(12) United States Patent
Lindsley et al.

(10) Patent No.: US 9,868,746 B2
(45) Date of Patent: *Jan. 16, 2018

(54) SUBSTITUTED 5-AMINOTHIENO[2,3-C] PYRIDAZINE-6-CARBOXAMIDE ANALOGS AS POSITIVE ALLOSTERIC MODULATORS OF THE MUSCARINIC ACETYLCHOLINE RECEPTOR M4

(71) Applicant: Vanderbilt University, Nashville, TN (US)

(72) Inventors: Craig W. Lindsley, Brentwood, TN (US); P. Jeffrey Conn, Nashville, TN (US); Michael R. Wood, Brentwood, TN (US); Bruce J. Melancon, Nashville, TN (US); James C. Tarr, Franklin, TN (US); James M. Salovich, Nashville, TN (US); Michael S. Poslusney, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,508

(22) Filed: Oct. 3, 2016

(65) Prior Publication Data

US 2017/0022216 A1 Jan. 26, 2017

Related U.S. Application Data

(63) Continuation of application No. 14/380,659, filed as application No. PCT/US2013/027534 on Feb. 23, 2013, now Pat. No. 9,493,481.

(60) Provisional application No. 61/602,481, filed on Feb. 23, 2012.

(51) Int. Cl.
  *C07D 495/04* (2006.01)
  *A61K 31/5025* (2006.01)
  *C07D 237/26* (2006.01)
  *C07D 409/04* (2006.01)
  *C07D 519/00* (2006.01)
  *C07F 7/18* (2006.01)

(52) U.S. Cl.
  CPC ......... *C07D 495/04* (2013.01); *C07D 237/26* (2013.01); *C07D 409/04* (2013.01); *C07D 519/00* (2013.01); *C07F 7/1804* (2013.01)

(58) Field of Classification Search
  None
  See application file for complete search history.

(56) References Cited

U.S. PATENT DOCUMENTS

| | | | |
|---|---|---|---|
| 4,496,725 A | 1/1985 | McCarthy, Jr. et al. | |
| 8,247,409 B2 | 8/2012 | Hong et al. | |
| 9,493,481 B2 * | 11/2016 | Lindsley | C07D 237/26 |
| 2007/0049603 A1 | 3/2007 | Miknis et al. | |
| 2009/0105244 A1 | 4/2009 | Rubio-Esteban et al. | |
| 2011/0077250 A1 | 3/2011 | Ryder | |
| 2013/0129677 A1 | 5/2013 | Dai et al. | |
| 2013/0210773 A1 | 8/2013 | Lindsley | |

FOREIGN PATENT DOCUMENTS

| | | |
|---|---|---|
| JP | 07-76586 | 3/1995 |
| WO | 1997/005139 | 2/1997 |
| WO | 2005/110410 | 11/2005 |
| WO | 2011/063415 | 5/2011 |
| WO | 2012/007593 | 1/2012 |
| WO | 2012/154731 | 11/2012 |
| WO | 2013/049255 | 4/2013 |
| WO | 2013/126856 | 8/2013 |
| WO | 2014/035829 | 3/2014 |
| WO | 2015/027204 | 2/2015 |
| WO | 2015/027214 | 2/2015 |

OTHER PUBLICATIONS 3-amino-4,5-diphenylthieno[2,3-c]pyridazine-2-carbohydrazide (CAS# 325170-33-0), EbuyChem.com, 2011, <http://www.ebuychem.com/product/325170-33-0.html>.
Almarsson, O. et al., "Crystal Engineering of the Composition of Pharmaceutical Phases. Do Pharmaceutical Co-crystal Represent a New path to Improved Medicines?," The Royal Society of Chemistry, 2004, 1889-1896.
Bodick et al., "Effects of Xanomeline, a Selective Muscarinic Receptor Agonist, on Cognitive Function and Behavioral Synptoms in Alzheimer Disease," Arch. Neurol., 1997, 54:465-473.
Brady et al., "Centrally Active Allosteric Potentiators of the M4 Muscarinic Acetylcholine Receptor Reverse Amphetamine-Induced Hyperlocomotor Activity in Rats," J Pharmacol Exp, 2008, vol. 327(3), pp. 941-955.
Bymaster et al., "Potential Role of Muscarinic Receptors in Schizophrenia," Life Sci. 1999, 64, 527-534.
Bymaster et al., "Unexpected antipsychotic-like activity with the muscarinic receptor ligand (5R, 6R)6-(3-propylthio-1,2,5-thiadiazol-4-yl)-1-azabicyclo[3.2.1]octane," Eur. J. Pharmocol, 1998, 356:109-119.

(Continued)

Primary Examiner — Emily Bernhardt
(74) Attorney, Agent, or Firm — Michael Best & Friedrich LLP

(57) ABSTRACT

In one aspect, the invention relates to substituted 5-aminothieno[2,3-c]pyridazine-6-carboxamide analogs, derivatives thereof, and related compounds, which are useful as positive allosteric modulators of the muscarinic acetylcholine receptor $M_4$ (mAChR $M_4$); synthesis methods for making the compounds; pharmaceutical compositions comprising the compounds; and methods of treating neurological and psychiatric disorders associated with muscarinic acetylcholine receptor dysfunction using the compounds and compositions. This abstract is intended as a scanning tool for purposes of searching in the particular art and is not intended to be limiting of the present invention.

8 Claims, 1 Drawing Sheet

(56) References Cited

OTHER PUBLICATIONS

Conn et al., "Subtype-Selective Allosteric Modulators Of Muscarinic Receptors For The Treatment Of CNS Disorders," Trends Pharmacol Sci., 2009, vol. 30, No. 3, pp. 148-155.
Fieser, L. F. and Fieser, M., "Reagents for Organic Synthesis," 1967, vol. 1, p. 584.
Jakubik et al., "Allosteric Modulation Of Muscarinic Acetylcholine Receptors," Pharmaceuticals, 2010, vol. 3, pp. 2838-2860.
Jeon, J. et al., "A Subpopulation of Neural M4 Muscarinic Acetylcholine Receptors Plays a Critical Role in Modulating Dopamine-Dependent Behaviors," J. Neurosci., 2010, 30(6):2396-2405.
Kennedy et al., "Synthesis And Structure—Activity Relationships Of Allosteric Potentiators Of The M4 Muscarinic Acetylcholine Receptors," ChemMedChem, 2009, vol. 4, No. 10, pp. 1600-1607.
Le et al., "Discovery of a selective M4 positive allosteric modulator based on the 3-amino-thieno[2,3-b]pyridine-2-carboxamide scaffold: development of ML253, a potent and brain penetrant compound that is active in a preclinical model of schizophrenia," Bioorg Med Chem Lett, 2013, vol. 23(1): pp. 346-350.
Le, "Optimization and Characterization of Muscarinic Acetylcholine Receptor M4 Positive Allosteric Modulators," Vandebilt University (2011), pp. 1-102.
Levy, A. et al., "Identification and localization of muscarinic acetylcholine receptor proteins in brain with subtype-specific antibodies," J. Neurosci., 1991, 11(10): 3218-3226.
Lewis et al., "Discovery Of A Highly Selective In Vitro And In Vivo M4 Positive Allosteric Modulator (PAM)." National Center for Biotechnology Information. U.S. National Library of Medicine; Bookshelf ID: NBK50687PMID: 21433380. Oct. 20, 2010; http://www.ncbi.nlm.nih.gov/books/NBK50687/; downloaded from the internet Apr. 4, 2013.
Morrison and Boyd, "Aromaticity," Organic Chemistry, (5th Ed., 1987) Chapter 13, pp. 477-497.
Pubchem-SID-17231431, May 5, 2011, pp. 1-2.
Shannon et al., "Muscarinic receptors Agonist, Like Dopamine Receptors Antagonist Antipsychotics, Inhibit Conditioned Avoidance, Response in Rats," J. Pharmacol. Exp. Ther., 1999, 290:901-907.
Shannon et al., "Xanomeline, an M1/M4 preferring muscarinic cholinergic receptor agonist, preoduces antipsychotic—like activity in rats," Schizophrenia Res., 2000, 42:249-259.
Uyen et al., Discovery of a Selective M4 Positive Allosteric Modulator Based on the 3-amino-thieno [2,3-b]pyridine-2-carboxamide Scaffold:Development of ML253, A Potent and Brain Penetrant Compound That is Active in a Preclinical Model of Schizophrenia, Bioorganic & Medicinal Chemistry Letters, Jan. 1, 2013, vol. 23, No. 1, pp. 346-350.
Shirey-Rice, "M1 And M4 Muscarinic Acetylcholine Receptor regulation Of Nuerotransmission And Cell Excitability In Rodent Hippocampus And Prefrontal Cortex," Dissertation, Submitted To The Faculty Of The Graduate School Of Vanderbilt University, 2010.
Yohannes et al., "Deconstructing cytisine: The syntheses of (+−)-cyfusine and (+−) -cyclopropylcyfusine, fused ring analogs of cytisine," Bioorganic & Medicinal Chemistry Letters, 2008, vol. 18, pp. 2316-2319.
ZINC03847009. National Center For Biotechnology Information. PubChem. Jul. 19, 2005 <http://pubchem.ncbi.nlm.nih.gov/summary/summary.cgi?cid=2751736>.
PCT/US2014/52379 International Search Report and Written Opinion dated Nov. 19, 2014 (8 pages).
PCT/US2014/52391 International Search Report and Written Opinion dated Nov. 7, 2014 (8 pages).
PCT/US2013/27534 International Search Report and Written Opinion dated May 28, 2013 (6 pages).
PCT/US2013/56441 International Search Report and Written Opinion dated Feb. 3, 2014 (13 pages).
PCT/US2014/52379 International Preliminary Report on Patentability dated Feb. 23, 2016 (1 page).
PCT/US2014/52391 International Preliminary Report on Patentability dated Feb. 23, 2016 (1 page).
PCT/US2013/56441 International Preliminary Report on Patentability dated Mar. 3, 2015 (1 page).
EP13751391.7 Extended European Search Report dated Jul. 28, 2015 (11 pages).
"Al-Kamali, Ahmed S. N.:""Synthesis and reactions of some new thieno [2,3-C] pyridazine derivatives,""The Phosphorus, Sulfur and Silicon Related Elements, vol. 184, No. 7, 2009, pp. 1812-1824, XP002741779, ISSN:1042-6507, DOI:10.1080/10426500802353213 *see compounds 5a, 5b and 5c in scheme 2 on p. 1841*".
"Radwan, Sh. M. et al:""Synthesis of some new pyrimidothienopyridazines and relatedheterocycles,""Journal of the Chinese Chemical Society (Taipei, Taiwan), vol. 52, No. 2, 2005, pp. 303-308, XP002741780, ISSN:0009-4536, DOI:10.1002/JCCS. 200500046 *see compound 2c in scheme I on p. 303*".
El-D Ean, A. M. Kamal et al: "Novel synthesis of thieno [2,3-c] pyridazine and pyrimido [4',5':4,5] thieno [2, 3-c] pyridazinederivatives," Phosphorus, Sulfur and Silicon and the Related Elements, vol. 180, No. 2, 2005, pp. 413-424, XP002741781, ISSN:1042-6507, DOI:10.1080/104265090509216 *see compounds 6c and 6d in scheme 2 on p. 415*.
"Radwan, Sh. M. et al:""Synthesis of pyridazothienothiazine and pyrimidothienopyridazines,""Phosphorus, Sulfur and Silicon and the Related Elements, vol. 164, 2000, pp. 299-313, XP002741782, ISSN: 1042-6507, DOI:10.1080/10426500008045255 *see compounds 2a-2c in scheme 1 on p.300*".
Abbady, M. S. et al: "Synthesis and some reactions of thieno [2,3-c] pyridazinederivatives and their antibacterial activity," Phosphorus, Sulfur and Silicon and the Related Elements, vol. 86, No. 1-4, 1994, pp. 203-209, XP009184922, ISSN:1042-6507, DOI:10.1080/10426509408018405 *see compound 4c on p. 204*.
"Gaber, Abdel-Aal M. et al :""Synthesis of novel polyfunctionally substituted thieno [2,3-c] pyridazines,""Journal of the Chinese Chemical Society (Taipei, Taiwan), vol. 51, No. 6, 2004, pp. 1325-1331, XP002741783, ISSN:0009-4536, DOI:10.1002/JCCS . 200400192 *see compound 14 in scheme IV on p. 1327*".
Radwan. Sh. M.: "Synthesis and reactions of some new heterocyclic compounds containing thieno [2,3-c] pyridazinemoiety," Phosphorus, Sulfur and Silicon and the Related Elements, 163, 153-169 CODEN:PSSLEC; ISSN:1042-6507, vol. 163, 2000, pp. 153-169, XP008169735, ISSN:1042-6507, DOI:10.1080/10426500008046617 *see compound 5 in scheme 1 on p. 154*.
Radwan, Sh. M. et al: "Synthesis of pyrrolo ["• 211 :1 ',2'] pyrazino [6'•5 ':4•5]thieno [2,3- c] pyridazinederivatives and related pentacyclicheterocycles," Phosphorus, Sulfur and Silicon and the Related Elements, 89 (1-4), 193-8 CODEN:PSSLEC; ISSN:1042-6507,1994, XP009184919, DOI:10.1080/10426509408020449 10.1080/10426509408020449 *see compound (6) on p. 194*.
Al-Kamali, Ahmed S. N. et al: "Synthesis and antibacterial activity of some novel thieno [2,3-c] pyridazinesusing 3-ami no-5-phenyl-2-ethoxycarbonylthieno [2, 3- c] pyridazine as a starting material," Arabi an Journal of Chemistry,vol. 7, No. 5, 2014, pp. 775-780, XP002741787, ISSN:1878-5352, DOI:10.1016/J.ARABJC.2010. 12.020 *see compound 10 in scheme 5 on p. 779*.
"A. E. Brady et al:""Centrally Active Allosteric Potentiators of the M4 Muscarinic Acetylcholine Receptor Reverse Amphetamine-Induced Hyperlocomotor Activity in Rats,""Journal of Pharmacology and Experimental Therapeutics, vol. 327, No. 3, Sep. 5, 2008 (Sep. 5, 2008), pp. 941-953, XP055081736,ISSN:0022-3565, DOI:10.1124/jpet.108.140350 *see table 1 and pharmacological activity*".
"Phillip Kennedy et al:""Synthesis and Structure-Activity Relationships of Allosteric Potentiators of the M4 Muscarinic Acetylcholine Receptor,""Chemmedchem, vol. 4, No. 10, Oct. 5, 2009 (Oct. 5, 2009), pp. 1600-1607, XP055081738, ISSN:1860-7179, DOI:10. 1002/cmdc.200900231 *see compounds of table 1 and pharmacological activity*".
Foster et al., "Neuropsychiatric Disease and Treatment," brochure (2014) 10, pp. 183-191.
Bridges et al., "Drug News Perspect," brochure (2010) 23(4) pp. 229-240.

* cited by examiner

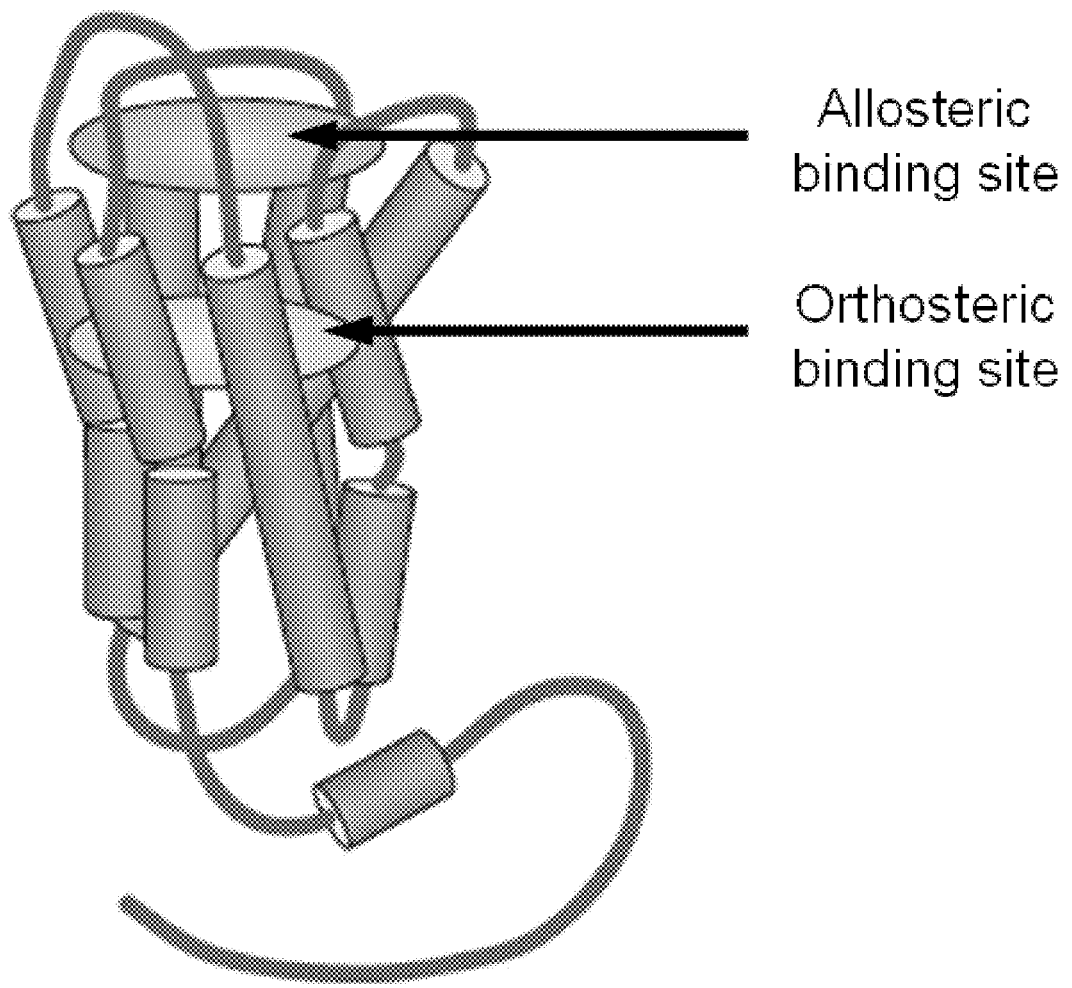

SUBSTITUTED 5-AMINOTHIENO[2,3-C] PYRIDAZINE-6-CARBOXAMIDE ANALOGS AS POSITIVE ALLOSTERIC MODULATORS OF THE MUSCARINIC ACETYLCHOLINE RECEPTOR M4

CROSS-REFERENCE TO RELATED APPLICATIONS

This application is a continuation of U.S. patent application Ser. No. 14/380,659, filed Aug. 22, 2014, now U.S. Pat. No. 9,493,481, which application is a U.S. national stage filing under 35 U.S.C. 371 of International Application No. PCT/US2013/027534, filed Feb. 23, 2013, which application claims priority to U.S. Provisional Patent Application No. 61/602,481, filed Feb. 23, 2012, each of which are incorporated herein by reference in their entireties.

STATEMENT REGARDING FEDERALLY SPONSORED RESEARCH

This invention was made with government support under grant numbers MH87965, MH86601, MH82867, MH73676, MH89870, NS65867, MH77607, MH84659 and MH74427 awarded by the National Institutes of Health. The United States government has certain rights in the invention.

BACKGROUND

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, that are critically involved in higher processes. Clinical data supports that cholinergic hypofunction contributes to the cognitive deficits of patients suffering from schizophrenia. Efforts to increase acetylcholine levels have focused on increasing levels of choline, the precursor for acetylcholine synthesis, and on blocking acetylcholinesterase (AChE), the enzyme that metabolizes acetylcholine. As a result, acetylcholinesterase (AChE) inhibitors, which inhibit the hydrolysis of ACh, have been approved in the United States for use in the palliative, but not disease-modifying, treatment of the cognitive deficits in AD patients.

Attempts to augment central cholinergic function through the administration of choline or phosphatidylcholine have not been successful. AChE inhibitors have shown therapeutic efficacy, but have been found to have frequent cholinergic side effects due to peripheral acetylcholine stimulation, including abdominal cramps, nausea, vomiting, and diarrhea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have severely limited their clinical utility. An alternative approach to pharmacologically target cholinergic hypofunction is the activation of mAChRs, which are widely expressed throughout the body.

The mAChRs are members of the family A GPCRs and include five subtypes, designated $M_1$-$M_5$. The $M_1$, $M_3$ and $M_5$ subtypes mainly couple to $G_q$ and activate phospholipase C, whereas the $M_2$ and $M_4$ subtypes mainly couple to $G_{i/o}$ and associated effector systems. These five distinct mAChR subtypes have been identified in the mammalian central nervous system where they are prevalent and differentially expressed. $M_1$-$M_5$ have varying roles in cognitive, sensory, motor and autonomic functions. Thus, without wishing to be bound by a particular theory, it is believed that selective agonists of mAChR subtypes that regulate processes involved in cognitive function could prove superior to be superior therapeutics for treatment of psychosis, schizophrenia and related disorders. The muscarinic $M_4$ receptor has been shown to have a major role in cognitive processing and is believed to have a major role in the pathophysiology of psychotic disorders, including schizophrenia.

Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_4$ has been viewed as the most likely subtype for mediating the effects of muscarinic acetylcholine receptor dysfunction in psychotic disorders, including schizophrenia, cognition disorders, and neuropathic pain. Because of this, considerable effort has been focused on developing selective $M_4$ agonists for treatment of these disorders. Unfortunately, these efforts have been largely unsuccessful because of an inability to develop compounds that are highly selective for the mAChR $M_4$. Because of this, mAChR agonists that have been tested in clinical studies induce a range adverse effects by activation of peripheral mAChRs. To fully understand the physiological roles of individual mAChR subtypes and to further explore the therapeutic utility of mAChR ligands in psychosis, including schizophrenia, cognition disorders and other disorders, it can be important to develop compounds that are highly selective activators of mAChR $M_4$ and other individual mAChR subtypes.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved. This approach is proving to be highly successful in developing selective ligands for multiple GPCR subtypes. In the case of mAChRs, a major goal has been to develop allosteric ligands that selectively increase activity of mAChR $M_4$ or other mAChR subtypes. Allosteric activators can include allosteric agonists, that act at a site removed from the orthosteric site to directly activate the receptor in the absence of ACh as well as positive allosteric modulators (PAMs), which do not activate the receptor directly but potentiate activation of the receptor by the endogenous orthosteric agonist ACh. Also, it is possible for a single molecule to have both allosteric potentiator and allosteric agonist activity.

Recently, muscarinic agonists including xanomeline have been shown to be active in animal models with similar profiles to known antipsychotic drugs, but without causing catalepsy (Bymaster et al., Eur. J. Pharmacol. 1998, 356, 109, Bymaster et al., Life Sci. 1999, 64, 527; Shannon et al., J. Pharmacol. Exp. Ther. 1999, 290, 901; Shannon et al., Schizophrenia Res. 2000, 42, 249.). Further, xanomeline was shown to reduce psychotic behavioral symptoms such as delusions, suspiciousness, vocal outbursts, and hallucinations in Alzheimer's disease patients (Bodick et al., Arch. Neurol. 1997, 54, 465.), however treatment induced side effects, e.g., gastrointestinal effects, have severely limited the clinical utility of this compound.

Despite advances in muscarinic acetylcholine receptor research, there is still a scarcity of compounds that are both potent, efficacious, and selective activators of the $M_4$ mAChR and also effective in the treatment of neurological and psychiatric disorders associated with cholinergic activity and diseases in which the muscarinic $M_4$ receptor is involved. These needs and other needs are satisfied by the present invention.

SUMMARY

In accordance with the purpose(s) of the invention, as embodied and broadly described herein, the invention, in one aspect, relates to compounds useful as positive allosteric modulators (i.e., potentiators) of the muscarinic acetylcholine receptor $M_4$ (mAChR $M_4$), methods of making same, pharmaceutical compositions comprising same, and methods of treating neurological and psychiatric disorders associated with muscarinic acetylcholine receptor dysfunction using same.

Disclosed are compounds having a structure represented by a formula:

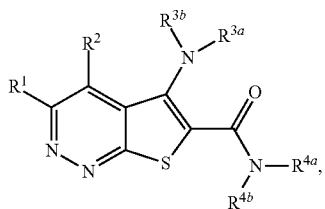

wherein $R^1$ is selected from hydrogen, halogen, —OH, —CN, —$NH_2$, —$CF_3$, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-$Ar^{10}$, $Ar^{10}$, —(C1-C3 alkyl)-$Cy^{10}$, and $Cy^{10}$; wherein each $Ar^{10}$, when present, is selected from phenyl and monocyclic heteroaryl; and wherein $Ar^{10}$ is substituted with 0, 1, 2, or 3 groups independently selected from halogen, —OH, —CN, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein each $Cy^{10}$, when present, is selected from C3-C9 cycloalkyl and C3-C8 heterocycloalkyl; and wherein $Cy^{10}$ is substituted with 0, 1, 2, or 3 groups independently selected from halogen, —OH, —CN, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^2$ is selected from hydrogen, halogen, —OH, —CN, —$NH_2$, —$CF_3$, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-$Ar^{11}$, $Ar^{11}$, —(C1-C3 alkyl)-$Cy^{11}$, and $Cy^{11}$; wherein each $Ar^{11}$, when present, is selected from phenyl and monocyclic heteroaryl; and wherein $Ar^{11}$ is substituted with 0, 1, 2, or 3 groups independently selected from halogen, —OH, —CN, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein each $Cy^{11}$, when present, is selected from C3-C9 cycloalkyl and C3-C8 heterocycloalkyl; and wherein $Cy^{11}$ is substituted with 0, 1, 2, or 3 groups independently selected from halogen, —OH, —CN, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein $R^1$ and $R^2$ are optionally covalently bonded and, together with the intermediate atoms, comprise a 3- to 7-membered cycle substituted with 0, 1, 2, or 3 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, $Ar^{10}$, $Ar^{11}$, $Cy^{10}$, and $Cy^{11}$; wherein each of $R^{3a}$ and $R^{3b}$ is independently selected from hydrogen, C1-C6 alkyl, C1-C6 haloalkyl, C1-C6 polyhaloalkyl, C3-C9 cycloalkyl, C2-C7 heterocycloalkyl, —(C1-C8 alkyl)-(C3-C9 cycloalkyl), and —(C1-C8 alkyl)-(C2-C7 heterocycloalkyl); wherein $R^{3a}$ and $R^{3b}$ are optionally covalently bonded and, together with the intermediate nitrogen, comprise a 3- to 7-membered heterocycloalkyl substituted with 0, 1, 2, or 3 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; wherein each of $R^{4a}$ and $R^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{20}R^{21}$, —(C1-C6 alkyl)-$NR^{20}$(C=O)$R^{21}$, —(C1-C6 alkyl)-$NR^{20}$(C=O)$OR^{21}$, —(C1-C6 alkyl)-$NR^{20}$(C=O)$NR^{21}$, —(C1-C6 monohaloalkyl)-$NR^{20}$(C=O)$OR^{21}$, —(C1-C6 polyhaloalkyl)-$NR^{20}$(C=O)$OR^{21}$, —(C1-C8 alkyl)-$Cy^1$, $Cy^1$, —($CH_2$)—$Ar^1$, —($CH_2$)$_2$—$Ar^3$, —(C3-C8 alkyl)-$Ar^1$, —(C2-C8 alkynyl)-$Ar^1$, and $Ar^2$; wherein $R^{4a}$ and $R^{4b}$ are not simultaneously hydrogen; wherein each $R^{20}$, when present, is independently selected from hydrogen and C1-C8 alkyl; wherein each $R^{21}$, when present, is independently selected from hydrogen, C1-C8 alkyl, C1-C8 monohaloalkyl, C1-C8 polyhaloalkyl, —(C1-C8 alkyl)-$Cy^1$, $Cy^1$, —(C1-C8 alkyl)-$Ar^1$, and $Ar^1$; wherein each $Ar^1$, when present, is independently selected from phenyl, naphthyl, and heteroaryl, and wherein each $Ar^1$ is independently substituted with 0, 1, 2, or 3 groups independently selected from halogen, —$NH_2$, —OH, —CN, —$N_3$, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{31}R^{32}$, —(C1-C6 alkyl)-$NR^{30}$(C=O)$R^{35}$, —(C1-C6 alkyl)-$NR^{30}$(C=O)$OR^{35}$, —(C1-C6 alkyl)-$NR^{30}$(C=O)$NR^{35}$, —(C1-C6 alkyl)-$NR^{30}S(O)_nR^{35}$, —$NR^{30}$(C1-C6 alkyl)-(C=O)$R^{35}$, —$NR^{30}$(C1-C6 alkyl)-(C=O)$OR^{35}$, —$NR^{30}$(C1-C6 alkyl)-(C=O)$NR^{35}$, —$NR^{30}$(C1-C6 alkyl)-$S(O)_nR^{35}$, —$NR^{30}$(C1-C6 alkyl)-$S(O)_nNR^{33}R^{34}$, —$NR^{30}$(C=O)$R^{35}$, —$NR^{30}$(C=O)$OR^{35}$, —$NR^{30}$(C=O)$NR^{35}$, —$NR^{30}S(O)_nR^{35}$, —(C1-C6 alkyl)-(C=O)$R^{35}$, —(C1-C6 alkyl)-(C=O)$OR^{35}$, —(C1-C6 alkyl)-(C=O)$NR^{35}$, —(C1-C6 alkyl)-$S(O)_nR^{35}$, —(C1-C6 alkyl)-$S(O)_nNR^{33}R^{34}$, —(C=O)$R^{35}$, —(C=O)$OR^{35}$, —$S(O)_nR^{35}$, —$S(O)_nNR^{33}R^{34}$, —(C1-C8 alkyl)-$Ar^{20}$, $Ar^{20}$, —(C1-C8 alkyl)-$Cy^{20}$, $Cy^{20}$, and $R^{37}$; wherein each n is an integer independently selected from 0, 1 and 2; wherein each $Ar^{20}$, when present, is independently selected from phenyl, naphthyl, and heteroaryl, and wherein each $Ar^{20}$ is independently substituted with 0, 1, 2, or 3 groups independently selected from halogen, —$NH_2$, —OH, —CN, —$S(O)_nR^{36}$, C1-C8 alkyl, C1-C8 monohaloalkyl, C1-C8 polyhaloalkyl, C1-C8 alkoxy, C1-C8 alkylamino, and C1-C8 dialkylamino; wherein each $Cy^{20}$, when present, is independently selected from C3-C9 cycloalkyl and C2-C7 heterocycloalkyl, and wherein each $Cy^{20}$ is independently substituted with 0, 1, 2, or 3 groups independently selected from halogen, —$NH_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{30}$, when present, is independently selected from hydrogen and C1-C8 alkyl; wherein each R$^{31}$, when present, is independently selected from hydrogen and C1-C8 alkyl; wherein each R$^{32}$, when present, is independently selected from hydrogen and C1-C8 alkyl; wherein each R$^{33}$, when present, is independently selected from hydrogen and C1-C8 alkyl; wherein each R$^{34}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{21}$, and Ar$^{21}$; wherein each Ar$^{21}$, when present, is independently selected from phenyl, naphthyl, and heteroaryl, and wherein each Ar$^{21}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{35}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{22}$, and Ar$^{22}$; wherein each Ar$^{22}$, when present, is independently selected from phenyl, naphthyl, and heteroaryl, and wherein each Ar$^{22}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{36}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{23}$, and Ar$^{23}$; wherein each Ar$^{23}$, when present, is independently selected from phenyl, naphthyl, and heteroaryl, and wherein each Ar$^{23}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{37}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN; wherein each Ar$^2$, when present, is a heteroaryl, and wherein each Ar$^2$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; wherein each Ar$^3$, when present, is a heteroaryl, and wherein each Ar$^3$ is independently substituted with 0, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; or and wherein each Ar$^3$ is independently monosubstituted with a groups selected from —Cl, —Br, —I, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; wherein each Cy$^1$, when present, is independently selected from C3-C9 cycloalkyl and C2-C7 heterocycloalkyl, and wherein each Cy$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; wherein R$^{4a}$ and R$^{4b}$ are optionally covalently bonded and, together with the intermediate nitrogen, comprise a 3- to 10-membered heterocycloalkyl substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$ (C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{30}$, Ar$^{30}$, —(C1-C8 alkyl)-Cy$^{30}$, Cy$^{30}$, and R$^{37}$; wherein each Ar$^{30}$, when present, is independently selected from phenyl, naphthyl, and heteroaryl, and wherein each Ar$^{30}$ is independently substituted with 0, 1, 2, or 3 groups independently selected from halogen, —NH$_2$, —OH, —CN, —S(O)$_n$R$^{45}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$; wherein each R$^{45}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Ar$^{40}$, when present, is independently selected from phenyl, naphthyl, and heteroaryl, and wherein each Ar$^{40}$ is independently substituted with 0, 1, 2, or 3 groups independently selected from halogen, —NH$_2$, —OH, —CN, —S(O)$_n$R$^{46}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{46}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Cy$^{40}$, when present, is independently selected from C3-C9 cycloalkyl and C2-C7 heterocycloalkyl, and wherein each Cy$^{40}$ is independently substituted with 0, 1, 2, or 3 groups independently selected from halogen, —NH$_2$, —OH, —CN, —S(O)$_n$R$^{46}$, C1-C8 alkyl, C1-C8 monohaloalkyl, C1-C8 polyhaloalkyl, C1-C8 alkoxy, C1-C8 alkylamino, and C1-C8 dialkylamino; wherein each Cy$^{30}$, when present, is independently selected from C3-C9 cycloalkyl and C2-C7 heterocycloalkyl, and wherein each Cy$^{30}$ is independently substituted with 0, 1, 2, or 3 groups independently selected from halogen, —NH$_2$, —OH, —CN, —S(O)$_n$R$^{45}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$; or a pharmaceutically acceptable salt, solvate, or polymorph thereof.

Also disclosed are compounds having a structure represented by a formula:

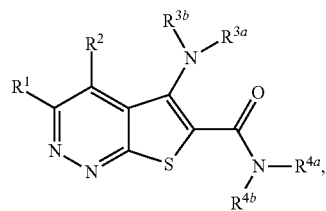

wherein R$^1$ is selected from hydrogen, halogen, C1-C6 alkyl, C1-C6 haloalkyl, C1-C6 polyhaloalkyl, C1-C6 alkoxy, C1-C6 alkylamino, and C1-C6 dialkylamino; wherein R$^2$ is selected from hydrogen, halogen, C1-C6 alkyl, C1-C6 haloalkyl, C1-C6 polyhaloalkyl, C1-C6 alkoxy, C1-C6 alkylamino, and C1-C6 dialkylamino; wherein R$^1$ and R$^2$ are optionally covalently bonded and, together with the intermediate atoms, comprise a 3- to 7-membered cycle substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; wherein each of R$^{3a}$ and R$^{3b}$ is independently selected from hydrogen, C1-C6 alkyl, C1-C6 haloalkyl, C1-C6 polyhaloalkyl, C3-C8 cycloalkyl, C2-C7 heterocycloalkyl, —(C1-C8 alkyl)-(C3-C8 cycloalkyl), and —(C1-C8 alkyl)-(C2-C7 heterocycloalkyl); wherein R$^{3a}$ and R$^{3b}$ are optionally covalently bonded and, together with the intermediate nitrogen, comprise a 3- to 7-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; wherein each of R$^{4a}$ and R$^{4b}$ is independently selected from hydrogen, C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; wherein R$^{4a}$ and R$^{4b}$ are not both hydrogen; wherein each of R$^{4a}$ and R$^{4b}$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein n is an integer from 0 to 2; wherein Ar$^1$ is selected from phenyl and heterocyclyl; wherein Ar$^2$ is heterocyclyl; wherein R4a and R4b are optionally covalently bonded and, together with the intermediate nitrogen, comprise a 3- to 10-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; and wherein R$^5$, when present, is selected from hydrogen, C1-C8 alkyl, C1-C8 haloalkyl, and C1-C8 polyhaloalkyl; or a pharmaceutically acceptable salt, hydrate, solvate, or polymorph thereof.

Also disclosed are pharmaceutical compositions comprising a therapeutically effective amount of one or more disclosed compounds, or pharmaceutically acceptable salt, hydrate, solvate, or polymorph thereof, and a pharmaceutically acceptable carrier.

Also disclosed are methods for the treatment of a neurological and/or psychiatric disorder associated with muscarinic acetylcholine receptor dysfunction in a mammal comprising the step of administering to the mammal a therapeutically effective amount of at least one disclosed compound or pharmaceutically acceptable salt, hydrate, solvate, or polymorph thereof.

Also disclosed are methods for potentiation of muscarinic acetylcholine receptor activity in a mammal comprising the step of administering to the mammal a therapeutically effective amount of at least one disclosed compound or pharmaceutically acceptable salt, hydrate, solvate, or polymorph thereof.

Also disclosed are methods for enhancing cognition in a mammal comprising the step of administering to the mammal an effective amount of at least one disclosed compound or pharmaceutically acceptable salt, hydrate, solvate, or polymorph thereof.

Also disclosed are methods for potentiation of muscarinic acetylcholine receptor activity in at least one cell, comprising the step of contacting the cell with an effective amount of at least one disclosed compound or pharmaceutically acceptable salt, hydrate, solvate, or polymorph thereof.

Also disclosed are uses of a disclosed compound, a disclosed product of making, or a pharmaceutically acceptable salt, hydrate, solvate, or polymorph thereof.

Also disclosed are uses of a disclosed compound, a disclosed product of making, or a pharmaceutically acceptable salt, hydrate, solvate, or polymorph thereof, in the manufacture of a medicament for the treatment of a disorder associated with a muscarinic acetylcholine receptor dysfunction in a mammal.

Also disclosed are methods for the manufacture of a medicament to activate the mAChR $M_4$ in a mammal comprising combining at least one disclosed compound or at least one disclosed product of making with a pharmaceutically acceptable carrier or diluent.

Also disclosed are kits comprising at least one disclosed compound, or a pharmaceutically acceptable salt, hydrate, solvate, or polymorph thereof, and one or more of: (a) at least one agent known to increase mAChR $M_4$ activity; (b) at least one agent known to decrease mAChR $M_4$ activity; (c) at least one agent known to treat a disorder associated with cholinergic activity; (d) instructions for treating a disorder associated with cholinergic activity; (e) instructions for treating a disorder associated with mAChR $M_4$ receptor activity; or (f) instructions for administering the compound in connection with cognitive or behavioral therapy.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying FIGURES, which are incorporated in and constitute a part of this specification, illustrate several aspects and together with the description serve to explain the principles of the invention.

FIG. 1 is a schematic illustration of ligand binding to the orthosteric site and an allosteric site in the muscarinic acetylcholine receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mAChR $M_4$ receptor is the site that acetylcholine binds.

As used herein, the term "mAChR $M_4$ receptor positive allosteric modulator" refers to any exogenously administered compound or agent that directly or indirectly augments the activity of the mAChR $M_4$ receptor in the presence or in the absence of acetylcholine, or another agonist, in an animal, in particular a mammal, for example a human. For example, a mAChR $M_4$ receptor positive allosteric modulator can increase the activity of the mAChR $M_4$ receptor in a cell in the presence of extracellular acetylcholine. The cell can be Chinese hamster ovary (CHO-K1) cells transfected with human mAChR $M_4$. The cell can be Chinese hamster ovary (CHO-K1) cells transfected with rat mAChR $M_4$ receptor. The cell can be Chinese hamster ovary (CHO-K1) cells transfected with a mammalian mAChR $M_4$. The term "mAChR $M_4$ receptor positive allosteric modulator" includes a compound that is a "mAChR $M_4$ receptor allosteric potentiator" or a "mAChR $M_4$ receptor allosteric agonist," as well as a compound that has mixed activity comprising pharmacology of both an "mAChR $M_4$ receptor allosteric potentiator" and an "mAChR $M_4$ receptor allosteric agonist". The term "mAChR $M_4$ receptor positive allosteric modulator also includes a compound that is a "mAChR $M_4$ receptor allosteric enhancer."

As used herein, the term "mAChR $M_4$ receptor allosteric potentiator" refers to any exogenously administered compound or agent that directly or indirectly augments the response produced by the endogenous ligand (such as acetylcholine) when the endogenous ligand binds to the orthosteric site of the mAChR $M_4$ receptor in an animal, in particular a human. The mAChR $M_4$ receptor allosteric potentiator binds to a site other than the orthosteric site, that is, an allosteric site, and positively augments the response of the receptor to an agonist or the endogenous ligand. In one aspect, an allosteric potentiator does not induce desensitization of the receptor, activity of a compound as an mAChR $M_4$ receptor allosteric potentiator provides advantages over the use of a pure mAChR $M_4$ receptor orthosteric agonist. Such advantages can include, for example, increased safety margin, higher tolerability, diminished potential for abuse, and reduced toxicity.

As used herein, the term "mAChR $M_4$ receptor allosteric enhancer" refers to any exogenously administered compound or agent that directly or indirectly augments the response produced by the endogenous ligand (such as acetylcholine) in an animal, in particular a mammal, for example a human. In one aspect, the allosteric enhancer increases the affinity of the natural ligand or agonist for the orthosteric site. In another aspect, an allosteric enhancer increases the agonist efficacy. The mAChR $M_4$ receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

As used herein, the term "mAChR $M_4$ receptor allosteric agonist" refers to any exogenously administered compound or agent that directly activates the activity of the mAChR $M_4$ receptor in the absence of the endogenous ligand (such as acetylcholine) in an animal, in particular a mammal, for example a human. The mAChR $M_4$ receptor allosteric agonist binds to a site that is distinct from the orthosteric acetylcholine site of the mAChR $M_4$ receptor. Because it does not require the presence of the endogenous ligand, activity of a compound as an mAChR $M_4$ receptor allosteric agonist provides advantages over the use of a pure mAChR $M_4$ receptor allosteric potentiator, such as more rapid onset of action.

As used herein, the term "mAChR $M_4$ receptor neutral allosteric ligand" refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with muscarinic acetylcholine receptor dysfunction prior to the administering step. In some aspects of the disclosed method, the subject has been diagnosed with a need for positive allosteric modulation of muscarinic acetylcholine receptor activity prior to the administering step. In some aspects of the disclosed method, the subject has been diagnosed with a need for partial agonism of muscarinic acetylcholine receptor activity prior to the administering step. In some aspects of the disclosed method, the subject has been diagnosed with a neurological and/or psychiatric disorder, e.g. schizophrenia, Alzheimer's disease, a cognitive disorder, or neuropathic pain prior to the administering step. In some aspects of the disclosed method, the subject has been identified with a disorder treatable by activation of the mAChR $M_4$ receptor and/or or a need for activation/agonism of mAChR $M_4$ activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mAChR $M_4$" means having been subjected to a physical examination by a person of skill, for example, a physician, and found to have a condition that can be diagnosed or treated by a compound or composition that can modulate mAChR $M_4$. As a further example, "diagnosed with a need for modulation of mAChR $M_4$" refers to having been subjected to a physical examination by a person of skill, for example, a physician, and found to have a condition characterized by mAChR $M_4$ activity. Such a diagnosis can be in reference to a disorder, such as a neurodegenerative disease, and the like, as discussed herein. For example, the term "diagnosed with a need for positive allosteric modulation of muscarinic acetylcholine receptor activity" refers to having been subjected to a physical examination by a person of skill, for example, a physician, and found to have a condition that can be diagnosed or treated by positive allosteric modulation of muscarinic acetylcholine receptor activity. For example, "diagnosed with a need for partial agonism of muscarinic acetylcholine receptor activity" means having been subjected to a physical examination by a person of skill, for example, a physician, and found to have a condition that can be diagnosed or treated by partial agonism of muscarinic acetylcholine receptor activity. For example, "diagnosed with a need for treatment of one or more neurological and/or psychiatric disorder associated with acetylcholine dysfunction" means having been subjected to a physical examination by a person of skill, for example, a physician, and found to have one or more neurological and/or psychiatric disorder associated with acetycholine dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mAChR $M_4$ activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. a muscarinic acetylcholine receptor), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "EC$_{50}$," is intended to refer to the concentration of a substance (e.g., a compound or a drug) that is required for 50% activation or enhancement of a biological process, or component of a process. For example, EC$_{50}$ can refer to the concentration of agonist that provokes a response halfway between the baseline and maximum response in an appropriate assay of the target activity. For example, an EC$_{50}$ for the mAChR M$_4$ receptor can be determined in an in vitro or cell-based assay system. Such in vitro assay systems frequently utilize a cell line that either expresses endogenously a target of interest, or has been transfected with a suitable expression vector that directs expression of a recombinant form of the target such as the mAChR M$_4$ receptor. For example, the EC$_{50}$ for mAChR M$_4$ can be determined using Chinese hamster ovary (CHO-K1) cells transfected with human mAChR M$_4$. Alternatively, the EC$_{50}$ for mAChR M$_4$ can be determined using Chinese hamster ovary (CHO-K1) cells transfected with rat mAChR M$_4$. In another example, the EC$_{50}$ for mAChR M$_4$ can be determined using Chinese hamster ovary (CHO-K1) cells transfected with a mammalian mAChR M$_4$.

As used herein, "IC$_{50}$," is intended to refer to the concentration of a substance (e.g., a compound or a drug) that is required for 50% inhibition of a biological process, or component of a process. For example, IC$_{50}$ refers to the half maximal (50%) inhibitory concentration (IC) of a substance as determined in a suitable assay. For example, an IC$_{50}$ for mAChR M$_4$ receptor can be determined in an in vitro or cell-based assay system. Frequently, receptor assays, including suitable assays for mAChR M$_4$, make use of a suitable cell-line, e.g. a cell line that either expresses endogenously a target of interest, or has been transfected with a suitable expression vector that directs expression of a recombinant form of the target such as mAChR $M_4$. For example, the $IC_{50}$ for mAChR $M_4$ can be determined using Chinese hamster ovary (CHO-K1) cells transfected with human mAChR $M_4$. Alternatively, the $IC_{50}$ for mAChR $M_4$ can be determined using Chinese hamster ovary (CHO-K1) cells transfected with rat mAChR $M_4$. In another example, the $IC_{50}$ for mAChR $M_4$ can be determined using Chinese hamster ovary (CHO-K1) cells transfected with a mammalian mAChR $M_4$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$", and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, bicyclo[1.1.1]pentanyl, adamantanyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide", as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. Additional representative heterocycloalkyl groups include, but are not limited to, 2,5-diazabicyclo[2.2.1]heptanyl, hexahydropyrrolo[3,4-c]pyrrolyl, and 2,6-diazaspiro[3.3]heptanyl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2$ $OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)$ OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$R°; —(CH$_2$)$_{0-4}$S(O)$_2$R°; —S(O)$_2$NR°$_2$; —(CH$_2$)$_{0-4}$S(O)$_2$R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^{\bullet}$, -(haloR$^{\bullet}$), —(CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$ wherein each R$^{\bullet}$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R° is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^{\dagger}$, —NR$^{\dagger}$$_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, or —N(R$^{\dagger}$)S(O)$_2$R$^{\dagger}$; wherein each R$^{\dagger}$ is independently hydrogen, C$_1$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^{\dagger}$, taken together with their intervening atom(s) form an unsubstituted 3-12-membered saturated, partially unsaturated, or aryl mono or bicyclic ring having 0-4 heteroatoms independently selected from nitrogen, oxygen, or sulfur.

Suitable substituents on the aliphatic group of R$^{\dagger}$ are independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

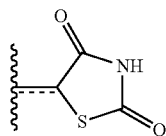

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$ respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

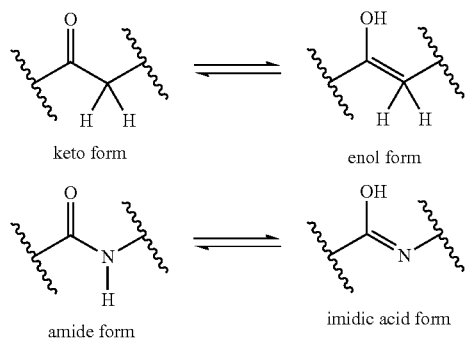

Likewise, amides with an N-hydrogen can exist in an equilibrium of the amide form and the imidic acid form. As another example, pyrazoles can exist in two tautomeric forms, N$^1$-unsubstituted, 3-A$^3$ and N$^1$-unsubstituted, 5-A$^3$ as shown below.

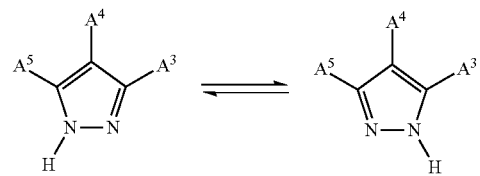

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

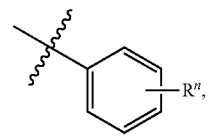

which is understood to be equivalent to a formula:

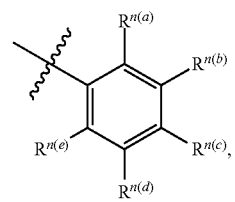

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as positive allosteric modulators of the muscarinic acetylcholine receptor $M_4$ (mAChR $M_4$). More specifically, in one aspect, the present invention relates to compounds that allosterically modulate mAChR $M_4$ receptor activity, affecting the sensitivity of mAChR $M_4$ receptors to agonists without acting as orthosteric agonists themselves. The compounds can, in one aspect, exhibit subtype selectivity.

In one aspect, the disclosed compounds exhibit positive allosteric modulation of mAChR $M_4$ response to acetylcholine as an increase in response to non-maximal concentrations of acetylcholine in Chinese hamster ovary (CHO-K1) cells transfected with rat mAChR $M_4$ in the presence of the compound, compared to the response to acetylcholine in the absence of the compound. In further aspect, the Chinese hamster ovary (CHO-K1) cells are transfected with human mAChR $M_4$. In yet a further aspect, Chinese hamster ovary (CHO-K1) cells are transfected with mAChR $M_4$ of a mammal.

In one aspect, the compounds of the invention are useful in the treatment neurological and psychiatric disorders associated with muscarinic acetylcholine receptor dysfunction and other diseases in which muscarinic acetylcholine receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

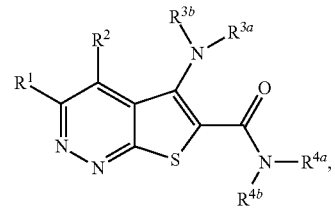

wherein $R^1$ is selected from hydrogen, halogen, —OH, —CN, —NH$_2$, —CF$_3$, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-Ar$^{10}$, Ar$^{10}$, —(C1-C3 alkyl)-Cy$^{10}$, and Cy$^{10}$; wherein each Ar$^{10}$, when present, is selected from phenyl and monocyclic heteroaryl; and wherein Ar$^{10}$ is substituted with 0, 1, 2, or 3 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein each Cy$^{10}$, when present, is selected from C3-C9 cycloalkyl and C3-C8 heterocycloalkyl; and wherein Cy$^{10}$ is substituted with 0, 1, 2, or 3 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^2$ is selected from hydrogen, halogen, —OH, —CN, —NH$_2$, —CF$_3$, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-Ar$^{11}$, Ar$^{11}$, —(C1-C3 alkyl)-Cy$^{11}$, and Cy$^{11}$; wherein each Ar$^{11}$, when present, is selected from phenyl and monocyclic heteroaryl; and wherein Ar$^{11}$ is substituted with 0, 1, 2, or 3 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein each Cy$^{11}$, when present, is selected from C3-C9 cycloalkyl and C3-C8 heterocycloalkyl; and wherein Cy$^{11}$ is substituted with 0, 1, 2, or 3 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein $R^1$ and $R^2$ are optionally covalently bonded and, together with the intermediate atoms, comprise a 3- to 7-membered cycle substituted with 0, 1, 2, or 3 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, Ar$^{10}$, Ar$^{11}$, Cy$^{10}$, and Cy$^{11}$; wherein each of R$^{3a}$ and R$^{3b}$ is independently selected from hydrogen, C1-C6 alkyl, C1-C6 haloalkyl, C1-C6 polyhaloalkyl, C3-C9 cycloalkyl, C2-C7 heterocycloalkyl, —(C1-C8 alkyl)-(C3-C9 cycloalkyl), and —(C1-C8 alkyl)-(C2-C7 heterocycloalkyl); wherein R$^{3a}$ and R$^{3b}$ are optionally covalently bonded and, together with the intermediate nitrogen, comprise a 3- to 7-membered heterocycloalkyl substituted with 0, 1, 2, or 3 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; wherein each of R$^{3a}$ and R$^{3b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{20}$R$^{21}$, —(C1-C6 alkyl)-NR$^{20}$(C=O)R$^{21}$, —(C1-C6 alkyl)-NR$^{20}$(C=O)OR$^{21}$, —(C1-C6 alkyl)-NR$^{20}$(C=O)NR$^{21}$, —(C1-C6 monohaloalkyl)-NR$^{20}$(C=O)OR$^{21}$, —(C1-C6 polyhaloalkyl)-NR$^{20}$(C=O)OR$^{21}$, —(C1-C8 alkyl)-Cy$^1$, Cy$^1$, —(CH$_2$)—Ar$^1$, —(CH$_2$)$_2$—Ar$^3$, —(C3-C8 alkyl)-Ar$^1$, —(C2-C8 alkynyl)-Ar$^1$, and Ar$^2$; wherein R$^{4a}$ and R$^{4b}$ are not simultaneously hydrogen; wherein each R$^{20}$, when present, is independently selected from hydrogen and C1-C8 alkyl; wherein each R$^{21}$, when present, is independently selected from hydrogen, C1-C8 alkyl, C1-C8 monohaloalkyl, C1-C8 polyhaloalkyl, —(C1-C8 alkyl)-Cy$^1$, Cy$^1$, —(C1-C8 alkyl)-Ar$^1$, and Ar$^1$; wherein each Ar$^1$, when present, is independently selected from phenyl, naphthyl, and heteroaryl, and wherein each Ar$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; wherein each n is an integer independently selected from 0, 1 and 2; wherein each Ar$^{20}$, when present, is independently selected from phenyl, naphthyl, and heteroaryl, and wherein each Ar$^{20}$ is independently substituted with 0, 1, 2, or 3 groups independently selected from halogen, —NH$_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino; wherein each Cy$^{20}$, when present, is independently selected from C3-C9 cycloalkyl and C2-C7 heterocycloalkyl, and wherein each Cy$^{20}$ is independently substituted with 0, 1, 2, or 3 groups independently selected from halogen, —NH$_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{30}$, when present, is independently selected from hydrogen and C1-C8 alkyl; wherein each R$^{31}$, when present, is independently selected from hydrogen and C1-C8 alkyl; wherein each R$^{32}$, when present, is independently selected from hydrogen and C1-C8 alkyl; wherein each R$^{33}$, when present, is independently selected from hydrogen and C1-C8 alkyl; wherein each R$^{34}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{21}$, and Ar$^{21}$; wherein each Ar$^{21}$, when present, is independently selected from phenyl, naphthyl, and heteroaryl, and wherein each Ar$^{21}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{35}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{22}$, and Ar$^{22}$; wherein each Ar$^{22}$, when present, is independently selected from phenyl, naphthyl, and heteroaryl, and wherein each Ar$^{22}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{36}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{23}$, and Ar$^{23}$; wherein each Ar$^{23}$, when present, is independently selected from phenyl, naphthyl, and heteroaryl, and wherein each Ar$^{23}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{37}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN; wherein each Ar$^2$, when present, is a heteroaryl, and wherein each Ar$^2$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{36}$S(O)$_n$R$^{35}$, —NR$^{36}$(C1-C6 alkyl)-(C=O)R$^{35}$, —NR$^{36}$(C1-C6 alkyl)-(C=O)OR$^{35}$, —NR$^{36}$(C1-C6 alkyl)-(C=O)NR$^{35}$, —NR$^{36}$(C1-C6 alkyl)-S(O)$_n$R$^{35}$, —NR$^{36}$(C1-C6 alkyl)-S(O)$_n$NR$^{33}$R$^{34}$, —NR$^{36}$(C=O)R$^{35}$, —NR$^{36}$(C=O)OR$^{35}$, —NR$^{36}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; wherein each Ar$^3$, when present, is a heteroaryl, and wherein each Ar$^3$ is independently substituted with 0, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-

NR³⁰S(O)ₙR³⁵, —NR³⁰(C1-C6 alkyl)-(C=O)R³⁵, —NR³⁰(C1-C6 alkyl)-(C=O)OR³⁵, —NR³⁰(C1-C6 alkyl)-(C=O)NR³⁵, —NR³⁰(C1-C6 alkyl)-S(O)ₙR³⁵, —NR³⁰(C1-C6 alkyl)-S(O)ₙNR³³R³⁴, —NR³⁰(C=O)R³⁵, —NR³⁰(C=O)OR³⁵, —NR³⁰(C=O)NR³⁵, —NR³⁰S(O)ₙR³⁵, —(C1-C6 alkyl)-(C=O)R³⁵, —(C1-C6 alkyl)-(C=O)OR³⁵, —(C1-C6 alkyl)-(C=O)NR³⁵, —(C1-C6 alkyl)-S(O)ₙR³⁵, —(C1-C6 alkyl)-S(O)ₙNR³³R³⁴, —(C=O)R³⁵, —(C=O)OR³⁵, —S(O)ₙR³⁵, —S(O)ₙNR³³R³⁴, —(C1-C8 alkyl)-Ar²⁰, Ar²⁰, —(C1-C8 alkyl)-Cy²⁰, Cy²⁰, and R³⁷; or and wherein each Ar³ is independently monosubstituted with a groups selected from —Cl, —Br, —I, —NH₂, —OH, —CN, —N₃, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR³¹R³², —(C1-C6 alkyl)-NR³⁰(C=O)R³⁵, —(C1-C6 alkyl)-NR³⁰(C=O)OR³⁵, —(C1-C6 alkyl)-NR³⁰(C=O)NR³⁵, —(C1-C6 alkyl)-NR³⁰S(O)ₙR³⁵, —NR³⁰(C1-C6 alkyl)-(C=O)R³⁵, —NR³⁰(C1-C6 alkyl)-(C=O)OR³⁵, —NR³⁰(C1-C6 alkyl)-(C=O)NR³⁵, —NR³⁰(C1-C6 alkyl)-S(O)ₙR³⁵, —NR³⁰(C1-C6 alkyl)-S(O)ₙNR³³R³⁴, —NR³⁰(C=O)R³⁵, —NR³⁰(C=O)OR³⁵, —NR³⁰(C=O)NR³⁵, —NR³⁰S(O)ₙR³⁵, —(C1-C6 alkyl)-(C=O)R³⁵, —(C1-C6 alkyl)-(C=O)OR³⁵, —(C1-C6 alkyl)-(C=O)NR³⁵, —(C1-C6 alkyl)-S(O)ₙR³⁵, —(C1-C6 alkyl)-S(O)ₙNR³³R³⁴, —(C=O)R³⁵, —(C=O)OR³⁵, —S(O)ₙR³⁵, —S(O)ₙNR³³R³⁴, —(C1-C8 alkyl)-Ar²⁰, Ar²⁰, —(C1-C8 alkyl)-Cy²⁰, Cy²⁰, and R³⁷; wherein each Cy¹, when present, is independently selected from C3-C9 cycloalkyl and C2-C7 heterocycloalkyl, and wherein each Cy¹ is independently substituted with 0, 1, 2, or 3 groups independently selected from halogen, —NH₂, —OH, —CN, —N₃, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR³¹R³², —(C1-C6 alkyl)-NR³⁰(C=O)R³⁵, —(C1-C6 alkyl)-NR³⁰(C=O)OR³⁵, —(C1-C6 alkyl)-NR³⁰(C=O)NR³⁵, —(C1-C6 alkyl)-NR³⁰S(O)ₙR³⁵, —NR³⁰(C1-C6 alkyl)-(C=O)R³⁵, —NR³⁰(C1-C6 alkyl)-(C=O)OR³⁵, —NR³⁰(C1-C6 alkyl)-(C=O)NR³⁵, —NR³⁰(C1-C6 alkyl)-S(O)ₙR³⁵, —NR³⁰(C1-C6 alkyl)-S(O)ₙNR³³R³⁴, —NR³⁰(C=O)R³⁵, —NR³⁰(C=O)OR³⁵, —NR³⁰(C=O)NR³⁵, —NR³⁰S(O)ₙR³⁵, —(C1-C6 alkyl)-(C=O)R³⁵, —(C1-C6 alkyl)-(C=O)OR³⁵, —(C1-C6 alkyl)-(C=O)NR³⁵, —(C1-C6 alkyl)-S(O)ₙR³⁵, —(C1-C6 alkyl)-S(O)ₙNR³³R³⁴, —(C=O)R³⁵, —(C=O)OR³⁵, —S(O)ₙR³⁵, —S(O)ₙNR³³R³⁴, —(C1-C8 alkyl)-Ar³⁰, Ar³⁰, —(C1-C8 alkyl)-Cy³⁰, Cy³⁰, and R³⁷; wherein each Ar³⁰, when present, is independently selected from phenyl, naphthyl, and heteroaryl, and wherein each Ar³⁰ is independently substituted with 0, 1, 2, or 3 groups independently selected from halogen, —NH₂, —OH, —CN, —S(O)ₙR⁴⁵, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar⁴⁰, Ar⁴⁰, —(C1-C8 alkyl)-Cy⁴⁰, and Cy⁴⁰; wherein each R⁴⁵, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Ar⁴⁰, when present, is independently selected from phenyl, naphthyl, and heteroaryl, and wherein each Ar⁴⁰ is independently substituted with 0, 1, 2, or 3 groups independently selected from halogen, —NH₂, —OH, —CN, —S(O)ₙR⁴⁶, C1-C8 alkyl, C1-C8 monohaloalkyl, C1-C8 polyhaloalkyl, C1-C8 alkoxy, C1-C8 alkylamino, and C1-C8 dialkylamino; wherein each R⁴⁶, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Cy⁴⁰, when present, is independently selected from C3-C9 cycloalkyl and C2-C7 heterocycloalkyl, and wherein each Cy⁴⁰ is independently substituted with 0, 1, 2, or 3 groups independently selected from halogen, —NH₂, —OH, —CN, —S(O)ₙR⁴⁶, C1-C8 alkyl, C1-C8 monohaloalkyl, C1-C8 polyhaloalkyl, C1-C8 alkoxy, C1-C8 alkylamino, and C1-C8 dialkylamino; wherein each Cy³⁰, when present, is independently selected from C3-C9 cycloalkyl and C2-C7 heterocycloalkyl, and wherein each Cy³⁰ is independently substituted with 0, 1, 2, or 3 groups independently selected from halogen, —NH₂, —OH, —CN, —S(O)ₙR⁴⁵, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar⁴⁰, Ar⁴⁰, —(C1-C8 alkyl)-Cy⁴⁰, and Cy⁴⁰; or a pharmaceutically acceptable salt, solvate, or polymorph thereof.

In one aspect, the invention relates to a compound having a structure represented by a formula:

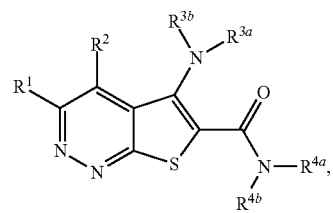

wherein R¹ is selected from hydrogen, halogen, C1-C6 alkyl, C1-C6 haloalkyl, C1-C6 polyhaloalkyl, C1-C6 alkoxy, C1-C6 alkylamino, and C1-C6 dialkylamino; wherein R² is selected from hydrogen, halogen, C1-C6 alkyl, C1-C6 haloalkyl, C1-C6 polyhaloalkyl, C1-C6 alkoxy, C1-C6 alkylamino, and C1-C6 dialkylamino; wherein R¹ and R² are optionally covalently bonded and, together with the intermediate atoms, comprise a 3- to 7-membered cycle substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, and C1-C6 dialkylamino; wherein each of R³ᵃ and R³ᵇ is independently selected from hydrogen, C1-C6 alkyl, C1-C6 haloalkyl, C1-C6 polyhaloalkyl, C3-C8 cycloalkyl, C2-C7 heterocycloalkyl, —(C1-C8 alkyl)-(C3-C8 cycloalkyl), and —(C1-C8 alkyl)-(C2-C7 heterocycloalkyl); wherein $R^{3a}$ and $R^{3b}$ are optionally covalently bonded and, together with the intermediate nitrogen, comprise a 3- to 7-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; wherein each of $R^{4a}$ and $R^{4b}$ is independently selected from hydrogen, C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; wherein $R^{4a}$ and $R^{4b}$ are not both hydrogen; wherein each of $R^{4a}$ and $R^{4b}$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein n is an integer from 0 to 2; wherein Ar$^1$ is selected from phenyl and heterocyclyl; wherein Ar$^2$ is heterocyclyl; wherein R4a and R4b are optionally covalently bonded and, together with the intermediate nitrogen, comprise a 3- to 10-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino; and wherein R$^5$, when present, is selected from hydrogen, C1-C8 alkyl, C1-C8 haloalkyl, and C1-C8 polyhaloalkyl; or a pharmaceutically acceptable salt, hydrate, solvate, or polymorph thereof.

In a further aspect, the compound has a structure represented by a formula listed below:

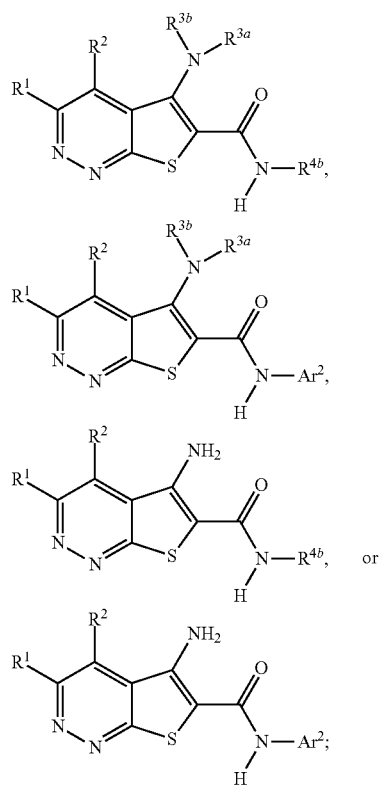

and wherein all variables are as defined herein.

In a further aspect, the compound has a structure represented by a formula listed below:

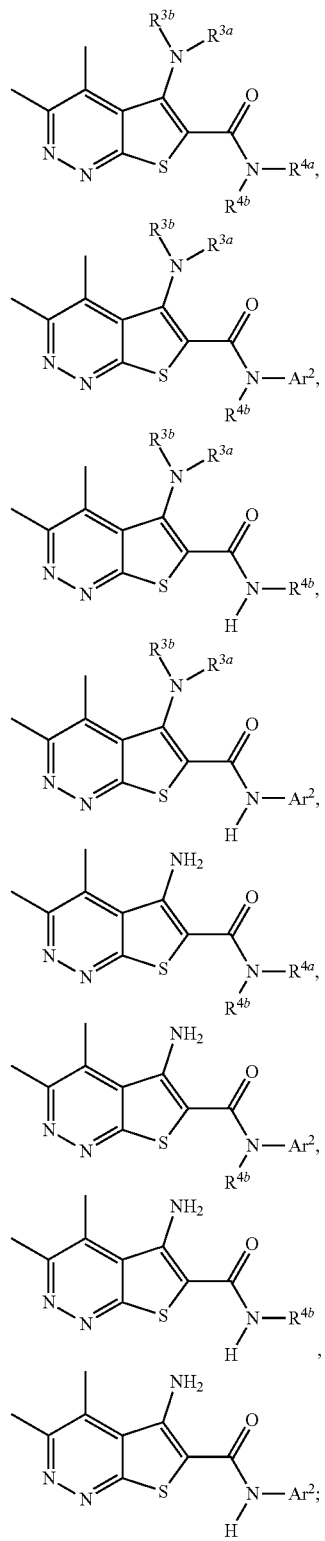

and wherein all variables are as defined herein.

In a further aspect, the compound has a structure represented by a formula listed below:

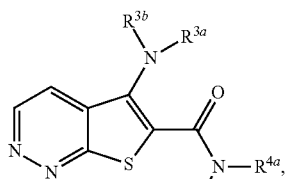
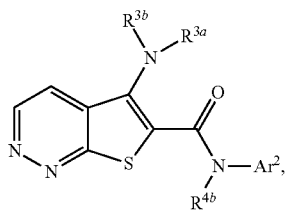
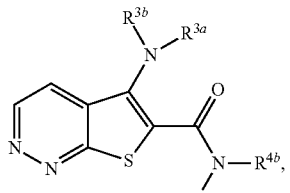
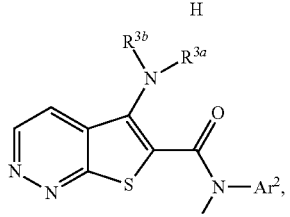
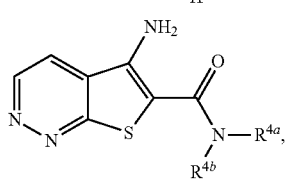
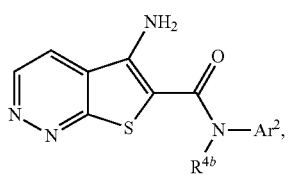
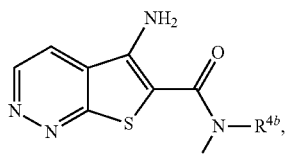
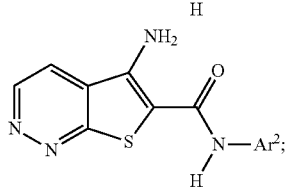

and wherein all variables are as defined herein.

In a further aspect, the compound has a structure represented by a formula listed below:

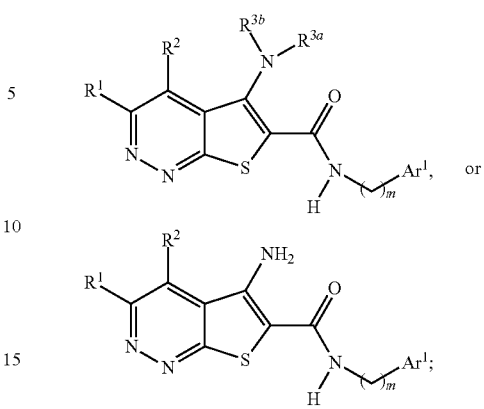

wherein m is an integer from 1 to 3; and wherein all other variables are as defined herein.

In various further aspects, m has a value of 1 or 2. In a yet further aspect, m has a value of 1 or 3. In an even further aspect, m has a value of 2 or 3. In a yet further aspect, m has a value of 1. In an even further aspect, m has a value of 2. In a still further aspect, m has a value of 3.

In a further aspect, the compound has a structure represented by a formula listed below:

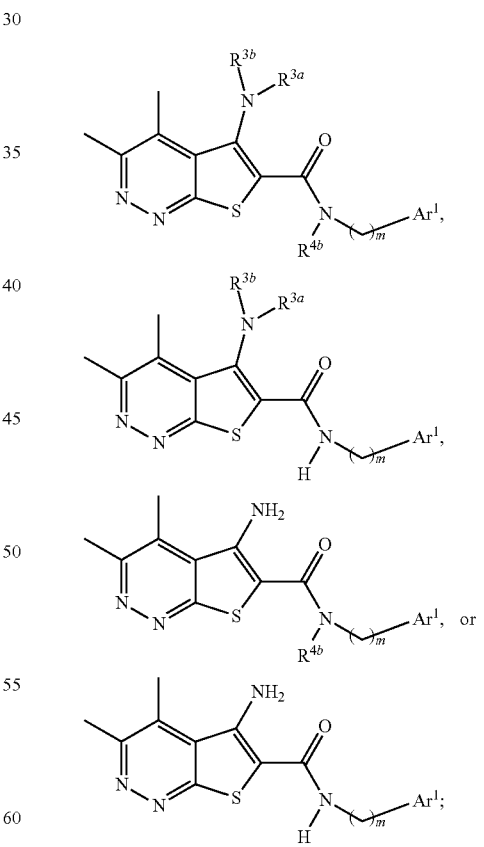

wherein m is an integer from 1 to 3; and wherein all other variables are as defined herein.

In a further aspect, the compound has a structure represented by a formula listed below:

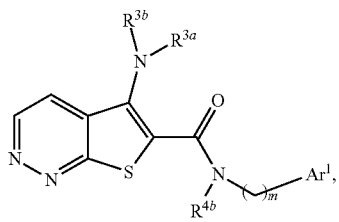

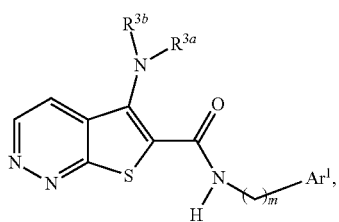

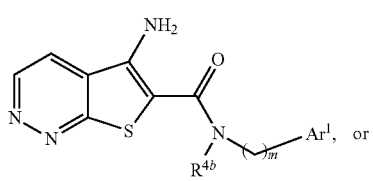

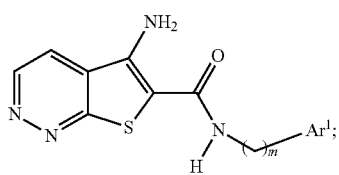

wherein m is an integer from 1 to 3; and wherein all other variables are as defined herein.

In a further aspect, the compound has a structure represented by a formula listed below:

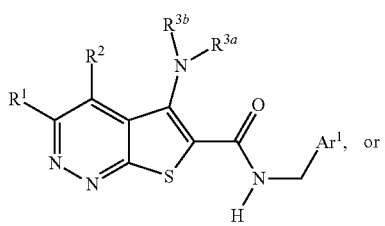

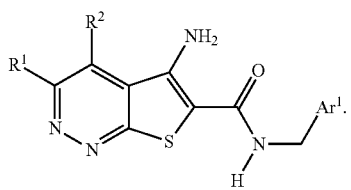

and wherein all variables are as defined herein.

In a further aspect, the compound has a structure represented by a formula listed below:

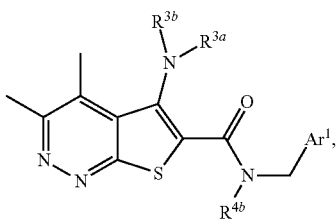

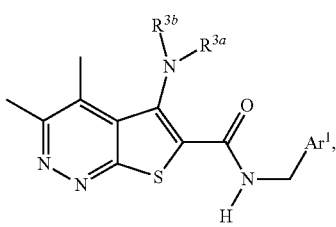

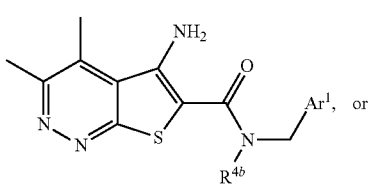

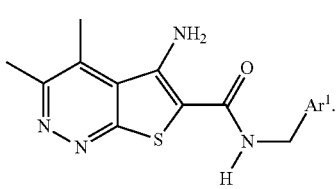

and wherein all variables are as defined herein.

In a further aspect, the compound has a structure represented by a formula listed below:

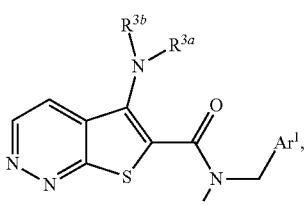

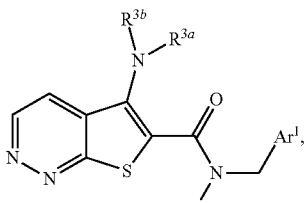

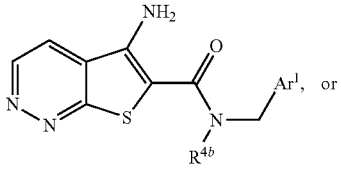

-continued

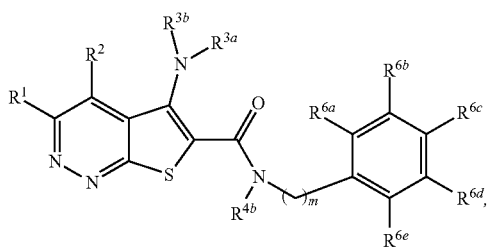

and wherein all variables are as defined herein.

In a further aspect, a compound can have a structure represented by the formula:

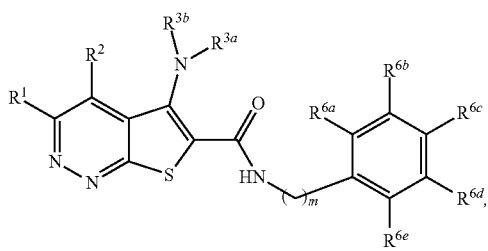

wherein m is an integer from 1 to 3; and wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

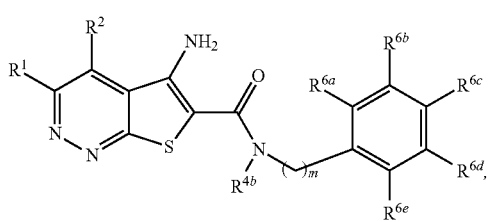

wherein m is an integer from 1 to 3; and wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

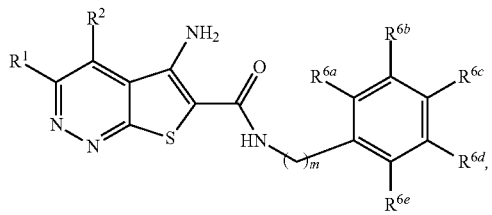

wherein m is an integer from 1 to 3; and wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

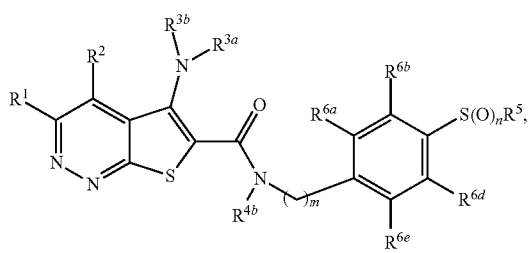

wherein m is an integer from 1 to 3; and wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

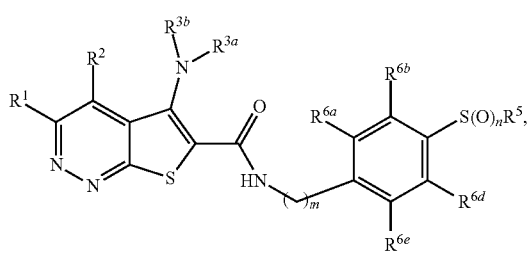

wherein m is an integer from 1 to 3; and wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

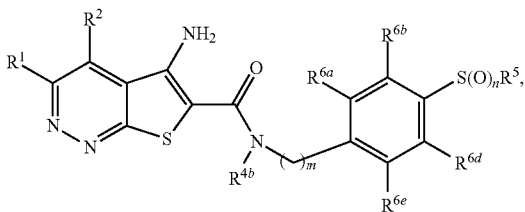

wherein m is an integer from 1 to 3; and wherein each of $R^{6a}$, $R^{6b}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

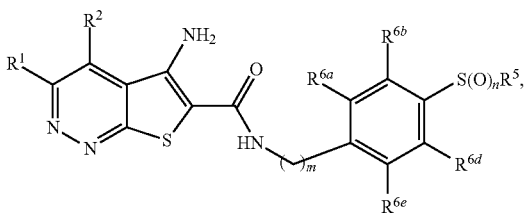

wherein m is an integer from 1 to 3; and wherein each of $R^{6a}$, $R^{6b}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

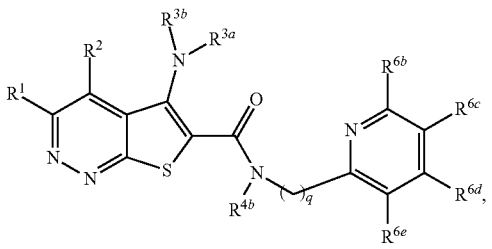

wherein q is an integer from 0 to 3; and wherein each of $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In various further aspects, q has a value of 0, 1, or 2. In a further aspect, q has a value of 0, 2, or 3. In a still further aspect, q has a value of 0, 1, or 3. In an even further aspect, q has a value of 1, 2, or 3. In a still further aspect, q has a value of 0 or 1. In a yet further aspect, q has a value of 0 or 2. In an even further aspect, q has a value of 0 or 3. In a still further aspect, q has a value of 1 or 2. In a yet further aspect, q has a value of 1 or 3. In an even further aspect, q has a value of 2 or 3. In a still further aspect, q has a value of 0. In a yet further aspect, q has a value of 1. In an even further aspect, q has a value of 2. In a still further aspect, q has a value of 3.

In a further aspect, a compound can have a structure represented by the formula:

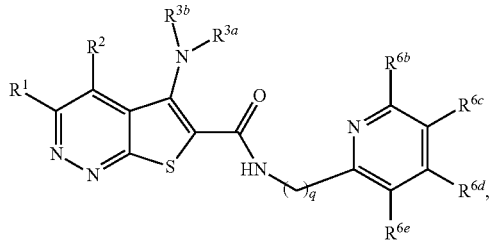

wherein q is an integer from 0 to 3; and wherein each of $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

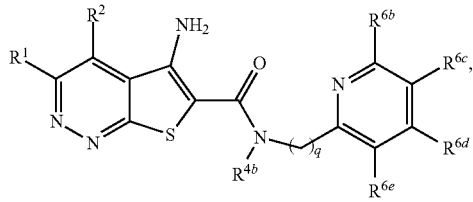

wherein q is an integer from 0 to 3; and wherein each of $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

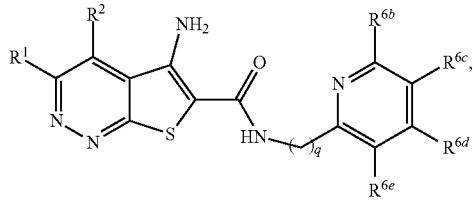

wherein q is an integer from 0 to 3; and wherein each of $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

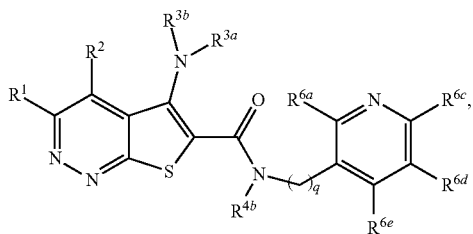

wherein q is an integer from 0 to 3; and wherein each of $R^{6a}$, $R^{6c}$, $R_{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

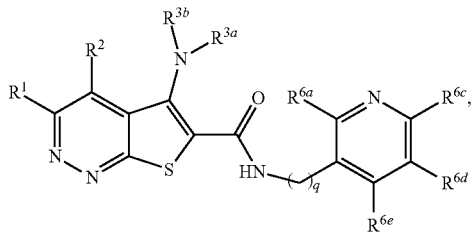

wherein q is an integer from 0 to 3; wherein each of $R^{6a}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

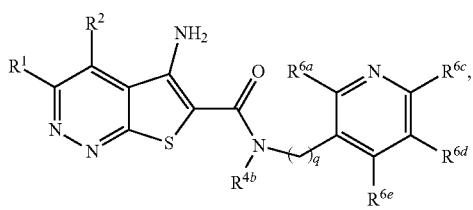

wherein q is an integer from 0 to 3; and wherein each of $R^{6a}$, $R^{6e}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

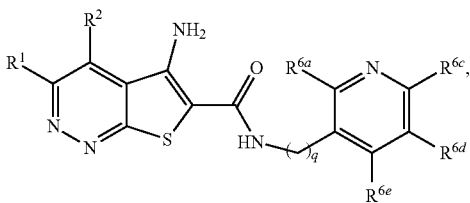

wherein q is an integer from 0 to 3; and wherein each of $R^{6a}$, $R^{6e}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

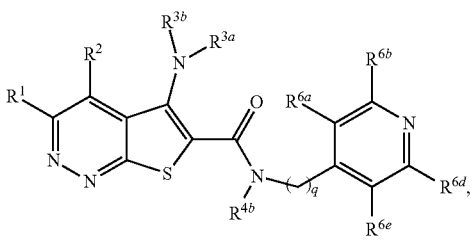

wherein q is an integer from 0 to 3; and wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

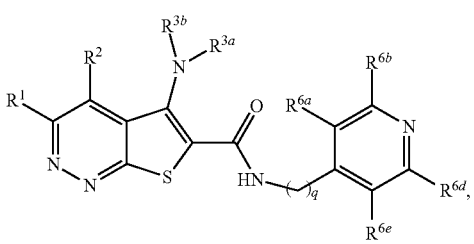

wherein q is an integer from 0 to 3; and wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

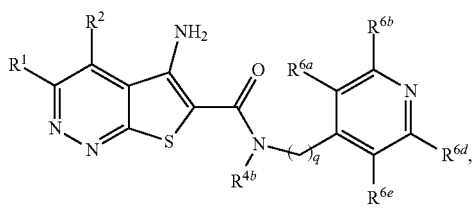

wherein q is an integer from 0 to 3; and wherein each of $R^{6a}$, $R^{6b}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_n R^5$; and wherein all other variables are as defined herein.

In a further aspect, a compound can have a structure represented by the formula:

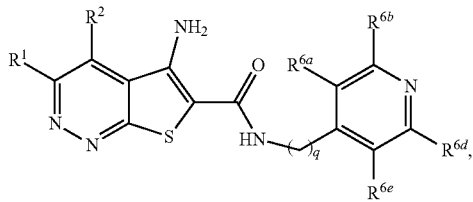

wherein q is an integer from 0 to 3; and wherein each of $R^{6a}$, $R^{6b}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_n R^5$; and wherein all other variables are as defined herein.

In a further aspect, a compound can have a structure represented by the formula:

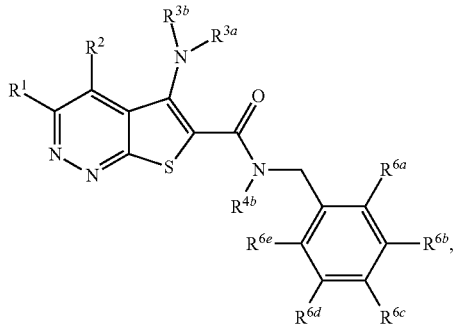

wherein each of $R^{6a}$, $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_n R^5$; and wherein all other variables are as defined herein.

In a further aspect, a compound can have a structure represented by the formula:

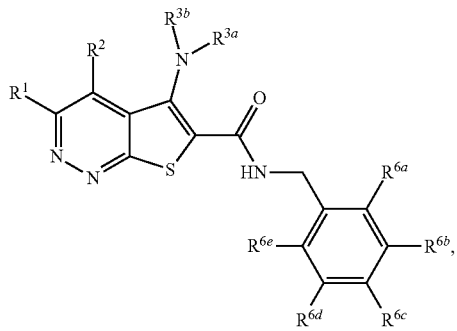

wherein each of $R^{6a}$, $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_n R^5$; and wherein all other variables are as defined herein.

In a further aspect, a compound can have a structure represented by the formula:

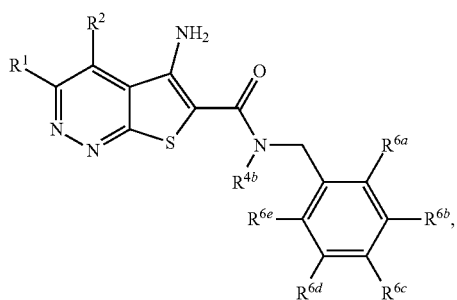

wherein each of $R^{6a}$, $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_n R^5$; and wherein all other variables are as defined herein.

In a further aspect, a compound can have a structure represented by the formula:

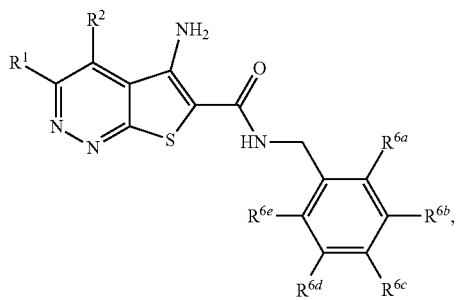

wherein each of $R^{6a}$, $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_n R^5$; and wherein all other variables are as defined herein.

In a further aspect, a compound can have a structure represented by the formula:

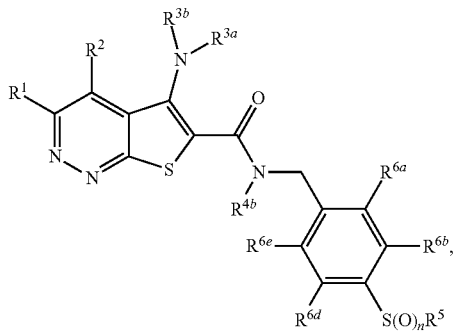

wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

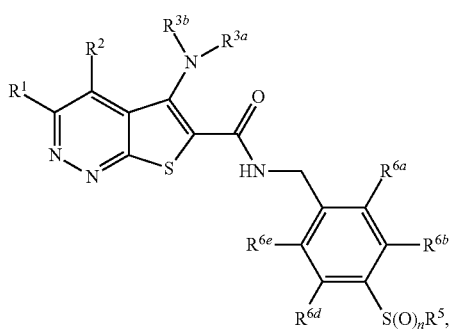

wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

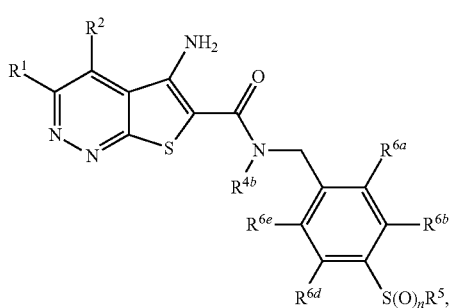

wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

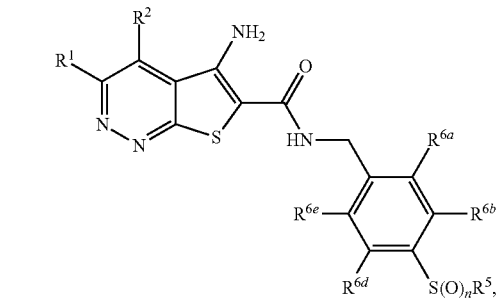

wherein each of $R^{6a}$, $R^{6b}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

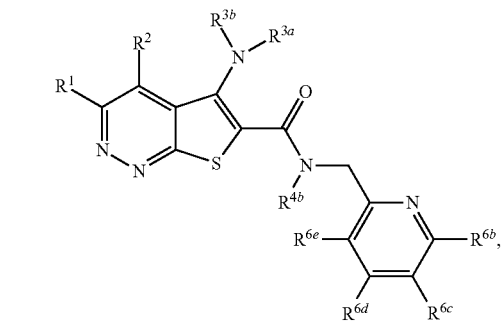

wherein each of $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

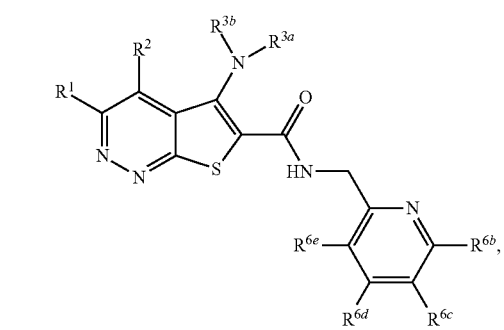

wherein each of $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

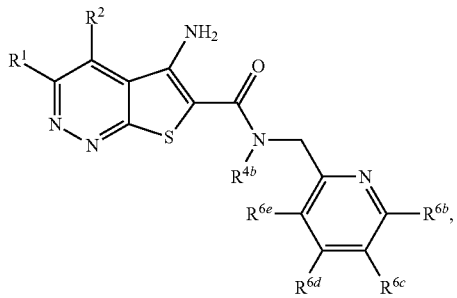

wherein each of R$^{6b}$, R$^{6c}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

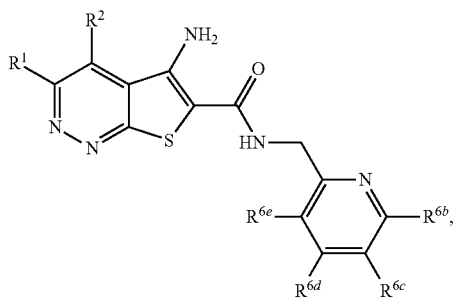

wherein each of R$^{6b}$, R$^{6c}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

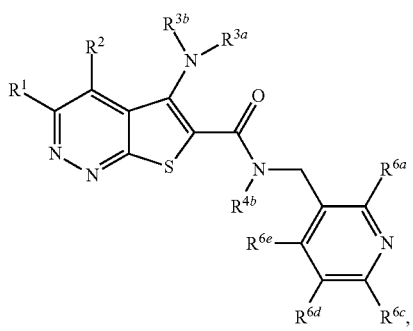

wherein each of R$^{6a}$, R$^{6c}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

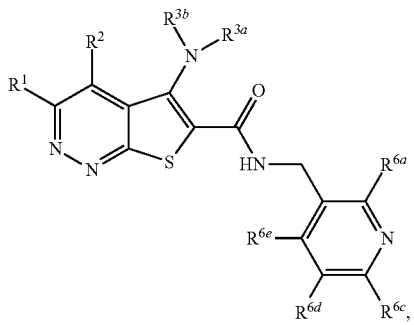

wherein each of R$^{6a}$, R$^{6c}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

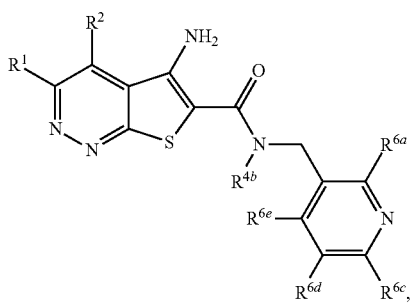

wherein each of R$^{6a}$, R$^{6c}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

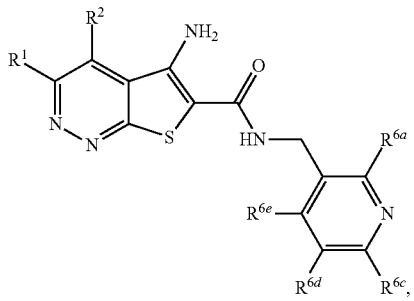

wherein each of R$^{6a}$, R$^{6c}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

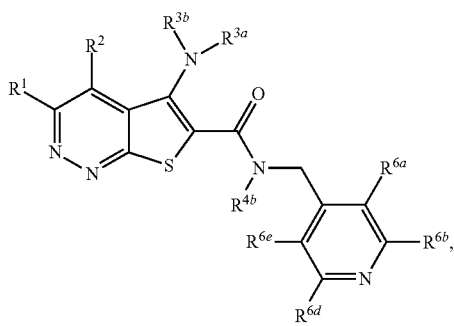

wherein each of R$^{6a}$, R$^{6b}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

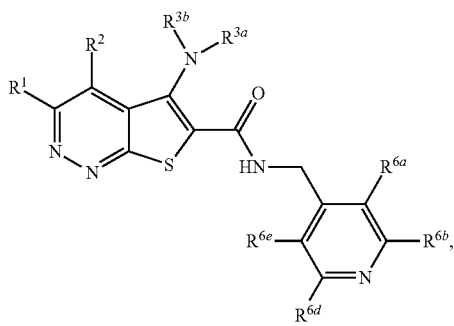

wherein each of R$^{6a}$, R$^{6b}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

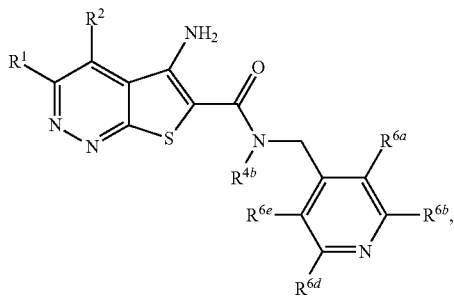

wherein each of R$^{6a}$, R$^{6b}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

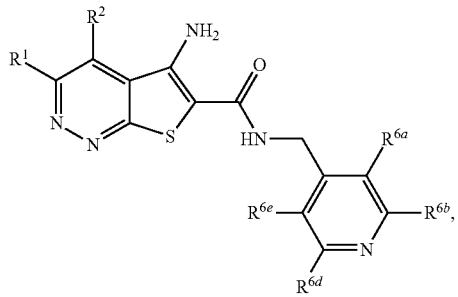

wherein each of R$^{6a}$, R$^{6b}$, R$^{6d}$, and R$^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

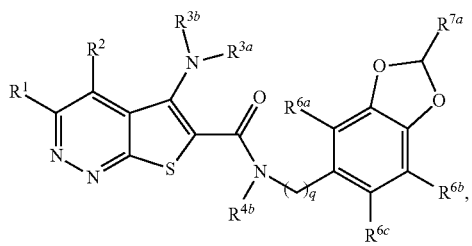

wherein q is an integer from 0 to 3; wherein each of R$^{6a}$, R$^{6b}$, and R$^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein R$^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

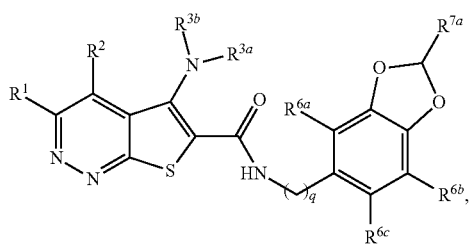

wherein q is an integer from 0 to 3; wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein $R^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

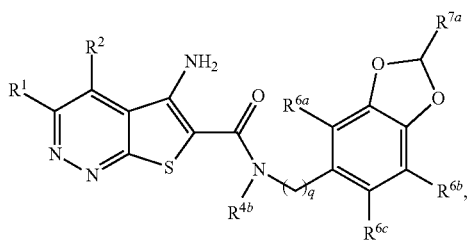

wherein q is an integer from 0 to 3; wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein $R^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

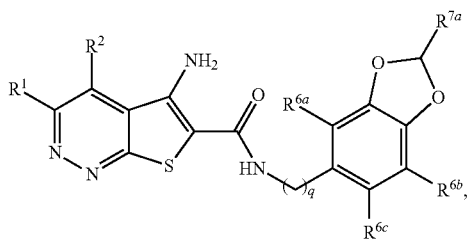

wherein q is an integer from 0 to 3; wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein $R^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

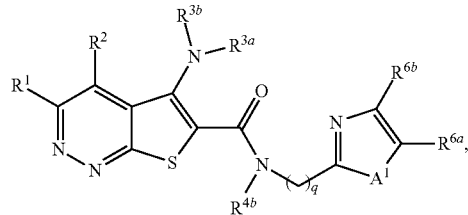

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

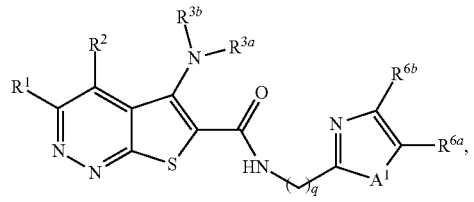

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

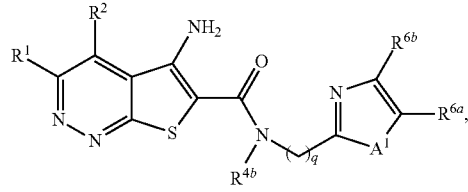

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of $R^{9a}$ and $R^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

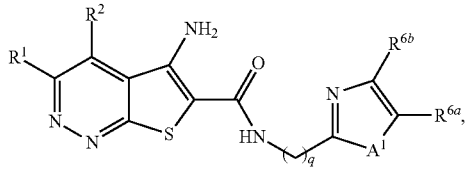

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of $R^{9a}$ and $R^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

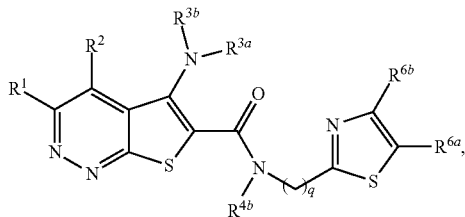

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

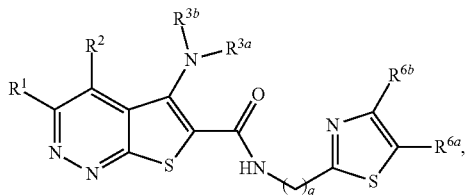

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

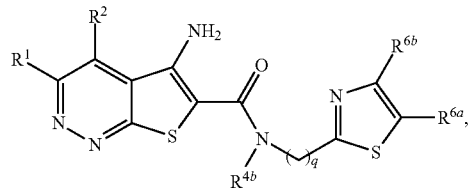

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

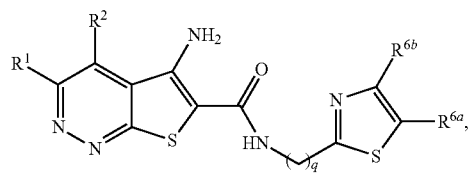

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

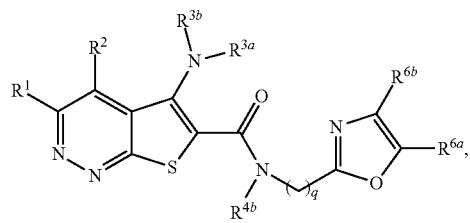

wherein q is an integer from 0 to 3; wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

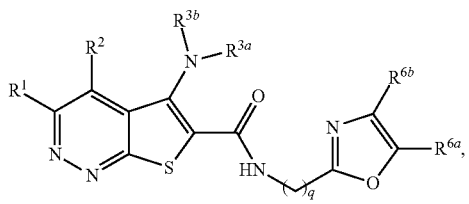

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

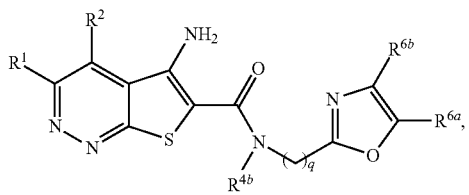

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

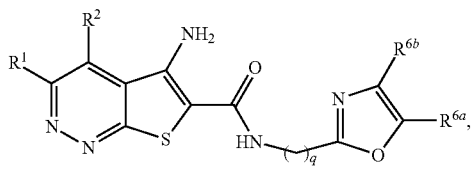

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

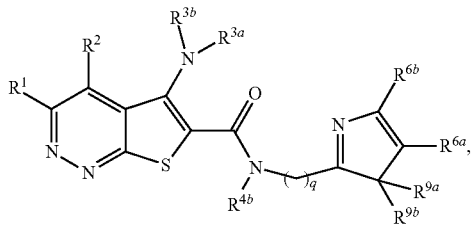

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

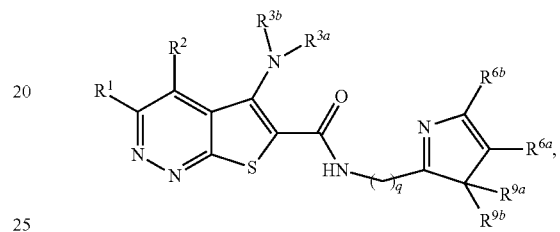

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

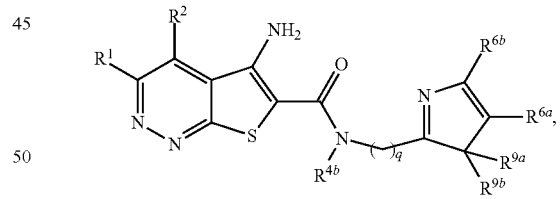

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

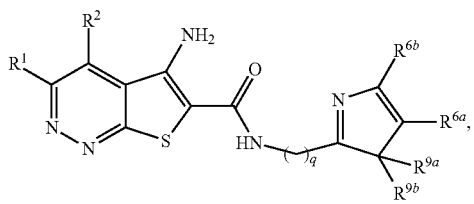

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

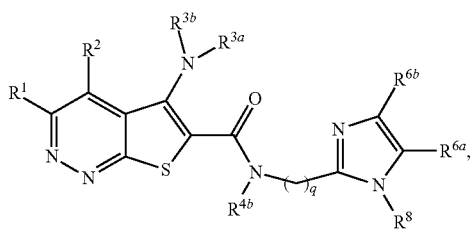

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^8$ is selected from hydrogen and C1-C8 alkyl; and wherein all other variables are as defined herein.

In a further aspect, a compound can have a structure represented by the formula:

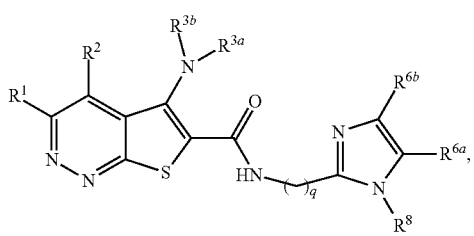

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^8$ is selected from hydrogen and C1-C8 alkyl; and wherein all other variables are as defined herein.

In a further aspect, a compound can have a structure represented by the formula:

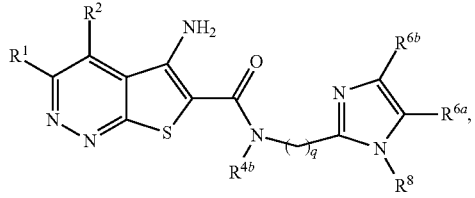

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^8$ is selected from hydrogen and C1-C8 alkyl; and wherein all other variables are as defined herein.

In a further aspect, a compound can have a structure represented by the formula:

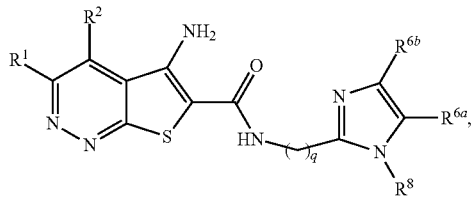

wherein q is an integer from 0 to 3; wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^8$ is selected from hydrogen and C1-C8 alkyl; and wherein all other variables are as defined herein.

In a further aspect, a compound can have a structure represented by the formula:

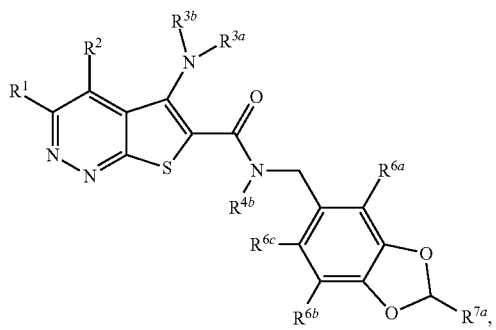

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^{7a}$ is selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

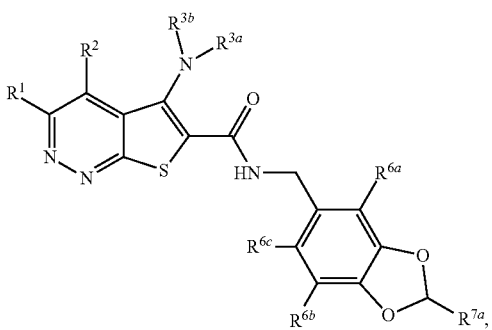

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein $R^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

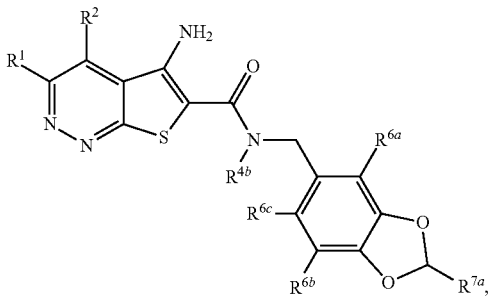

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein $R^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

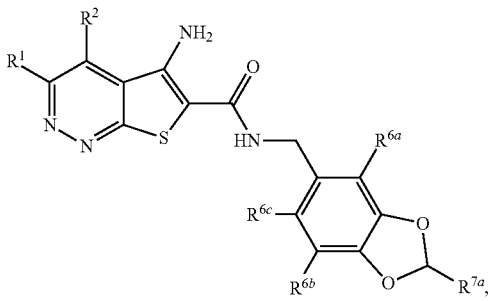

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein $R^{7a}$ is selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

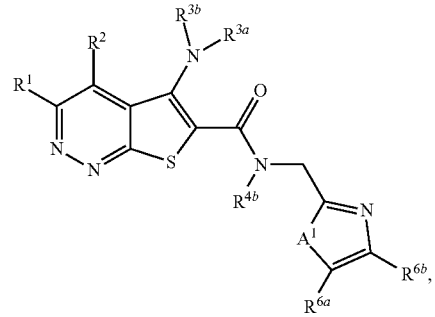

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

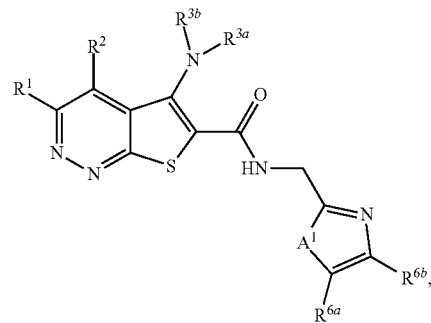

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

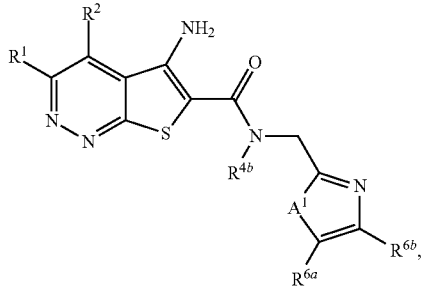

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

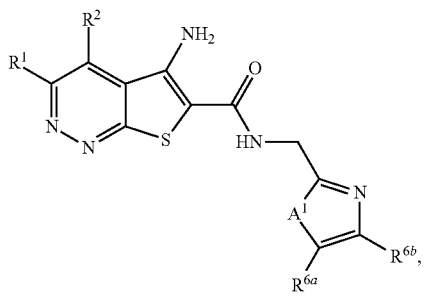

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein A$^1$ is selected from S, O, NR$^8$, and CR$^{9a}$R$^{9b}$; wherein R$^8$, when present, is selected from hydrogen and C1-C8 alkyl; wherein each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

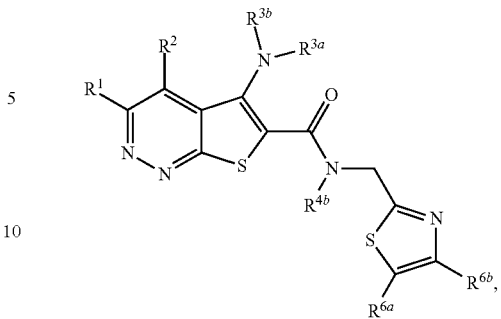

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

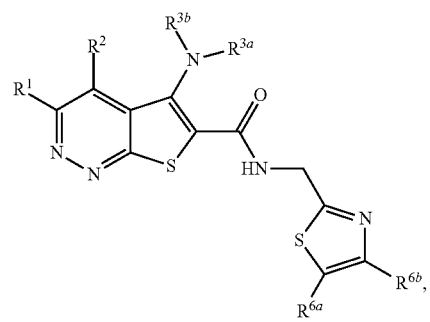

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

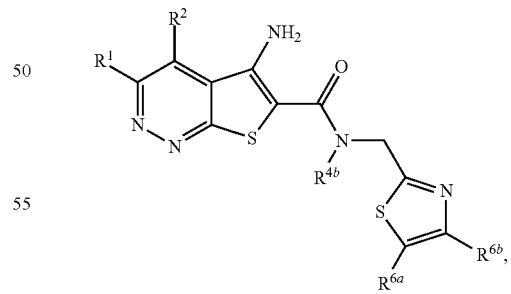

wherein each of $R^{6a}$ and $R^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein all other variables are as defined herein.

In a further aspect, a compound can have a structure represented by the formula:

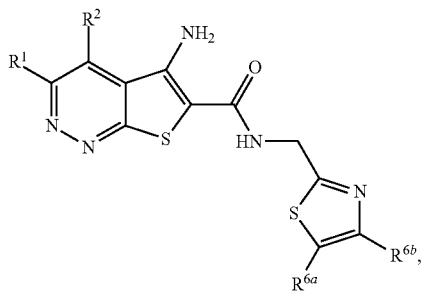

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

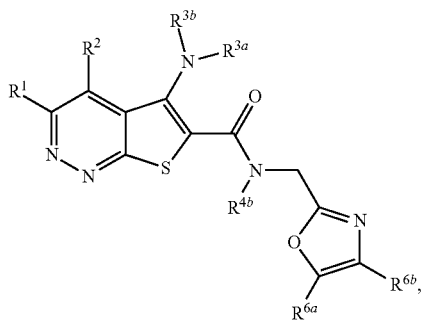

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

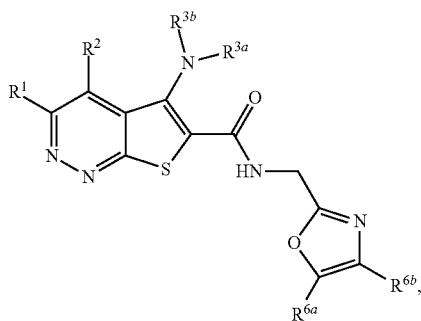

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

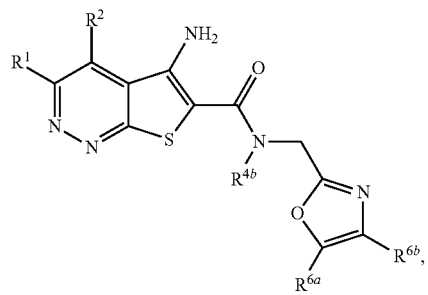

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

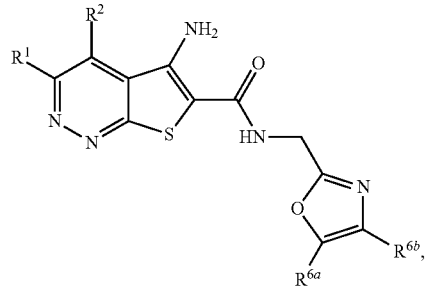

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

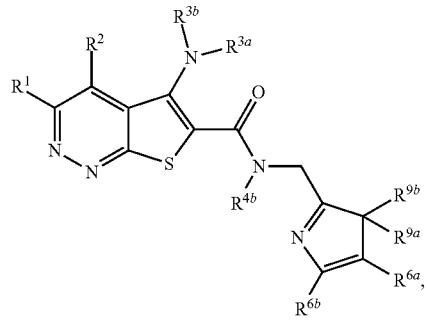

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

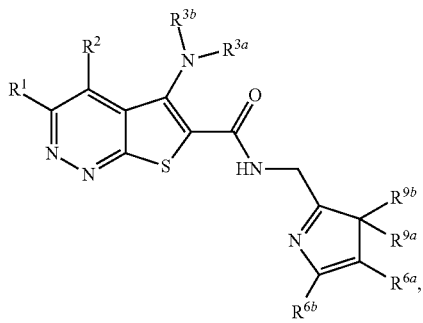

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

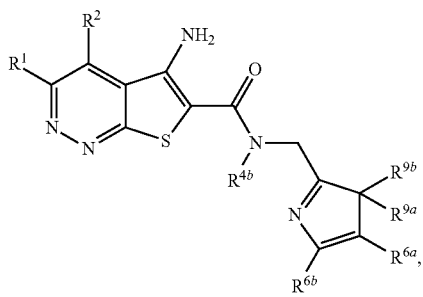

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

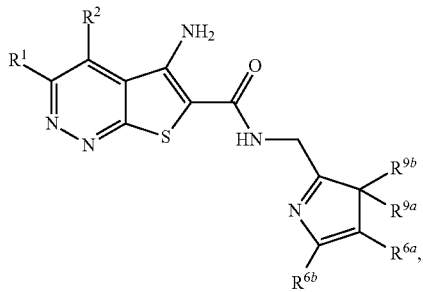

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{9a}$ and $R^{9b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein all other variables are as defined herein.

In a further aspect, a compound can have a structure represented by the formula:

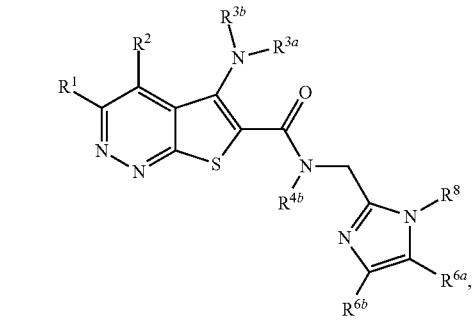

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^8$ is selected from hydrogen and C1-C8 alkyl; and wherein all other variables are as defined herein.

In a further aspect, a compound can have a structure represented by the formula:

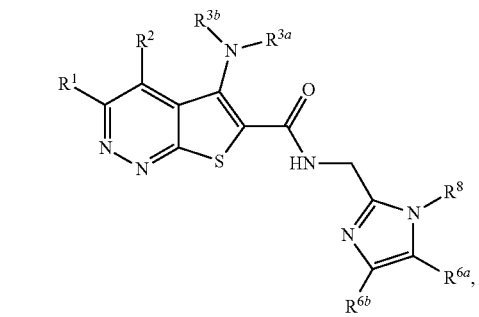

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein $R^8$ is selected from hydrogen and C1-C8 alkyl; and wherein all other variables are as defined herein.

In a further aspect, a compound can have a structure represented by the formula:

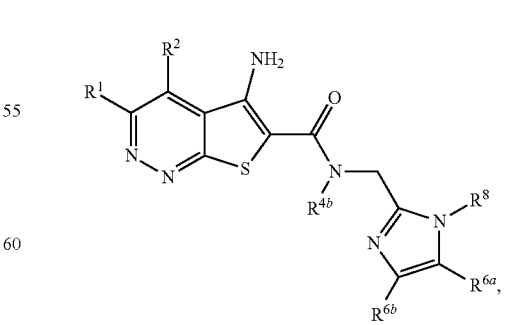

wherein each of $R^{6a}$ and $R^{6b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein R$^8$ is selected from hydrogen and C1-C8 alkyl; and wherein all other variables are as defined herein.

In a further aspect, a compound can have a structure represented by the formula:

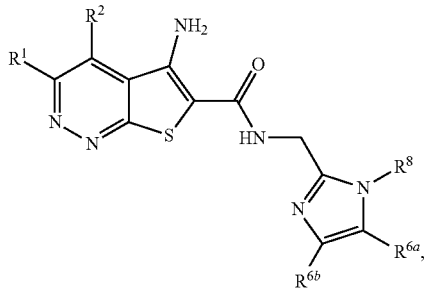

wherein each of R$^{6a}$ and R$^{6b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein R$^8$ is selected from hydrogen and C1-C8 alkyl; and wherein all other variables are as defined herein.

In a further aspect, a compound can have a structure represented by the formula:

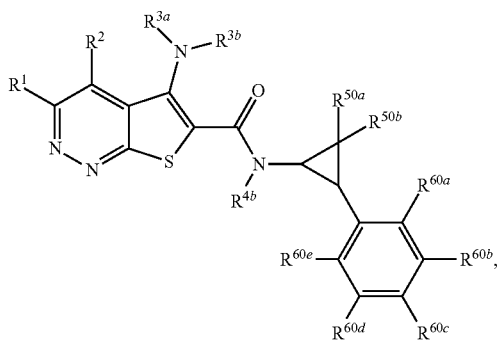

wherein each of R$^{50a}$ and R$^{50b}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of R$^{60a}$, R$^{60b}$, R$^{60c}$, R$^{60d}$ and R$^{60e}$ are independently selected from halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, and C1-C3 dialkylamino; provided that at least two of R$^{60a}$, R$^{60b}$, R$^{60c}$, R$^{60d}$, and R$^{60e}$ are hydrogen; and wherein all other variables are as defined herein.

In a further aspect, a compound can have a structure represented by the formula:

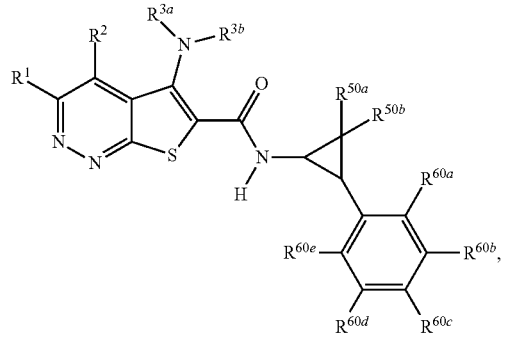

wherein each of R$^{50a}$ and R$^{50b}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of R$^{60a}$, R$^{60b}$, R$^{60c}$, R$^{60d}$ and R$^{60e}$ are independently selected from halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, and C1-C3 dialkylamino; provided that at least two of R$^{60a}$, R$^{60b}$, R$^{60c}$, R$^{60d}$, and R$^{60e}$ are hydrogen; and wherein all other variables are as defined herein.

In a further aspect, a compound can have a structure represented by the formula:

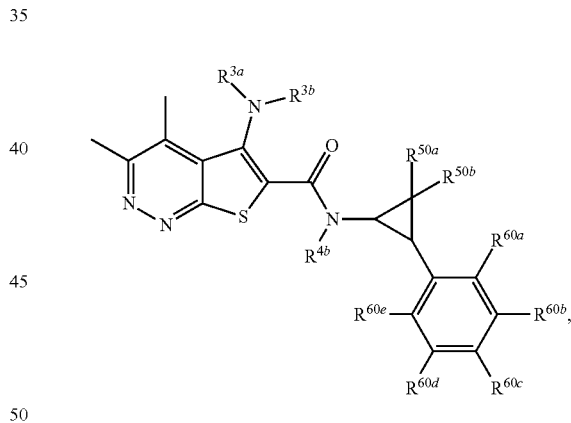

wherein each of R$^{50a}$ and R$^{50b}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of R$^{60a}$, R$^{60b}$, R$^{60c}$, R$^{60d}$ and R$^{60e}$ are independently selected from halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, and C1-C3 dialkylamino; provided that at least two of R$^{60a}$, R$^{60b}$, R$^{60c}$, R$^{60d}$, and R$^{60e}$ are hydrogen; and wherein all other variables are as defined herein.

In a further aspect, a compound can have a structure represented by the formula:

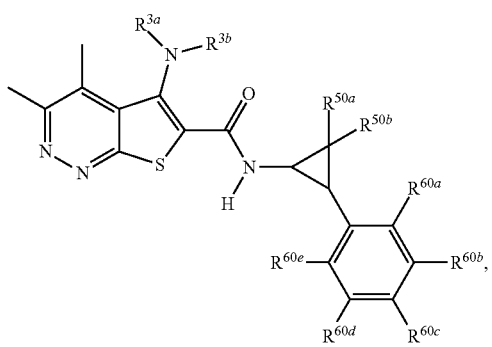

wherein each of R⁵⁰ᵃ and R⁵⁰ᵇ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of R⁶⁰ᵃ, R⁶⁰ᵇ, R⁶⁰ᶜ, R⁶⁰ᵈ, and R⁶⁰ᵉ are independently selected from halogen, —NH$_2$, —OH, —CN, —S(O)$_n$R³⁶, C1-C3 alkyl, C1-C3 monohaloalkyl, C1-C3 polyhaloalkyl, C1-C3 alkoxy, C1-C3 alkylamino, and C1-C3 dialkylamino; provided that at least two of R⁶⁰ᵃ, R⁶⁰ᵇ, R⁶⁰ᶜ, R⁶⁰ᵈ, and R⁶⁰ᵉ are hydrogen; and wherein all other variables are as defined herein.

In a further aspect, a compound can have a structure represented by the formula:

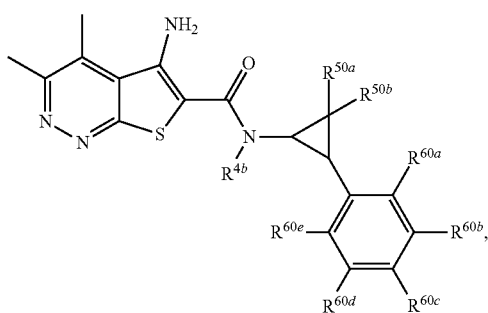

wherein each of R⁵⁰ᵃ and R⁵⁰ᵇ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of R⁶⁰ᵃ, R⁶⁰ᵇ, R⁶⁰ᶜ, R⁶⁰ᵈ, and R⁶⁰ᵉ are independently selected from halogen, —NH$_2$, —OH, —CN, —S(O)$_n$R³⁶, C1-C3 alkyl, C1-C3 monohaloalkyl, C1-C3 polyhaloalkyl, C1-C3 alkoxy, C1-C3 alkylamino, and C1-C3 dialkylamino; provided that at least two of R⁶⁰ᵃ, R⁶⁰ᵇ, R⁶⁰ᶜ, R⁶⁰ᵈ, and R⁶⁰ᵉ are hydrogen; and wherein all other variables are as defined herein.

In a further aspect, a compound can have a structure represented by the formula:

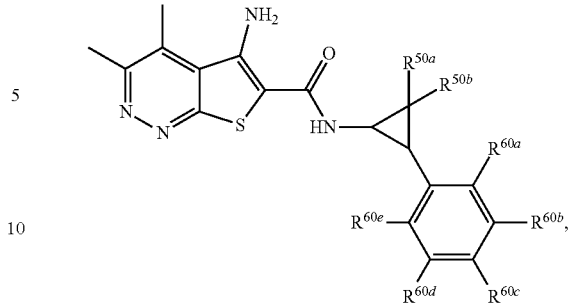

wherein each of R⁵⁰ᵃ and R⁵⁰ᵇ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of R⁶⁰ᵃ, R⁶⁰ᵇ, R⁶⁰ᶜ, R⁶⁰ᵈ, and R⁶⁰ᵉ are independently selected from halogen, —NH$_2$, —OH, —CN, —S(O)$_n$R³⁶, C1-C3 alkyl, C1-C3 monohaloalkyl, C1-C3 polyhaloalkyl, C1-C3 alkoxy, C1-C3 alkylamino, and C1-C3 dialkylamino; provided that at least two of R⁶⁰ᵃ, R⁶⁰ᵇ, R⁶⁰ᶜ, R⁶⁰ᵈ, and R⁶⁰ᵉ are hydrogen; and wherein all other variables are as defined herein.

In a further aspect, a compound can have a structure represented by the formula:

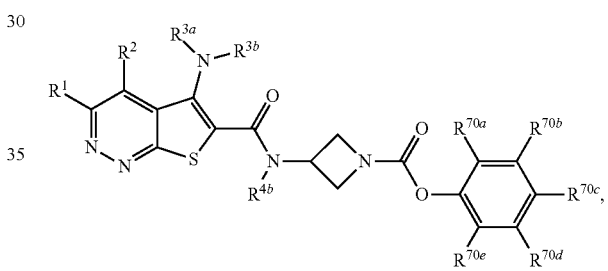

wherein each of R⁷⁰ᵃ, R⁷⁰ᵇ, R⁷⁰ᶜ, R⁷⁰ᵈ, and R⁷⁰ᵉ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of R⁷⁰ᵃ, R⁷⁰ᵇ, R⁷⁰ᶜ, R⁷⁰ᵈ, and R⁷⁰ᵉ are hydrogen; and wherein all other variables are as defined herein.

In a further aspect, a compound can have a structure represented by the formula:

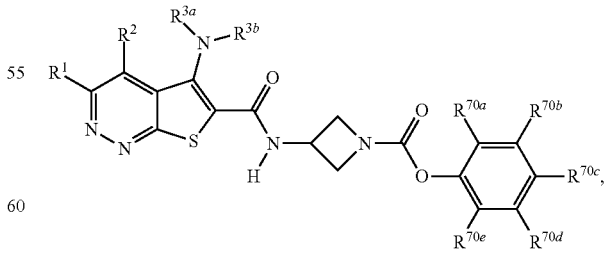

wherein each of R⁷⁰ᵃ, R⁷⁰ᵇ, R⁷⁰ᶜ, R⁷⁰ᵈ, and R⁷⁰ᵉ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino;

provided that at least two of $R^{70}$, $R^{70b}$, $R^{70c}$, $R^{70d}$, and $R^{70e}$ are hydrogen; and wherein all other variables are as defined herein.

In a further aspect, a compound can have a structure represented by the formula:

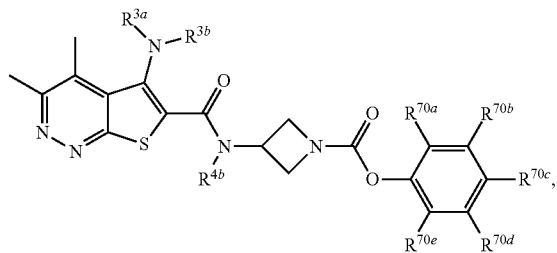

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

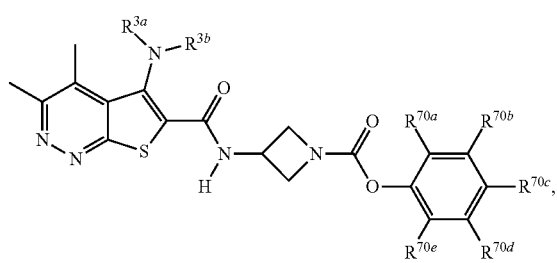

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

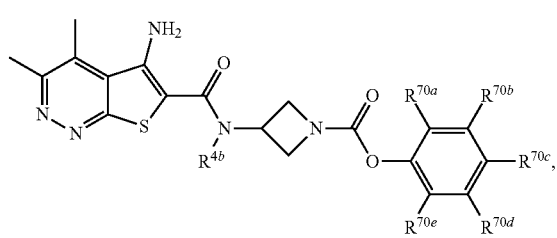

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

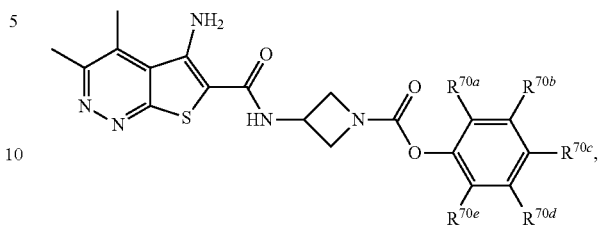

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

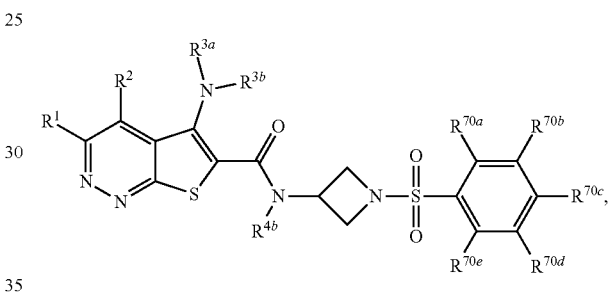

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

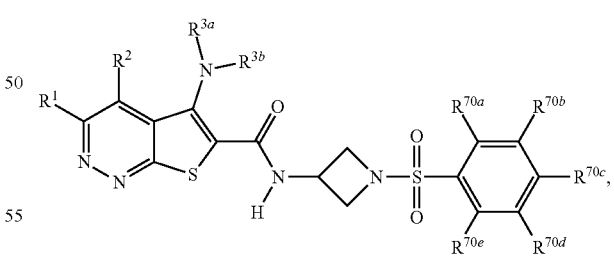

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

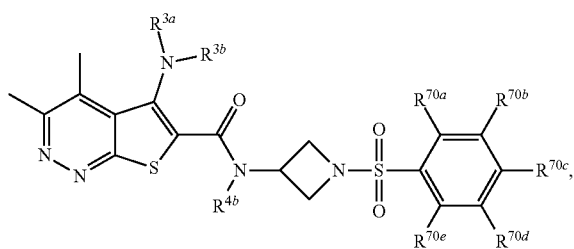

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

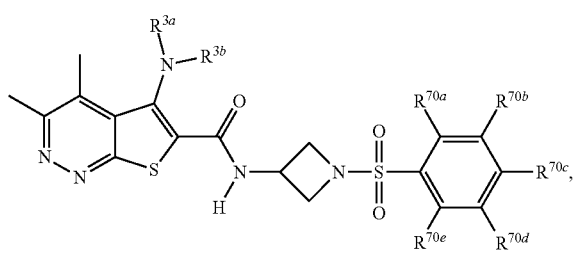

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

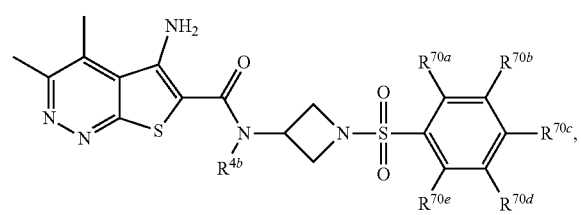

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

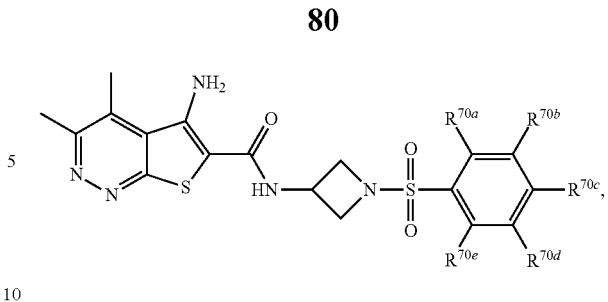

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:


wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; wherein $R^{80}$ is selected from hydrogen and C1-C6 alkyl; and wherein all other variables are as defined herein.

In a further aspect, a compound can have a structure represented by the formula:


wherein each of $R^{70a}$, $R^{70b}$, $R^{70c}$, $R^{70d}$ and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; wherein $R^{80}$ is selected from hydrogen and C1-C6 alkyl; and wherein all other variables are as defined herein.

In a further aspect, a compound can have a structure represented by the formula:

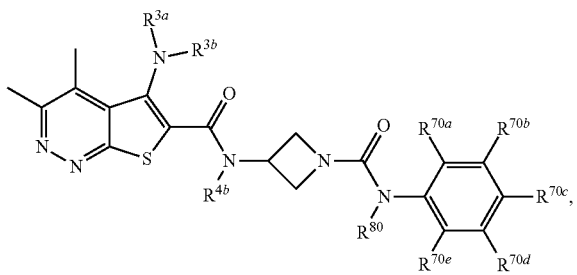

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; wherein $R^{80}$ is selected from hydrogen and C1-C6 alkyl; and wherein all other variables are as defined herein.

In a further aspect, a compound can have a structure represented by the formula:

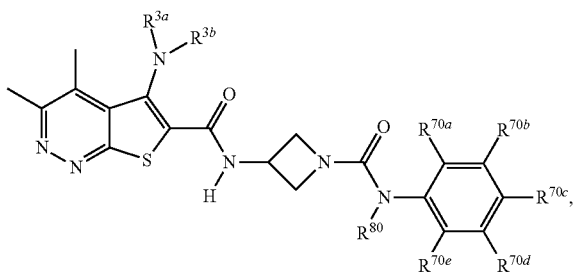

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; wherein $R^{80}$ is selected from hydrogen and C1-C6 alkyl; and wherein all other variables are as defined herein.

In a further aspect, a compound can have a structure represented by the formula:

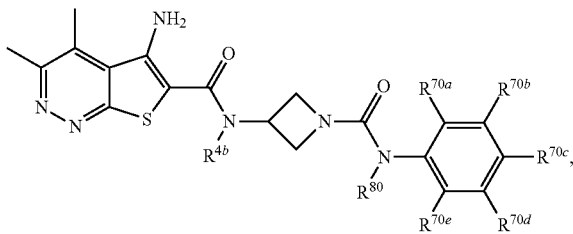

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; wherein $R^{80}$ is selected from hydrogen and C1-C6 alkyl; and wherein all other variables are as defined herein.

In a further aspect, a compound can have a structure represented by the formula:

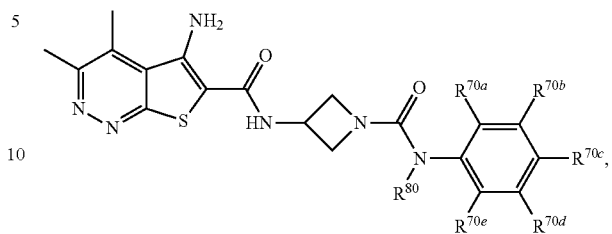

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; wherein $R^{80}$ is selected from hydrogen and C1-C6 alkyl; and wherein all other variables are as defined herein.

In a further aspect, a compound can have a structure represented by the formula:

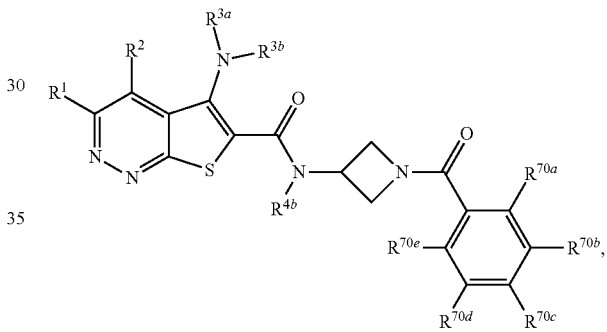

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

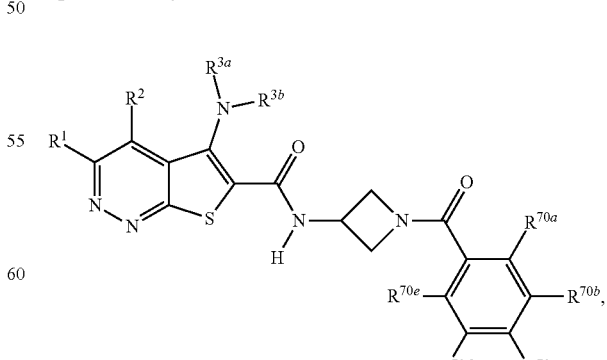

wherein each of $R^{70a}$, $R^{70b}$, $R^{70c}$, $R^{70d}$, and $R^{70e}$ are independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

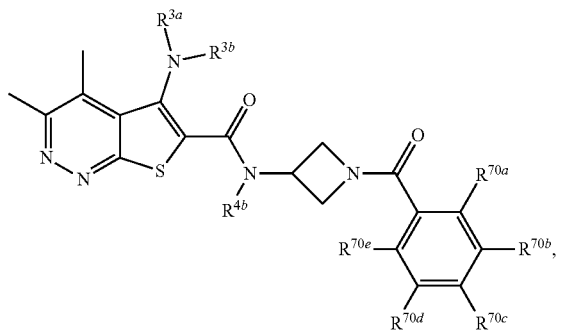

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

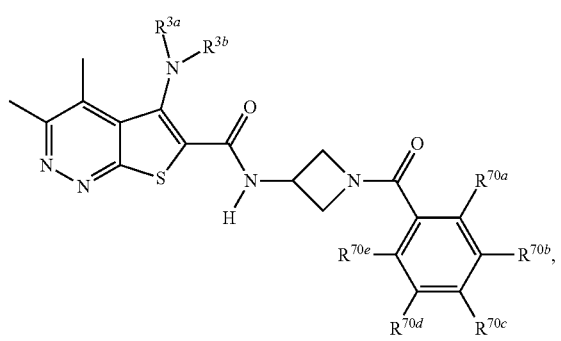

wherein each of $R^{70a}$, $R^{70b}$, $R^{70c}$, $R^{70d}$, and $R^{70e}$ are independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

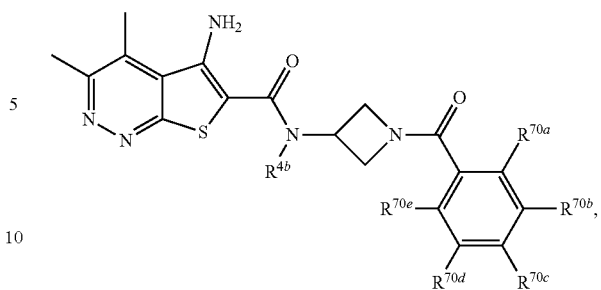

wherein each of $R^{70a}$, $R^{70b}$, $R^{70c}$, $R^{70d}$, and $R^{70e}$ is independently selected from halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen; and wherein all other variables are as defined herein.

In a further aspect, a compound can have a structure represented by the formula:

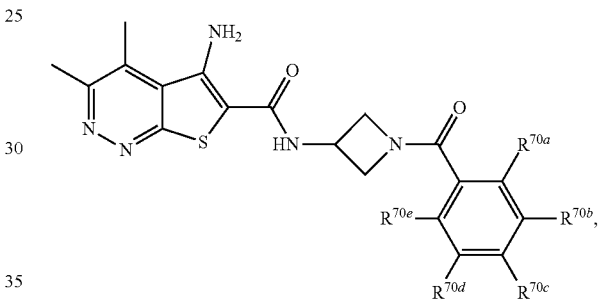

wherein each of $R^{70a}$, $R^{70b}$, $R^{70c}$, $R^{70d}$, and $R^{70e}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and ee are hydrogen; and wherein all other variables are as defined herein.

In a further aspect, a compound can have a structure represented by the formula:

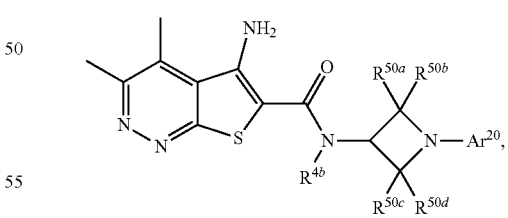

wherein each of $R^{50a}$, $R^{50b}$, $R^{50c}$, and $R^{50d}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of $R^{50a}$, $R^{50b}$, $R^{50c}$, and $R^{50d}$ is hydrogen; and wherein all other variables are as defined herein.

In a further aspect, a compound can have a structure represented by the formula:

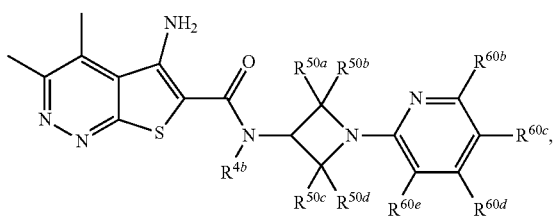

wherein each of $R^{50a}$, $R^{50b}$, $R^{50c}$, and $R^{50d}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of $R^{50a}$, $R^{50b}$, $R^{50c}$, and $R^{50d}$ is hydrogen; and wherein each of $R^{60b}$, $R^{60c}$, $R^{60d}$, and $R^{60e}$ is independently selected from halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, and C1-C3 dialkylamino; provided that at least one of $R^{60b}$, $R^{60c}$, $R^{60d}$, and $R^{60e}$ is hydrogen; and wherein all other variables are as defined herein.

In a further aspect, a compound can have a structure represented by the formula:

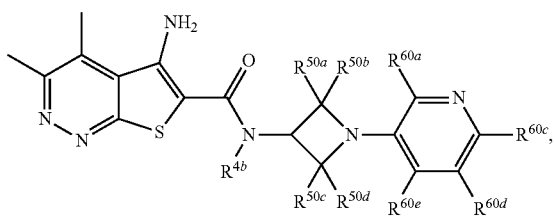

wherein each of $R^{50a}$, $R^{50b}$, $R^{50c}$, and $R^{50d}$ are independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of $R^{50a}$, $R^{50b}$, $R^{50c}$, and $R^{50d}$ is hydrogen; and wherein each of $R^{60a}$, $R^{60c}$, $R^{60d}$, and $R^{60e}$ is independently selected from halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, and C1-C3 dialkylamino; provided that at least one of $R^{60a}$, $R^{60c}$, $R^{60d}$, and $R^{60e}$ are hydrogen; and wherein all other variables are as defined herein.

In a further aspect, a compound can have a structure represented by the formula:

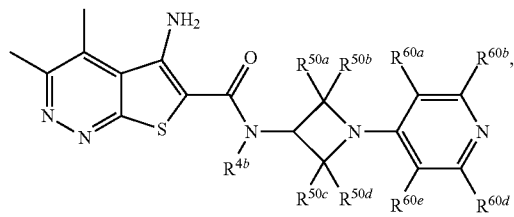

wherein each of $R^{50a}$, $R^{50b}$, $R^{50c}$, and $R^{50d}$ are independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of $R^{50a}$, $R^{50b}$, $R^{50c}$, and $R^{50d}$ is hydrogen; and wherein each of $R^{60a}$, $R^{60b}$, $R^{60d}$, and $R^{60e}$ is independently selected from halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, and C1-C3 dialkylamino; provided that at least one of $R^{60a}$, $R^{60b}$, $R^{60d}$, and $R^{60e}$ are hydrogen; and wherein all other variables are as defined herein.

In a further aspect, a compound can have a structure represented by the formula:

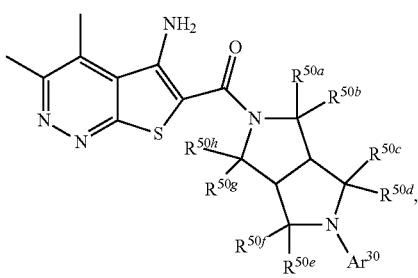

wherein each of $R^{50a}$, $R^{50b}$, $R^{50c}$, $R^{50d}$, $R^{50e}$, $R^{50f}$, $R^{50g}$, and $R^{50h}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least five of $R^{50a}$, $R^{50b}$, $R^{50c}$, $R^{50d}$, $R^{50e}$, $R^{50f}$, $R^{50g}$, and $R^{50h}$ are hydrogen; and wherein all other variables are as defined herein.

In a further aspect, a compound can have a structure represented by the formula:

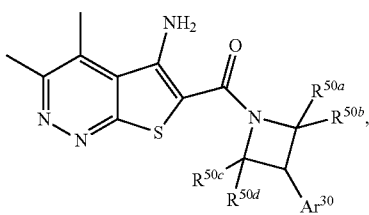

wherein each of $R^{50a}$, $R^{50b}$, $R^{50c}$, and $R^{50d}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of $R^{50a}$, $R^{50b}$, $R^{50c}$, and $R^{50d}$ is hydrogen; and wherein all other variables are as defined herein.

In a further aspect, a compound can have a structure represented by the formula:

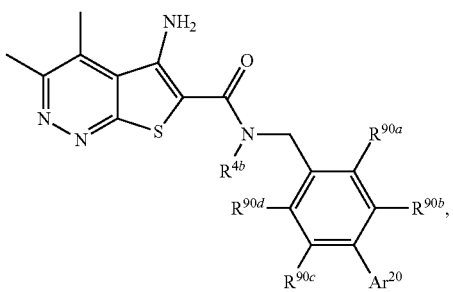

wherein each of $R^{90a}$, $R^{90b}$, $R^{90c}$, and $R^{90d}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least two of $R^{90a}$, $R^{90b}$, $R^{90c}$, and $R^{90d}$ are hydrogen; and wherein all other variables are as defined herein.

In a further aspect, a compound can have a structure represented by the formula:

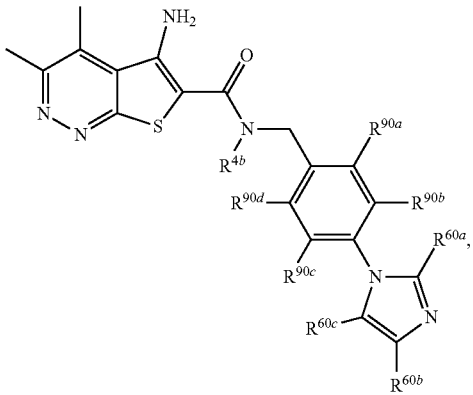

wherein each of $R^{90a}$, $R^{90b}$, $R^{90c}$, and $R^{90d}$ is independently selected from halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; and wherein each of $R^{60a}$, $R^{60b}$, and $R^{60c}$ are independently selected from halogen, —$NH_2$, —OH, —CN, —$S(O)_nR^{36}$, C1-C3 alkyl, C1-C3 monohaloalkyl, C1-C3 polyhaloalkyl, C1-C3 alkoxy, C1-C3 alkylamino, and C1-C3 dialkylamino, provided that at least two of $R^{90a}$, $R^{90b}$, $R^{90c}$, and $R^{90d}$ are hydrogen; and wherein all other variables are as defined herein.

Suitable substituents are described below.

a. $R^1$ Groups

In various aspects, $R^1$ is selected from hydrogen, halogen, —OH, —CN, —$NH_2$, —$CF_3$, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-$Ar^{10}$, $Ar^{10}$, —(C1-C3 alkyl)-$Cy^{10}$, and $Cy^{10}$. In a further aspect, $R^1$ is hydrogen.

In a further aspect, $R^1$ is selected from hydrogen, —(C1-C3 alkyl)-$Ar^{10}$, $Ar^{10}$, —(C1-C3 alkyl)-$Cy^{10}$, and $Cy^{10}$. In a still further aspect, $R^1$ is selected from hydrogen, —$CH_2$—$Ar^{10}$, —$(CH_2)_2$—$Ar^{10}$, —$(CH_2)_3$—$Ar^{10}$, $Ar^{10}$, —$CH_2Cy^{10}$, —$(CH_2)_2$—$Cy^{10}$, —$(CH_2)_3$—$Cy^{10}$, and $Cy^{10}$. In a yet further aspect, $R^1$ is selected from hydrogen, —$CH_2$—$Ar^{10}$, $Ar^{10}$, —$CH_2$—$Cy^{10}$, and —$Cy^{10}$.

In a further aspect, $R^1$ is selected from —(C1-C3 alkyl)-$Ar^{10}$, $Ar^{10}$, —(C1-C3 alkyl)-$Cy^{10}$, and $Cy^{10}$. In a still further aspect, $R^1$ is selected from —$CH_2$—$Ar^{10}$, —$(CH_2)_2$—$Ar^{10}$, —$(CH_2)_3$—$Ar^{10}$, $Ar^{10}$, —$CH_2$-$Cy^{10}$, —$(CH_2)_2$—$Cy^{10}$, —$(CH_2)_3$—$Cy^{10}$, and $Cy^{10}$. In a yet further aspect, $R^1$ is selected from —$CH_2$—$Ar^{10}$, $Ar^{10}$, —$CH_2$—$Cy^{10}$, and $Cy^{10}$. In an even further aspect, $R^1$ is selected from —$CH_2$-phenyl and phenyl. In a still further aspect, $R^1$ is selected from —$CH_2$-morpholinyl and morpholinyl.

In a further aspect, $R^1$ is selected from methyl, —$CH_2$-phenyl, phenyl, —$CH_2$-morpholinyl, and morpholinyl. In a still further aspect, $R^1$ is selected from methyl, phenyl, and morpholinyl.

In various aspects, $R^1$ is selected from hydrogen, halogen, C1-C6 alkyl, C1-C6 haloalkyl, C1-C6 polyhaloalkyl, C1-C6 alkoxy, C1-C6 alkylamino, and C1-C6 dialkylamino. In a further aspect, $R^1$ is selected from hydrogen, halogen, C1-C3 alkyl, C1-C3 haloalkyl, C1-C3 polyhaloalkyl, C1-C3 alkoxy, C1-C3 alkylamino, and C1-C3 dialkylamino. In a still further aspect, $R^1$ is selected from hydrogen, —F, —Cl, C1-C6 alkyl, C1-C6 haloalkyl, C1-C6 polyhaloalkyl, C1-C6 alkoxy, C1-C6 alkylamino, and C1-C6 dialkylamino. In a yet further aspect, $R^1$ is selected from hydrogen, —F, —Cl, C1-C3 alkyl, C1-C3 haloalkyl, C1-C3 polyhaloalkyl, C1-C3 alkoxy, C1-C3 alkylamino, and C1-C3 dialkylamino.

In various further aspects, $R^1$ is selected from hydrogen, —F, —Cl, —Br, —I, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, and —$N(CH_2CH_3)(CH(CH_3)_2)$. In a still further aspect, $R^1$ is selected from hydrogen, —F, —Cl, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$. In a yet further aspect, $R^1$ is selected from hydrogen, —F, —Cl, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$.

In a further aspect, $R^1$ is selected from halogen, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^1$ is selected from —F, —Cl, C1-C6 alkyl, C1-C6 haloalkyl, C1-C6 polyhaloalkyl, C1-C6 alkoxy, C1-C6 alkylamino, and C1-C6 dialkylamino. In a yet further aspect, $R^1$ is selected from —F, —Cl, C1-C3 alkyl, C1-C3 haloalkyl, C1-C3 polyhaloalkyl, C1-C3 alkoxy, C1-C3 alkylamino, and C1-C3 dialkylamino. In an even further aspect, $R^1$ is selected from —F, —Cl, —Br, —I, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, and —N(CH$_2$CH$_3$)(CH(CH$_3$)$_2$). In a still further aspect, R$^1$ is selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In a yet further aspect, R$^1$ is selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$.

In a further aspect, R$^1$ is selected from hydrogen, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ is selected from hydrogen, C1-C3 alkyl, C1-C3 haloalkyl, C1-C3 polyhaloalkyl, C1-C3 alkoxy, C1-C3 alkylamino, and C1-C3 dialkylamino. In a yet further aspect, R$^1$ is selected from hydrogen, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, R$^1$ is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^1$ is selected from hydrogen, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$.

In a further aspect, R$^1$ is methyl. In an even further aspect, R$^1$ is ethyl. In a still further aspect, R$^1$ is propyl. In a yet further aspect, R$^1$ is isopropyl. In a still further aspect, R$^1$ is —CH$_2$F. In a yet further aspect, R$^1$ is —CH$_2$Cl. In an even further aspect, R$^1$ is —CHF$_2$. In a still further aspect, R$^1$ is CF$_3$. In a yet further aspect, R$^1$ is —CHCl$_2$. In an even further aspect, R$^1$ is —CCl$_3$. In a still further aspect, R$^1$ is —OCH$_3$. In a yet further aspect, R$^1$ is —NHCH$_3$. In an even further aspect, R$^1$ is —N(CH$_3$)$_2$.

In various further aspects, R$^1$ is selected from hydrogen, —F, —Cl, —Br, and —I. In a further aspect, R$^1$ is selected from hydrogen, —F, and —Cl. In a still further aspect, R$^1$ is selected from hydrogen and —F. In a yet further aspect, R$^1$ is hydrogen. In an even further aspect, R$^1$ is —F. In a still further aspect, R$^1$ is —Cl. In a yet further aspect, R$^1$ is methyl. In an even further aspect, R$^1$ is ethyl. In a still further aspect, R$^1$ is propyl.

In various further aspects, R$^1$ is selected from hydrogen, —F, —Cl, —Br, —I, and C1-C6 alkyl. In a further aspect, R$^1$ is selected from hydrogen, —F, —Cl, and C1-C6 alkyl. In a yet further aspect, R$^1$ is selected from hydrogen, —F, —Cl, and C1-C3 alkyl. In a still further aspect, R$^1$ is selected from hydrogen, —F, —Cl, methyl, ethyl, propyl, and isopropyl.

In a further aspect, R$^1$ is selected from hydrogen, —F, and C1-C6 alkyl. In a still further aspect, R$^1$ is selected from hydrogen, —F, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, and 2,3-dimethylpentan-2-yl. In a yet further aspect, R$^1$ is selected from hydrogen, —F, methyl, ethyl, propyl, isopropyl, tert-butyl, sec-butyl, isobutyl, tert-butyl, neopentyl, isopentyl, sec-pentyl, and tert-pentyl. In an even further aspect, R$^1$ is selected from hydrogen, —F, methyl, ethyl, propyl, and isopropyl.

In various further aspects, each of R$^1$ and R$^2$ is hydrogen. In a further aspect, each of R$^1$, R$^2$, R$^{3a}$, and R$^{3b}$ is hydrogen. In a still further aspect, each of R$^1$, R$^2$, R$^{3a}$, R$^{3b}$, and R$^{4a}$ is hydrogen. In a yet further aspect, each of R$^1$ and R$^2$ is methyl; and wherein each of R$^{3a}$, R$^{3b}$, and R$^{4a}$ is hydrogen. In an even further aspect, each of R$^1$ and R$^2$ is methyl.

In one aspect, R$^1$ and R$^2$ are optionally covalently bonded and, together with the intermediate atoms, comprise a 3- to 7-membered cycle substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a further aspect, R$^1$ and R$^2$ are covalently bonded and, together with the intermediate atoms, comprise an unsubstituted 3- to 7-membered cycle.

In a further aspect, R$^1$ and R$^2$ are covalently bonded and, together with the intermediate atoms, comprise a 3- to 7-membered cycle monosubstituted with a group selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a yet further aspect, R$^1$ and R$^2$ are covalently bonded and, together with the intermediate atoms, comprise a 3- to 7-membered cycle substituted with a 0-1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In an even further aspect, R$^1$ and R$^2$ are covalently bonded and, together with the intermediate atoms, comprise a 3- to 7-membered cycle substituted with a 1-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino.

In a further aspect, R$^1$ and R$^2$ are covalently bonded and, together with the intermediate atoms, comprise a 3- to 7-membered cycle substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 3- to 7-membered cycle substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 3- to 7-membered cycle substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 3- to 7-membered cycle substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 3- to 7-membered cycle substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 3- to 7-membered cycle substituted with 0-2 groups independently selected from —F, methyl, ethyl, propyl, and isopropyl. In an even further aspect, R$^1$ and R$^2$ are covalently bonded and, together with the intermediate atoms, comprise a 3- to 7-membered cycle substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 3- to 7-membered cycle substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 3- to 7-membered cycle substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 4- to 6-membered cycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 4- to 6-membered cycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 4- to 6-membered cycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 4- to 6-membered cycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 4- to 6-membered cycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 4- to 6-membered cycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 4- to 6-membered cycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 4- to 6-membered cycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 4- to 6-membered cycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 4- to 6-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 4- to 6-membered heterocycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 4- to 6-membered heterocycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 4- to 6-membered heterocycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 4- to 6-membered heterocycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 4- to 6-membered heterocycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 4- to 6-membered heterocycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 4- to 6-membered heterocycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 4- to 6-membered heterocycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 4-membered cycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 4-membered cycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 4-membered cycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 4-membered cycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 4-membered cycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 4-membered cycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 4-membered cycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 4-membered cycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 4-membered cycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 4-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 4-membered heterocycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 4-membered heterocycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 4-membered heterocycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 4-membered heterocycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 4-membered heterocycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 4-membered heterocycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 4-membered heterocycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 4-membered heterocycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 5-membered cycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 5-membered cycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 5-membered cycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 5-membered cycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 5-membered cycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 5-membered cycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 5-membered cycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 5-membered cycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 5-membered cycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 5-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 5-membered heterocycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 5-membered heterocycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 5-membered heterocycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 5-membered heterocycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 5-membered heterocycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 5-membered heterocycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 5-membered heterocycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 6-membered cycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 6-membered cycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 6-membered cycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 6-membered cycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 6-membered cycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 6-membered cycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 6-membered cycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 6-membered cycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 6-membered cycloalkyl substituted with 0-2 groups independently selected from —NH$_2$, —OH, —CN, —F, —Cl, methyl, —CF$_3$, and —CCl$_3$.

In a further aspect, R$^1$ and R$^2$ are covalently bonded and, together with the intermediate atoms, comprise a 6-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^1$ and R$^2$ are covalently bonded and, together with the intermediate atoms, comprise a 6-membered heterocycloalkyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, and C1-C3 dialkylamino. In a yet further aspect, R$^1$ and R$^2$ are covalently bonded and, together with the intermediate atoms, comprise a 6-membered heterocycloalkyl substituted with 0-2 groups independently selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In an even further aspect, R$^1$ and R$^2$ are covalently bonded and, together with the intermediate atoms, comprise a 6-membered heterocycloalkyl substituted with 0-2 groups independently selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, R$^1$ and R$^2$ are covalently bonded and, together with the intermediate atoms, comprise a 6-membered heterocycloalkyl substituted with 0-2 groups independently selected from —F, —Cl, —Br, —I, and C1-C6 alkyl. In a yet further aspect, R$^1$ and R$^2$ are covalently bonded and, together with the intermediate atoms, comprise a 6-membered heterocycloalkyl substituted with 0-2 groups independently selected from —F, methyl, ethyl, propyl, and isopropyl. In an even further aspect, R$^1$ and R$^2$ are covalently bonded and, together with the intermediate atoms, comprise a 6-membered heterocycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$. In a still further aspect, R$^1$ and R$^2$ are covalently bonded and, together with the intermediate atoms, comprise a 6-membered heterocycloalkyl substituted with 0-2 groups independently selected from —NH$_2$, —OH, —CN, —F, —Cl, methyl, —CH$_2$F, —CH$_2$Cl, —CHF$_2$, —CF$_3$, —CHCl$_2$, and —CCl$_3$. In a yet further aspect, R$^1$ and R$^2$ are covalently bonded and, together with the intermediate atoms, comprise a 6-membered heterocycloalkyl substituted with 0-2 groups independently selected from —NH$_2$, —OH, —CN, —F, —Cl, methyl, —CF$_3$, and —CCl$_3$.

b. R$^2$ Groups

In various aspects, R$^2$ is selected from hydrogen, halogen, —OH, —CN, —NH$_2$, —CF$_3$, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-Ar$^{11}$, Ar$^{11}$, —(C1-C3 alkyl)-Cy$^{11}$, and Cy$^{11}$. In a further aspect, R$^2$ is hydrogen.

In a further aspect, R$^2$ is selected from hydrogen, —(C1-C3 alkyl)-Ar$^{11}$, Ar$^{11}$, —(C1-C3 alkyl)-Cy$^{11}$, and Cy$^{11}$. In a still further aspect, R$^2$ is selected from hydrogen, —CH$_2$—Ar$^{11}$, —(CH$_2$)$_2$—Ar$^{11}$, —(CH$_2$)$_3$—Ar$^{11}$, Ar$^{11}$, —CH$_2$—Cy$^{11}$, —(CH$_2$)$_2$—Cy$^{11}$, —(CH$_2$)$_3$—Cy$^{11}$, and Cy$^{11}$. In a yet further aspect, R$^2$ is selected from hydrogen, —CH$_2$—Ar$^{11}$, Ar$^{11}$, —CH$_2$—Cy$^{11}$, and Cy$^{11}$.

In a further aspect, R$^2$ is selected from —(C1-C3 alkyl)-Ar$^{11}$, Ar$^{11}$, —(C1-C3 alkyl)-Cy$^{11}$, and Cy$^{11}$. In a still further aspect, R$^2$ is selected from —CH$_2$—Ar$^{11}$, —(CH$_2$)$_2$—Ar$^{11}$, —(CH$_2$)$_3$—Ar$^{11}$, Ar$^{11}$, —CH$_2$-Cy$^{11}$, —(CH$_2$)$_2$—Cy$^{11}$, —(CH$_2$)$_3$—Cy$^{11}$, and Cy$^{11}$. In a yet further aspect, R$^2$ is selected from —CH$_2$—Ar$^{11}$, Ar$^{11}$, —CH$_2$-Cy$^{11}$, and Cy$^{11}$. In an even further aspect, R$^2$ is selected from —CH$_2$-phenyl and phenyl. In a still further aspect, R$^2$ is selected from —CH$_2$-morpholinyl and morpholinyl.

In a further aspect, R$^2$ is selected from methyl, —CH$_2$-phenyl, phenyl, —CH$_2$-morpholinyl, and morpholinyl. In a still further aspect, R$^2$ is selected from methyl, phenyl, and morpholinyl.

In various aspects, R$^2$ is selected from hydrogen, halogen, C1-C6 alkyl, C1-C6 haloalkyl, C1-C6 polyhaloalkyl, C1-C6 alkoxy, C1-C6 alkylamino, and C1-C6 dialkylamino. In a further aspect, R$^2$ is selected from hydrogen, halogen, C1-C3 alkyl, C1-C3 haloalkyl, C1-C3 polyhaloalkyl, C1-C3 alkoxy, C1-C3 alkylamino, and C1-C3 dialkylamino. In a still further aspect, R$^2$ is selected from hydrogen, —F, —Cl, C1-C6 alkyl, C1-C6 haloalkyl, C1-C6 polyhaloalkyl, C1-C6 alkoxy, C1-C6 alkylamino, and C1-C6 dialkylamino. In a yet further aspect, R$^2$ is selected from hydrogen, —F, —Cl, C1-C3 alkyl, C1-C3 haloalkyl, C1-C3 polyhaloalkyl, C1-C3 alkoxy, C1-C3 alkylamino, and C1-C3 dialkylamino.

In various further aspects, R$^2$ is selected from hydrogen, —F, —Cl, —Br, —I, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, R$^2$ is selected from hydrogen, —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In a yet further aspect, R$^2$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$.

In a further aspect, R$^2$ is selected from halogen, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^2$ is selected from —F, —Cl, C1-C6 alkyl, C1-C6 haloalkyl, C1-C6 polyhaloalkyl, C1-C6 alkoxy, C1-C6 alkylamino, and C1-C6 dialkylamino. In a yet further aspect, $R^2$ is selected from —F, —Cl, C1-C3 alkyl, C1-C3 haloalkyl, C1-C3 polyhaloalkyl, C1-C3 alkoxy, C1-C3 alkylamino, and C1-C3 dialkylamino. In an even further aspect, $R^2$ is selected from —F, —Cl, —Br, —I, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, $R^2$ is selected from —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$. In a yet further aspect, $R^2$ is selected from —F, —Cl, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$.

In a further aspect, $R^2$ is selected from hydrogen, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^2$ is selected from hydrogen, C1-C3 alkyl, C1-C3 haloalkyl, C1-C3 polyhaloalkyl, C1-C3 alkoxy, C1-C3 alkylamino, and C1-C3 dialkylamino. In a yet further aspect, $R^2$ is selected from hydrogen, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, $R^2$ is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^2$ is selected from hydrogen, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$.

In a further aspect, $R^2$ is methyl. In an even further aspect, $R^2$ is ethyl. In a still further aspect, $R^2$ is propyl. In a yet further aspect, $R^2$ is isopropyl. In a still further aspect, $R^2$ is —CH$_2$F. In a yet further aspect, $R^2$ is —CH$_2$Cl. In an even further aspect, $R^2$ is —CHF$_2$. In a still further aspect, $R^2$ is —CF$_3$. In a yet further aspect, $R^2$ is —CHCl$_2$. In an even further aspect, $R^2$ is —CCl$_3$. In a still further aspect, $R^2$ is —OCH$_3$. In a yet further aspect, $R^2$ is —NHCH$_3$. In an even further aspect, $R^2$ is —N(CH$_3$)$_2$.

In various further aspects, $R^2$ is selected from hydrogen, —F, —Cl, —Br, and —I. In a further aspect, $R^2$ is selected from hydrogen, —F, and —Cl. In a still further aspect, $R^2$ is selected from hydrogen and —F. In a yet further aspect, $R^2$ is hydrogen. In an even further aspect, $R^2$ is —F. In a still further aspect, $R^2$ is —Cl. In a yet further aspect, $R^2$ is methyl. In an even further aspect, $R^2$ is ethyl. In a still further aspect, $R^2$ is propyl.

In various further aspects, $R^2$ is selected from hydrogen, —F, —Cl, —Br, —I, and C1-C6 alkyl. In a further aspect, $R^2$ is selected from hydrogen, —F, —Cl, and C1-C6 alkyl. In a yet further aspect, $R^2$ is selected from hydrogen, —F, —Cl, and C1-C3 alkyl. In a still further aspect, $R^2$ is selected from hydrogen, —F, —Cl, methyl, ethyl, propyl, and isopropyl.

In a further aspect, $R^2$ is selected from hydrogen, —F, and C1-C6 alkyl. In a still further aspect, $R^2$ is selected from hydrogen, —F, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, and 2,3-dimethylpentan-2-yl. In a yet further aspect, $R^2$ is selected from hydrogen, —F, methyl, ethyl, propyl, isopropyl, tert-butyl, sec-butyl, isobutyl, tert-butyl, neopentyl, isopentyl, sec-pentyl, and tert-pentyl. In an even further aspect, $R^2$ is selected from hydrogen, —F, methyl, ethyl, propyl, and isopropyl.

c. $R^{3A}$ and $R^{3B}$ Groups

In one aspect, each of $R^{3a}$ and $R^{3b}$ is independently selected from hydrogen, C1-C6 alkyl, C1-C6 haloalkyl, C1-C6 polyhaloalkyl, C3-C8 cycloalkyl, C2-C7 heterocloalkyl, —(C1-C8 alkyl)-(C3-C8 cycloalkyl), and —(C1-C8 alkyl)-(C2-C7 heterocycloalkyl). In a further aspect, each of $R^{3a}$ and $R^{3b}$ is hydrogen. In a still further aspect, each of $R^{3a}$, $R^{3b}$, and $R^{4a}$ is hydrogen.

In a further aspect, each of $R^{3a}$ and $R^{3b}$ is independently selected from C1-C6 alkyl, C1-C6 haloalkyl, C1-C6 polyhaloalkyl, C3-C8 cycloalkyl, C2-C7 heterocycloalkyl, —(C1-C8 alkyl)-(C3-C8 cycloalkyl), and —(C1-C8 alkyl)-(C2-C7 heterocycloalkyl). In a still further aspect, each of $R^{3a}$ and $R^{3b}$ is independently selected from hydrogen, C1-C6 alkyl, C1-C6 haloalkyl, C1-C6 polyhaloalkyl, C3-C8 cycloalkyl, C2-C7 heterocycloalkyl, —(C1-C8 alkyl)-(C3-C6 cycloalkyl), and —(C1-C8 alkyl)-(C2-C5 heterocycloalkyl). In a yet further aspect, each of $R^{3a}$ and $R^{3b}$ is independently selected from hydrogen, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl. In an even further aspect, each of $R^{3a}$ and $R^{3b}$ is independently selected from hydrogen, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl.

In a further aspect, each of $R^{3a}$ and $R^{3b}$ is independently selected from hydrogen, methyl, ethyl, —CH₂F, —CH₂Cl, —CHF₂, —CF₃, —CHCl₂, —CCl₃, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl. In a still further aspect, each of $R^{3a}$ and $R^{3b}$ is independently selected from hydrogen, cyclopropyl, cyclobutyl, cyclopentyl, and cyclohexyl. In a yet further aspect, each of $R^{3a}$ and $R^{3b}$ is independently selected from hydrogen, pyrollidinyl, tetrahydrofuranyl, tetrahydrothiophenyl, piperidinyl, tetrahydro-2H-pyranyl, and tetrahydro-2H-thiopyranyl. In an even further aspect, each of $R^{3a}$ and $R^{3b}$ is independently selected from hydrogen, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl.

In a further aspect, each of $R^{3a}$ and $R^{3b}$ is independently selected from hydrogen, methyl, ethyl, —CH₂F, —CH₂Cl, —CHF₂, —CF₃, —CHCl₂, and —CCl₃. In an even further aspect, each of $R^{3a}$ and $R^{3b}$ is independently selected from hydrogen, —CH₂F, —CH₂Cl, —CHF₂, —CF₃, —CHCl₂, and —CCl₃. In a still further aspect, each of $R^{3a}$ and $R^{3b}$ is independently selected from hydrogen, methyl, ethyl, and isopropyl. In a yet further aspect, each of $R^{3a}$ and $R^{3b}$ is independently selected from hydrogen and methyl. In an even further aspect, each of $R^{3a}$ and $R^{3b}$ is methyl.

In a further aspect, $R^{3a}$ is hydrogen and $R^{3b}$ is selected from hydrogen, C1-C6 alkyl, C1-C6 haloalkyl, C1-C6 polyhaloalkyl, C3-C8 cycloalkyl, C2-C7 heterocycloalkyl, —(C1-C8 alkyl)-(C3-C8 cycloalkyl), and —(C1-C8 alkyl)-(C2-C7 heterocycloalkyl). In a still further aspect, $R^{3a}$ is hydrogen and $R^{3b}$ is selected from hydrogen, C1-C3 alkyl, C1-C3 haloalkyl, C1-C3 polyhaloalkyl, C3-C6 cycloalkyl, C2-C5 heterocycloalkyl, —(C1-C8 alkyl)-(C3-C6 cycloalkyl), and —(C1-C8 alkyl)-(C2-C5 heterocycloalkyl). In a yet further aspect, $R^{3a}$ is hydrogen and $R^{3b}$ is selected from hydrogen, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl. In an even further aspect, $R^{3a}$ is hydrogen and $R^{3b}$ is selected from hydrogen, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl.

In a further aspect, $R^{3a}$ is hydrogen and $R^{3b}$ is selected from hydrogen, cyclopropyl, cyclobutyl, cyclopentyl, and cyclohexyl. In an even further aspect, $R^{3a}$ is hydrogen and $R^{3b}$ is selected from hydrogen, pyrollidinyl, tetrahydrofuranyl, tetrahydrothiophenyl, piperidinyl, tetrahydro-2H-pyranyl, and tetrahydro-2H-thiopyranyl. In a still further aspect, $R^{3a}$ is hydrogen and $R^{3b}$ is selected from hydrogen, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl.

In a further aspect, $R^{3a}$ is hydrogen and $R^{3b}$ is selected from hydrogen, methyl, ethyl, —CH₂F, —CH₂Cl, —CHF₂, —CF₃, —CHCl₂, and —CCl₃. In a still further aspect, $R^{3a}$ is hydrogen and $R^{3b}$ is selected from hydrogen, —CH₂F, —CH₂Cl, —CHF₂, —CF₃, —CHCl₂, and CCl₃. In a yet further aspect, $R^{3a}$ is hydrogen and $R^{3b}$ is methyl. In an even further aspect, $R^{3a}$ is hydrogen and $R^{3b}$ is ethyl. In a still further aspect, $R^{3a}$ is hydrogen and $R^{3b}$ is cyclopropyl.

In a further aspect, $R^{3a}$ is hydrogen and $R^{3b}$ is cyclopentyl. In a still further aspect, $R^{3a}$ is hydrogen and $R^{3b}$ is cyclohexyl. In a yet further aspect, $R^{3a}$ is hydrogen and $R^{3b}$ is pyrollidinyl. In an even further aspect, $R^{3a}$ is hydrogen and $R^{3b}$ is piperidinyl. In a still further aspect, $R^{3a}$ is hydrogen and $R^{3b}$ is —(C1-C3)-pyrollidinyl. In a yet further aspect, $R^{3a}$ is hydrogen and $R^{3b}$ is —(C1-C3)-piperidinyl.

In one aspect, $R^{3a}$ and $R^{3b}$ are optionally covalently bonded and, together with the intermediate nitrogen, comprise a 3- to 7-membered heterocycloalkyl substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, and C1-C6 dialkylamino. In a further aspect, $R^{3a}$ and $R^{3b}$ are covalently bonded and, together with the intermediate nitrogen, comprise a 3- to 7-membered heterocycloalkyl substituted with 0-2 groups independently selected from —F, —Cl, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{3a}$ and $R^{3b}$ are covalently bonded and, together with the intermediate nitrogen, comprise a 3- to 7-membered heterocycloalkyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, $R^{3a}$ and $R^{3b}$ are covalently bonded and, together with the intermediate nitrogen, comprise a 3- to 7-membered heterocycloalkyl substituted with 0-2 groups independently selected from —F, —Cl, —NH$_2$, —OH, —CN, methyl, —CF$_3$, —CCl$_3$, —OCH$_3$, and —NHCH$_3$. In an even further aspect, wherein $R^{3a}$ and $R^{3b}$ are covalently bonded and, together with the intermediate nitrogen, comprise a 3- to 7-membered heterocycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$.

In a further aspect, $R^{3a}$ and $R^{3b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{3a}$ and $R^{3b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, $R^{3a}$ and $R^{3b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from —F, —Cl, —NH$_2$, —OH, —CN, methyl, —CF$_3$, —CCl$_3$, —OCH$_3$, and —NHCH$_3$. In an even further aspect, $R^{3a}$ and $R^{3b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from —F, —Cl, methyl, —CH$_2$F, —CH$_2$Cl, —CHF$_2$, —CF$_3$, —CHCl$_2$, and —CCl$_3$.

In a further aspect, $R^{3a}$ and $R^{3b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{3a}$ and $R^{3b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, $R^{3a}$ and $R^{3b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from —F, —Cl, —NH$_2$, —OH, —CN, methyl, —CF$_3$, —CCl$_3$, —OCH$_3$, and —NHCH$_3$. In an even further aspect, $R^{3a}$ and $R^{3b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from —F, —Cl, methyl, —CH$_2$F, —CH$_2$Cl, —CHF$_2$, —CF$_3$, —CHCl$_2$, and —CCl$_3$.

In a further aspect, $R^{3a}$ and $R^{3b}$ are covalently bonded and, together with the intermediate nitrogen, comprise a pyrrolidinyl group substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{3a}$ and $R^{3b}$ are covalently bonded and, together with the intermediate nitrogen, comprise a pyrrolidinyl group substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, $R^{3a}$ and $R^{3b}$ are covalently bonded and, together with the intermediate nitrogen, comprise a pyrrolidinyl group substituted with 0-2 groups independently selected from —F, —Cl, —NH$_2$, —OH, —CN, methyl, —CF$_3$, —CCl$_3$, —OCH$_3$, and —NHCH$_3$. In an even further aspect, $R^{3a}$ and $R^{3b}$ are covalently bonded and, together with the intermediate nitrogen, comprise a pyrrolidinyl group substituted with 0-2 groups independently selected from —F, —Cl, methyl, —CH$_2$F, —CH$_2$Cl, —CHF$_2$, —CF$_3$, —CHCl$_2$, and —CCl$_3$.

In a further aspect, $R^{3a}$ and $R^{3b}$ are covalently bonded and, together with the intermediate nitrogen, comprise a piperidinyl group substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{3a}$ and $R^{3b}$ are covalently bonded and, together with the intermediate nitrogen, comprise a piperidinyl group substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, $R^{3a}$ and $R^{3b}$ are covalently bonded and, together with the intermediate nitrogen, comprise a piperidinyl group substituted with 0-2 groups independently selected from —F, —Cl, —NH$_2$, —OH, —CN, methyl, —CF$_3$, —CCl$_3$, —OCH$_3$, and —NHCH$_3$. In an even further aspect, $R^{3a}$ and $R^{3b}$ are covalently bonded and, together with the intermediate nitrogen, comprise a piperidinyl group substituted with 0-2 groups independently selected from —F, —Cl, methyl, —CH$_2$F, —CH$_2$Cl, —CHF$_2$, —CF$_3$, —CHCl$_2$, and —CCl$_3$.

d. $R^{4A}$ and $R^{4B}$ Groups

In one aspect, each of $R^{4a}$ and $R^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{20}$R$^{21}$, —(C1-C6 alkyl)-NR$^{20}$(C=O)R$^{21}$, —(C1-C6 alkyl)-NR$^{20}$(C=O)OR$^{21}$, —(C1-C6 alkyl)-NR$^{20}$(C=O)NR$^{21}$, —(C1-C6 monohaloalkyl)-NR$^{20}$(C=O)OR$^{21}$, —(C1-C6 polyhaloalkyl)-NR$^{20}$(C=O)OR$^{21}$, —(C1-C8 alkyl)-Cy$^1$, Cy$^1$, —(CH$_2$)—Ar$^1$, —(CH$_2$)$_2$—Ar$^3$, —(C3-C8 alkyl)-Ar$^1$, —(C2-C8 alkynyl)-Ar$^1$, and Ar$^2$; and R$^{4a}$ and R$^{4b}$ are not simultaneously hydrogen.

In a further aspect, R$^{4a}$ is hydrogen; and R$^{4b}$ is selected from C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{20}$R$^{21}$, —(C1-C6 alkyl)-NR$^{20}$(C=O)R$^{21}$, —(C1-C6 alkyl)-NR$^{20}$(C=O)OR$^{21}$, —(C1-C6 alkyl)-NR$^{20}$(C=O)NR$^{21}$, —(C1-C6 monohaloalkyl)-NR$^{20}$(C=O)OR$^{21}$, —(C1-C6 polyhaloalkyl)-NR$^{20}$(C=O)OR$^{21}$, —(C1-C8 alkyl)-Cy$^1$, Cy$^1$, —(CH$_2$)—Ar$^1$, —(CH$_2$)$_2$—Ar$^3$, —(C3-C8 alkyl)-Ar$^1$, —(C2-C8 alkynyl)-Ar$^1$, and Ar$^2$.

In a further aspect, each of R$^{4a}$ and R$^{4b}$ is independently selected from hydrogen, C1-C6 alkyl, C1-C6 monohaloalkyl, C1-C6 polyhaloalkyl, C3-C6 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{20}$NR$^{21}$, —(C1-C6 alkyl)-NR$^{20}$(C=O)R$^{21}$, —(C1-C6 alkyl)-NR$^{20}$(C=O)OR$^{21}$, —(C1-C6 alkyl)-NR$^{20}$(C=O)NR$^{21}$, —(C1-C6 monohaloalkyl)-NR$^{20}$(C=O)OR$^{21}$, —(C1-C6 polyhaloalkyl)-NR$^{20}$(C=O)OR$^{21}$, —(C1-C6 alkyl)-Cy$^1$, Cy$^1$, —(CH$_2$)—Ar$^1$, —(CH$_2$)$_2$—Ar$^3$, —(C3-C6 alkyl)-Ar$^1$, —(C2-C6 alkynyl)-Ar$^1$, and Ar$^2$; and R$^{4a}$ and R$^{4b}$ are not simultaneously hydrogen.

In a further aspect, R$^{4a}$ is hydrogen; and R$^{4b}$ is selected from C1-C6 alkyl, C1-C6 monohaloalkyl, C1-C6 polyhaloalkyl, C3-C6 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{20}$R$^{21}$, —(C1-C6 alkyl)-NR$^{20}$(C=O)R$^{21}$, —(C1-C6 alkyl)-NR$^{20}$(C=O)OR$^{21}$, —(C1-C6 alkyl)-NR$^{20}$(C=O)NR$^{21}$, —(C1-C6 monohaloalkyl)-NR$^{20}$(C=O)OR$^{21}$, —(C1-C6 polyhaloalkyl)-NR$^{20}$(C=O)OR$^{21}$, —(C1-C6 alkyl)-Cy$^1$, Cy$^1$, —(CH$_2$)—Ar$^1$, —(CH$_2$)$_2$—Ar$^3$, —(C3-C6 alkyl)-Ar$^1$, —(C2-C6 alkynyl)-Ar$^1$, and Ar$^2$.

In a further aspect, each of R$^{4a}$ and R$^{4b}$ is independently selected from hydrogen, C1-C3 alkyl, C1-C3 monohaloalkyl, C1-C3 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{20}$R$^{21}$, —(C1-C3 alkyl)-NR$^{20}$(C=O)R$^{21}$, —(C1-C3 alkyl)-NR$^{20}$(C=O)OR$^{21}$, —(C1-C3 alkyl)-NR$^{20}$(C=O)NR$^{21}$, —(C1-C3 monohaloalkyl)-NR$^{20}$(C=O)OR$^{21}$, —(C1-C3 polyhaloalkyl)-NR$^{20}$(C=O)OR$^{21}$, —(C1-C3 alkyl)-Cy$^1$, Cy$^1$, —(CH$_2$)—Ar$^1$, —(CH$_2$)$_2$—Ar$^3$, —(C3-C6 alkyl)-Ar$^1$, —(C2-C6 alkynyl)-Ar$^1$, and Ar$^2$; and R$^{4a}$ and R$^{4b}$ are not simultaneously hydrogen.

In a further aspect, R$^{4a}$ is hydrogen; and R$^{4b}$ is selected from C1-C3 alkyl, C1-C3 monohaloalkyl, C1-C3 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{20}$R$^{21}$, —(C1-C3 alkyl)-NR$^{20}$(C=O)R$^{21}$, —(C1-C3 alkyl)-NR$^{20}$(C=O)OR$^{21}$, —(C1-C3 alkyl)-NR$^{20}$(C=O)NR$^{21}$, —(C1-C3 monohaloalkyl)-NR$^{20}$(C=O)OR$^{21}$, —(C1-C3 polyhaloalkyl)-NR$^{20}$(C=O)OR$^{21}$, —(C1-C3 alkyl)-Cy$^1$, Cy$^1$, —(CH$_2$)—Ar$^1$, —(CH$_2$)$_2$—Ar$^3$, —(C3-C6 alkyl)-Ar$^1$, —(C2-C6 alkynyl)-Ar$^1$, and Ar$^2$; and R$^{4a}$ and R$^{4b}$ are not simultaneously hydrogen.

In a further aspect, each of R$^{4a}$ and R$^{4b}$ is independently selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CH$_2$OH, —(CH$_2$)$_3$CH$_2$OH, —(CH$_2$)$_4$CH$_2$OH, —(CH$_2$)$_2$CH(CH$_3$)OH, —CH(CH$_3$)(CH$_2$)2CH$_2$OH, —CH(CH$_3$)CH$_2$CH$_2$OH, —CH(CH$_3$)CH$_2$OH, —CH$_2$OCH$_3$, —(CH$_2$)$_2$OCH$_3$, —(CH$_2$)$_2$OCH$_2$CH$_3$, —(CH$_2$)$_3$OCH$_3$, —(CH$_2$)$_3$OCH$_2$CH$_3$, —CH$_2$OCH$_2$CH$_3$, —(CH$_2$)$_2$OCH$_2$OCH$_3$, —(CH$_2$)$_2$OCH$_2$OCH$_2$CH$_3$, —(CH$_2$)$_3$OCH$_2$OCH$_3$, —(CH$_2$)$_3$OCH$_2$OCH$_2$CH$_3$, —CH$_2$O(CH$_2$)$_2$OCH$_3$, —(CH$_2$)$_2$(CH$_2$)$_2$OCH$_3$, —(CH$_2$)$_2$O(CH$_2$)$_2$OCH$_2$CH$_3$, —(CH$_2$)$_3$O(CH$_2$)$_2$OCH$_3$, —(CH$_2$)$_3$O(CH$_2$)$_2$OCH$_2$CH$_3$, —CH$_2$NR$^{20}$R$^{21}$, —CH$_2$NHR$^{21}$, —(CH$_2$)$_2$NR$^{20}$R$^{21}$, —(CH$_2$)$_2$NHR$^{21}$, —(CH$_2$)$_3$NR$^{20}$R$^{21}$, —(CH$_2$)$_3$NHR$^{21}$, —(CH$_2$)$_4$NR$^{20}$R$^{21}$, —(CH$_2$)$_4$NHR$^{21}$, —CH$_2$NR$^{20}$(C=O)R$^{21}$, —CH$_2$NH(C=O)R$^{21}$, —(CH$_2$)$_2$NR$^{20}$(C=O)R$^{21}$, —(CH$_2$)$_2$NH(C=O)R$^{21}$, —(CH$_2$)$_3$NR$^{20}$(C=O)R$^{21}$, —(CH$_2$)$_3$NH(C=O)R$^{21}$, —(CH$_2$)$_4$NR$^{20}$(C=O)R$^{21}$, —(CH$_2$)$_4$NH(C=O)R$^{21}$, —CH$_2$NR$^{20}$(C=O)OR$^{21}$, —CH$_2$NH(C=O)OR$^{21}$, —(CH$_2$)$_2$NR$^{20}$(C=O)OR$^{21}$, —(CH$_2$)$_2$NH(C=O)OR$^{21}$, —(CH$_2$)$_3$NR$^{20}$(C=O)OR$^{21}$, —(CH$_2$)$_3$NH(C=O)OR$^{21}$, —(CH$_2$)$_4$NR$^{20}$(C=O)OR$^{21}$, —(CH$_2$)$_4$NH(C=O)OR$^{21}$, —CH$_2$NR$^{20}$(C=O)NHR$^{21}$, —CH$_2$NH(C=O)NHR$^{21}$, —(CH$_2$)$_2$NR$^{20}$(C=O)NHR$^{21}$, —(CH$_2$)$_2$NH(C=O)NHR$^{21}$, —(CH$_2$)$_3$NR$^{20}$(C=O)NHR$^{21}$, —(CH$_2$)$_3$NH(C=O)NHR$^{21}$, —(CH$_2$)$_4$NR$^{20}$(C=O)NHR$^{21}$, —(CH$_2$)$_4$NH(C=O)NHR$^{21}$, —CH$_2$—Cy$^1$, —(CH$_2$)$_2$—Cy$^1$, —(CH$_2$)$_3$—Cy$^1$, Cy$^1$, —(CH$_2$)—Ar$^1$, —(CH$_2$)$_2$—Ar$^3$, —(CH$_2$)$_3$—Ar$^1$, —CH$_2$(C≡C)—Ar$^1$, and Ar$^2$; and R$^{4a}$ and R$^{4b}$ are not simultaneously hydrogen.

In a further aspect, R$^{4a}$ is hydrogen; and R$^{4b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CH$_2$OH, —(CH$_2$)$_3$CH$_2$OH, —(CH$_2$)$_4$CH$_2$OH, —(CH$_2$)$_2$CH(CH$_3$)OH, —CH(CH$_3$)(CH$_2$)2CH$_2$OH, —CH(CH$_3$)CH$_2$CH$_2$OH, —CH(CH$_3$)CH$_2$OH, —CH$_2$OCH$_3$, —(CH$_2$)$_2$OCH$_3$, —(CH$_2$)$_2$OCH$_2$CH$_3$, —(CH$_2$)$_3$OCH$_3$, —(CH$_2$)$_3$OCH$_2$CH$_3$, —CH$_2$OCH$_2$OCH$_3$, —(CH$_2$)$_2$OCH$_2$OCH$_3$, —(CH$_2$)$_2$OCH$_2$OCH$_2$CH$_3$, —(CH$_2$)$_3$OCH$_2$OCH$_3$, —(CH$_2$)$_3$OCH$_2$OCH$_2$CH$_3$, —CH$_2$O(CH$_2$)$_2$OCH$_3$, —(CH$_2$)$_2$(CH$_2$)$_2$OCH$_3$, —(CH$_2$)$_2$O(CH$_2$)$_2$OCH$_3$, —(CH$_2$)$_2$O(CH$_2$)$_2$OCH$_2$CH$_3$, —(CH$_2$)$_3$O(CH$_2$)$_2$OCH$_3$, —(CH$_2$)$_3$O(CH$_2$)$_2$OCH$_2$CH$_3$, —CH$_2$NR$^{20}$R$^{21}$, —CH$_2$NHR$^{21}$, —(CH$_2$)$_2$NR$^{20}$R$^{21}$, —(CH$_2$)$_2$NHR$^{21}$, —(CH$_2$)$_3$NR$^{20}$R$^{21}$, —(CH$_2$)$_3$NHR$^{21}$, —(CH$_2$)$_4$NR$^{20}$R$^{21}$, —(CH$_2$)$_4$NHR$^{21}$, —CH$_2$NR$^{20}$(C=O)R$^{21}$, —CH$_2$NH(C=O)R$^{21}$, —(CH$_2$)$_2$NR$^{20}$(C=O)R$^{21}$, —(CH$_2$)$_2$NH(C=O)R$^{21}$, —(CH$_2$)$_3$NR$^{20}$(C=O)R$^{21}$, —(CH$_2$)$_3$NH(C=O)R$^{21}$, —(CH$_2$)$_4$NR$^{20}$(C=O)R$^{21}$, —(CH$_2$)$_4$NH(C=O)R$^{21}$, —CH$_2$NR$^{20}$(C=O)OR$^{21}$, —CH$_2$NH(C=O)OR$^{21}$, —(CH$_2$)$_2$NR$^{20}$(C=O)OR$^{21}$, —(CH$_2$)$_2$NH(C=O)OR$^{21}$, —(CH$_2$)$_3$NR$^{20}$(C=O)OR$^{21}$, —(CH$_2$)$_3$NH(C=O)OR$^{21}$, —(CH$_2$)$_4$NR$^{20}$(C=O)OR$^{21}$, —(CH$_2$)$_4$NH(C=O)OR$^{21}$, —CH$_2$NR$^{20}$(C=O)NHR$^{21}$, —CH$_2$NH(C=O)NHR$^{21}$, —(CH$_2$)$_2$NR$^{20}$(C=O)NHR$^{21}$, —(CH$_2$)$_2$NH(C=O)NHR$^{21}$, —(CH$_2$)$_3$NR$^{20}$(C=O)NHR$^{21}$, —(CH$_2$)$_3$NH(C=O)NHR$^{21}$, —(CH$_2$)$_4$NR$^{20}$(C=O)NHR$^{21}$, —(CH$_2$)$_4$NH(C=O)NHR$^{21}$, —CH$_2$—Cy$^1$, —(CH$_2$)$_2$—Cy$^1$, —(CH$_2$)$_3$—Cy$^1$, Cy$^1$, —(CH$_2$)—Ar$^1$, —(CH$_2$)$_2$—Ar$^3$, —(CH$_2$)$_3$—Ar$^1$, —CH$_2$(C≡C)—Ar$^1$, and Ar$^2$.

In a further aspect, each of R$^{4a}$ and R$^{4b}$ is independently selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CH$_2$OH, —(CH$_2$)$_3$CH$_2$OH, —(CH$_2$)$_4$CH$_2$OH, —(CH$_2$)$_2$CH(CH$_3$)OH, —CH(CH$_3$)(CH$_2$)$_2$CH$_2$OH, —CH(CH$_3$)CH$_2$CH$_2$OH, —CH(CH$_3$)CH$_2$OH, —CH$_2$OCH$_3$, —(CH$_2$)$_2$OCH$_3$, —(CH$_2$)$_2$OCH$_2$CH$_3$, —(CH$_2$)$_3$OCH$_3$, —(CH$_2$)$_3$OCH$_2$CH$_3$, —CH$_2$OCH$_2$CH$_3$, —CH$_2$OCH$_2$OCH$_3$, —(CH$_2$)$_2$OCH$_2$OCH$_3$, —(CH$_2$)$_2$OCH$_2$OCH$_2$CH$_3$, —(CH$_2$)$_3$OCH$_2$OCH$_3$, —(CH$_2$)$_3$OCH$_2$OCH$_2$CH$_3$, —CH$_2$O(CH$_2$)$_2$OCH$_3$, —(CH$_2$)$_2$(CH$_2$)$_2$OCH$_3$, —(CH$_2$)$_2$O(CH$_2$)$_2$OCH$_2$CH$_3$, —(CH$_2$)$_3$O(CH$_2$)$_2$OCH$_3$, —(CH$_2$)$_3$O(CH$_2$)$_2$OCH$_2$CH$_3$, —CH$_2$NR$^{20}$R$^{21}$, —CH$_2$NHR$^{21}$, —(CH$_2$)$_2$NR$^{20}$R$^{21}$, —(CH$_2$)$_2$NHR$^{21}$, —(CH$_2$)$_3$NR$^{20}$R$^{21}$, —(CH$_2$)$_3$NHR$^{21}$, —(CH$_2$)$_4$NR$^{20}$R$^{21}$, —(CH$_2$)$_4$NHR$^{21}$, —CH$_2$NR$^{20}$(C=O)R$^{21}$, —CH$_2$NH(C=O)R$^{21}$, —(CH$_2$)$_2$NR$^{20}$(C=O)R$^{21}$, —(CH$_2$)$_2$NH(C=O)R$^{21}$, —(CH$_2$)$_3$NR$^{20}$(C=O)R$^{21}$, —(CH$_2$)$_3$NH(C=O)R$^{21}$, —(CH$_2$)$_4$NR$^{20}$(C=O)R$^{21}$, —(CH$_2$)$_4$NH(C=O)R$^{21}$, —CH$_2$NR$^{20}$(C=O)OR$^{21}$, —CH$_2$NH(C=O)OR$^{21}$, —(CH$_2$)$_2$NR$^{20}$(C=O)OR$^{21}$, —(CH$_2$)$_2$NH(C=O)OR$^{21}$, —(CH$_2$)$_3$NR$^{20}$(C=O)OR$^{21}$, —(CH$_2$)$_3$NH(C=O)OR$^{21}$, —(CH$_2$)$_4$NR$^{20}$(C=O)OR$^{21}$, —(CH$_2$)$_4$NH(C=O)OR$^{21}$, —CH$_2$NR$^{20}$(C=O)NHR$^{21}$, —CH$_2$NH(C=O)NHR$^{21}$, —(CH$_2$)$_2$NR$^{20}$(C=O)NHR$^{21}$, —(CH$_2$)$_2$NH(C=O)NHR$^{21}$, —(CH$_2$)$_3$NR$^{20}$(C=O)NHR$^{21}$, —(CH$_2$)$_3$NH(C=O)NHR$^{21}$, —(CH$_2$)$_4$NR$^{20}$(C=O)NHR$^{21}$, and —(CH$_2$)$_4$NH(C=O)NHR$^{21}$; and R$^{4a}$ and R$^{4b}$ are not simultaneously hydrogen.

In a further aspect, R$^{4a}$ is hydrogen; and R$^{4b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CH$_2$OH, —(CH$_2$)$_3$CH$_2$OH, —(CH$_2$)$_4$CH$_2$OH, —(CH$_2$)$_2$CH(CH$_3$)OH, —CH(CH$_3$)(CH$_2$)$_2$CH$_2$OH, —CH(CH$_3$)CH$_2$CH$_2$OH, —CH(CH$_3$)CH$_2$OH, —CH$_2$OCH$_3$, —(CH$_2$)$_2$OCH$_3$, —(CH$_2$)$_2$OCH$_2$CH$_3$, —(CH$_2$)$_3$OCH$_3$, —(CH$_2$)$_3$OCH$_2$CH$_3$, —CH$_2$OCH$_2$OCH$_3$, —(CH$_2$)$_2$OCH$_2$OCH$_3$, —(CH$_2$)$_2$OCH$_2$OCH$_2$CH$_3$, —(CH$_2$)$_3$OCH$_2$OCH$_3$, —(CH$_2$)$_3$OCH$_2$OCH$_2$CH$_3$, —CH$_2$O(CH$_2$)$_2$OCH3, —(CH$_2$)$_2$(CH$_2$)$_2$OCH$_3$, —(CH$_2$)$_2$O(CH$_2$)$_2$OCH$_2$CH$_3$, —(CH$_2$)$_3$O(CH$_2$)$_2$OCH$_3$, —(CH$_2$)$_3$O(CH$_2$)$_2$OCH$_2$CH$_3$, —CH$_2$NR$^{20}$R$^{21}$, —CH$_2$NHR$^{21}$, —(CH$_2$)$_2$NR$^{20}$R$^{21}$, —(CH$_2$)$_2$NHR$^{21}$, —(CH$_2$)$_3$NR$^{20}$R$^{21}$, —(CH$_2$)$_3$NHR$^{21}$, —(CH$_2$)$_4$NR$^{20}$R$^{21}$, —(CH$_2$)$_4$NHR$^{21}$, —CH$_2$NR$^{20}$(C=O)R$^{21}$, —CH$_2$NH(C=O)R$^{21}$, —(CH$_2$)$_2$NR$^{20}$(C=O)R$^{21}$, —(CH$_2$)$_2$NH(C=O)R$^{21}$, —(CH$_2$)$_3$NR$^{20}$(C=O)R$^{21}$, —(CH$_2$)$_3$NH(C=O)R$^{21}$, —(CH$_2$)$_4$NR$^{20}$(C=O)R$^{21}$, —(CH$_2$)$_4$NH(C=O)R$^{21}$, —CH$_2$NR$^{20}$(C=O)OR$^{21}$, —CH$_2$NH(C=O)OR$^{21}$, —(CH$_2$)$_2$NR$^{20}$(C=O)OR$^{21}$, —(CH$_2$)$_2$NH(C=O)OR$^{21}$, —(CH$_2$)$_3$NR$^{20}$(C=O)OR$^{21}$, —(CH$_2$)$_3$NH(C=O)OR$^{21}$, —(CH$_2$)$_4$NR$^{20}$(C=O)OR$^{21}$, —(CH$_2$)$_4$NH(C=O)OR$^{21}$, —CH$_2$NR$^{20}$(C=O)NHR$^{21}$, —CH$_2$NH(C=O)NHR$^{21}$, —(CH$_2$)$_2$NR$^{20}$(C=O)NHR$^{21}$, —(CH$_2$)$_2$NH(C=O)NHR$^{21}$, —(CH$_2$)$_3$NR$^{20}$(C=O)NHR$^{21}$, —(CH$_2$)$_3$NH(C=O)NHR$^{21}$, —(CH$_2$)$_4$NR$^{20}$(C=O)NHR$^{21}$, and —(CH$_2$)$_4$NH(C=O)NHR$^{21}$.

In a further aspect, each of R$^{4a}$ and R$^{4b}$ is independently selected from hydrogen, —CH$_2$—Cy$^1$, —(CH$_2$)$_2$—Cy$^1$, —(CH$_2$)$_3$—Cy$^1$, Cy$^1$, —(CH$_2$)—Ar$^1$, —(CH$_2$)$_2$—Ar$^3$, —(CH$_2$)$_3$—Ar$^1$, —CH$_2$(C≡C)—Ar$^1$, and Ar$^2$; and R$^{4a}$ and R$^{4b}$ are not simultaneously hydrogen.

In a further aspect, R$^{4a}$ is hydrogen; and R$^{4b}$ is selected from —CH$_2$—Cy$^1$, —(CH$_2$)$_2$—Cy$_1^1$, —(CH$_2$)$_3$—Cy$^1$, Cy$^1$, —(CH$_2$)—Ar$^1$, —(CH$_2$)$_2$—Ar$^3$, —(CH$_2$)$_3$—Ar$^1$, —CH$_2$(C≡C)—Ar$^1$, and Ar$^2$; and R$^{4a}$ and R$^{4b}$ are not simultaneously hydrogen.

In a further aspect, R$^{4a}$ is selected from hydrogen, methyl and ethyl; and R$^{4b}$ has a structure represented by a formula selected from:

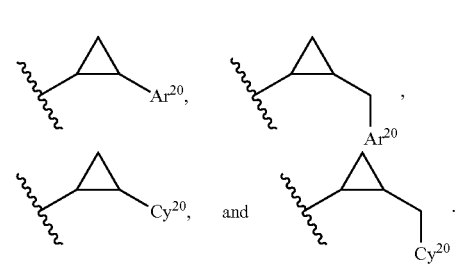

In a further aspect, R$^{4a}$ is selected from hydrogen, methyl and ethyl; and R$^{4b}$ has a structure represented by a formula selected from:

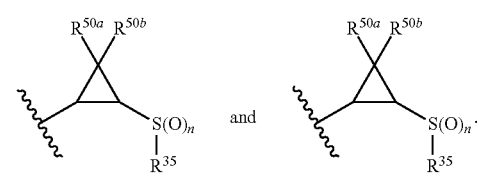

In a further aspect, R$^{4a}$ is selected from hydrogen, methyl and ethyl; and R$^{4b}$ has a structure represented by a formula selected from:

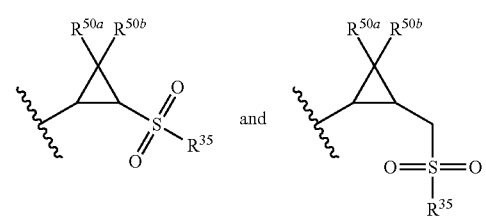

In a further aspect, R$^{4a}$ is selected from hydrogen, methyl and ethyl; and R$^{4b}$ has a structure represented by a formula selected from:

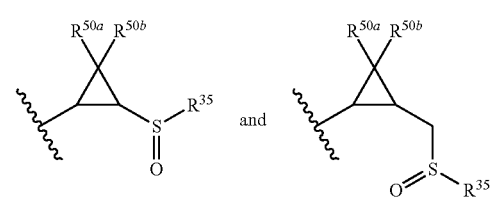

In a further aspect, R$^{4a}$ is selected from hydrogen, methyl and ethyl; and R$^{4b}$ has a structure represented by a formula selected from:

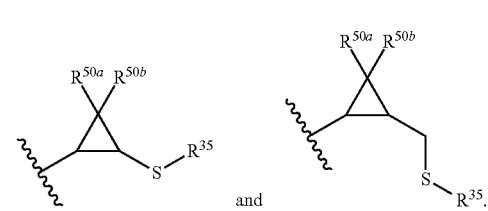

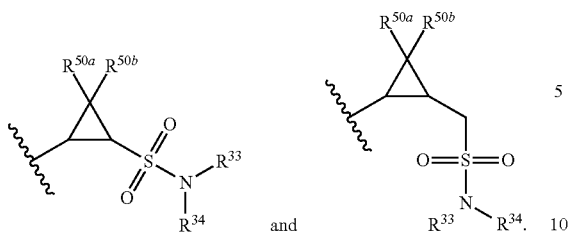 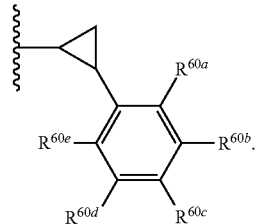

In a further aspect, $R^{4a}$ is selected from hydrogen, methyl and ethyl; and $R^{4b}$ has a structure represented by a formula selected from:

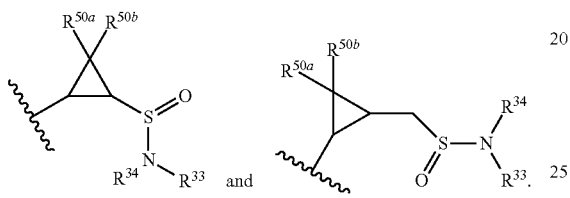

In a further aspect, $R^{4a}$ is selected from hydrogen, methyl and ethyl; and $R^{4b}$ has a structure represented by a formula selected from:

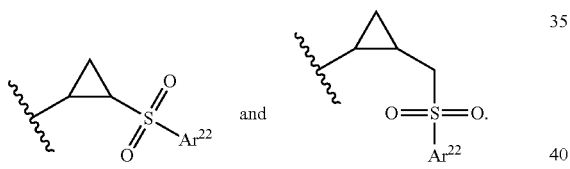

In a further aspect, $R^{4a}$ is selected from hydrogen, methyl and ethyl; and $R^{4b}$ has a structure represented by a formula selected from:

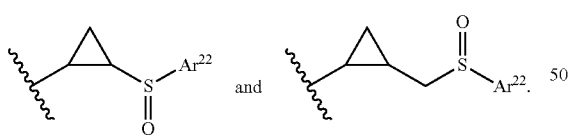

In a further aspect, $R^{4a}$ is selected from hydrogen, methyl and ethyl; and $R^{4b}$ has a structure represented by a formula selected from:

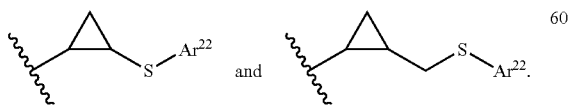

In a further aspect, $R^{4a}$ is selected from hydrogen, methyl and ethyl; $R^{4b}$ has a structure represented by a formula:

In a further aspect, $R^{4a}$ is selected from hydrogen, methyl and ethyl; and $R^{4b}$ has a structure represented by a formula selected from:

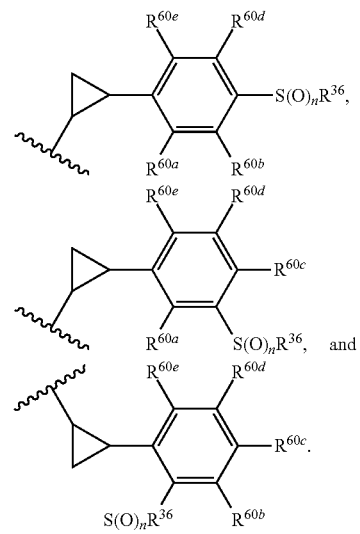

In a further aspect, $R^{4a}$ is selected from hydrogen, methyl and ethyl; and $R^{4b}$ has a structure represented by a formula selected from:

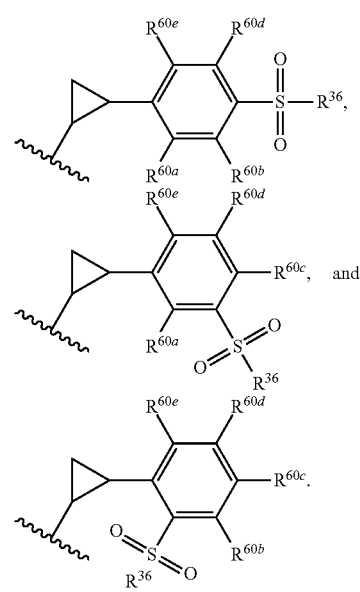

In a further aspect, $R^{4a}$ is selected from hydrogen, methyl and ethyl; and $R^{4b}$ has a structure represented by a formula selected from:

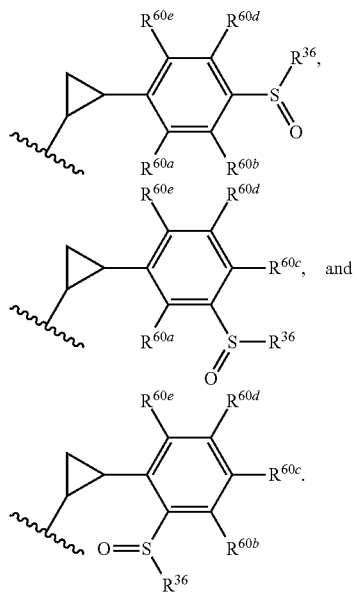

In a further aspect, $R^{4a}$ is selected from hydrogen, methyl and ethyl; and $R^{4b}$ has a structure represented by a formula selected from:

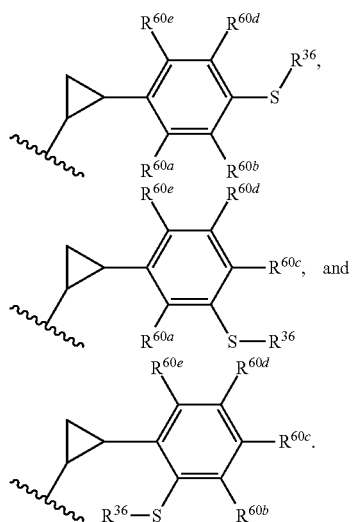

In a further aspect, $R^{4a}$ is selected from hydrogen, methyl and ethyl; and $R^{4b}$ has a structure represented by a formula:

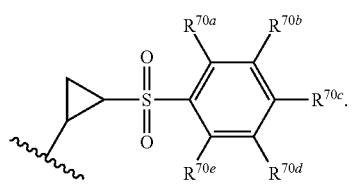

In a further aspect, $R^{4a}$ is hydrogen and $R^{4b}$ has a structure represented by a formula selected from:

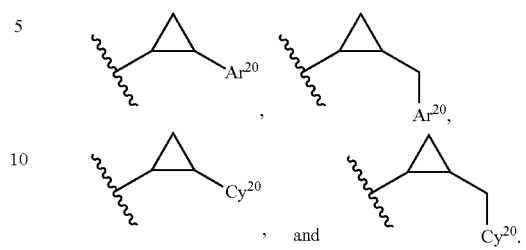

In a further aspect, $R^{4a}$ is hydrogen and $R^{4b}$ has a structure represented by a formula selected from:

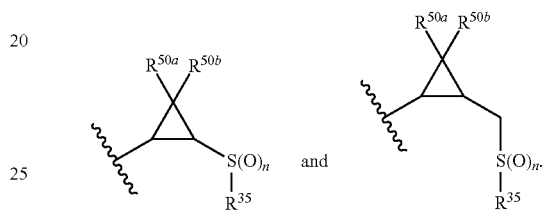

In a further aspect, $R^{4a}$ is hydrogen and $R^{4b}$ has a structure represented by a formula selected from:

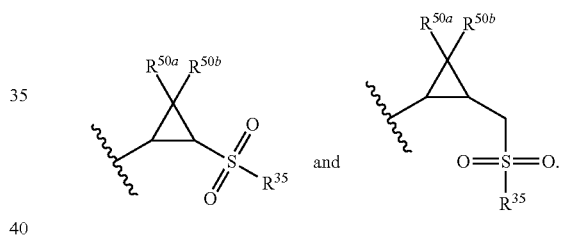

In a further aspect, $R^{4a}$ is hydrogen and $R^{4b}$ has a structure represented by a formula selected from:

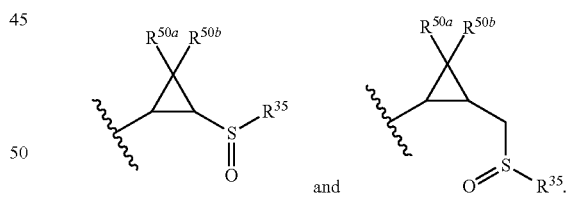

In a further aspect, $R^{4a}$ is hydrogen and $R^{4b}$ has a structure represented by a formula selected from:

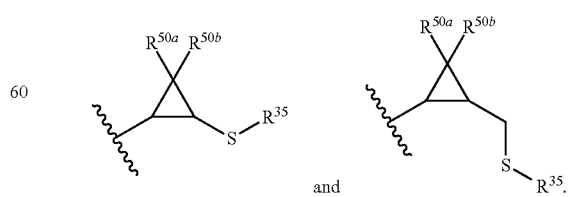

In a further aspect, $R^{4a}$ is hydrogen and $R^{4b}$ has a structure represented by a formula selected from:

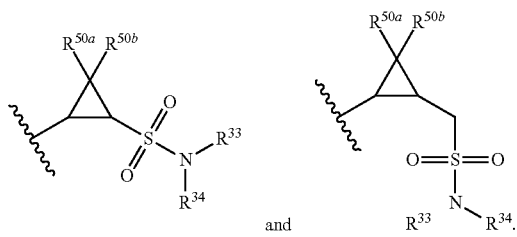

In a further aspect, $R^{4a}$ is hydrogen and $R^{4b}$ has a structure represented by a formula selected from:

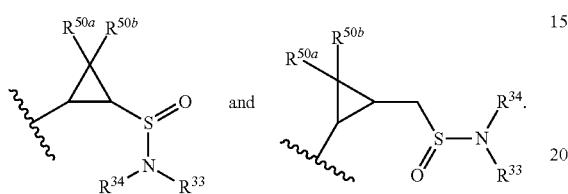

In a further aspect, $R^{4a}$ is hydrogen and $R^{4b}$ has a structure represented by a formula selected from:

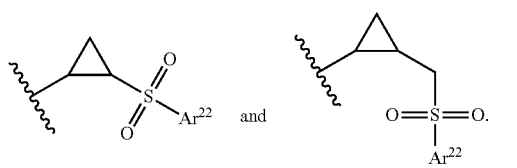

In a further aspect, $R^{4a}$ is hydrogen and $R^{4b}$ has a structure represented by a formula selected from:

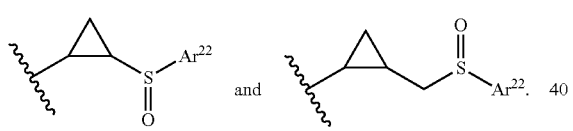

In a further aspect, $R^{4a}$ is hydrogen and $R^{4b}$ has a structure represented by a formula selected from:

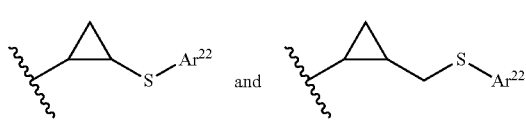

In a further aspect, $R^{4a}$ is hydrogen and $R^{4b}$ has a structure represented by a formula:

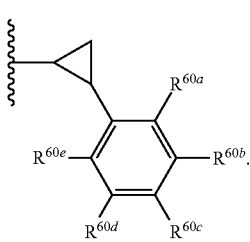

In a further aspect, $R^{4a}$ is hydrogen and $R^{4b}$ has a structure represented by a formula selected from:

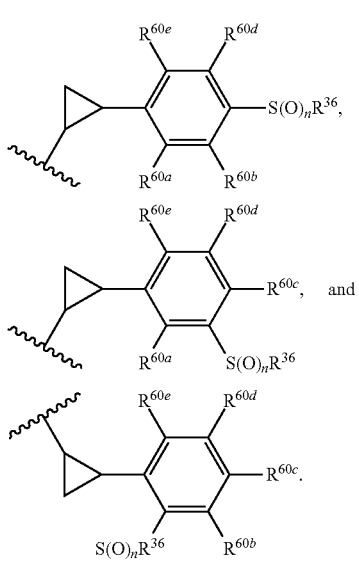

In a further aspect, $R^{4a}$ is hydrogen and $R^{4b}$ has a structure represented by a formula selected from:

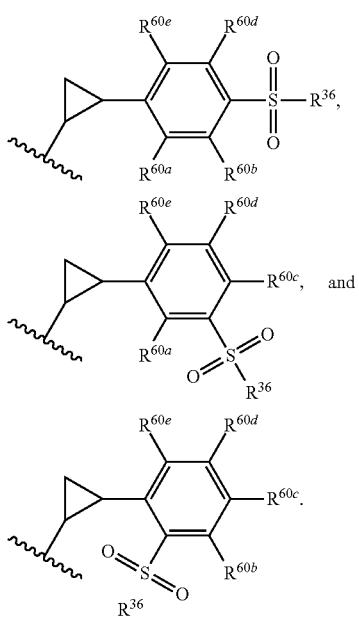

In a further aspect, $R^{4a}$ is hydrogen and $R^{4b}$ has a structure represented by a formula selected from:

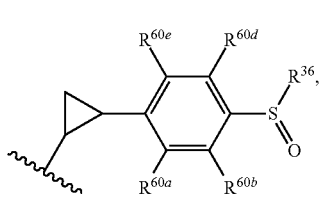

-continued

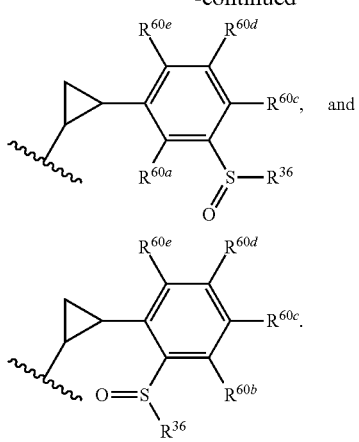

In a further aspect, $R^{4a}$ is hydrogen and $R^{4b}$ has a structure represented by a formula selected from:

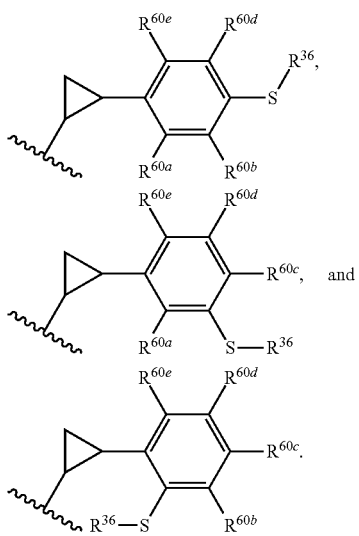

In a further aspect, $R^{4a}$ is hydrogen and $R^{4b}$ has a structure represented by a formula:

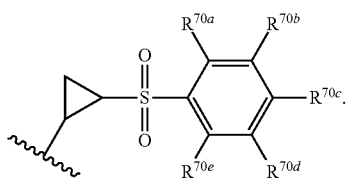

In a further aspect, $R^{4a}$ is selected from hydrogen, methyl and ethyl; $R^{4b}$ has a structure represented by a formula selected from:

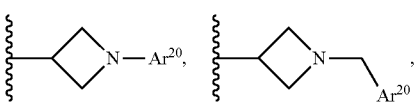

-continued

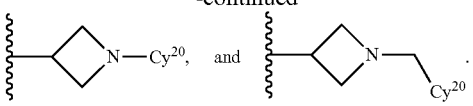

In a further aspect, $R^{4a}$ is selected from hydrogen, methyl and ethyl; $R^{4b}$ has a structure represented by a formula selected from:

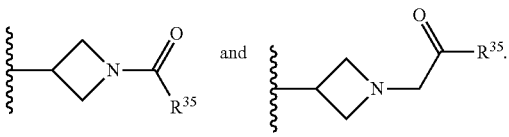

In a further aspect, $R^{4a}$ is selected from hydrogen, methyl and ethyl; $R^{4b}$ has a structure represented by a formula selected from:

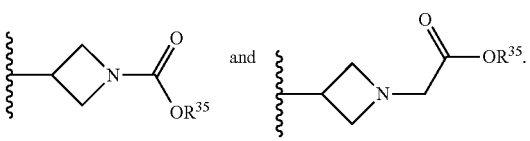

In a further aspect, $R^{4a}$ is selected from hydrogen, methyl and ethyl; $R^{4b}$ has a structure represented by a formula selected from:

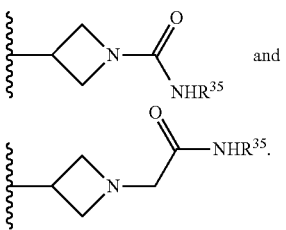

In a further aspect, $R^{4a}$ is selected from hydrogen, methyl and ethyl; $R^{4b}$ has a structure represented by a formula selected from:

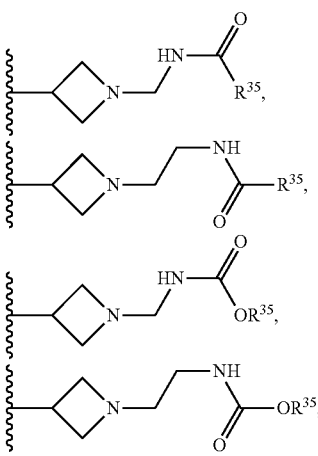

-continued

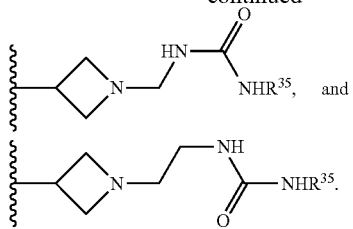

In a further aspect, $R^{4a}$ is selected from hydrogen, methyl, and ethyl; and $R^{4b}$ has a structure represented by a formula selected from:

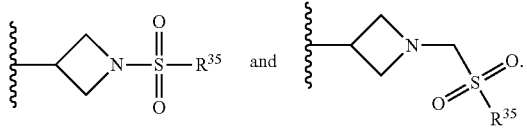

In a further aspect, $R^{4a}$ is selected from hydrogen, methyl, and ethyl; and $R^{4b}$ has a structure represented by a formula selected from:

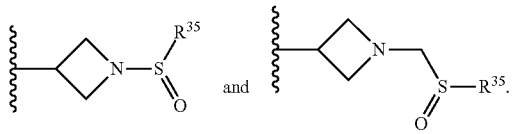

In a further aspect, $R^{4a}$ is selected from hydrogen, methyl, and ethyl; and $R^{4b}$ has a structure represented by a formula selected from:

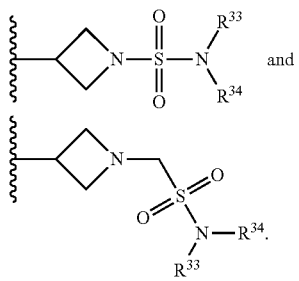

In a further aspect, $R^{4a}$ is selected from hydrogen, methyl, and ethyl; and $R^{4b}$ has a structure represented by a formula selected from:

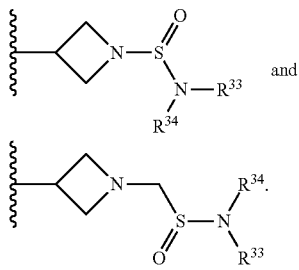

In a further aspect, $R^{4a}$ is selected from hydrogen, methyl, and ethyl; and $R^{4b}$ has a structure represented by a formula selected from:

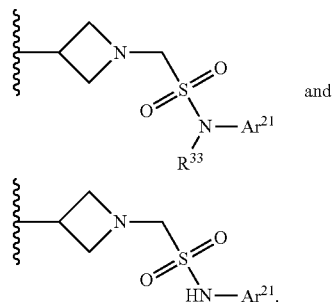

In a further aspect, $R^{4a}$ is selected from hydrogen, methyl, and ethyl; and $R^{4b}$ has a structure represented by a formula selected from:

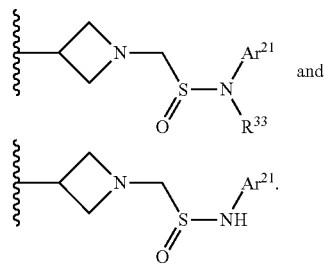

In a further aspect, $R^{4a}$ is selected from hydrogen, methyl, and ethyl; and $R^{4b}$ has a structure represented by a formula selected from:

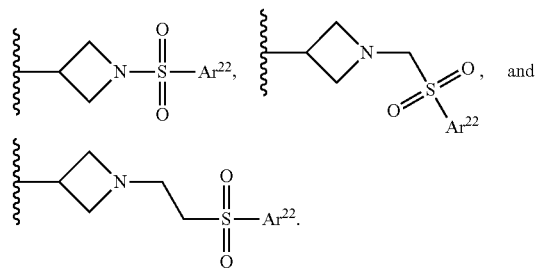

In a further aspect, $R^{4a}$ is selected from hydrogen, methyl, and ethyl; and $R^{4b}$ has a structure represented by a formula:

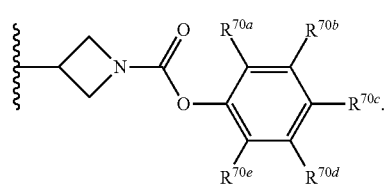

In a further aspect, $R^{4a}$ is selected from hydrogen, methyl, and ethyl; and $R^{4b}$ has a structure represented by a formula selected from:

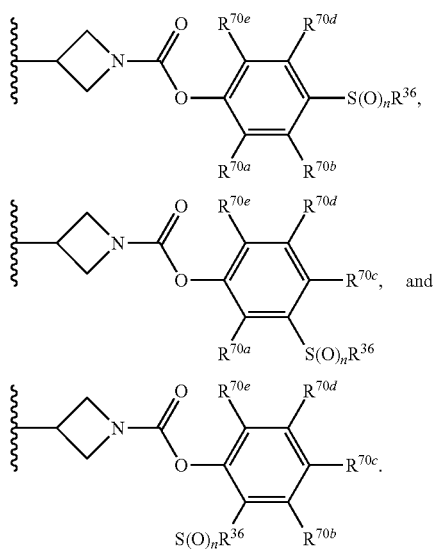

In a further aspect, $R^{4a}$ is selected from hydrogen, methyl, and ethyl; and $R^{4b}$ has a structure represented by a formula selected from:

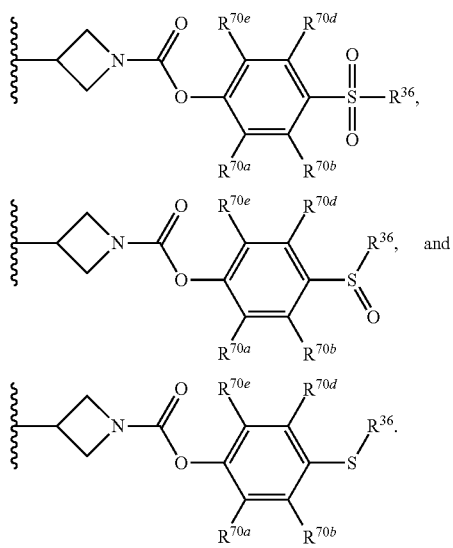

In a further aspect, $R^{4a}$ is selected from hydrogen, methyl, and ethyl; and $R^{4b}$ has a structure represented by a formula selected from:

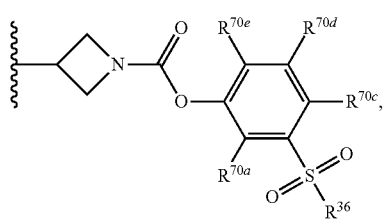

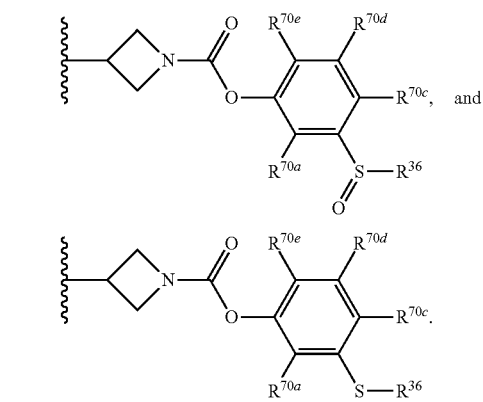

In a further aspect, $R^{4a}$ is selected from hydrogen, methyl, and ethyl; and $R^{4b}$ has a structure represented by a formula selected from:

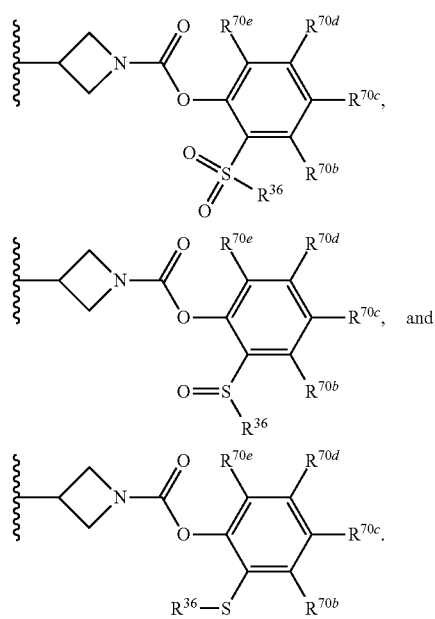

In a further aspect, $R^{4a}$ is selected from hydrogen, methyl, and ethyl; and has a structure represented by a formula selected from:

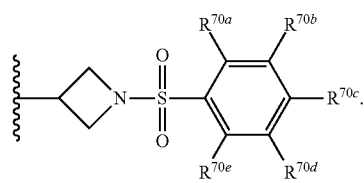

In a further aspect, $R^{4a}$ is hydrogen and $R^{4b}$ has a structure represented by a formula selected from:

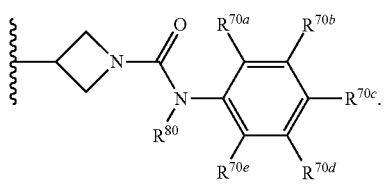

In a further aspect, $R^{4a}$ is hydrogen and $R^{4b}$ has a structure represented by a formula selected from:

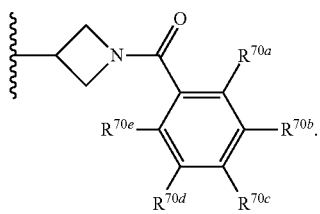

In a further aspect, $R^{4a}$ is hydrogen and $R^{4b}$ has a structure represented by a formula selected from:

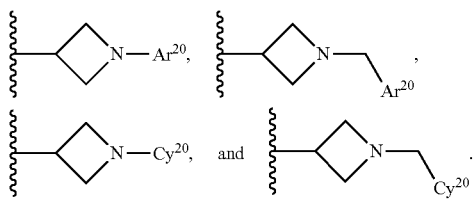

In a further aspect, $R^{4a}$ is hydrogen and $R^{4b}$ has a structure represented by a formula selected from:

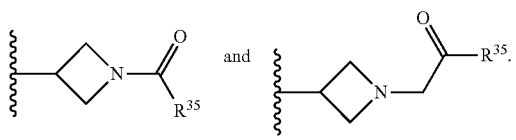

In a further aspect, $R^{4a}$ is hydrogen and $R^{4b}$ has a structure represented by a formula selected from:

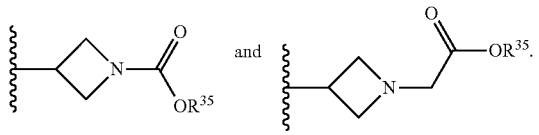

In a further aspect, $R^{4a}$ is hydrogen and $R^{4b}$ has a structure represented by a formula selected from:

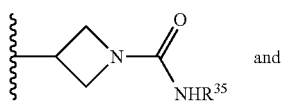

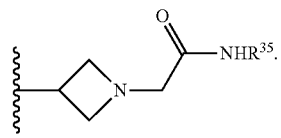

In a further aspect, $R^{4a}$ is hydrogen and $R^{4b}$ has a structure represented by a formula selected from:

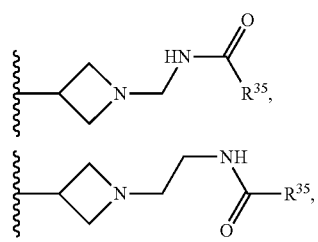

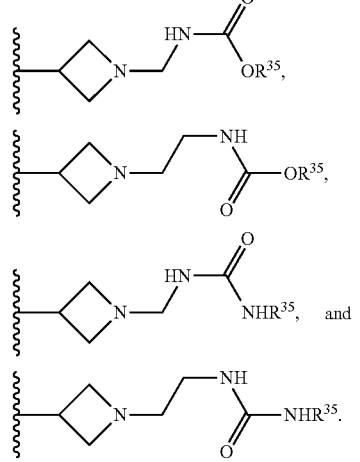

In a further aspect, $R^{4a}$ is hydrogen and $R^{4b}$ has a structure represented by a formula selected from:

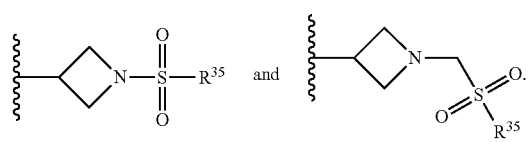

In a further aspect, $R^{4a}$ is hydrogen and $R^{4b}$ has a structure represented by a formula selected from:

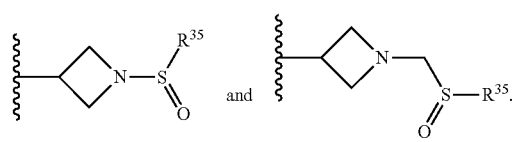

In a further aspect, $R^{4a}$ is hydrogen and $R^{4b}$ has a structure represented by a formula selected from:

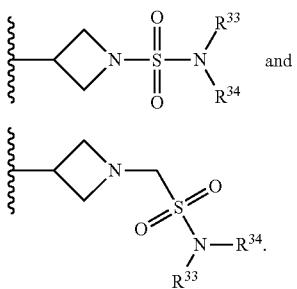

In a further aspect, $R^{4a}$ is hydrogen and $R^{4b}$ has a structure represented by a formula selected from:

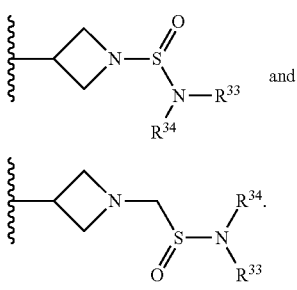

In a further aspect, $R^{4a}$ is hydrogen and $R^{4b}$ has a structure represented by a formula selected from:

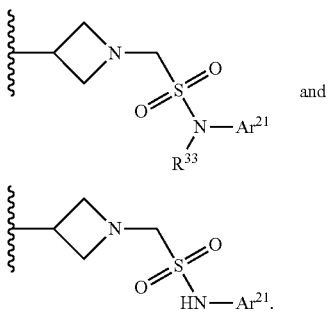

In a further aspect, $R^{4a}$ is hydrogen and $R^{4b}$ has a structure represented by a formula selected from:

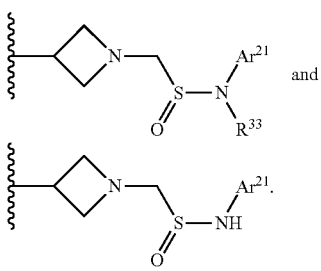

In a further aspect, $R^{4a}$ is hydrogen and $R^{4b}$ has a structure represented by a formula selected from:

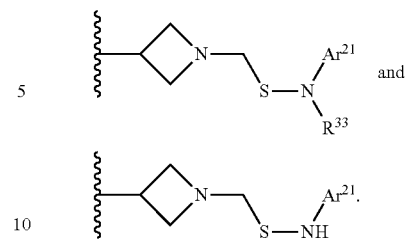

In a further aspect, $R^{4a}$ is hydrogen and $R^{4b}$ has a structure represented by a formula selected from:

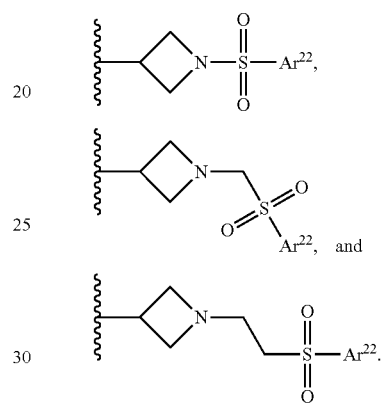

In a further aspect, $R^{4a}$ is hydrogen and $R^{4b}$ has a structure represented by a formula:

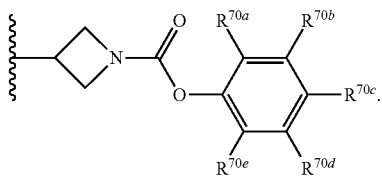

In a further aspect, $R^{4a}$ is hydrogen and $R^{4b}$ has a structure represented by a formula selected from:

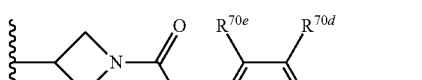
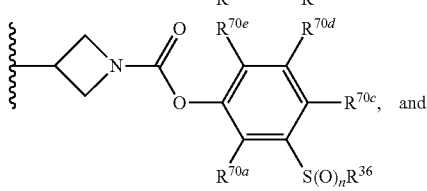

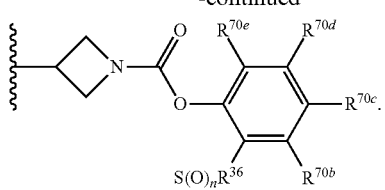

In a further aspect, $R^{4a}$ is hydrogen and $R^{4b}$ has a structure represented by a formula selected from:

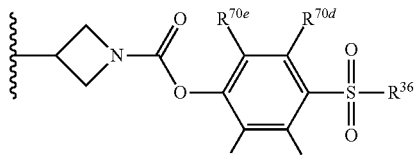

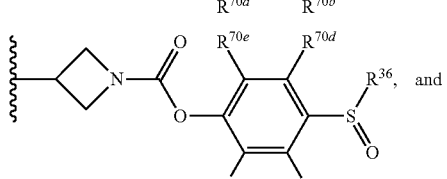

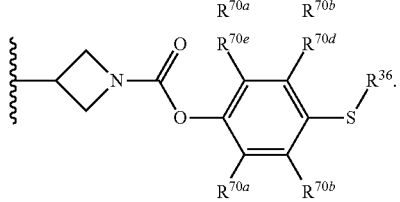

In a further aspect, $R^{4a}$ is hydrogen and $R^{4b}$ has a structure represented by a formula selected from:

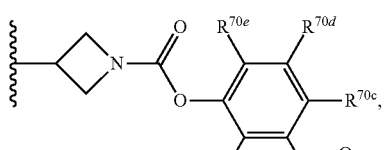

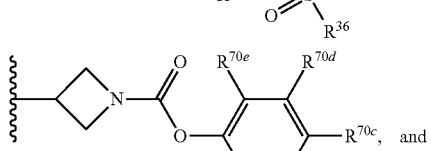

In a further aspect, $R^{4a}$ is hydrogen and $R^{4b}$ has a structure represented by a formula selected from:

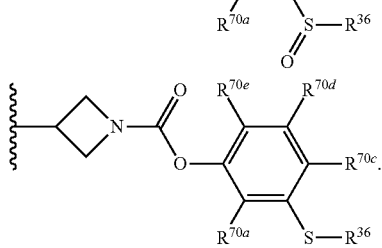

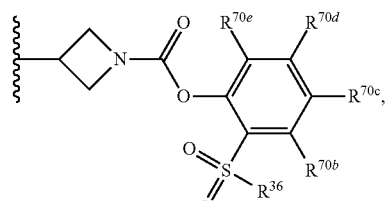

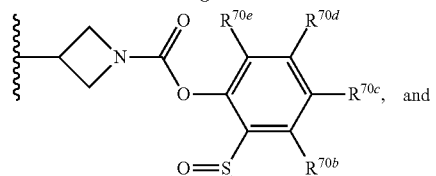

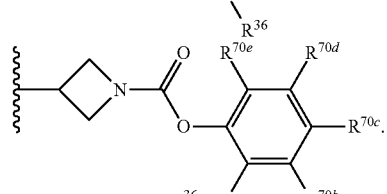

In a further aspect, $R^{4a}$ is hydrogen and $R^{4b}$ has a structure represented by a formula selected from:

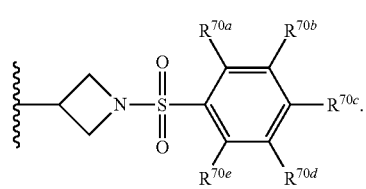

In one aspect, each of $R^{4a}$ and $R^{4b}$ is independently selected from hydrogen, C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$, provided that $R^{4a}$ and $R^{4b}$ are not both hydrogen; and each of $R^{4a}$ and $R^{4b}$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a further aspect, each of $R^{4a}$ and $R^{4b}$ is independently selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein each of $R^{4a}$ and $R^{4b}$ is unsubstituted.

In a further aspect, each of $R^{4a}$ and $R^{4b}$ is independently selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein each of $R^{4a}$ and $R^{4b}$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, each of $R^{4a}$ and $R^{4b}$ is independently selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and $Ar^2$; and wherein each of $R^{4a}$ and $R^{4b}$ is substituted with 0-1 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a yet further aspect, each of $R^{4a}$ and $R^{4b}$ is independently selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein each of $R^{4a}$ and $R^{4b}$ is substituted with 1-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In an even further aspect, each of $R^{4a}$ and $R^{4b}$ is independently selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein each of $R^{4a}$ and $R^{4b}$ is monosubstituted with a group selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_3$)CH(CH$_3$)$_2$, —N(CH$_2$CH$_3$)$_2$, and —S(O)$_n$R$^5$. In an even further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-1 groups selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein $R^{4b}$ is substituted with 0-1 groups selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, $R^{4a}$ is hydrogen and $R^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is substituted with 0-1 groups selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is substituted with 0-1 groups selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is substituted with 0-1 groups selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is substituted with 0-1 groups selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is independently substituted with 1-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is independently substituted with 1-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is independently substituted with 1-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is independently substituted with 1-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is independently substituted with 1-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is independently substituted with 1-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is monosubstituted with a group selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is monosubstituted with a group selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and wherein R$^{4b}$ is monosubstituted with a group selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, R$^{4a}$ is hydrogen and R$^{4b}$ is selected from C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), —(C1-C6 alkyl)-Ar$^1$, and Ar$^2$; and R$^{4b}$ is unsubstituted. In a still further aspect, R$^{4a}$ is hydrogen and R$^{4b}$ is selected from C1-C6 alkyl, C1-C6 haloalkyl, C1-C6 polyhaloalkyl, C3-C6 cycloalkyl, C2-C5 heterocycloalkyl, —(C1-C6 alkyl)-(C3-C6 cycloalkyl), —(C1-C6 alkyl)-(C2-C5 heterocycloalkyl), —(C1-C3 alkyl)-Ar$^1$, and Ar$^2$; and R$^{4b}$ is unsubstituted. In a yet further aspect, R$^{4a}$ is hydrogen and R$^{4b}$ is selected from C1-C3 alkyl, C1-C3 haloalkyl, C1-C3 polyhaloalkyl, C3-C6 cycloalkyl, C2-C5 heterocycloalkyl, —(C1-C3 alkyl)-(C3-C6 cycloalkyl), —(C1-C3 alkyl)-(C2-C5 heterocycloalkyl), —(C1-C3 alkyl)-Ar$^1$, and Ar$^2$; and R$^{4b}$ is unsubstituted.

In a further aspect, each of R$^{4a}$ and R$^{4b}$ is independently selected from hydrogen and —(C1-C6 alkyl)-Ar$^1$, provided that R$^{4a}$ and R$^{4b}$ are not both hydrogen. In a still further aspect, each of R$^{4a}$ and R$^{4b}$ is independently selected from hydrogen and —(C1-C3 alkyl)-Ar$^1$, provided that R$^{4a}$ and R$^{4b}$ are not both hydrogen. In a yet further aspect, each of R$^{4a}$ and R$^{4b}$ is independently selected from hydrogen and —((CH$_2$)$_2$)—Ar$^1$, provided that R$^{4a}$ and R$^{4b}$ are not both hydrogen. In an even further aspect, each of R$^{4a}$ and R$^{4b}$ is independently selected from hydrogen and —(CH$_2$)—Ar$^1$, provided that R$^{4a}$ and R$^{4b}$ are not both hydrogen.

In a further aspect, each of R$^{4a}$ and R$^{4b}$ is independently selected from hydrogen and —(C1-C6 alkyl)-phenyl, provided that R$^{4a}$ and R$^{4b}$ are not both hydrogen. In a still further aspect, each of R$^{4a}$ and R$^{4b}$ is independently selected from hydrogen and —(C1-C3 alkyl)-phenyl, provided that R$^{4a}$ and R$^{4b}$ are not both hydrogen. In a yet further aspect, each of R$^{4a}$ and R$^{4b}$ is independently selected from hydrogen and —((CH$_2$)$_2$)-phenyl, provided that R$^{4a}$ and R$^{4b}$ are not both hydrogen. In an even further aspect, each of R$^{4a}$ and R$^{4b}$ is independently selected from hydrogen and —(CH$_2$)-phenyl, provided that R$^{4a}$ and R$^{4b}$ are not both hydrogen.

In a further aspect, each of R$^{4a}$ and R$^{4b}$ is independently selected from hydrogen and —(C1-C6 alkyl)-heterocyclyl, provided that R$^{4a}$ and R$^{4b}$ are not both hydrogen. In a still further aspect, each of R$^{4a}$ and R$^{4b}$ is independently selected from hydrogen and —(C1-C3 alkyl)-heterocyclyl, provided that R$^{4a}$ and R$^{4b}$ are not both hydrogen. In a yet further aspect, each of R$^{4a}$ and R$^{4b}$ is independently selected from hydrogen and —((CH$_2$)$_2$)-heterocyclyl, provided that R$^{4a}$ and R$^{4b}$ are not both hydrogen. In an even further aspect, each of R$^{4a}$ and R$^{4b}$ is independently selected from hydrogen and —(CH$_2$)-heterocyclyl, provided that R$^{4a}$ and R$^{4b}$ are not both hydrogen.

In a further aspect, each of R$^{4a}$ and R$^{4b}$ is independently selected from hydrogen and —(C1-C6 alkyl)-Ar$^1$, provided that R$^{4a}$ and R$^{4b}$ are not both hydrogen; and wherein —(C1-C6 alkyl)-Ar$^1$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, R$^{4a}$ is hydrogen and R$^{4b}$ is —(C1-C6 alkyl)-Ar$^1$ substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is —(C1-C6 alkyl)-Ar$^1$ substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —(C1-C6 alkyl)-Ar$^1$ substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —(C1-C6 alkyl)-Ar$^1$ substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —(C1-C6 alkyl)-Ar$^1$ substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —(C1-C6 alkyl)-Ar$^1$ substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, each of R$^{4a}$ and R$^{4b}$ is independently selected from hydrogen and —(C1-C3 alkyl)-Ar$^1$, provided that R$^{4a}$ and R$^{4b}$ are not both hydrogen; and wherein —(C1-C3 alkyl)-Ar$^1$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, R$^{4a}$ is hydrogen and R$^{4b}$ is —(C1-C3 alkyl)-Ar$^1$ substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is —(C1-C3 alkyl)-Ar$^1$ substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —(C1-C3 alkyl)-Ar$^1$ substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —(C1-C3 alkyl)-Ar$^1$ substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —(C1-C3 alkyl)-Ar$^1$ substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —(C1-C3 alkyl)-Ar$^1$ substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, each of R$^{4a}$ and R$^{4b}$ is independently selected from hydrogen and —((CH$_2$)$_2$)—Ar$^1$, provided that R$^{4a}$ and R$^{4b}$ are not both hydrogen; and wherein —((CH$_2$)$_2$)—Ar$^1$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, R$^{4a}$ is hydrogen and R$^{4b}$ is —((CH$_2$)$_2$)—Ar$^1$ substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is —((CH$_2$)$_2$)—Ar$^1$ substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —((CH$_2$)$_2$)—Ar$^1$ substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —((CH$_2$)$_2$)—Ar$^1$ substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —((CH$_2$)$_2$)—Ar$^1$ substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, $R^{4a}$ is hydrogen and $R^{4b}$ is —(($CH_2$)$_2$)—$Ar^1$ substituted with 0-2 groups independently selected from —F, —Cl, methyl, —$CH_2F$, —$CH_2Cl$, —$CHF_2$, —$CF_3$, —$CHCl_2$, —$CCl_3$, and —$S(O)_nR^5$.

In a further aspect, each of $R^{4a}$ and $R^{4b}$ is independently selected from hydrogen and —($CH_2$)—$Ar^1$, provided that $R^{4a}$ and $R^{4b}$ are not both hydrogen; and wherein —($CH_2$)—$Ar^1$ is substituted with 0-2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $R^{4a}$ is hydrogen and $R^{4b}$ is —($CH_2$)—$Ar^1$ substituted with 0-2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$. In a still further aspect, $R^{4a}$ is hydrogen and $R^{4b}$ is —($CH_2$)—$Ar^1$ substituted with 0-2 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —($CH_2$)$_2CH_2F$, —($CH_2$)$_2CH_2Cl$, —($CH_2$)$_2CH_2Br$, —($CH_2$)$_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —($CH_2$)$_2CHF_2$, —($CH_2$)$_2CF_3$, —($CH_2$)$_2CHCl_2$, —($CH_2$)$_2CCl_3$, —($CH_2$)$_2CHBr_2$, —($CH_2$)$_2CBr_3$, —($CH_2$)$_2CHI_2$, —($CH_2$)$_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, and —$S(O)_nR^5$. In a yet further aspect, $R^{4a}$ is hydrogen and $R^{4b}$ is —($CH_2$)—$Ar^1$ substituted with 0-2 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —($CH_2$)$_2CH_2F$, —($CH_2$)$_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —($CH_2$)$_2CHF_2$, —($CH_2$)$_2CF_3$, —($CH_2$)$_2CHCl_2$, —($CH_2$)$_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, and —$S(O)_nR^5$. In an even further aspect, $R^{4a}$ is hydrogen and $R^{4b}$ is —($CH_2$)—$Ar^1$ substituted with 0-2 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, and —$S(O)_nR^5$. In a still further aspect, $R^{4a}$ is hydrogen and $R^{4b}$ is —($CH_2$)—$Ar^1$ substituted with 0-2 groups independently selected from —F, —Cl, —$NH_2$, —OH, —CN, methyl, —$CF_3$, —$CCl_3$, —$OCH_3$, —$NHCH_3$, and —$S(O)_nR^5$. In a yet further aspect, $R^{4a}$ is hydrogen and $R^{4b}$ is —($CH_2$)—$Ar^1$ substituted with 0-2 groups independently selected from —F, —Cl, methyl, —$CH_2F$, —$CH_2Cl$, —$CHF_2$, —$CF_3$, —$CHCl_2$, —$CCl_3$, and —$S(O)_nR^5$.

In a further aspect, each of $R^{4a}$ and $R^{4b}$ is independently selected from hydrogen and —(($CH_2$)$_2$)-phenyl, provided that $R^{4a}$ and $R^{4b}$ are not both hydrogen; and wherein —(($CH_2$)$_2$)-phenyl is substituted with 0-2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $R^{4a}$ is hydrogen and $R^{4b}$ is —(($CH_2$)$_2$)-phenyl substituted with 0-2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$. In a still further aspect, $R^{4a}$ is hydrogen and $R^{4b}$ is —(($CH_2$)$_2$)-phenyl substituted with 0-2 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —($CH_2$)$_2CH_2F$, —($CH_2$)$_2CH_2Cl$, —($CH_2$)$_2CH_2Br$, —($CH_2$)$_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —($CH_2$)$_2CHF_2$, —($CH_2$)$_2CF_3$, —($CH_2$)$_2CHCl_2$, —($CH_2$)$_2CCl_3$, —($CH_2$)$_2CHBr_2$, —($CH_2$)$_2CBr_3$, —($CH_2$)$_2CHI_2$, —($CH_2$)$_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, and —$S(O)_nR^5$. In a yet further aspect, $R^{4a}$ is hydrogen and $R^{4b}$ is —(($CH_2$)$_2$)-phenyl substituted with 0-2 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —($CH_2$)$_2CH_2F$, —($CH_2$)$_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —($CH_2$)$_2CHF_2$, —($CH_2$)$_2CF_3$, —($CH_2$)$_2CHCl_2$, —($CH_2$)$_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, and —$S(O)_nR^5$. In an even further aspect, $R^{4a}$ is hydrogen and $R^{4b}$ is —(($CH_2$)$_2$)-phenyl substituted with 0-2 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, and —$S(O)_nR^5$. In a still further aspect, $R^{4a}$ is hydrogen and $R^{4b}$ is —(($CH_2$)$_2$)-phenyl substituted with 0-2 groups independently selected from —F, —Cl, —$NH_2$, —OH, —CN, methyl, —$CF_3$, —$CCl_3$, —$OCH_3$, —$NHCH_3$, and —$S(O)_nR^5$. In a yet further aspect, $R^{4a}$ is hydrogen and $R^{4b}$ is —(($CH_2$)$_2$)-phenyl substituted with 0-2 groups independently selected from —F, —Cl, methyl, —$CH_2F$, —$CH_2Cl$, —$CHF_2$, —$CF_3$, —$CHCl_2$, —$CCl_3$, and —$S(O)_nR^5$.

In a further aspect, each of $R^{4a}$ and $R^{4b}$ is independently selected from hydrogen and —($CH_2$)-phenyl, provided that $R^{4a}$ and $R^{4b}$ are not both hydrogen; and wherein —($CH_2$)-phenyl is substituted with 0-2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $R^{4a}$ is hydrogen and $R^{4b}$ is —($CH_2$)-phenyl substituted with 0-2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$. In a still further aspect, $R^{4a}$ is hydrogen and $R^{4b}$ is —($CH_2$)-phenyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —(CH$_2$)-phenyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —(CH$_2$)-phenyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —(CH$_2$)-phenyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —(CH$_2$)-phenyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, each of R$^{4a}$ and R$^{4b}$ is independently selected from hydrogen and —((CH$_2$)$_2$)-heterocyclyl, provided that R$^{4a}$ and R$^{4b}$ are not both hydrogen; and wherein —((CH$_2$)$_2$)-heterocyclyl is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, R$^{4a}$ is hydrogen and R$^{4b}$ is —((CH$_2$)$_2$)-heterocyclyl substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is —((CH$_2$)$_2$)-heterocyclyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —((CH$_2$)$_2$)-heterocyclyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —((CH$_2$)$_2$)-heterocyclyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —((CH$_2$)$_2$)-heterocyclyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —((CH$_2$)$_2$)-heterocyclyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, each of R$^{4a}$ and R$^{4b}$ is independently selected from hydrogen and —(CH$_2$)-heterocyclyl, provided that R$^{4a}$ and R$^{4b}$ are not both hydrogen; and wherein —(CH$_2$)-heterocyclyl, when present, is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, R$^{4a}$ is hydrogen and R$^{4b}$ is —(CH$_2$)-heterocyclyl substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, R$^{4a}$ is hydrogen and R$^{4b}$ is —(CH$_2$)-heterocyclyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —(CH$_2$)-heterocyclyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —(CH$_2$)-heterocyclyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —(CH$_2$)-heterocyclyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —(CH$_2$)-heterocyclyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, each of R$^{4a}$ and R$^{4b}$ is independently selected from hydrogen and Ar$^2$, provided that R$^{4a}$ and R$^{4b}$ are not both hydrogen. In a yet further aspect, R$^{4a}$ is hydrogen and R$^{4b}$ is Ar$^2$.

In a further aspect, each of R$^{4a}$ and R$^{4b}$ is independently selected from hydrogen and Ar$^2$, provided that R$^{4a}$ and R$^{4b}$ are not both hydrogen; and wherein Ar$^2$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, each of R$^{4a}$ is hydrogen and R$^{4b}$ is independently selected from hydrogen and Ar$^2$; and wherein Ar$^2$, when present, is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, each of R$^{4a}$ is hydrogen and R$^{4b}$ is Ar$^2$ substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, each of R$^{4a}$ is hydrogen and R$^{4b}$ is Ar$^2$ substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, each of R$^{4a}$ is hydrogen and R$^{4b}$ is Ar$^2$ substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, each of R$^{4a}$ is hydrogen and R$^{4b}$ is Ar$^2$ substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —S(O)$_n$R$^5$. In a still further aspect, each of R$^{4a}$ is hydrogen and R$^{4b}$ is Ar$^2$ substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, each of R$^{4a}$ is hydrogen and R$^{4b}$ is Ar$^2$ substituted with 0-2 groups independently selected from —F, —Cl, methyl, —CH$_2$F, —CH$_2$Cl, —CHF$_2$, —CF$_3$, —CHCl$_2$, —CCl$_3$. and —S(O)$_n$R$^5$.

In a further aspect, each of R$^{4a}$ and R$^{4b}$ is independently selected from hydrogen, C1-C8 alkyl, C1-C8 haloalkyl, C1-C8 polyhaloalkyl, C3-C8 cycloalkyl, C2-C7 heterocycloalkyl, —(C1-C8 alkyl)-(C3-C8 cycloalkyl), —(C1-C8 alkyl)-(C2-C7 heterocycloalkyl), provided that R$^{4a}$ and R$^{4b}$ are not both hydrogen; and wherein each of R$^{4a}$ and R$^{4b}$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, each of R$^{4a}$ and R$^{4b}$ is independently selected from hydrogen, C1-C6 alkyl, C1-C6 haloalkyl, C1-C6 polyhaloalkyl, C3-C8 cycloalkyl, C2-C7 heterocycloalkyl, —(C1-C8 alkyl)-(C3-C8 cycloalkyl), and —(C1-C8 alkyl)-(C2-C7 heterocycloalkyl), provided that R$^{4a}$ and R$^{4b}$ are not both hydrogen. In a yet further aspect, each of R$^{4a}$ and R$^{4b}$ is independently selected from hydrogen, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl, provided that R$^{4a}$ and R$^{4b}$ are not both hydrogen.

In a further aspect, each of R$^{4a}$ and R$^{4b}$ is independently selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl, provided that R$^{4a}$ and R$^{4b}$ are not both hydrogen. In a yet further aspect, each of R$^{4a}$ and R$^{4b}$ is independently selected from hydrogen, methyl, ethyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl, provided that R$^{4a}$ and R$^{4b}$ are not both hydrogen.

In a further aspect, each of R$^{4a}$ and R$^{4b}$ is independently selected from hydrogen, methyl, ethyl, —CH$_2$F, —CH$_2$Cl, —CHF$_2$, —CF$_3$, —CHCl$_2$, and —CCl$_3$, provided that R$^{4a}$ and R$^{4b}$ are not both hydrogen. In a still further aspect, each of R$^{4a}$ and R$^{4b}$ is independently selected from hydrogen, —CH$_2$F, —CH$_2$Cl, —CHF$_2$, —CF$_3$, —CHCl$_2$, and —CCl$_3$, provided that R$^{4a}$ and R$^{4b}$ are not both hydrogen. In a yet further aspect, each of R$^{4a}$ and R$^{4b}$ is independently selected from hydrogen, methyl, ethyl, and isopropyl, provided that R$^{4a}$ and R$^{4b}$ are not both hydrogen. In an even further aspect, each of R$^{4a}$ and R$^{4b}$ is independently selected from hydrogen and methyl, provided that R$^{4a}$ and R$^{4b}$ are not both hydrogen. In a still further aspect, each of R$^{4a}$ and R$^{4b}$ is methyl.

In a further aspect, each of R$^{4a}$ and R$^{4b}$ is independently selected from hydrogen, cyclopropyl, cyclobutyl, cyclopentyl, and cyclohexyl, provided that R$^{4a}$ and R$^{4b}$ are not both hydrogen. In a still further aspect, each of R$^{4a}$ and R$^{4b}$ is independently selected from hydrogen, pyrollidinyl, tetrahydrofuranyl, tetrahydrothiophenyl, piperidinyl, tetrahydro-2H-pyranyl, and tetrahydro-2H-thiopyranyl, provided that R$^{4a}$ and R$^{4b}$ are not both hydrogen. In a yet further aspect, each of R$^{4a}$ and R$^{4b}$ is independently selected from hydrogen, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl, provided that R$^{4a}$ and R$^{4b}$ are not both hydrogen.

In an even further aspect, R$^{4a}$ is hydrogen and R$^{4b}$ is selected from C1-C6 alkyl, C1-C6 haloalkyl, C1-C6 polyhaloalkyl, C3-C8 cycloalkyl, C2-C7 heterocycloalkyl, —(C1-C8 alkyl)-(C3-C8 cycloalkyl), and —(C1-C8 alkyl)-(C2-C7 heterocycloalkyl). In a still further aspect, R$^{4a}$ is hydrogen and R$^{4b}$ is selected from hydrogen, C1-C3 alkyl, C1-C3 haloalkyl, C1-C3 polyhaloalkyl, C3-C6 cycloalkyl, C2-C5 heterocycloalkyl, —(C1-C8 alkyl)-(C3-C6 cycloalkyl), and —(C1-C8 alkyl)-(C2-C5 heterocycloalkyl). In a yet further aspect, R$^{4a}$ is hydrogen and R$^{4b}$ is selected from methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl. In an even further aspect, R$^{4a}$ is hydrogen and R$^{4b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl. In a still further aspect, R$^{4a}$ is hydrogen and R$^{4b}$ is selected from methyl, ethyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrollidinyl, tetrahydrofuranyl, tetrahydrothiophenyl, piperidinyl, tetrahydro-2H-pyranyl, tetrahydro-2H-thiopyranyl, —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl.

In a further aspect, R$^{4a}$ is hydrogen and R$^{4b}$ is selected from methyl, ethyl, —CH$_2$F, —CH$_2$Cl, —CHF$_2$, —CF$_3$, —CHCl$_2$, and —CCl$_3$. In a still further aspect, R$^{4a}$ is hydrogen and R$^{4b}$ is selected from hydrogen, —CH$_2$F, —CH$_2$Cl, —CHF$_2$, —CF$_3$, —CHCl$_2$, and —CCl$_3$. In a yet further aspect, R$^{4a}$ is hydrogen and R$^{4b}$ is methyl. In an even further aspect, R$^{4a}$ is hydrogen and R$^{4b}$ is ethyl.

In a further aspect, R$^{4a}$ is hydrogen and R$^{4b}$ is selected from cyclopropyl, cyclobutyl, cyclopentyl, and cyclohexyl. In a still further aspect, R$^{4a}$ is hydrogen and R$^{4b}$ is selected from pyrollidinyl, tetrahydrofuranyl, tetrahydrothiophenyl, piperidinyl, tetrahydro-2H-pyranyl, and tetrahydro-2H-thiopyranyl. In a yet further aspect, R$^{4a}$ is hydrogen and R$^{4b}$ is selected from —(C1-C3)-pyrollidinyl, —(C1-C3)-tetrahydrofuranyl, —(C1-C3)-tetrahydrothiophenyl, —(C1-C3)-piperidinyl, —(C1-C3)-tetrahydro-2H-pyranyl, and —(C1-C3)-tetrahydro-2H-thiopyranyl.

In a further aspect, R$^{4a}$ is hydrogen and R$^{4b}$ is cyclopropyl. In a still further aspect, R$^{4a}$ is hydrogen and R$^{4b}$ is cyclopropyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, $R^{4a}$ is hydrogen and $R^{4b}$ is cyclopropyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, $R^{4a}$ is hydrogen and $R^{4b}$ is cyclopropyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, $R^{4a}$ is hydrogen and $R^{4b}$ is cyclopropyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, $R^{4a}$ is hydrogen and $R^{4b}$ is cyclopropyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, $R^{4a}$ is hydrogen and $R^{4b}$ is cyclobutyl. In a still further aspect, $R^{4a}$ is hydrogen and $R^{4b}$ is cyclobutyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, $R^{4a}$ is hydrogen and $R^{4b}$ is cyclobutyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, $R^{4a}$ is hydrogen and $R^{4b}$ is cyclobutyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, $R^{4a}$ is hydrogen and $R^{4b}$ is cyclobutyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, $R^{4a}$ is hydrogen and $R^{4b}$ is cyclobutyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, $R^{4a}$ is hydrogen and $R^{4b}$ is cyclopentyl. In a still further aspect, $R^{4a}$ is hydrogen and $R^{4b}$ is cyclopentyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, $R^{4a}$ is hydrogen and $R^{4b}$ is cyclopentyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, $R^{4a}$ is hydrogen and $R^{4b}$ is cyclopentyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, $R^{4a}$ is hydrogen and $R^{4b}$ is cyclopentyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, $R^{4a}$ is hydrogen and $R^{4b}$ is cyclopentyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, $R^{4a}$ is hydrogen and $R^{4b}$ is cyclohexyl. In a still further aspect, $R^{4a}$ is hydrogen and $R^{4b}$ is cyclohexyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH₂CH₃)(CH(CH₃)₂), and —S(O)ₙR⁵. In a yet further aspect, R⁴ᵃ is hydrogen and R⁴ᵇ is cyclohexyl substituted with 0-2 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, and —S(O)ₙR⁵. In an even further aspect, R⁴ᵃ is hydrogen and R⁴ᵇ is cyclohexyl substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, and —S(O)ₙR⁵. In a still further aspect, R⁴ᵃ is hydrogen and R⁴ᵇ is cyclohexyl substituted with 0-2 groups independently selected from —F, —Cl, —NH₂, —OH, —CN, methyl, —CF₃, —CCl₃, —OCH₃, —NHCH₃, and —S(O)ₙR⁵. In a yet further aspect, R⁴ᵃ is hydrogen and R⁴ᵇ is cyclohexyl substituted with 0-2 groups independently selected from —F, —Cl, methyl, —CH₂F, —CH₂Cl, —CHF₂, —CF₃, —CHCl₂, —CCl₃, and —S(O)ₙR⁵.

In a further aspect, R⁴ᵃ is hydrogen and R⁴ᵇ is pyrollidinyl. In a still further aspect, R⁴ᵃ is hydrogen and R⁴ᵇ is pyrollidinyl substituted with 0-2 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), and —S(O)ₙR⁵. In a yet further aspect, R⁴ᵃ is hydrogen and R⁴ᵇ is pyrollidinyl substituted with 0-2 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, and —S(O)ₙR⁵. In an even further aspect, R⁴ᵃ is hydrogen and R⁴ᵇ is pyrollidinyl substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, and —S(O)ₙR⁵. In a still further aspect, R⁴ᵃ is hydrogen and R⁴ᵇ is pyrollidinyl substituted with 0-2 groups independently selected from —F, —Cl, —NH₂, —OH, —CN, methyl, —CF₃, —CCl₃, —OCH₃, —NHCH₃, and —S(O)ₙR⁵. In a yet further aspect, R⁴ᵃ is hydrogen and R⁴ᵇ is pyrollidinyl substituted with 0-2 groups independently selected from —F, —Cl, methyl, —CH₂F, —CH₂Cl, —CHF₂, —CF₃, —CHCl₂, —CCl₃, and —S(O)ₙR⁵.

In a further aspect, R⁴ᵃ is hydrogen and R⁴ᵇ is piperidinyl. In a still further aspect, R⁴ᵃ is hydrogen and R⁴ᵇ is piperidinyl substituted with 0-2 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), and —S(O)ₙR⁵. In a yet further aspect, R⁴ᵃ is hydrogen and R⁴ᵇ is piperidinyl substituted with 0-2 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, and —S(O)ₙR⁵. In an even further aspect, R⁴ᵃ is hydrogen and R⁴ᵇ is piperidinyl substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, and —S(O)ₙR⁵. In a still further aspect, R⁴ᵃ is hydrogen and R⁴ᵇ is piperidinyl substituted with 0-2 groups independently selected from —F, —Cl, —NH₂, —OH, —CN, methyl, —CF₃, —CCl₃, —OCH₃, —NHCH₃, and —S(O)ₙR⁵. In a yet further aspect, R⁴ᵃ is hydrogen and R⁴ᵇ is piperidinyl substituted with 0-2 groups independently selected from —F, —Cl, methyl, —CH₂F, —CH₂Cl, —CHF₂, —CF₃, —CHCl₂, —CCl₃, and —S(O)ₙR⁵.

In a further aspect, R⁴ᵃ is hydrogen and R⁴ᵇ is —(C1-C3)-pyrollidinyl. In a still further aspect, R⁴ᵃ is hydrogen and R⁴ᵇ is —(C1-C3)-pyrollidinyl substituted with 0-2 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —(C1-C3)-pyrollidinyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —(C1-C3)-pyrollidinyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —(C1-C3)-pyrollidinyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —(C1-C3)-pyrollidinyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In a further aspect, R$^{4a}$ is hydrogen and R$^{4b}$ is —(C1-C3)-piperidinyl. In a still further aspect, R$^{4a}$ is hydrogen and R$^{4b}$ is —(C1-C3)-piperidinyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a yet further aspect, R$^{4a}$ is hydrogen and R$^{4b}$ is —(C1-C3)-piperidinyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In an even further aspect, R$^{4a}$ is hydrogen and R$^{4b}$ is —(C1-C3)-piperidinyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a still further aspect, R$^{4a}$ is hydrogen and R$^{4b}$ is —(C1-C3)-piperidinyl substituted with 0-2 groups independently selected from —F, —Cl, —NH$_2$, —OH, —CN, methyl, —CF$_3$, —CCl$_3$, —OCH$_3$, —NHCH$_3$, and —S(O)$_n$R$^5$. In a yet further aspect, R$^{4a}$ is hydrogen and R$^{4b}$ is —(C1-C3)-piperidinyl substituted with 0-2 groups independently selected from —F, —Cl, methyl, —CH$_2$F, —CH$_2$Cl, —CHF$_2$, —CF$_3$, —CHCl$_2$, —CCl$_3$, and —S(O)$_n$R$^5$.

In one aspect, R$^{4a}$ and R$^{4b}$ are optionally covalently bonded and, together with the intermediate nitrogen, comprise a 3- to 7-membered heterocycloalkyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a further aspect, R$^{4a}$ and R$^{4b}$ are covalently bonded and, together with the intermediate nitrogen, comprise a 3- to 7-membered heterocycloalkyl substituted with 0-2 groups independently selected from —F, —Cl, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^{4a}$ and R$^{4b}$ are covalently bonded and, together with the intermediate nitrogen, comprise a 3- to 7-membered heterocycloalkyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, R$^{4a}$ and R$^{4b}$ are covalently bonded and, together with the intermediate nitrogen, comprise a 3- to 7-membered heterocycloalkyl substituted with 0-2 groups independently selected from —F, —Cl, —NH$_2$, —OH, —CN, methyl, —CF$_3$, —CCl$_3$, —OCH$_3$, and —NHCH$_3$. In an even further aspect, wherein R$^{4a}$ and R$^{4b}$ are covalently bonded and, together with the intermediate nitrogen, comprise a 3- to 7-membered heterocycloalkyl substituted with 0-2 groups independently selected from —F, —Cl, methyl, —CH$_2$F, —CH$_2$Cl, —CHF$_2$, —CF$_3$, —CHCl$_2$, and —CCl$_3$.

In a further aspect, R$^{4a}$ and R$^{4b}$ are covalently bonded and, together with the intermediate nitrogen, comprise a heterocycloalkyl selected from aziridinyl, azetidinyl, pyrolidinyl, and piperidinyl; and wherein the heterocycloalkyl is substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, R$^{4a}$ and R$^{4b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a yet further aspect, R$^{4a}$ and R$^{4b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from —F, —Cl, —NH$_2$, —OH, —CN, methyl, —CF$_3$, —CCl$_3$, —OCH$_3$, and —NHCH$_3$. In an even further aspect, R$^{4a}$ and R$^{4b}$ are covalently bonded and, together with the intermediate nitrogen, comprise a heterocycloalkyl selected from aziridinyl, azetidinyl, pyrrolidinyl, and piperidinyl; and wherein the heterocycloalkyl is substituted with 0-2 groups independently selected from —F, —C, methyl, —CH$_2$F, —CH$_2$Cl, —CHF$_2$, —CHCl$_2$, and —CCl$_3$.

In a further aspect, R$^{4a}$ and R$^{4b}$ are covalently bonded and, together with the intermediate nitrogen, comprise a heterocycloalkyl selected from pyrrolidinyl and piperidinyl;

and wherein the heterocycloalkyl is substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{4a}$ and $R^{4b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In a yet further aspect, $R^{4a}$ and $R^{4b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from —F, —Cl, —NH₂, —OH, —CN, methyl, —CF₃, —CCl₃, —OCH₃, and —NHCH₃. In an even further aspect, $R^{4a}$ and $R^{4b}$ are covalently bonded and, together with the intermediate nitrogen, comprise a heterocycloalkyl selected from pyrrolidinyl and piperidinyl; and wherein the heterocycloalkyl is substituted with 0-2 groups independently selected from —F, —Cl, methyl, —CH₂F, —CH₂Cl, —CHF₂, —CF₃, —CHCl₂, and —CCl₃.

In a further aspect, $R^{4a}$ and $R^{4b}$ are covalently bonded and, together with the intermediate nitrogen, comprise a pyrrolidinyl group substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{4a}$ and $R^{4b}$ are covalently bonded and, together with the intermediate nitrogen, comprise a pyrrolidinyl group substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In a yet further aspect, $R^{4a}$ and $R^{4b}$ are covalently bonded and, together with the intermediate nitrogen, comprise a pyrrolidinyl group substituted with 0-2 groups independently selected from —F, —Cl, —NH₂, —OH, —CN, methyl, —CF₃, —CCl₃, —OCH₃, and —NHCH₃. In an even further aspect, $R^{4a}$ and $R^{4b}$ are covalently bonded and, together with the intermediate nitrogen, comprise a pyrrolidinyl group substituted with 0-2 groups independently selected from —F, —Cl, methyl, —CH₂F, —CH₂Cl, —CHF₂, —CF₃, —CHCl₂, and —CCl₃.

In a further aspect, $R^{4a}$ and $R^{4b}$ are covalently bonded and, together with the intermediate nitrogen, comprise a piperidinyl group substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, and C1-C6 dialkylamino. In a still further aspect, $R^{4a}$ and $R^{4b}$ are covalently bonded and, together with the intermediate nitrogen, comprise a piperidinyl group substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In a yet further aspect, $R^{4a}$ and $R^{4b}$ are covalently bonded and, together with the intermediate nitrogen, comprise a piperidinyl group substituted with 0-2 groups independently selected from —F, —Cl, —NH₂, —OH, —CN, methyl, —CF₃, —CCl₃, —OCH₃, and —NHCH₃. In an even further aspect, $R^{4a}$ and $R^{4b}$ are covalently bonded and, together with the intermediate nitrogen, comprise a piperidinyl group substituted with 0-2 groups independently selected from —F, —Cl, methyl, —CH₂F, —CH₂Cl, —CHF₂, —CF₃, —CHCl₂, and —CCl₃.

In a further aspect, $R^{4a}$ and $R^{4b}$ are covalently bonded and, together with the intermediate nitrogen, comprise a structure represented by a formula:

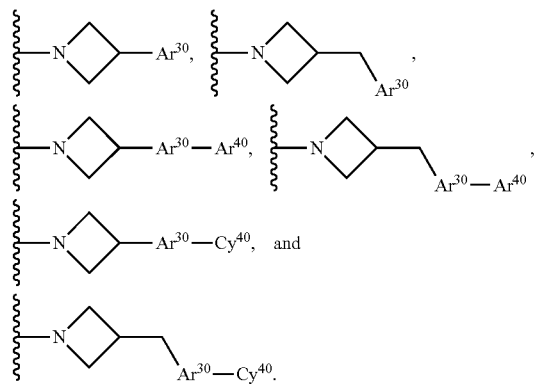

In a further aspect, $R^{4a}$ and $R^{4b}$ are covalently bonded and, together with the intermediate nitrogen, comprise a structure represented by a formula:

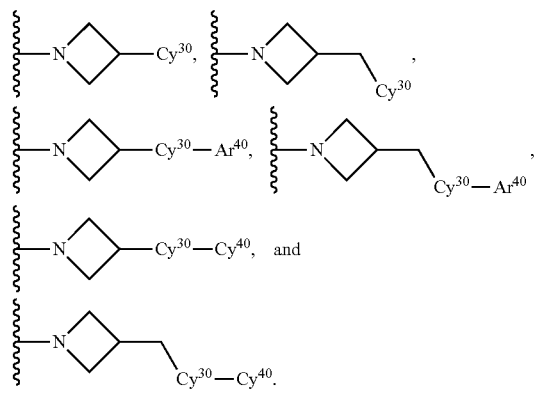

In a further aspect, $R^{4a}$ and $R^{4b}$ are covalently bonded and, together with the intermediate nitrogen, comprise a structure represented by a formula:

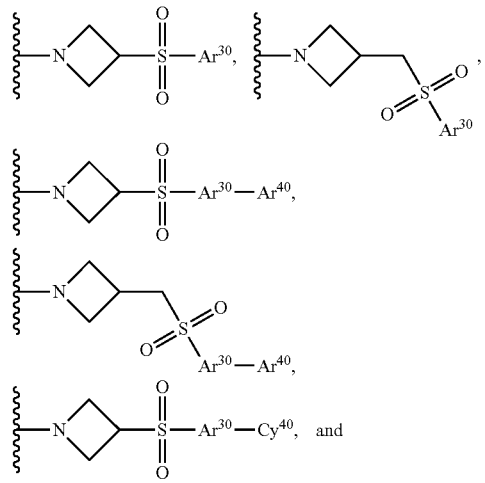

-continued

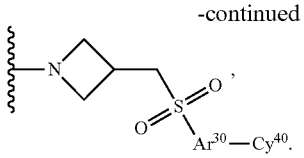

In a further aspect, $R^{4a}$ and $R^{4b}$ are covalently bonded and, together with the intermediate nitrogen, comprise a structure represented by a formula:

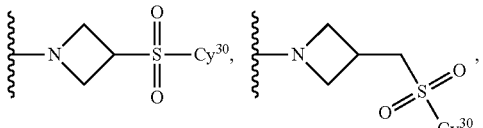

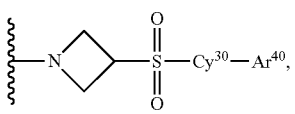

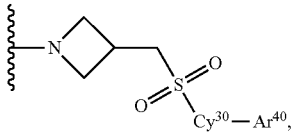

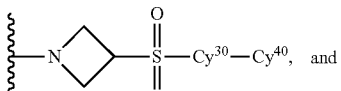

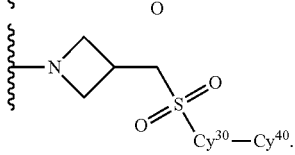

In a further aspect, $R^{4a}$ and $R^{4b}$ are covalently bonded and, together with the intermediate nitrogen, comprise a structure represented by a formula:

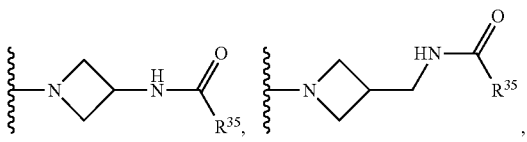

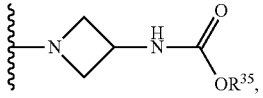

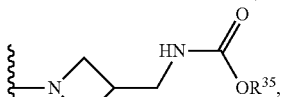

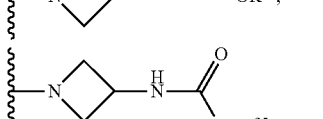

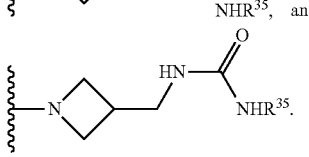

In a further aspect, $R^{4a}$ and $R^{4b}$ are covalently bonded and, together with the intermediate nitrogen, comprise a structure represented by a formula:

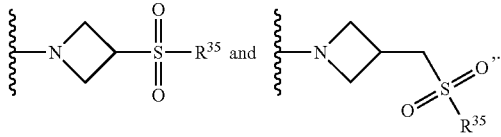

In a further aspect, $R^{4a}$ and $R^{4b}$ are covalently bonded and, together with the intermediate nitrogen, comprise a structure represented by a formula:

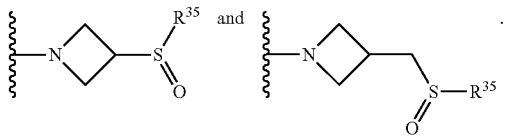

In a further aspect, $R^{4a}$ and $R^{4b}$ are covalently bonded and, together with the intermediate nitrogen, comprise a structure represented by a formula:

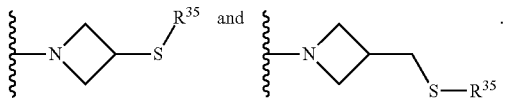

In a further aspect, $R^{4a}$ and $R^{4b}$ are covalently bonded and, together with the intermediate nitrogen, comprise a structure represented by a formula:

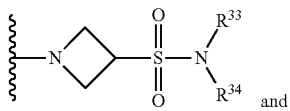

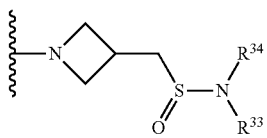

In a further aspect, $R^{4a}$ and $R^{4b}$ are covalently bonded and, together with the intermediate nitrogen, comprise a structure represented by a formula:

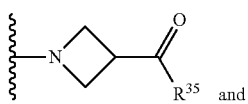

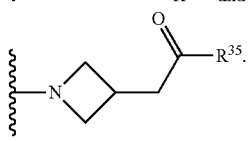

In a further aspect, $R^{4a}$ and $R^{4b}$ are covalently bonded and, together with the intermediate nitrogen, comprise a structure represented by a formula:

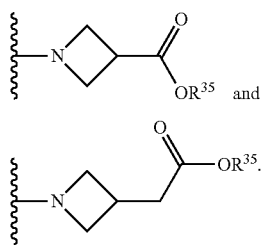

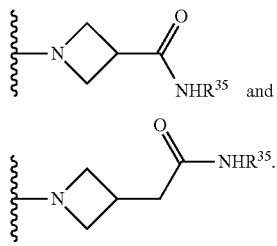

In a further aspect, $R^{4a}$ and $R^{4b}$ are covalently bonded and, together with the intermediate nitrogen, comprise a structure represented by a formula:

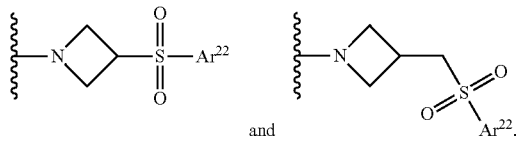

In a further aspect, $R^{4a}$ and $R^{4b}$ are covalently bonded and, together with the intermediate nitrogen, comprise a structure represented by a formula:

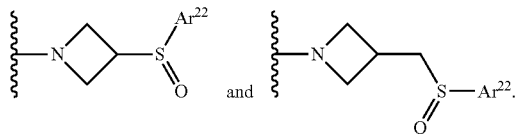

In a further aspect, $R^{4a}$ and $R^{4b}$ are covalently bonded and, together with the intermediate nitrogen, comprise a structure represented by a formula:

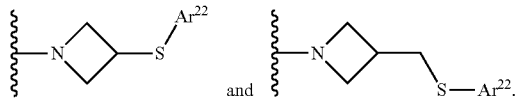

In a further aspect, $R^{4a}$ and $R^{4b}$ are covalently bonded and, together with the intermediate nitrogen, comprise a structure represented by a formula:

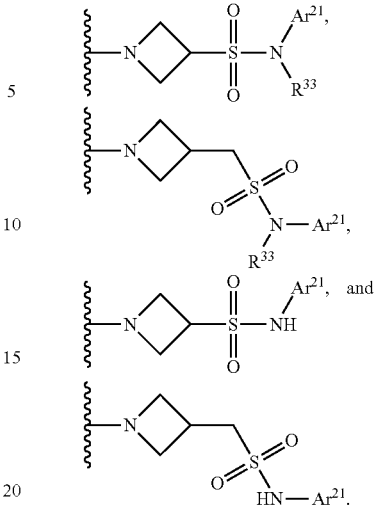

In a further aspect, $R^{4a}$ and $R^{4b}$ are covalently bonded and, together with the intermediate nitrogen, comprise a structure represented by a formula:

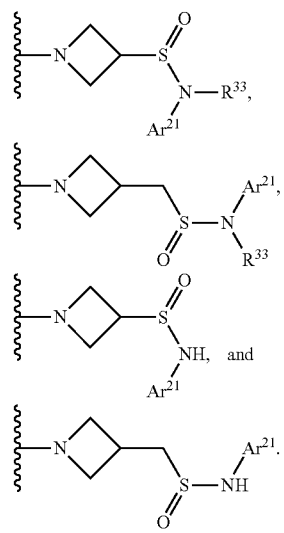

e. $R^5$ Groups

In one aspect, $R^5$, when present, is selected from hydrogen, C1-C8 alkyl, C1-C8 haloalkyl, and C1-C8 polyhaloalkyl. In a further aspect, $R^5$, when present, is selected from C1-C8 alkyl, C1-C8 haloalkyl, and C1-C8 polyhaloalkyl. In a still further aspect, $R^5$, when present, is hydrogen.

In a further aspect, $R^5$, when present, is selected from C1-C6 alkyl, C1-C6 haloalkyl, and C1-C6 polyhaloalkyl. In a yet further aspect, $R^5$, when present, is selected from C1-C3 alkyl, C1-C3 haloalkyl, and C1-C3 polyhaloalkyl. In an even further aspect, $R^5$, when present, is selected from methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, R$^5$, when present, is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, R$^5$, when present, is selected from methyl, —CH$_2$F, —CH$_2$Cl, —CHF$_2$, —CF$_3$, —CHCl$_2$, and —CCl$_3$. In an even further aspect, R$^5$, when present, is selected from methyl, —CF$_3$, and —CCl$_3$. In a still further aspect, R$^5$, when present, is selected from —CH$_2$F, —CH$_2$Cl, —CHF$_2$, —CF$_3$, —CHCl$_2$, and —CCl$_3$.

In a further aspect, R$^5$, when present, is selected from hydrogen, C1-C6 alkyl, C1-C6 haloalkyl, and C1-C6 polyhaloalkyl. In a still further aspect, R$^5$, when present, is selected from hydrogen, C1-C3 alkyl, C1-C3 haloalkyl, and C1-C3 polyhaloalkyl. In a yet further aspect, R$^5$, when present, is selected from hydrogen, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a yet further aspect, R$^5$, when present, is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$.

In a further aspect, R$^5$, when present, is selected from hydrogen, methyl, —CH$_2$F, —CH$_2$Cl, —CHF$_2$, —CF$_3$, —CHCl$_2$, and —CCl$_3$. In a still further aspect, R$^5$, when present, is selected from hydrogen, methyl, —CF$_3$, and —CCl$_3$. In a yet further aspect, R$^5$, when present, is selected from hydrogen, —CH$_2$F, —CH$_2$Cl, —CHF$_2$, —CF$_3$, —CHCl$_2$, and —CCl$_3$. In an even further aspect, R$^5$, when present, is selected from hydrogen, methyl, and —CF$_3$. In a still further aspect, R$^5$, when present, is selected from hydrogen and methyl. In a yet further aspect, R$^5$, when present, is selected from hydrogen and —CF$_3$.

In a further aspect, R$^5$, when present, is methyl. In a still further aspect, R$^5$, when present, is —CH$_2$F. In a yet further aspect, R$^5$, when present, is —CH$_2$Cl. In an even further aspect, R$^5$, when present, is —CHF$_2$. In a still further aspect, R$^5$, when present, is —CF$_3$. In a yet further aspect, R$^5$, when present, is —CHCl$_2$. In an even further aspect, R$^5$, when present, is —CCl$_3$.

f. R$^{6A}$, R$^{6B}$, R$^{6C}$, R$^{6D}$, and R$^{6E}$ Groups

In one aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a further aspect, each of R$^{6a}$, R$^{6b}$, R$^{6c}$, R$^{6d}$, and R$^{6e}$, when present, is hydrogen.

In a further aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_n$R$^5$. In a still further aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, and —S(O)$_n$R$^5$. In a yet further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In an even further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In a still further aspect, wherein each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a yet further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, —CF$_3$, —CCl$_3$, —OCH$_3$, —NHCH$_3$, and —S(O)$_n$R$^5$. In an even further aspect, each of R$^{6a}$, R$^{6b}$, R$^{6c}$, R$^{6d}$, and R$^{6e}$, when present, is independently selected from hydrogen, —F, —Cl, methyl, —CH$_2$F, —CH$_2$Cl, —CHF$_2$, —CF$_3$, —CHCl$_2$, —CCl$_3$, and —S(O)$_n$R$^5$.

In various aspects, each of R$^{6a}$, R$^{6b}$, R$^{6c}$, R$^{6d}$, and R$^{6e}$, when present, is independently selected from hydrogen, halogen, —NH$_2$, —OH, —CN, C1-C8 alkyl, C1-C8 haloalkyl, and C1-C8 polyhaloalkyl. In a further aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C6 alkyl, C1-C6 haloalkyl, and C1-C6 polyhaloalkyl. In a still further aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C3 alkyl, C1-C3 haloalkyl, and C1-C3 polyhaloalkyl. In an even further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, and —CCl$_3$. In an even further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, methyl, —CF$_3$, and —CCl$_3$.

In various aspects, each of R$^{6a}$, R$^{6b}$, R$^{6c}$, R$^{6d}$, and R$^{6e}$, when present, is independently selected from hydrogen, halogen, C1-C8 alkyl, C1-C8 haloalkyl, and C1-C8 polyhaloalkyl. In a further aspect, each of R$^{6a}$, R$^{6b}$, R$^{6c}$, R$^{6d}$, and R$^{6e}$, when present, is independently selected from hydrogen, halogen, C1-C6 alkyl, C1-C6 haloalkyl, and C1-C6 polyhaloalkyl. In a still further aspect, each of R$^{6a}$, R$^{6b}$, R$^{6c}$, R$^{6d}$, and R$^{6e}$, when present, is independently selected from hydrogen, halogen, C1-C3 alkyl, C1-C3 haloalkyl, and C1-C3 polyhaloalkyl. In an even further aspect, each of R$^{6a}$, R$^{6b}$, R$^{6c}$, R$^{6d}$, and R$^{6e}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of R$^{6a}$, R$^{6b}$, R$^{6c}$, R$^{6d}$, and R$^{6e}$, when present, is independently selected from hydrogen, —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{6a}$, R$^{6b}$, R$^{6c}$, R$^{6d}$, and R$^{6e}$, when present, is independently selected from hydrogen, —F, —Cl, methyl, —CH$_2$F, —CH$_2$Cl, —CHF$_2$, —CF$_3$, —CHCl$_2$, and —CCl$_3$. In an even further aspect, each of R$^{6a}$, R$^{6b}$, R$^{6c}$, R$^{6d}$, and R$^{6e}$, when present, is independently selected from hydrogen, —F, —Cl, methyl, —CF$_3$, and —CCl$_3$.

In various aspects, each of R$^{6a}$, R$^{6b}$, R$^{6c}$, R$^{6d}$, and R$^{6e}$, when present, is independently selected from hydrogen, halogen, —NH$_2$, —OH, —CN, C1-C8 haloalkyl, and C1-C8 polyhaloalkyl. In a further aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C6 haloalkyl, and C1-C6 polyhaloalkyl. In a still further aspect, each of R$^{6a}$, R$^{6b}$, R$^{6c}$, R$^{6d}$, and R$^{6e}$, when present, is independently selected from hydrogen, halogen, —NH$_2$, —OH, —CN, C1-C3 haloalkyl, and C1-C3 polyhaloalkyl. In an even further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, —CH$_2$F, —CH$_2$Cl, —CHF$_2$, —CF$_3$, —CHCl$_2$, and —CCl$_3$. In an even further aspect, each of R$^{6a}$, R$^{6b}$, R$^{6c}$, R$^{6d}$, and R$^{6e}$, when present, is independently selected from hydrogen, —F, —Cl, —NH$_2$, —OH, —CN, —CF$_3$, and —CCl$_3$. In a still further aspect, each of R$^{6a}$, R$^{6b}$, R$^{6c}$, R$^{6d}$, and R$^{6e}$, when present, is independently selected from hydrogen, —F, —Cl, —CH$_2$F, —CH$_2$Cl, —CHF$_2$, —CF$_3$, —CHCl$_2$, and —CCl$_3$.

In various aspects, each of R$^{6a}$, R$^{6b}$, R$^{6c}$, R$^{6d}$, and R$^{6e}$, when present, is independently selected from hydrogen, halogen, and C1-C8 alkyl. In a further aspect, each of R$^{6a}$, R$^{6b}$, R$^{6c}$, R$^{6d}$, and R$^{6e}$, when present, is independently selected from hydrogen, halogen, and C1-C6 alkyl. In a still further aspect, each of R$^{6a}$, R$^{6b}$, R$^{6c}$, R$^{6d}$, and R$^{6e}$, when present, is independently selected from hydrogen, halogen, and C1-C3 alkyl. In an even further aspect, each of R$^{6a}$, R$^{6b}$, R$^{6c}$, R$^{6d}$, and R$^{6e}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, and tert-pentyl. In a still further aspect, each of R$^{6a}$, R$^{6b}$, R$^{6c}$, R$^{6d}$, and R$^{6e}$, when present, is independently selected from hydrogen, —F, —Cl, methyl, ethyl, propyl, and isopropyl. In a yet further aspect, each of R$^{6a}$, R$^{6b}$, R$^{6c}$, R$^{6d}$, and R$^{6e}$, when present, is independently selected from hydrogen, —F, —Cl, and methyl.

In various aspects, each of R$^{6a}$, R$^{6b}$, R$^{6c}$, R$^{6d}$, and R$^{6e}$, when present, is independently selected from hydrogen and C1-C8 alkyl. In a further aspect, each of R$^{6a}$, R$^{6b}$, R$^{6c}$, R$^{6d}$, and R$^{6e}$, when present, is independently selected from hydrogen and C1-C6 alkyl. In a still further aspect, each of R$^{6a}$, R$^{6b}$, R$^{6c}$, R$^{6d}$, and R$^{6e}$ when present, is independently selected from hydrogen and C1-C3 alkyl. In an even further aspect, each of R$^{6a}$, R$^{6b}$, R$^{6c}$, R$^{6d}$, and R$^{6e}$, when present, is independently selected from hydrogen, methyl, ethyl, propyl, isopropyl, tert-butyl, sec-butyl, isobutyl, tert-butyl, neopentyl, isopentyl, sec-pentyl, and tert-pentyl. In a still further aspect, each of R$^{6a}$, R$^{6b}$, R$^{6c}$, R$^{6d}$, and R$^{6e}$, when present, is independently selected from hydrogen, methyl, ethyl, propyl, and isopropyl. In a yet further aspect, each of R$^{6a}$, R$^{6b}$, R$^{6c}$, R$^{6d}$, and R$^{6e}$, when present, is independently selected from hydrogen and methyl.

In various aspects, each of R$^{6a}$, R$^{6b}$, R$^{6c}$, R$^{6d}$, and R$^{6e}$, when present, is independently selected from hydrogen, halogen, —NH$_2$, —OH, —CN, C1-C8 alkoxy, C1-C8 alkylamino, C1-C8 dialkylamino, and —S(O)$_n$R$^5$. In a further aspect, each of $R^{6a}$, $R^{6b}$, $R^{6c}$, $R^{6d}$, and $R^{6e}$, when present, is independently selected from hydrogen, halogen, —NH$_2$, —OH, —CN, C1-C6 alkoxy, C1-C6 alkylamino, C1-C6 dialkylamino, and —S(O)$_n$R$^5$. In a still further aspect, each of $R^{6a}$, $R^{6b}$, $R^{6c}$, $R^{6d}$, and $R^{6e}$, when present, is independently selected from hydrogen, halogen, —NH$_2$, —OH, —CN, C1-C3 alkoxy, C1-C3 alkylamino, C1-C3 dialkylamino, and —S(O)$_n$R$^5$. In an even further aspect, each of $R^{6a}$, $R^{6b}$, $R^{6c}$, $R^{6d}$, and $R^{6e}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a still further aspect, each of $R^{6a}$, $R^{6b}$, $R^{6e}$, $R^{6d}$, and $R^{6e}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In a yet further aspect, each of $R^{6a}$, $R^{6b}$, $R^{6c}$, $R^{6d}$, and $R^{6e}$, when present, is independently selected from hydrogen, —NH$_2$, —OH, —CN, —OCH$_3$, —NHCH$_3$, —N(CH$_3$)$_2$, and —S(O)$_n$R$^5$. In an even further aspect, each of $R^{6a}$, $R^{6b}$, $R^{6c}$, $R^{6d}$, and $R^{6e}$, when present, is independently selected from hydrogen, —NH$_2$, —OH, —CN, —OCH$_3$, —NHCH$_3$, and —S(O)$_n$R$^5$.

In a further aspect, each of $R^{6a}$, $R^{6b}$, $R^{6c}$, $R^{6d}$, and $R^{6e}$, when present, is independently selected from hydrogen and —S(O)$_n$R$^5$.

g. $R^{7A}$, $R^{7B}$, $R^{7C}$, and $R^{7D}$ Groups

In one aspect, each of $R^{7a}$, $R^{7b}$, $R^{7c}$, and $R^{7d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a further aspect, each of $R^{7a}$, $R^{7b}$, $R^{7c}$, and $R^{7d}$, when present, is hydrogen.

In a further aspect, each of $R^{7a}$, $R^{7b}$, $R^{7c}$, and $R^{7d}$, when present, is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_n$R$^5$. In a still further aspect, each of $R^{7a}$, $R^{7b}$, $R^{7c}$, and $R^{7d}$, when present, is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, and —S(O)$_n$R$^5$. In a yet further aspect, each of $R^{7a}$, $R^{7b}$, $R^{7c}$, and $R^{7d}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In an even further aspect, each of $R^{7a}$, $R^{7b}$, $R^{7c}$, and $R^{7d}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In a still further aspect, wherein each of $R^{7a}$, $R^{7b}$, $R^{7c}$, and $R^{7d}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a yet further aspect, each of $R^{7a}$, $R^{7b}$, $R^{7c}$, and $R^{7d}$, when present, is independently selected from hydrogen, —F, —Cl, —NH$_2$, —OH, —CN, methyl, —CF$_3$, —CCl$_3$, —OCH$_3$, —NHCH$_3$, and —S(O)$_n$R$^5$. In an even further aspect, each of $R^{7a}$, $R^{7b}$, $R^{7c}$, and $R^{7d}$, when present, is independently selected from hydrogen, —F, —Cl, methyl, —CH$_2$F, —CH$_2$Cl, —CHF$_2$, —CF$_3$, —CHCl$_2$, —CCl$_3$, and —S(O)$_n$R$^5$.

In various aspects, each of $R^{7a}$, $R^{7b}$, $R^{7c}$, and $R^{7d}$, when present, is independently selected from hydrogen, halogen, —NH$_2$, —OH, —CN, C1-C8 alkyl, C1-C8 haloalkyl, and C1-C8 polyhaloalkyl. In a further aspect, each of $R^{7a}$, $R^{7b}$, $R^{7c}$, and $R^{7d}$, when present, is independently selected from hydrogen, halogen, —NH$_2$, —OH, —CN, C1-C6 alkyl, C1-C6 haloalkyl, and C1-C6 polyhaloalkyl. In a still further aspect, each of $R^{7a}$, $R^{7b}$, $R^{7c}$, and $R^{7d}$, when present, is independently selected from hydrogen, halogen, —NH$_2$, —OH, —CN, C1-C3 alkyl, C1-C3 haloalkyl, and C1-C3 polyhaloalkyl. In an even further aspect, each of $R^{7a}$, $R^{7b}$, $R^{7c}$, and $R^{7d}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of $R^{7a}$, $R^{7b}$, $R^{7c}$, and $R^{7d}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of $R^{7a}$, $R^{7b}$, $R^{7c}$, and $R^{7d}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, and —CCl$_3$. In an even further aspect, each of $R^{7a}$, $R^{7b}$, $R^{7c}$, and $R^{7d}$, when present, is independently selected from hydrogen, —F, —Cl, —NH$_2$, —OH, —CN, methyl, —CF$_3$, and —CCl$_3$.

In various aspects, each of $R^{7a}$, $R^{7b}$, $R^{7c}$, and $R^{7d}$, when present, is independently selected from hydrogen, halogen, C1-C8 alkyl, C1-C8 haloalkyl, and C1-C8 polyhaloalkyl. In a further aspect, each of $R^{7a}$, $R^{7b}$, $R^{7c}$, and $R^{7d}$, when present, is independently selected from hydrogen, halogen, C1-C6 alkyl, C1-C6 haloalkyl, and C1-C6 polyhaloalkyl. In a still further aspect, each of $R^{7a}$, $R^{7b}$, $R^{7c}$, and $R^{7d}$, when present, is independently selected from hydrogen, halogen, C1-C3 alkyl, C1-C3 haloalkyl, and C1-C3 polyhaloalkyl. In an even further aspect, each of $R^{7a}$, $R^{7b}$, $R^{7c}$, and $R^{7d}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of $R^{7a}$, $R^{7b}$, $R^{7c}$, and $R^{7d}$, when present, is independently selected from hydrogen, —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of $R^{7a}$, $R^{7b}$, $R^{7c}$, and $R^{7d}$, when present, is independently selected from hydrogen, —F, —Cl, methyl, —CH$_2$F, —CH$_2$Cl, —CHF$_2$, —CF$_3$, —CHCl$_2$, and —CCl$_3$. In an even further aspect, each of $R^{7a}$, $R^{7b}$, $R^{7c}$, and $R^{7d}$, when present, is independently selected from hydrogen, —F, —Cl, methyl, —CF$_3$, and —CCl$_3$.

In various aspects, each of $R^{7a}$, $R^{7b}$, $R^{7c}$, and $R^{7d}$, when present, is independently selected from hydrogen, halogen, —NH$_2$, —OH, —CN, C1-C8 haloalkyl, and C1-C8 polyhaloalkyl. In a further aspect, each of $R^{7a}$, $R^{7b}$, $R^{7c}$, and $R^{7d}$, when present, is independently selected from hydrogen, halogen, —NH$_2$, —OH, —CN, C1-C6 haloalkyl, and C1-C6 polyhaloalkyl. In a still further aspect, each of $R^{7a}$, $R^{7b}$, $R^{7c}$, and $R^{7d}$, when present, is independently selected from hydrogen, halogen, —NH$_2$, —OH, —CN, C1-C3 haloalkyl, and C1-C3 polyhaloalkyl. In an even further aspect, each of $R^{7a}$, $R^{7b}$, $R^{7c}$, and $R^{7d}$, when present, is independently selected from hydrogen, —F, —Cl, —NH$_2$, —OH, —CN, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of $R^{7a}$, $R^{7b}$, $R^{7c}$, and $R^{7d}$, when present, is independently selected from hydrogen, —F, —Cl, —NH$_2$, —OH, —CN, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of $R^{7a}$, $R^{7b}$, $R^{7c}$, and $R^{7d}$, when present, is independently selected from hydrogen, —F, —Cl, —NH$_2$, —OH, —CN, —CH$_2$F, —CH$_2$Cl, —CHF$_2$, —CF$_3$, —CHCl$_2$, and —CCl$_3$. In an even further aspect, each of $R^{7a}$, $R^{7b}$, $R^{7c}$, and $R^{7d}$, when present, is independently selected from hydrogen, —F, —Cl, —NH$_2$, —OH, —CN, —CF$_3$, and —CCl$_3$. In a still further aspect, each of $R^{7a}$, $R^{7b}$, $R^{7c}$, and $R^{7d}$, when present, is independently selected from hydrogen, —F, —Cl, —CH$_2$F, —CH$_2$Cl, —CHF$_2$, —CF$_3$, —CHCl$_2$, and —CCl$_3$.

In various aspects, each of $R^{7a}$, $R^{7b}$, $R^{7c}$, and $R^{7d}$, when present, is independently selected from hydrogen, halogen, and C1-C8 alkyl. In a further aspect, each of $R^{7a}$, $R^{7b}$, $R^{7c}$, and $R^{7d}$, when present, is independently selected from hydrogen, halogen, and C1-C6 alkyl. In a still further aspect, each of $R^{7a}$, $R^{7b}$, $R^{7c}$, and $R^{7d}$, when present, is independently selected from hydrogen, halogen, and C1-C3 alkyl. In an even further aspect, each of $R^{7a}$, $R^{7b}$, $R^{7c}$, and $R^{7d}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, and tert-pentyl. In a still further aspect, each of $R^{7a}$, $R^{7b}$, $R^{7c}$, and $R^{7d}$, when present, is independently selected from hydrogen, —F, —Cl, methyl, ethyl, propyl, and isopropyl. In a yet further aspect, each of $R^{7a}$, $R^{7b}$, $R^{7c}$, and $R^{7d}$, when present, is independently selected from hydrogen, —F, —Cl, and methyl.

In various aspects, each of $R^{7a}$, $R^{7b}$, $R^{7c}$, and $R^{7d}$, when present, is independently selected from hydrogen and C1-C8 alkyl. In a further aspect, each of $R^{7a}$, $R^{7b}$, $R^{7c}$, and $R^{7d}$, when present, is independently selected from hydrogen and C1-C6 alkyl. In a still further aspect, each of $R^{7a}$, $R^{7b}$, $R^{7c}$, and $R^{7d}$, when present, is independently selected from hydrogen and C1-C3 alkyl. In an even further aspect, each of $R^{7a}$, $R^{7b}$, $R^{7c}$, and $R^{7d}$, when present, is independently selected from hydrogen, methyl, ethyl, propyl, isopropyl, tert-butyl, sec-butyl, isobutyl, tert-butyl, neopentyl, isopentyl, sec-pentyl, and tert-pentyl. In a still further aspect, each of $R^{7a}$, $R^{7b}$, $R^{7c}$, and $R^{7d}$, when present, is independently selected from hydrogen, methyl, ethyl, propyl, and isopropyl. In a yet further aspect, each of $R^{7a}$, $R^{7b}$, $R^{7c}$, and $R^{7d}$, when present, is independently selected from hydrogen and methyl.

In various aspects, each of $R^{7a}$, $R^{7b}$, $R^{7c}$, and $R^{7d}$, when present, is independently selected from hydrogen, halogen, —NH$_2$, —OH, —CN, C1-C8 alkoxy, C1-C8 alkylamino, C1-C8 dialkylamino, and —S(O)$_n$R$^5$. In a further aspect, each of $R^{7a}$, $R^{7b}$, $R^{7c}$, and $R^{7d}$, when present, is independently selected from hydrogen, halogen, —NH$_2$, —OH, —CN, C1-C6 alkoxy, C1-C6 alkylamino, C1-C6 dialkylamino, and —S(O)$_n$R$^5$. In a still further aspect, each of $R^{7a}$, $R^{7b}$, $R^{7c}$, and $R^{7d}$, when present, is independently selected from hydrogen, halogen, —NH$_2$, —OH, —CN, C1-C3 alkoxy, C1-C3 alkylamino, C1-C3 dialkylamino, and —S(O)$_n$R$^5$. In an even further aspect, each of $R^{7a}$, $R^{7b}$, $R^{7c}$, and $R^{7d}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a still further aspect, each of $R^{7a}$, $R^{7b}$, $R^{7c}$, and $R^{7d}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In a yet further aspect, each of $R^{7a}$, $R^{7b}$, $R^{7c}$, and $R^{7d}$, when present, is independently selected from hydrogen, —NH$_2$, —OH, —CN, —OCH$_3$, —NHCH$_3$, —N(CH$_3$)$_2$, and —S(O)$_n$R$^5$. In an even further aspect, each of $R^{7a}$, $R^{7b}$, $R^{7c}$, and $R^{7d}$, when present, is independently selected from hydrogen, —NH$_2$, —OH, —CN, —OCH$_3$, —NHCH$_3$, and —S(O)$_n$R$^5$.

In a further aspect, each of R$^{7a}$, R$^{7b}$, R$^{7c}$, and R$^{7d}$, when present, is independently selected from hydrogen and —S(O)$_n$R$^5$.

h. R$^8$ Groups

In one aspect, R$^8$, when present, is selected from hydrogen and C1-C8 alkyl. In a further aspect, R$^8$, when present, is selected from hydrogen and C1-C6 alkyl. In a still further aspect, R$^8$, when present, is selected from hydrogen and C1-C3 alkyl. In a yet further aspect, R$^8$, when present, is selected from hydrogen, methyl, ethyl, propyl, isopropyl, tert-butyl, sec-butyl, isobutyl, tert-butyl, neopentyl, isopentyl, sec-pentyl, and tert-pentyl. In an even further aspect, R$^8$, when present, is selected from hydrogen, methyl, ethyl, propyl, and isopropyl. In a still further aspect, R$^8$, when present, is selected from hydrogen, methyl, and ethyl. In a yet further aspect, R$^8$, when present, is selected from hydrogen and methyl. In an even further aspect, R$^8$, when present, is hydrogen. In a still further aspect, R$^8$, when present, is methyl. In a yet further aspect, R$^8$, when present, is ethyl.

i. R$^{9A}$ and R$^{9B}$ Groups

In one aspect, each of R$^{9a}$ and R$^{9b}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a further aspect, each of R$^{9a}$ and R$^{9b}$, when present, is hydrogen.

In a further aspect, each of R$^{9a}$ and R$^{9b}$, when present, is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_n$R$^5$. In a still further aspect, each of R$^{9a}$ and R$^{9b}$, when present, is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, and —S(O)$_n$R$^5$. In a yet further aspect, each of R$^{9a}$ and R$^{9b}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In an even further aspect, each of R$^{9a}$ and R$^{9b}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$) (CH$_2$)$_2$CH$_3$, —N(CH$_3$)CH(CH$_3$)$_2$, —N(CH$_2$CH$_3$)$_2$, and —S(O)$_n$R$^5$. In a still further aspect, wherein each of R$^{9a}$ and R$^{9b}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_n$R$^5$. In a yet further aspect, each of R$^{9a}$ and R$^{9b}$, when present, is independently selected from hydrogen, —F, —Cl, —NH$_2$, —OH, —CN, methyl, —CF$_3$, —CCl$_3$, —OCH$_3$, —NHCH$_3$, and —S(O)$_n$R$^5$. In an even further aspect, each of R$^{9a}$ and R$^{9b}$, when present, is independently selected from hydrogen, —F, —Cl, methyl, —CH$_2$F, —CH$_2$Cl, —CHF$_2$, —CF$_3$, —CHCl$_2$, —CCl$_3$, and —S(O)$_n$R$^5$.

In various aspects, each of R$^{9a}$ and R$^{9b}$, when present, is independently selected from hydrogen, halogen, —NH$_2$, —OH, —CN, C1-C8 alkyl, C1-C8 haloalkyl, and C1-C8 polyhaloalkyl. In a further aspect, each of R$^{9a}$ and R$^{9b}$, when present, is independently selected from hydrogen, halogen, —NH$_2$, —OH, —CN, C1-C6 alkyl, C1-C6 haloalkyl, and C1-C6 polyhaloalkyl. In a still further aspect, each of R$^{9a}$ and R$^{9b}$, when present, is independently selected from hydrogen, halogen, —NH$_2$, —OH, —CN, C1-C3 alkyl, C1-C3 haloalkyl, and C1-C3 polyhaloalkyl. In an even further aspect, each of R$^{9a}$ and R$^{9b}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of R$^{9a}$ and R$^{9b}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{9a}$ and R$^{9b}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, and —CCl$_3$. In an even further aspect, each of R$^{9a}$ and R$^{9b}$, when present, is independently selected from hydrogen, —F, —Cl, —NH$_2$, —OH, —CN, methyl, —CF$_3$, and —CCl$_3$.

In various aspects, each of R$^{9a}$ and R$^{9b}$, when present, is independently selected from hydrogen, halogen, C1-C8 alkyl, C1-C8 haloalkyl, and C1-C8 polyhaloalkyl. In a further aspect, each of R$^{9a}$ and R$^{9b}$, when present, is independently selected from hydrogen, halogen, C1-C6 alkyl, C1-C6 haloalkyl, and C1-C6 polyhaloalkyl. In a still further aspect, each of R$^{9a}$ and R$^{9b}$, when present, is independently selected from hydrogen, halogen, C1-C3 alkyl, C1-C3 haloalkyl, and C1-C3 polyhaloalkyl. In an even further aspect, each of R$^{9a}$ and R$^{9b}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of R$^{9a}$ and R$^{9b}$, when present, is independently selected from hydrogen, —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{9a}$ and R$^{9b}$, when present, is independently selected from hydrogen, —F, —Cl, methyl, —CH$_2$F, —CH$_2$Cl, —CHF$_2$, —CF$_3$, —CHCl$_2$, and —CCl$_3$. In an even further aspect, each of R$^{9a}$ and R$^{9b}$, when present, is independently selected from hydrogen, —F, —Cl, methyl, —CF$_3$, and —CCl$_3$.

In various aspects, each of R$^{9a}$ and R$^{9b}$, when present, is independently selected from hydrogen, halogen, —NH$_2$, —OH, —CN, C1-C8 haloalkyl, and C1-C8 polyhaloalkyl. In a further aspect, each of R$^{9a}$ and R$^{9b}$, when present, is independently selected from hydrogen, halogen, —NH$_2$, —OH, —CN, C1-C6 haloalkyl, and C1-C6 polyhaloalkyl. In a still further aspect, each of R$^{9a}$ and R$^{9b}$, when present, is independently selected from hydrogen, halogen, —NH$_2$, —OH, —CN, C1-C3 haloalkyl, and C1-C3 polyhaloalkyl. In an even further aspect, each of R$^{9a}$ and R$^{9b}$, when present, is independently selected from hydrogen, —F, —Cl, —NH$_2$, —OH, —CN, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of R$^{9a}$ and R$^{9b}$, when present, is independently selected from hydrogen, —F, —Cl, —NH$_2$, —OH, —CN, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{9a}$ and R$^{9b}$, when present, is independently selected from hydrogen, —F, —Cl, —NH$_2$, —OH, —CN, —CH$_2$F, —CH$_2$Cl, —CHF$_2$, —CF$_3$, —CHCl$_2$, and —CCl$_3$. In an even further aspect, each of R$^{9a}$ and R$^{9b}$, when present, is independently selected from hydrogen, —F, —Cl, —NH$_2$, —OH, —CN, —CF$_3$, and —CCl$_3$. In a still further aspect, each of R$^{9a}$ and R$^{9b}$, when present, is independently selected from hydrogen, —F, —Cl, —CH$_2$F, —CH$_2$Cl, —CHF$_2$, —CF$_3$, —CHCl$_2$, and —CCl$_3$.

In various aspects, each of R$^{9a}$ and R$^{9b}$, when present, is independently selected from hydrogen, halogen, and C1-C8 alkyl. In a further aspect, each of R$^{9a}$ and R$^{9b}$, when present, is independently selected from hydrogen, halogen, and C1-C6 alkyl. In a still further aspect, each of R$^{9a}$ and R$^{9b}$, when present, is independently selected from hydrogen, halogen, and C1-C3 alkyl. In an even further aspect, each of R$^{9a}$ and R$^{9b}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, and tert-pentyl. In a still further aspect, each of R$^{9a}$ and R$^{9b}$, when present, is independently selected from hydrogen, —F, —Cl, methyl, ethyl, propyl, and isopropyl. In a yet further aspect, each of R$^{9a}$ and R$^{9b}$, when present, is independently selected from hydrogen, —F, —Cl, and methyl.

In various aspects, each of R$^{9a}$ and R$^{9b}$, when present, is independently selected from hydrogen and C1-C8 alkyl. In a further aspect, each of R$^{9a}$ and R$^{9b}$, when present, is independently selected from hydrogen and C1-C6 alkyl. In a still further aspect, each of R$^{9a}$ and R$^{9b}$, when present, is independently selected from hydrogen and C1-C3 alkyl. In an even further aspect, each of R$^{9a}$ and R$^{9b}$, when present, is independently selected from hydrogen, methyl, ethyl, propyl, isopropyl, tert-butyl, sec-butyl, isobutyl, tert-butyl, neopentyl, isopentyl, sec-pentyl, and tert-pentyl. In a still further aspect, each of R$^{9a}$ and R$^{9b}$, when present, is independently selected from hydrogen, methyl, ethyl, propyl, and isopropyl. In a yet further aspect, each of R$^{9a}$ and R$^{9b}$, when present, is independently selected from hydrogen and methyl.

In various aspects, each of R$^{9a}$ and R$^{9b}$, when present, is independently selected from hydrogen, halogen, —NH$_2$, —OH, —CN, C1-C8 alkoxy, C1-C8 alkylamino, C1-C8 dialkylamino, and —S(O)$_n$R$^5$. In a further aspect, each of R$^{9a}$ and R$^{9b}$, when present, is independently selected from hydrogen, halogen, —NH$_2$, —OH, —CN, C1-C6 alkoxy, C1-C6 alkylamino, C1-C6 dialkylamino, and —S(O)$_n$R$^5$. In a still further aspect, each of R$^{9a}$ and R$^{9b}$, when present, is independently selected from hydrogen, halogen, —NH$_2$, —OH, —CN, C1-C3 alkoxy, C1-C3 alkylamino, C1-C3 dialkylamino, and —S(O)$_n$R$^5$. In an even further aspect, each of R$^{9a}$ and R$^{9b}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_n$R$^5$. In a still further aspect, each of R$^{9a}$ and R$^{9b}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_n$R$^5$. In a yet further aspect, each of R$^{9a}$ and R$^{9b}$, when present, is independently selected from hydrogen, —NH$_2$, —OH, —CN, —OCH$_3$, —NHCH$_3$, —N(CH$_3$)$_2$, and —S(O)$_n$R$^5$. In an even further aspect, each of R$^{9a}$ and R$^{9b}$, when present, is independently selected from hydrogen, —NH$_2$, —OH, —CN, —OCH$_3$, —NHCH$_3$, and —S(O)$_n$R$^5$.

In a further aspect, each of R$^{9a}$ and R$^{9b}$, when present, is independently selected from hydrogen and —S(O)$_n$R$^5$.

j. R$^{20}$ Groups

In one aspect, each R$^{20}$, when present, is independently selected from hydrogen and C1-C8 alkyl. In a further aspect, each R$^{20}$, when present, is hydrogen. In a still further aspect, each R$^{20}$, when present, is methyl.

In various aspects, each R$^{20}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each R$^{20}$, when present, is independently selected from hydrogen, methyl, ethyl, propyl, isopropyl, tert-butyl, sec-butyl, and isobutyl. In a still further aspect, each R$^{20}$, when present, is independently selected from hydrogen, methyl, ethyl, propyl, and isopropyl. In a yet further aspect, each R$^{20}$, when present, is independently selected from hydrogen, methyl, and ethyl. In an even further aspect, each $R^{20}$, when present, is independently selected from hydrogen and methyl.

k. $R^{21}$ Groups

In one aspect, each $R^{21}$, when present, is independently selected from hydrogen, C1-C8 alkyl, C1-C8 monohaloalkyl, C1-C8 polyhaloalkyl, —(C1-C8 alkyl)-$Cy^1$, $Cy^1$, —(C1-C8 alkyl)-$Ar^1$, and $Ar^1$. In a further aspect, each $R^{21}$, when present, is hydrogen.

In various aspects, each $R^{21}$, when present, is independently selected from hydrogen, C1-C8 alkyl, C1-C8 monohaloalkyl, and C1-C8 polyhaloalkyl.

In various aspects, each $R^{21}$, when present, is independently selected from hydrogen, C1-C8 alkyl, —(C1-C8 alkyl)-$Cy^1$, $Cy^1$, —(C1-C8 alkyl)-$Ar^1$, and $Ar^1$.

In various aspects, each $R^{21}$, when present, is independently selected from —(C1-C8 alkyl)-$Cy^1$, $Cy^1$, —(C1-C8 alkyl)-$Ar^1$, and $Ar^1$.

l. $R^{30}$ Groups

In one aspect, each $R^{30}$, when present, is independently selected from hydrogen and C1-C8 alkyl. In a further aspect, each $R^{30}$, when present, is hydrogen. In a still further aspect, each $R^{30}$, when present, is methyl.

In various aspects, each $R^{30}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{30}$, when present, is independently selected from hydrogen, methyl, ethyl, propyl, isopropyl, tert-butyl, sec-butyl, and isobutyl. In a still further aspect, each $R^{30}$, when present, is independently selected from hydrogen, methyl, ethyl, propyl, and isopropyl. In a yet further aspect, each $R^{30}$, when present, is independently selected from hydrogen, methyl, and ethyl. In an even further aspect, each $R^{30}$, when present, is independently selected from hydrogen and methyl.

m. $R^{31}$ Groups

In one aspect, each $R^{31}$, when present, is independently selected from hydrogen and C1-C8 alkyl. In a further aspect, each $R^{31}$, when present, is hydrogen. In a still further aspect, each $R^{31}$, when present, is methyl.

In various aspects, each $R^{31}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{31}$, when present, is independently selected from hydrogen, methyl, ethyl, propyl, isopropyl, tert-butyl, sec-butyl, and isobutyl. In a still further aspect, each $R^{31}$, when present, is independently selected from hydrogen, methyl, ethyl, propyl, and isopropyl. In a yet further aspect, each $R^{31}$, when present, is independently selected from hydrogen, methyl, and ethyl. In an even further aspect, each $R^{31}$, when present, is independently selected from hydrogen and methyl.

n. $R^{32}$ Groups

In one aspect, each $R^{32}$, when present, is independently selected from hydrogen and C1-C8 alkyl. In a further aspect, each $R^{32}$, when present, is hydrogen. In a still further aspect, each $R^{32}$, when present, is methyl.

In various aspects, each $R^{32}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{32}$, when present, is independently selected from hydrogen, methyl, ethyl, propyl, isopropyl, tert-butyl, sec-butyl, and isobutyl. In a still further aspect, each $R^{32}$, when present, is independently selected from hydrogen, methyl, ethyl, propyl, and isopropyl. In a yet further aspect, each $R^{32}$, when present, is independently selected from hydrogen, methyl, and ethyl. In an even further aspect, each $R^{32}$, when present, is independently selected from hydrogen and methyl.

o. $R^{33}$ Groups

In one aspect, each $R^{33}$, when present, is independently selected from hydrogen and C1-C8 alkyl. In a further aspect, each $R^{33}$, when present, is hydrogen. In a still further aspect, each $R^{33}$, when present, is methyl.

In various aspects, each $R^{33}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{33}$, when present, is independently selected from hydrogen, methyl, ethyl, propyl, isopropyl, tert-butyl, sec-butyl, and isobutyl. In a still further aspect, each $R^{33}$, when present, is independently selected from hydrogen, methyl, ethyl, propyl, and isopropyl. In a yet further aspect, each $R^{33}$, when present, is independently selected from hydrogen, methyl, and ethyl. In an even further aspect, each $R^{33}$, when present, is independently selected from hydrogen and methyl.

p. $R^{34}$ Groups

In one aspect, each $R^{34}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-$Ar^{21}$, and $Ar^{21}$. In a further aspect, each $R^{34}$, when present, is hydrogen.

In a further aspect, each $R^{34}$, when present, is independently selected from hydrogen, C1-C6 alkyl, C1-C6 monohaloalkyl, C1-C6 polyhaloalkyl, C3-C6 cycloalkyl, C2-C5 heterocycloalkyl, —(C1-C6)-$Ar^{21}$, and $Ar^{21}$. In a still further aspect, each $R^{34}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, —(C1-C6)-$Ar^{21}$, and $Ar^{21}$.

In a further aspect, each $R^{34}$, when present, is independently selected from hydrogen, —(C1-C6)-$Ar^{21}$, and $Ar^{21}$. In a still further aspect, each $R^{34}$, when present, is independently selected from hydrogen, —(CH$_2$)—$Ar^{21}$, —(CH$_2$)$_2$—$Ar^{21}$, —(CH$_2$)$_3$—$Ar^{21}$, —(CH(CH$_3$)CH$_2$)—$Ar^{21}$, and $Ar^{21}$. In a yet further aspect, each $R^{34}$, when present, is independently selected from hydrogen, —(CH$_2$)—$Ar^{21}$, —(CH$_2$)$_2$—$Ar^{21}$, and $Ar^{21}$. In an even further aspect, each $R^{34}$, when present, is independently selected from hydrogen, —(CH$_2$)—$Ar^{21}$, and $Ar^{21}$. In various further aspects, each $Ar^{21}$ can be substituted with 0-3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino. In a yet further aspect, each $Ar^{21}$ can be substituted with 0-3 groups independently selected from —F, —Cl, —NH$_2$, —OH, —CN, —CH$_3$, —CF$_3$, —CHF$_2$, —CH$_2$F, —OCH$_3$, —N(CH$_3$)$_2$, and —NHCH$_3$.

In a further aspect, each $R^{34}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{34}$, when present, is independently selected from hydrogen, C1-C8 alkyl, C1-C8 monohaloalkyl, and C1-C8 polyhaloalkyl. In a still further aspect, each $R^{34}$, when present, is independently selected from hydrogen, C1-C6 alkyl, C1-C6 monohaloalkyl, and C1-C6 polyhaloalkyl. In a yet further aspect, each $R^{34}$, when present, is independently selected from hydrogen, C1-C3 alkyl, C1-C3 monohaloalkyl, and C1-C38 polyhaloalkyl.

In a further aspect, each $R^{34}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, each $R^{34}$, when present, is independently selected from hydrogen, methyl, ethyl, propyl, isopropyl, tert-butyl, sec-butyl, isobutyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each $R^{34}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each $R^{34}$, when present, is independently selected from hydrogen, methyl, —CH$_2$F, —CHF$_2$, and —CF$_3$.

q. $R^{35}$ Groups

In one aspect, each $R^{35}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{22}$, and Ar$^{22}$. In a further aspect, each $R^{35}$, when present, is hydrogen.

In a further aspect, each $R^{35}$, when present, is independently selected from hydrogen, C1-C6 alkyl, C1-C6 monohaloalkyl, C1-C6 polyhaloalkyl, C3-C6 cycloalkyl, C2-C5 heterocycloalkyl, —(C1-C6)-Ar$^{22}$, and Ar$^{22}$. In a still further aspect, each $R^{35}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, —(C1-C6)-Ar$^{22}$, and Ar$^{22}$.

In a further aspect, each $R^{35}$, when present, is independently selected from hydrogen, —(C1-C6)-Ar$^{22}$, and Ar$^{22}$. In a still further aspect, each $R^{35}$, when present, is independently selected from hydrogen, —(CH$_2$)—Ar$^{22}$, —(CH$_2$)$_2$—Ar$^{22}$, —(CH$_2$)$_3$—Ar$^{22}$, —(CH(CH$_3$)CH$_2$)—Ar$^{22}$, and Ar$^{22}$. In a yet further aspect, each $R^{35}$, when present, is independently selected from hydrogen, —(CH$_2$)—Ar$^{22}$, —(CH$_2$)$_2$—Ar$^{22}$, and Ar$^{22}$. In an even further aspect, each $R^{35}$, when present, is independently selected from hydrogen, —(CH$_2$)—Ar$^{22}$, and Ar$^{22}$. In various further aspects, each Ar$^{22}$ can be substituted with 0-3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino. In a yet further aspect, each Ar$^{22}$ can be substituted with 0-3 groups independently selected from —F, —Cl, —NH$_2$, —OH, —CN, —CH$_3$, —CF$_3$, —CHF$_2$, —CH$_2$F, —OCH$_3$, —N(CH$_3$)$_2$, and —NHCH$_3$.

In a further aspect, each $R^{35}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{35}$, when present, is independently selected from hydrogen, C1-C8 alkyl, C1-C8 monohaloalkyl, and C1-C8 polyhaloalkyl. In a still further aspect, each $R^{35}$, when present, is independently selected from hydrogen, C1-C6 alkyl, C1-C6 monohaloalkyl, and C1-C6 polyhaloalkyl. In a yet further aspect, each $R^{35}$, when present, is independently selected from hydrogen, C1-C3 alkyl, C1-C3 monohaloalkyl, and C1-C38 polyhaloalkyl.

In a further aspect, each $R^{35}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, each $R^{35}$, when present, is independently selected from hydrogen, methyl, ethyl, propyl, isopropyl, tert-butyl, sec-butyl, isobutyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each $R^{35}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each $R^{35}$, when present, is independently selected from hydrogen, methyl, —CH$_2$F, —CHF$_2$, and —CF$_3$.

r. $R^{36}$ Groups

In one aspect, each $R^{36}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{23}$, and Ar$^{23}$. In a further aspect, each $R^{36}$, when present, is hydrogen.

In a further aspect, each $R^{36}$, when present, is independently selected from hydrogen, C1-C6 alkyl, C1-C6 monohaloalkyl, C1-C6 polyhaloalkyl, C3-C6 cycloalkyl, C2-C5 heterocycloalkyl, —(C1-C6)-Ar$^{23}$, and Ar$^{23}$. In a still further aspect, each $R^{36}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, —(C1-C6)-Ar$^{23}$, and Ar$^{23}$.

In a further aspect, each $R^{36}$, when present, is independently selected from hydrogen, —(C1-C6)-Ar$^{23}$, and Ar$^{23}$. In a still further aspect, each $R^{36}$, when present, is independently selected from hydrogen, —(CH$_2$)—Ar$^{23}$, —(CH$_2$)$_2$—Ar$^{23}$, —(CH$_2$)$_3$—Ar$^{23}$, —(CH(CH$_3$)CH$_2$)—Ar$^{23}$, and Ar$^{23}$. In a yet further aspect, each $R^{36}$, when present, is independently selected from hydrogen, —(CH$_2$)—Ar$^{23}$, —(CH$_2$)$_2$—Ar$^{23}$, and Ar$^{23}$. In an even further aspect, each $R^{36}$, when present, is independently selected from hydrogen, —(CH$_2$)—Ar$^{23}$, and Ar$^{23}$. In various further aspects, each Ar$^{23}$ can be substituted with 0-3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino. In a yet further aspect, each Ar$^{23}$ can be substituted with 0-3 groups independently selected from —F, —Cl, —NH$_2$, —OH, —CN, —CH$_3$, —CF$_3$, —CHF$_2$, —CH$_2$F, —OCH$_3$, —N(CH$_3$)$_2$, and —NHCH$_3$.

In a further aspect, each $R^{36}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{36}$, when present, is independently selected from hydrogen, C1-C8 alkyl, C1-C8 monohaloalkyl, and C1-C8 polyhaloalkyl. In a still further aspect, each $R^{36}$, when present, is independently selected from hydrogen, C1-C6 alkyl, C1-C6 monohaloalkyl, and C1-C6 polyhaloalkyl. In a yet further aspect, each $R^{36}$, when present, is independently selected from hydrogen, C1-C3 alkyl, C1-C3 monohaloalkyl, and C1-C38 polyhaloalkyl.

In a further aspect, each $R^{36}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, each $R^{36}$, when present, is independently selected from hydrogen, methyl, ethyl, propyl, isopropyl, tert-butyl, sec-butyl, isobutyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each $R^{36}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each $R^{36}$, when present, is independently selected from hydrogen, methyl, —CH$_2$F, —CHF$_2$, and —CF$_3$.

s. $R^{37}$ Groups

In one aspect, each $R^{37}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN.

In one aspect, each $R^{37}$, when present, is independently selected from C1-C4 alkyl, C1-C4 alkoxy, C1-C4 monoalkylamino, or C1-C4 dialkylamino substituted with 1 or 2 groups selected from —CH$_3$, —CF$_3$, —F, —OH, —NH$_2$, and —CN.

In a further aspect, each $R^{37}$, when present, is independently selected from C1-C3 alkyl, C1-C3 alkoxy, C1-C3 monoalkylamino, and C1-C3 dialkylamino substituted with 1 or 2 groups independently selected from —CH$_3$, —CF$_3$, —F, —OH, —NH$_2$, and —CN.

In a further aspect, each $R^{37}$, when present, is independently selected from —CH$_2$R$^{38}$, —CHR$^{38}$R$^{39}$, —CHR$^{38}$CH$_2$R$^{39}$, —CR$^{38}$R$^{39}$CH$_3$, and —CH$_2$CHR$^{38}$R$^{39}$; and wherein each of R$^{38}$ and R$^{39}$, when present, is independently selected from —CH$_3$, —CF$_3$, —F, —OH, —NH$_2$, and —CN. In a still further aspect, each $R^{37}$, when present, is independently selected from —CH$_2$R$^{38}$ and —CHR$^{38}$R$^{39}$; and wherein each of R$^{38}$ and R$^{39}$, when present, is independently selected from —CH$_3$, —CF$_3$, —F, —OH, —NH$_2$, and —CN. In a yet further aspect, each $R^{37}$, when present, is —CH$_2$R$^{38}$; and each R$^{38}$ is independently selected from —CH$_3$, —CF$_3$, —F, —OH, —NH$_2$, and —CN. In an even further aspect, each $R^{37}$, when present, is independently selected from —CH$_2$CF$_3$, —CH$_2$CH$_3$, —CH$_2$F, —CH$_2$OH, —CH$_2$NH$_2$, and —CH$_2$CN. In a yet further aspect, each $R^{37}$, when present, is independently selected from —CH$_2$CF$_3$, —CH$_2$F, —CH$_2$OH, —CH$_2$NH$_2$, and —CH$_2$CN. In a still further aspect, each $R^{37}$, when present, is —CHR$^{38}$R$^{39}$; and each of R$^{38}$ and R$^{39}$, when present, is independently selected from —CH$_3$, —CF$_3$, —F, —OH, —NH$_2$, and —CN.

In a further aspect, each $R^{37}$, when present, is —CHR$^{38}$CH$_2$R$^{39}$; and each of R$^{38}$ and R$^{39}$, when present, is independently selected from —CH$_3$, —CF$_3$, —F, —OH, —NH$_2$, and —CN. In a yet further aspect, each $R^{37}$, when present, is —CH$_2$CHR$^{38}$R$^{39}$; and each of R$^{38}$ and R$^{39}$, when present, is independently selected from —CH$_3$, —CF$_3$, —F, —OH, —NH$_2$, and —CN. In an even further aspect, each $R^{37}$, when present, is —CR$^{38}$R$^{39}$CH$_3$; and each of R$^{38}$ and R$^{39}$, when present, is independently selected from —CH$_3$, —CF$_3$, —F, —OH, —NH$_2$, and —CN.

In a further aspect, each $R^{37}$, when present, is independently selected from —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each $R^{37}$, when present, is —CH$_2$CF$_3$. In a yet further aspect, each $R^{37}$, when present, is —CH$_2$F. In an even further aspect, each $R^{37}$, when present, is —CH$_2$OH. In a still further aspect, each $R^{37}$, when present, is —CH$_2$NH$_2$. In a yet further aspect, each $R^{37}$, when present, is —CH$_2$CN.

t. $R^{38}$ Groups

In one aspect, each $R^{38}$, when present, is independently selected from —CH$_3$, —CF$_3$, —F, —OH, —NH$_2$, and —CN. In a further aspect, each $R^{38}$, when present, is independently selected from —CF$_3$, —F, —OH, —NH$_2$, and —CN. In a still further aspect, each $R^{38}$, when present, is independently selected from —CH$_3$, —F, —OH, —NH$_2$, and —CN. In a yet further aspect, each $R^{38}$, when present, is independently selected from —CH$_3$, —CF$_3$, —OH, —NH$_2$, and —CN. In an even further aspect, each $R^{38}$, when present, is independently selected from —CH$_3$, —CF$_3$, —F, —NH$_2$, and —CN. In a still further aspect, each $R^{38}$, when present, is independently selected from —CH$_3$, —CF$_3$, —F, —OH, and —CN. In a yet further aspect, each $R^{38}$, when present, is independently selected from —CH$_3$, —CF$_3$, —F, —OH, and —NH$_2$.

In a further aspect, each $R^{38}$, when present, is —CH$_3$. In a still further aspect, each $R^{38}$, when present, is —CF$_3$. In a yet further aspect, each $R^{38}$, when present, is —F. In an even further aspect, each $R^{38}$, when present, is —OH. In a still further aspect, each $R^{38}$, when present, is —NH$_2$. In a yet further aspect, each $R^{38}$, when present, is —CN.

u. $R^{39}$ Groups

In one aspect, each $R^{39}$, when present, is independently selected from —CH$_3$, —CF$_3$, —F, —OH, —NH$_2$, and —CN. In a further aspect, each $R^{39}$, when present, is independently selected from —CF$_3$, —F, —OH, —NH$_2$, and —CN. In a still further aspect, each $R^{39}$, when present, is independently selected from —CH$_3$, —F, —OH, —NH$_2$, and —CN. In a yet further aspect, each $R^{39}$, when present, is independently selected from —CH$_3$, —CF$_3$, —OH, —NH$_2$, and —CN. In an even further aspect, each $R^{39}$, when present, is independently selected from —CH$_3$, —CF$_3$, —F, —NH$_2$, and —CN. In a still further aspect, each $R^{39}$, when present, is independently selected from —CH$_3$, —CF$_3$, —F, —OH, and —CN. In a yet further aspect, each $R^{39}$, when present, is independently selected from —CH$_3$, —CF$_3$, —F, —OH, and —NH$_2$.

In a further aspect, each $R^{39}$, when present, is —CH$_3$. In a still further aspect, each $R^{39}$, when present, is —CF$_3$. In a yet further aspect, each $R^{39}$, when present, is —F. In an even further aspect, each $R^{39}$, when present, is —OH. In a still further aspect, each $R^{39}$, when present, is —NH$_2$. In a yet further aspect, each $R^{39}$, when present, is —CN.

v. $R^{45}$ Groups

In one aspect, each $R^{45}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl. In a further aspect, each $R^{45}$, when present, is hydrogen.

In a further aspect, each $R^{45}$, when present, is independently selected from hydrogen, C1-C6 alkyl, C1-C6 hydroxyalkyl, C1-C6 monohaloalkyl, C1-C6 polyhaloalkyl, C3-C6 cycloalkyl, C2-C5 heterocycloalkyl, phenyl, and monocyclic heteroaryl. In a still further aspect, each $R^{45}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, phenyl, and monocyclic heteroaryl.

In a further aspect, each $R^{45}$, when present, is independently selected from hydrogen, substituted phenyl, and substituted monocyclic heteroaryl. In a still further aspect, each phenyl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a yet further aspect, each phenyl can be substituted with 0-3 groups independently selected from —F, —Cl, —NH$_2$, —OH, —CN, —CH$_3$, —CF$_3$, —CHF$_2$, —CH$_2$F, and —OCH$_3$. In an even further aspect, each monocyclic heteroaryl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, each monocyclic heteroaryl can be substituted with 0-3 groups independently selected from —F, —Cl, —NH$_2$, —OH, —CN, —CH$_3$, —CF$_3$, —CHF$_2$, —CH$_2$F, and —OCH$_3$. In various further aspects, each monocyclic heteroaryl is independently selected from pyridine, pyrimidine, and pyradazine, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, each monocyclic heteroaryl is independently selected from pyridine, pyrimidine, and pyradazine, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{45}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{45}$, when present, is independently selected from hydrogen, C1-C8 alkyl, C1-C8 hydroxyalkyl, C1-C8 monohaloalkyl, and C1-C8 polyhaloalkyl. In a still further aspect, each $R^{45}$, when present, is independently selected from hydrogen, C1-C6 alkyl, C1-C6 hydroxyalkyl, C1-C6 monohaloalkyl, and C1-C6 polyhaloalkyl. In a yet further aspect, each $R^{45}$, when present, is independently selected from hydrogen, C1-C3 alkyl, C1-C3 hydroxyalkyl, C1-C3 monohaloalkyl, and C1-C38 polyhaloalkyl.

In a further aspect, each $R^{45}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$ CHBr$_2$, —(CH$_2$)$_2$CBr$_3$, —(CH$_2$)$_2$CHI$_2$, —(CH$_2$)$_2$CI$_3$, 1-hydroxyethyl, 2-hydroxyethyl, 1-hydroxypropyl, 2-hydroxypropyl, 3 hydroxypropyl, 1-hydroxybutyl, 2-hydroxybutyl, 3-hydroxybutyl, and 4-hydroxybutyl.

w. $R^{46}$ Groups

In one aspect, each $R^{46}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl. In a further aspect, each $R^{46}$, when present, is hydrogen.

In a further aspect, each $R^{46}$, when present, is independently selected from hydrogen, C1-C6 alkyl, C1-C6 hydroxyalkyl, C1-C6 monohaloalkyl, C1-C6 polyhaloalkyl, C3-C6 cycloalkyl, C2-C5 heterocycloalkyl, phenyl, and monocyclic heteroaryl. In a still further aspect, each $R^{46}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, phenyl, and monocyclic heteroaryl.

In a further aspect, each $R^{46}$, when present, is independently selected from hydrogen, substituted phenyl, and substituted monocyclic heteroaryl. In a still further aspect, each phenyl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a yet further aspect, each phenyl can be substituted with 0-3 groups independently selected from —F, —Cl, —NH$_2$, —OH, —CN, —CH$_3$, —CF$_3$, —CHF$_2$, —CH$_2$F, and —OCH$_3$. In an even further aspect, each monocyclic heteroaryl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, each monocyclic heteroaryl can be substituted with 0-3 groups independently selected from —F, —Cl, —NH$_2$, —OH, —CN, —CH$_3$, —CF$_3$, —CHF$_2$, —CH$_2$F, and —OCH$_3$. In various further aspects, each monocyclic heteroaryl is independently selected from pyridine, pyrimidine, and pyradazine, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, each monocyclic heteroaryl is independently selected from pyridine, pyrimidine, and pyradazine, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{46}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{46}$, when present, is independently selected from hydrogen, C1-C8 alkyl, C1-C8 hydroxyalkyl, C1-C8 monohaloalkyl, and C1-C8 polyhaloalkyl. In a still further aspect, each $R^{46}$, when present, is independently selected from hydrogen, C1-C6 alkyl, C1-C6 hydroxyalkyl, C1-C6 monohaloalkyl, and C1-C6 polyhaloalkyl. In a yet further aspect, each $R^{46}$, when present, is independently selected from hydrogen, C1-C3 alkyl, C1-C3 hydroxyalkyl, C1-C3 monohaloalkyl, and C1-C38 polyhaloalkyl.

In a further aspect, each $R^{46}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, 1-hydroxyethyl, 2-hydroxyethyl, 1-hydroxypropyl, 2-hydroxypropyl, 3 hydroxypropyl, 1-hydroxybutyl, 2-hydroxybutyl, 3-hydroxybutyl, and 4-hydroxybutyl.

x. $R^{50A}$, $R^{50B}$, $R^{50C}$, $R^{50D}$, $R^{50E}$, $R^{50F}$, $R^{50G}$, and $R^{50H}$ Groups In one aspect, each of $R^{50A}$ and $R^{50B}$ are independently selected from C3-C9 cycloalkyl and C2-C7 heterocycloalkyl, and wherein each $Cy^1$ is independently substituted with 0, 1, 2, or 3 groups independently selected from hydrogen, halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$.

In various aspects, each of R$^{50A}$ and R$^{50B}$ are independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino. In a further aspect, each of R$^{50A}$ and R$^{50B}$ are independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$. In a still further aspect, each of R$^{50A}$ and R$^{50B}$ are independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, each of R$^{50A}$ and R$^{50B}$ are independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$.

In a further aspect, each of R$^{50A}$ and R$^{50B}$ are independently selected from hydrogen, —F, and —Cl. In a still further aspect, each of R$^{50A}$ and R$^{50B}$ are independently selected from hydrogen and —F. In a yet further aspect, each of R$^{50A}$ and R$^{50B}$ are hydrogen.

In one aspect, each of R$^{50a}$, R$^{50b}$, R$^{50c}$, and R$^{50d}$ is independently selected from C3-C9 cycloalkyl and C2-C7 heterocycloalkyl, and wherein each Cy$^1$ is independently substituted with 0, 1, 2, or 3 groups independently selected from hydrogen, halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$, provided that at least one of R$^{50a}$, R$^{50b}$, R$^{50c}$, and R$^{50d}$ is hydrogen.

In various aspects, each of R$^{50a}$, R$^{50b}$, R$^{50c}$, and R$^{50d}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of R$^{50a}$, R$^{50b}$, R$^{50c}$, and R$^{50d}$ is hydrogen. In a further aspect, each of R$^{50a}$, R$^{50b}$, R$^{50c}$, and R$^{50d}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$, provided that at least one of R$^{50a}$, R$^{50b}$, R$^{50c}$, and R$^{50d}$ is hydrogen. In a still further aspect, each of each of R$^{50a}$, R$^{50b}$, R$^{50c}$, and R$^{50d}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$, provided that at least one of R$^{50a}$, R$^{50b}$, R$^{50c}$, and R$^{50d}$ is hydrogen. In a still further aspect, each of R$^{50a}$, R$^{50b}$, R$^{50c}$, and R$^{50d}$ independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$, provided that at least one of R$^{50a}$, R$^{50b}$, R$^{50c}$, and R$^{50d}$ is hydrogen.

In a further aspect, each of R$^{50a}$, R$^{50b}$, R$^{50c}$, and R$^{50d}$ is independently selected from hydrogen, —F, and —Cl, provided that at least one of R$^{50a}$, R$^{50b}$, R$^{50c}$, and R$^{50d}$ is hydrogen. In a still further aspect, each of R$^{50a}$, R$^{50b}$, R$^{50c}$, and R$^{50d}$ is independently selected from hydrogen and —F, provided that at least one of R$^{50a}$, R$^{50b}$, R$^{50c}$, and R$^{50d}$ is hydrogen. In a yet further aspect, each of R$^{50a}$, R$^{50b}$, R$^{50c}$, and R$^{50d}$ is hydrogen.

In one aspect, each of R$^{50a}$, R$^{50b}$, R$^{50c}$, R$^{50d}$, R$^{50e}$, R$^{50f}$, R$^{50g}$, and R$^{50h}$ is independently selected from C3-C9 cycloalkyl and C2-C7 heterocycloalkyl, and wherein each Cy$^1$ is independently substituted with 0, 1, 2, or 3 groups independently selected from hydrogen, halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$, provided that at least five of R$^{50a}$, R$^{50b}$, R$^{50c}$, R$^{50d}$, R$^{50e}$, R$^{50f}$, R$^{50g}$, and R$^{50h}$ are hydrogen.

In various aspects, each of R$^{50a}$, R$^{50b}$, R$^{50c}$, R$^{50d}$, R$^{50e}$, R$^{50f}$, R$^{50g}$, and R$^{50h}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino, provided that at least one of R$^{50a}$, R$^{50b}$, R$^{50c}$, and R$^{50d}$ is hydrogen. In a further aspect, each of R$^{50a}$, R$^{50b}$, R$^{50c}$, R$^{50d}$, R$^{50e}$, R$^{50f}$, R$^{50g}$, and R$^{50h}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$, provided that at least one of R$^{50a}$, R$^{50b}$, R$^{50c}$, and R$^{50d}$ is hydrogen. In a still further aspect, each of R$^{50a}$, R$^{50b}$, R$^{50c}$, R$^{50d}$, R$^{50e}$, R$^{50f}$, R$^{50g}$, and R$^{50h}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$, provided that at least one of R$^{50a}$, R$^{50b}$, R$^{50c}$, and R$^{50d}$ is hydrogen. In a still further aspect, each of R$^{50a}$, R$^{50b}$, R$^{50c}$, R$^{50d}$, R$^{50e}$, R$^{50f}$, R$^{50g}$, and R$^{50h}$ is independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$, provided that at least one of R$^{50a}$, R$^{50b}$, R$^{50c}$, and R$^{50d}$ is hydrogen.

In a further aspect, each of R$^{50a}$, R$^{50b}$, R$^{50c}$, R$^{50d}$, R$^{50e}$, R$^{50f}$, R$^{50g}$, and R$^{50h}$ is independently selected from hydrogen, —F, and —Cl, provided that at least one of R$^{50a}$, R$^{50b}$, R$^{50c}$, and R$^{50d}$ is hydrogen. In a still further aspect, each of R$^{50a}$, R$^{50b}$, R$^{50c}$, R$^{50d}$, R$^{50e}$, R$^{50f}$, R$^{50g}$, and R$^{50h}$ is independently selected from hydrogen and —F, provided that at least one of R$^{50a}$, R$^{50b}$, R$^{50c}$, and R$^{50d}$ is hydrogen. In a yet further aspect, each of R$^{50a}$, R$^{50b}$, R$^{50c}$, R$^{50d}$, R$^{50e}$, R$^{50f}$, R$^{50g}$, and R$^{50h}$ are hydrogen.

y. R$^{60A}$, R$^{60B}$, R$^{60C}$, R$^{60D}$, and R$^{60E}$ Groups

In one aspect, each of R$^{60a}$, R$^{60b}$, R$^{60c}$, R$^{60d}$, and R$^{60e}$ is independently selected from hydrogen, halogen, —NH$_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino, provided that at least two of R$^{60a}$, R$^{60b}$, R$^{60c}$, R$^{60d}$, and R$^{60e}$ are hydrogen. In one aspect, each of R$^{60a}$, R$^{60b}$, R$^{60c}$, R$^{60d}$, and R$^{60e}$ are independently selected from hydrogen, halogen, —NH$_2$, —OH, —CN, —S(O). R$^{36}$, C1-C6 alkyl, C1-C6 monohaloalkyl, C1-C6 polyhaloalkyl, C1-C6 alkoxy, C1-C6 alkylamino, and C1-C6 dialkylamino, provided that at least two of R$^{60a}$, R$^{60b}$, R$^{60c}$, R$^{60d}$, and R$^{60e}$ are hydrogen.

In various aspects, each of R$^{60a}$, R$^{60b}$, R$^{60c}$, R$^{60d}$, and R$^{60e}$ is independently selected from hydrogen, halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, C1-C3 dialkylamino; provided that at least two of R$^{60a}$, R$^{60b}$, R$^{60c}$, R$^{60d}$, and R$^{60e}$ are hydrogen. In a further aspect, each of R$^{60a}$, R$^{60b}$, R$^{60c}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —(S=O)CH$_3$, and —SO$_2$CH$_3$, provided that at least two of R$^{60a}$, R$^{60b}$, R$^{60c}$, R$^{60d}$, and R$^{60e}$ are hydrogen. In a still further aspect, each of R$^{60a}$, R$^{60b}$, R$^{60c}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$, provided that at least two of R$^{60a}$, R$^{60b}$, R$^{60c}$, R$^{60d}$, and R$^{60e}$ are hydrogen. In a yet further aspect, each of R$^{60a}$, R$^{60b}$, R$^{60c}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, —N(CH$_3$)$_2$, —(S=O)CH$_3$, and —SO$_2$CH$_3$, provided that at least two of R$^{60a}$, R$^{60b}$, R$^{60c}$, R$^{60d}$, and R$^{60e}$ are hydrogen.

In various aspects, each of R$^{60a}$, R$^{60b}$, R$^{60c}$, R$^{60d}$, and R$^{60e}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of R$^{60a}$, R$^{60b}$, R$^{60c}$, R$^{60d}$, and R$^{60e}$ are hydrogen. In a further aspect, each of R$^{60a}$, R$^{60b}$, R$^{60c}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$, provided that at least two of R$^{60a}$, R$^{60b}$, R$^{60c}$, R$^{60d}$, and R$^{60e}$ are hydrogen. In a still further aspect, each of R$^{60a}$, R$^{60b}$, R$^{60c}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$, provided that at least two of R$^{60a}$, R$^{60b}$, R$^{60c}$, R$^{60d}$, and R$^{60e}$ are hydrogen. In a yet further aspect, each of R$^{60a}$, R$^{60b}$, R$^{60c}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$, provided that at least two of R$^{60a}$, R$^{60b}$, R$^{60c}$, R$^{60d}$, and R$^{60e}$ are hydrogen.

In a further aspect, each of R$^{60a}$, R$^{60b}$, R$^{60c}$, R$^{60d}$, and R$^{60e}$ is independently selected from hydrogen, —F, —Cl, —CH$_2$F, —CHF$_2$, —CF$_3$, and —OCH$_3$, provided that at least two of R$^{60a}$, R$^{60b}$, R$^{60c}$, R$^{60d}$, and R$^{60e}$ are hydrogen. In a yet further aspect, each of R$^{60a}$, R$^{60b}$, R$^{60c}$, R$^{60d}$, and R$^{60e}$ is hydrogen.

In one aspect, each of R$^{60b}$, R$^{60c}$, R$^{60d}$, and R$^{60e}$ is independently selected from hydrogen, halogen, —NH$_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino, provided that at least one of R$^{60b}$, R$^{60c}$, R$^{60d}$, and R$^{60e}$ is hydrogen. In one aspect, each of R$^{60b}$, R$^{60c}$, R$^{60d}$, and R$^{60e}$ is independently selected from hydrogen, halogen, —NH$_2$, —OH, —CN, —S(O)$_n$R$^{36}$, C1-C6 alkyl, C1-C6 monohaloalkyl, C1-C6 polyhaloalkyl, C1-C6 alkoxy, C1-C6 alkylamino, and C1-C6 dialkylamino, provided that at least one of R$^{60b}$, R$^{60c}$, R$^{60d}$, and R$^{60e}$ is hydrogen.

In various aspects, each of R$^{60b}$, R$^{60c}$, R$^{60d}$, and R$^{60e}$ is independently selected from hydrogen, halogen, —NH$_2$, —OH, —CN, —S(O). R$^{36}$, C1-C3 alkyl, C1-C3 monohaloalkyl, C1-C3 polyhaloalkyl, C1-C3 alkoxy, C1-C3 alkylamino, C1-C3 dialkylamino; provided that at least one of R$^{60b}$, R$^{60c}$, R$^{60d}$, and R$^{60e}$ is hydrogen. In a further aspect, each of R$^{60b}$, R$^{60c}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —(S=O)CH$_3$, and —SO$_2$CH$_3$, provided that at least one of R$^{60b}$, R$^{60c}$, R$^{60d}$, and R$^{60e}$ is hydrogen. In a still further aspect, each of R$^{60b}$, R$^{60c}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$, provided that at least one of R$^{60b}$, R$^{60c}$, R$^{60d}$, and R$^{60e}$ is hydrogen. In a yet further aspect, each of R$^{60b}$, R$^{60c}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, —N(CH$_3$)$_2$, —(S=O)CH$_3$, and —SO$_2$CH$_3$, provided that at least one of R$^{60b}$, R$^{60c}$, R$^{60d}$, and R$^{60e}$ is hydrogen.

In various aspects, each of R$^{60b}$, R$^{60c}$, R$^{60d}$, and R$^{60e}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least one of R$^{60b}$, R$^{60c}$, R$^{60d}$, and R$^{60e}$ is hydrogen. In a further aspect, each of R$^{60b}$, R$^{60c}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$, provided that at least one of R$^{60b}$, R$^{60c}$, R$^{60d}$, and R$^{60e}$ is hydrogen. In a still further aspect, each of R$^{60b}$, R$^{60c}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$, provided that at least one of R$^{60b}$, R$^{60c}$, R$^{60d}$, and R$^{60e}$ is hydrogen. In a yet further aspect, each of R$^{60b}$, R$^{60c}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$, provided that at least one of R$^{60b}$, R$^{60c}$, R$^{60d}$, and R$^{60e}$ is hydrogen.

In a further aspect, each of R$^{60b}$, R$^{60c}$, R$^{60d}$, and R$^{60e}$ is independently selected from hydrogen, —F, —Cl, —CH$_2$F, —CHF$_2$, —CF$_3$, and —OCH$_3$, provided that at least one of R$^{60b}$, R$^{60c}$, R$^{60d}$, and R$^{60e}$ is hydrogen. In a yet further aspect, each of R$^{60b}$, R$^{60c}$, R$^{60d}$, and R$^{60e}$ is hydrogen.

In one aspect, each of R$^{60a}$, R$^{60c}$, R$^{60d}$, and R$^{60e}$ is independently selected from hydrogen, halogen, —NH$_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino, provided that at least one of R$^{60a}$, R$^{60c}$, R$^{60d}$, and R$^{60e}$ is hydrogen. In one aspect, each of R$^{60a}$, R$^{60c}$, R$^{60d}$, and R$^{60e}$ is independently selected from hydrogen, halogen, —NH$_2$, —OH, —CN, —S(O)$_n$R$^{36}$, C1-C6 alkyl, C1-C6 monohaloalkyl, C1-C6 polyhaloalkyl, C1-C6 alkoxy, C1-C6 alkylamino, and C1-C6 dialkylamino, provided that at least one of R$^{60a}$, R$^{60c}$, R$^{60d}$, and R$^{60e}$ is hydrogen.

In various aspects, each of R$^{60a}$, R$^{60c}$, R$^{60d}$, and R$^{60e}$ is independently selected from hydrogen, halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, C1-C3 dialkylamino; provided that at least one of R$^{60a}$, R$^{60c}$, R$^{60d}$, and R$^{60e}$ is hydrogen. In a further aspect, each of R$^{60a}$, R$^{60c}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —(S=O)CH$_3$, and —SO$_2$CH$_3$, provided that at least one of R$^{60a}$, R$^{60c}$, R$^{60d}$, and R$^{60e}$ is hydrogen. In a still further aspect, each of R$^{60a}$, R$^{60c}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$, provided that at least one of R$^{60a}$, R$^{60c}$, R$^{60d}$, and R$^{60e}$ is hydrogen. In a yet further aspect, each of R$^{60a}$, R$^{60c}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, —N(CH$_3$)$_2$, —(S=O)CH$_3$, and —SO$_2$CH$_3$, provided that at least one of R$^{60a}$, R$^{60c}$, R$^{60d}$, and R$^{60e}$ is hydrogen.

In various aspects, each of R$^{60a}$, R$^{60c}$, R$^{60d}$, and R$^{60e}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least one of R$^{60a}$, R$^{60c}$, R$^{60d}$, and R$^{60e}$ is hydrogen. In a further aspect, each of R$^{60a}$, R$^{60c}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$, provided that at least one of R$^{60a}$, R$^{60c}$, R$^{60d}$, and R$^{60e}$ is hydrogen. In a still further aspect, each of R$^{60a}$, R$^{60c}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$, provided that at least one of R$^{60a}$, R$^{60c}$, R$^{60d}$, and R$^{60e}$ is hydrogen. In a yet further aspect, each of R$^{60a}$, R$^{60c}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$, provided that at least one of R$^{60a}$, R$^{60c}$, R$^{60d}$, and R$^{60e}$ is hydrogen.

In a further aspect, each of R$^{60a}$, R$^{60c}$, R$^{60d}$, and R$^{60e}$ is independently selected from hydrogen, —F, —Cl, —CH$_2$F, —CHF$_2$, —CF$_3$, and —OCH$_3$, provided that at least one of R$^{60a}$, R$^{60c}$, R$^{60d}$, and R$^{60e}$ is hydrogen. In a yet further aspect, each of R$^{60a}$, R$^{60c}$, R$^{60d}$, and R$^{60e}$ is hydrogen.

In one aspect, each of R$^{60a}$, R$^{60b}$, R$^{60d}$, and R$^{60e}$ is independently selected from hydrogen, halogen, —NH$_2$, —OH, —CN, —S(O)$_n$R$^{36}$, C1-C8 alkyl, C1-C8 monohaloalkyl, C1-C8 polyhaloalkyl, C1-C8 alkoxy, C1-C8 alkylamino, and C1-C8 dialkylamino, provided that at least one of R$^{60a}$, R$^{60b}$, R$^{60d}$, and R$^{60e}$ is hydrogen. In one aspect, each of R$^{60a}$, R$^{60b}$, R$^{60d}$, and R$^{60e}$ is independently selected from hydrogen, halogen, —NH$_2$, —OH, —CN, —S(O)$_n$R$^{36}$, C1-C6 alkyl, C1-C6 monohaloalkyl, C1-C6 polyhaloalkyl, C1-C6 alkoxy, C1-C6 alkylamino, and C1-C6 dialkylamino, provided that at least one of R$^{60a}$, R$^{60b}$, R$^{60d}$, and R$^{60e}$ is hydrogen.

In various aspects, each of R$^{60a}$, R$^{60b}$, R$^{60d}$, and R$^{60e}$ is independently selected from hydrogen, halogen, —NH$_2$, —OH, —CN, —S(O)$_n$R$^{36}$, C1-C3 alkyl, C1-C3 monohaloalkyl, C1-C3 polyhaloalkyl, C1-C3 alkoxy, C1-C3 alkylamino, C1-C3 dialkylamino; provided that at least one of R$^{60a}$, R$^{60b}$, R$^{60d}$, and R$^{60e}$ is hydrogen. In a further aspect, each of R$^{60a}$, R$^{60b}$, R$^{60d}$, and R$^{60e}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —(S=O)CH$_3$, and —SO$_2$CH$_3$, provided that at least one of R$^{60a}$, R$^{60b}$, R$^{60d}$, and R$^{60e}$ is hydrogen. In a still further aspect, each of R$^{60a}$, R$^{60b}$, R$^{60d}$, and R$^{60e}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$, provided that at least one of R$^{60a}$, R$^{60b}$, R$^{60d}$, and R$^{60e}$ is hydrogen. In a yet further aspect, each of R$^{60a}$, R$^{60b}$, R$^{60d}$, and R$^{60e}$ is independently selected from hydrogen, —F, —Cl, —NH$_2$, —OH, —CN, methyl, —CH$_2$F, —CHF$_2$, —CF$_3$, —OCH$_3$, —NHCH$_3$, —N(CH$_3$)$_2$, —(S=O)CH$_3$, and —SO$_2$CH$_3$, provided that at least one of R$^{60a}$, R$^{60b}$, R$^{60d}$, and R$^{60e}$ is hydrogen.

In various aspects, each of R$^{60a}$, R$^{60b}$, R$^{60d}$, and R$^{60e}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least one of R$^{60a}$, R$^{60b}$, R$^{60d}$, and R$^{60e}$ is hydrogen. In a further aspect, each of R$^{60a}$, R$^{60b}$, R$^{60d}$, and R$^{60e}$ is independently selected from hydrogen, —F, —Cl, —NH$_2$, —OH, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$N(CH_3)_2$, and —$N(CH_3)$ $CH_2CH_3$, provided that at least one of $R^{60a}$, $R^{60b}$, $R^{60d}$, and $R^{60e}$ is hydrogen. In a still further aspect, each of $R^{60a}$, $R^{60b}$, $R^{60d}$, and $R^{60e}$ is independently selected from hydrogen, —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$, provided that at least one of $R^{60a}$, $R^{60b}$, $R^{60d}$, and $R^{60e}$ is hydrogen. In a yet further aspect, each of $R^{60a}$, $R^{60b}$, $R^{60d}$, and $R^{60e}$ is independently selected from hydrogen, —F, —Cl, —$NH_2$, —OH, —CN, methyl, —$CH_2F$, —$CHF_2$, —$CF_3$, —$OCH_3$, —$NHCH_3$, and —$N(CH_3)_2$, provided that at least one of $R^{60a}$, $R^{60b}$, $R^{60d}$, and $R^{60e}$ is hydrogen.

In a further aspect, each of $R^{60a}$, $R^{60b}$, $R^{60d}$, and $R^{60e}$ is independently selected from hydrogen, —F, —Cl, —$CH_2F$, —$CHF_2$, —$CF_3$, and —$OCH_3$, provided that at least one of $R^{60a}$, $R^{60b}$, $R^{60d}$, and $R^{60e}$ is hydrogen. In a yet further aspect, each of $R^{60a}$, $R^{60b}$, $R^{60d}$, and $R^{60e}$ is hydrogen.

In one aspect, each of each of $R^{60a}$, $R^{60b}$, and $R^{60c}$ is independently selected from hydrogen, halogen, —$NH_2$, —OH, —CN, —$S(O)_nR^{36}$, C1-C8 alkyl, C1-C8 monohaloalkyl, C1-C8 polyhaloalkyl, C1-C8 alkoxy, C1-C8 alkylamino, and C1-C8 dialkylamino. In one aspect, each of each of $R^{60a}$, $R^{60b}$, and $R^{60c}$ is independently selected from hydrogen, halogen, —$NH_2$, —OH, —CN, —$S(O)_nR^{36}$, C1-C6 alkyl, C1-C6 monohaloalkyl, C1-C6 polyhaloalkyl, C1-C6 alkoxy, C1-C6 alkylamino, and C1-C6 dialkylamino.

In various aspects, each of each of $R^{60a}$, $R^{60b}$, and $R^{60c}$ is independently selected from hydrogen, halogen, —$NH_2$, —OH, —CN, —$S(O)_nR^{36}$, C1-C3 alkyl, C1-C3 monohaloalkyl, C1-C3 polyhaloalkyl, C1-C3 alkoxy, C1-C3 alkylamino, C1-C3 dialkylamino. In a further aspect, each of each of $R^{60a}$, $R^{60b}$, and $R^{60c}$ is independently selected from hydrogen, —F, —Cl, —$NH_2$, —OH, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$N(CH_3)_2$, —$N(CH_3)$ $CH_2CH_3$, —$(S=O)CH_3$, and —$SO_2CH_3$. In a still further aspect, each of each of $R^{60a}$, $R^{60b}$, and $R^{60c}$ is independently selected from hydrogen, —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$(S=O)CH_3$, and —$SO_2CH_3$. In a yet further aspect, each of each of $R^{60a}$, $R^{60b}$, and $R^{60c}$ is independently selected from hydrogen, —F, —Cl, —$NH_2$, —OH, —CN, methyl, —$CH_2F$, —$CHF_2$, —$CF_3$, —$OCH_3$, —$NHCH_3$, —$N(CH_3)_2$, —$(S=O)CH_3$, and —$SO_2CH_3$.

In various aspects, each of each of $R^{60a}$, $R^{60b}$, and $R^{60c}$ is independently selected from hydrogen, halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino. In a further aspect, each of each of $R^{60a}$, $R^{60b}$, and $R^{60c}$ is independently selected from hydrogen, —F, —Cl, —$NH_2$, —OH, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$N(CH_3)_2$, and —$N(CH_3)$ $CH_2CH_3$. In a still further aspect, each of each of $R^{60a}$, $R^{60b}$, and $R^{60c}$ is independently selected from hydrogen, —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$. In a yet further aspect, each of each of $R^{60a}$, $R^{60b}$, and $R^{60c}$ is independently selected from hydrogen, —F, —Cl, —$NH_2$, —OH, —CN, methyl, —$CH_2F$, —$CHF_2$, —$CF_3$, —$OCH_3$, —$NHCH_3$, and —$N(CH_3)_2$.

In a further aspect, each of each of $R^{60a}$, $R^{60b}$, and $R^{60c}$ is independently selected from hydrogen, —F, —Cl, —$CH_2F$, —$CHF_2$, —$CF_3$, and —$OCH_3$. In a yet further aspect, each of each of $R^{60a}$, $R^{60b}$, and $R^{60c}$ is hydrogen.

z. $R^{70A}$, $R^{70B}$, $R^{70C}$, $R^{70D}$, and $R^{70E}$ Groups

In one aspect, each of $R^{70a}$, $R^{70b}$, $R^{70c}$, $R^{70d}$, and $R^{70e}$ are independently selected from hydrogen, halogen, —$NH_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino, provided that at least two of $R^{70a}$, $R^{70b}$, $R^{70c}$, $R^{70d}$, and $R^{70e}$ are hydrogen. In one aspect, each of $R^{70a}$, $R^{70b}$, $R^{70c}$, $R^{70d}$, and $R^{70e}$ are independently selected from hydrogen, halogen, —$NH_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino, provided that at least two of $R^{70a}$, $R^{70b}$, $R^{70c}$, $R^{70d}$, and $R^{70e}$ are hydrogen.

In various aspects, each of $R^{70a}$, $R^{70b}$, $R^{70c}$, $R^{70d}$, and $R^{70e}$ are independently selected from hydrogen, halogen, —$NH_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of $R^{70a}$, $R^{70b}$, $R^{70c}$, $R^{70d}$, and $R^{70e}$ are hydrogen. In a further aspect, each of $R^{70a}$, $R^{70b}$, $R^{70c}$, $R^{70d}$, and $R^{70e}$ are independently selected from hydrogen, —F, —Cl, —$NH_2$, —OH, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$N(CH_3)_2$, and —$N(CH_3)CH_2CH_3$, provided that at least two of $R^{70a}$, $R^{70b}$, $R^{70c}$, $R^{70d}$, and $R^{70e}$ are hydrogen. In a still further aspect, each of $R^{70a}$, $R^{70b}$, $R^{70c}$, $R^{70d}$, and $R^{70e}$ are independently selected from hydrogen, —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$, provided that at least two of $R^{70a}$, $R^{70b}$, $R^{70c}$, $R^{70d}$, and $R^{70e}$ are hydrogen. In a yet further aspect, each of $R^{70a}$, $R^{70b}$, $R^{70c}$, $R^{70d}$, and $R^{70e}$ are independently selected from hydrogen, —F, —Cl, —$NH_2$, —OH, —CN, methyl, —$CH_2F$, —$CHF_2$, —$CF_3$, —$OCH_3$, —$NHCH_3$, and —$N(CH_3)_2$, provided that at least two of $R^{70a}$, $R^{70b}$, $R^{70c}$, $R^{70d}$, and $R^{70e}$ are hydrogen.

aa. $R^{80}$ Groups

In one aspect, $R^{80}$ is selected from hydrogen and C1-C6 alkyl. In a further aspect, $R^{80}$ is selected from hydrogen, methyl, ethyl, propyl, and isopropyl. In a still further aspect, $R^{80}$ is selected from hydrogen, methyl, and ethyl. In a yet further aspect, $R^{80}$ is selected from hydrogen and methyl. In an even further aspect, $R^{80}$ is hydrogen. In a still further aspect, $R^{80}$ is methyl.

a. $R^{90A}$, $R^{90B}$, $R^{90C}$, and $R^{90D}$ Groups

In one aspect, each of $R^{90a}$, $R^{90b}$, $R^{90c}$, and $R^{90d}$ is independently selected from hydrogen, halogen, —$NH_2$, —OH, —CN, —$N_3$, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{31}R^{32}$, —(C1-C6 alkyl)-$NR^{30}$ (C=O)$R^{35}$, —(C1-C6 alkyl)-$NR^{30}$(C=O)O$R^{35}$, —(C1-C6 alkyl)-$NR^{30}$(C=O)$NR^{35}$, —(C1-C6 alkyl)-$NR^{30}S(O)_nR^{35}$, —$NR^{30}$(C1-C6 alkyl)-(C=O)$R^{35}$, —$NR^{30}$(C1-C6 alkyl)-(C=O)O$R^{35}$, —$NR^{30}$(C1-C6 alkyl)-(C=O)$NR^{35}$, —$NR^{30}$ (C1-C6 alkyl)-$S(O)_nR^{35}$, —$NR^{30}$(C1-C6 alkyl)-$S(O)_n$ $NR^{33}R^{34}$, —$NR^{30}$(C=O)$R^{35}$, —$NR^{30}$(C=O)O$R^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$, provided that at least two of R$^{90a}$, R$^{90b}$, R$^{90c}$, and R$^{90d}$ are hydrogen.

In various aspects, each of R$^{90a}$, R$^{90b}$, R$^{90c}$, and R$^{90d}$ is independently selected from hydrogen, halogen, —NH$_2$, —OH, —CN, C1-C3 alkyl, C1-C3 monohaloalkyl, C1-C3 polyhaloalkyl, C1-C3 alkoxy, C1-C3 alkylamino, and C1-C3 dialkylamino; provided that at least two of R$^{90a}$, R$^{90b}$, R$^{90c}$, and R$^{90d}$ are hydrogen. In a further aspect, each of R$^{90a}$, R$^{90b}$, R$^{90c}$, and R$^{90d}$ is independently selected from hydrogen, —F, —Cl, —NH$_2$, —OH, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$, provided that at least two of R$^{90a}$, R$^{90b}$, R$^{90c}$, and R$^{90d}$ are hydrogen. In a still further aspect, each of R$^{90a}$, R$^{90b}$, R$^{90c}$, and R$^{90d}$ is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$, provided that at least two of R$^{90a}$, R$^{90b}$, R$^{90c}$, and R$^{90d}$ are hydrogen. In a yet further aspect, each of R$^{90a}$, R$^{90b}$, R$^{90c}$, and R$^{90d}$ is independently selected from hydrogen, —F, —Cl, —NH$_2$, —OH, —CN, methyl, —CH$_2$F, —CHF$_2$, —CF$_3$, —OCH$_3$, —NHCH$_3$, and —N(CH$_3$)$_2$, provided that at least two of R$^{90a}$, R$^{90b}$, R$^{90c}$, and and R$^{90d}$ are hydrogen.

In a further aspect, each of R$^{90a}$, R$^{90b}$, R$^{90c}$, and R$^{90d}$ is independently selected from hydrogen, —F, —Cl, —CH$_2$F, —CHF$_2$, —CF$_3$, and —OCH$_3$, provided that at least two of R$^{90a}$, R$^{90b}$, R$^{90c}$, and R$^{90d}$ are hydrogen. In a yet further aspect, each of R$^{90a}$, R$^{90b}$, R$^{90c}$, and R$^{90d}$ is hydrogen.

b. Ar$^1$ Groups

In one aspect, Ar$^1$ is selected from phenyl and heterocyclyl, and Ar$^1$ is substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a further aspect, Ar$^1$ is phenyl. In a still further aspect, Ar$^1$ is heterocyclyl.

In various aspects, each Ar$^1$, when present, is independently selected from phenyl, naphthyl, and heteroaryl, and wherein each Ar$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$.

In a further aspect, Ar$^1$ is phenyl substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$. In a still further aspect, Ar$^1$ is phenyl substituted with 0-2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_n$R$^5$. In a yet further aspect, Ar$^1$ is phenyl substituted with 0-2 groups independently selected from halogen, —NH$_2$, —OH, —CN, C1-C6 alkyl, C1-C3 haloalkyl, C1-C3 polyhaloalkyl, C1-C3 alkoxy, C1-C3 alkylamino, C1-C3 dialkylamino, and —S(O)$_n$R$^5$. In an even further aspect, Ar$^1$ is phenyl substituted with 0-2 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, Ar$^1$ is phenyl substituted with 0-2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is phenyl substituted with 0-2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, Ar$^1$ is phenyl substituted with 0-2 groups independently selected from —F, —Cl, —NH$_2$, —OH, —CN, methyl, —CHF$_2$, and —CF$_3$. In a yet further aspect, Ar$^1$ is phenyl substituted with 0-2 —F groups. In an even further aspect, Ar$^1$ is phenyl substituted with 0-2 —Cl groups. In a still further aspect, Ar$^1$ is phenyl substituted with 0-2 methyl groups. In a yet further aspect, Ar$^1$ is phenyl substituted with 0-2 —CF$_3$ groups. In an even further aspect, Ar$^1$ is phenyl substituted with 0-2 —NH$_2$ groups. In a still further aspect, Ar$^1$ is phenyl substituted with 0-2 —OH groups. In a yet further aspect, Ar$^1$ is phenyl substituted with 0-2 —CN groups.

In a further aspect, Ar$^1$ is phenyl substituted with 0-2 groups independently selected from —F, —Cl, —NH$_2$, —OH, —CN, methyl, —CF$_3$, —CCl$_3$, —OCH$_3$, and —NHCH$_3$. In a yet further aspect, Ar$^1$ is phenyl substituted with 0-1 groups selected from —F, —Cl, —NH$_2$, —OH, —CN, methyl, —CF$_3$, —CCl$_3$, —OCH$_3$, and —NHCH$_3$. In a still further aspect, Ar$^1$ is phenyl substituted with 1-2 groups independently selected from —F, —Cl, —NH$_2$, —OH, —CN, methyl, —CF$_3$, —CCl$_3$, —OCH$_3$, and —NHCH₃. In a yet further aspect, Ar¹ is phenyl substituted with 1-2 groups independently selected from —F, —Cl, methyl, —CH₂F, —CH₂Cl, —CHF₂, —CF₃, —CHCl₂, and —CCl₃. In an even further aspect, Ar¹ is phenyl monosubstituted with a group selected from —F, —Cl, methyl, —CH₂F, —CH₂Cl, —CHF₂, —CF₃, —CHCl₂, and —CCl₃.

In a further aspect, Ar¹ is heterocyclyl substituted with 0-2 groups independently selected from halogen, —NH₂, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)ₙR⁵. In a still further aspect, Ar¹ is heterocyclyl substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)ₙR⁵. In a yet further aspect, Ar¹ is heterocyclyl substituted with 0-2 groups independently selected from halogen, —NH₂, —OH, —CN, C1-C6 alkyl, C1-C3 haloalkyl, C1-C3 polyhaloalkyl, C1-C3 alkoxy, C1-C3 alkylamino, C1-C3 dialkylamino, and —S(O)ₙR⁵. In an even further aspect, Ar¹ is heterocyclyl substituted with 0-2 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, Ar¹ is heterocyclyl substituted with 0-2 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂.

In a further aspect, Ar¹ is heterocyclyl substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In a still further aspect, Ar¹ is heterocyclyl substituted with 0-2 groups independently selected from —F, —Cl, —NH₂, —OH, —CN, methyl, —CHF₂, and —CF₃. In a yet further aspect, Ar¹ is heterocyclyl substituted with 0-2 —F groups. In an even further aspect, Ar¹ is heterocyclyl substituted with 0-2 —Cl groups. In a still further aspect, Ar¹ is heterocyclyl substituted with 0-2 methyl groups. In a yet further aspect, Ar¹ is heterocyclyl substituted with 0-2 —CF₃ groups. In an even further aspect, Ar¹ is heterocyclyl substituted with 0-2 —NH₂ groups. In a still further aspect, Ar¹ is heterocyclyl substituted with 0-2 —OH groups. In a yet further aspect, Ar¹ is heterocyclyl substituted with 0-2 —CN groups.

In a further aspect, Ar¹ is heterocyclyl substituted with 0-2 groups independently selected from —F, —Cl, —NH₂, —OH, —CN, methyl, —CF₃, —CCl₃, —OCH₃, and —NHCH₃. In a yet further aspect, Ar¹ is heterocyclyl substituted with 0-1 groups selected from —F, —Cl, —NH₂, —OH, —CN, methyl, —CF₃, —CCl₃, —OCH₃, and —NHCH₃. In a still further aspect, Ar¹ is heterocyclyl substituted with 1-2 groups independently selected from —F, —Cl, —NH₂, —OH, —CN, methyl, —CF₃, —CCl₃, —OCH₃, and —NHCH₃. In a yet further aspect, Ar¹ is heterocyclyl substituted with 1-2 groups independently selected from —F, —Cl, methyl, —CH₂F, —CH₂Cl, —CHF₂, —CF₃, —CHCl₂, and —CCl₃. In an even further aspect, Ar¹ is heterocyclyl monosubstituted with a group selected from —F, —Cl, methyl, —CH₂F, —CH₂Cl, —CHF₂, —CF₃, —CHCl₂, and —CCl₃.

In a further aspect, Ar¹ has a structure represented by a formula selected from:

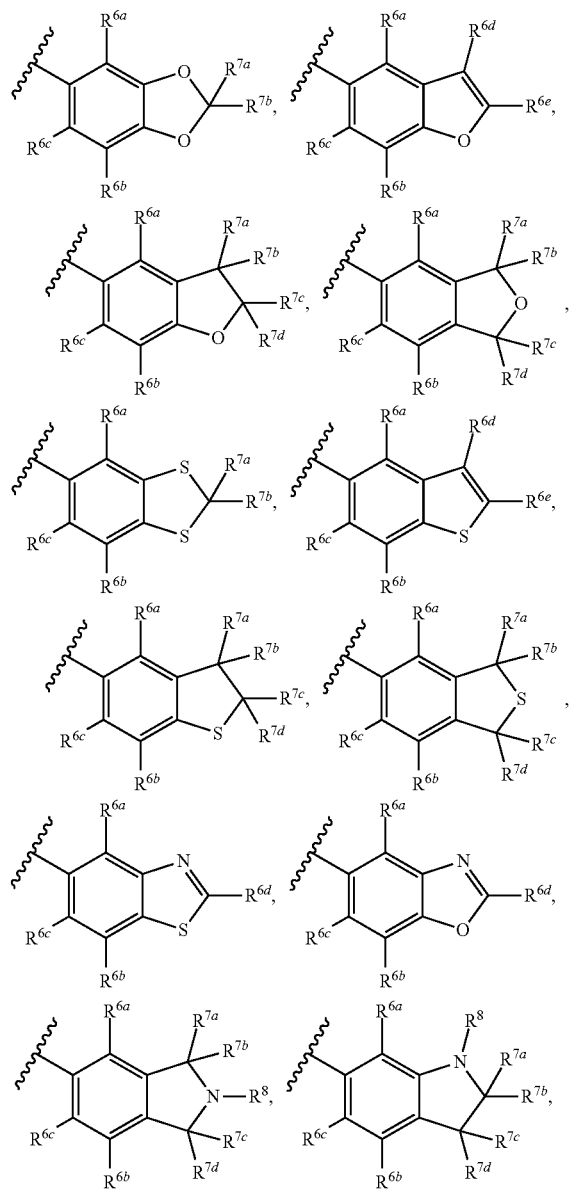

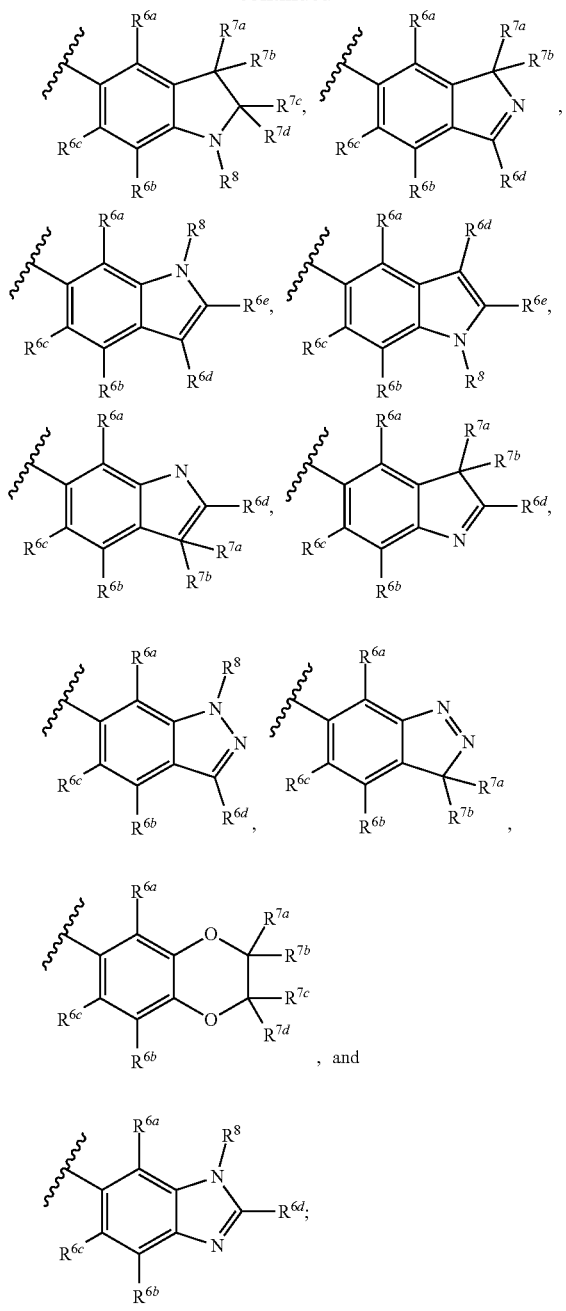

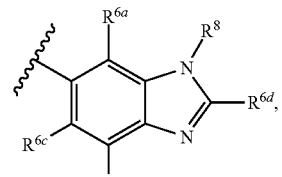

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein R$^8$ is selected from hydrogen and C1-C8 alkyl.

In a further aspect, Ar$^1$ has a structure represented by a formula selected from:

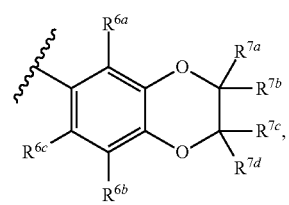

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of R$^{7a}$, R$^{7b}$, R$^{7c}$, and R$^{7d}$, when present is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

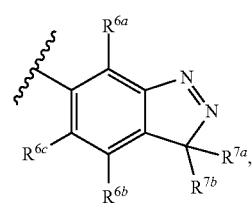

wherein each of R$^{6a}$, R$^{6b}$, R$^{6c}$, R$^{6d}$, and R$^{6e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein each of R$^{7a}$, R$^{7b}$, R$^{7c}$, and R$^{7d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein R$^8$, when present, is selected from hydrogen and C1-C8 alkyl.

In a further aspect, Ar$^1$ has a structure represented by a formula selected from:

wherein each of R$^{6a}$, R$^{6b}$, and R$^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of R$^{7a}$ and R$^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

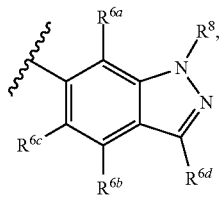

wherein each of $R^{6a}$, $R^{6b}$, and $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein R$^8$ is selected from hydrogen and C1-C8 alkyl.

In a further aspect, Ar$^1$ has a structure represented by a formula selected from:

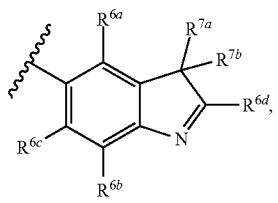

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of R$^{7a}$ and R$^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

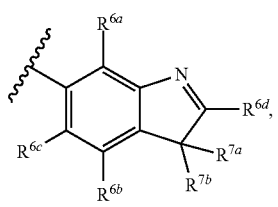

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of R$^{7a}$ and R$^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

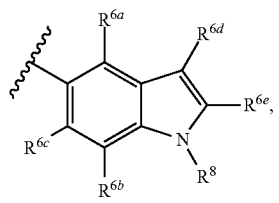

wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein R$^8$ is selected from hydrogen and C1-C8 alkyl.

In a further aspect, Ar$^1$ has a structure represented by a formula selected from:

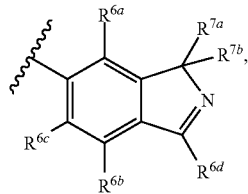

wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein R$^8$ is selected from hydrogen and C1-C8 alkyl.

In a further aspect, Ar$^1$ has a structure represented by a formula selected from:

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of R$^{7a}$ and R$^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

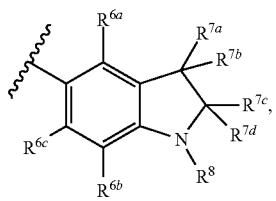

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{7a}$, $R^{7b}$, $R^{7c}$, and $R^{7d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^1$ has a structure represented by a formula selected from:

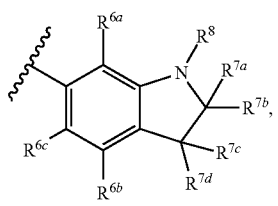

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{7a}$, $R^{7b}$, $R^{7c}$, and $R^{7d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^1$ has a structure represented by a formula selected from:

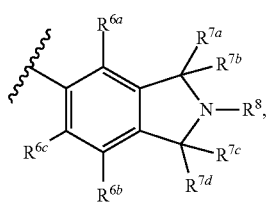

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{7a}$, $R^{7b}$, $R^{7c}$, and $R^{7d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^1$ has a structure represented by a formula selected from:

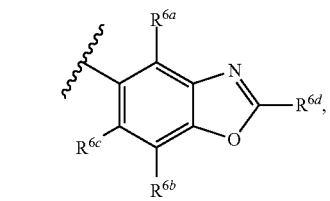

wherein each of $R^{6a}$, $R^{6b}$, $R^{6c}$, and $R^{6d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $Ar^1$ has a structure represented by a formula selected from:

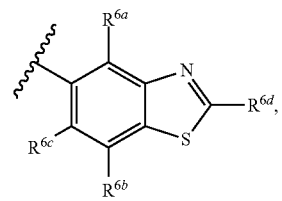

wherein each of $R^{6a}$, $R^{6b}$, $R^{6c}$, and $R^{6d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $Ar^1$ has a structure represented by a formula selected from:

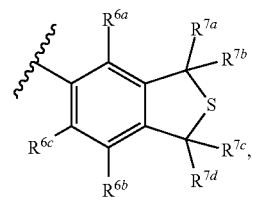

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein each of $R^{7a}$, $R^{7b}$, $R^{7c}$, and $R^{7d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $Ar^1$ has a structure represented by a formula selected from:

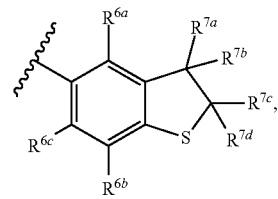

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

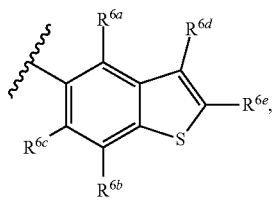

wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

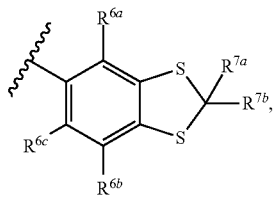

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$ and $R^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

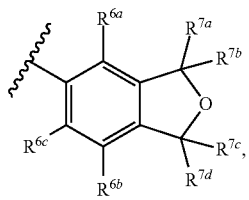

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

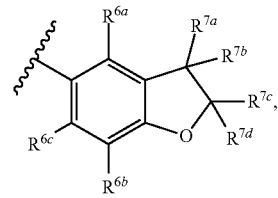

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

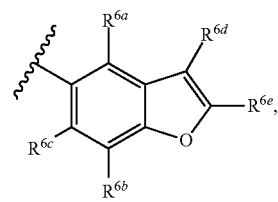

wherein each of $R^{6a}$, $R^{6b}$, $R^{6c}$, $R^{6d}$, and $R^{6e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^1$ has a structure represented by a formula selected from:

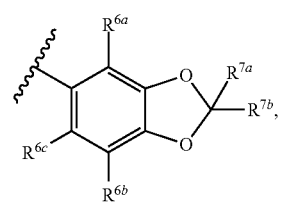

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$ and $R^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

c. Ar² Groups

In one aspect, Ar² is heterocyclyl substituted with 0-2 groups independently selected from halogen, —NH₂, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R⁵.

In various aspects, each Ar², when present, is a heteroaryl, and wherein each Ar² is independently substituted with 0, 1, 2, or 3 groups independently selected from halogen, —NH₂, —OH, —CN, —N₃, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR³¹R³², —(C1-C6 alkyl)-NR³⁰(C═O)R³⁵, —(C1-C6 alkyl)-NR³⁰(C═O)OR³⁵, —(C1-C6 alkyl)-NR³⁰(C═O)NR³⁵, —(C1-C6 alkyl)-NR³⁰S(O)$_n$R³⁵, —NR³⁰(C1-C6 alkyl)-(C═O)R³⁵, —NR³⁰(C1-C6 alkyl)-(C═O)OR³⁵, —NR³⁰(C1-C6 alkyl)-(C═O)NR³⁵, —NR³⁰(C1-C6 alkyl)-S(O)$_n$R³⁵, —NR³⁰(C1-C6 alkyl)-S(O)$_n$NR³³R³⁴, —NR³⁰(C═O)R³⁵, —NR³⁰(C═O)OR³⁵, —NR³⁰(C═O)NR³⁵, —NR³⁰S(O)$_n$R³⁵, —(C1-C6 alkyl)-(C═O)R³⁵, —(C1-C6 alkyl)-(C═O)OR³⁵, —(C1-C6 alkyl)-(C═O)NR³⁵, —(C1-C6 alkyl)-S(O)$_n$R³⁵, —(C1-C6 alkyl)-S(O)$_n$NR³³R³⁴, —(C═O)R³⁵, —(C═O)OR³⁵, —S(O)$_n$R³⁵, —S(O)$_n$NR³³R³⁴, —(C1-C8 alkyl)-Ar²⁰, Ar²⁰, —(C1-C8 alkyl)-Cy²⁰, Cy²⁰, and R³⁷.

In a further aspect, Ar² is heterocyclyl substituted with 0-2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_n$R⁵. In a yet further aspect, Ar² is heterocyclyl substituted with 0-2 groups independently selected from halogen, —NH₂, —OH, —CN, C1-C6 alkyl, C1-C3 haloalkyl, C1-C3 polyhaloalkyl, C1-C3 alkoxy, C1-C3 alkylamino, C1-C3 dialkylamino, and —S(O)$_n$R⁵. In an even further aspect, Ar² is heterocyclyl substituted with 0-2 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, Ar² is heterocyclyl substituted with 0-2 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂.

In a further aspect, Ar² is heterocyclyl substituted with 0-2 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In a still further aspect, Ar² is heterocyclyl substituted with 0-2 groups independently selected from —F, —Cl, —NH₂, —OH, —CN, methyl, —CHF₂, and —CF₃. In a yet further aspect, Ar² is heterocyclyl substituted with 0-2 —F groups. In an even further aspect, Ar² is heterocyclyl substituted with 0-2 —Cl groups. In a still further aspect, Ar² is heterocyclyl substituted with 0-2 methyl groups. In a yet further aspect, Ar² is heterocyclyl substituted with 0-2 —CF₃ groups. In an even further aspect, Ar² is heterocyclyl substituted with 0-2 —NH₂ groups. In a still further aspect, Ar² is heterocyclyl substituted with 0-2 —OH groups. In a yet further aspect, Ar² is heterocyclyl substituted with 0-2 —CN groups.

In a further aspect, Ar² is heterocyclyl substituted with 0-2 groups independently selected from —F, —Cl, —NH₂, —OH, —CN, methyl, —CF₃, —CCl₃, —OCH₃, and —NHCH₃. In a yet further aspect, Ar² is heterocyclyl substituted with 0-1 groups selected from —F, —Cl, —NH₂, —OH, —CN, methyl, —CF₃, —CCl₃, —OCH₃, and —NHCH₃. In a still further aspect, Ar² is heterocyclyl substituted with 1-2 groups independently selected from —F, —Cl, —NH₂, —OH, —CN, methyl, —CF₃, —CCl₃, —OCH₃, and —NHCH₃. In a yet further aspect, Ar² is heterocyclyl substituted with 1-2 groups independently selected from —F, —Cl, methyl, —CH₂F, —CH₂Cl, —CHF₂, —CF₃, —CHCl₂, and —CCl₃. In an even further aspect, Ar² is heterocyclyl monosubstituted with a group selected from —F, —Cl, methyl, —CH₂F, —CH₂Cl, —CHF₂, —CF₃, —CHCl₂, and —CCl₃.

In a further aspect, Ar² has a structure represented by a formula selected from:

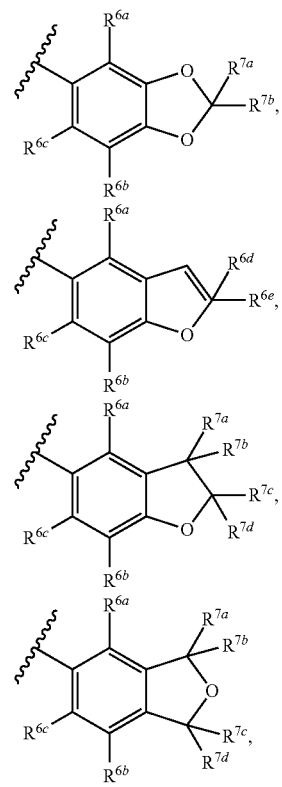

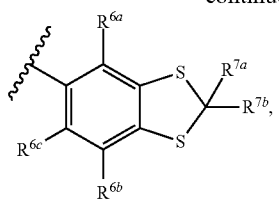
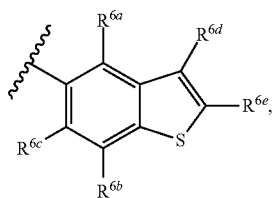
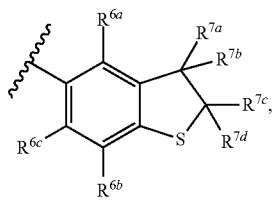
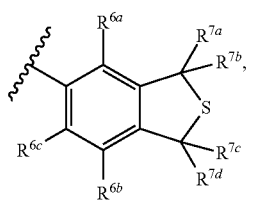
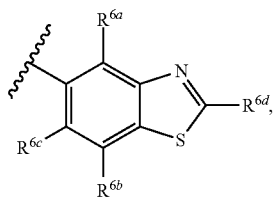

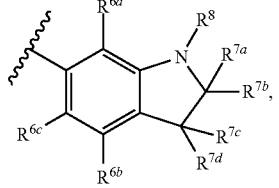
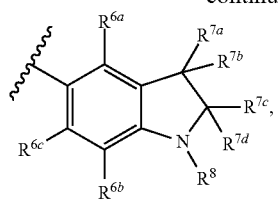
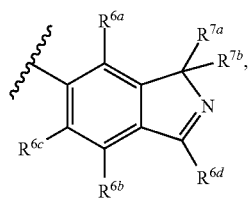
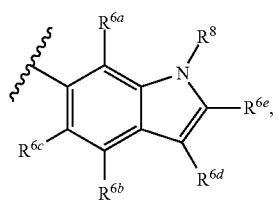
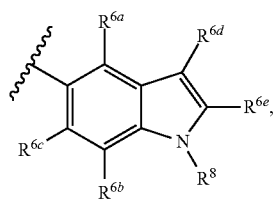
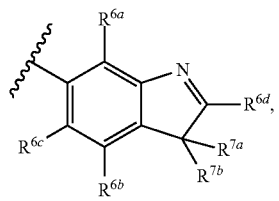
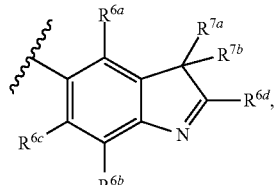
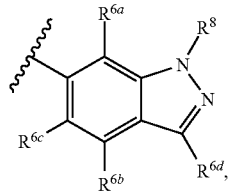
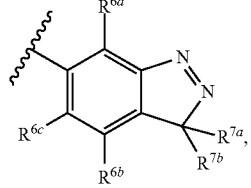

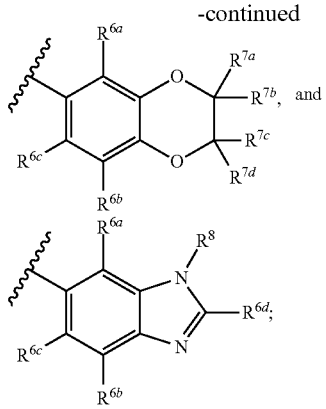

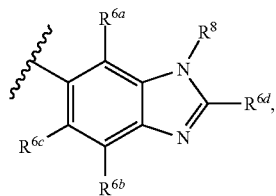

wherein each of $R^{6a}$, $R^{6b}$, $R^{6c}$, $R^{6d}$, and $R^{6e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; each of $R^{7a}$, $R^{7b}$, $R^{7c}$, and $R^{7d}$, when present is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein $R^8$, when present, is selected from hydrogen and C1-C8 alkyl.

In a further aspect, Ar$^2$ has a structure represented by a formula selected from:

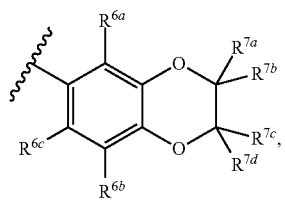

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein $R^8$ is selected from hydrogen and C1-C8 alkyl.

In a further aspect, Ar$^2$ has a structure represented by a formula selected from:

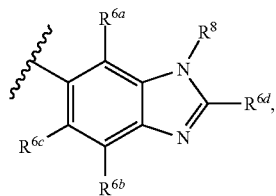

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$, when present is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

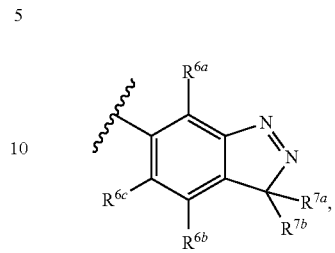

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$ and $R^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

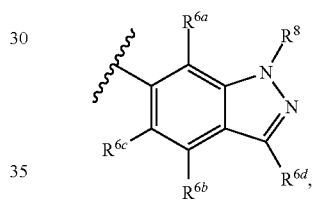

wherein each of $R^{6a}$, $R^{6b}$, and $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein $R^8$ is selected from hydrogen and C1-C8 alkyl.

In a further aspect, Ar$^2$ has a structure represented by a formula selected from:

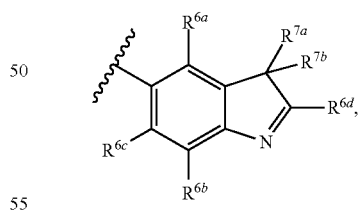

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$ and $R^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

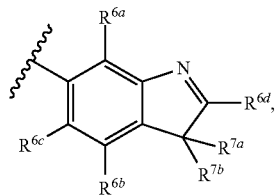

wherein each of $R^{6a}$, $R^{6b}$, $R^{6c}$, and $R^{6d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein each of $R^{7a}$ and $R^{7b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $Ar^2$ has a structure represented by a formula selected from:

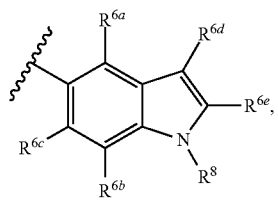

wherein each of $R^{6a}$, $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^2$ has a structure represented by a formula selected from:

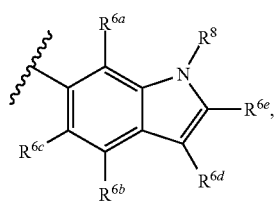

wherein each of $R^{6a}$, $R^{6b}$, $R^{6c}$, $R^{6d}$, and $R^{6e}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^2$ has a structure represented by a formula selected from:

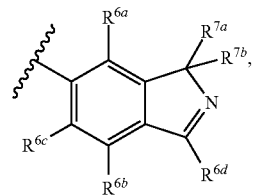

wherein each of $R^{6a}$, $R^{6b}$, $R^{6c}$, and $R^{6d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein each of $R^{7a}$ and $R^{7b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$.

In a further aspect, $Ar^2$ has a structure represented by a formula selected from:

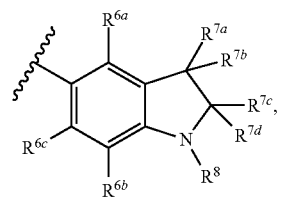

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{7a}$, $R^{7b}$, $R^{7c}$, and $R^{7d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^2$ has a structure represented by a formula selected from:

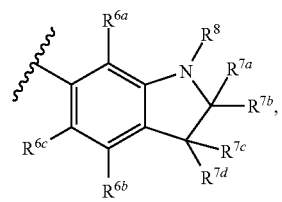

wherein each of $R^{6a}$, $R^{6b}$, and $R^{6c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; wherein each of $R^{7a}$, $R^{7b}$, $R^{7c}$, and $R^{7d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_nR^5$; and wherein $R^8$ is selected from hydrogen and C1-C8 alkyl.

In a further aspect, $Ar^2$ has a structure represented by a formula selected from:

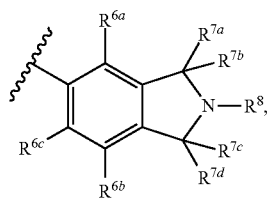

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; wherein each of $R^{7a}$, $R^{7b}$, $R^{7c}$, and $R^{7d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein R$^8$ is selected from hydrogen and C1-C8 alkyl.

In a further aspect, Ar$^2$ has a structure represented by a formula selected from:

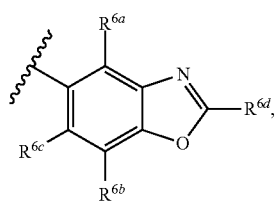

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

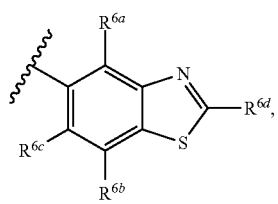

wherein each of $R^{6a}$, $R^{6b}$, $R^{6c}$, and $R^{6d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

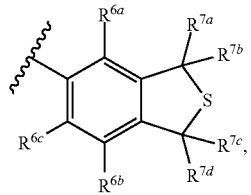

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

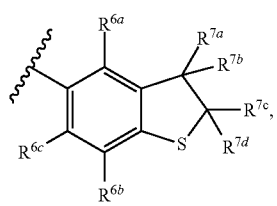

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

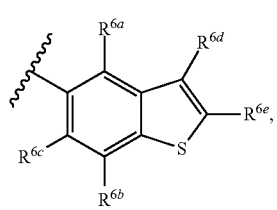

wherein each of $R^{6a}$, $R^{6b}$, $R^{6c}$, $R^{6d}$, and $R^{6e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

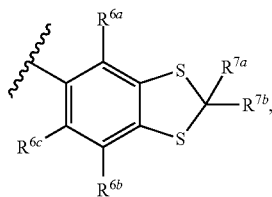

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$ and $R^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

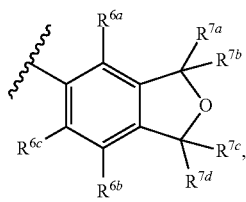

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

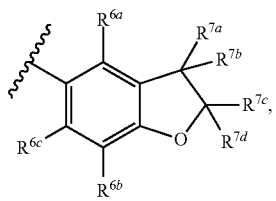

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$, $R^{7b}$, $R^{7c}$, and $R^{7d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

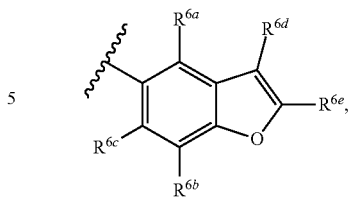

wherein each of $R^{6a}$, $R^{6b}$, $R^{6c}$, $R^{6d}$, and $R^{6e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

In a further aspect, Ar$^2$ has a structure represented by a formula selected from:

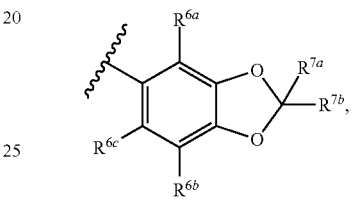

wherein each of $R^{6a}$, $R^{6b}$, and $R^{6c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and wherein each of $R^{7a}$ and $R^{7b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

d. Ar$^3$ Groups

In one aspect, each Ar$^3$, when present, is a heteroaryl, and wherein each Ar$^3$ is independently substituted with 0, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)NR$^{30}$(C=O)R$^{35}$, —(C1-C6 alkyl)NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$; or and wherein each Ar$^3$ is independently monosubstituted with a groups selected from —Cl, —Br, —I, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl), —NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$.

e. Ar$^{10}$ Groups

In one aspect, each Ar$^{10}$, when present, is selected from phenyl and monocyclic heteroaryl; and wherein Ar$^{10}$ is substituted with 0, 1, 2, or 3 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In one aspect, each Ar$^{10}$, when present, is selected from phenyl and monocyclic heteroaryl; and wherein Ar$^{10}$ is unsubstituted.

In a further aspect, each Ar$^{10}$, when present, is selected from phenyl and monocyclic heteroaryl; and wherein Ar$^{10}$ is substituted with 0, 1, or 2 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, each Ar$^{10}$, when present, is selected from phenyl and monocyclic heteroaryl; and wherein Ar$^{10}$ is substituted with 0 or 1 group selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, each Ar$^{10}$, when present, is selected from phenyl and monocyclic heteroaryl; and wherein Ar$^{10}$ is substituted with 1 or 2 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, each Ar$^{10}$, when present, is selected from phenyl and monocyclic heteroaryl; and wherein Ar$^{10}$ is monosubstituted with a group selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, each Ar$^{10}$, when present, is selected from phenyl and monocyclic heteroaryl; and wherein Ar$^{10}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{10}$, when present, is selected from phenyl and monocyclic heteroaryl; and wherein Ar$^{10}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{10}$, when present, is selected from phenyl and monocyclic heteroaryl; and wherein Ar$^{10}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{10}$, when present, is selected from phenyl and monocyclic heteroaryl; and wherein Ar$^{10}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{10}$, when present, is selected from phenyl, pyridinyl, pyrimidinyl, and pyrazinyl; and wherein Ar$^{10}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{10}$, when present, is selected from phenyl, pyridinyl, pyrimidinyl, and pyrazinyl; and wherein Ar$^{10}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{10}$, when present, is selected from phenyl, pyridinyl, pyrimidinyl, and pyrazinyl; and wherein Ar$^{10}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{10}$, when present, is selected from phenyl, pyridinyl, pyrimidinyl, and pyrazinyl; and wherein Ar$^{10}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{10}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{10}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{10}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{10}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{10}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{10}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{10}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{10}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{10}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{10}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)CH(CH$_3$)$_2$, and —N(CH$_2$CH$_3$)$_2$. In a yet further aspect, each Ar$^{10}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{10}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{10}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{10}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{10}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{10}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

f. Ar$^{11}$ Groups

In one aspect, each Ar$^{11}$, when present, is selected from phenyl and monocyclic heteroaryl; and wherein Ar$^{11}$ is substituted with 0, 1, 2, or 3 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In one aspect, each Ar$^{11}$, when present, is selected from phenyl and monocyclic heteroaryl; and wherein Ar$^{11}$ is unsubstituted.

In a further aspect, each Ar$^{11}$, when present, is selected from phenyl and monocyclic heteroaryl; and wherein Ar$^{11}$ is substituted with 0, 1, or 2 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, each Ar$^{11}$, when present, is selected from phenyl and monocyclic heteroaryl; and wherein Ar$^{11}$ is substituted with 0 or 1 group selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, each Ar$^{11}$, when present, is selected from phenyl and monocyclic heteroaryl; and wherein Ar$^{11}$ is substituted with 1 or 2 groups independently selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, each Ar$^{11}$, when present, is selected from phenyl and monocyclic heteroaryl; and wherein Ar$^{11}$ is monosubstituted with a group selected from halogen, —OH, —CN, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, each Ar$^{11}$, when present, is selected from phenyl and monocyclic heteroaryl; and wherein Ar$^{11}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{11}$, when present, is selected from phenyl and monocyclic heteroaryl; and wherein Ar$^{11}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{11}$, when present, is selected from phenyl and monocyclic heteroaryl; and wherein Ar$^{11}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{11}$, when present, is selected from phenyl and monocyclic heteroaryl; and wherein Ar$^{11}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{11}$, when present, is selected from phenyl, pyridinyl, pyrimidinyl, and pyrazinyl; and wherein Ar$^{11}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{11}$, when present, is selected from phenyl, pyridinyl, pyrimidinyl, and pyrazinyl; and wherein Ar$^{11}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{11}$, when present, is selected from phenyl, pyridinyl, pyrimidinyl, and pyrazinyl; and wherein Ar$^{11}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{11}$, when present, is selected from phenyl, pyridinyl, pyrimidinyl, and pyrazinyl; and wherein Ar$^{11}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{11}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{11}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{11}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{11}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{11}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{11}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{11}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{11}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{11}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{11}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{11}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{11}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{11}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, and —$N(CH_2CH_3)(CH(CH_3)_2)$. In a still further aspect, each $Ar^{11}$, when present, is pyridinyl and is monosubstituted with a group selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In a yet further aspect, each $Ar^{11}$, when present, is pyridinyl and is monosubstituted with a group selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$. In an even further aspect, each $Ar^{11}$, when present, is pyridinyl and is monosubstituted with a group selected from —F, —Cl, —$NH_2$, —OH, —CN, methyl, —$CF_3$, —$CCl_3$, —$OCH_3$, and —$NHCH_3$.

g. $Ar^{20}$ Groups

In one aspect, each $Ar^{20}$, when present, is independently selected from phenyl, naphthyl, and heteroaryl; and wherein $Ar^{20}$ is substituted with 0, 1, 2, or 3 groups independently selected from halogen, —OH, —CN, —$NH_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{20}$, when present, is independently selected from phenyl, naphthyl, and heteroaryl; and wherein $Ar^{20}$ is substituted with 0, 1, 2, or 3 groups independently selected from halogen, —OH, —CN, —$NH_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{20}$, when present, is independently selected from phenyl, naphthyl, and heteroaryl; and wherein $Ar^{20}$ is substituted with 0, 1, 2, or 3 groups independently selected from halogen, —OH, —CN, —$NH_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{20}$, when present, is selected from phenyl, naphthyl, and heteroaryl; and wherein $Ar^{20}$ is unsubstituted.

In one aspect, each $Ar^{20}$, when present, is independently selected from phenyl and monocyclic heteroaryl; and wherein $Ar^{20}$ is substituted with 0, 1, 2, or 3 groups independently selected from halogen, —OH, —CN, —$NH_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{20}$, when present, is independently selected from phenyl and monocyclic heteroaryl; and wherein $Ar^{20}$ is substituted with 0, 1, 2, or 3 groups independently selected from halogen, —OH, —CN, —$NH_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{20}$, when present, is independently selected from phenyl and monocyclic heteroaryl; and wherein $Ar^{20}$ is substituted with 0, 1, 2, or 3 groups independently selected from halogen, —OH, —CN, —$NH_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{20}$, when present, is selected from phenyl and monocyclic heteroaryl; and wherein $Ar^{20}$ is unsubstituted.

In a further aspect, each $Ar^{20}$, when present, is selected from phenyl, naphthyl, and heteroaryl; and wherein $Ar^{20}$ is substituted with 0, 1, or 2 groups independently selected from halogen, —OH, —CN, —$NH_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each $Ar^{20}$, when present, is selected from phenyl, naphthyl, and heteroaryl; and wherein $Ar^{20}$ is substituted with 0 or 1 group selected from halogen, —OH, —CN, —$NH_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each $Ar^{20}$, when present, is selected from phenyl, naphthyl, and heteroaryl; and wherein $Ar^{20}$ is substituted with 1 or 2 groups independently selected from halogen, —OH, —CN, —$NH_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{20}$, when present, is selected from phenyl, naphthyl, and heteroaryl; and wherein $Ar^{20}$ is monosubstituted with a group selected from halogen, —OH, —CN, —$NH_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{20}$, when present, is selected from phenyl, naphthyl, and heteroaryl; and wherein $Ar^{20}$ is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, and —$N(CH_2CH_3)(CH(CH_3)_2)$. In a still further aspect, each $Ar^{20}$, when present, is selected from phenyl, naphthyl, and heteroaryl; and wherein $Ar^{20}$ is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In a yet further aspect, each $Ar^{20}$, when present, is selected from phenyl, naphthyl, and heteroaryl; and wherein $Ar^{20}$ is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$. In an even further aspect, each $Ar^{20}$, when present, is selected from phenyl and monocyclic heteroaryl; and wherein $Ar^{20}$ is substituted with 0, 1, 2, or 3 groups independently selected from —F, —Cl, —$NH_2$, —OH, —CN, methyl, —$CF_3$, —$CCl_3$, —$OCH_3$, and —$NHCH_3$.

In various further aspects, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$(CH_3)CH(CH_3)_2$, —$N(CH_2CH_3)_2$, —$N(CH_2CH_3)((CH_2)_2CH_3)$, and —$N(CH_2CH_3)(CH(CH_3)_2)$. In a still further aspect, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In a yet further aspect, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$. In an even further aspect, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —$NH_2$, —OH, —CN, methyl, —$CF_3$, —$CCl_3$, —$OCH_3$, and —$NHCH_3$.

In various further aspects, each $Ar^{20}$, when present, is phenyl and is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, and —$N(CH_2CH_3)(CH(CH_3)_2)$. In a still further aspect, each $Ar^{20}$, when present, is phenyl and is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In a yet further aspect, each $Ar^{20}$, when present, is phenyl and is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$. In an even further aspect, each $Ar^{20}$, when present, is phenyl and is substituted with 0, 1, 2, or 3 groups independently selected from —F, —Cl, —$NH_2$, —OH, —CN, methyl, —$CF_3$, —$CCl_3$, —$OCH_3$, and —$NHCH_3$.

In various further aspects, each $Ar^{20}$, when present, is phenyl and is monosubstituted with a group selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In a yet further aspect, each $Ar^{20}$, when present, is phenyl and is monosubstituted with a group selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, and —$N(CH_3)_2$. In an even further aspect, each $Ar^{20}$, when present, is phenyl and is monosubstituted with a group selected from —F, —Cl, —$NH_2$, —OH, —CN, methyl, —$CF_3$, —$CCl_3$, —$OCH_3$, and —$NHCH_3$.

In various further aspects, each $Ar^{20}$, when present, is pyridinyl and is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{20}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{20}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{20}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{20}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{20}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{20}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{20}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

h. Ar$^{21}$ Groups

In one aspect, each Ar$^{21}$, when present, is independently selected from phenyl, naphthyl, and heteroaryl; and wherein Ar$^{21}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{21}$, when present, is independently selected from phenyl, naphthyl, and heteroaryl; and wherein Ar$^{21}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{21}$, when present, is independently selected from phenyl, naphthyl, and heteroaryl; and wherein Ar$^{21}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{21}$, when present, is selected from phenyl, naphthyl, and heteroaryl; and wherein Ar$^{21}$ is unsubstituted.

In one aspect, each Ar$^{21}$, when present, is independently selected from phenyl and monocyclic heteroaryl; and wherein Ar$^{21}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{21}$, when present, is independently selected from phenyl and monocyclic heteroaryl; and wherein Ar$^{21}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{21}$, when present, is independently selected from phenyl and monocyclic heteroaryl; and wherein Ar$^{21}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{21}$, when present, is selected from phenyl and monocyclic heteroaryl; and wherein Ar$^{21}$ is unsubstituted.

In a further aspect, each Ar$^{21}$, when present, is from phenyl, naphthyl, and heteroaryl; and wherein Ar$^{21}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each Ar$^{21}$, when present, is selected from phenyl, naphthyl, and heteroaryl; and wherein Ar$^{21}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each Ar$^{21}$, when present, is selected from phenyl, naphthyl, and heteroaryl; and wherein Ar$^{21}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{21}$, when present, is selected from phenyl, naphthyl, and heteroaryl; and wherein $Ar^{21}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{21}$, when present, is selected from phenyl, naphthyl, and heteroaryl; and wherein $Ar^{21}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{21}$, when present, is selected from phenyl, naphthyl, and heteroaryl; and wherein $Ar^{21}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{21}$, when present, is selected from phenyl, naphthyl, and heteroaryl; and wherein $Ar^{21}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{21}$, when present, is selected from phenyl and monocyclic heteroaryl; and wherein $Ar^{21}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{21}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{21}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{21}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{21}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{21}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{21}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{21}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{21}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{21}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{21}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{21}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{21}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{21}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{21}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{21}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

i. Ar$^{22}$ Groups

In one aspect, each Ar$^{22}$, when present, is independently selected from phenyl, naphthyl, and heteroaryl; and wherein Ar$^{22}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{22}$, when present, is independently selected from phenyl, naphthyl, and heteroaryl; and wherein Ar$^{22}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{22}$, when present, is independently selected from phenyl, naphthyl, and heteroaryl; and wherein $Ar^{22}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{22}$, when present, is selected from phenyl, naphthyl, and heteroaryl; and wherein $Ar^{22}$ is unsubstituted.

In one aspect, each $Ar^{22}$, when present, is independently selected from phenyl and monocyclic heteroaryl; and wherein $Ar^{22}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{22}$, when present, is independently selected from phenyl and monocyclic heteroaryl; and wherein $Ar^{22}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{22}$, when present, is independently selected from phenyl and monocyclic heteroaryl; and wherein $Ar^{22}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{22}$, when present, is selected from phenyl and monocyclic heteroaryl; and wherein $Ar^{22}$ is unsubstituted.

In a further aspect, each $Ar^{22}$, when present, is selected from phenyl, naphthyl, and heteroaryl; and wherein $Ar^{22}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each $Ar^{22}$, when present, is selected from phenyl, naphthyl, and heteroaryl; and wherein $Ar^{22}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each $Ar^{22}$, when present, is selected from phenyl, naphthyl, and heteroaryl; and wherein $Ar^{22}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{22}$, when present, is selected from phenyl, naphthyl, and heteroaryl; and wherein $Ar^{22}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{22}$, when present, is selected from phenyl, naphthyl, and heteroaryl; and wherein $Ar^{22}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{22}$, when present, is selected from phenyl, naphthyl, and heteroaryl; and wherein $Ar^{22}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{22}$, when present, is selected from phenyl, naphthyl, and heteroaryl; and wherein $Ar^{22}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{22}$, when present, is selected from phenyl and monocyclic heteroaryl; and wherein $Ar^{22}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each Ar²², when present, is selected from phenyl, naphthyl, pyridinyl, pyrimidinyl, and pyrazinyl; and wherein Ar²² is substituted with 0, 1, 2, or 3 groups independently selected from —F, —Cl, —NH₂, —OH, —CN, methyl, —CF₃, —CCl₃, —OCH₃, and —NHCH₃.

In various further aspects, each Ar²², when present, is phenyl and is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each Ar²², when present, is phenyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each Ar²², when present, is phenyl and is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each Ar²², when present, is phenyl and is substituted with 0, 1, 2, or 3 groups independently selected from —F, —Cl, —NH₂, —OH, —CN, methyl, —CF₃, —CCl₃, —OCH₃, and —NHCH₃.

In various further aspects, each Ar²², when present, is phenyl and is monosubstituted with a group selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each Ar²², when present, is phenyl and is monosubstituted with a group selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each Ar²², when present, is phenyl and is monosubstituted with a group selected from —F, —Cl, —NH₂, —OH, —CN, methyl, —CF₃, —CCl₃, —OCH₃, and —NHCH₃.

In various further aspects, each Ar²², when present, is pyridinyl and is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each Ar²², when present, is pyridinyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each Ar²², when present, is pyridinyl and is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each Ar²², when present, is pyridinyl and is substituted with 0, 1, 2, or 3 groups independently selected from —F, —Cl, —NH₂, —OH, —CN, methyl, —CF₃, —CCl₃, —OCH₃, and —NHCH₃.

In various further aspects, each Ar²², when present, is pyridinyl and is monosubstituted with a group selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{22}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{22}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{22}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

j. Ar$^{23}$ Groups

In one aspect, each Ar$^{23}$, when present, is independently selected from phenyl, naphthyl, and heteroaryl; and wherein Ar$^{23}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{23}$, when present, is independently selected from phenyl, naphthyl, and heteroaryl; and wherein Ar$^{23}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{23}$, when present, is independently selected from phenyl, naphthyl, and heteroaryl; and wherein Ar$^{23}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{23}$, when present, is selected from phenyl, naphthyl, and heteroaryl; and wherein Ar$^{23}$ is unsubstituted.

In one aspect, each Ar$^{23}$, when present, is independently selected from phenyl and monocyclic heteroaryl; and wherein Ar$^{23}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{23}$, when present, is independently selected from phenyl and monocyclic heteroaryl; and wherein Ar$^{23}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{23}$, when present, is independently selected from phenyl and monocyclic heteroaryl; and wherein Ar$^{23}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{23}$, when present, is selected from phenyl and monocyclic heteroaryl; and wherein Ar$^{23}$ is unsubstituted.

In a further aspect, each Ar$^{23}$, when present, is selected from phenyl, naphthyl, and heteroaryl; and wherein Ar$^{23}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each Ar$^{23}$, when present, is selected from phenyl, naphthyl, and heteroaryl; and wherein Ar$^{23}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each Ar$^{23}$, when present, is selected from phenyl, naphthyl, and heteroaryl; and wherein Ar$^{23}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each Ar$^{23}$, when present, is selected from phenyl, naphthyl, and heteroaryl; and wherein Ar$^{23}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each Ar$^{23}$, when present, is selected from phenyl, naphthyl, and heteroaryl; and wherein Ar$^{23}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is selected from phenyl, naphthyl, and heteroaryl; and wherein Ar$^{23}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is selected from phenyl, naphthyl, and heteroaryl; and wherein Ar$^{23}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is selected from phenyl and monocyclic heteroaryl; and wherein Ar$^{23}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is selected from phenyl, naphthyl, pyridinyl, pyrimidinyl, and pyrazinyl; and wherein Ar$^{23}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is selected from phenyl, naphthyl, pyridinyl, pyrimidinyl, and pyrazinyl; and wherein Ar$^{23}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is selected from phenyl, naphthyl, pyridinyl, pyrimidinyl, and pyrazinyl; and wherein Ar$^{23}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is selected from phenyl, naphthyl, pyridinyl, pyrimidinyl, and pyrazinyl; and wherein Ar$^{23}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, Ar$^{23}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, Ar$^{23}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

k. Ar$^{30}$ Groups

In one aspect, each Ar$^{30}$, when present, is independently selected from phenyl, naphthyl, and heteroaryl; and wherein Ar$^{30}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{30}$, when present, is independently selected from phenyl, naphthyl, and heteroaryl; and wherein Ar$^{30}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{30}$, when present, is independently selected from phenyl, naphthyl, and heteroaryl; and wherein Ar$^{30}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{30}$, when present, is selected from phenyl, naphthyl, and heteroaryl; and wherein Ar$^{30}$ is unsubstituted.

In one aspect, each Ar$^{30}$, when present, is independently selected from phenyl and monocyclic heteroaryl; and wherein Ar$^{30}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{30}$, when present, is independently selected from phenyl and monocyclic heteroaryl; and wherein Ar$^{30}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{30}$, when present, is independently selected from phenyl and monocyclic heteroaryl; and wherein Ar$^{30}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{30}$, when present, is selected from phenyl and monocyclic heteroaryl; and wherein Ar$^{30}$ is unsubstituted.

In a further aspect, each Ar$^{30}$, when present, is from phenyl, naphthyl, and heteroaryl; and wherein Ar$^{30}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each Ar$^{30}$, when present, is selected from phenyl, naphthyl, and heteroaryl; and wherein Ar$^{30}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each Ar$^{30}$, when present, is selected from phenyl, naphthyl, and heteroaryl; and wherein Ar$^{30}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{30}$, when present, is selected from phenyl, naphthyl, and heteroaryl; and wherein $Ar^{30}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{30}$, when present, is selected from phenyl, naphthyl, and heteroaryl; and wherein $Ar^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{30}$, when present, is selected from phenyl, naphthyl, and heteroaryl; and wherein $Ar^{30}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{30}$, when present, is selected from phenyl, naphthyl, and heteroaryl; and wherein $Ar^{30}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{30}$, when present, is selected from phenyl and monocyclic heteroaryl; and wherein $Ar^{30}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{30}$, when present, is selected from phenyl, naphthyl, pyridinyl, pyrimidinyl, and pyrazinyl; and wherein $Ar^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{30}$, when present, is selected from phenyl, naphthyl, pyridinyl, pyrimidinyl, and pyrazinyl; and wherein $Ar^{30}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{30}$, when present, is selected from phenyl, naphthyl, pyridinyl, pyrimidinyl, and pyrazinyl; and wherein $Ar^{30}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{30}$, when present, is selected from phenyl, naphthyl, pyridinyl, pyrimidinyl, and pyrazinyl; and wherein $Ar^{30}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{30}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{30}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{30}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{30}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$,—(CH$_2$)$_2$CHF$_2$,—(CH$_2$)$_2$CF$_3$,—(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$,—OCH(CH$_2$CH$_3$)$_2$(CH$_3$),—NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$ CH$_2$F,—(CH$_2$)$_2$CH$_2$Cl—CHF$_2$,—CF$_3$,—CHCl$_2$,—CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$ CCl$_3$, —OCH$_3$, —OCH$_2$CH$_3$, —O(CH$_2$)$_2$CH$_3$, —OCH (CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$) CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$ CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$ CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH (CH$_2$)$_3$CH$_3$, —NH(CH$_2$)$_4$CH$_3$, —N(CH$_3$)$_2$, —N(CH$_3$) CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$ CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH (CH$_2$)$_3$CH$_3$, —N(CH$_3$)$_2$, —N(CH$_3$)CH$_2$CH$_3$, —N(CH$_3$) (CH$_2$)$_2$CH$_3$, —N(CH$_3$)CH(CH$_3$)$_2$, and —N(CH$_2$CH$_3$)$_2$. In a yet further aspect, each Ar$^{30}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

1. Ar$^{40}$ Groups

In one aspect, each Ar$^{40}$, when present, is independently selected from phenyl, naphthyl, and heteroaryl; and wherein Ar$^{40}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{40}$, when present, is independently selected from phenyl, naphthyl, and heteroaryl; and wherein Ar$^{40}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{40}$, when present, is independently selected from phenyl, naphthyl, and heteroaryl; and wherein $Ar^{40}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{40}$, when present, is selected from phenyl, naphthyl, and heteroaryl; and wherein $Ar^{40}$ is unsubstituted.

In one aspect, each $Ar^{40}$, when present, is independently selected from phenyl and monocyclic heteroaryl; and wherein $Ar^{40}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{40}$, when present, is independently selected from phenyl and monocyclic heteroaryl; and wherein $Ar^{40}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{40}$, when present, is independently selected from phenyl and monocyclic heteroaryl; and wherein $Ar^{40}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{40}$, when present, is selected from phenyl and monocyclic heteroaryl; and wherein $Ar^{40}$ is unsubstituted.

In a further aspect, each $Ar^{40}$, when present, is selected from phenyl, naphthyl, and heteroaryl; and wherein $Ar^{40}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each $Ar^{40}$, when present, is selected from phenyl, naphthyl, and heteroaryl; and wherein $Ar^{40}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each $Ar^{40}$, when present, is selected from phenyl, naphthyl, and heteroaryl; and wherein $Ar^{40}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{40}$, when present, is selected from phenyl, naphthyl, and heteroaryl; and wherein $Ar^{40}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{40}$, when present, is selected from phenyl, naphthyl, and heteroaryl; and wherein $Ar^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{40}$, when present, is selected from phenyl, naphthyl, and heteroaryl; and wherein $Ar^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{40}$, when present, is selected from phenyl, naphthyl, and heteroaryl; and wherein $Ar^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{40}$, when present, is selected from phenyl and monocyclic heteroaryl; and wherein $Ar^{40}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is selected from phenyl, naphthyl, pyridinyl, pyrimidinyl, and pyrazinyl; and wherein Ar$^{40}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{40}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{40}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{40}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{40}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{40}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{40}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{40}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{40}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{40}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{40}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$ CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{40}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{40}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

m. Cy$^1$ Groups

In one aspect, each Cy$^1$, when present, is independently selected from C3-C9 cycloalkyl and C2-C7 heterocycloalkyl, and wherein each Cy$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{31}$R$^{32}$, —(C1-C6 alkyl)-NR$^{30}$(C=O)R$^{35}$, —(C1-C6 alkyl)-NR$^{30}$(C=O)OR$^{35}$, —(C1-C6 alkyl)-NR$^{30}$(C=O)NR$^{35}$, —(C1-C6 alkyl)-NR$^{30}$S(O)$_n$R$^{35}$, —NR$^{30}$(C1-C6 alkyl)-(C=O)R$^{35}$, —NR$^{30}$(C1-C6 alkyl)-(C=O)OR$^{35}$, —NR$^{30}$(C1-C6 alkyl)-(C=O)NR$^{35}$, —NR$^{30}$(C1-C6 alkyl)-S(O)$_n$R$^{35}$, —NR$^{30}$(C1-C6 alkyl)-S(O)$_n$NR$^{33}$R$^{34}$, —NR$^{30}$(C=O)R$^{35}$, —NR$^{30}$(C=O)OR$^{35}$, —NR$^{30}$(C=O)NR$^{35}$, —NR$^{30}$S(O)$_n$R$^{35}$, —(C1-C6 alkyl)-(C=O)R$^{35}$, —(C1-C6 alkyl)-(C=O)OR$^{35}$, —(C1-C6 alkyl)-(C=O)NR$^{35}$, —(C1-C6 alkyl)-S(O)$_n$R$^{35}$, —(C1-C6 alkyl)-S(O)$_n$NR$^{33}$R$^{34}$, —(C=O)R$^{35}$, —(C=O)OR$^{35}$, —S(O)$_n$R$^{35}$, —S(O)$_n$NR$^{33}$R$^{34}$, —(C1-C8 alkyl)-Ar$^{20}$, Ar$^{20}$, —(C1-C8 alkyl)-Cy$^{20}$, Cy$^{20}$, and R$^{37}$.

In a further aspect, XXX.

n. Cy$^{10}$ Groups

In one aspect, each Cy$^{10}$, when present, is independently selected from C3-C9 cycloalkyl and C2-C7 heterocycloalkyl, and wherein each Cy$^{10}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a further aspect, each Cy$^{10}$, when present, is independently selected from C3-C9 cycloalkyl and C2-C7 heterocycloalkyl, and wherein each Cy$^{10}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Cy$^{10}$, when present, is independently selected from C3-C9 cycloalkyl and C2-C7 heterocycloalkyl, and wherein each Cy$^{10}$ is unsubstituted.

In a further aspect, each Cy$^{10}$, when present, is independently selected from C3-C9 cycloalkyl and C2-C7 heterocycloalkyl, and wherein each Cy$^{10}$ is substituted with 0, 1, or 2 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Cy$^{10}$, when present, is independently selected from C3-C9 cycloalkyl and C2-C7 heterocycloalkyl, and wherein each Cy$^{10}$ is substituted with 0 or 1 group selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a yet further aspect, each Cy$^{10}$, when present, is independently selected from C3-C9 cycloalkyl and C2-C7 heterocycloalkyl, and wherein each Cy$^{10}$ is substituted with 1 or 2 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In an even further aspect, each Cy$^{10}$, when present, is independently selected from C3-C9 cycloalkyl and C2-C7 heterocycloalkyl, and wherein each Cy$^{10}$ is monosubstituted with a group selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino.

In a further aspect, each Cy$^{10}$, when present, is independently selected from C3-C9 cycloalkyl and C2-C7 heterocycloalkyl, and wherein each Cy$^{10}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Cy$^{10}$, when present, is independently selected from C3-C9 cycloalkyl and C2-C7 heterocycloalkyl, and wherein each Cy$^{10}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Cy$^{10}$, when present, is independently selected from C3-C9 cycloalkyl and C2-C7 heterocycloalkyl, and wherein each $Cy^{10}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Cy^{10}$, when present, is independently selected from C3-C9 cycloalkyl and C2-C7 heterocycloalkyl, and wherein each $Cy^{10}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Cy^{10}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{10}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Cy^{10}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{10}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Cy^{10}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{10}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Cy^{10}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{10}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Cy^{10}$, when present, is cyclohexyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Cy^{10}$, when present, is cyclohexyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Cy^{10}$, when present, is cyclohexyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Cy^{10}$, when present, is cyclohexyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Cy^{10}$, when present, is cyclohexyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Cy^{10}$, when present, is cyclohexyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH $-(CH_2)_3CH_3$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In a yet further aspect, each $Cy^{10}$, when present, is cyclohexyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Cy^{10}$, when present, is cyclohexyl and is monosubstituted with a group selected from —F, —Cl, —NH$_2$, —OH, —CN, methyl, —CF$_3$, —CCl$_3$, —OCH$_3$, and —NHCH$_3$. In a still further aspect, each $Cy^{10}$, when present, is cyclohexyl and is unsubstituted In various further aspects, each $Cy^{10}$, when present, is morpholinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Cy^{10}$, when present, is morpholinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Cy^{10}$, when present, is morpholinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Cy^{10}$, when present, is morpholinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Cy^{10}$, when present, is morpholinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Cy^{10}$, when present, is morpholinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Cy^{10}$, when present, is morpholinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Cy^{10}$, when present, is morpholinyl and is monosubstituted with a group selected from —F, —Cl, —NH$_2$, —OH, —CN, methyl, —CF$_3$, —CCl$_3$, —OCH$_3$, and —NHCH$_3$.

o. $Cy^{11}$ Groups

In one aspect, each $Cy^{11}$, when present, is independently selected from C3-C9 cycloalkyl and C2-C7 heterocycloalkyl, and wherein each $Cy^{11}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a further aspect, each $Cy^{11}$, when present, is independently selected from C3-C9 cycloalkyl and C2-C7 heterocycloalkyl, and wherein each $Cy^{11}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Cy^{11}$, when present, is independently selected from C3-C9 cycloalkyl and C2-C7 heterocycloalkyl, and wherein each $Cy^{11}$ is unsubstituted.

In a further aspect, each $Cy^{11}$, when present, is independently selected from C3-C9 cycloalkyl and C2-C7 heterocycloalkyl, and wherein each $Cy^{11}$ is substituted with 0, 1, or 2 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Cy^{11}$, when present, is independently selected from C3-C9 cycloalkyl and C2-C7 heterocycloalkyl, and wherein each $Cy^{11}$ is substituted with 0 or 1 group selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a yet further aspect, each $Cy^{11}$, when present, is independently selected from C3-C9 cycloalkyl and C2-C7 heterocycloalkyl, and wherein each $Cy^{11}$ is substituted with 1 or 2 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In an even further aspect, each $Cy^{11}$, when present, is independently selected from C3-C9 cycloalkyl and C2-C7 heterocycloalkyl, and wherein each $Cy^{11}$ is monosubstituted with a group selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino.

In a further aspect, each $Cy^{11}$, when present, is independently selected from C3-C9 cycloalkyl and C2-C7 heterocycloalkyl, and wherein each $Cy^{11}$ is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each $Cy^{11}$, when present, is independently selected from C3-C9 cycloalkyl and C2-C7 heterocycloalkyl, and wherein each $Cy^{11}$ is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each $Cy^{11}$, when present, is independently selected from C3-C9 cycloalkyl and C2-C7 heterocycloalkyl, and wherein each $Cy^{11}$ is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each $Cy^{11}$, when present, is independently selected from C3-C9 cycloalkyl and C2-C7 heterocycloalkyl, and wherein each $Cy^{11}$ is substituted with 0, 1, 2, or 3 groups independently selected from —F, —Cl, —NH₂, —OH, —CN, —CF₃, —CCl₃, —OCH₃, and —NHCH₃.

In various further aspects, each $Cy^{11}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{11}$ is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each $Cy^{11}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{11}$ is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each $Cy^{11}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{11}$ is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each $Cy^{11}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{11}$ is substituted with 0, 1, 2, or 3 groups independently selected from —F, —Cl, —NH₂, —OH, —CN, methyl, —CF₃, —CCl₃, —OCH₃, and —NHCH₃.

In various further aspects, each $Cy^{11}$, when present, is cyclohexyl and is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each $Cy^{11}$, when present, is cyclohexyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each $Cy^{11}$, when present, is cyclohexyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Cy$^{11}$, when present, is cyclohexyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Cy$^{11}$, when present, is cyclohexyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Cy$^{11}$, when present, is cyclohexyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Cy$^{11}$, when present, is cyclohexyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Cy$^{11}$, when present, is cyclohexyl and is monosubstituted with a group selected from —F, —Cl, —NH$_2$, —OH, —CN, methyl, —CF$_3$, —CCl$_3$, —OCH$_3$, and —NHCH$_3$. In a still further aspect, each Cy$^{11}$, when present, is cyclohexyl and is unsubstituted In various further aspects, each Cy$^{11}$, when present, is morpholinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Cy$^{11}$, when present, is morpholinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Cy$^{11}$, when present, is morpholinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Cy$^{11}$, when present, is morpholinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Cy$^{11}$, when present, is morpholinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Cy$^{11}$, when present, is morpholinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Cy$^{11}$, when present, is morpholinyl and is monosubstituted with a group selected from —F, —Cl, —NH$_2$, —OH, —CN, methyl, —CF$_3$, —CCl$_3$, —OCH$_3$, and —NHCH$_3$.

p. Cy$^{20}$ Groups

In one aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{36}$. In a further aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, C1-C6 dialkylamino, and —S(O)$_n$R$^{36}$. In a still further aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, C1-C3 dialkylamino, and —S(O)$_n$R$^{36}$. In a yet further aspect, each Cy$^{20}$, when present, is independently selected from C3-C9 cycloalkyl and C2-C7 heterocycloalkyl, and wherein each Cy$^{20}$ is unsubstituted.

In a further aspect, each Cy$^{20}$, when present, is independently selected from C3-C9 cycloalkyl and C2-C7 heterocycloalkyl, and wherein each Cy$^{20}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{36}$. In a still further aspect, each Cy$^{20}$, when present, is independently selected from C3-C9 cycloalkyl and C2-C7 heterocycloalkyl, and wherein each Cy$^{20}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{36}$. In a yet further aspect, each Cy$^{20}$, when present, is independently selected from C3-C9 cycloalkyl and C2-C7 heterocycloalkyl, and wherein each Cy$^{20}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{36}$. In an even further aspect, each Cy$^{20}$, when present, is independently selected from C3-C9 cycloalkyl and C2-C7 heterocycloalkyl, and wherein each Cy$^{20}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{36}$.

In a further aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{20}$, when present, is independently selected from C3-C9 cycloalkyl and C2-C7 heterocycloalkyl, and wherein each Cy$^{20}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{20}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{20}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —(S═O)CH$_3$, and —SO$_2$CH$_3$. In a yet further aspect, each Cy$^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{20}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{20}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{20}$, when present, is cyclopropyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each $Cy^{20}$, when present, is cyclopropyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{20}$, when present, is cyclopropyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{20}$, when present, is cyclopropyl and is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{20}$, when present, is cyclopropyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each $Cy^{20}$, when present, is cyclopropyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{20}$, when present, is cyclopropyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{20}$, when present, is cyclopropyl and is monosubstituted with a group selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{20}$, when present, is azetidinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each $Cy^{20}$, when present, is azetidinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{20}$, when present, is azetidinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{20}$, when present, is azetidinyl and is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{20}$, when present, is azetidinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{20}$, when present, is azetidinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{20}$, when present, is azetidinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{20}$, when present, is azetidinyl and is monosubstituted with a group selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

q. Cy$^{30}$ Groups

In one aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{45}$. In a further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, C1-C6 dialkylamino, and —S(O)$_n$R$^{45}$. In a still further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, C1-C3 dialkylamino, and —S(O)$_n$R$^{45}$. In a yet further aspect, each Cy$^{30}$, when present, is independently selected from C3-C9 cycloalkyl and C2-C7 heterocycloalkyl, and wherein each Cy$^{30}$ is unsubstituted.

In a further aspect, each Cy$^{30}$, when present, is independently selected from C3-C9 cycloalkyl and C2-C7 heterocycloalkyl, and wherein each Cy$^{30}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{45}$. In a still further aspect, each Cy$^{30}$, when present, is independently selected from C3-C9 cycloalkyl and C2-C7 heterocycloalkyl, and wherein each Cy$^{30}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{45}$. In a yet further aspect, each Cy$^{30}$, when present, is independently selected from C3-C9 cycloalkyl and C2-C7 heterocycloalkyl, and wherein each Cy$^{30}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{45}$. In an even further aspect, each Cy$^{30}$, when present, is independently selected from C3-C9 cycloalkyl and C2-C7 heterocycloalkyl, and wherein each Cy$^{30}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{45}$.

In a further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —(S═O)

CH₃, and —SO₂CH₃. In a yet further aspect, each Cy³⁰, when present, is independently selected from C3-C9 cycloalkyl and C2-C7 heterocycloalkyl, and wherein each Cy³⁰ is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy³⁰, when present, is independently selected from C3-C9 cycloalkyl and C2-C7 heterocycloalkyl, and wherein each Cy³⁰ is substituted with 0, 1, 2, or 3 groups independently selected from —F, —Cl, —NH₂, —OH, —CN, methyl, —CF₃, —CCl₃, —OCH₃, —NHCH₃, —(S=O)CH₃, and —SO₂CH₃.

In various further aspects, each Cy³⁰, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy³⁰ is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy³⁰, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy³⁰ is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃) CH₂CH₃, —N(CH₃)(CH₂)₂CH₃, —N(CH₃)CH(CH₃)₂, —N(CH₂CH₃)₂, —(S=O)CH₃, and —SO₂CH₃. In a yet further aspect, each Cy³⁰, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy³⁰ is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy³⁰, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy³⁰ is substituted with 0, 1, 2, or 3 groups independently selected from —F, —Cl, —NH₂, —OH, —CN, methyl, —CF₃, —CCl₃, —OCH₃, —NHCH₃, —(S=O)CH₃, and —SO₂CH₃.

In various further aspects, each Cy³⁰, when present, is cyclopropyl and is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃) CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy³⁰, when present, is cyclopropyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂ CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃) (CH₂)₂CH₃, —N(CH₃)CH(CH₃)₂, —N(CH₂CH₃)₂, —(S=O)CH₃, and —SO₂CH₃. In a yet further aspect, each Cy³⁰, when present, is cyclopropyl and is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy³⁰, when present, is cyclopropyl and is substituted with 0, 1, 2, or 3 groups independently selected from —F, —Cl, —NH₂, —OH, —CN, methyl, —CF₃, —CCl₃, —OCH₃, —NHCH₃, —(S=O)CH₃, and —SO₂CH₃.

In various further aspects, each Cy³⁰, when present, is cyclopropyl and is monosubstituted with a group selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂ CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂ CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃) CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃.

In a still further aspect, each $Cy^{30}$, when present, is cyclopropyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{30}$, when present, is cyclopropyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{30}$, when present, is cyclopropyl and is monosubstituted with a group selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{30}$, when present, is azetidinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each $Cy^{30}$, when present, is azetidinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{30}$, when present, is azetidinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{30}$, when present, is azetidinyl and is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{30}$, when present, is azetidinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each $Cy^{30}$, when present, is azetidinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{30}$, when present, is azetidinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{30}$, when present, is azetidinyl and is monosubstituted with a group selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

r. $Cy^{40}$ Groups

In one aspect, each $Cy^{40}$, when present, is independently selected from C3-C9 cycloalkyl and C2-C7 heterocycloalkyl, and wherein each $Cy^{40}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{46}$. In a further aspect, each $Cy^{40}$, when present, is independently selected from C3-C9 cycloalkyl and C2-C7 heterocycloalkyl, and wherein each $Cy^{40}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, C1-C6 dialkylamino, and —S(O)$_n$R$^{46}$. In a still further aspect, each $Cy^{40}$, when present, is independently selected from C3-C9 cycloalkyl and C2-C7 heterocycloalkyl, and wherein each $Cy^{40}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, C1-C3 dialkylamino, and —S(O)$_n$R$^{46}$. In a yet further aspect, each $Cy^{40}$, when present, is independently selected from C3-C9 cycloalkyl and C2-C7 heterocycloalkyl, and wherein each $Cy^{40}$ is unsubstituted.

In a further aspect, each $Cy^{40}$, when present, is independently selected from C3-C9 cycloalkyl and C2-C7 heterocycloalkyl, and wherein each $Cy^{40}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{46}$. In a still further aspect, each Cy$^{40}$, when present, is independently selected from C3-C9 cycloalkyl and C2-C7 heterocycloalkyl, and wherein each Cy$^{40}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{46}$. In a yet further aspect, each Cy$^{40}$, when present, is independently selected from C3-C9 cycloalkyl and C2-C7 heterocycloalkyl, and wherein each Cy$^{40}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{46}$. In an even further aspect, each Cy$^{40}$, when present, is independently selected from C3-C9 cycloalkyl and C2-C7 heterocycloalkyl, and wherein each Cy$^{40}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_n$R$^{46}$.

In a further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{40}$, when present, is cyclopropyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{40}$, when present, is cyclopropyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —(S═O)CH$_3$, and —SO$_2$CH$_3$. In a yet further aspect, each Cy$^{40}$, when present, is cyclopropyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{40}$, when present, is cyclopropyl and is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{40}$, when present, is cyclopropyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{40}$, when present, is cyclopropyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —NHCH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{40}$, when present, is cyclopropyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{40}$, when present, is cyclopropyl and is monosubstituted with a group selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{40}$, when present, is azetidinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{40}$, when present, is azetidinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{40}$, when present, is azetidinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{40}$, when present, is azetidinyl and is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{40}$, when present, is azetidinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each Cy$^{40}$, when present, is azetidinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each Cy$^{40}$, when present, is azetidinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each Cy$^{40}$, when present, is azetidinyl and is monosubstituted with a group selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

s. A$^1$ Groups

In one aspect, A$^1$ is selected from S, O, NR$^8$, and CR$^{9a}$R$^{9b}$. In a further aspect, A$^1$ is selected from S, O, and NR$^8$. In a still further aspect, A$^1$ is selected from S, O, and CR$^{9a}$R$^{9b}$. In a yet further aspect, A$^1$ is selected from O, NR$^8$, and CR$^{9a}$R$^{9b}$. In an even further aspect, A$^1$ is selected from S and O. In a still further aspect, A$^1$ is selected from S and NR$^8$. In a yet further aspect, A$^1$ is selected from S and CR$^{9a}$R$^{9b}$. In an even further aspect, A$^1$ is selected from O and NR$^8$. In a still further aspect, A$^1$ is selected from O and CR$^{9a}$R$^{9b}$. In a yet further aspect, A$^1$ is selected from NR$^8$ and CR$^{9a}$R$^{9b}$.

In a further aspect, A$^1$ is S. In a still further aspect, A$^1$ is O. In a yet further aspect, A$^1$ is NR$^8$. In an even further aspect, A$^1$ is CR$^{9a}$R$^{9b}$.

2. Example Compounds

In one aspect, a compound can be present as one or more of the following structures:

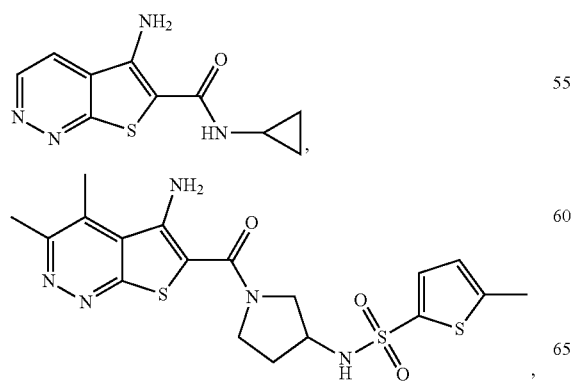

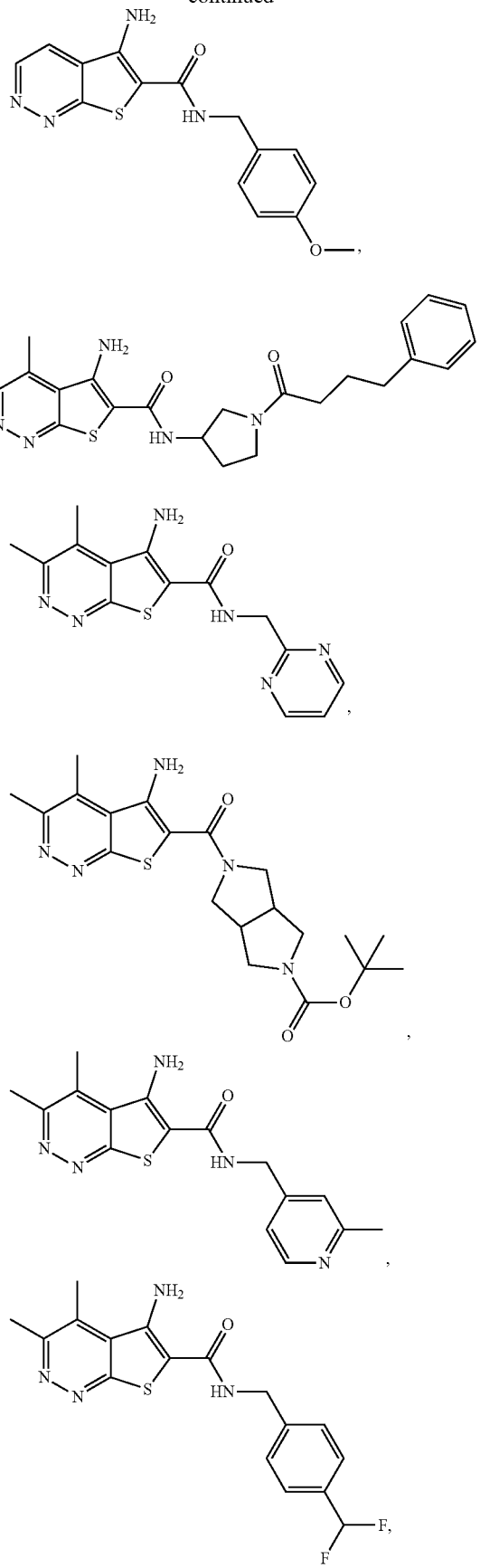

273
-continued
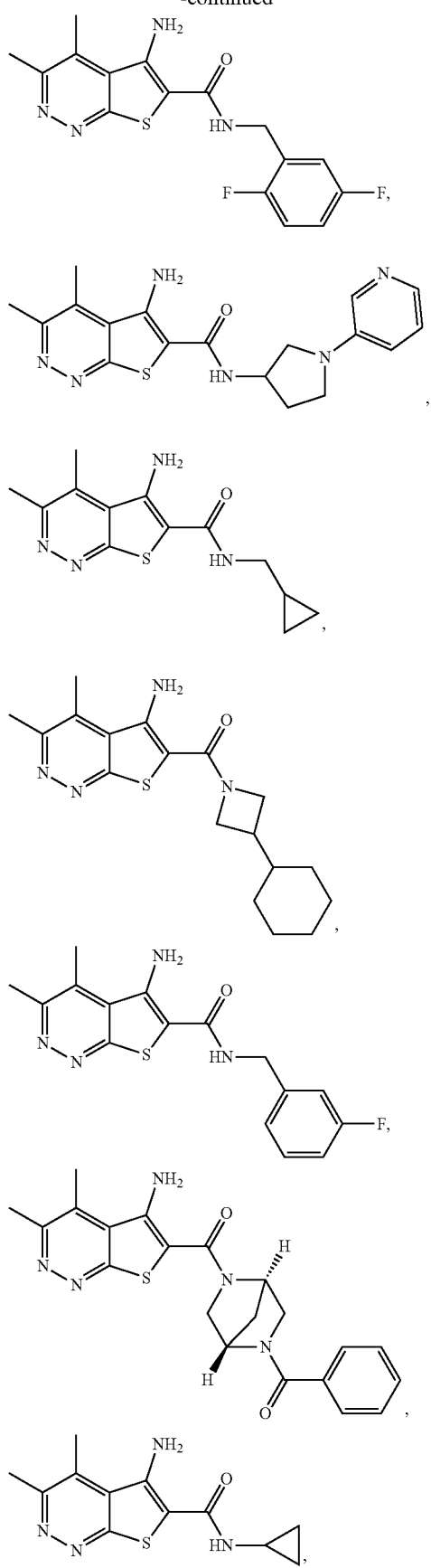
274
-continued
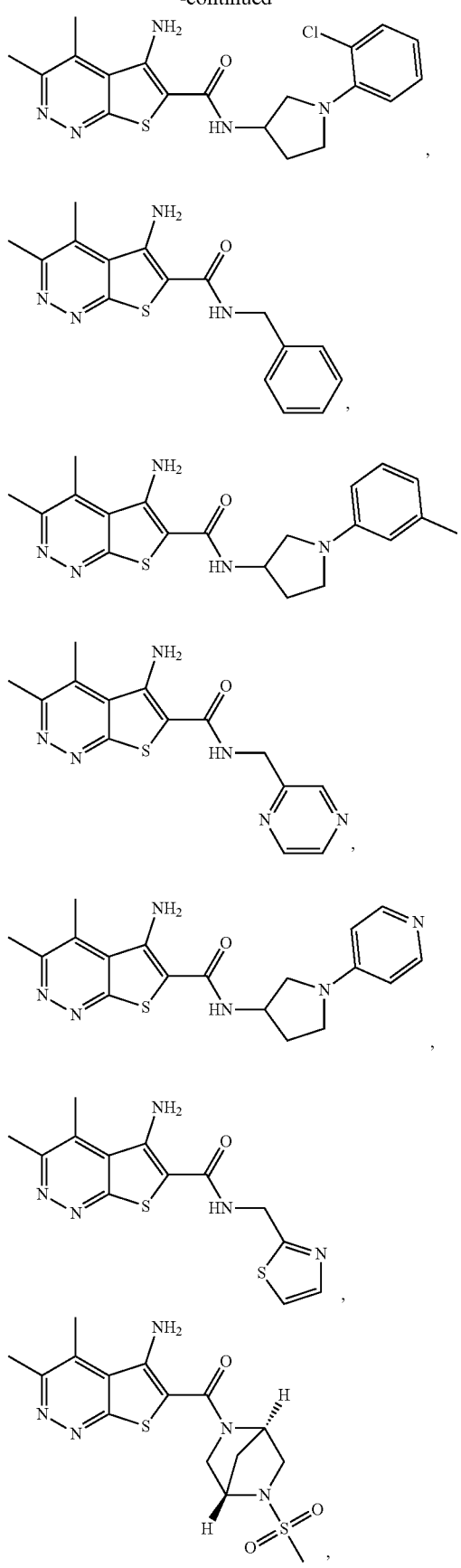

275
-continued
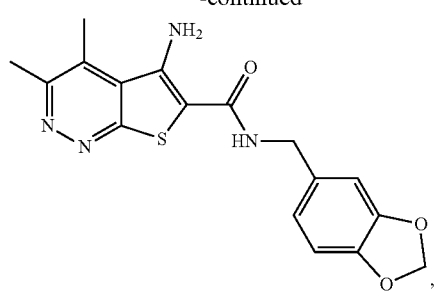
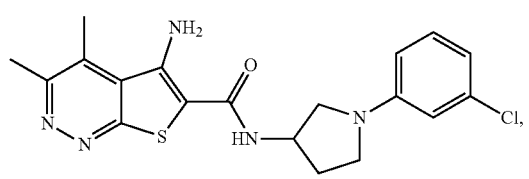
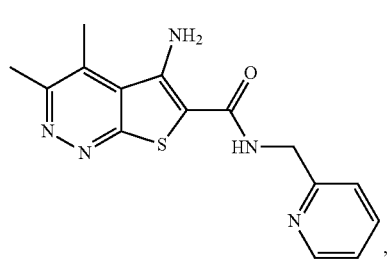
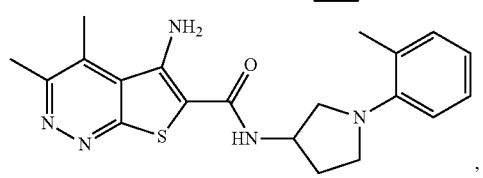
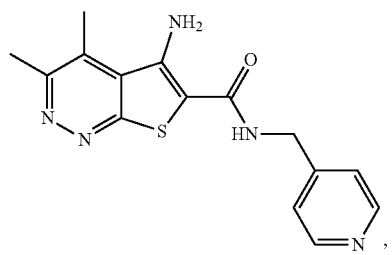
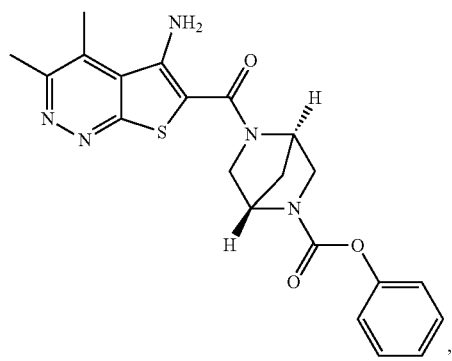
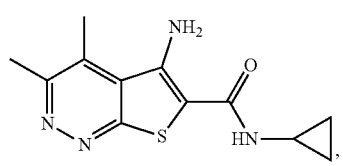
276
-continued
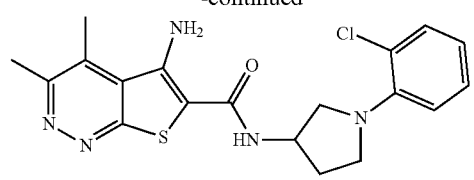
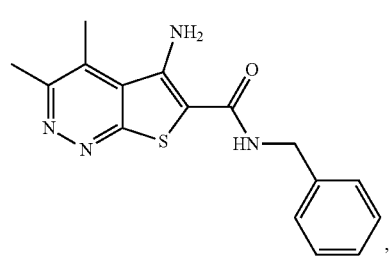
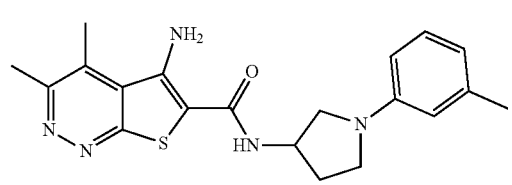
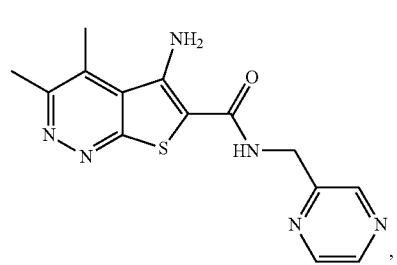
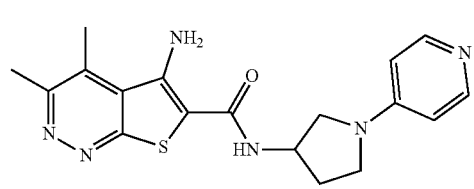
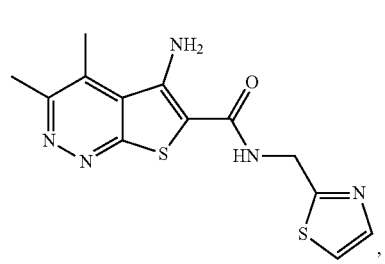
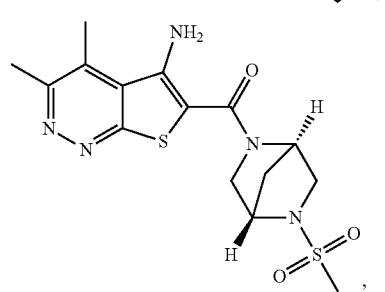

277
-continued
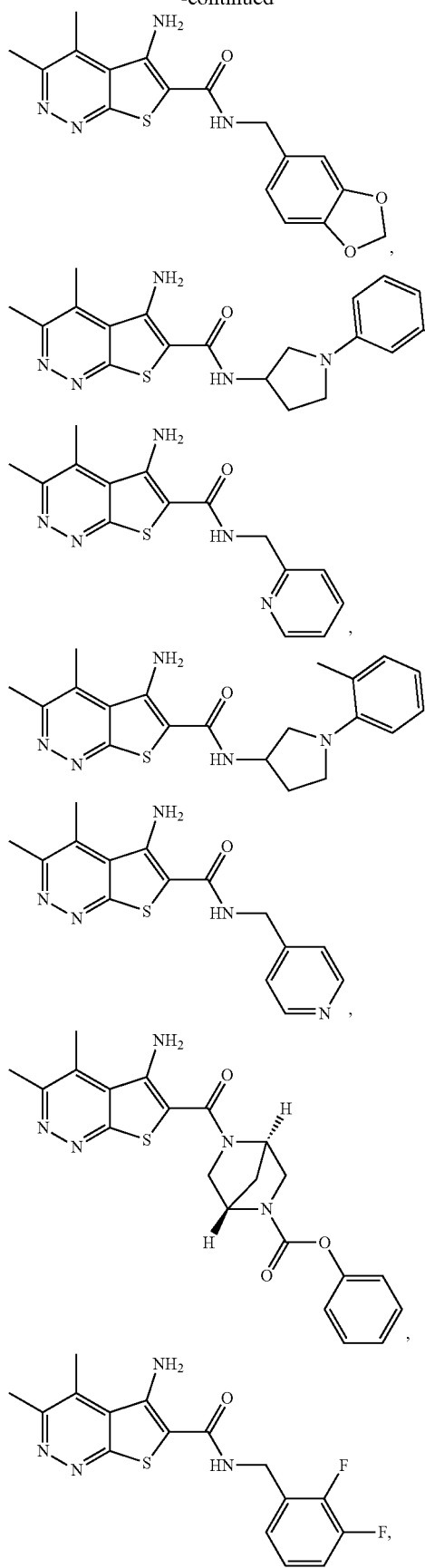
278
-continued
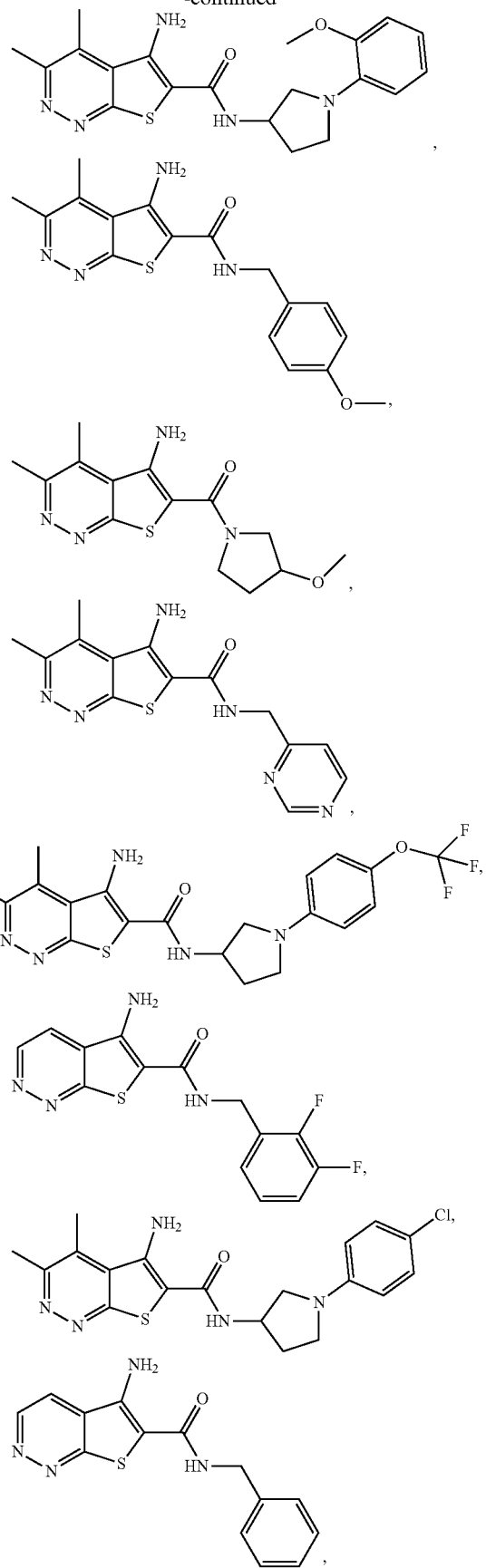

279
-continued
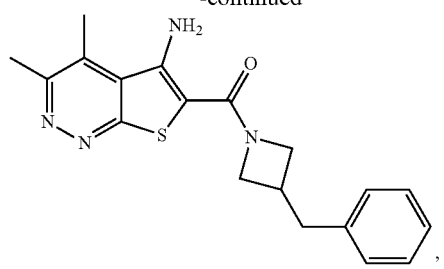
,
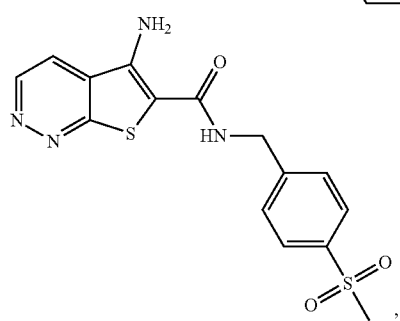
,
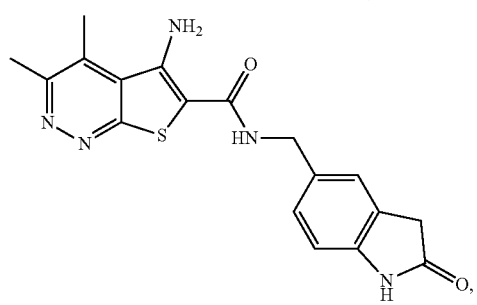
,
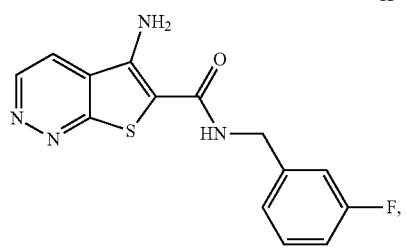
,
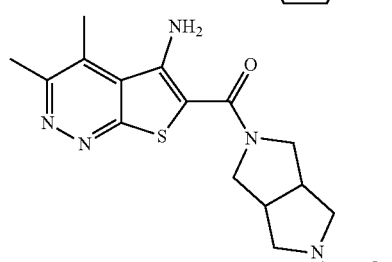
,
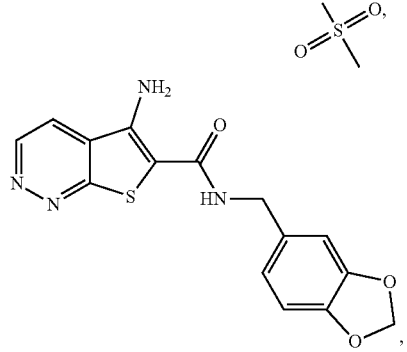
,
280
-continued
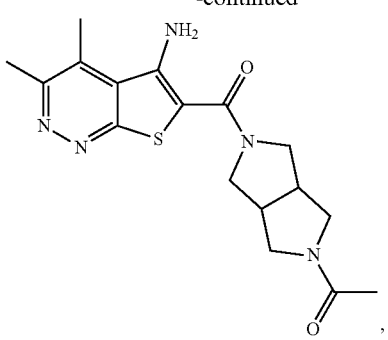
,
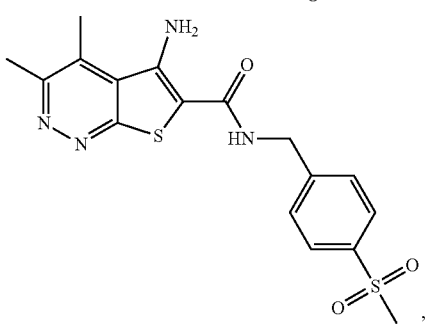
,
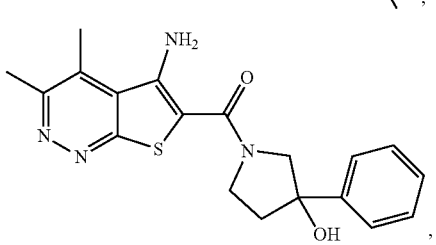
,
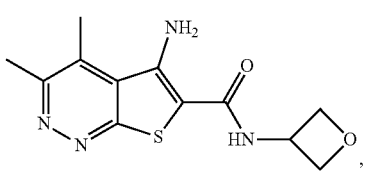
,
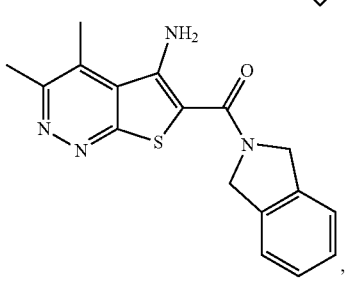
,
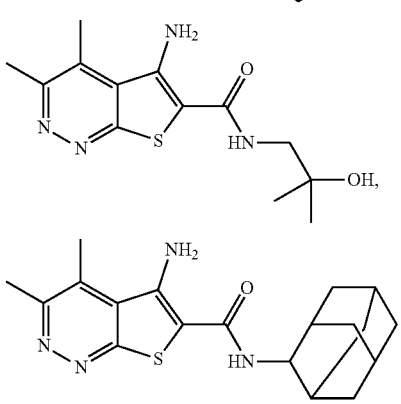
, 281
-continued
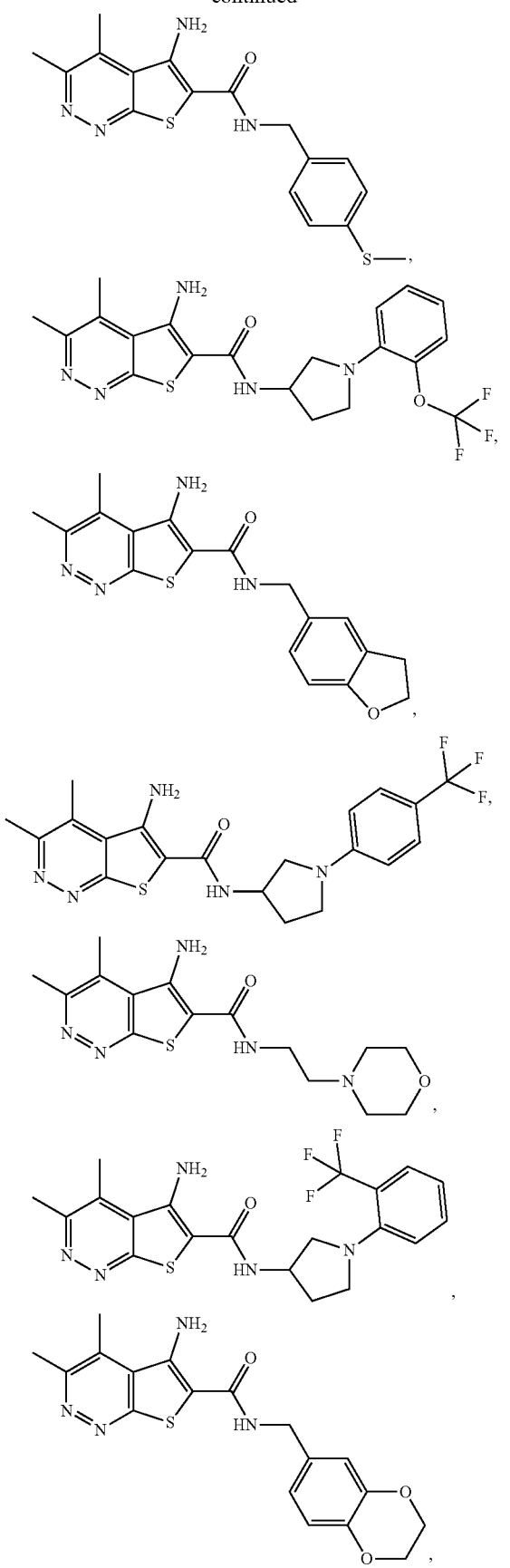
282
-continued
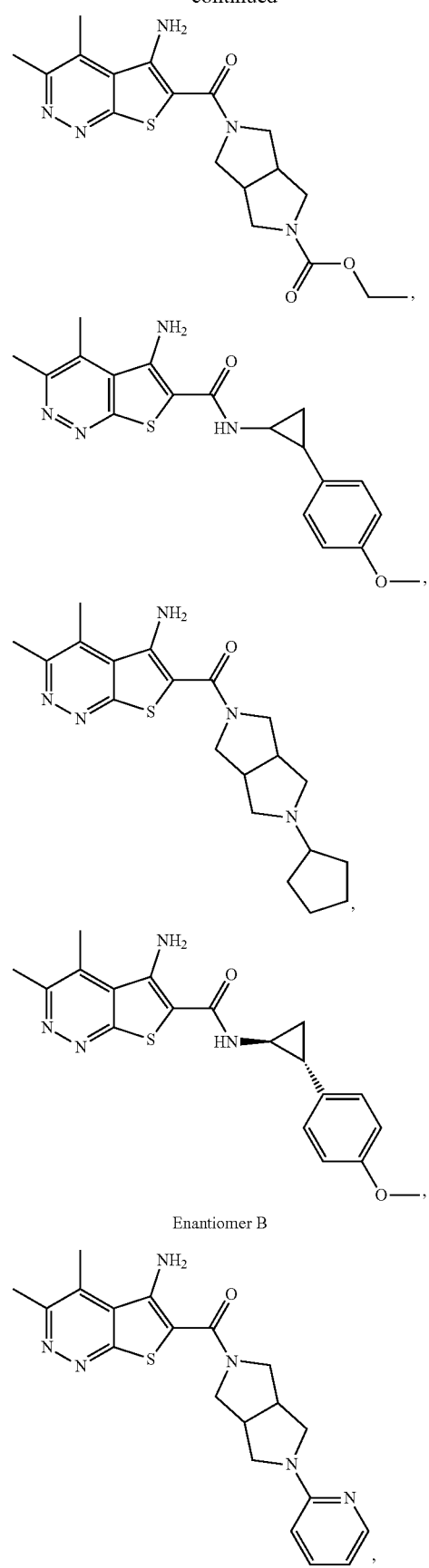
Enantiomer B

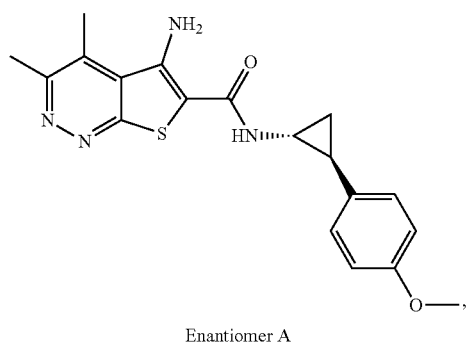
Enantiomer A
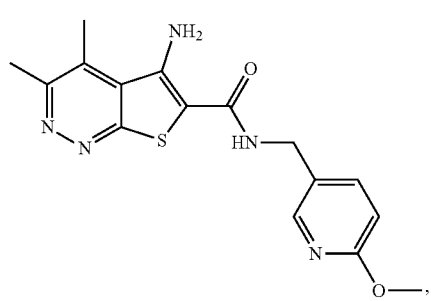
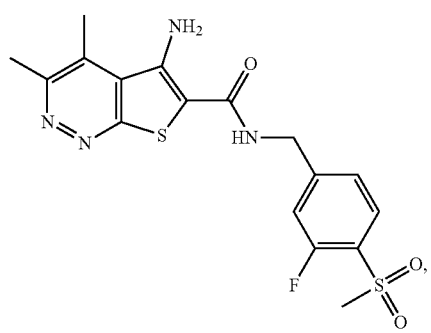
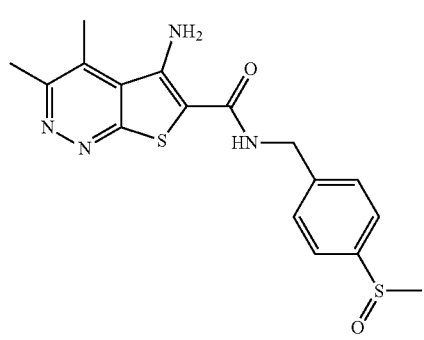
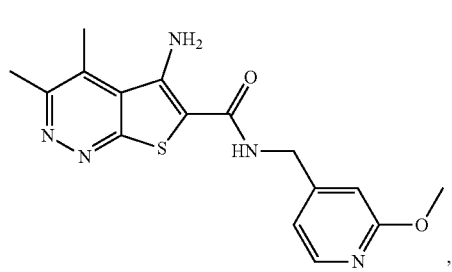
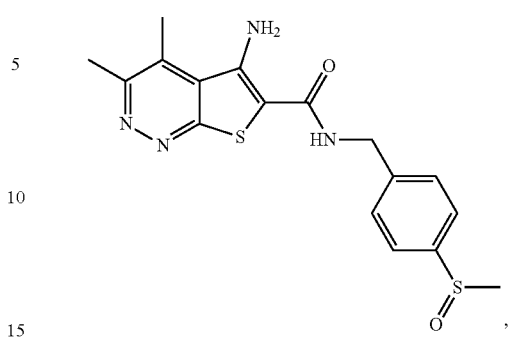
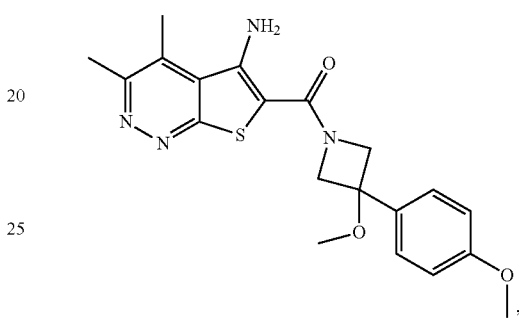
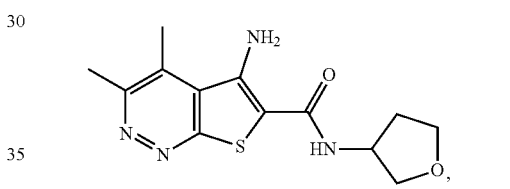
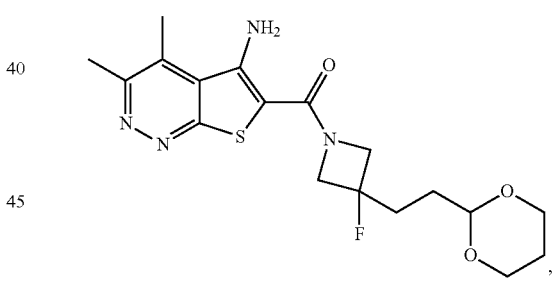
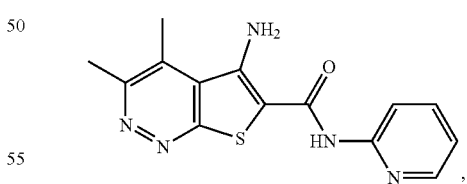
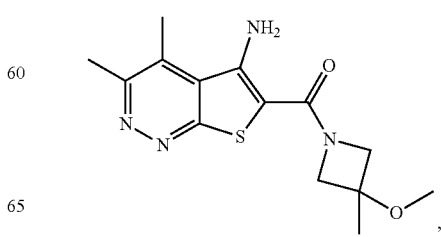

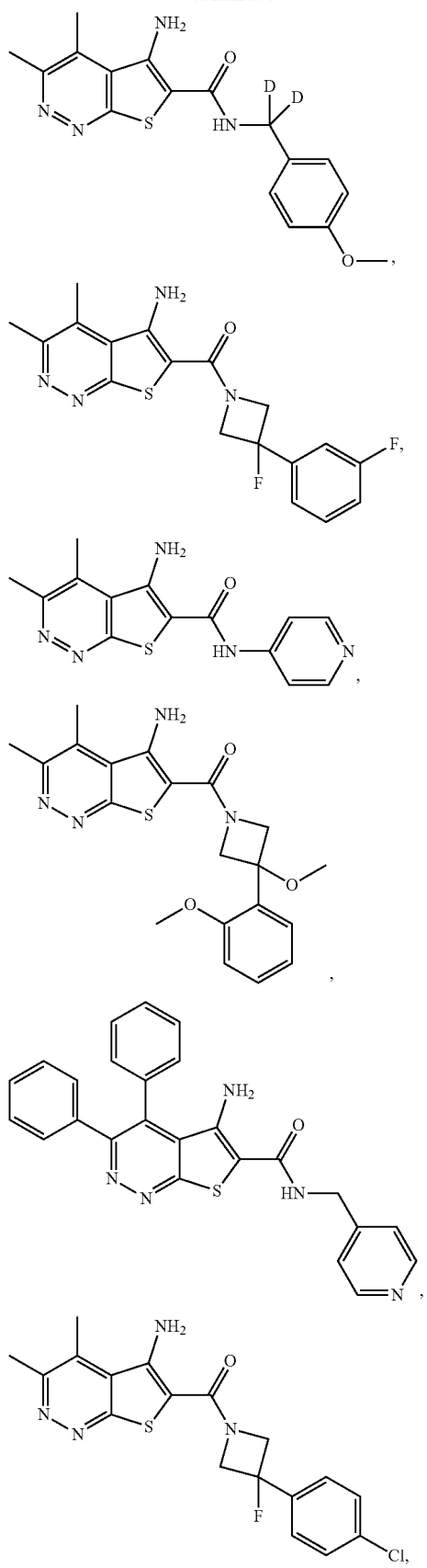
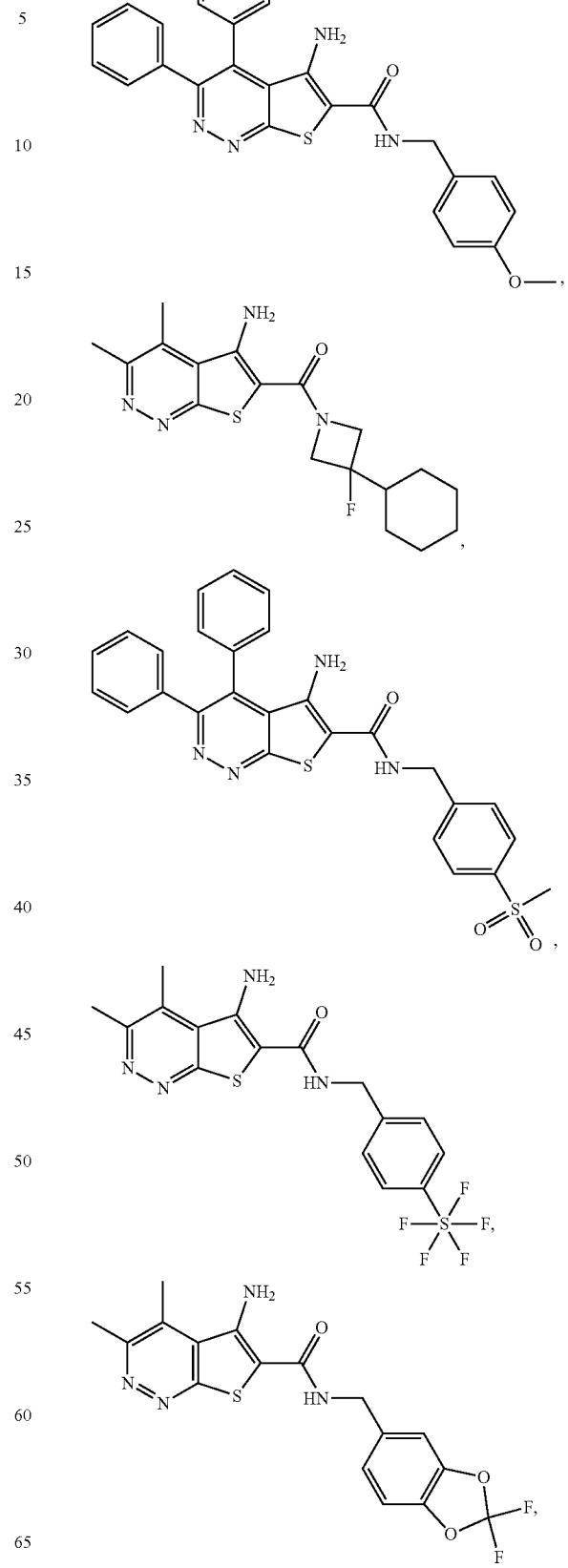

287
-continued
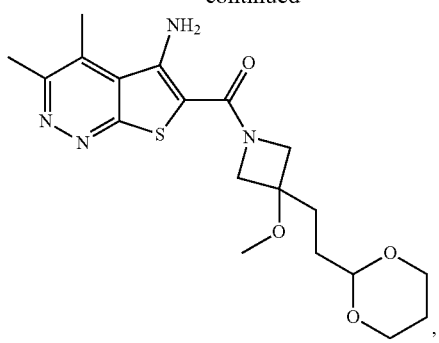
288
-continued
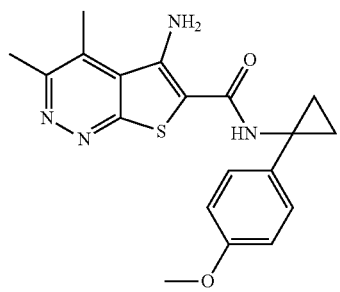
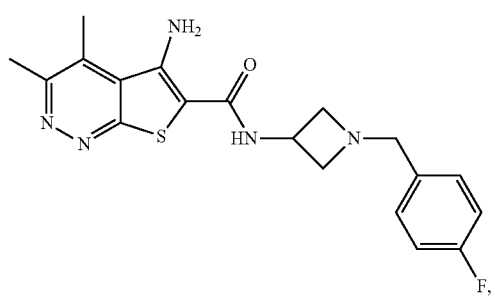
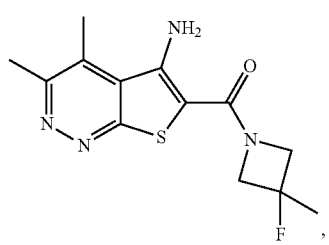
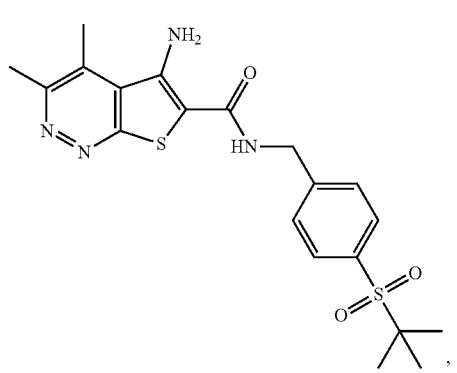
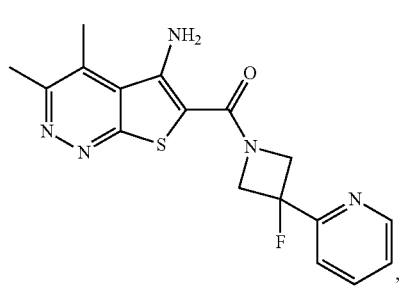

289
-continued
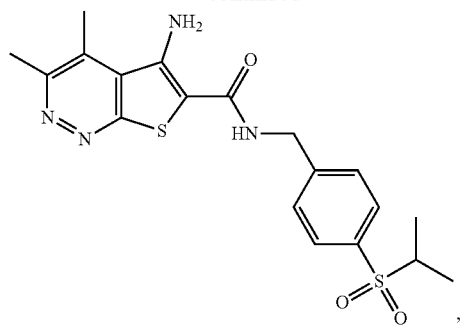
,
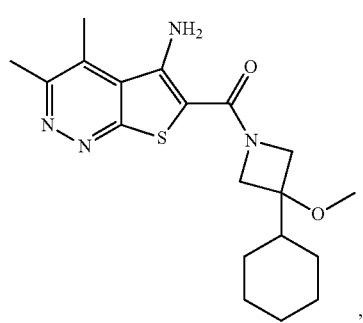
,
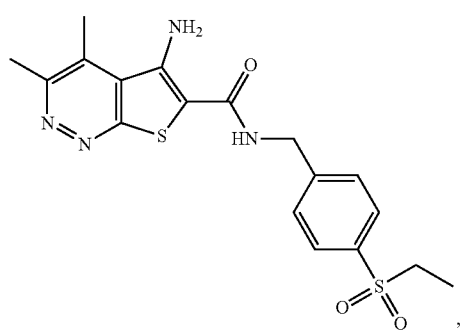
,
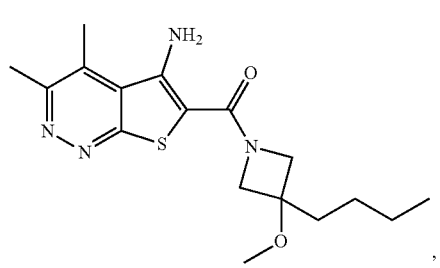
,
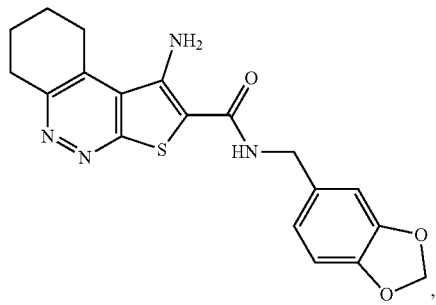
,
290
-continued
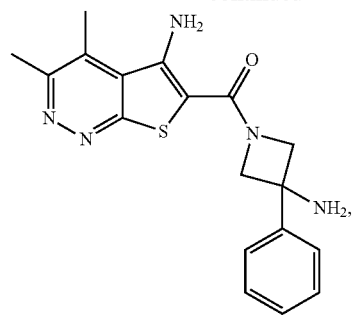
,
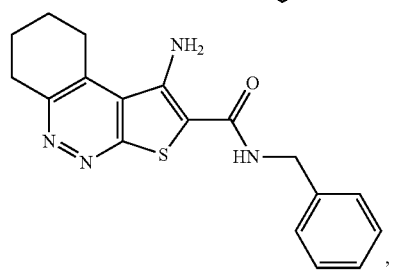
,
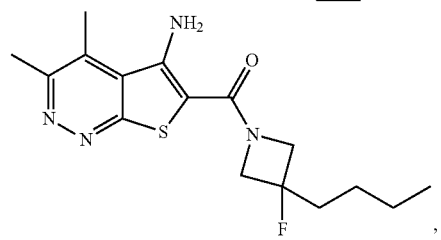
,
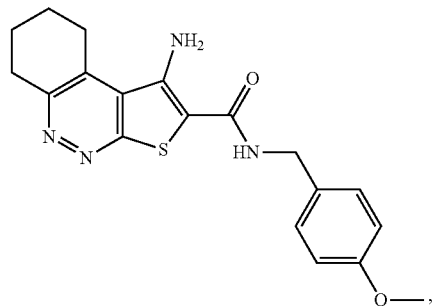
,
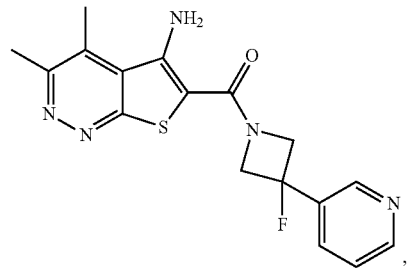
,
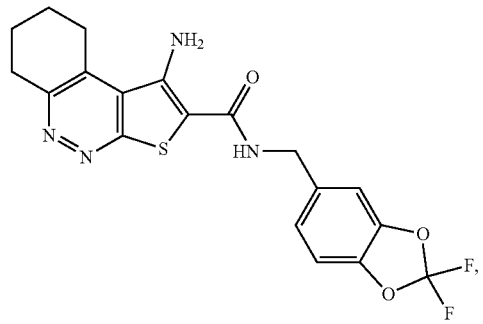
, 291
-continued
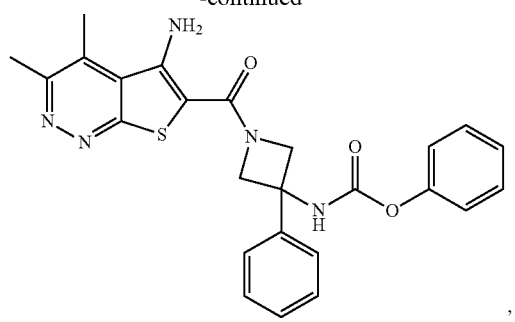,
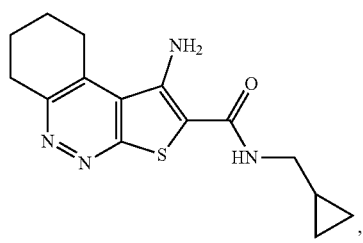,
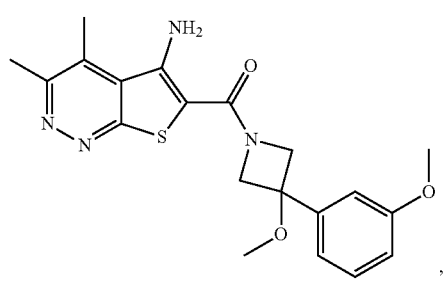,
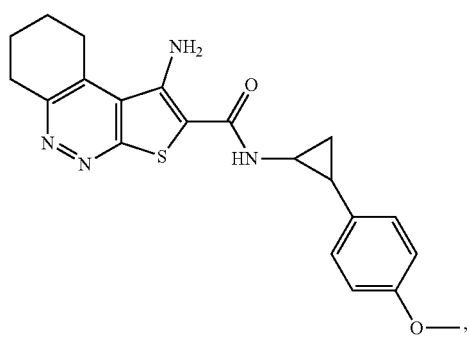,
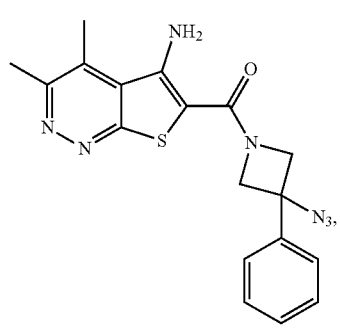,
292
-continued
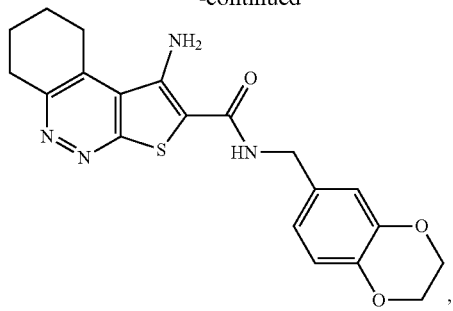,
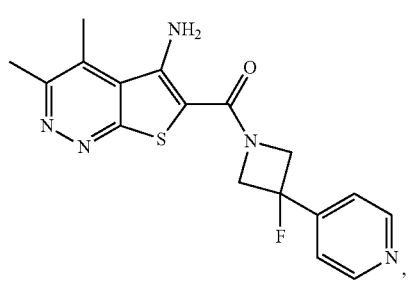,
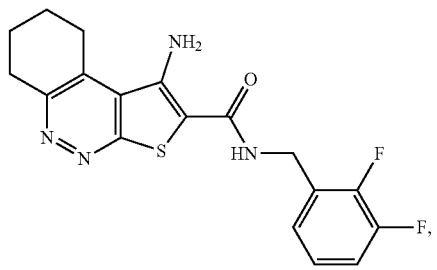,
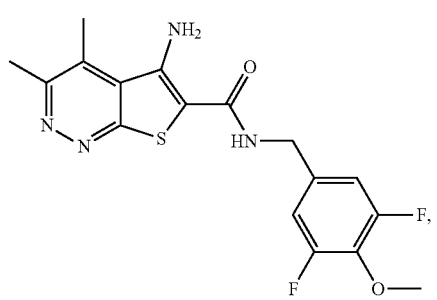,
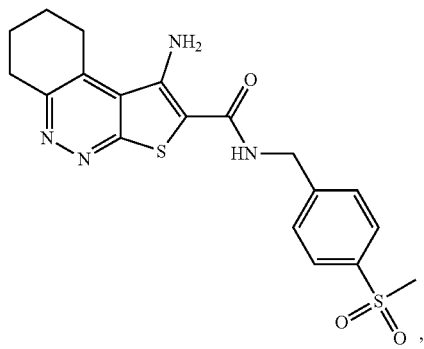, 293
-continued
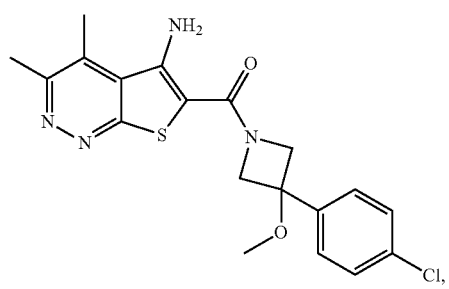
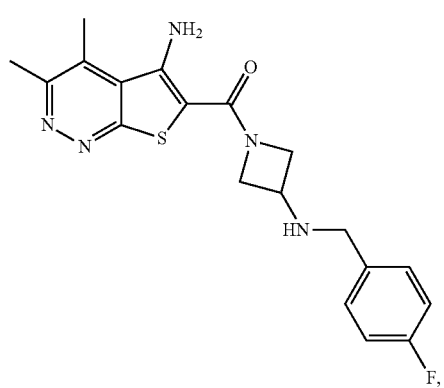
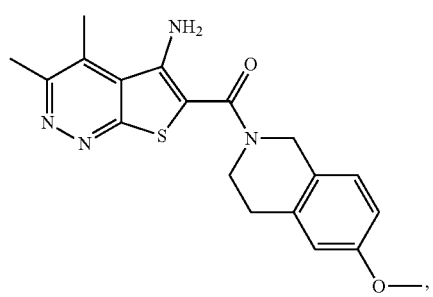
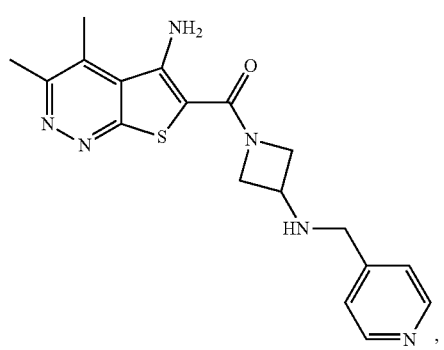
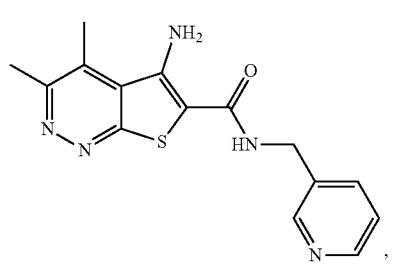
294
-continued
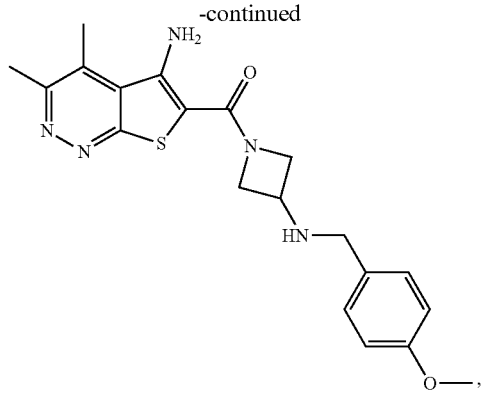
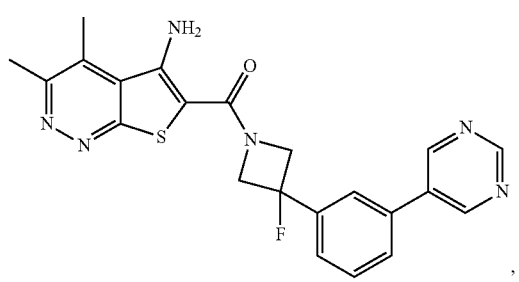
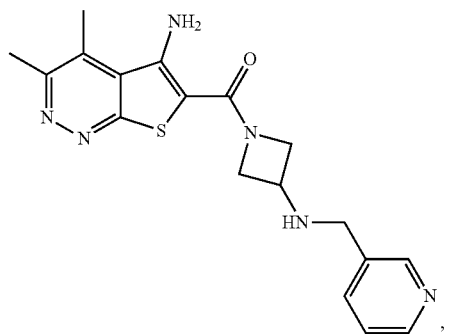
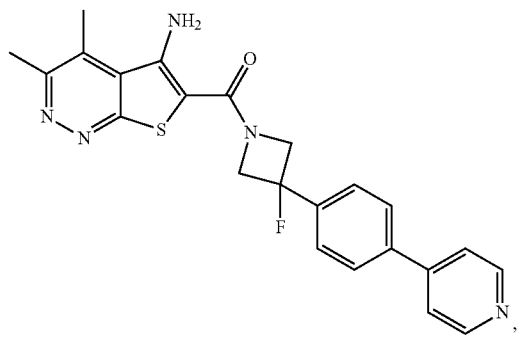
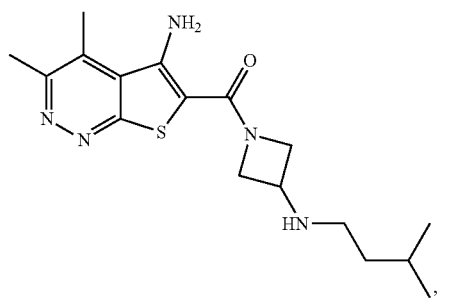

295
-continued
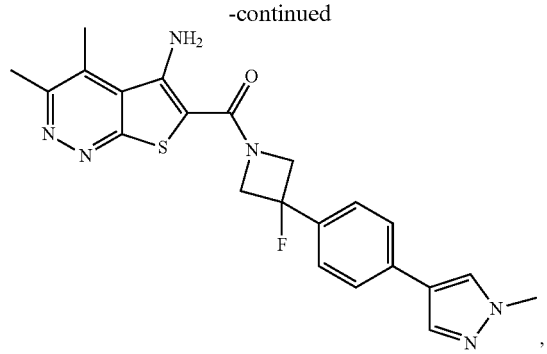
,
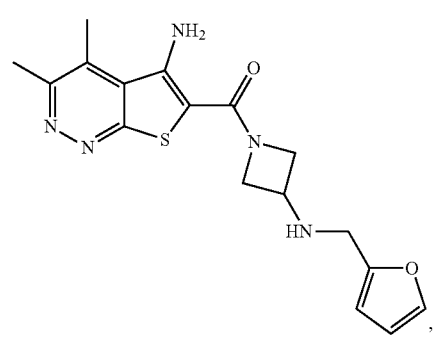
,
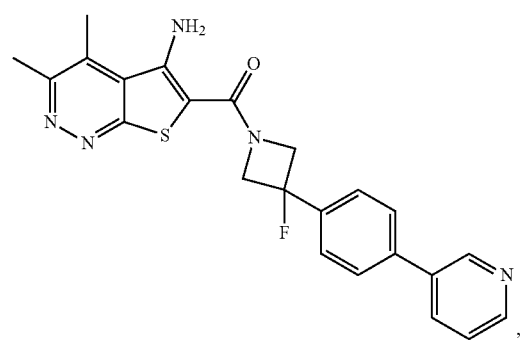
,
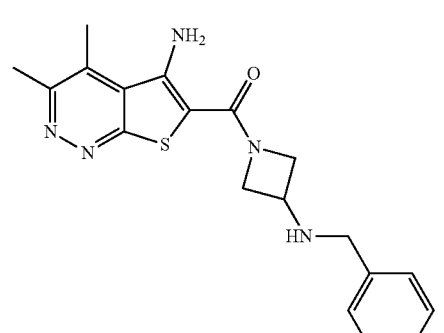
,
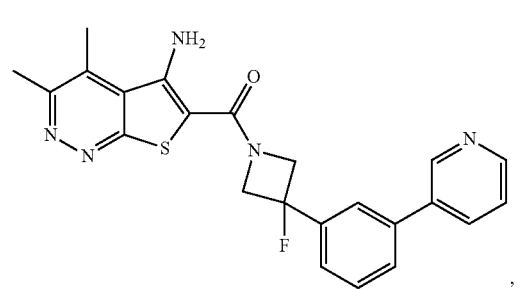
,
296
-continued
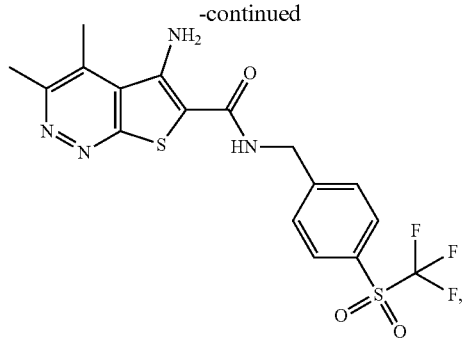
,
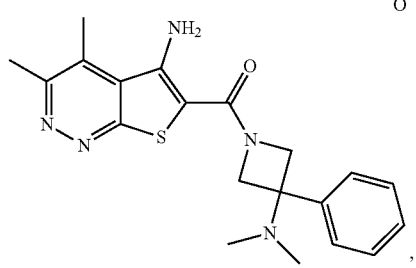
,
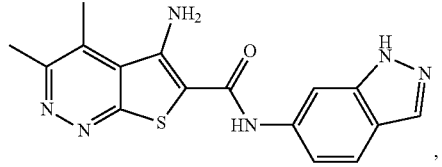
,
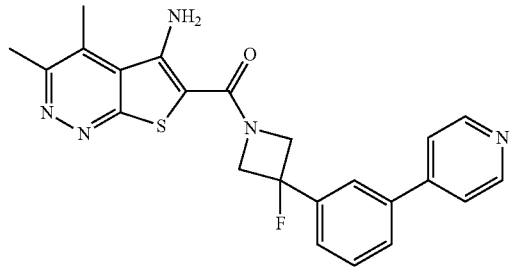
,
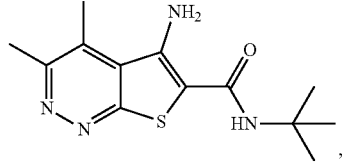
,
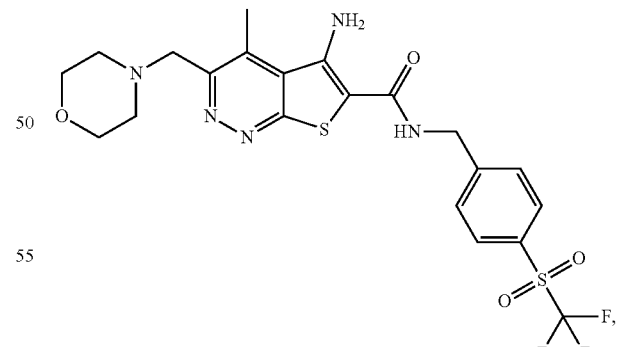
,
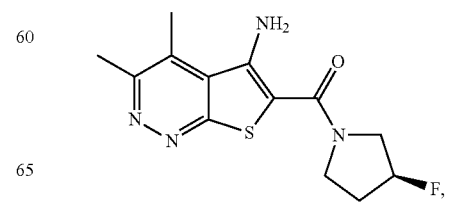
,

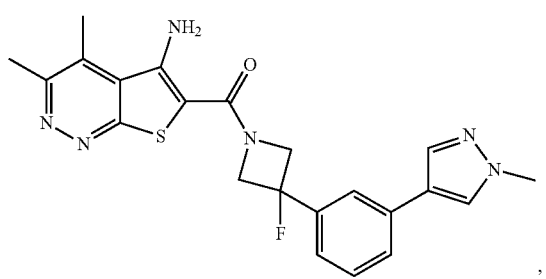
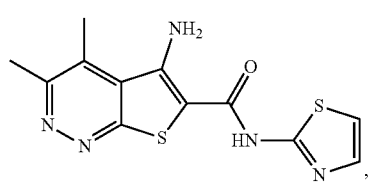
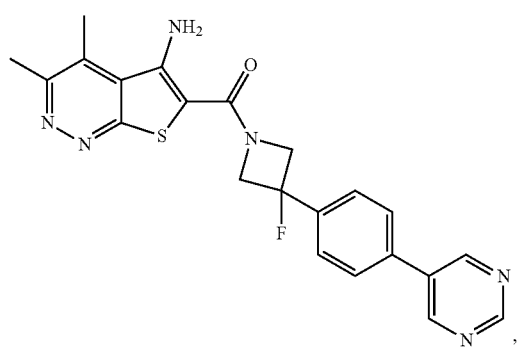
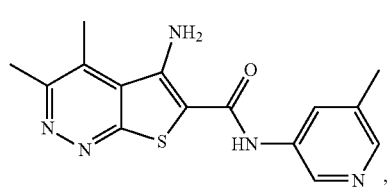
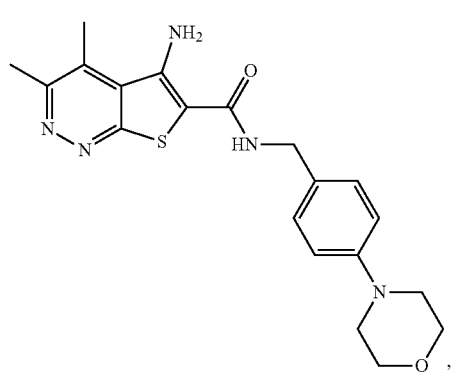
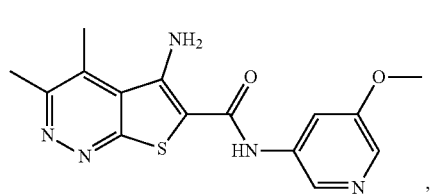
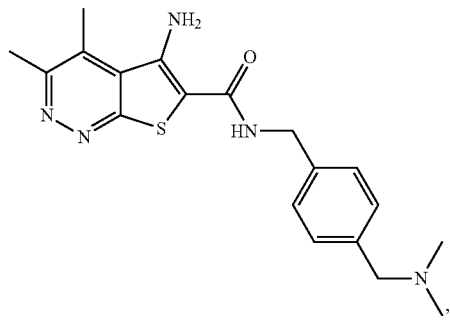
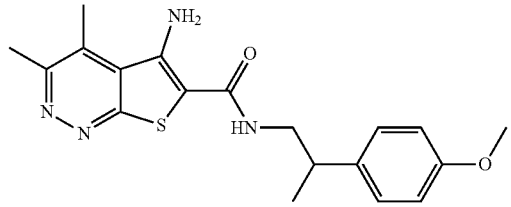
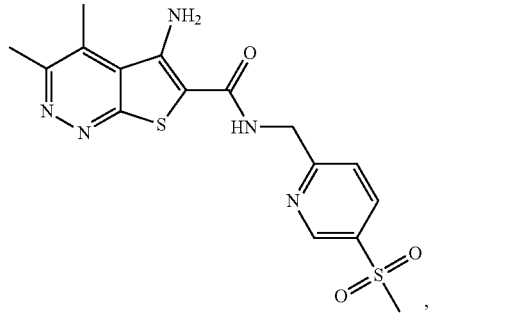
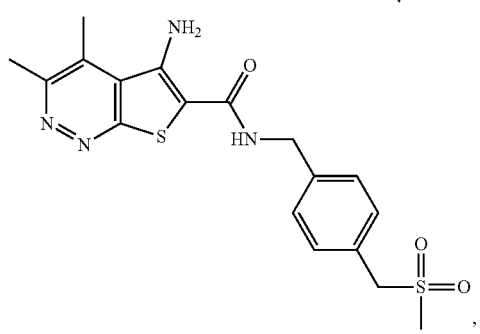
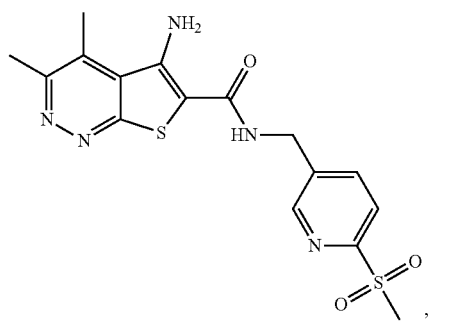
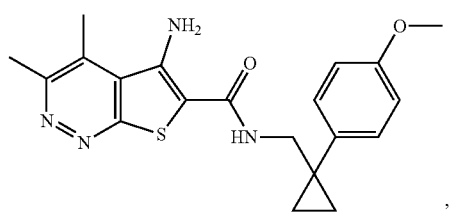

299
-continued
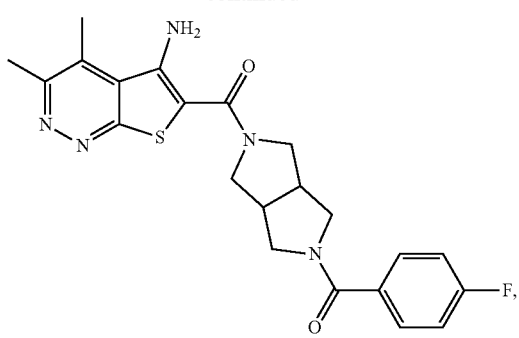
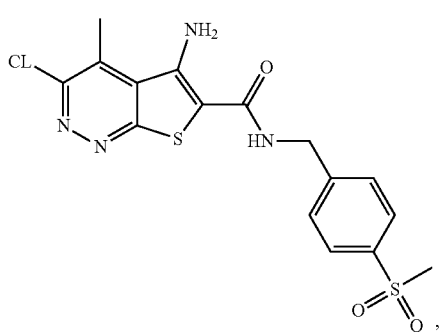
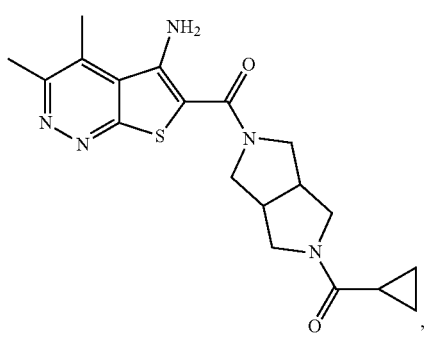
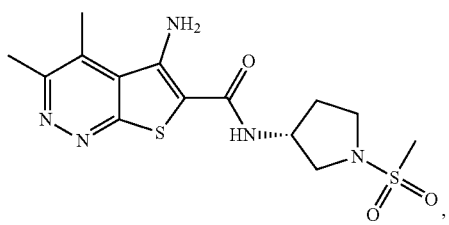
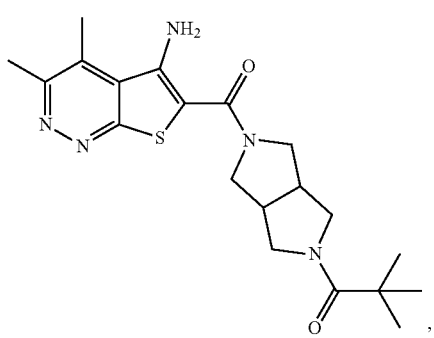
300
-continued
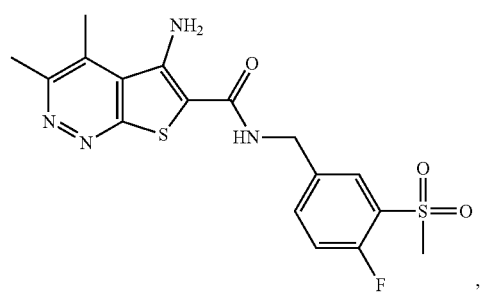
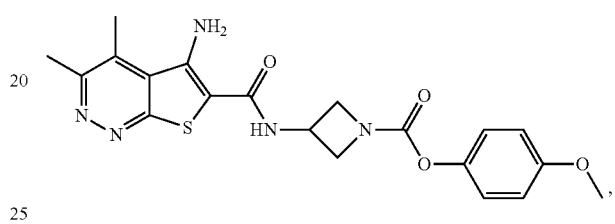
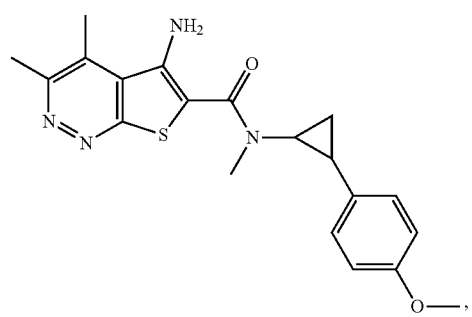
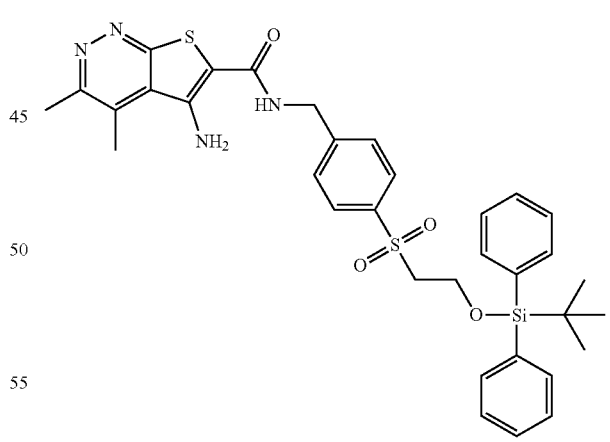
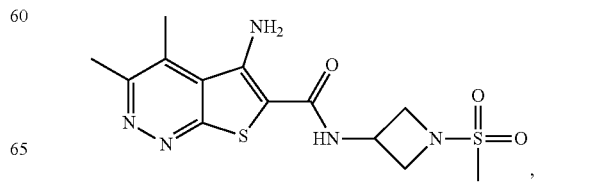

301
-continued
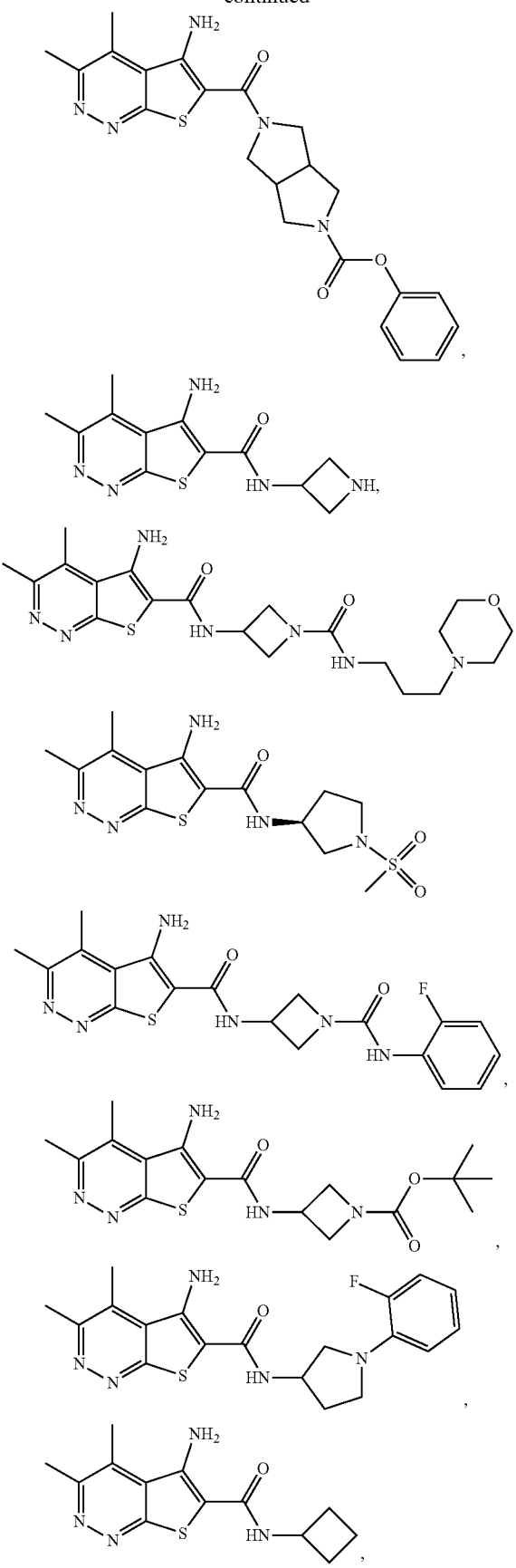
302
-continued
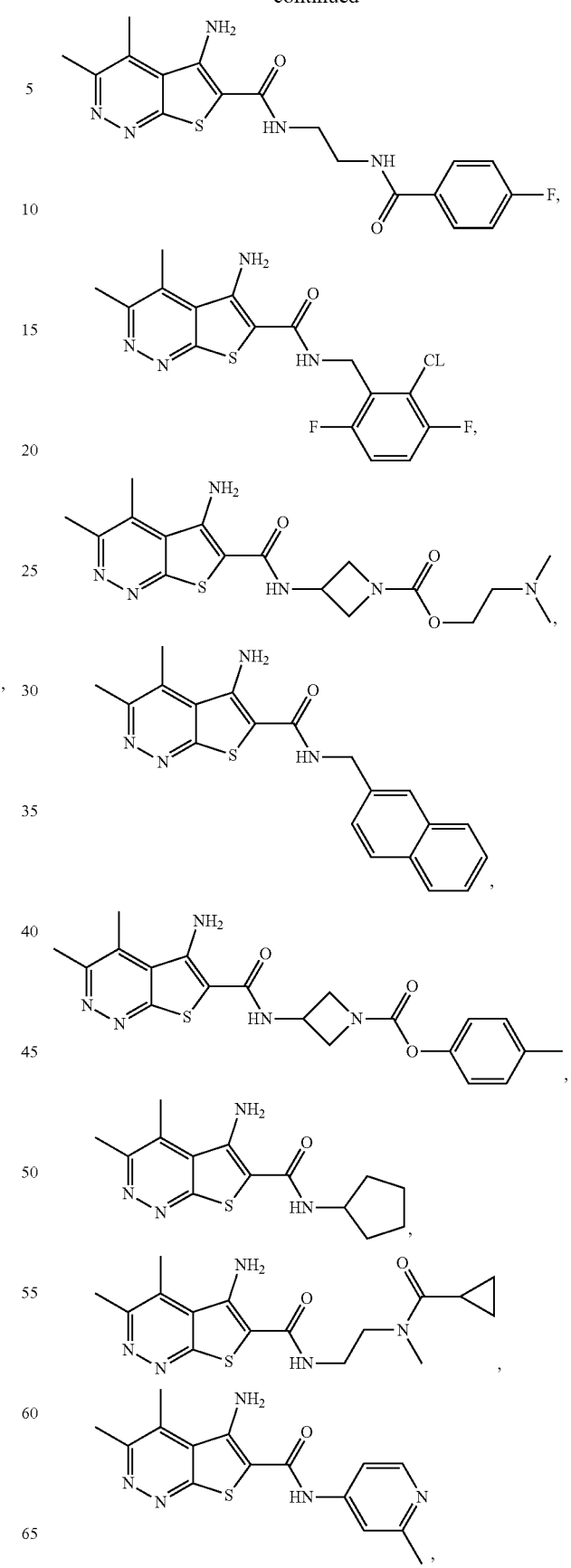

303
-continued
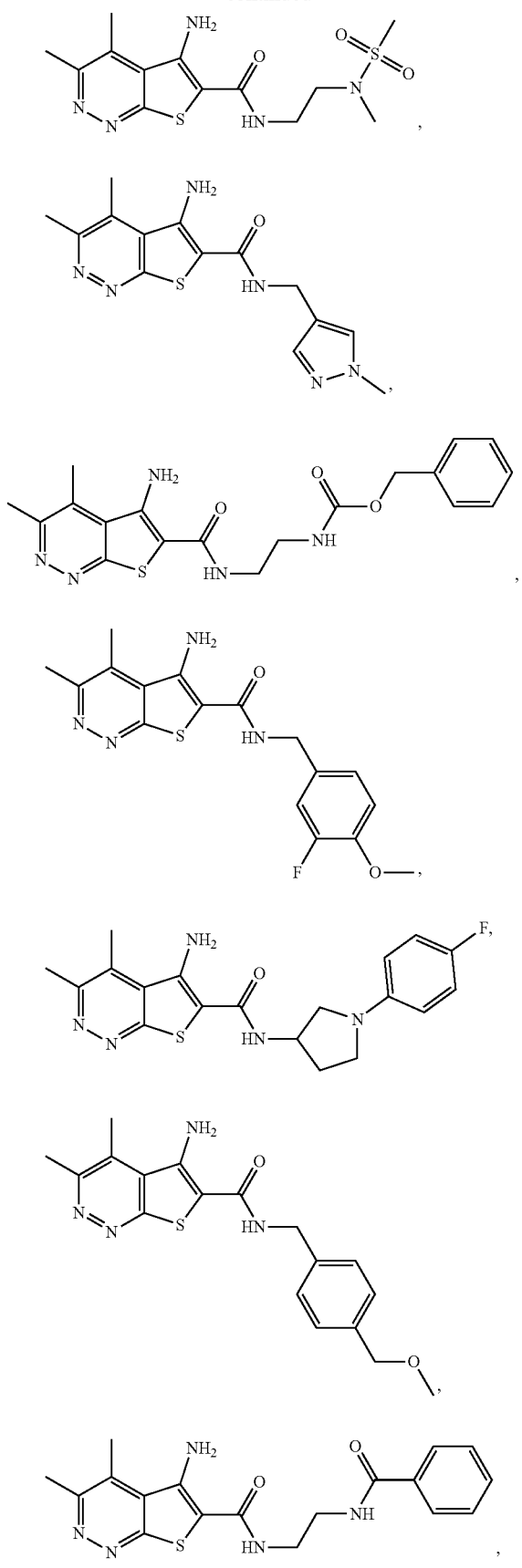
304
-continued
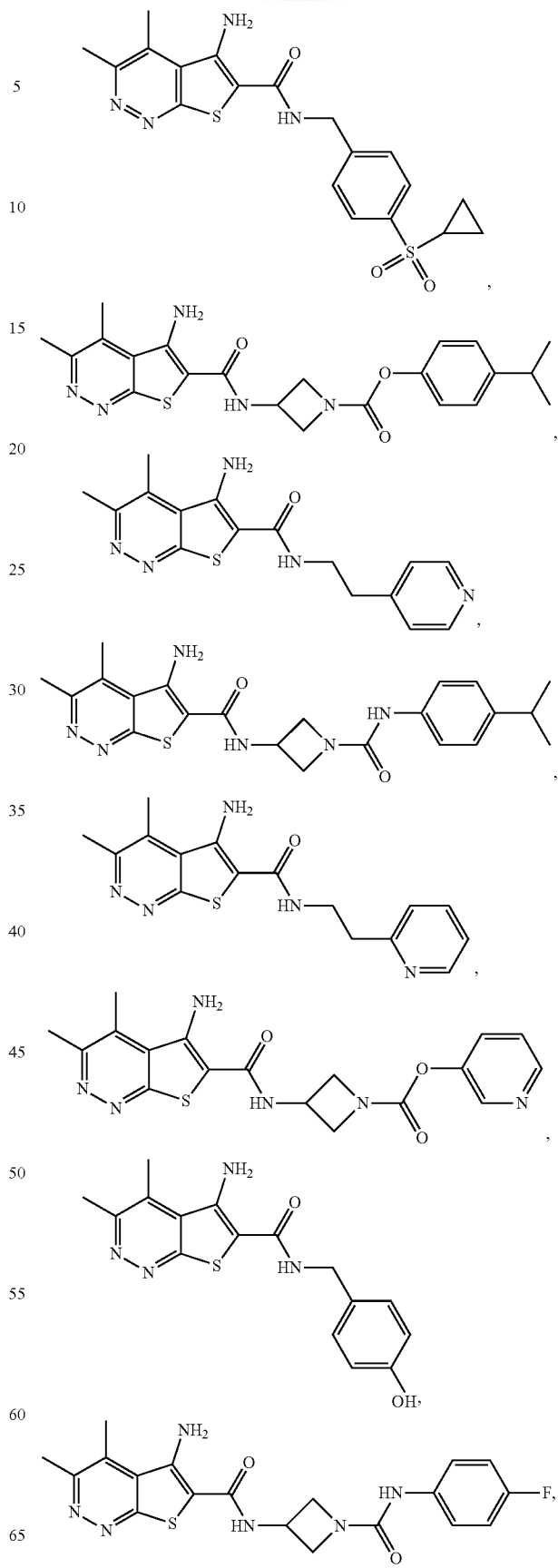

305
-continued
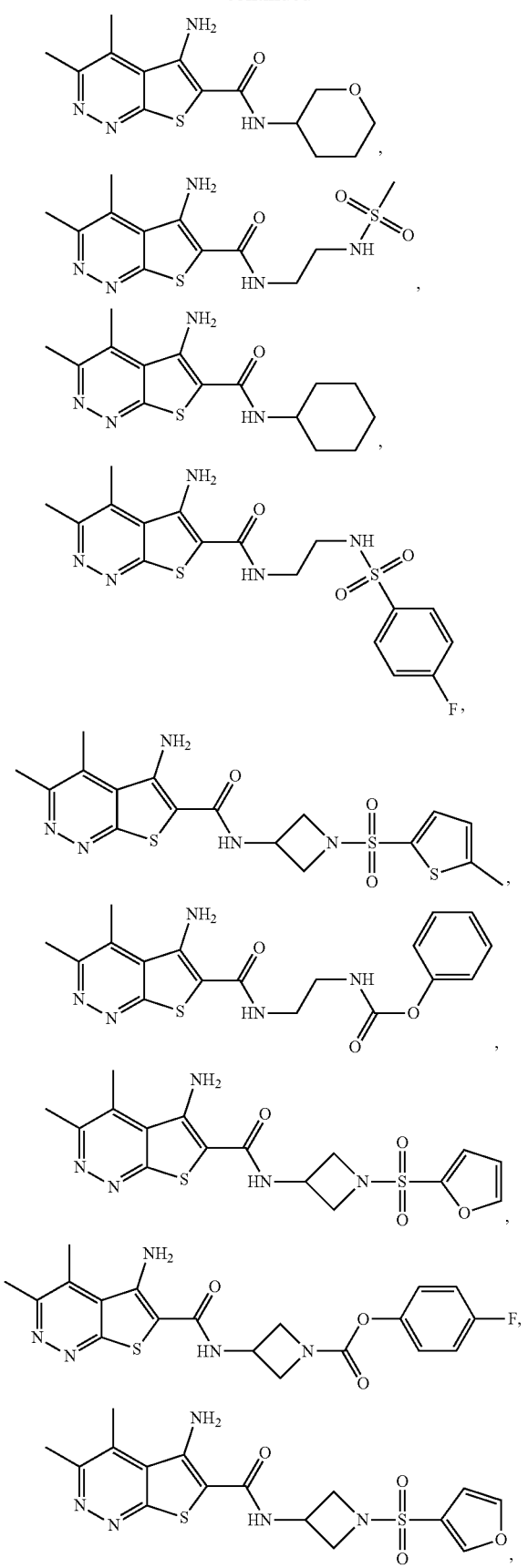
306
-continued
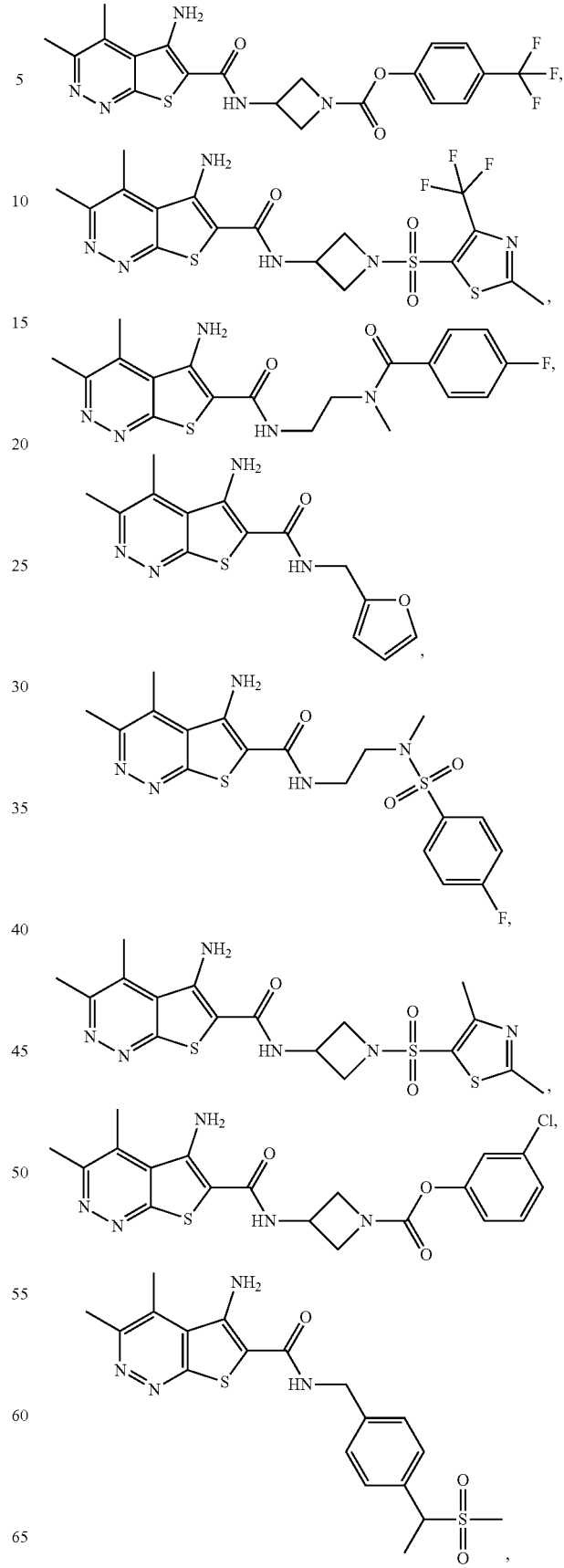

307
-continued
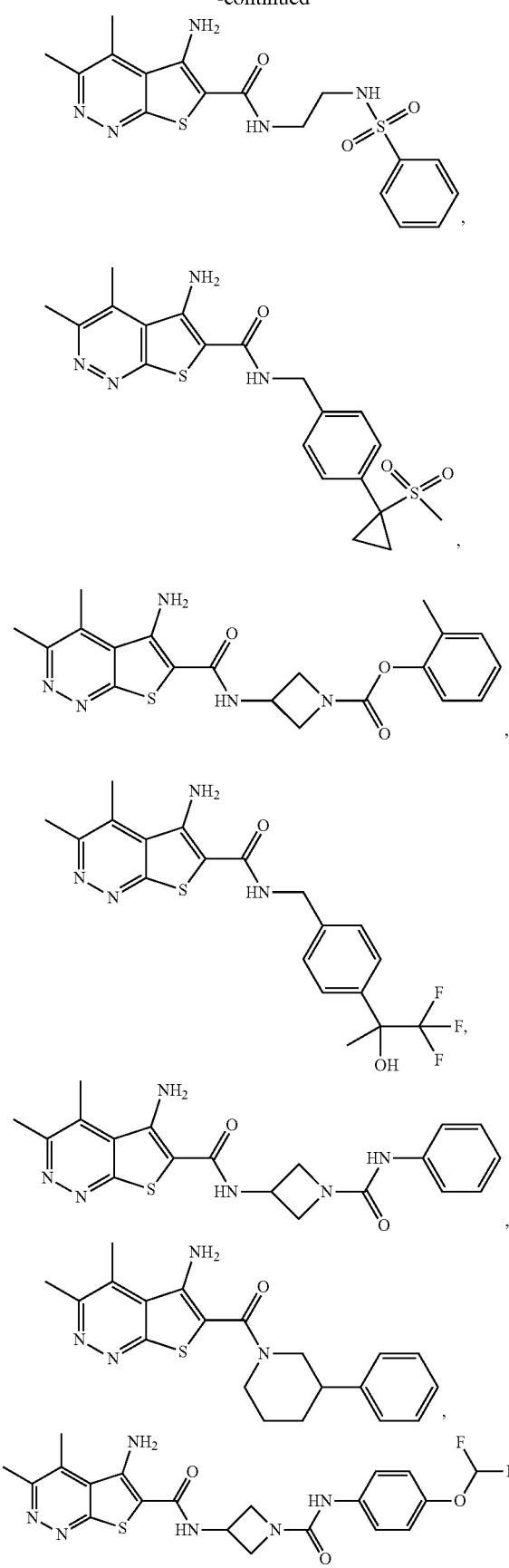
308
-continued
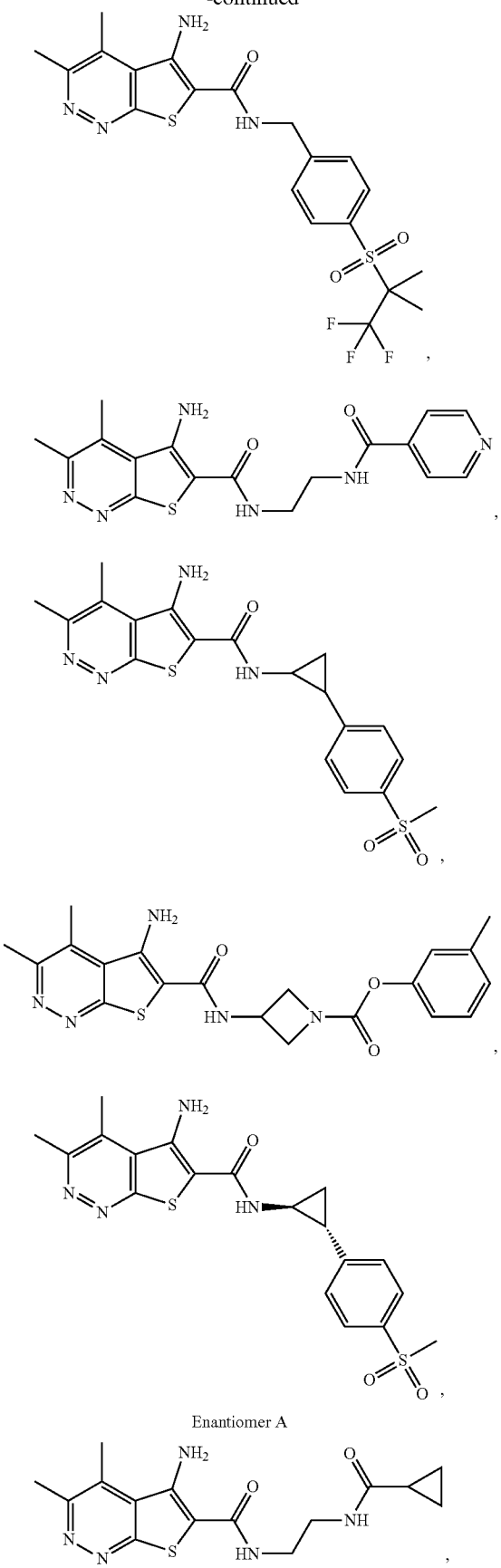

309
-continued
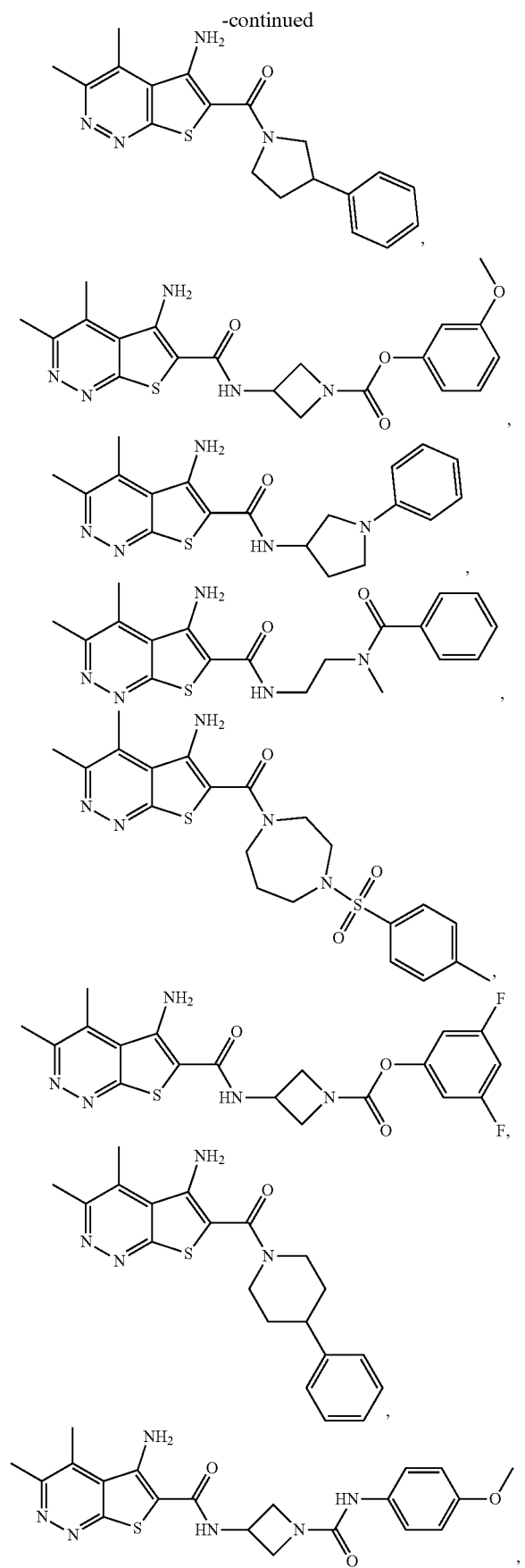
310
-continued
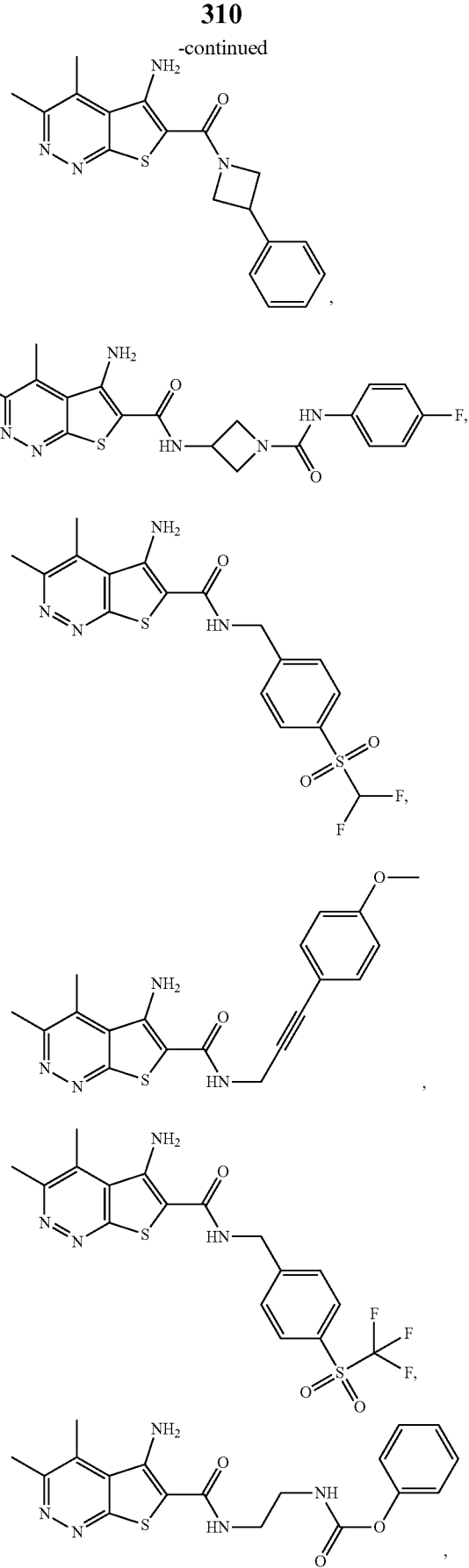

311
-continued
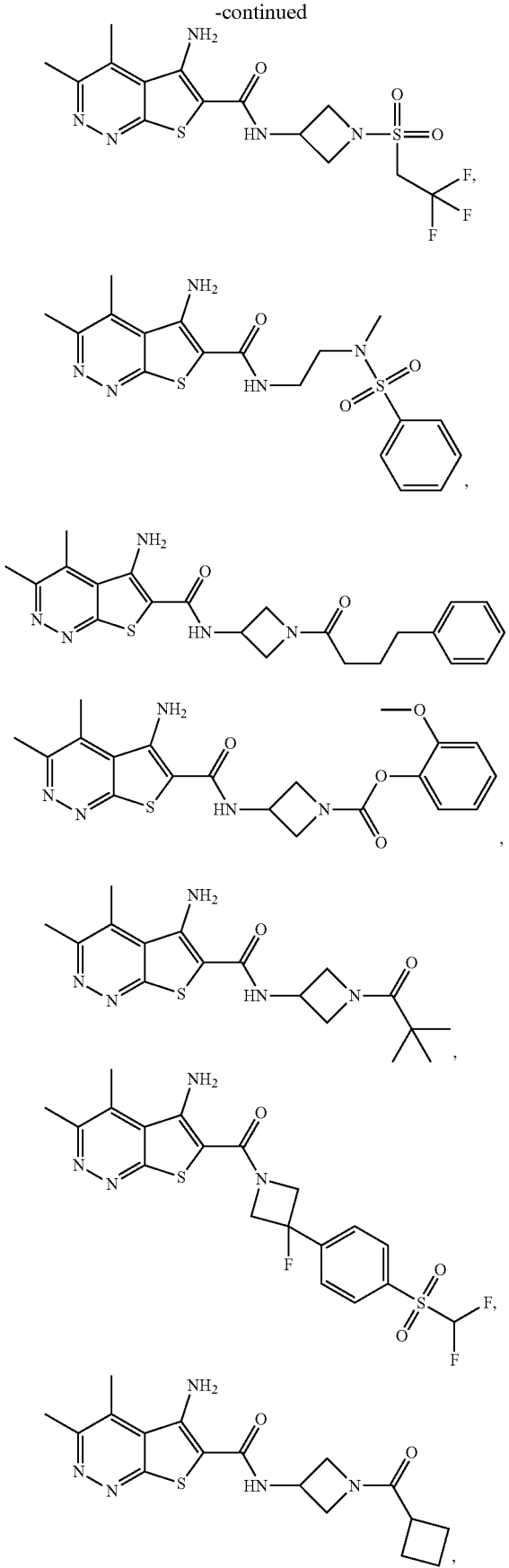
312
-continued
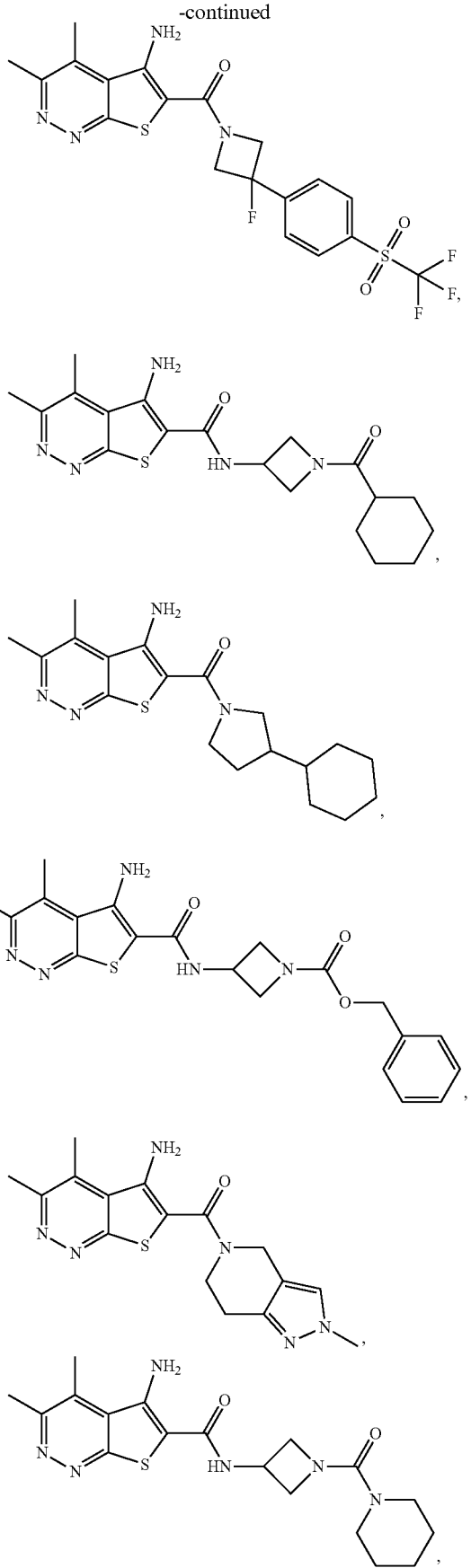

313
-continued
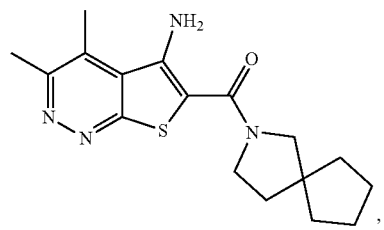
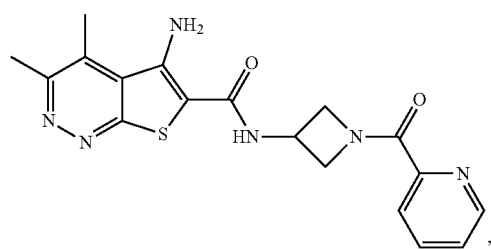
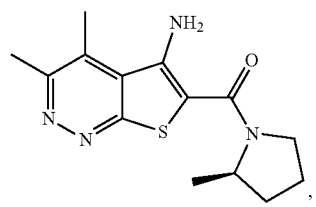
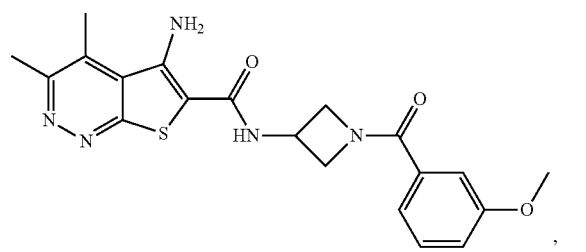
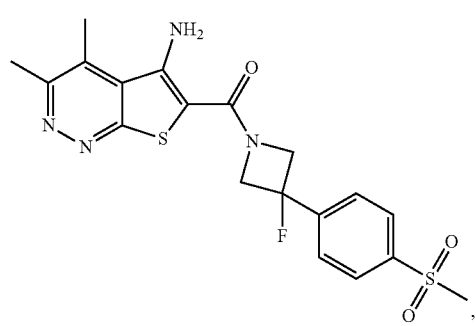
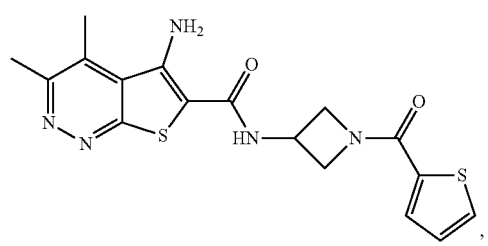
314
-continued
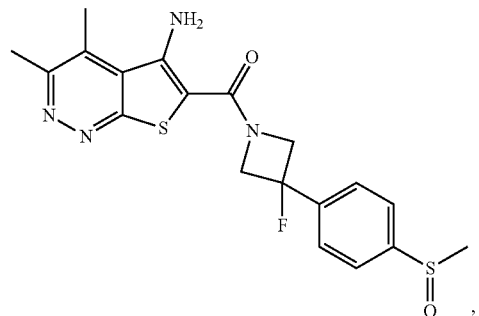
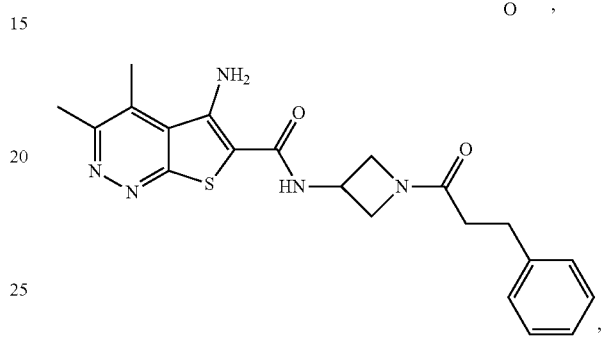
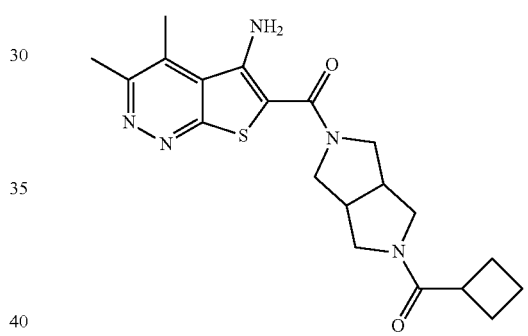
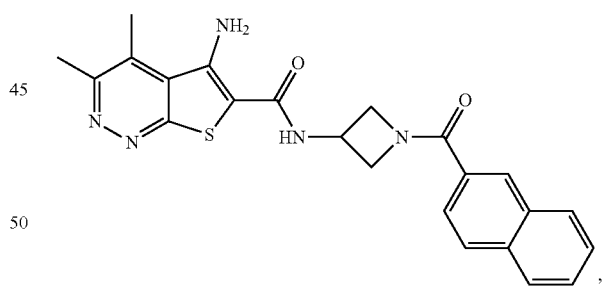
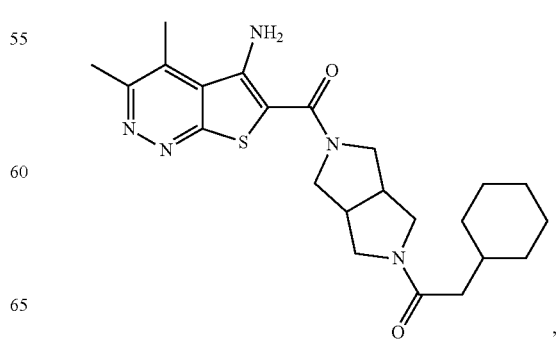

315
-continued
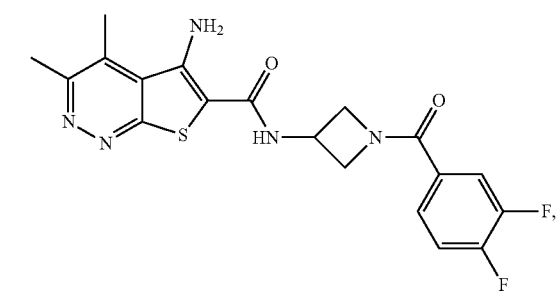
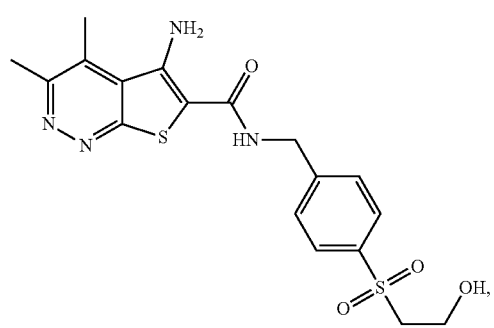
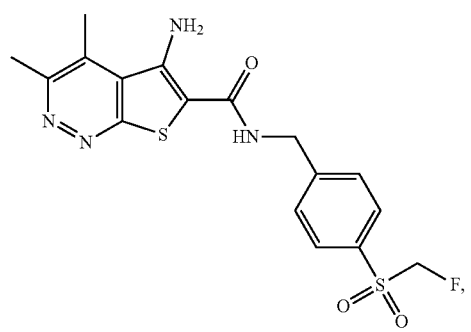
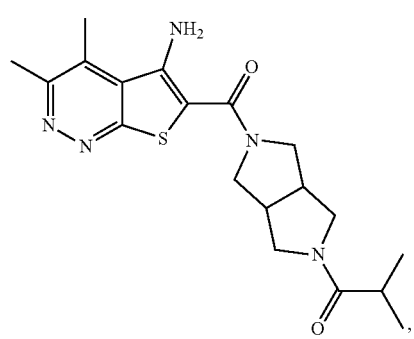
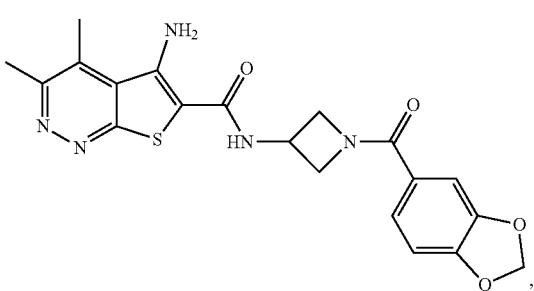
316
-continued
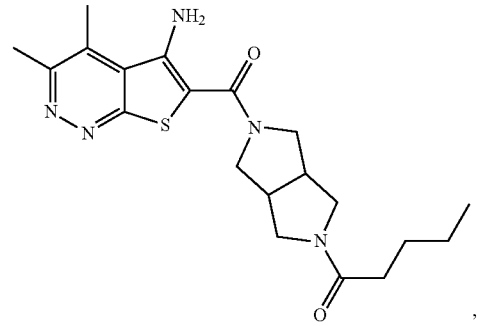
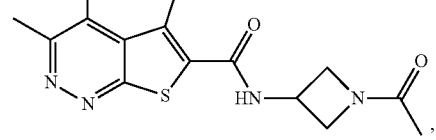
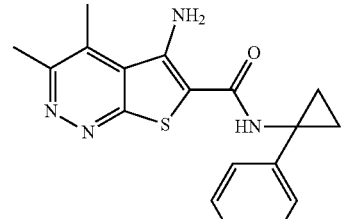
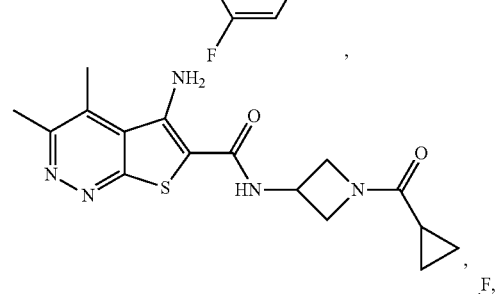
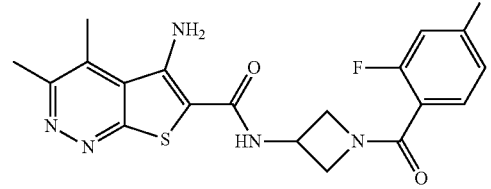
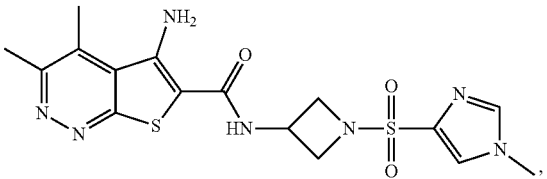
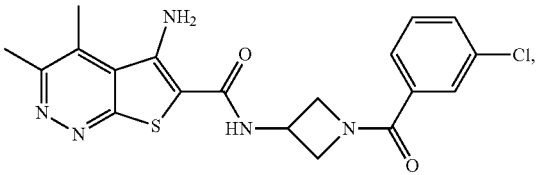
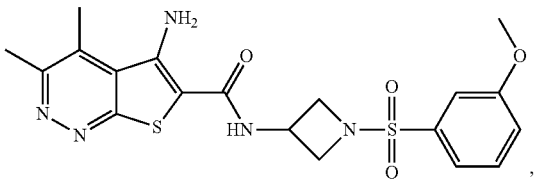

317
-continued
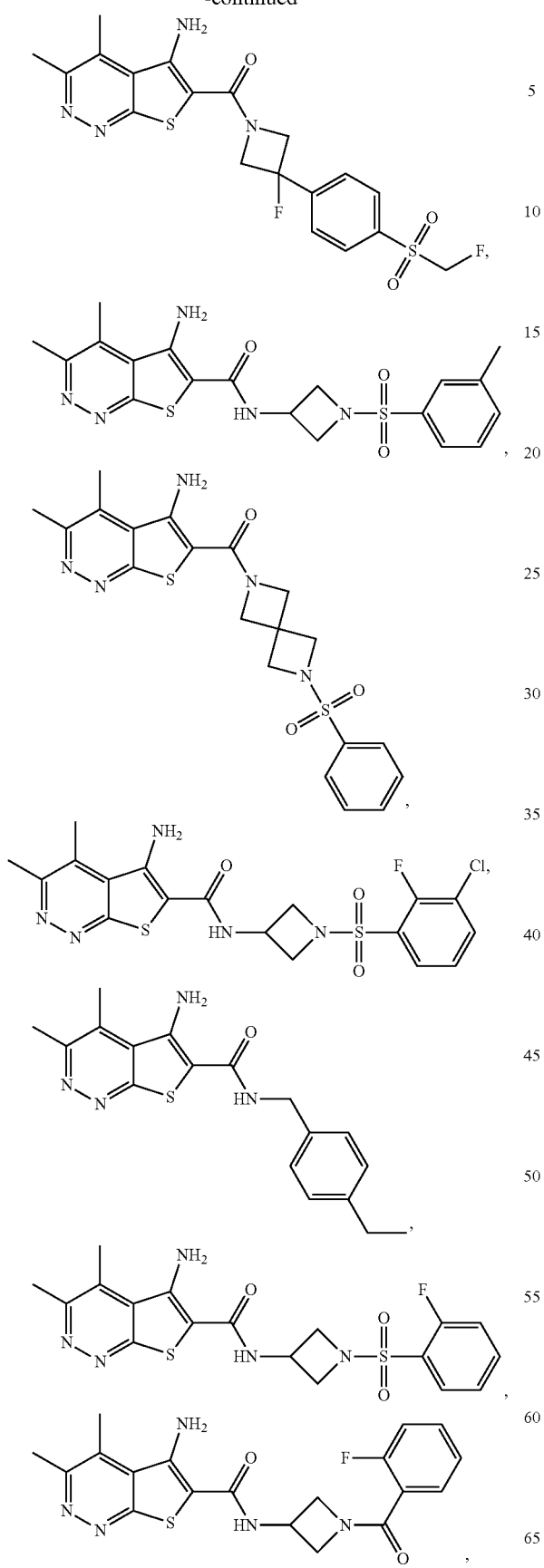
318
-continued
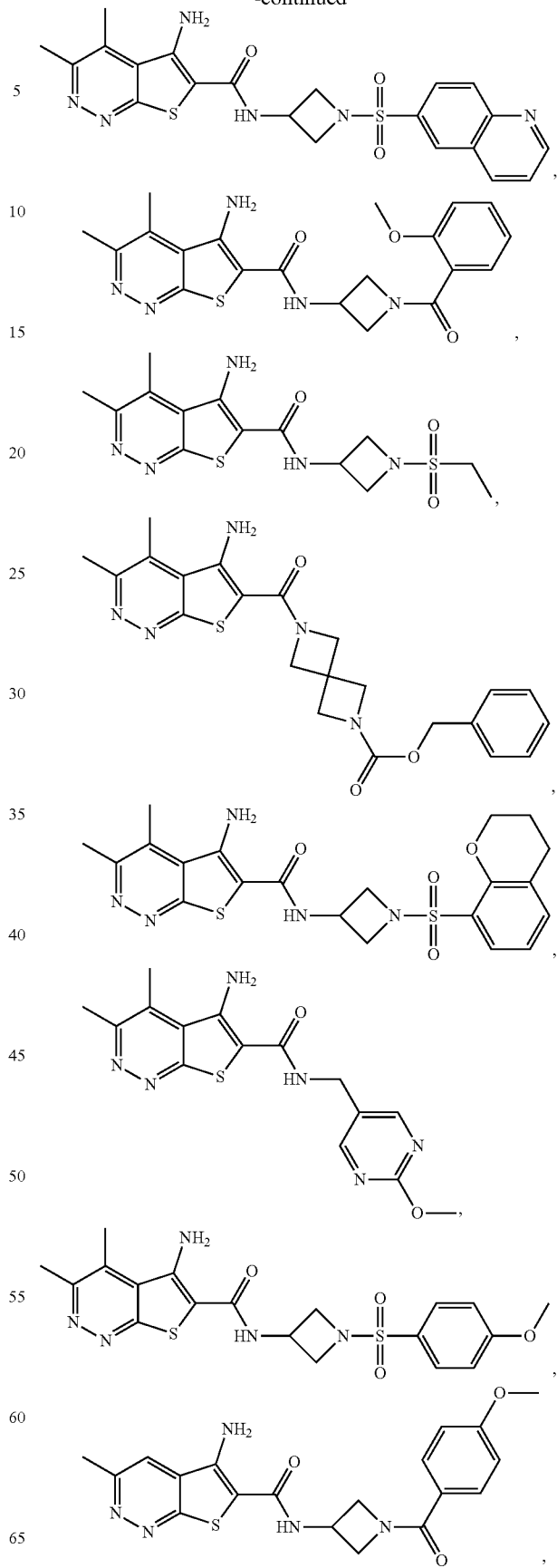

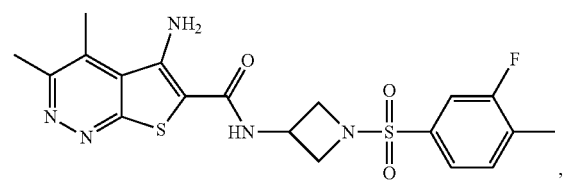
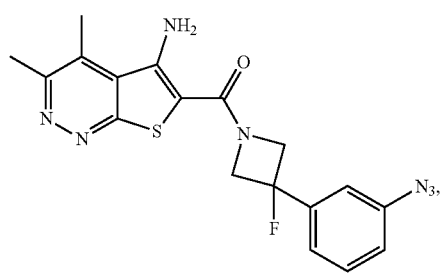
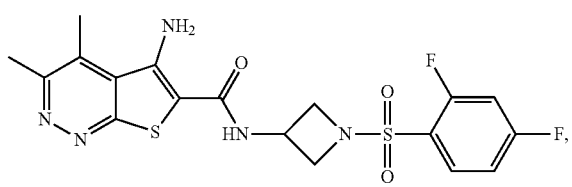
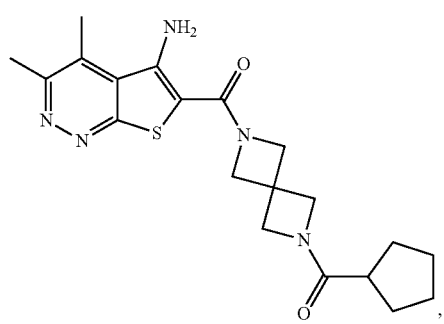
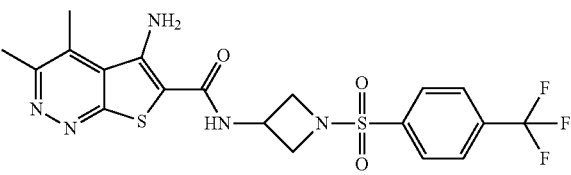
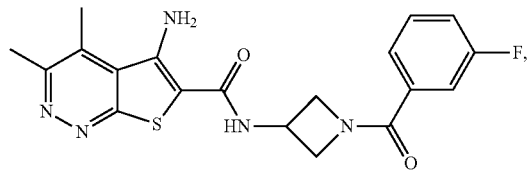
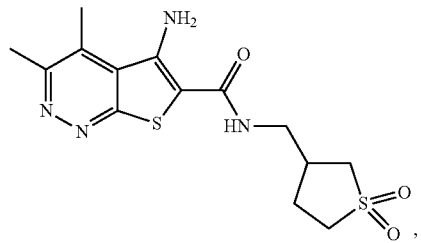
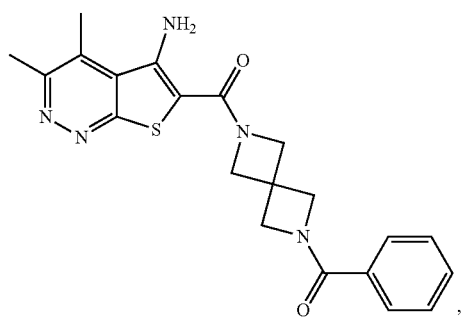
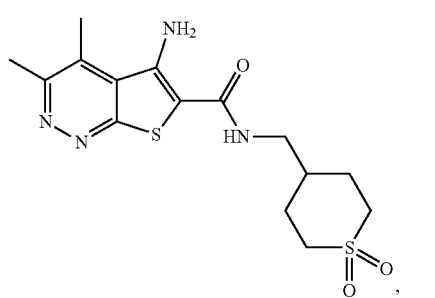
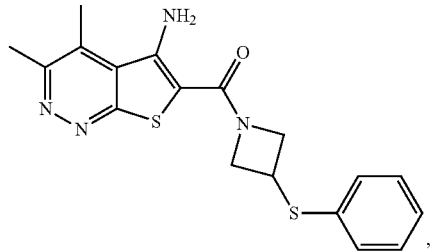
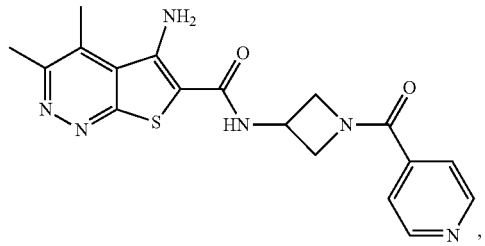
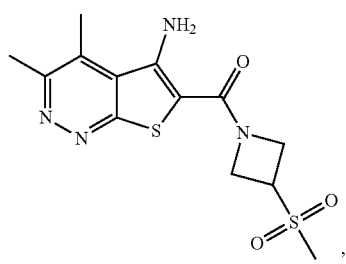
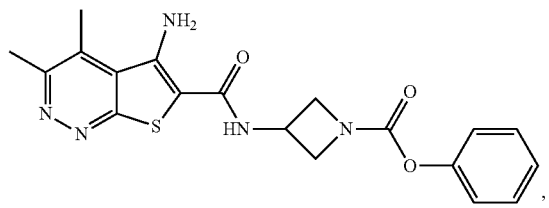

321
-continued
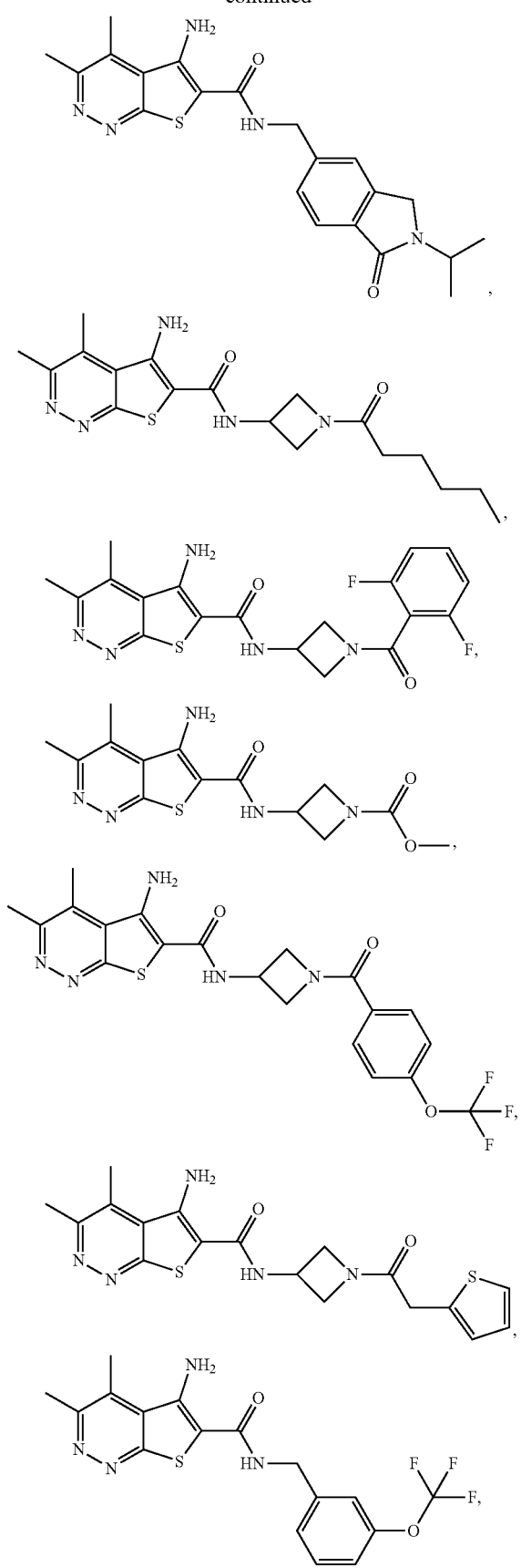
322
-continued
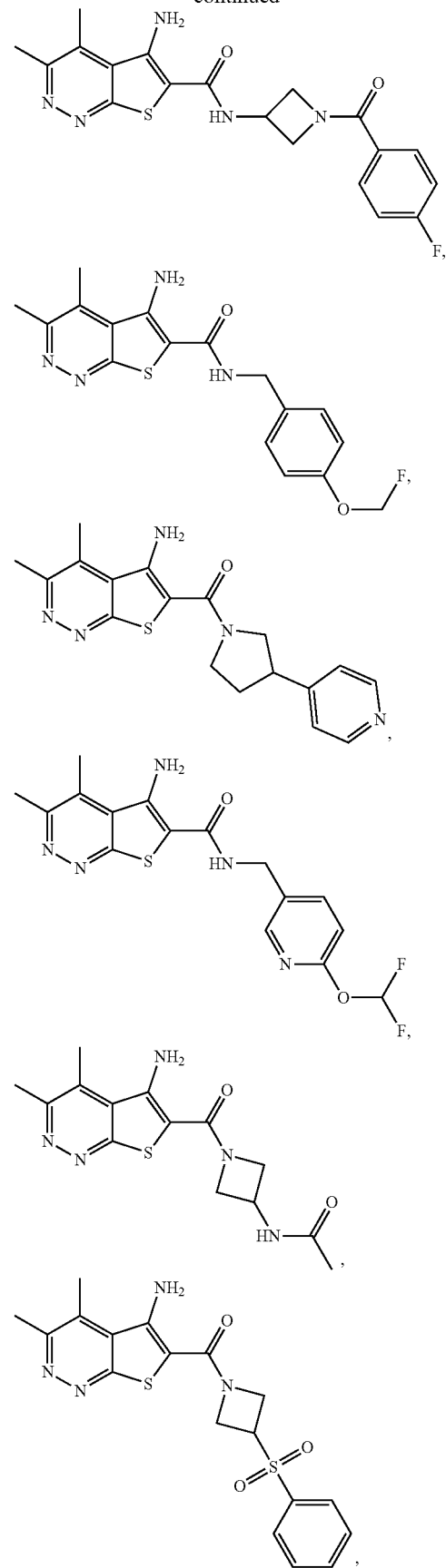

323
-continued
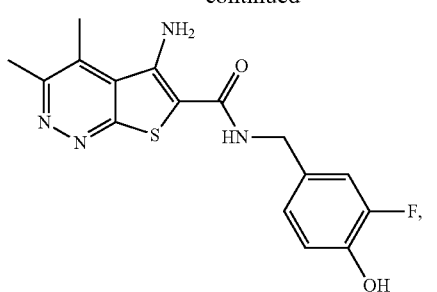
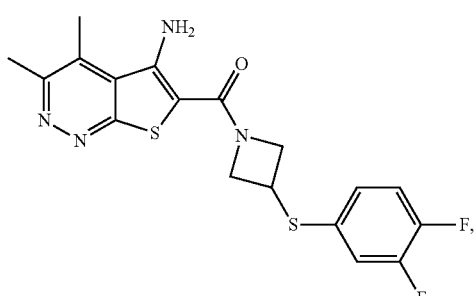
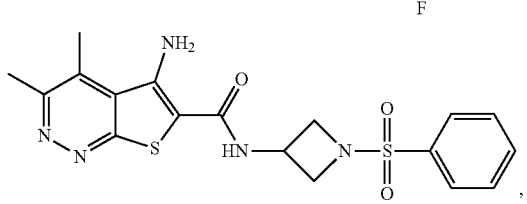
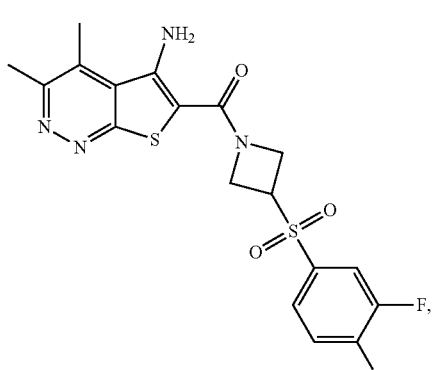
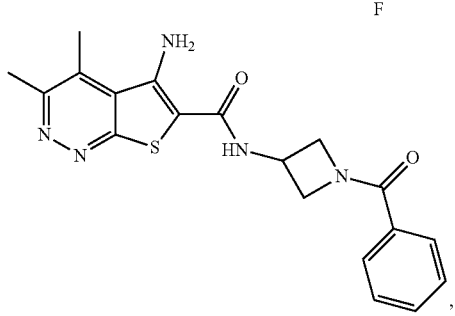
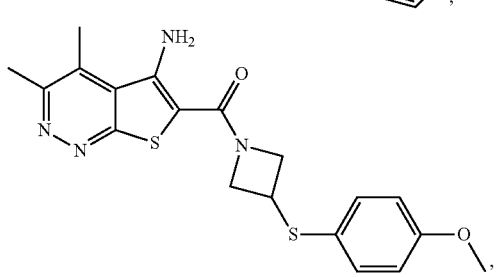
324
-continued
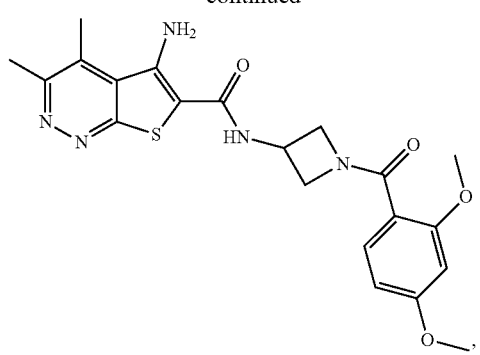
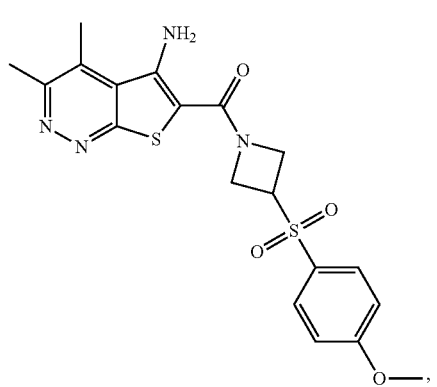
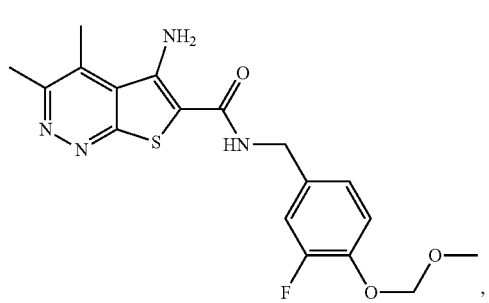
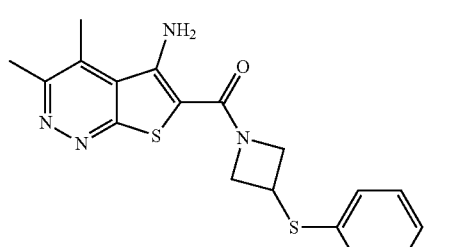
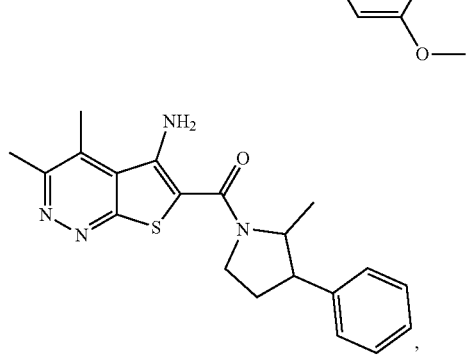

325
-continued
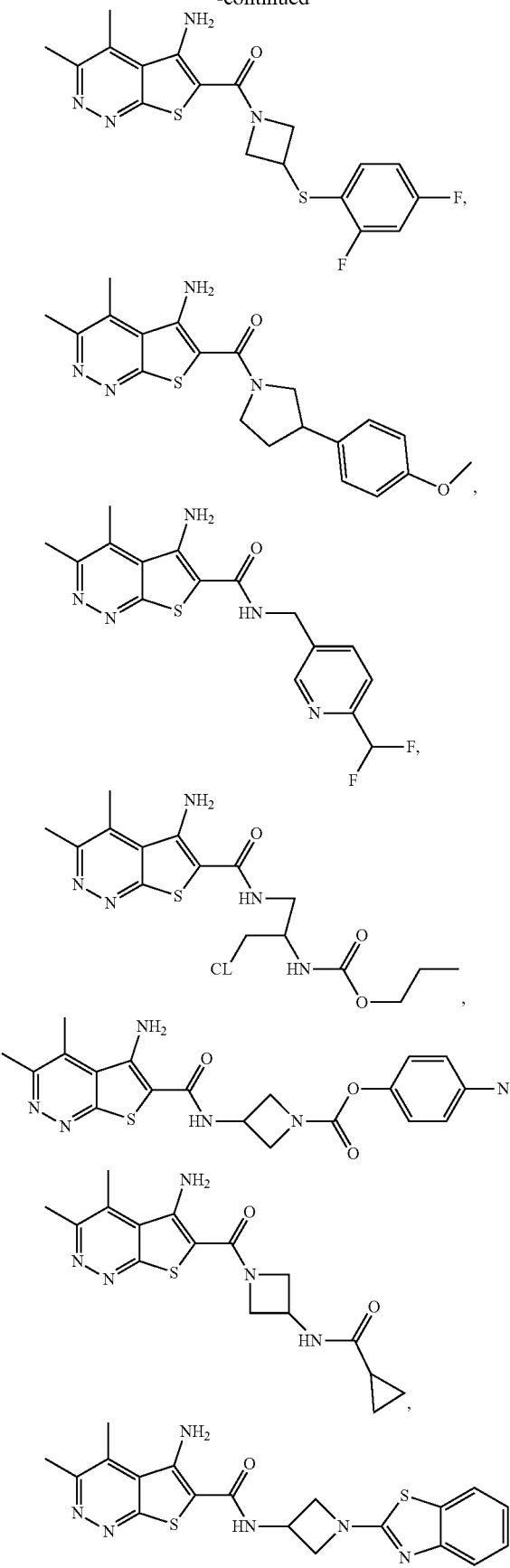
326
-continued
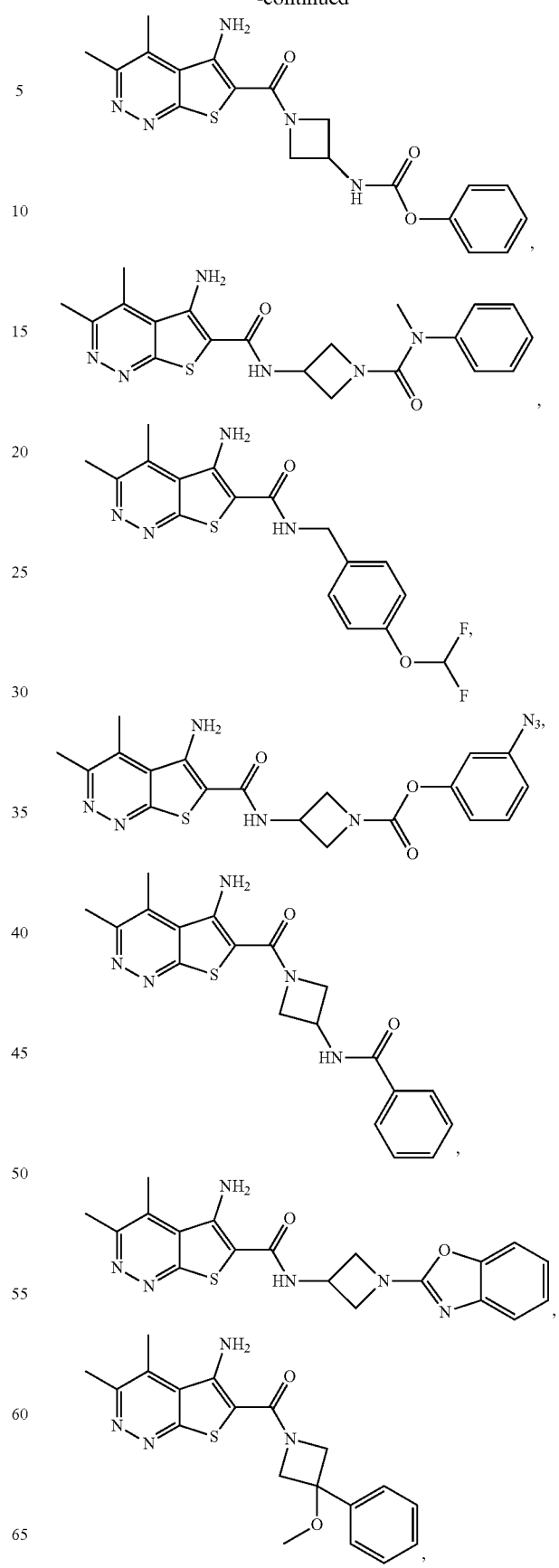

327
-continued
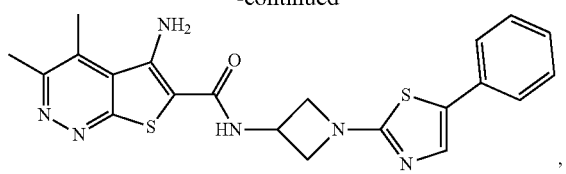
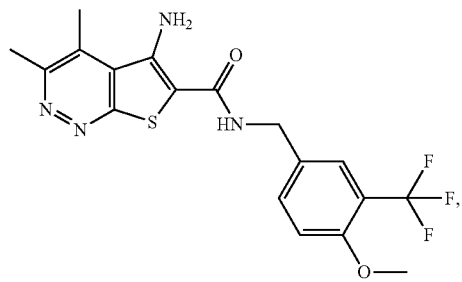
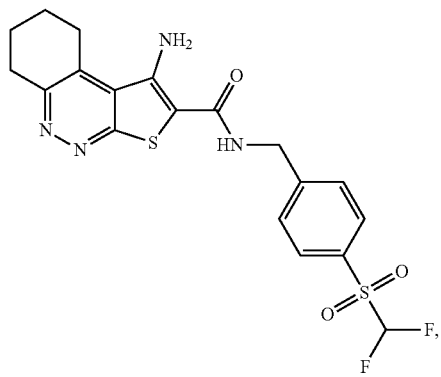
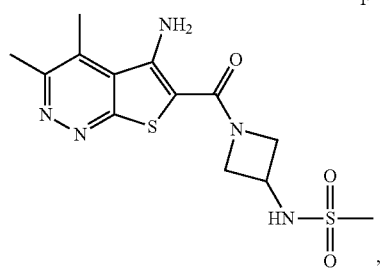
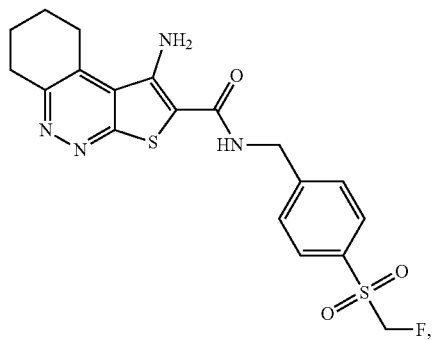
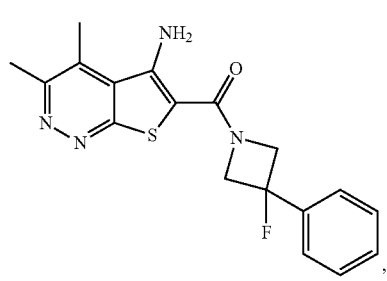
328
-continued
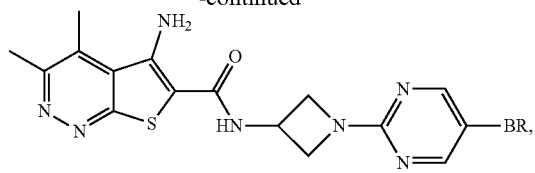
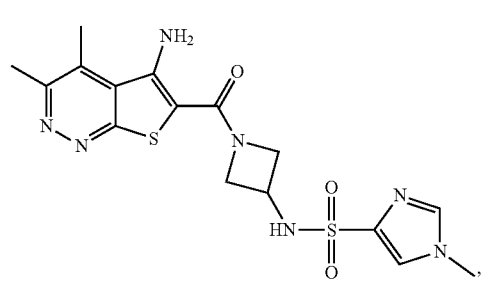
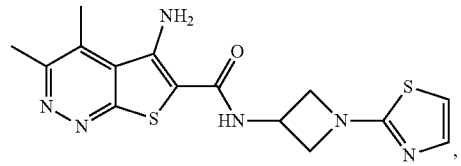
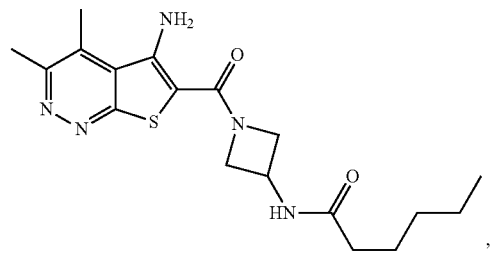
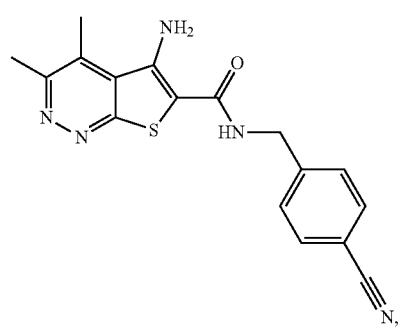
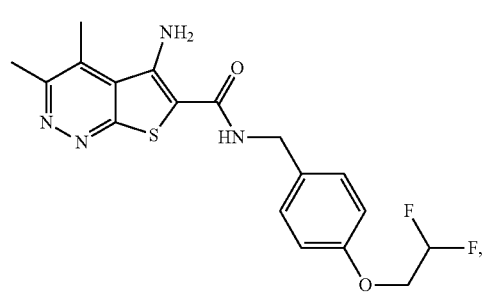

329
-continued
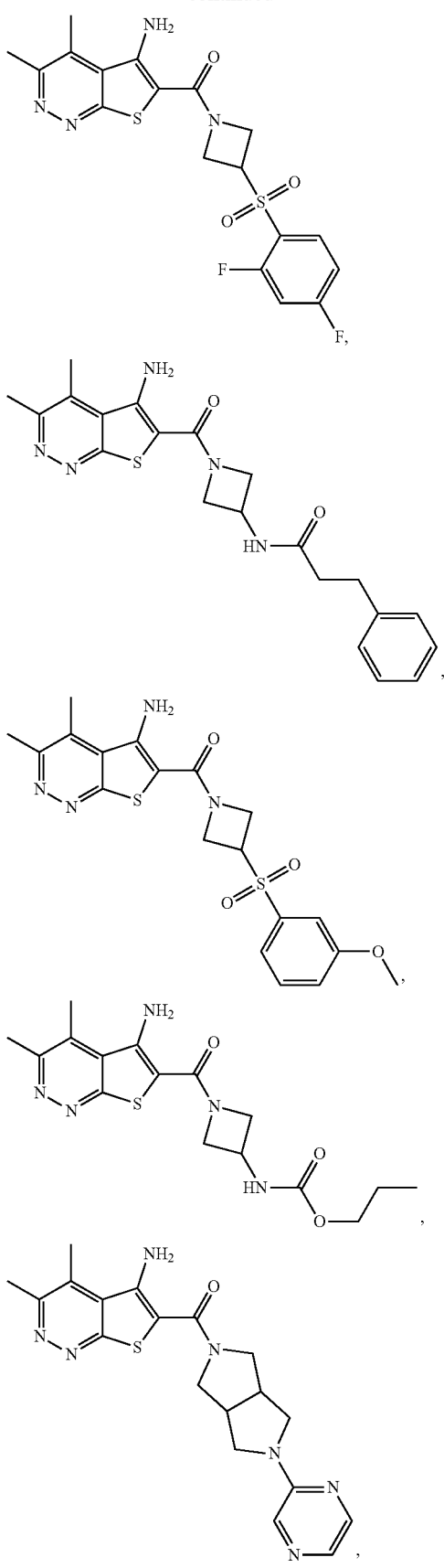
330
-continued
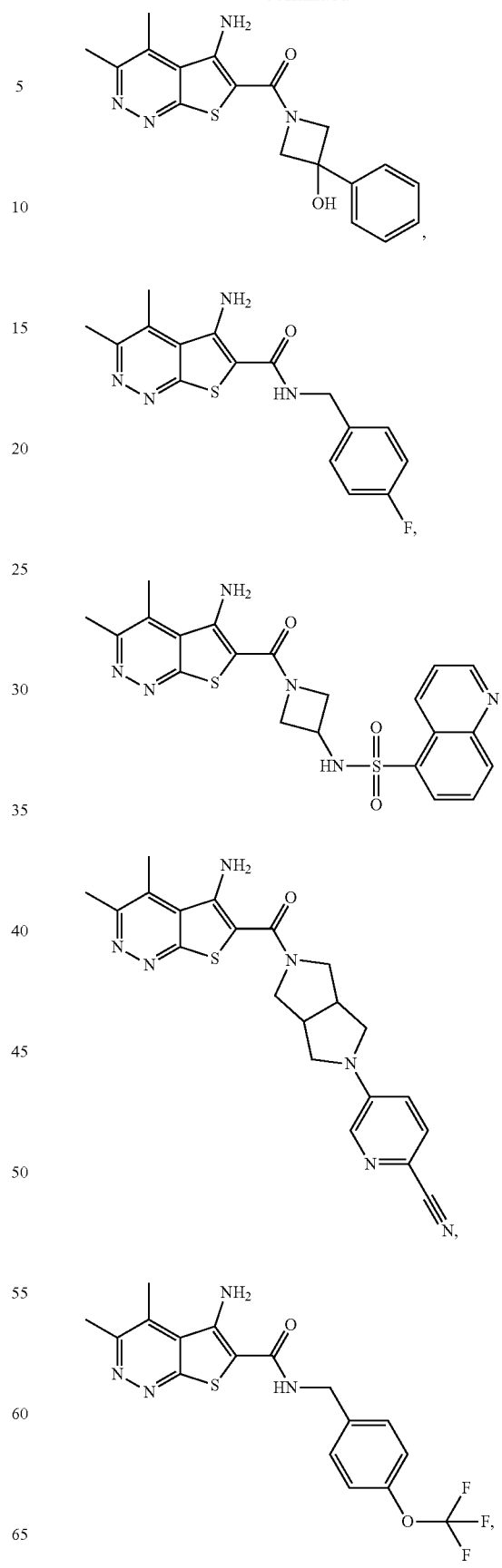

331
-continued
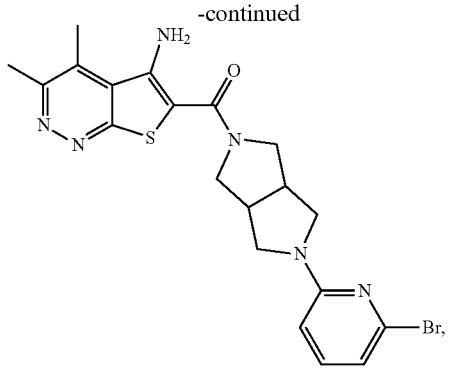
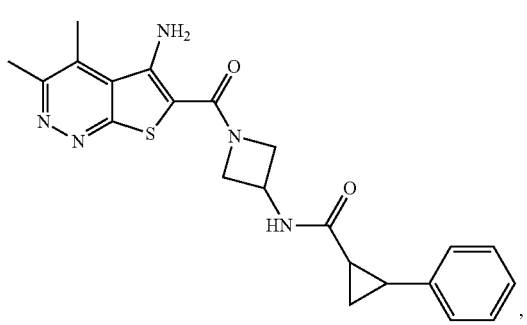
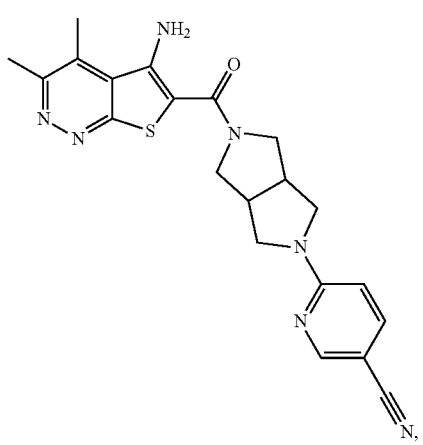
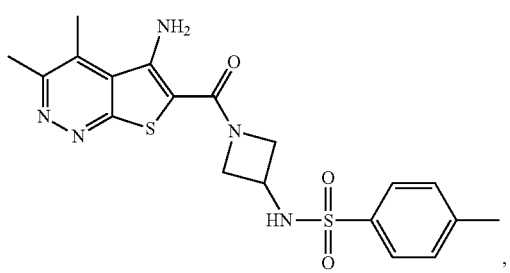
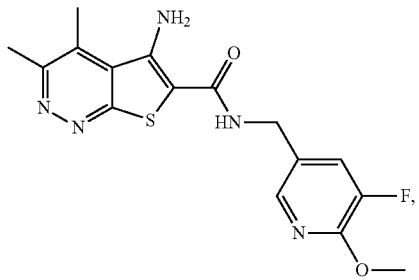
332
-continued
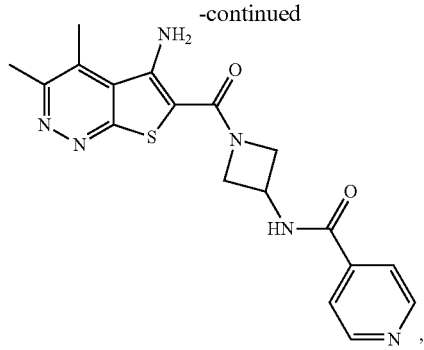
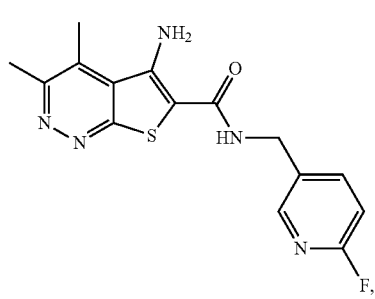
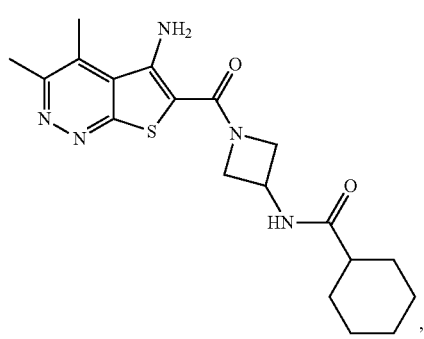
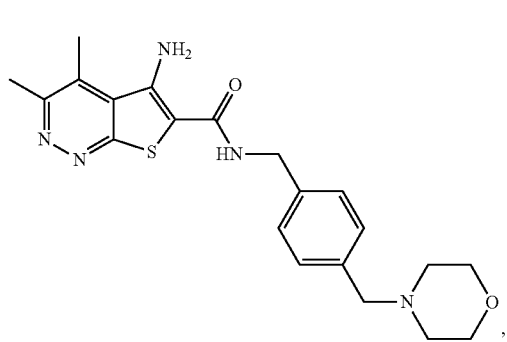
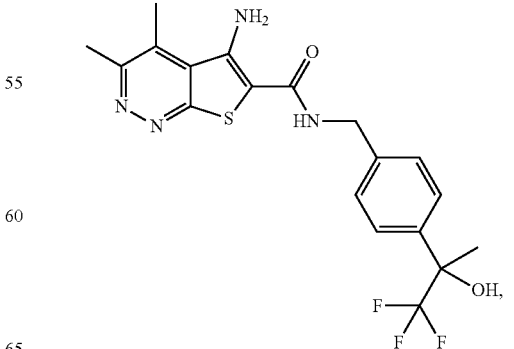
Enantiomer A 333
-continued
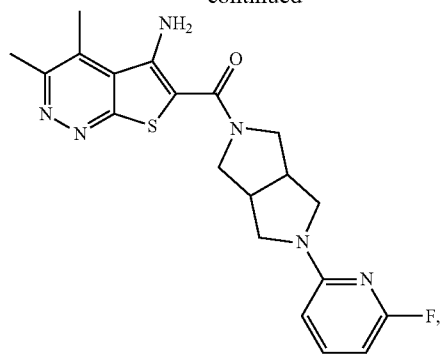
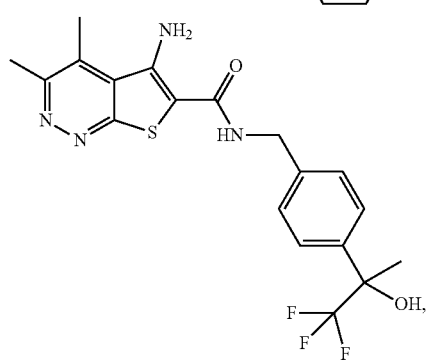
Enantiomer B
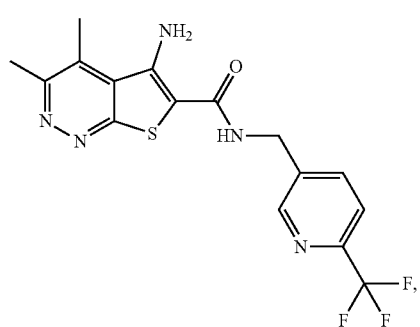
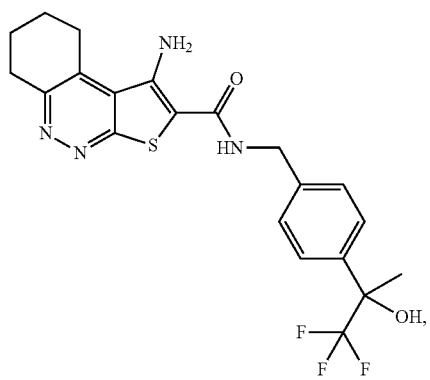
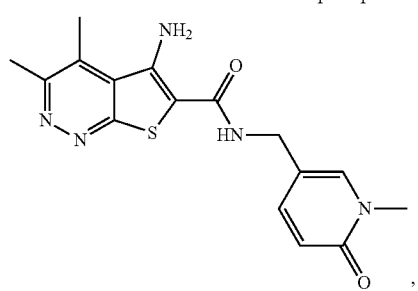
334
-continued
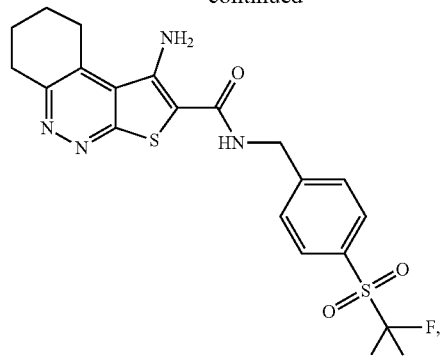
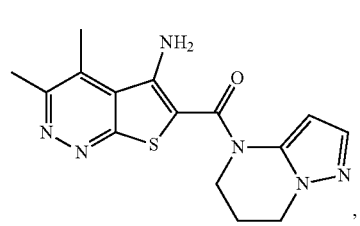
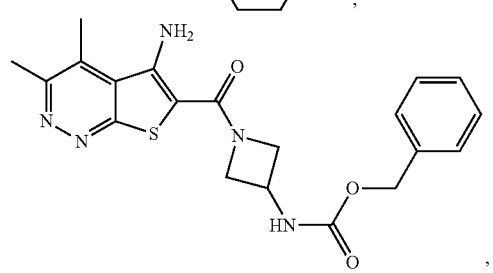
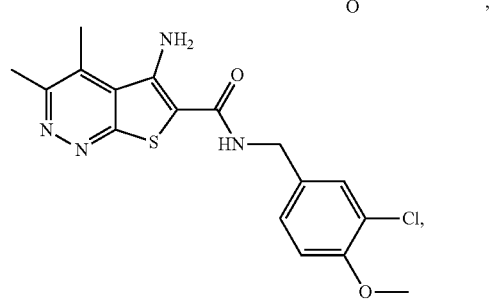
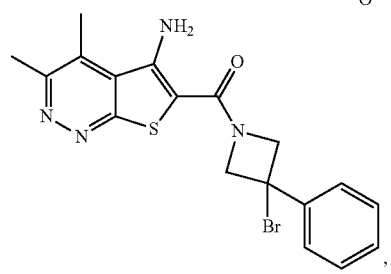
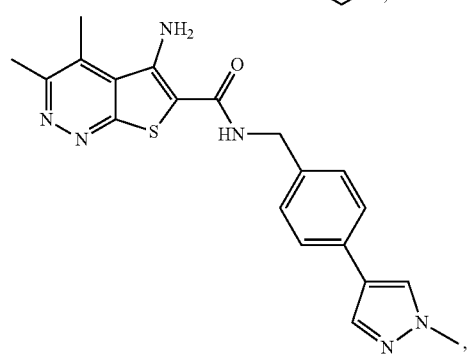

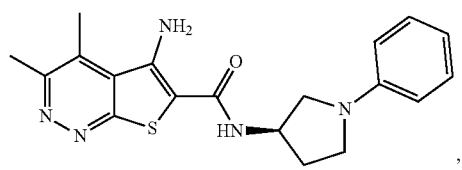
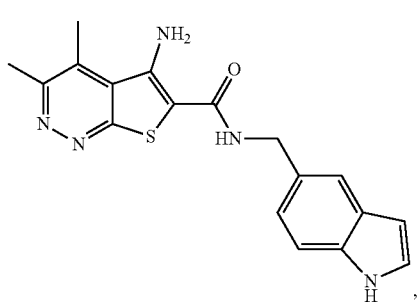
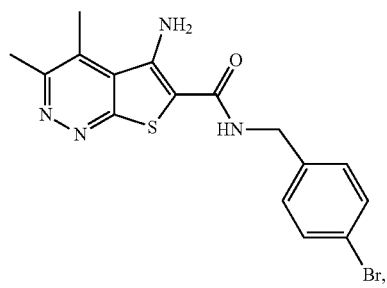
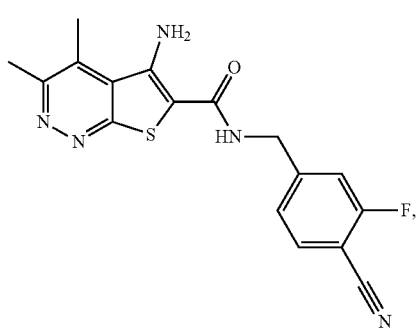
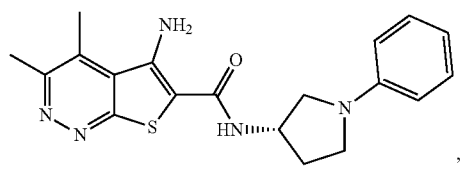
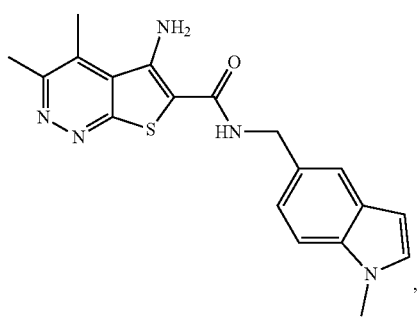
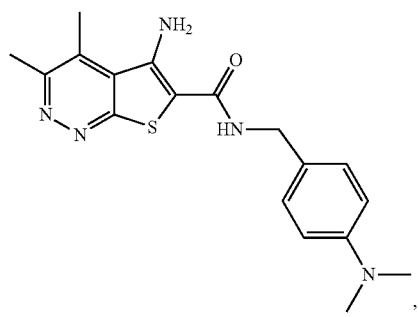
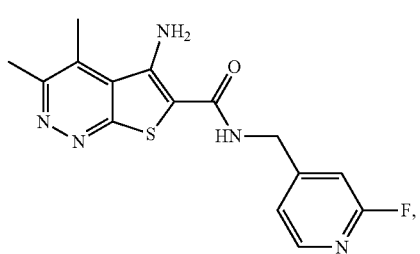
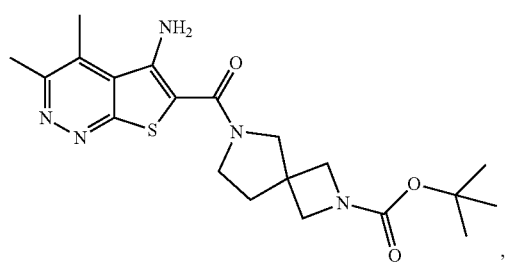
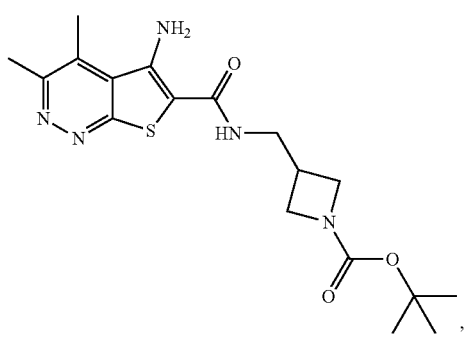
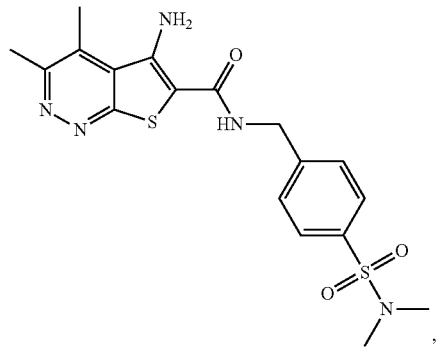

337
-continued
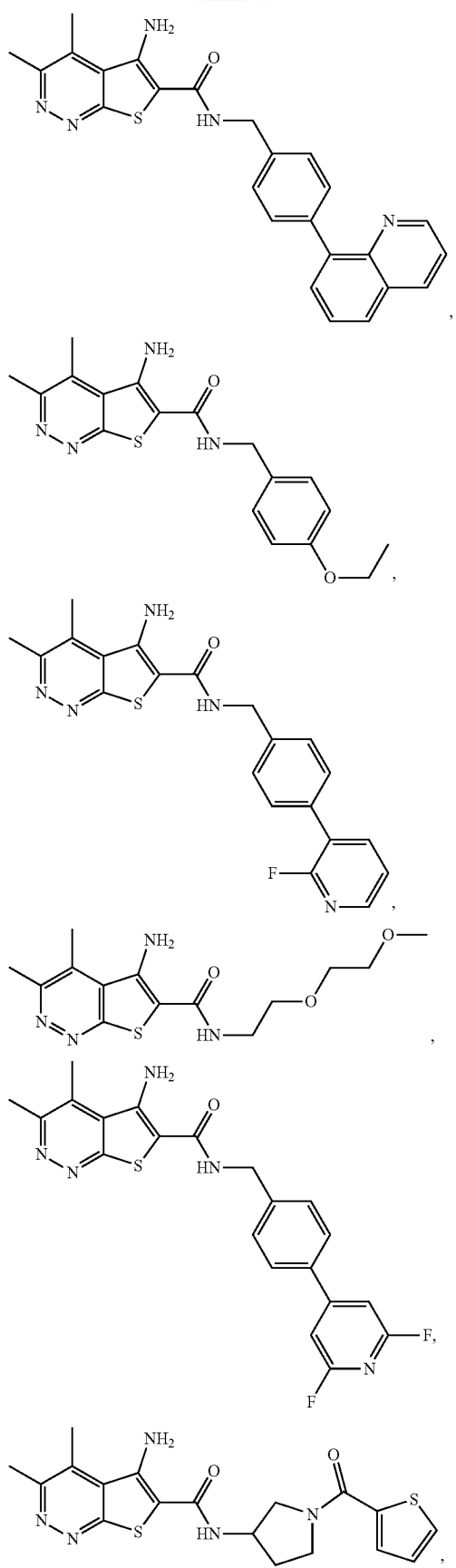
338
-continued
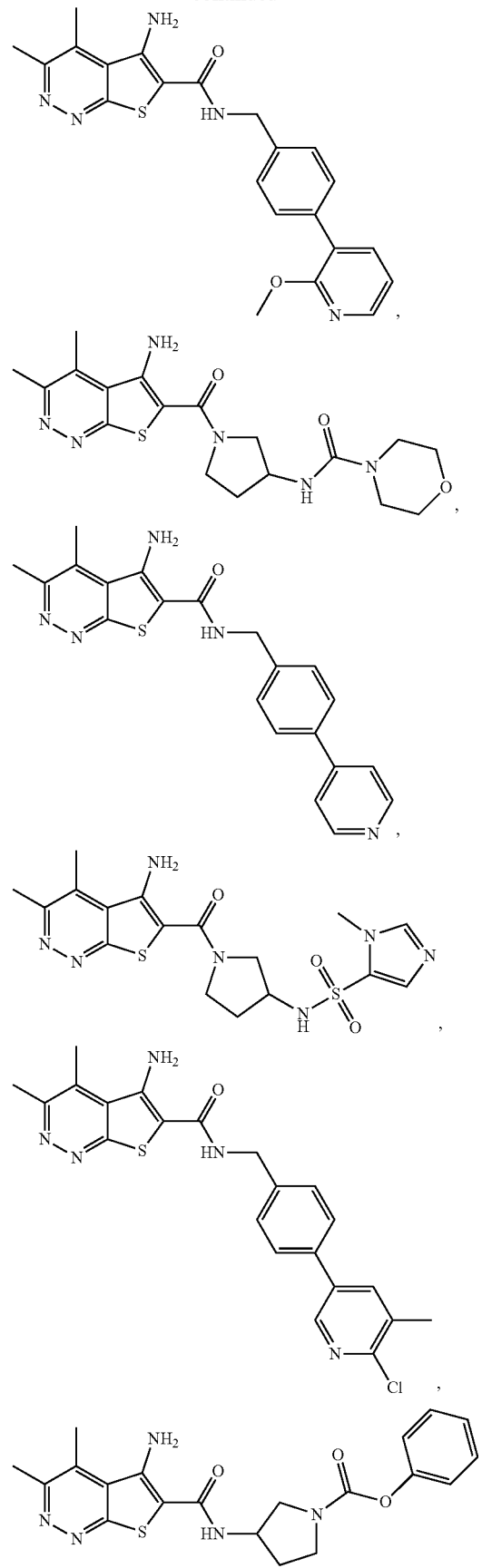

339
-continued
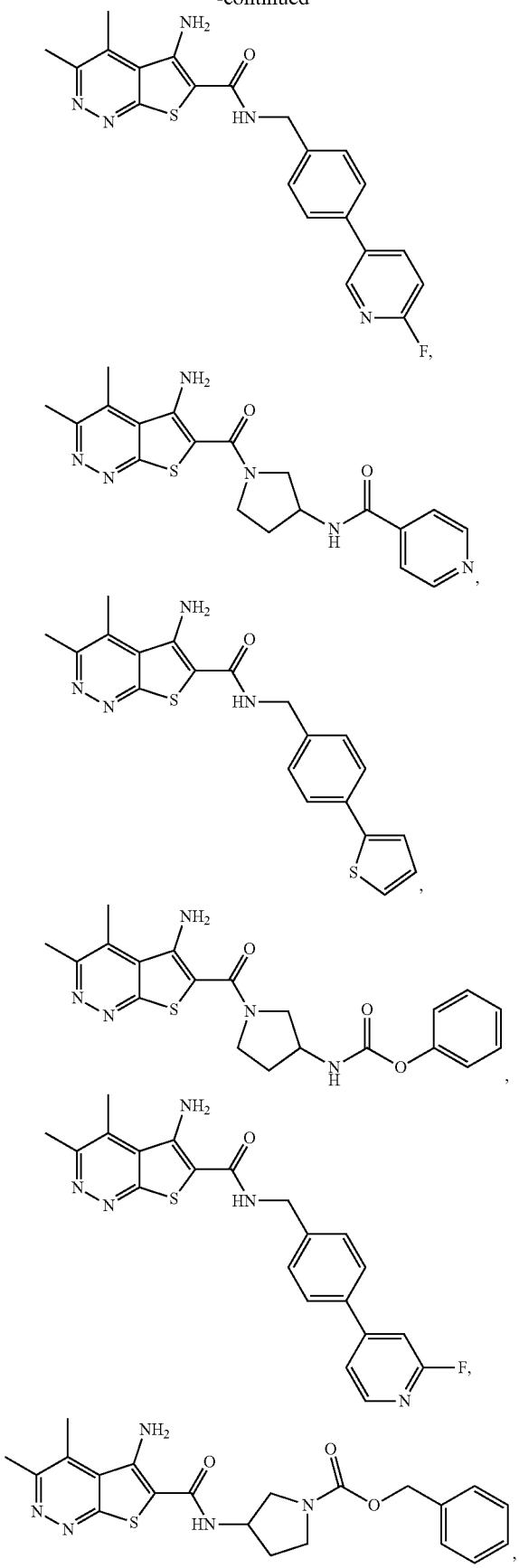
340
-continued
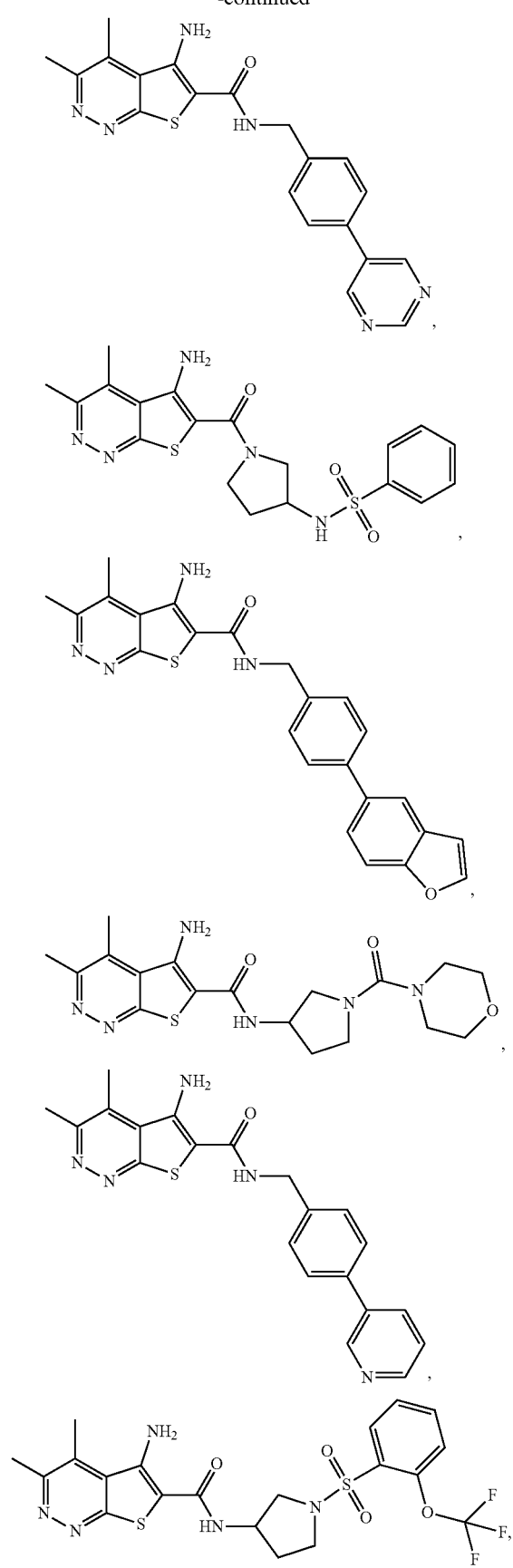

341
-continued
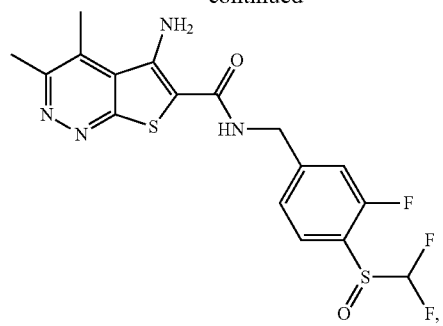
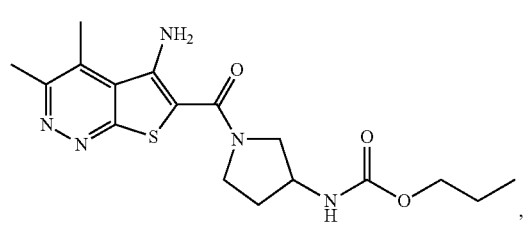
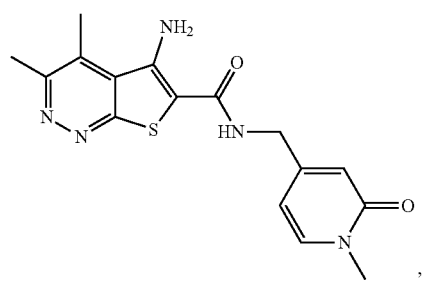
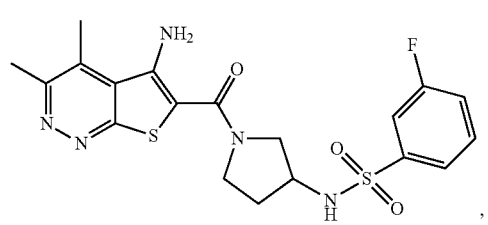
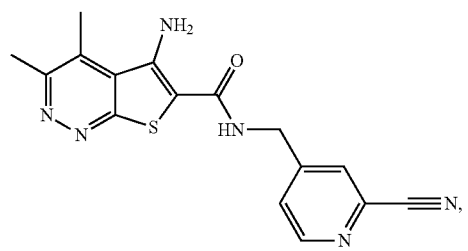
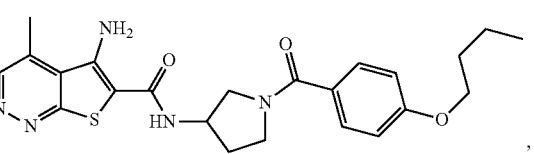
342
-continued
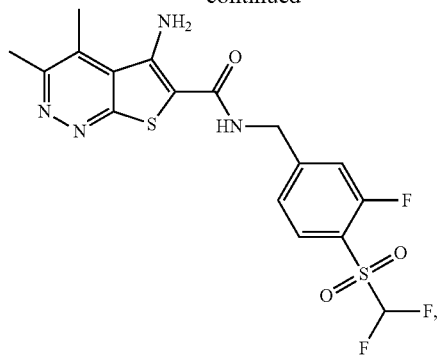
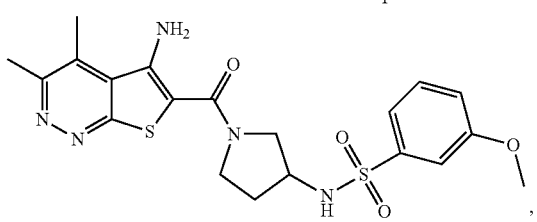
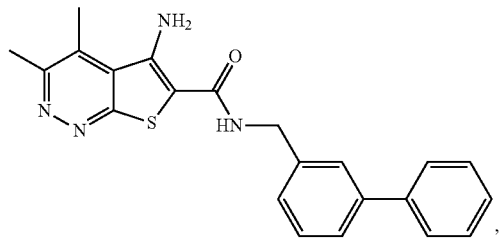
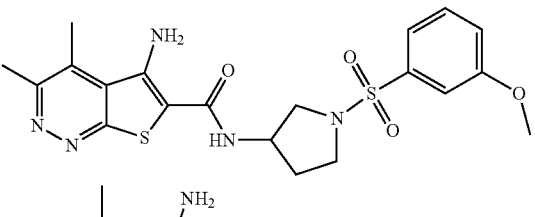
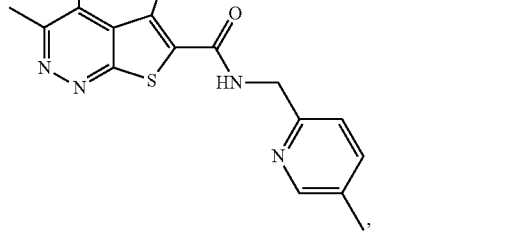
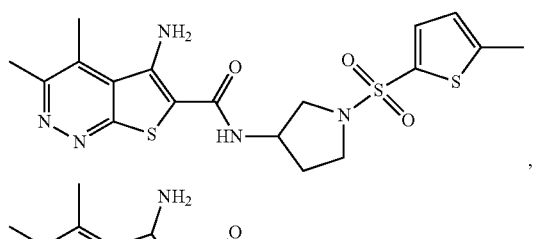
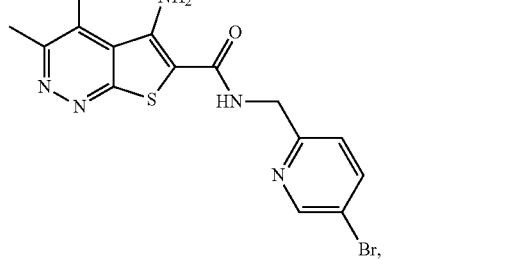

343
-continued
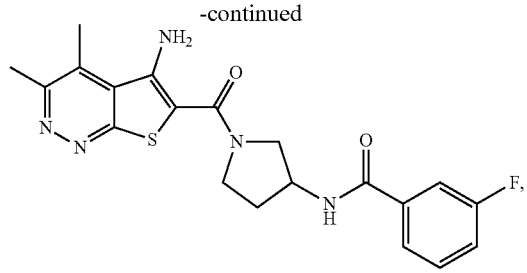
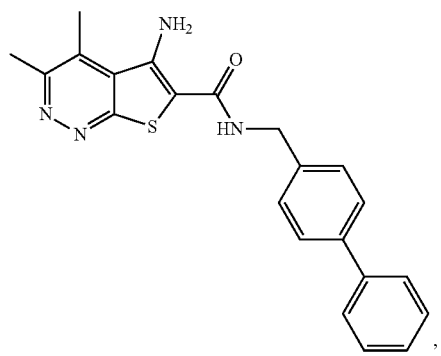
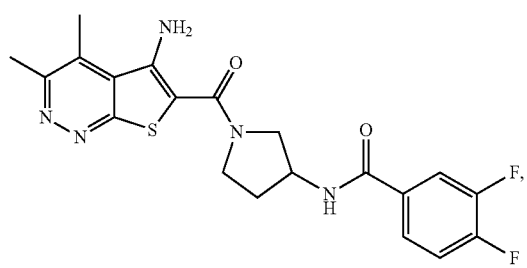
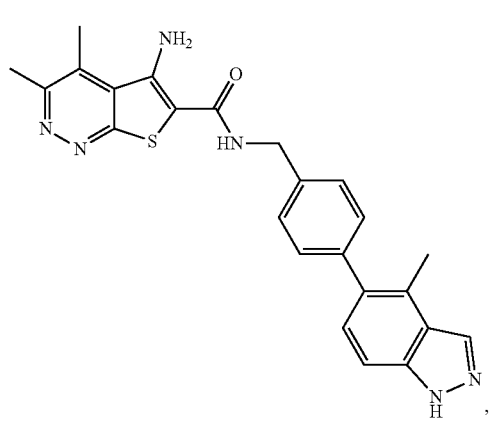
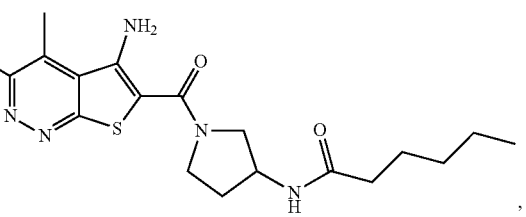
344
-continued
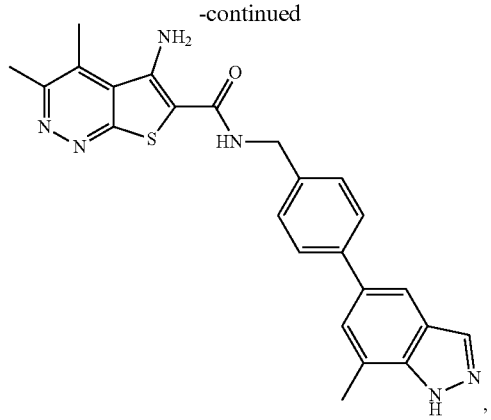
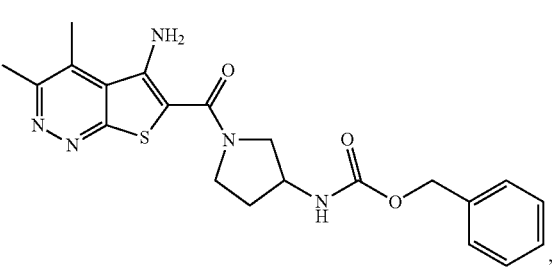

345
-continued
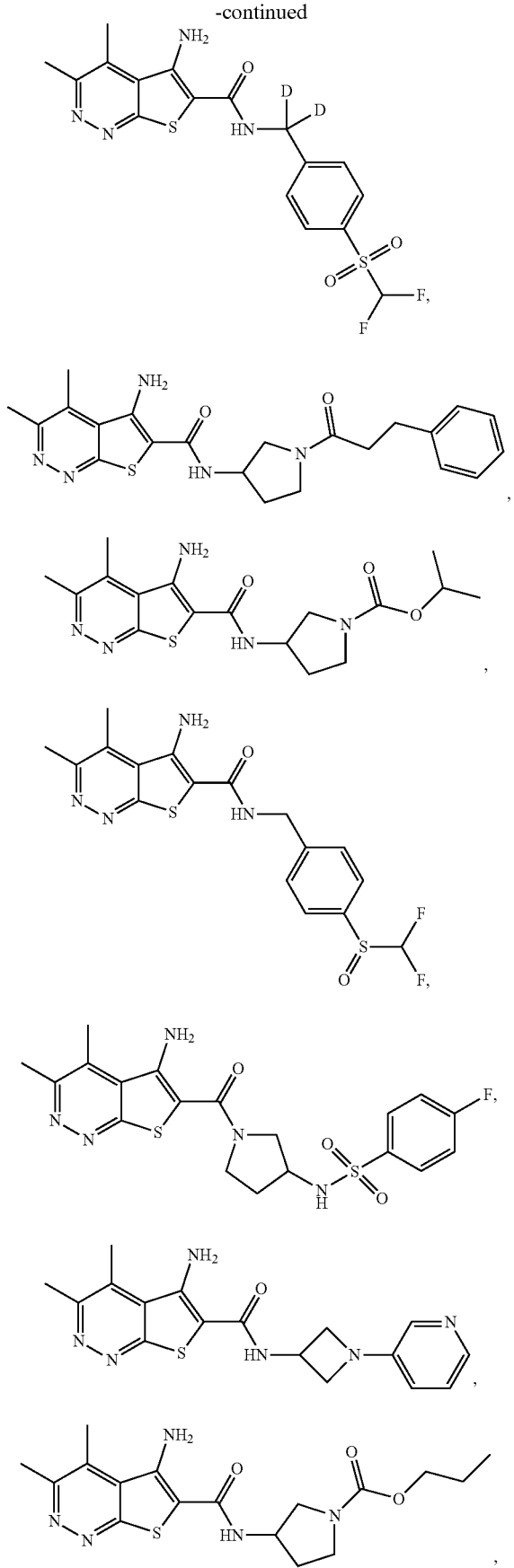
346
-continued
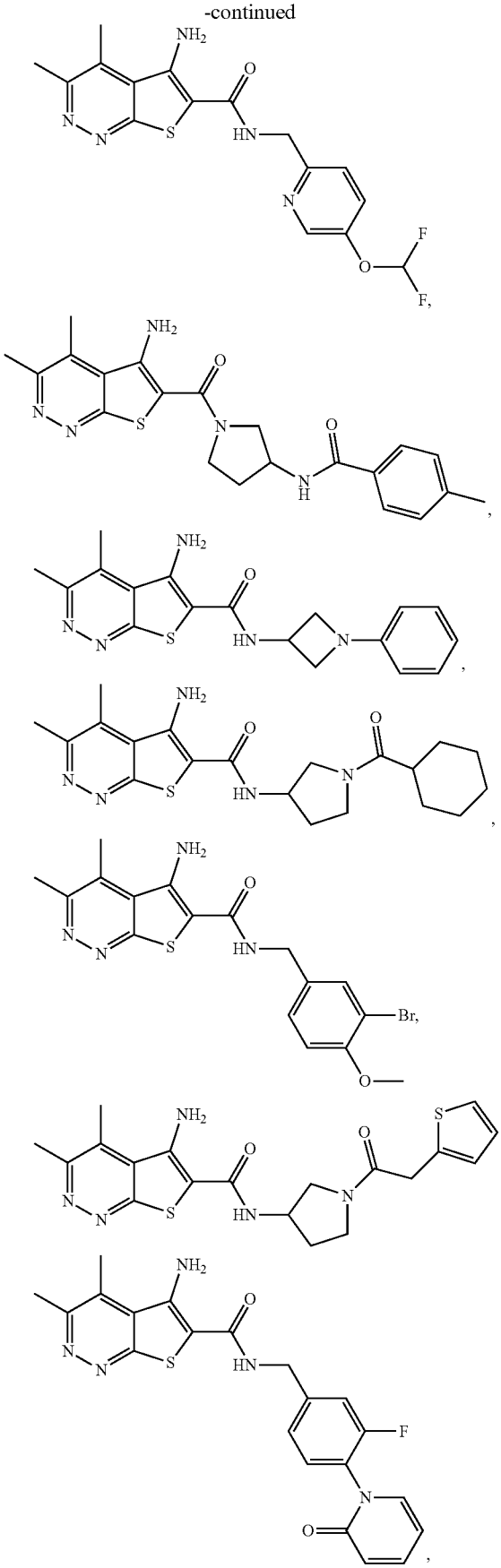

347
-continued
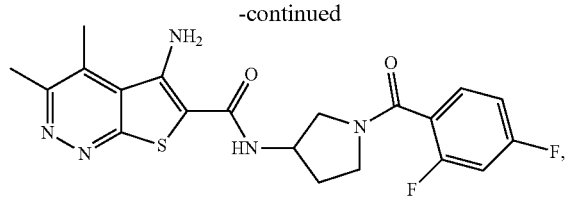
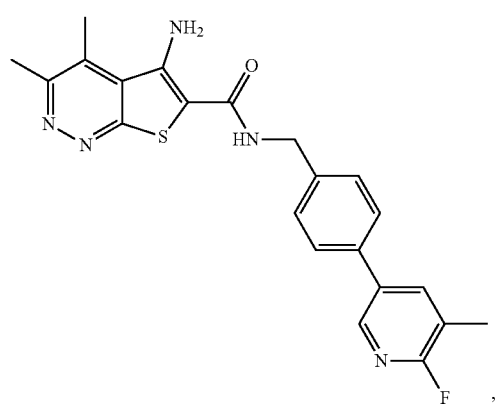
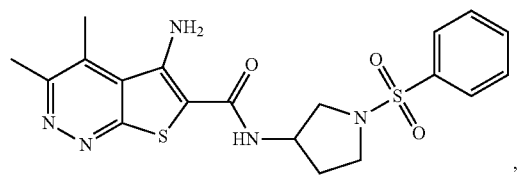
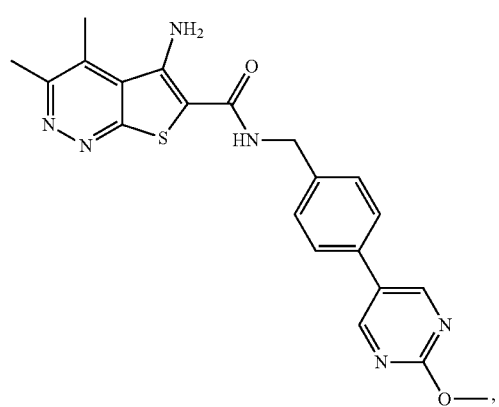
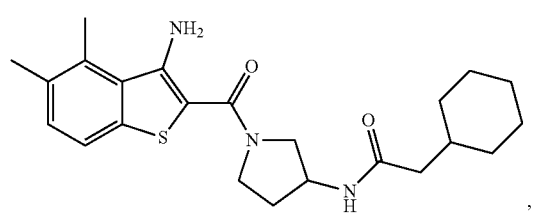
348
-continued
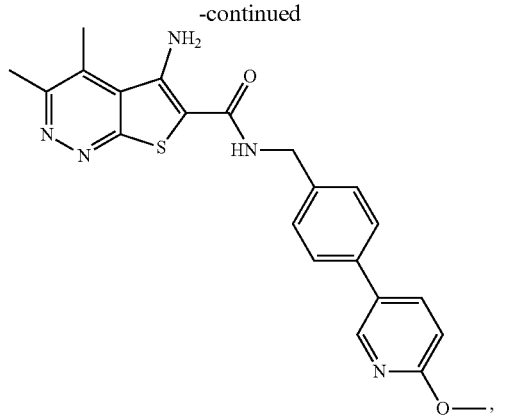
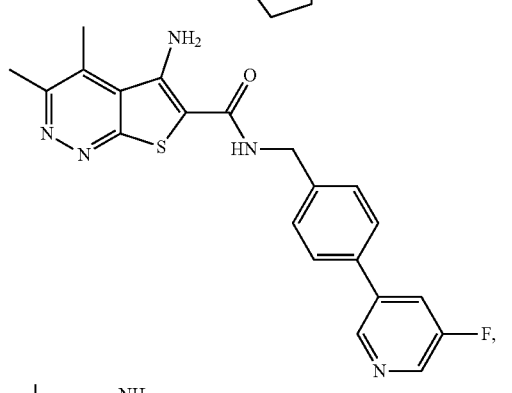
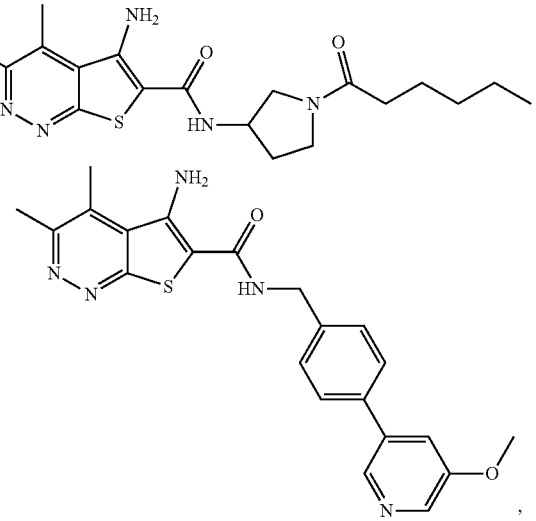
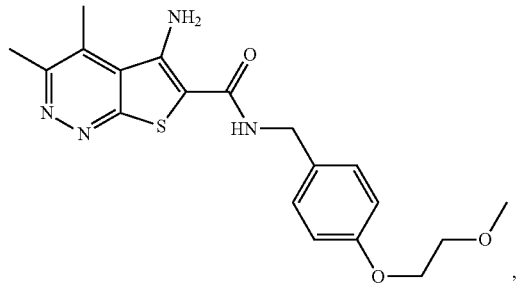

349
-continued
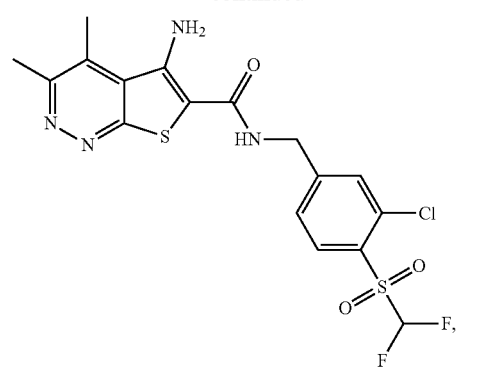
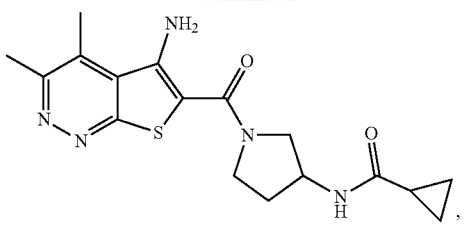
Enantiomer B
350
-continued
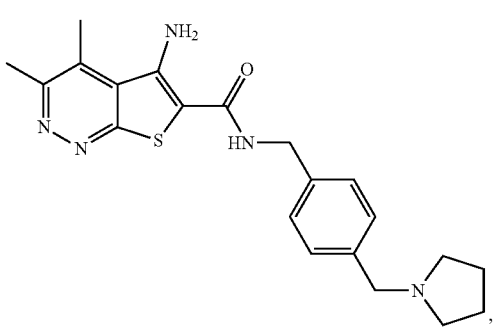
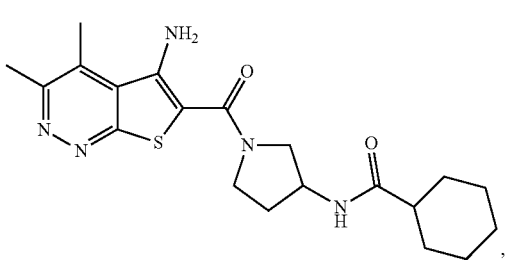
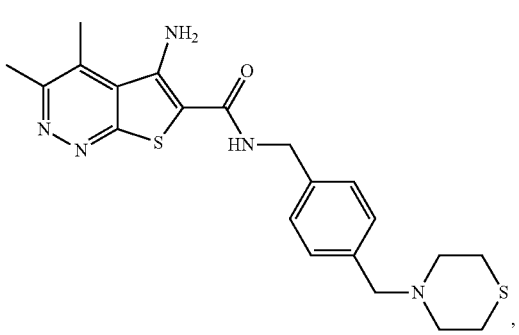
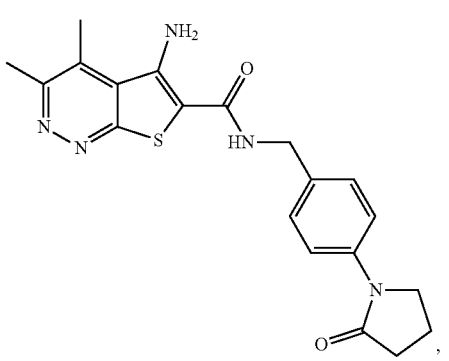

-continued
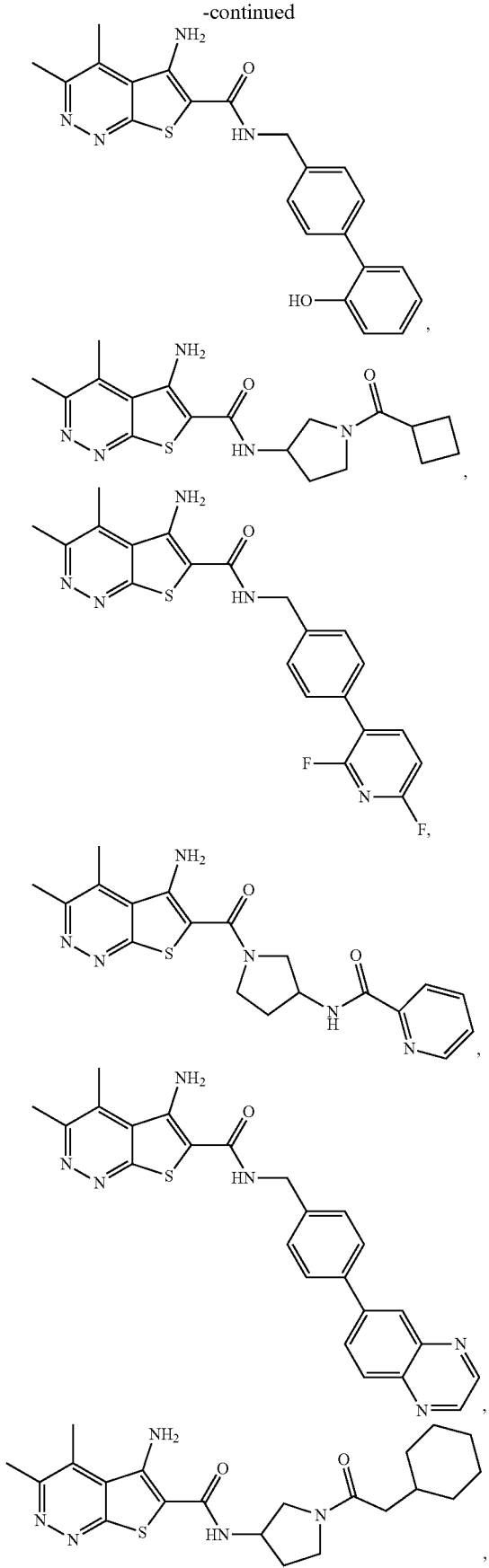
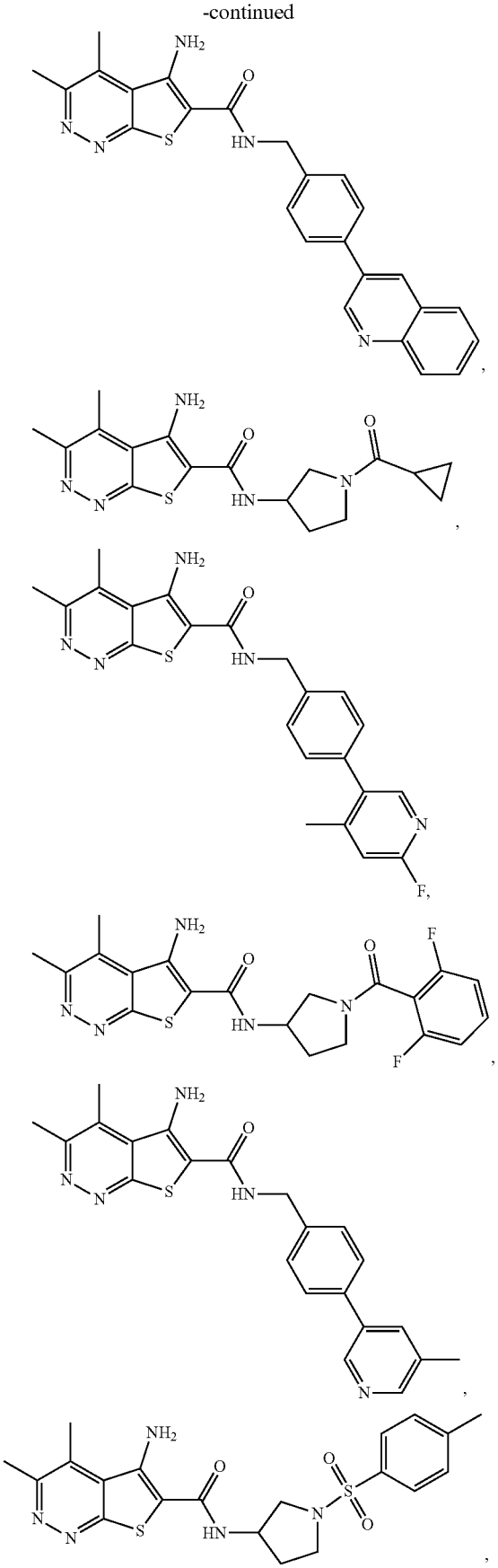

353
-continued
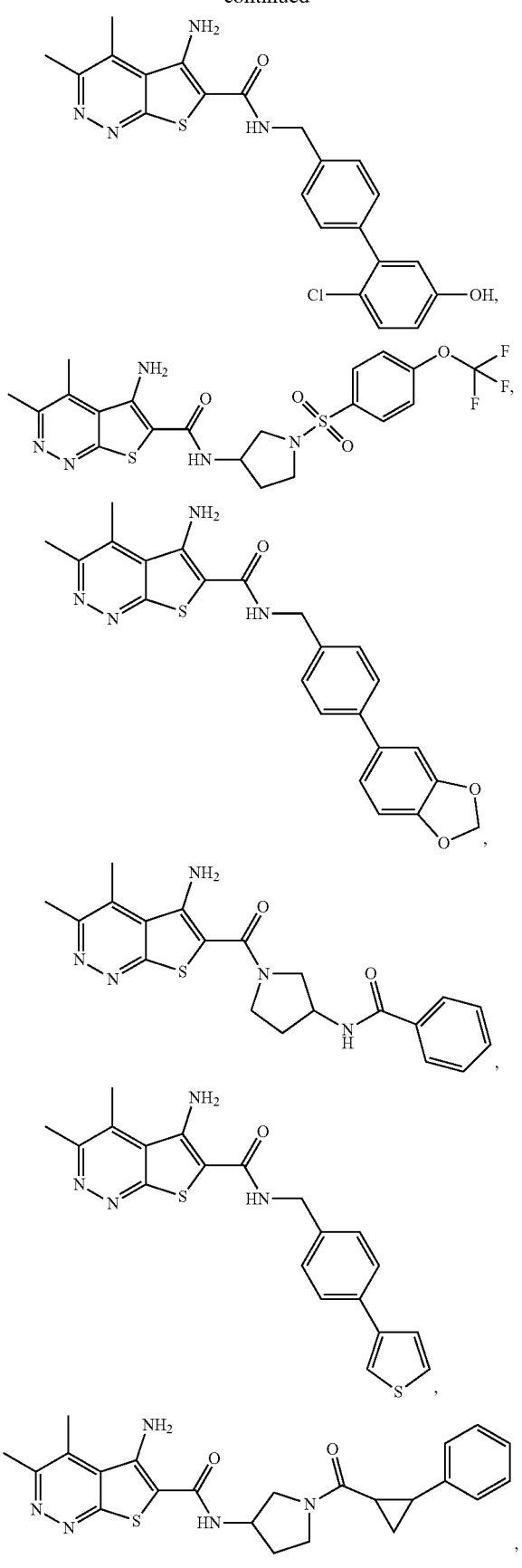
354
-continued
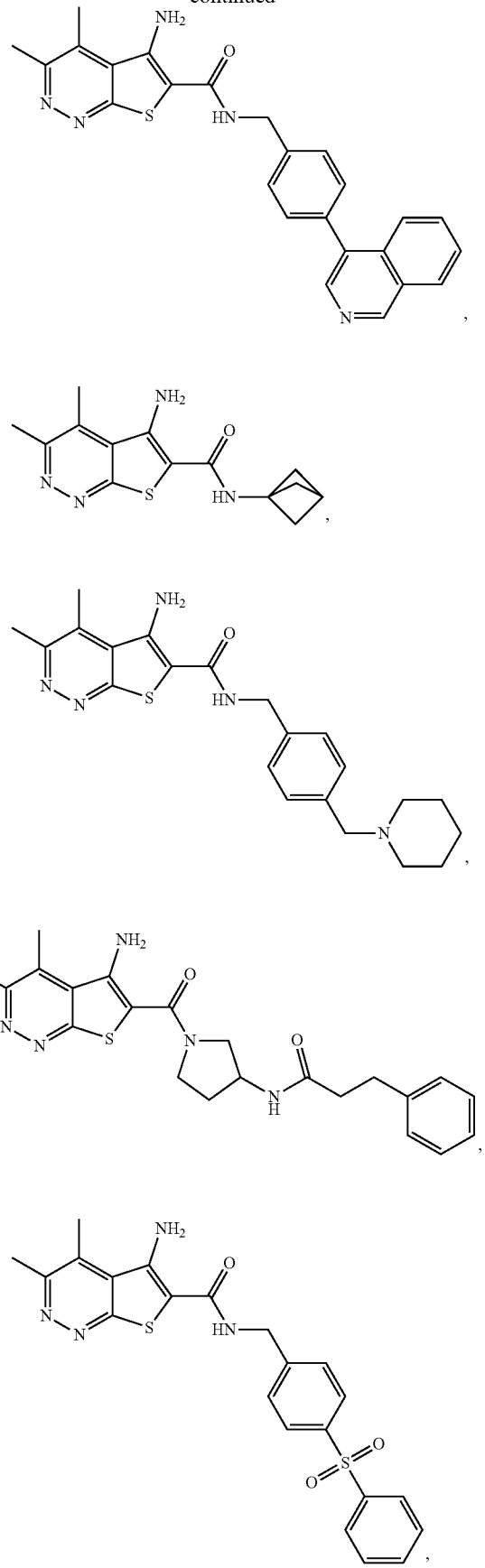

355
-continued
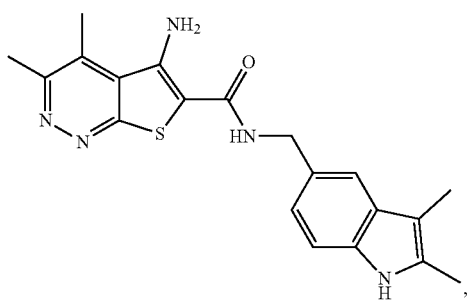
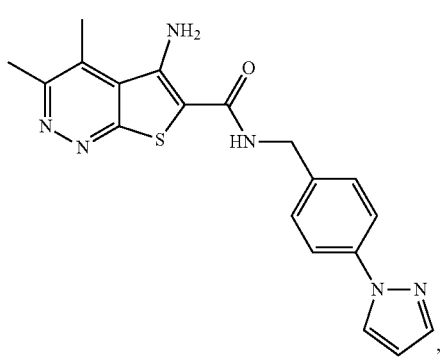
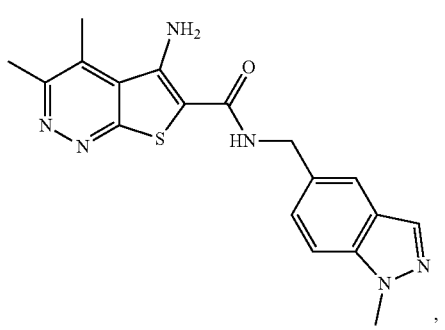
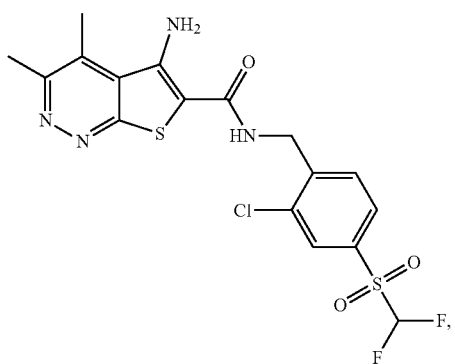
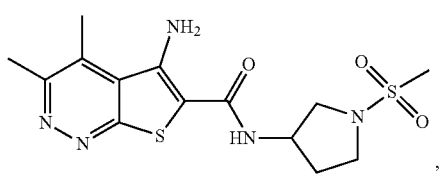
356
-continued
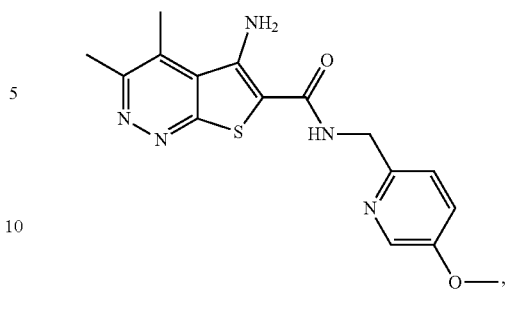
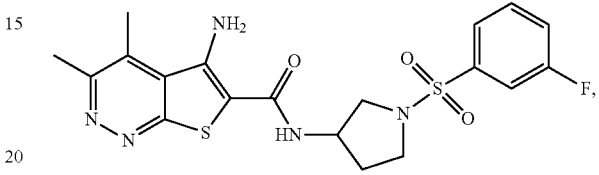
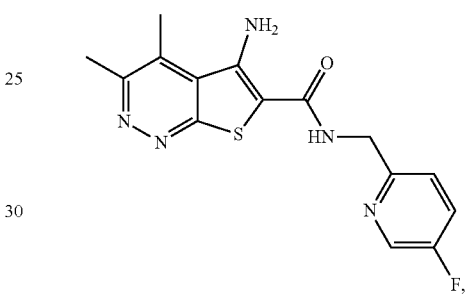
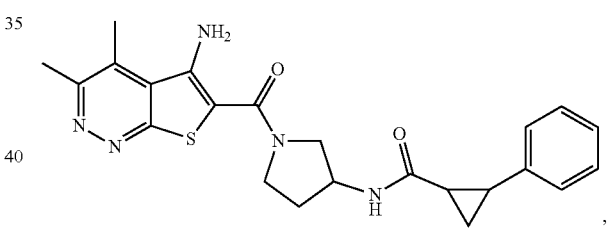
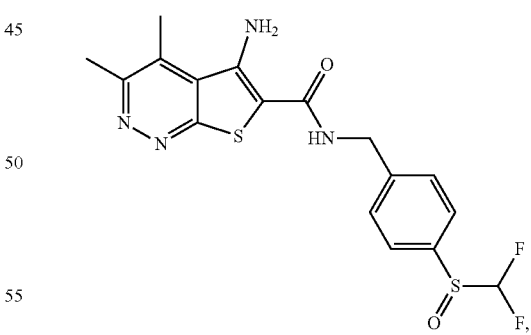
Enantiomer A
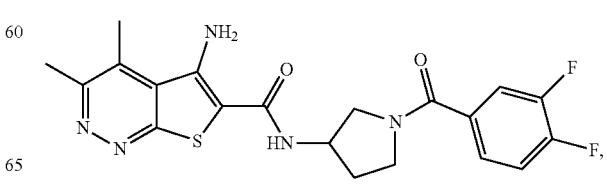

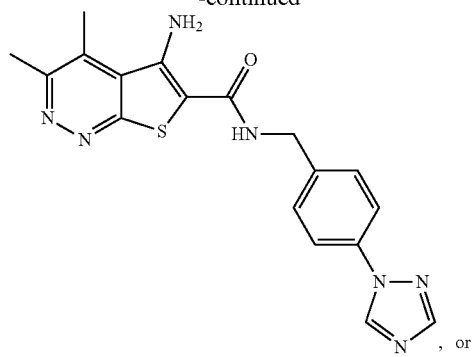
, or
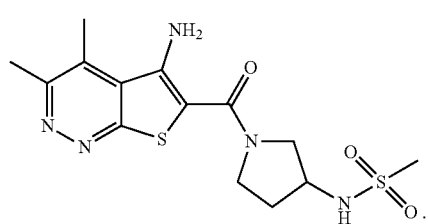
.
In one aspect, a compound can be present as one or more of the following structures:
Enantiomer B
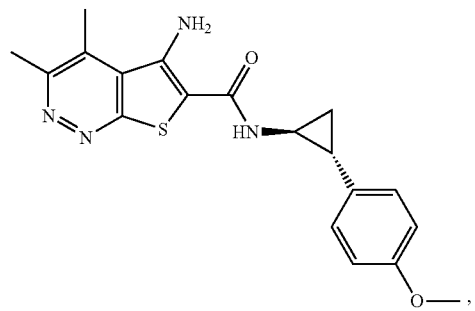
,
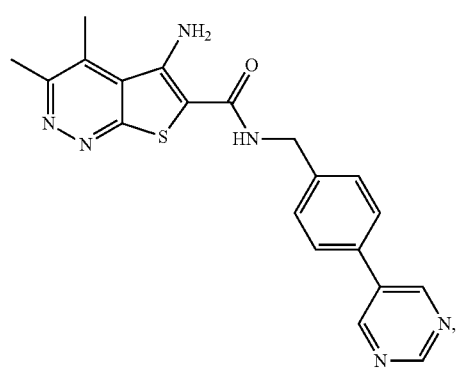
,
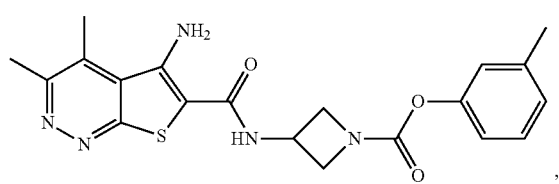
,
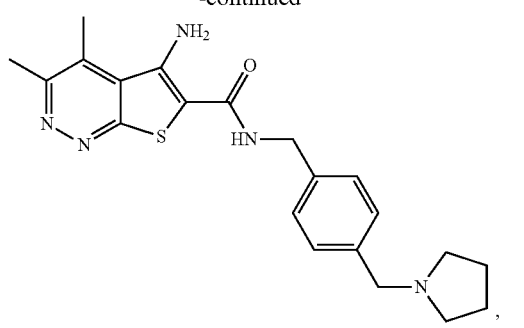
,
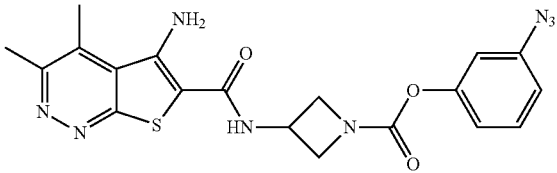
,
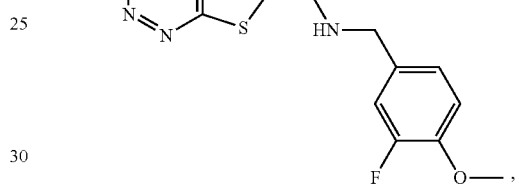
,
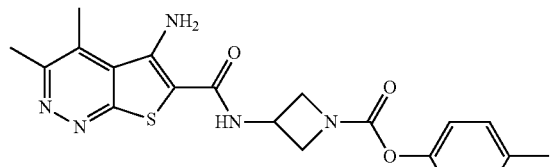
,
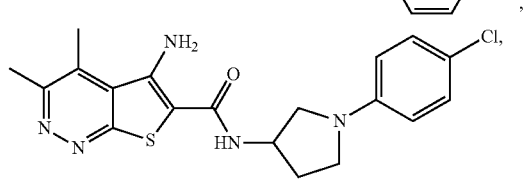
,
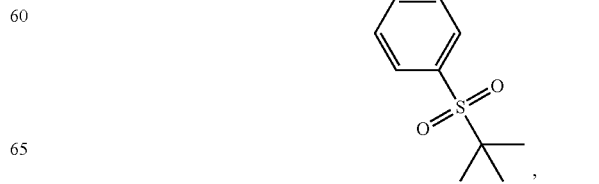
, 359
-continued
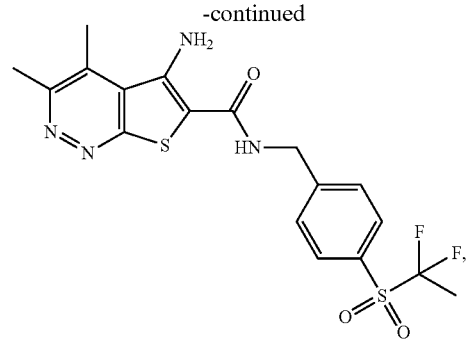
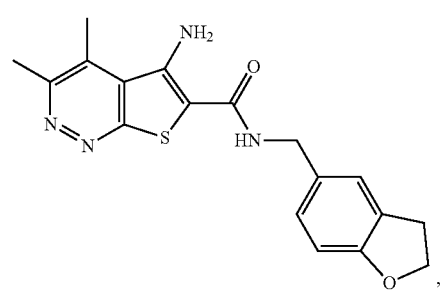
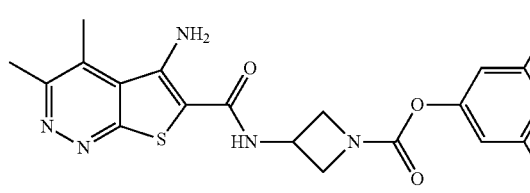
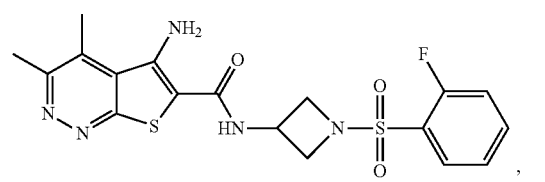
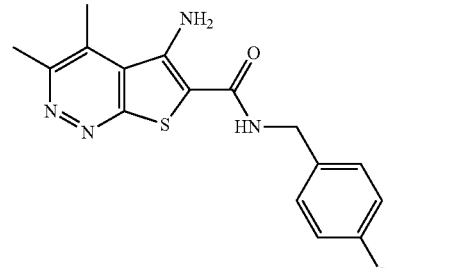
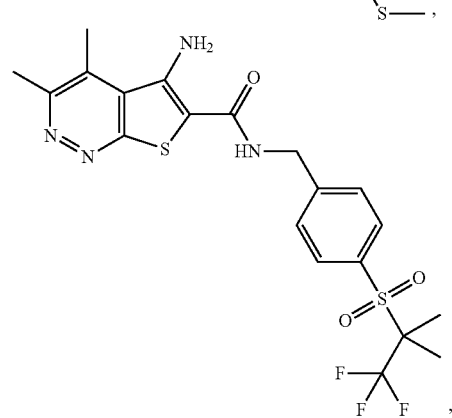
360
-continued
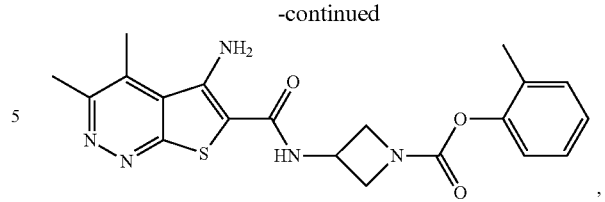
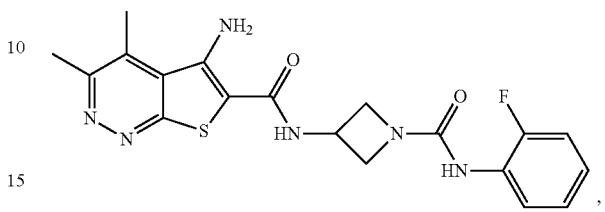
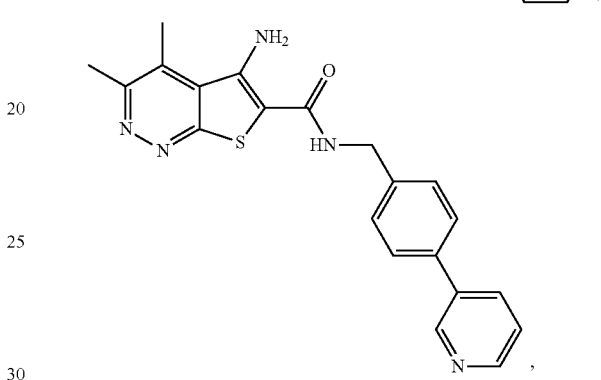
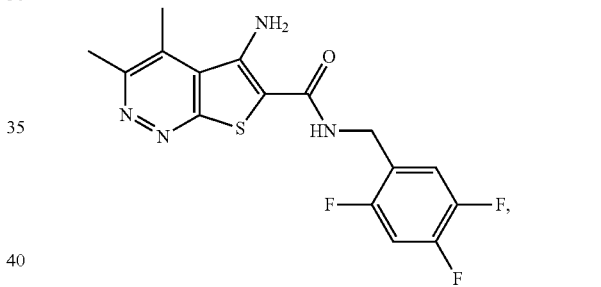
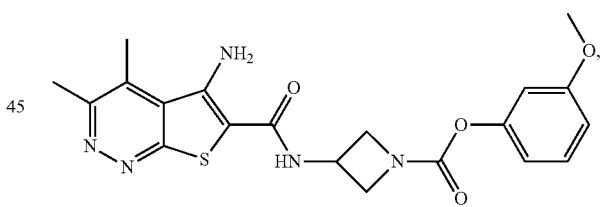
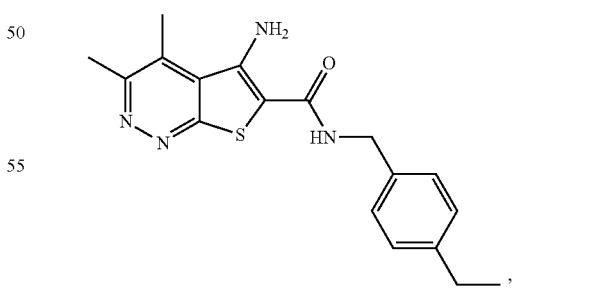
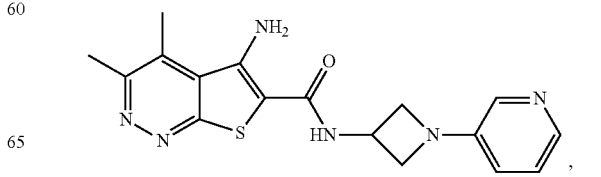

361
-continued
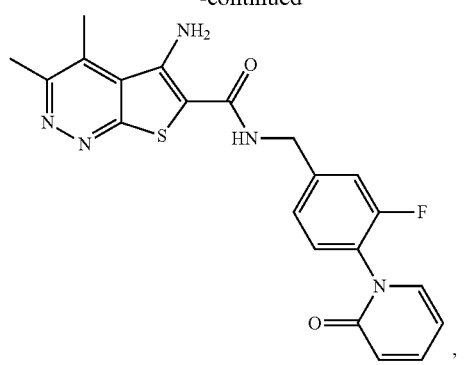
362
-continued
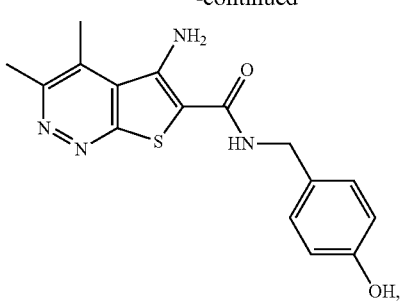
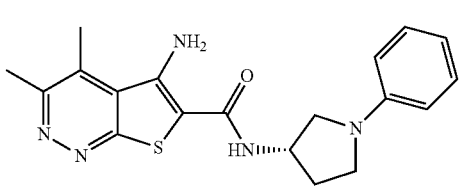
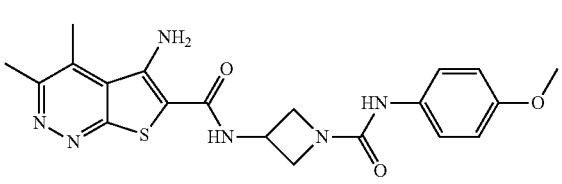
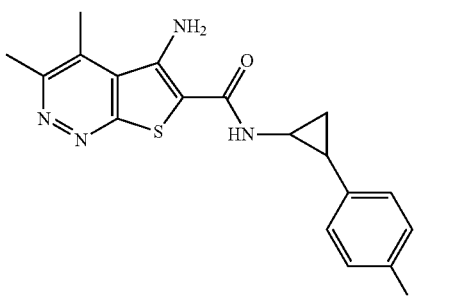
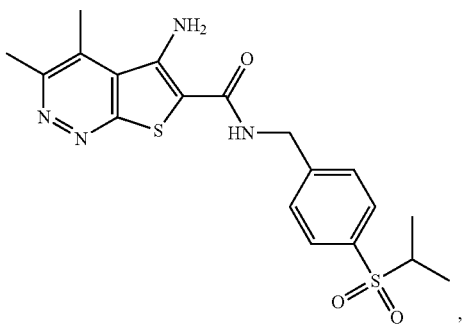
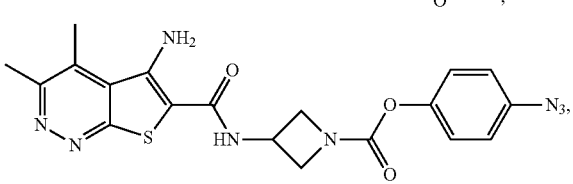

363
-continued
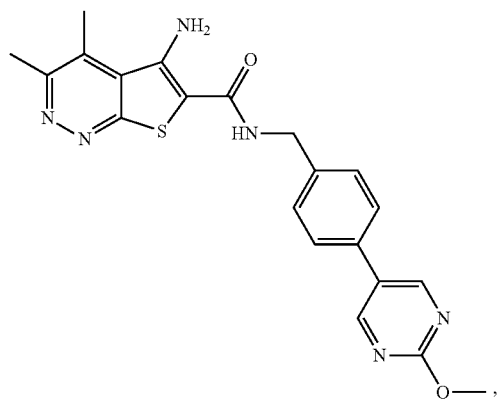
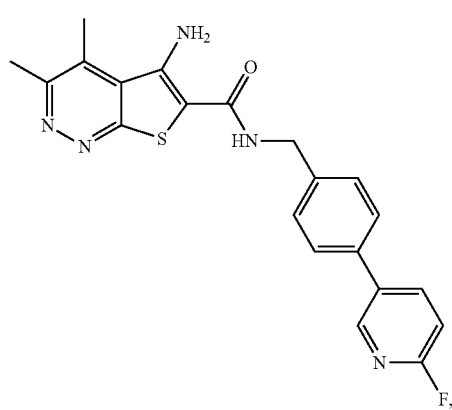
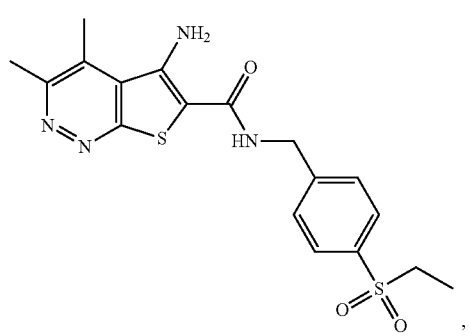
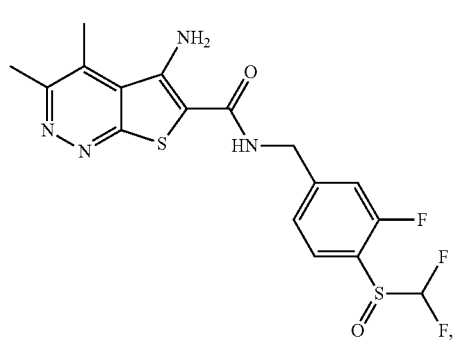
364
-continued
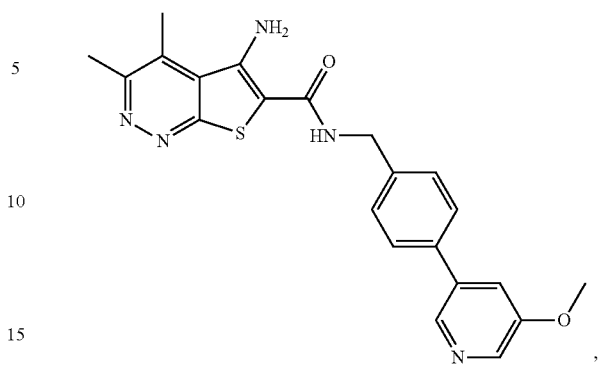
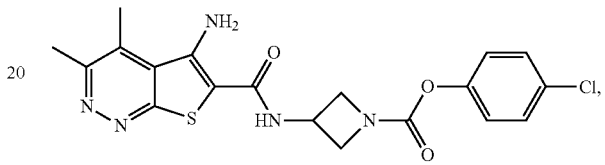
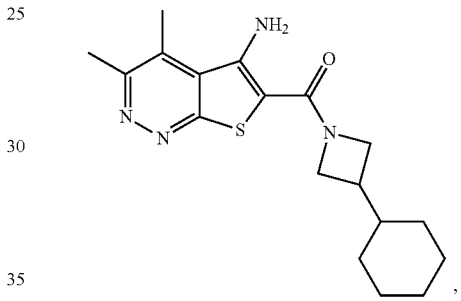
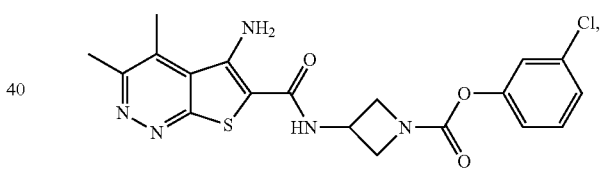
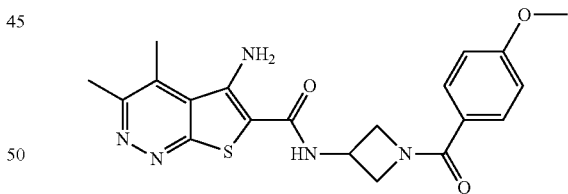
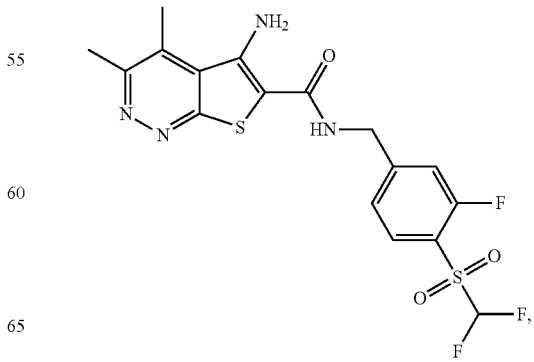

365
-continued
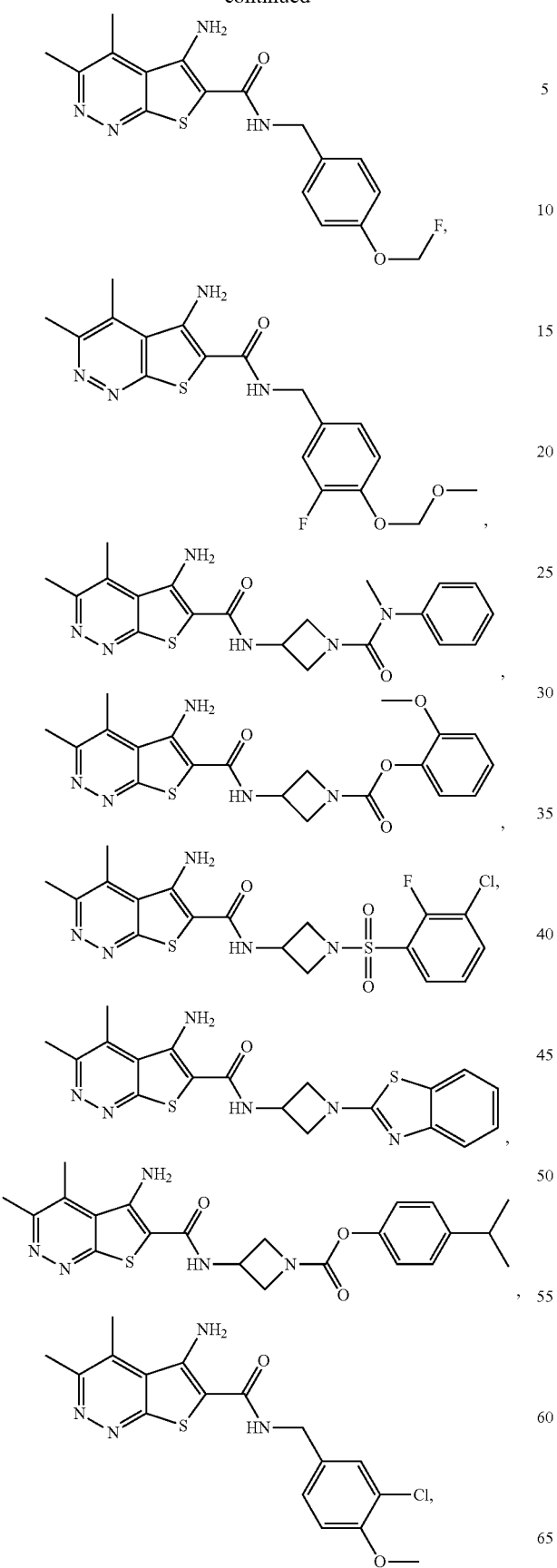
366
-continued
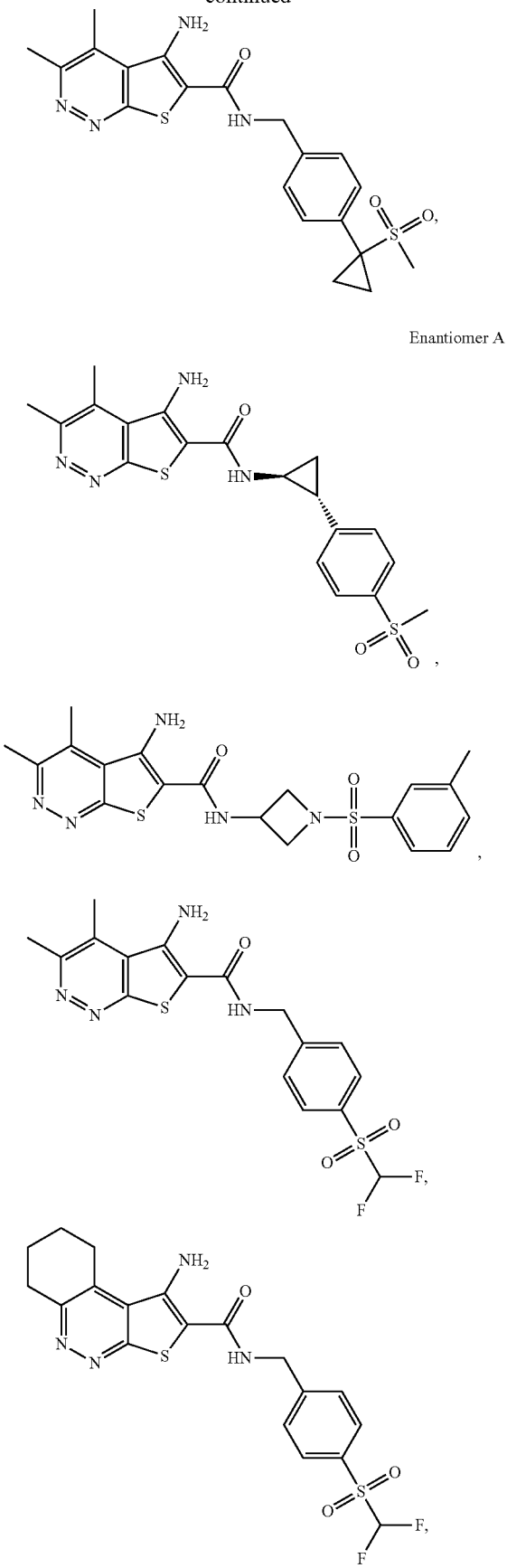

367
-continued
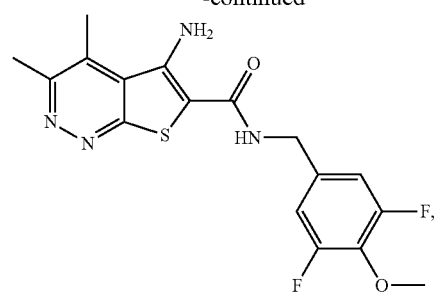
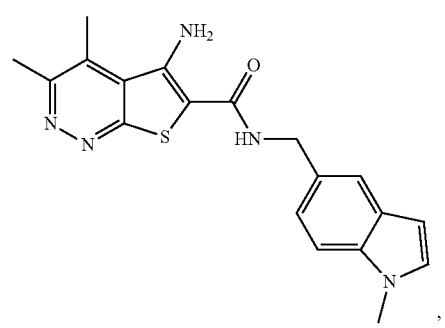
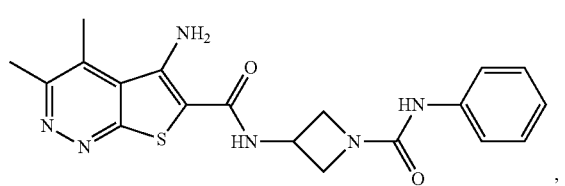
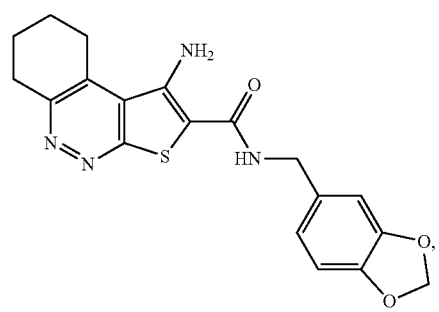
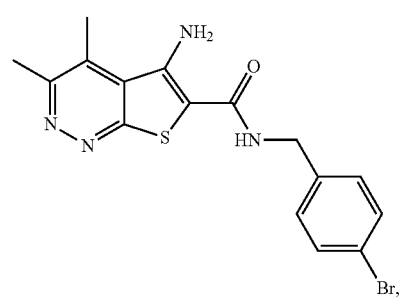
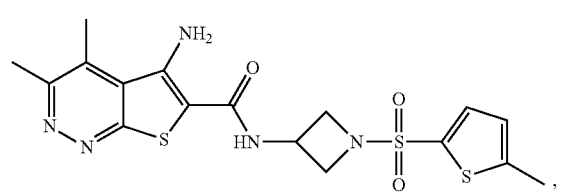
368
-continued
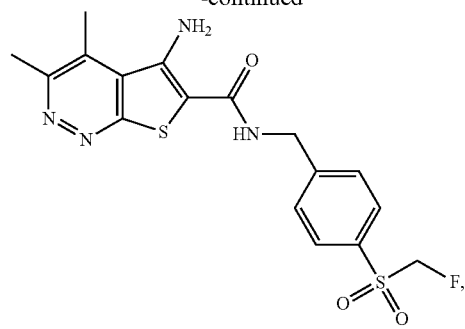
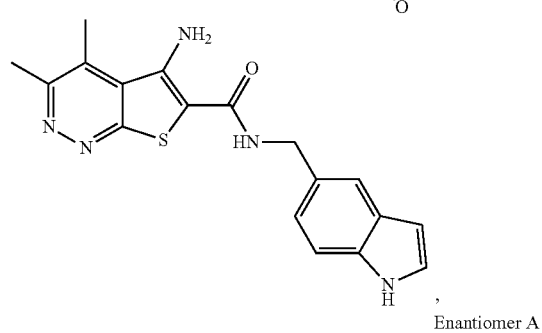
Enantiomer A
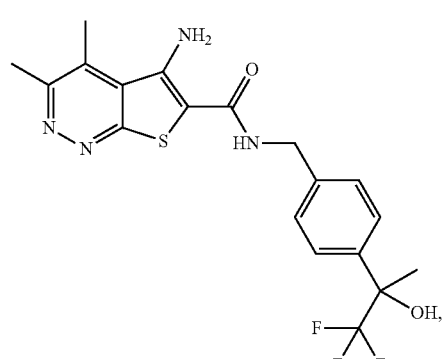
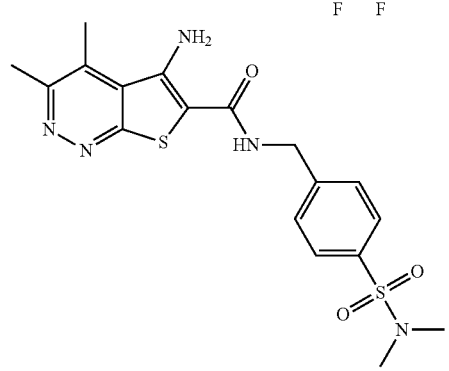
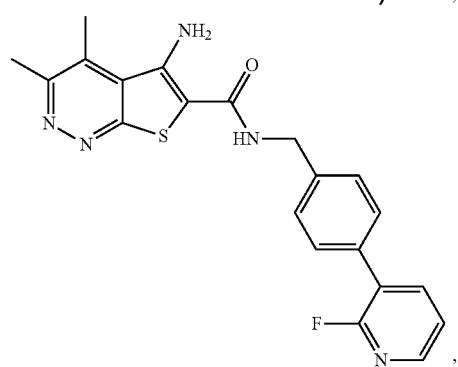

369
-continued
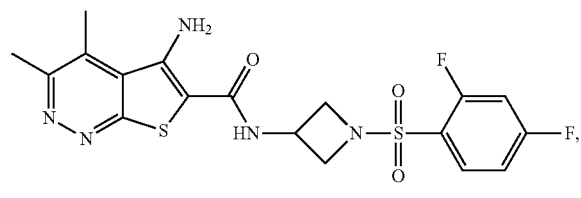
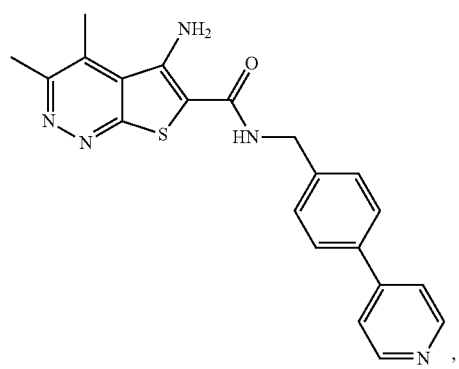
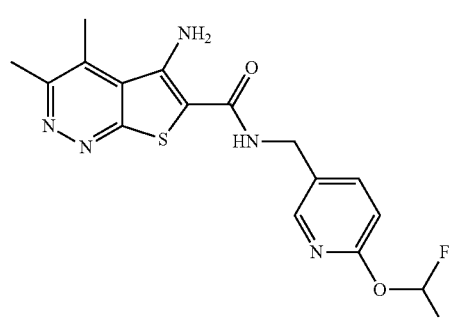
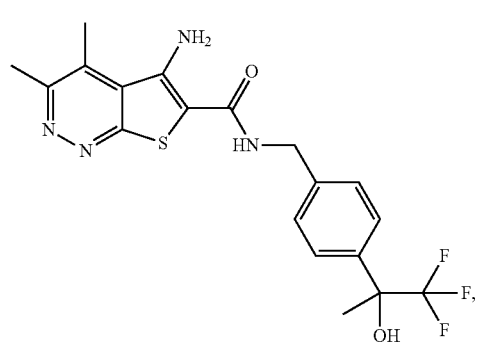
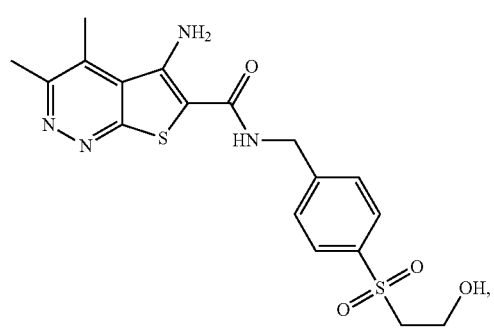
370
-continued
Enantiomer B
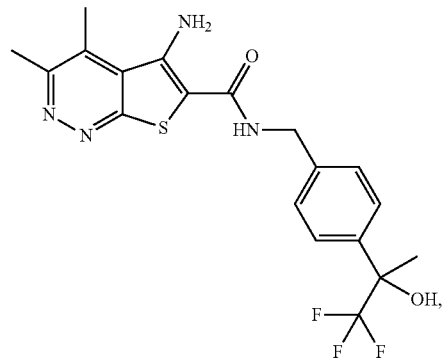
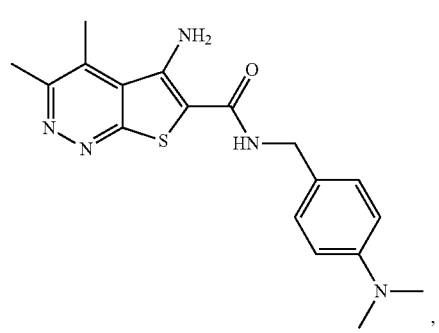
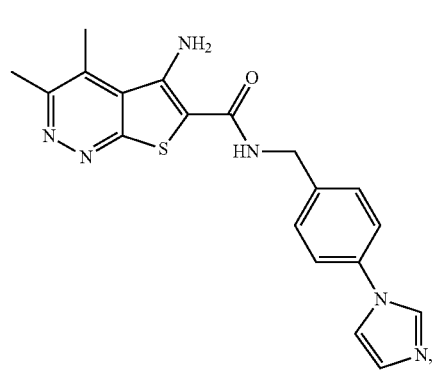
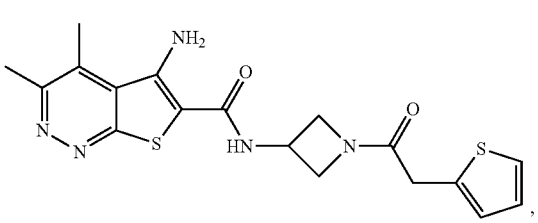
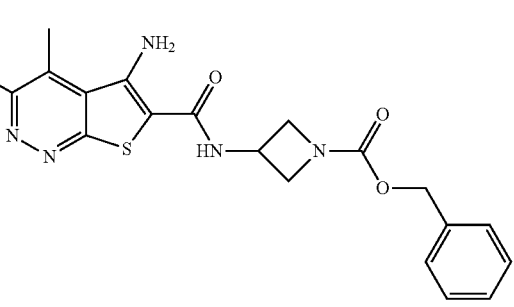

-continued
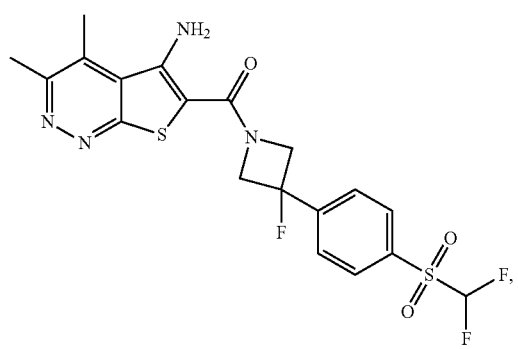
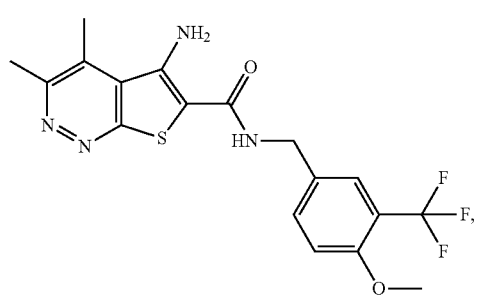
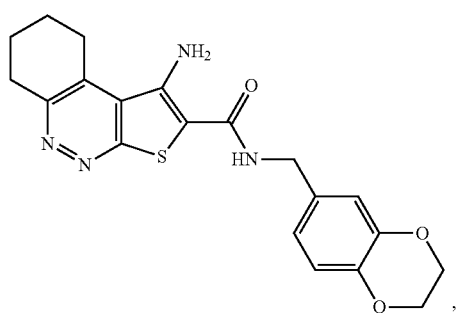
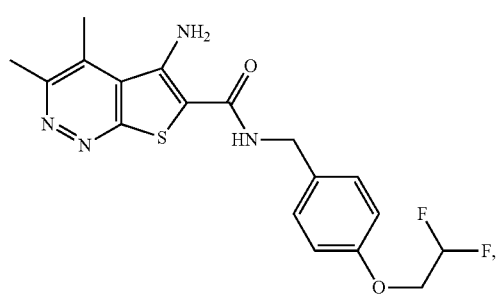
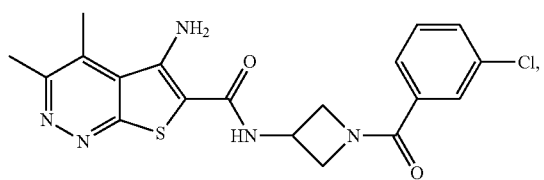
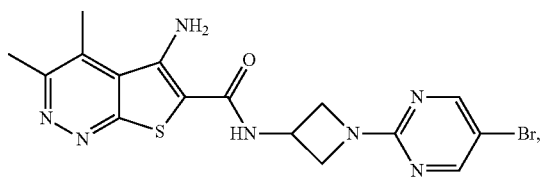
-continued
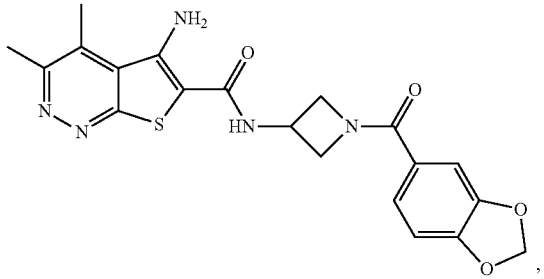
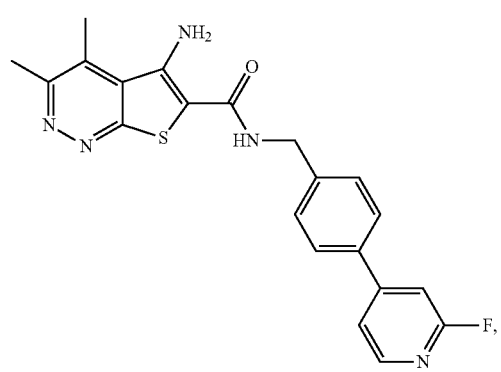
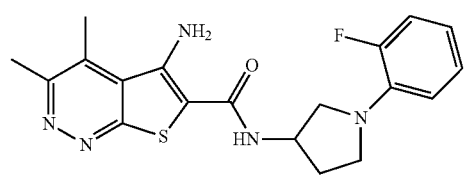
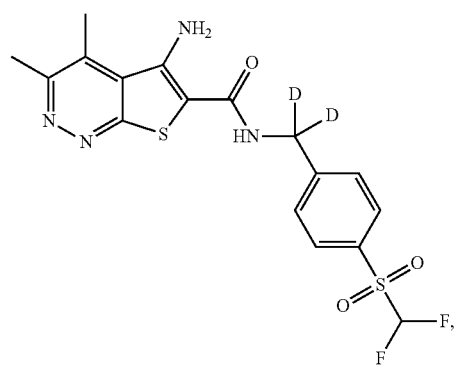
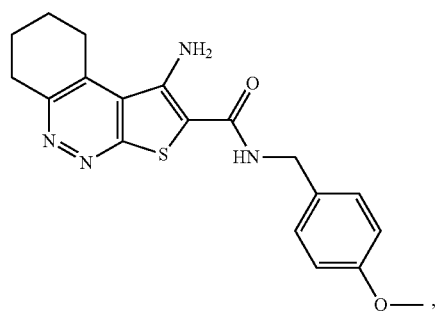

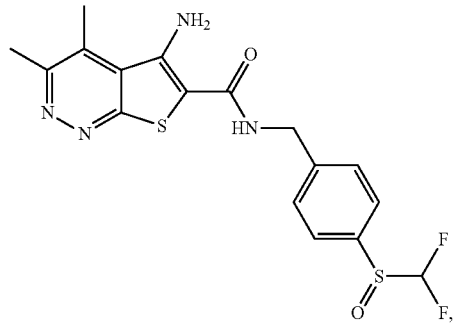
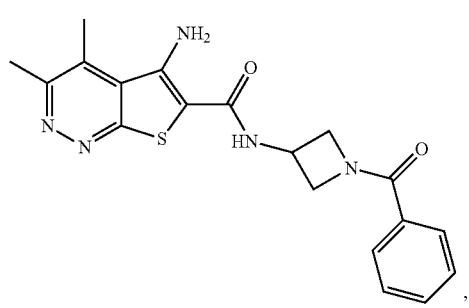
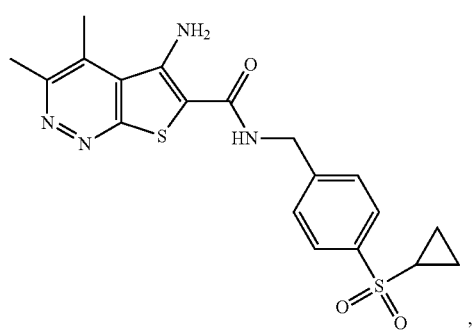
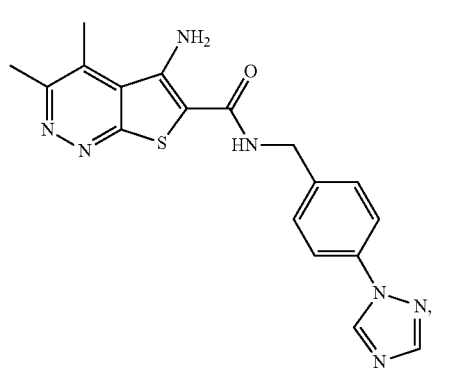
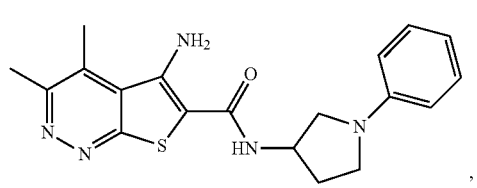
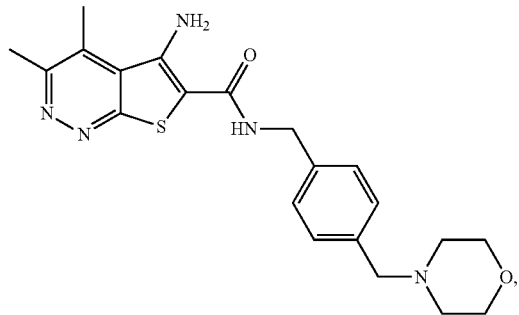
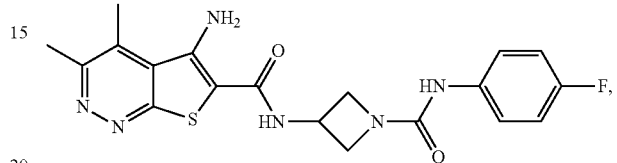
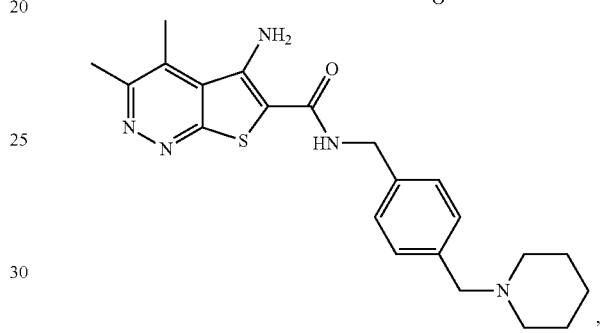
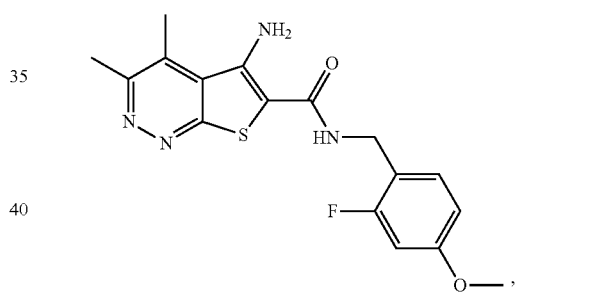
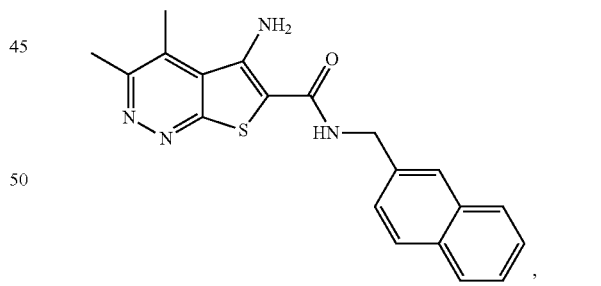
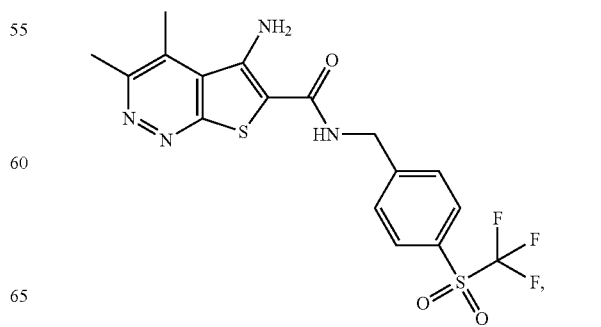

375
-continued
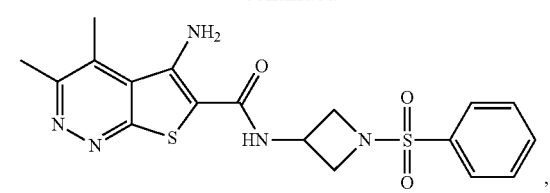
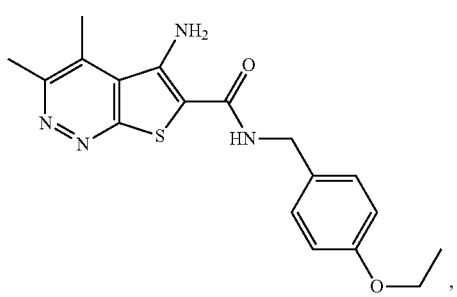
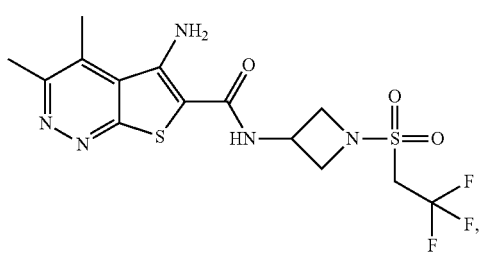
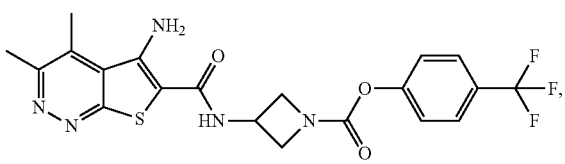
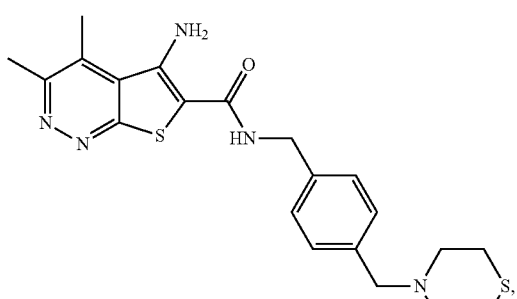
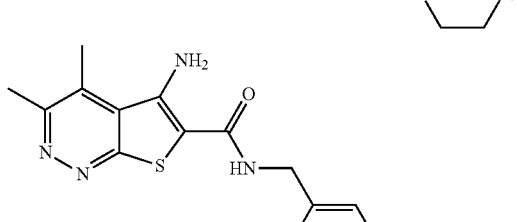
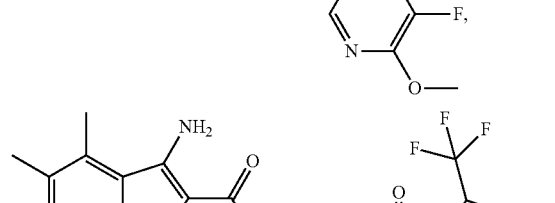
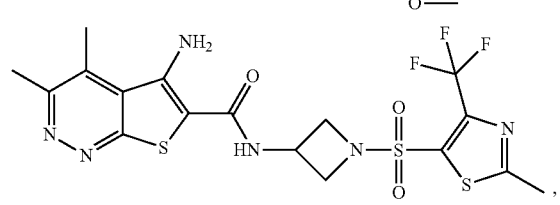
376
-continued
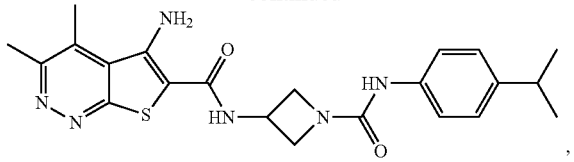
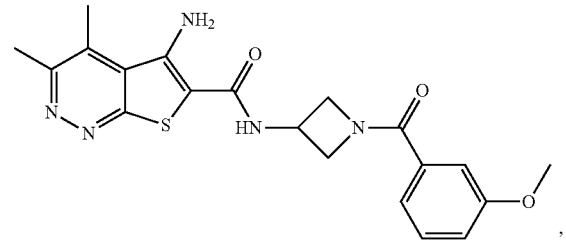
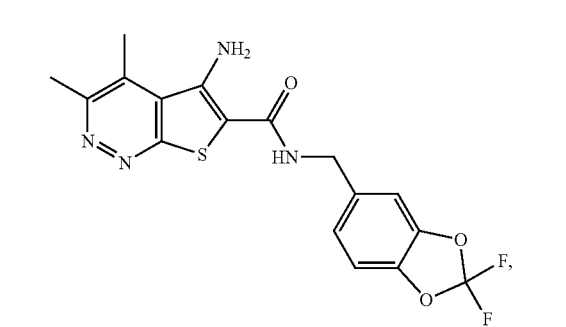
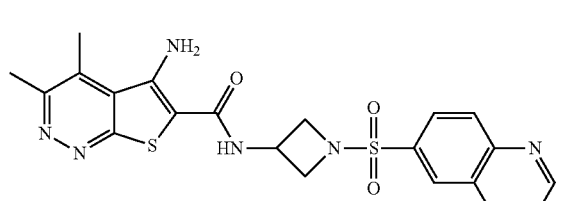
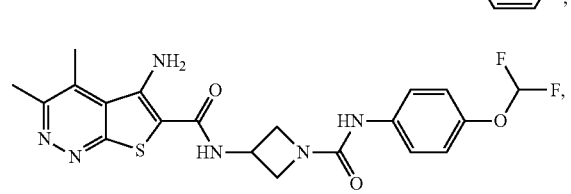
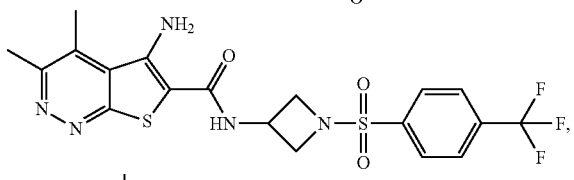
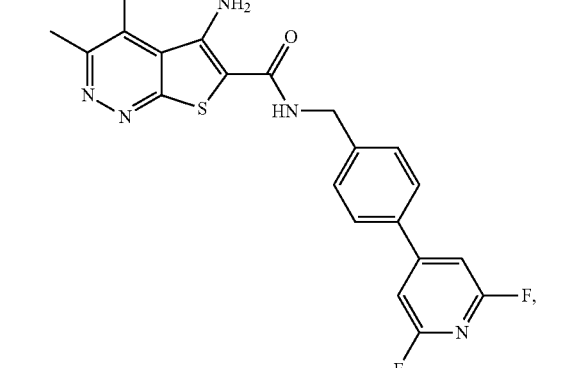

377
-continued
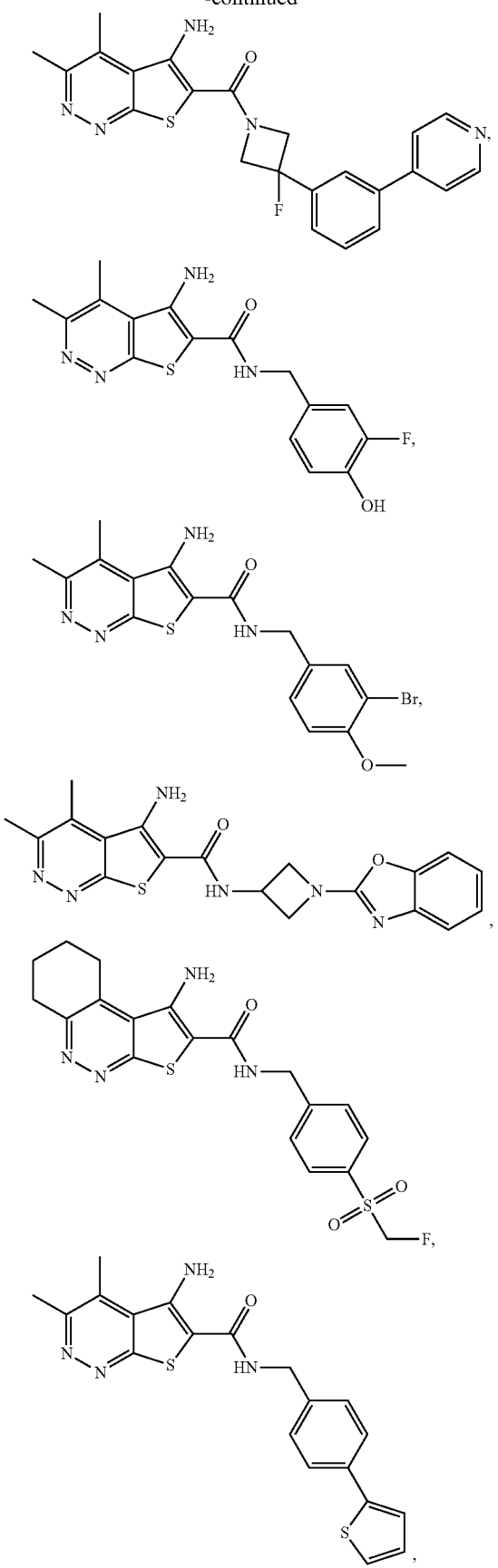
378
-continued
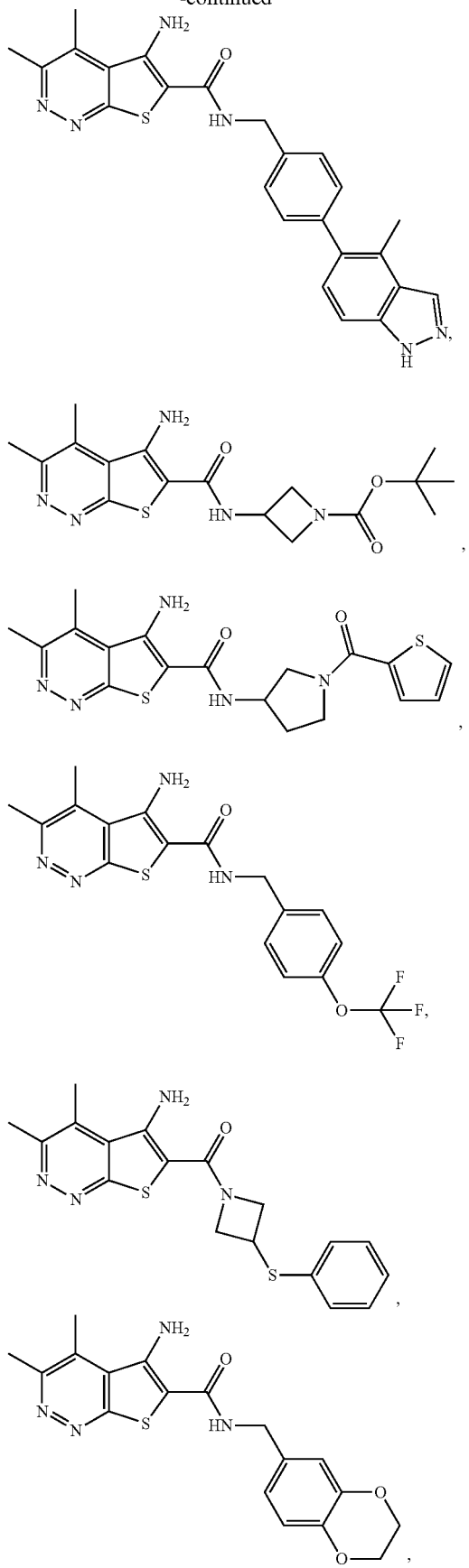

379
-continued
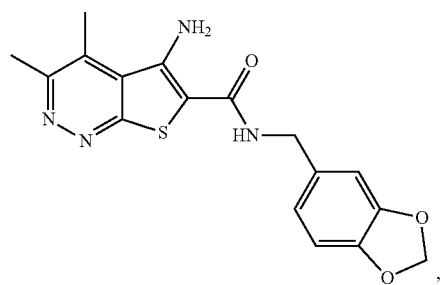
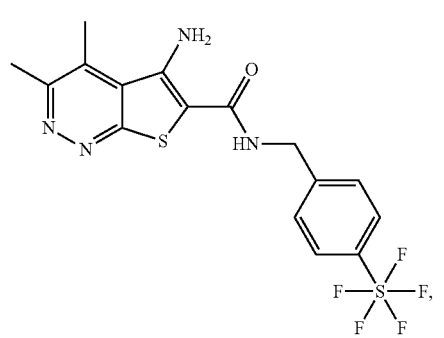
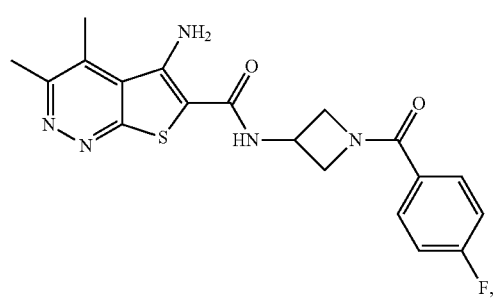
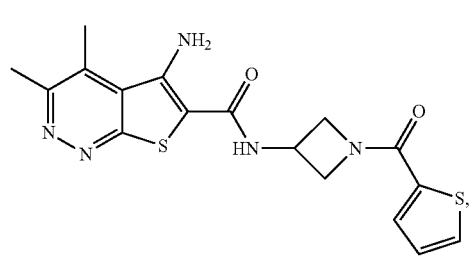
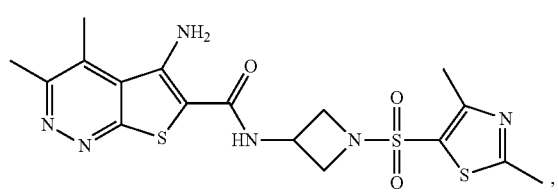
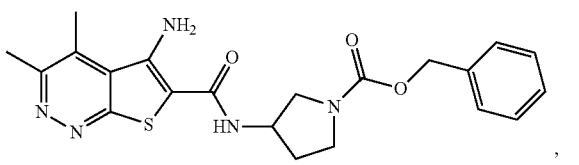
380
-continued
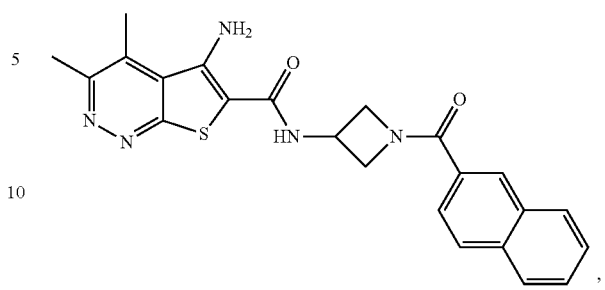
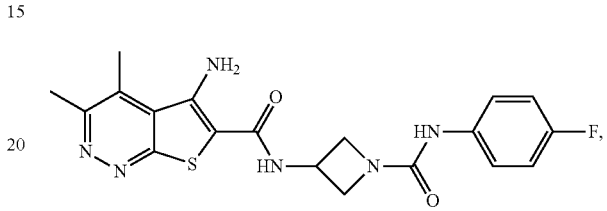
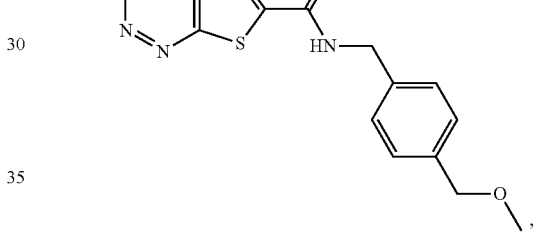
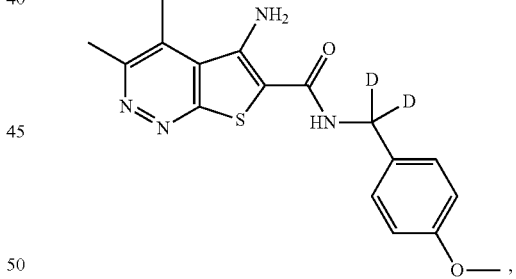

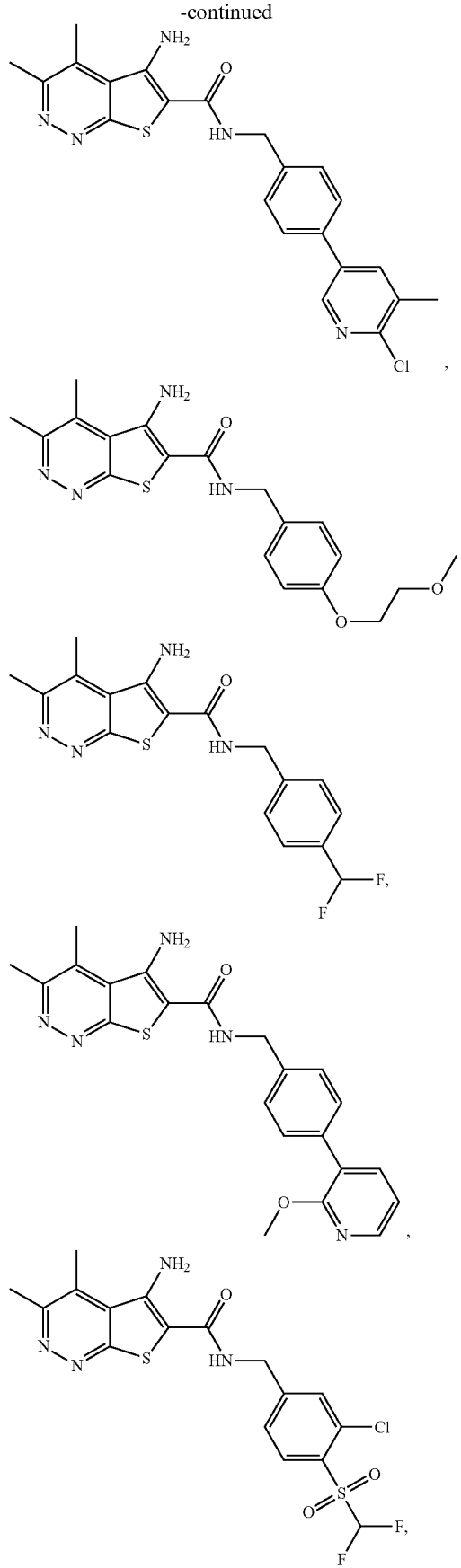

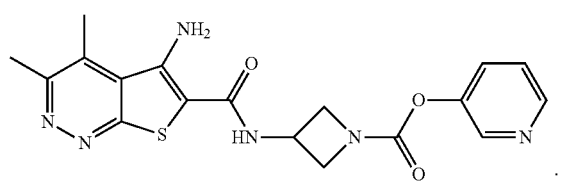
In one aspect, a compound can be present as one or more of the following structures:
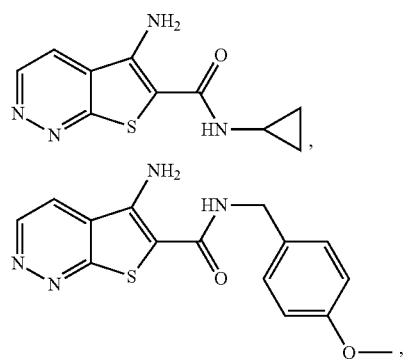
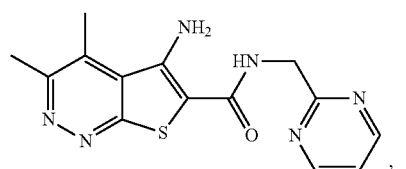
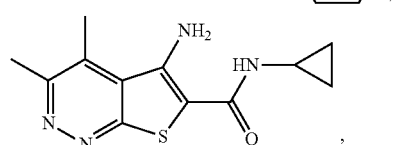
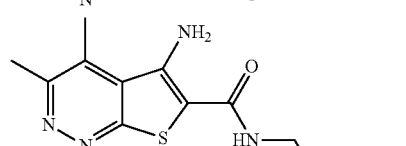
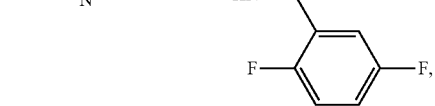
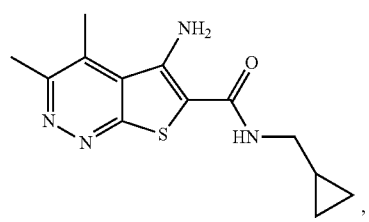
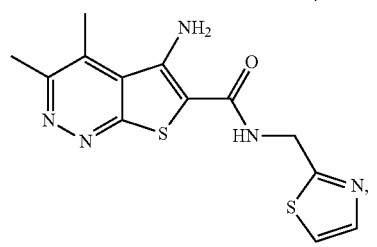
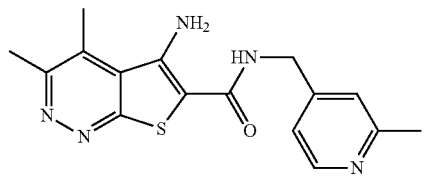
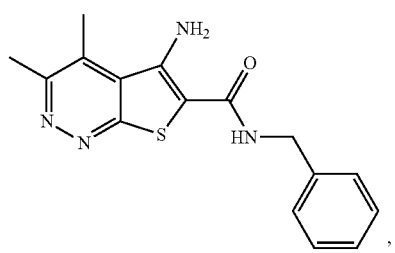
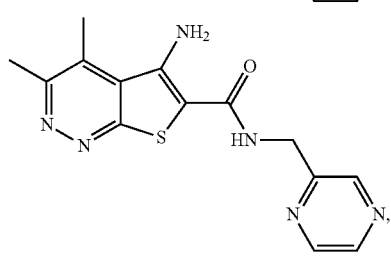
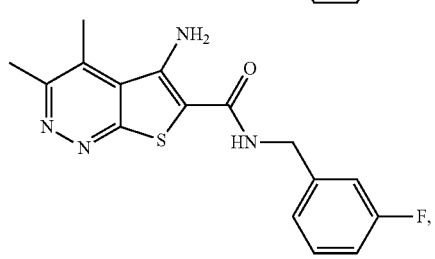
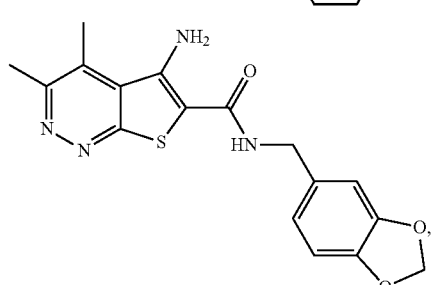
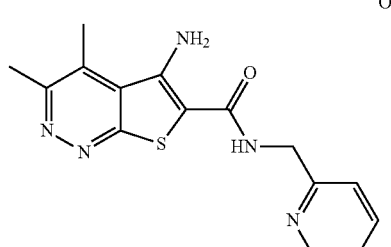
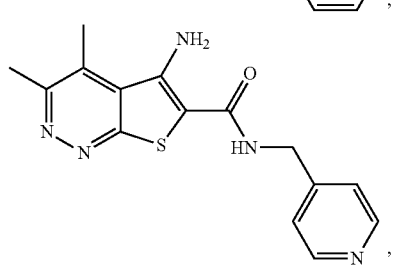

-continued
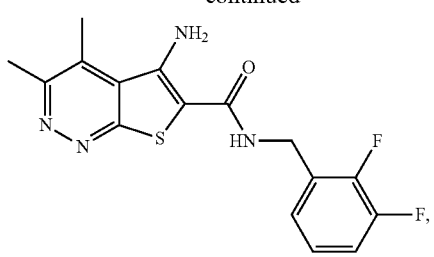
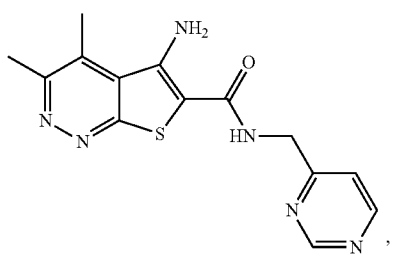
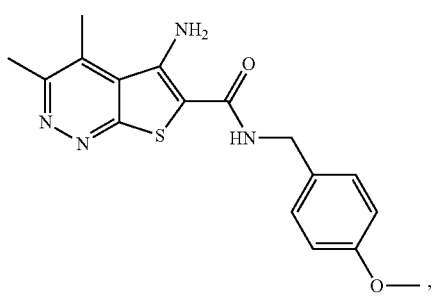
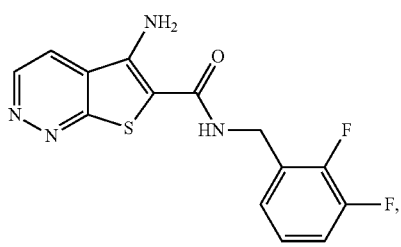
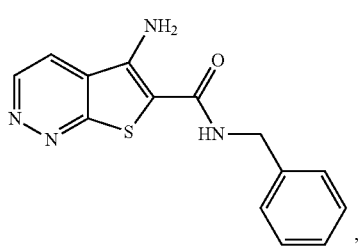
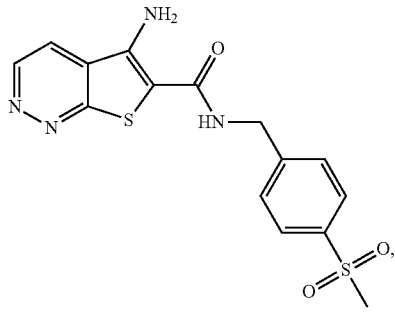
-continued
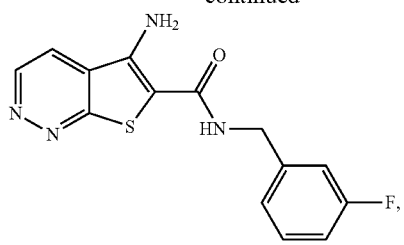
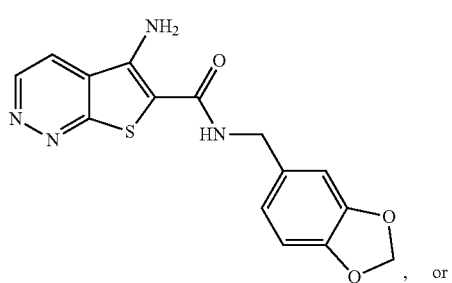
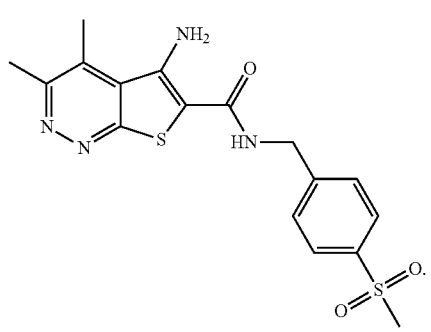, or
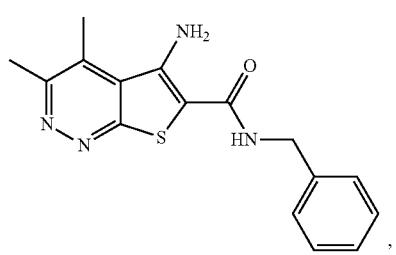.
In one aspect, a compound can be present as one or more of the following structures:
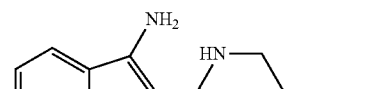
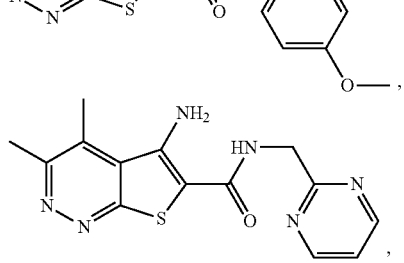

387
-continued
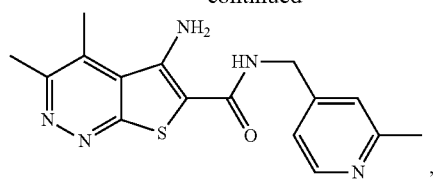,
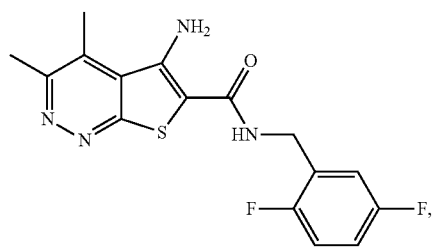,
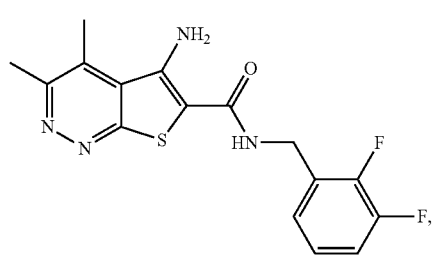,
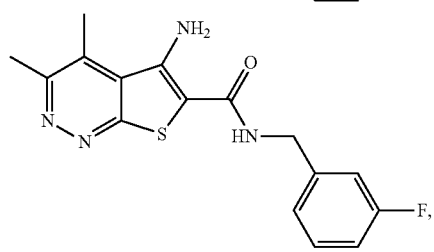,
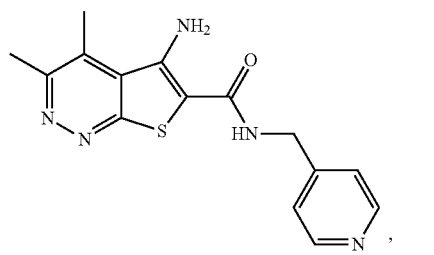,
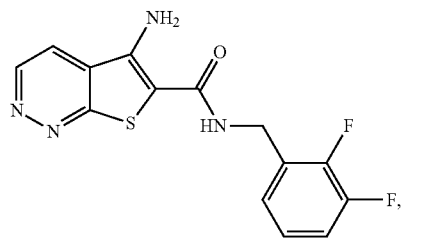,
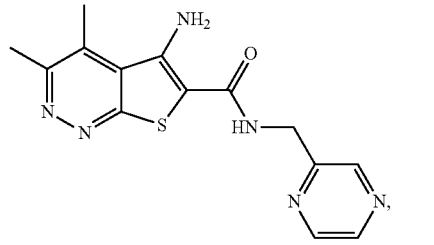,
388
-continued
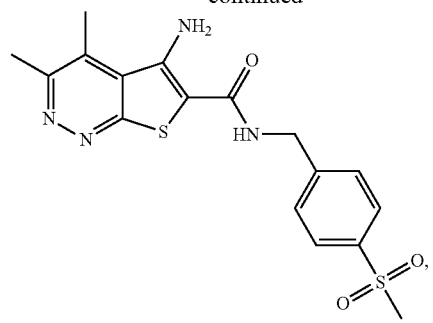,
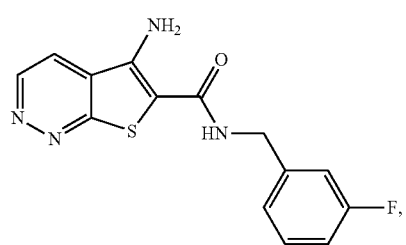,
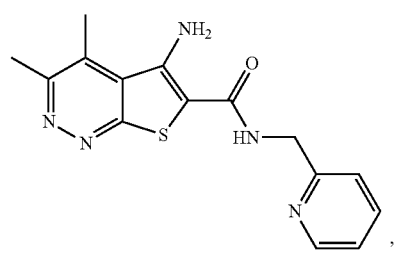,
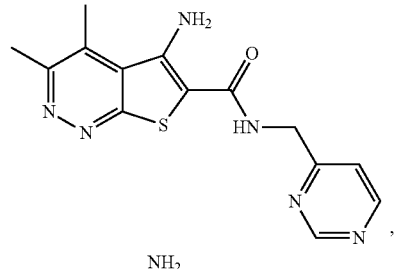,
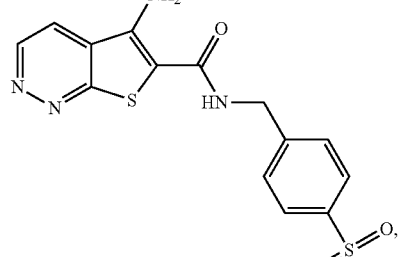,
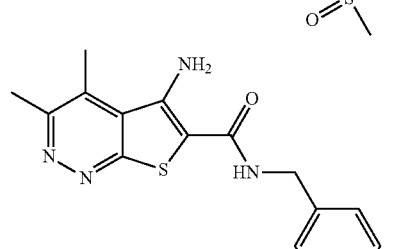 or -continued
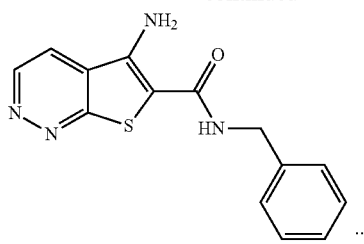
In one aspect, a compound can be present as one or more of the following structures:
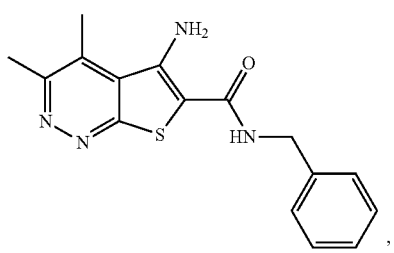
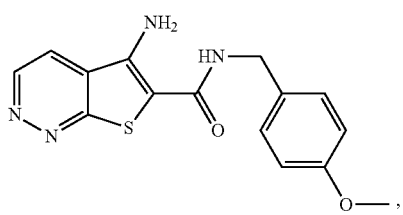
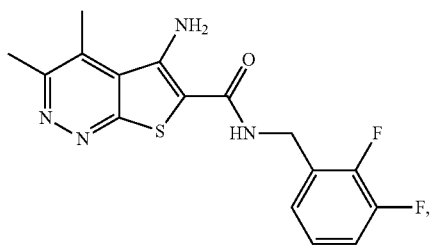
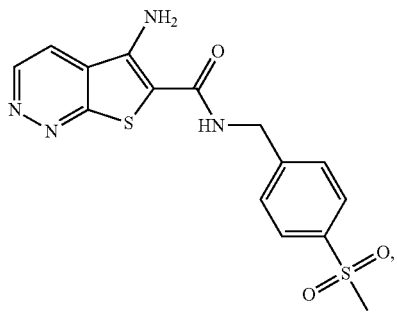
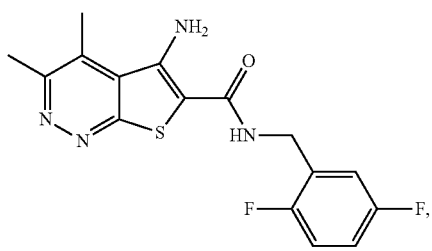
-continued
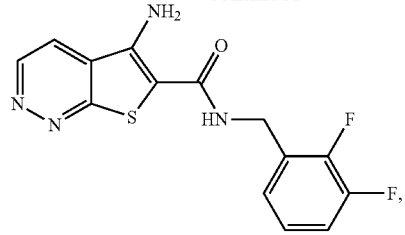
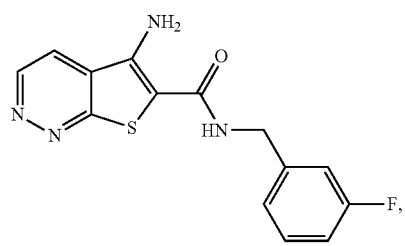
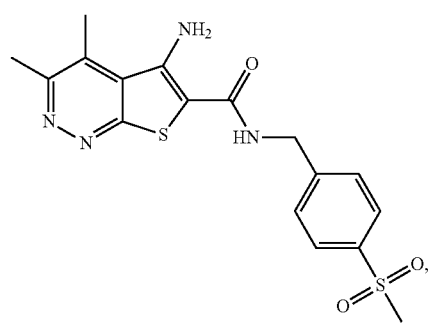
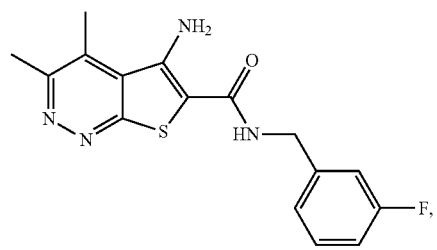
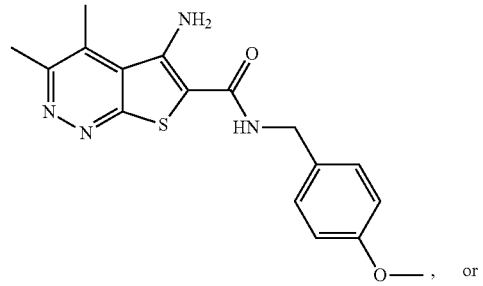 or
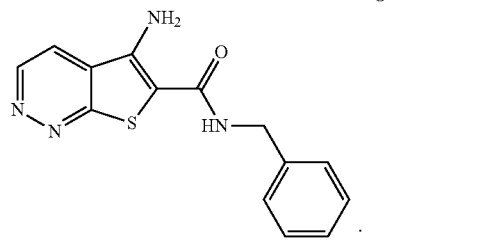
In one aspect, a compound can be present as one or more of the following structures:

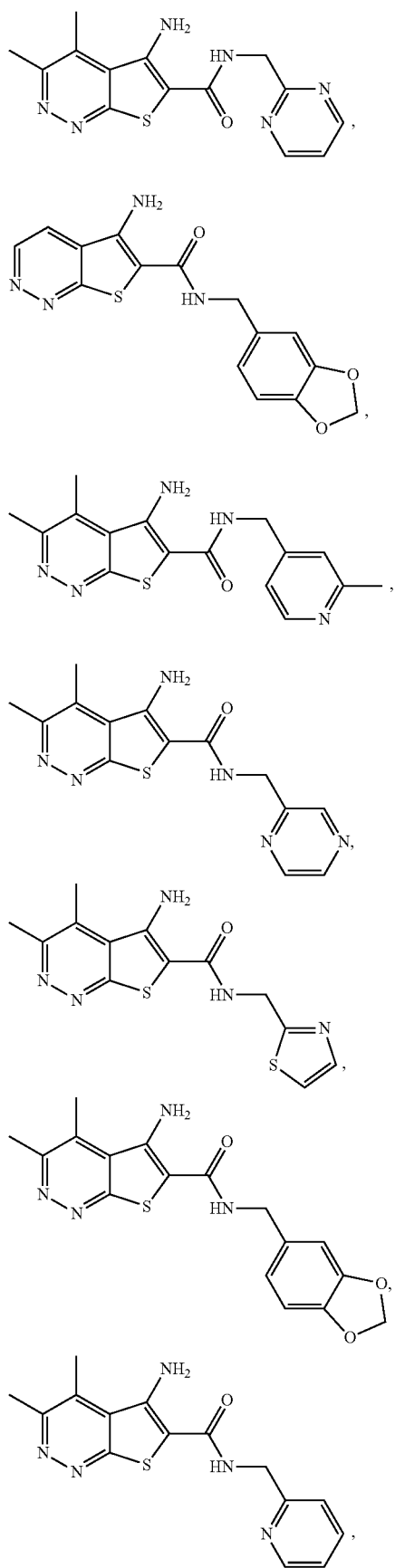
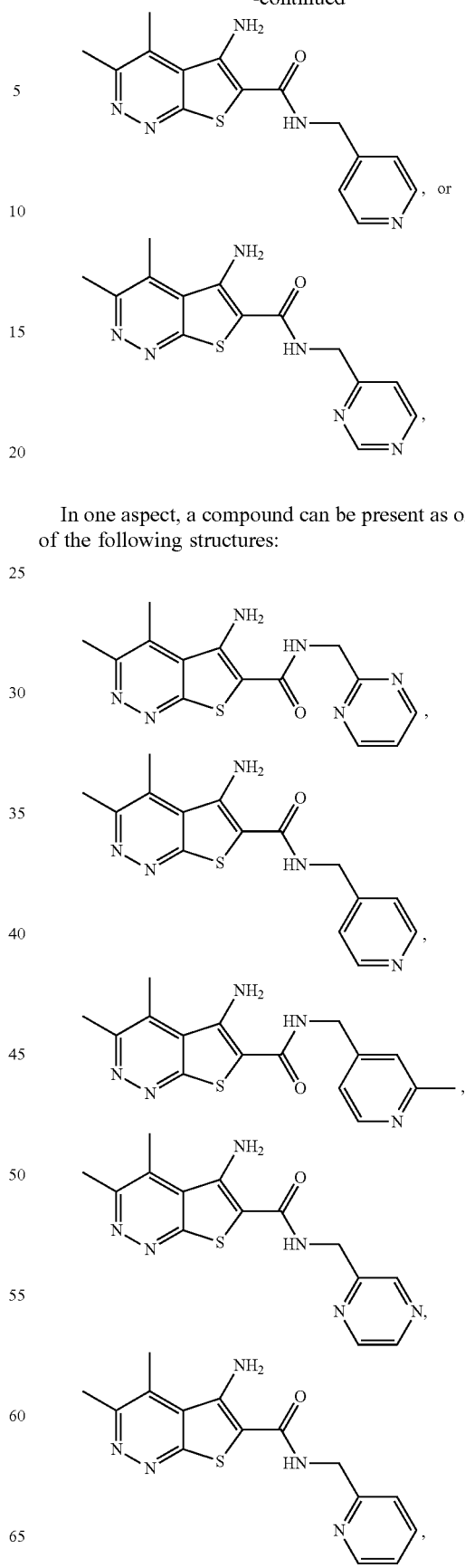
In one aspect, a compound can be present as one or more of the following structures:

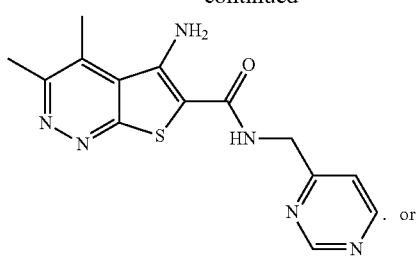
or
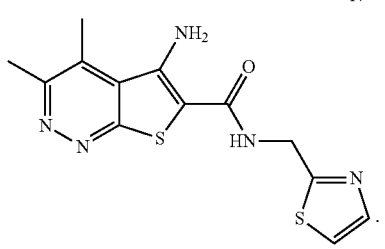
In one aspect, a compound can be present as one or more of the following structures:
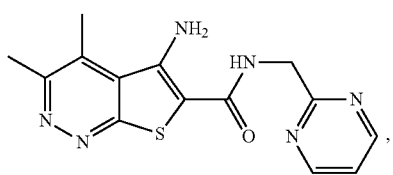
,
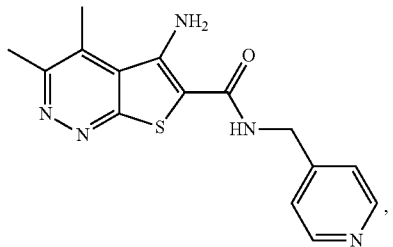
,
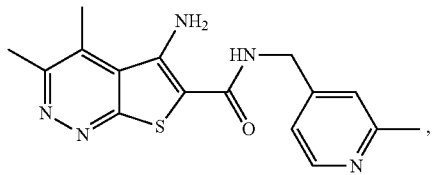
,
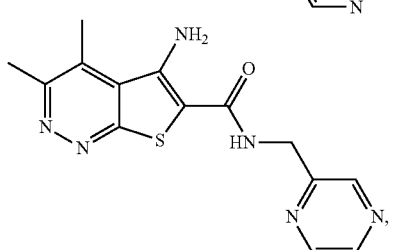
,
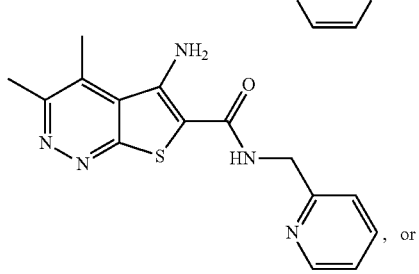
, or
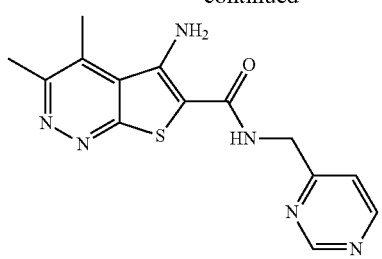
In one aspect, a compound can be present as one or more of the following structures:
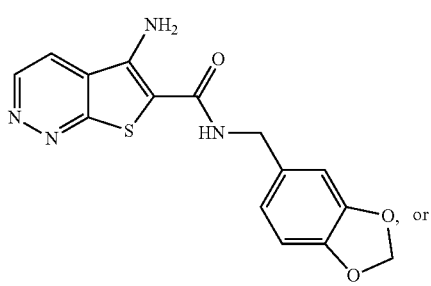
, or
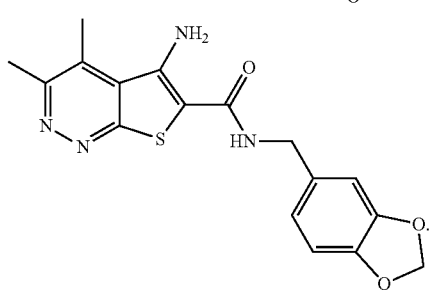
In one aspect, a compound can be present as one or more of the following structures:
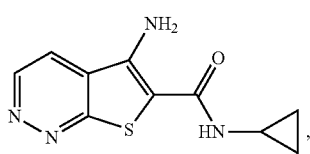
,
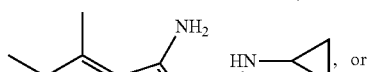
, or
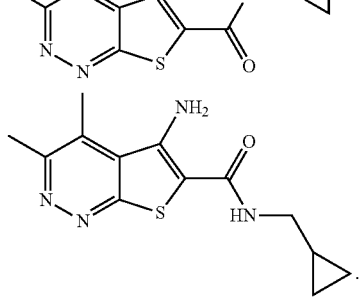
.
In one aspect, a compound can be present as one or more of the following structures:

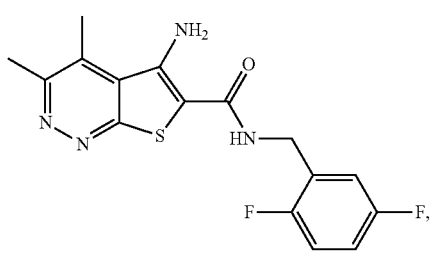
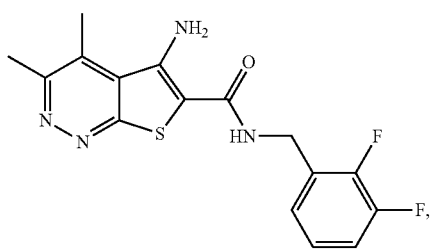
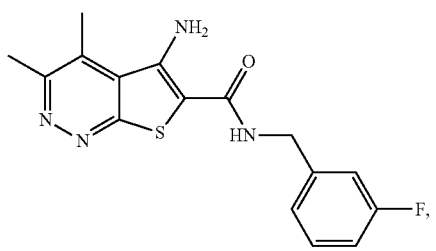
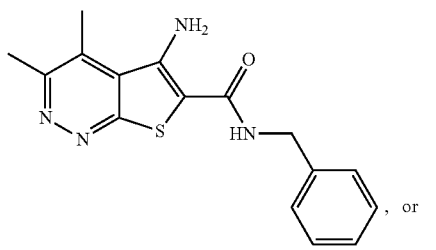, or
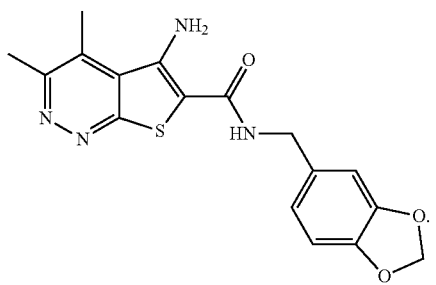
In one aspect, a compound can be present as one or more of the following structures:
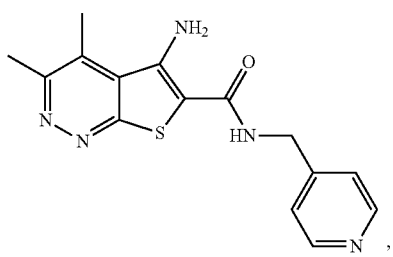
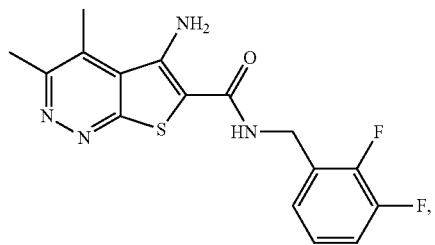
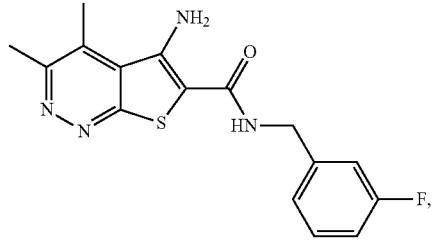
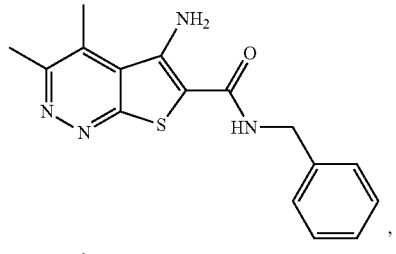
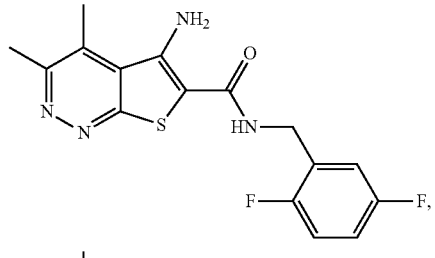
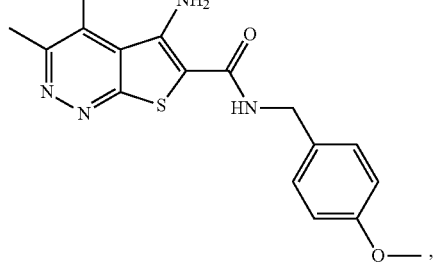
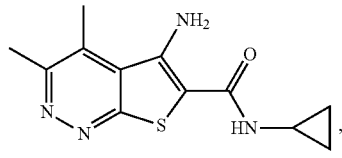
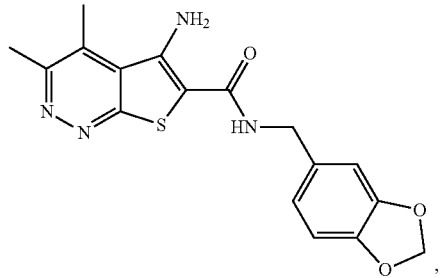

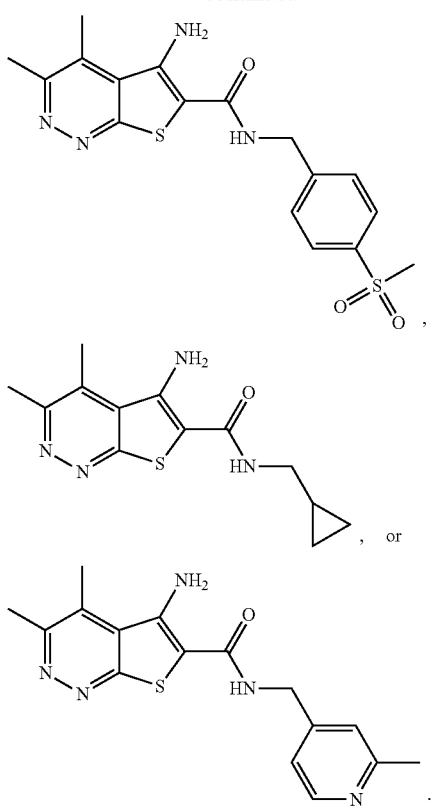
In one aspect, a compound can be present as one or more of the following structures:
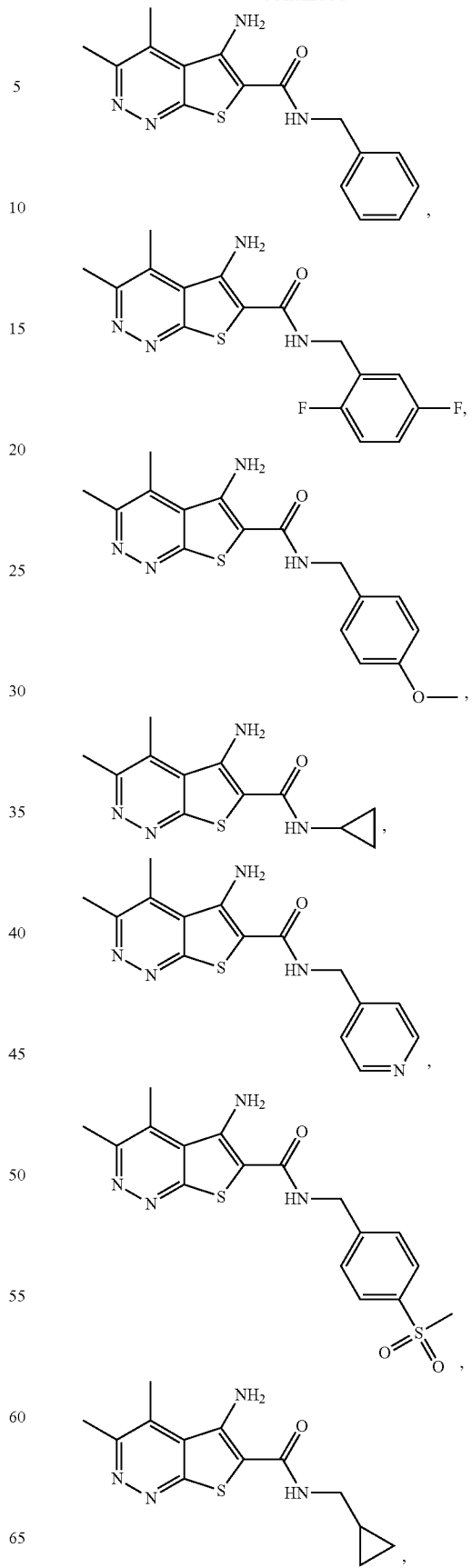

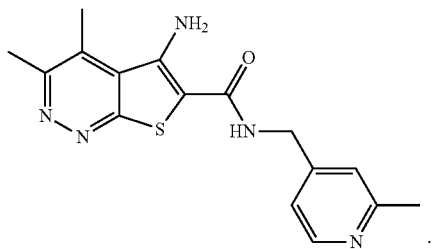
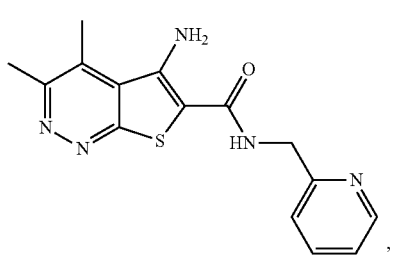
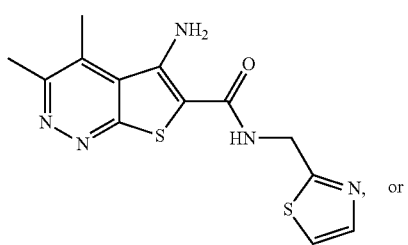 or
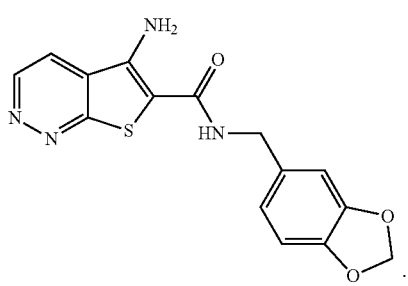 [SMILES: Nc1c(C(=O)NCc2ccc3c(c2)OCO3)sc2nnccc12]
In one aspect, a compound can be present as one or more of the following structures:
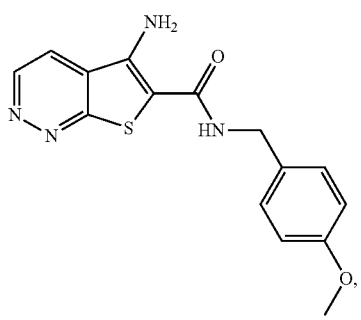
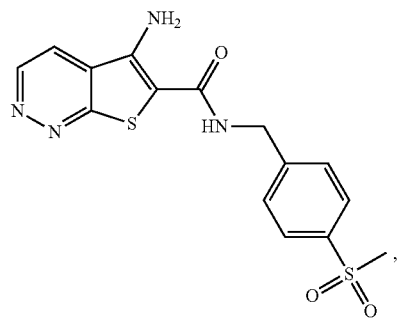
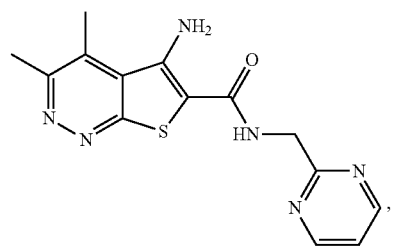
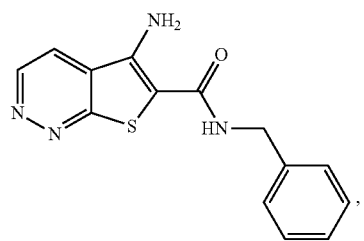
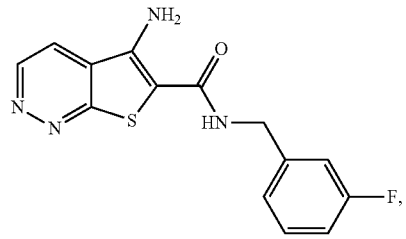
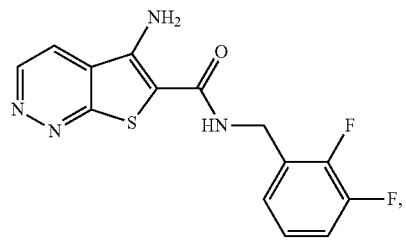
, or -continued
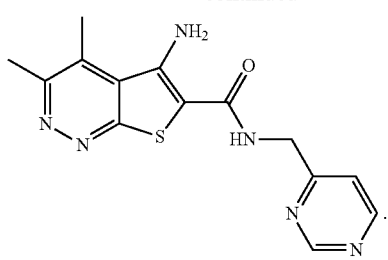
In one aspect, a compound can be present as one or more of the following structures:
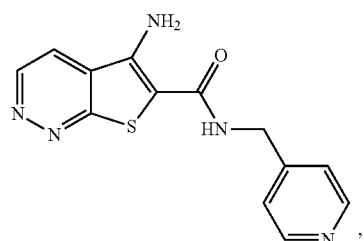
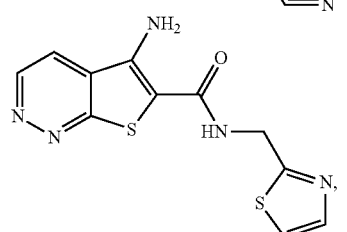
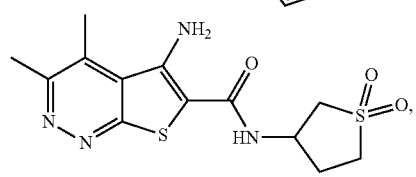
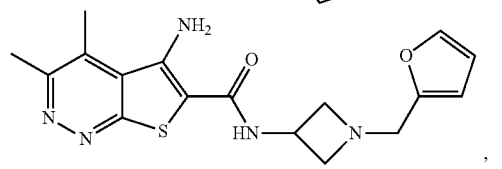
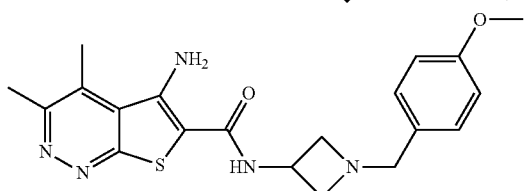
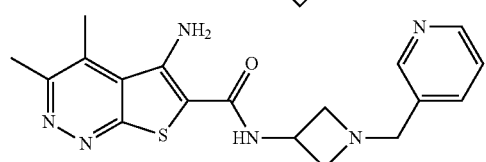
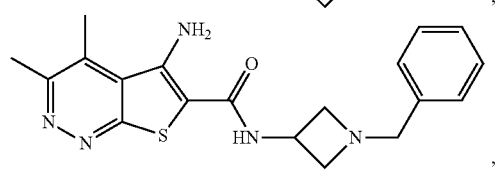
-continued
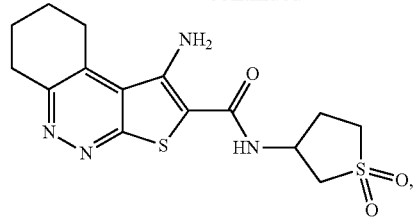
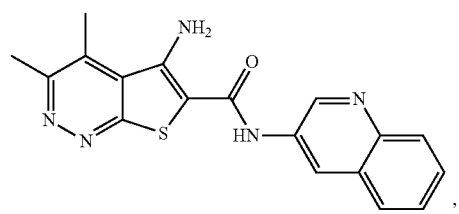
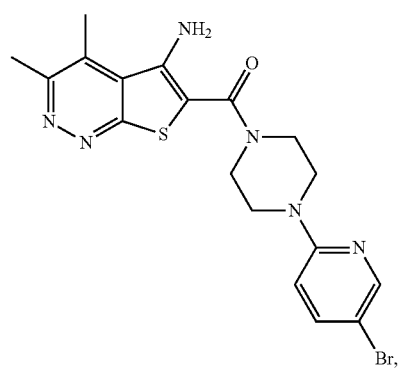
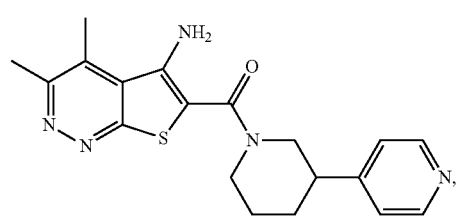
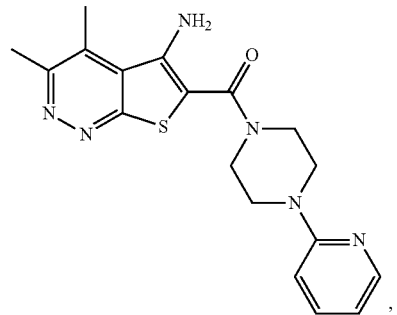
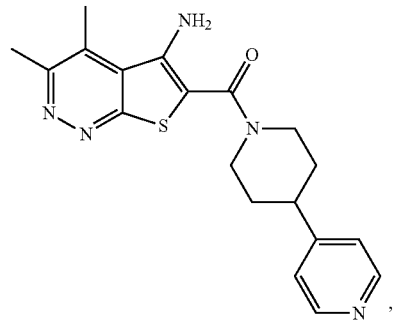

403
-continued
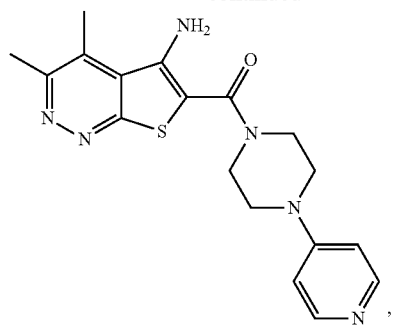,
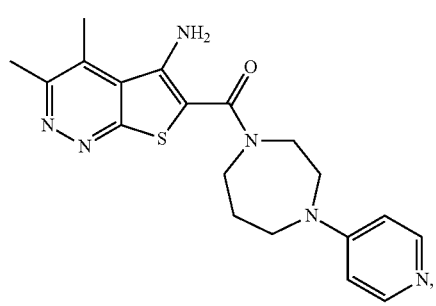,
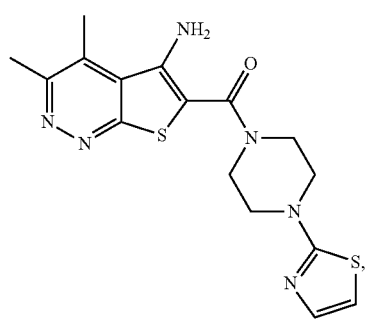,
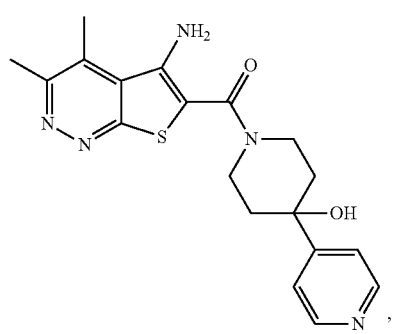,
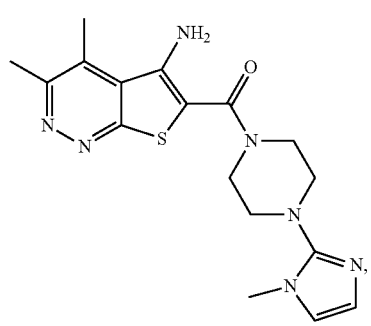,
404
-continued
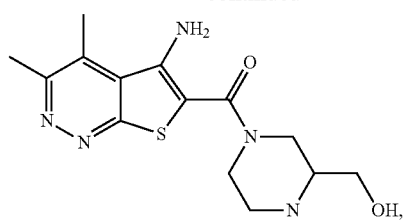,
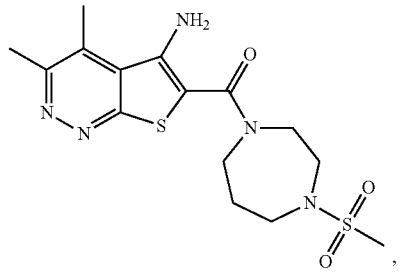,
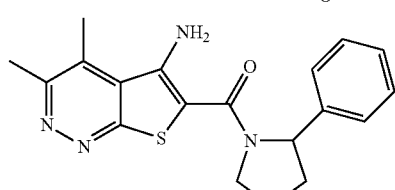,
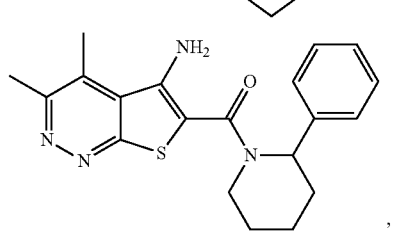,
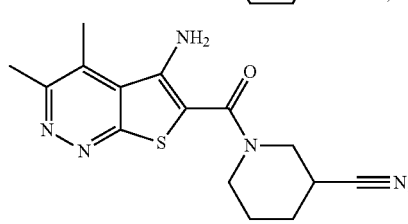, 405
-continued
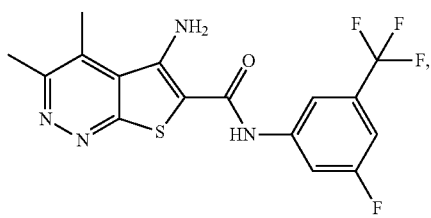
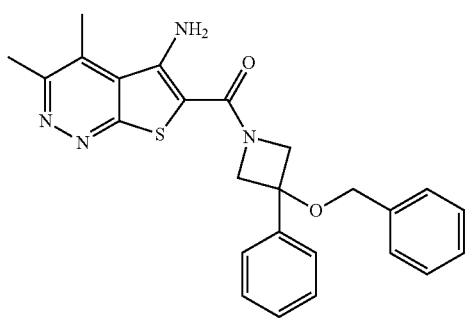
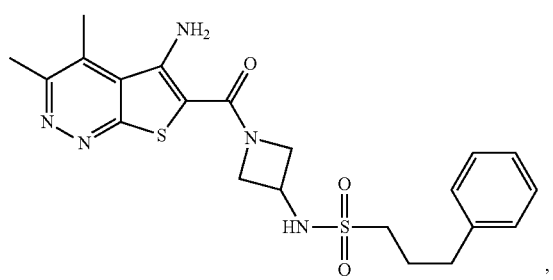
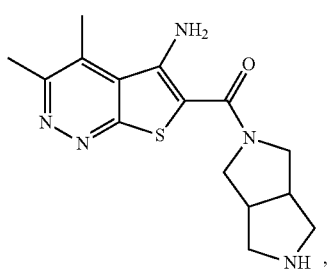
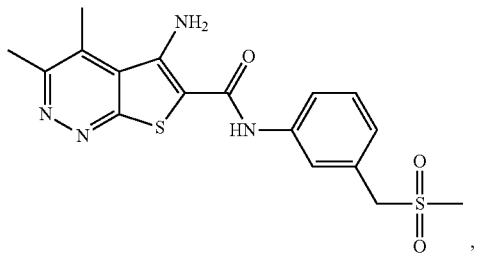
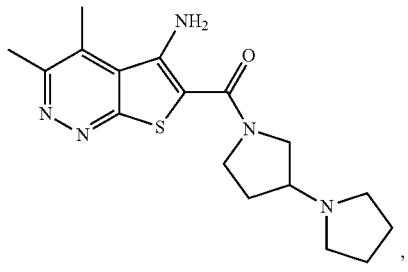
406
-continued
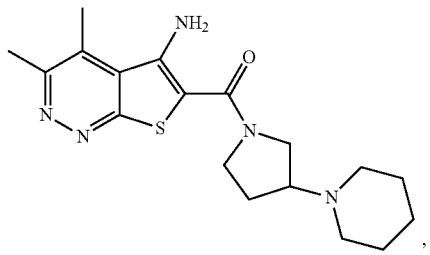
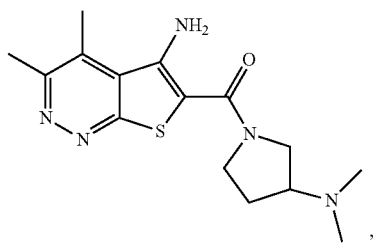
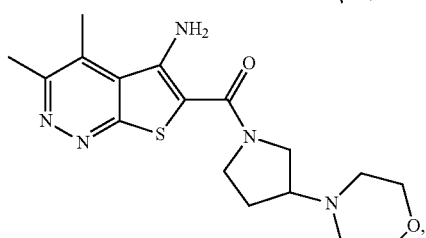
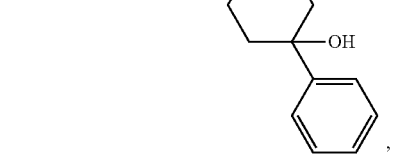
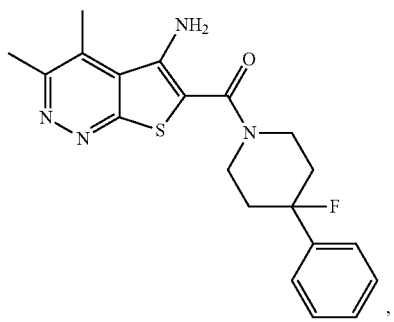
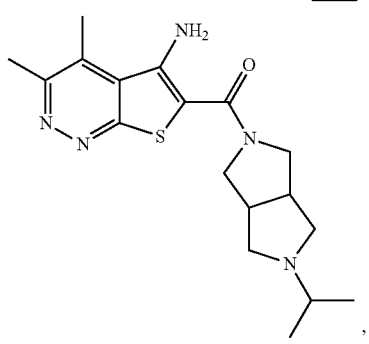

407
-continued
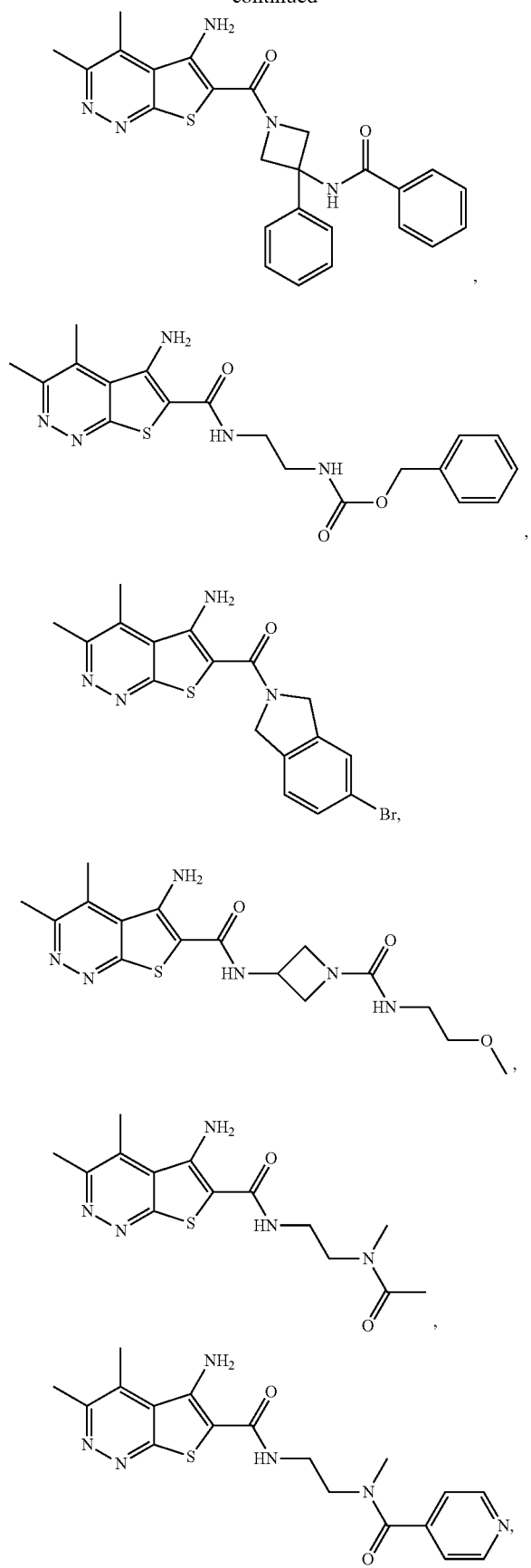
408
-continued
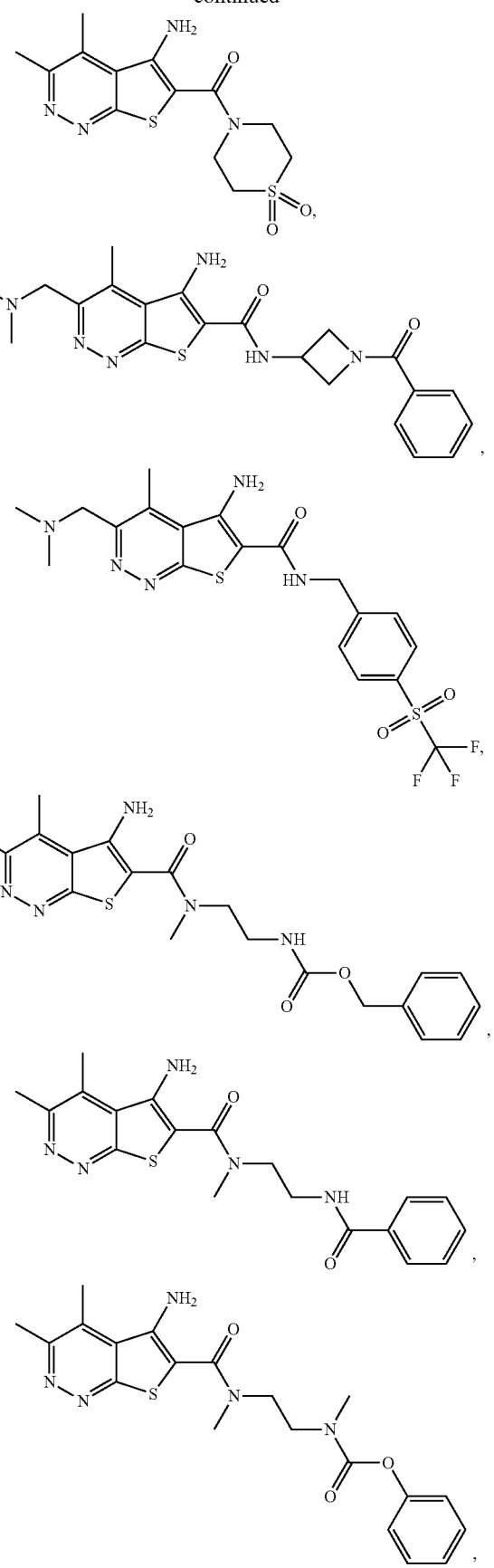

409
-continued

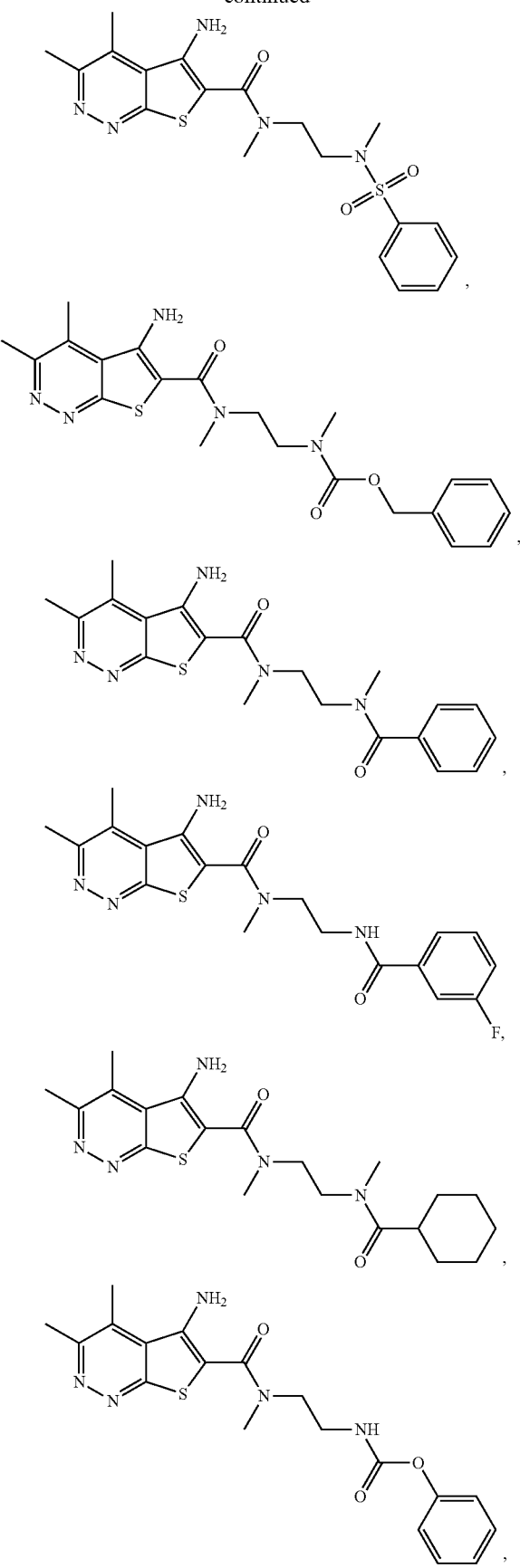

410
-continued

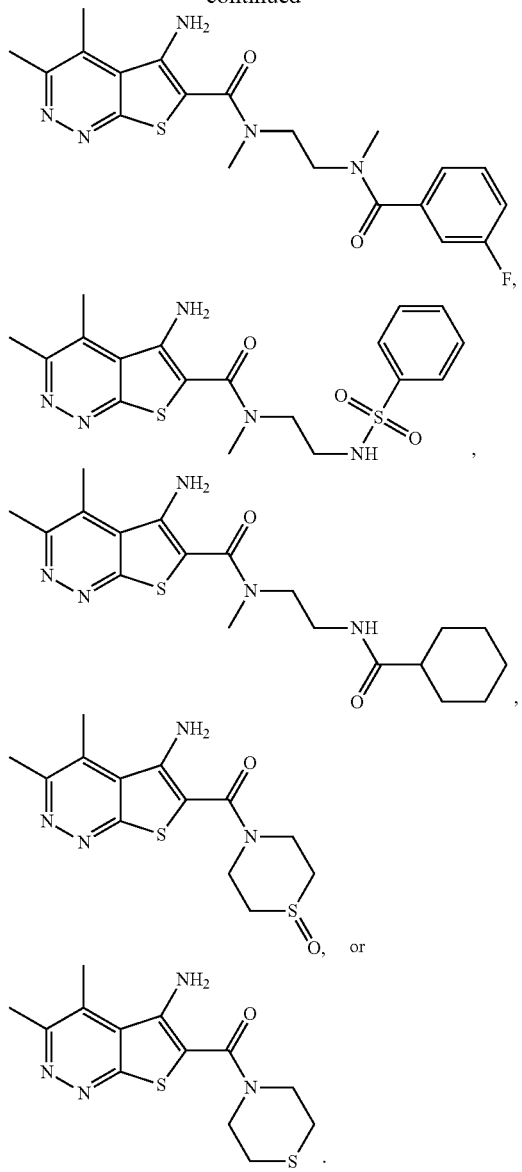

It is understood that the disclosed compounds can be used in connection with the disclosed methods, compositions, kits, and uses.

3. Muscarinic Acetylcholine Receptor $M_4$ Activity

The human muscarinic acetylcholine receptor $M_4$ (mAChR $M_4$) is a protein of 479 amino acids encoded by the CHRM4 gene. The molecular weight of the unglycosylated protein is about 54 kDa and it is a transmembrane GPCR. As described above, the mAChR $M_4$ is a member of the GPCR Class 1 family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face. A schematic of the structure of mAChR $M_4$ is shown in FIG. 1, with the transmembrane segments shown as cylindrical shapes (which span the lipid bilayer of the cell membrane). The orthosteric binding for natural ligand, acetylcholine, for mAChRs is within a pocket located in the transmembrane segments as depicted in FIG. 1.

In one aspect, the disclosed compounds potentiate the agonist response (e.g., acetylcholine) of mAChR $M_4$. In a further aspect, the disclosed compounds increase mAChR $M_4$ response to non-maximal concentrations of agonist in the presence of compound compared to the response to agonist in the absence of compound. The potentiation of mAChR $M_4$ activity, can be demonstrated by methodology known in the art. For example, activation of mAChR $M_4$ activity can be determined by measurement of calcium flux in response to agonist, e.g. acetylcholine, in cells loaded with a $Ca^{2+}$-sensitive fluorescent dye (e.g., Fluo-4). In a further aspect, the calcium flux was measured as an increase in fluorescent static ratio. In a yet further aspect, positive allosteric modulator activity was analyzed as a concentration-dependent increase in the $EC_{20}$ acetylcholine response (i.e. the response of mAChR $M_4$. at a concentration of acetylcholine that yields 20% of the maximal response).

In one aspect, the disclosed compounds activate mAChR $M_4$ response as an increase in calcium fluorescence in mAChR $M_4$-transfected CHO-K1 cells in the presence of the compound, compared to the response of equivalent CHO-K1 cells in the absence of the compound. In a further aspect, a disclosed compound activates the mAChR $M_4$ response with an $EC_{50}$ of less than about 10 µM, of less than about 5 µM, of less than about 1 µM, of less than about 500 nM, of less than about 100 nM, or of less than about 50 nM. In a further aspect, the mAChR $M_4$-transfected CHO-K1 cells are transfected with human mAChR $M_4$. In a still further aspect, the mAChR $M_4$-transfected CHO-K1 cells are transfected with rat mAChR $M_4$.

In one aspect, the disclosed compounds exhibit positive allosteric modulation of mAChR $M_4$ response to acetylcholine as an increase in response to non-maximal concentrations of acetylcholine in CHO-K1 cells transfected with a mAChR $M_4$ in the presence of the compound, compared to the response to acetylcholine in the absence of the compound. In a yet further aspect, the disclosed compounds exhibit positive allosteric modulation of the mAChR $M_4$ response to acetylcholine with an $EC_{50}$ of less than about 10,000 nM. In an even further aspect, the disclosed compounds exhibit positive allosteric modulation of the mAChR $M_4$ response to acetylcholine with an $EC_{50}$ of less than about 5,000 nM. In a still further aspect, the disclosed compounds exhibit positive allosteric modulation of the mAChR $M_4$ response to acetylcholine with an $EC_{50}$ of less than about 1,000 nM. In a yet further aspect, the disclosed compounds exhibit positive allosteric modulation of the mAChR $M_4$ response to acetylcholine with an $EC_{50}$ of less than about 500 nM. In an even further aspect, the disclosed compounds exhibit positive allosteric modulation of the mAChR $M_4$ response to acetylcholine with an $EC_{50}$ of less than about 100 nM. In a still further aspect, the $EC_{50}$ for positive allosteric modulation is determined in CHO-K1 cells are transfected with a mAChR $M_4$. In a yet further aspect, the mAChR $M_4$ transfected human mAChR $M_4$. In a still further aspect, the mAChR $M_4$ transfected rat mAChR $M_4$.

Without wishing to be bound by a particular theory, the disclosed compounds and products of the disclosed methods are believed to bind to an allosteric site distinct from the orthosteric binding site. Further, without wishing to be bound by particular theory, the disclosed compounds and products of the disclosed methods bind to an allosteric site that comprises portions of one or more extracellular loops and transmembrane segments distinct from the orthosteric binding site. For example, a disclosed compound can bind at the binding site as illustrated in FIG. 1.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved.

In various further aspects, the compound activates mAChR $M_4$ response in mAChR $M_4$-transfected CHO-K1 cells with an $EC_{50}$ less than the $EC_{50}$ for one or more of mAChR $M_1$, $M_2$, $M_3$ or $M_5$-transfected CHO-K1 cells That is, a disclosed compound can have selectivity for the mAChR $M_4$ receptor vis-à-vis one or more of the mAChR $M_1$, $M_2$, $M_3$ or $M_5$ receptors. For example, in one aspect, a disclosed compound can activate mAChR $M_4$ response with an $EC_{50}$ of about 5-fold less than that for mAChR $M_1$, of about 10-fold less than that for mAChR $M_1$, of about 20-fold less than that for mAChR $M_1$, of about 30-fold less than that for mAChR $M_1$, of about 50-fold less than that for mAChR $M_1$, of about 100-fold less than that for mAChR $M_1$, of about 200-fold less than that for mAChR $M_1$, of about 300-fold less than that for mAChR $M_1$, of about 400-fold less than that for mAChR $M_1$, or greater than about 500-fold less than that for mAChR $M_1$. In a further aspect, a disclosed compound can activate mAChR $M_4$ response with an $EC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, of about 50-fold less than that for mAChR $M_2$, of about 100-fold less than that for mAChR $M_2$, of about 200-fold less than that for mAChR $M_2$, of about 300-fold less than that for mAChR $M_2$, of about 400-fold less than that for mAChR $M_2$, or greater than about 500-fold less than that for mAChR $M_2$. In a further aspect, a disclosed compound can activate mAChR $M_4$ response with an $EC_{50}$ of about 5-fold less than that for mAChR $M_3$, of about 10-fold less than that for mAChR $M_3$, of about 20-fold less than that for mAChR $M_3$, of about 30-fold less than that for mAChR $M_3$, of about 50-fold less than that for mAChR $M_3$, of about 100-fold less than that for mAChR $M_3$, of about 200-fold less than that for mAChR $M_3$, of about 300-fold less than that for mAChR $M_3$, of about 400-fold less than that for mAChR $M_3$, or greater than about 500-fold less than that for mAChR $M_3$. In a further aspect, a disclosed compound can activate mAChR $M_4$ response with an $EC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, of about 50-fold less than that for mAChR $M_5$, of about 100-fold less than that for mAChR $M_5$, of about 200-fold less than that for mAChR $M_5$, of about 300-fold less than that for mAChR $M_5$, of about 400-fold less than that for mAChR $M_5$, or greater than about 500-fold less than that for mAChR $M_5$. In a further aspect, a disclosed compound can activate mAChR $M_4$ response with an $EC_{50}$ of 5-fold less than that for the mAChR $M_1$, $M_2$, $M_3$, or $M_5$ receptors, of about 10-fold less than that for the mAChR $M_1$, $M_2$, $M_3$, or $M_5$ receptors, of about 20-fold less than that for the mAChR $M_1$, $M_2$, $M_3$, or $M_5$ receptors, of about 30-fold less than that for the $M_2$-$M_5$ receptors, of about 50-fold less than that for the mAChR $M_1$, $M_2$, $M_3$, or $M_5$ receptors, of about 100-fold less than that for the mAChR $M_1$, $M_2$, $M_3$, or $M_5$ receptors, of about 200-fold less than that for the mAChR $M_1$, $M_2$, $M_3$, or $M_5$ receptors, of about 300-fold less than that for the mAChR $M_1$, $M_2$, $M_3$, or $M_5$ receptors, of about 400-fold less than that for the mAChR $M_1$, $M_2$, $M_3$, or $M_5$ receptors, or greater than about 500-fold less than that for the mAChR $M_1$, $M_2$, $M_3$, or $M_5$ receptors.

In various further aspects, the compound activates mAChR $M_4$ response in $M_1$-transfected CHO-K1 cells with an $EC_{50}$ of less than about 10 µM and exhibits a selectivity for the $M_1$ receptor vis-à-vis one or more of the mAChR $M_1$, $M_2$, $M_3$, or $M_5$ receptors. For example, in one aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_1$, of about 10-fold less than that for mAChR $M_1$, of about 20-fold less than that for mAChR $M_1$, of about 30-fold less than that for mAChR $M_1$, of about 50-fold less than that for mAChR $M_1$, of about 100-fold less than that for mAChR $M_1$, of about 200-fold less than that for mAChR $M_1$, of about 300-fold less than that for mAChR $M_1$, of about 400-fold less than that for mAChR $M_1$, or greater than about 500-fold less than that for mAChR $M_1$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, of about 50-fold less than that for mAChR $M_2$, of about 100-fold less than that for mAChR $M_2$, of about 200-fold less than that for mAChR $M_2$, of about 300-fold less than that for mAChR $M_2$, of about 400-fold less than that for mAChR $M_2$, or greater than about 500-fold less than that for mAChR $M_2$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_3$, of about 10-fold less than that for mAChR $M_3$, of about 20-fold less than that for mAChR $M_3$, of about 30-fold less than that for mAChR $M_3$, of about 50-fold less than that for mAChR $M_3$, of about 100-fold less than that for mAChR $M_3$, of about 200-fold less than that for mAChR $M_3$, of about 300-fold less than that for mAChR $M_3$, of about 400-fold less than that for mAChR $M_3$, or greater than about 500-fold less than that for mAChR $M_3$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, of about 50-fold less than that for mAChR $M_5$, of about 100-fold less than that for mAChR $M_5$, of about 200-fold less than that for mAChR $M_5$, of about 300-fold less than that for mAChR $M_5$, of about 400-fold less than that for mAChR $M_5$, or greater than about 500-fold less than that for mAChR $M_5$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with $EC_{50}$ of 5-fold less than that for the mAChR $M_1$, $M_2$, $M_3$, or $M_5$ receptors, of about 10-fold less than that for the mAChR $M_1$, $M_2$, $M_3$, or $M_5$ receptors, of about 20-fold less than that for the mAChR $M_1$, $M_2$, $M_3$, or $M_5$ receptors, of about 30-fold less than that for the $M_2$-$M_5$ receptors, of about 50-fold less than that for the mAChR $M_1$, $M_2$, $M_3$, or $M_5$ receptors, of about 100-fold less than that for the mAChR $M_1$, $M_2$, $M_3$, or $M_5$ receptors, of about 200-fold less than that for the mAChR $M_1$, $M_2$, $M_3$, or $M_5$ receptors, of about 300-fold less than that for the mAChR $M_1$, $M_2$, $M_3$, or $M_5$ receptors, of about 400-fold less than that for the mAChR $M_1$, $M_2$, $M_3$, or $M_5$ receptors, or greater than about 500-fold less than that for the mAChR $M_1$, $M_2$, $M_3$, or $M_5$ receptors.

In vivo efficacy for disclosed compounds can be measured in a number of preclinical rat behavioral models where known, clinically useful antipsychotics display similar positive responses. For example, disclosed compounds are anticipated to reverse amphetamine-induced hyperlocomotion in male Sprague-Dawley rats at doses ranging from 1 to 100 mg/kg p.o.

C. Methods of Making the Compounds

In one aspect, the invention relates to methods of making compounds useful as positive allosteric activators of the mAChR $M_4$ receptor, which can be useful in the treatment neurological and psychiatric disorders associated with muscarinic acetylcholine dysfunction and other diseases in which muscarinic acetylcholine receptors are involved. In one aspect, the invention relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, substituted 5-aminothieno[2,3-c]pyridazine-6-carboxamide analogs of the present invention can be prepared generically by the synthetic scheme as shown below.

SCHEME 1A

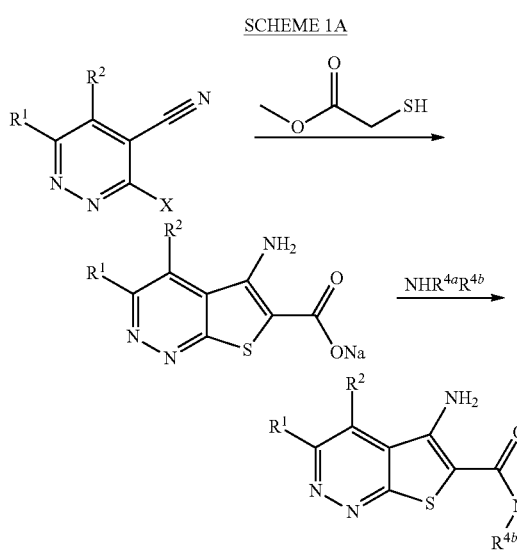

Compounds are represented in generic form, with substituents as noted in compound descriptions elsewhere herein. A more specific example is set forth below.

SCHEME 1B

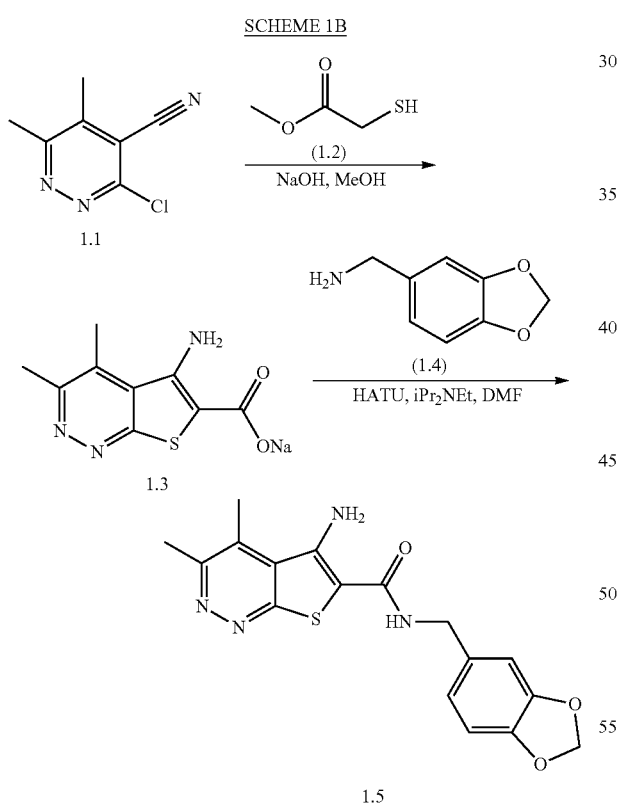

In one aspect, compounds of the present invention, e.g. compounds of Formula (1.5) and other substituted 5-aminothieno[2,3-c]pyridazine-6-carboxamide analogs, can be prepared according to Scheme 1B as shown above beginning with a compound of Formula (1.1) and subsequent reaction steps as outlined. Compounds of Formula (1.3) can be prepared by reaction of compounds of Formula (1.1), i.e. a 3-halo-4-carbonitrile derivative of pyridazine, and compounds of Formula (1.2), i.e. a thioglycolate, in the presence of an appropriate base, e.g. sodium hydroxide, and an appropriate solvent, e.g. methanol, and heated at an appropriate temperature, e.g. microwave heating at about 150° C., until the reaction is completed, e.g. about 30-90 min. Compounds of Formula (1.5) can be prepared by reaction of compounds of Formula (1.3), i.e. a substituted thieno[2,3-c]pyridazine-6-carboxylate, and compounds of Formula (1.4), i.e. a heterocyclyl, in the presence of Hünig's base and O-(7-azabenzotriazol-1-yl)-N,N,N',N'-tetramethyluronium hexafluorophosphate (HATU) reacting at an appropriate temperature, e.g. ambient temperature or about 15° C. to about 30° C., until the reaction is completed, e.g. about 60-180 min. As can be appreciated by one skilled in the art, the above reaction provides an example of a generalized approach wherein compounds similar in structure to the specific reactants illustrated above, i.e. compounds of Formulas (1.1), (1.2), (1.3) and (1.4), and appropriate reagents, can be substituted in the reaction to provide substituted 5-aminothieno[2,3-c]pyridazine-6-carboxamide analogs similar to Formula (1.5).

2. Route II

In one aspect, substituted analogs of the present invention can be prepared generically by the synthetic scheme as shown below.

SCHEME 2A

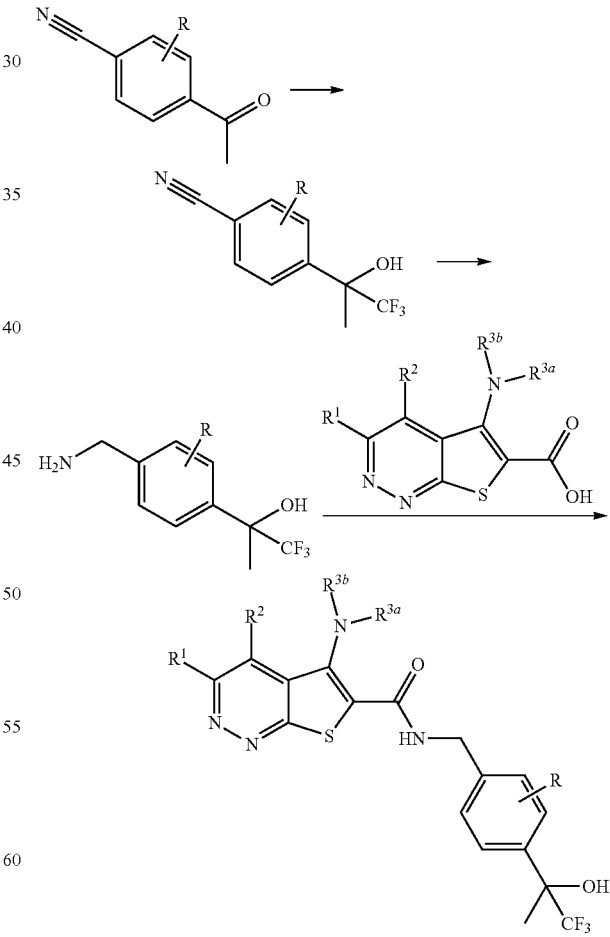

Compounds are represented in generic form, with substituents as noted in compound descriptions elsewhere herein. A more specific example is set forth below.

SCHEME 2B

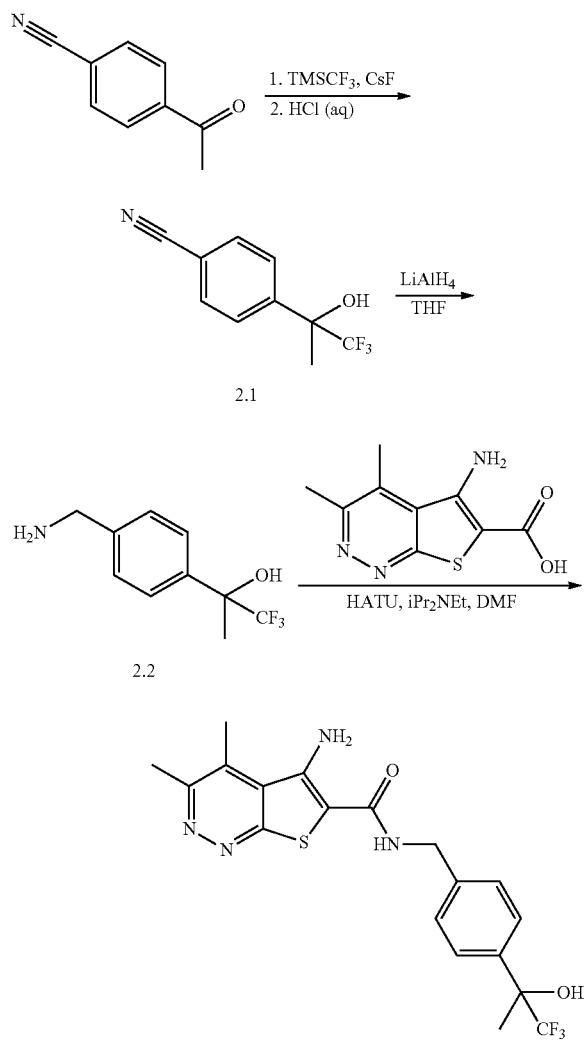

Example 2
(Compound B106, Table I)

In one aspect, compounds of the present invention, e.g. compounds of Formula (2) and other substituted analogs, can be prepared according to Scheme 2b as shown above beginning with an optionally substituted 4-acetylbenzonitrile and subsequent reaction steps as outlined. Addition reaction at the carbonyl to provide the corresponding alcohol, followed by reduction of the nitrile to yield the optionally substituted benzyl amine, produces a compound of Formula (2.2), which can be used in a amidation reaction with a compound of Formula (1.3), or an analog thereof, to form the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

3. Route III

In one aspect, substituted analogs of the present invention can be prepared generically by the synthetic scheme as shown below.

SCHEME 3A

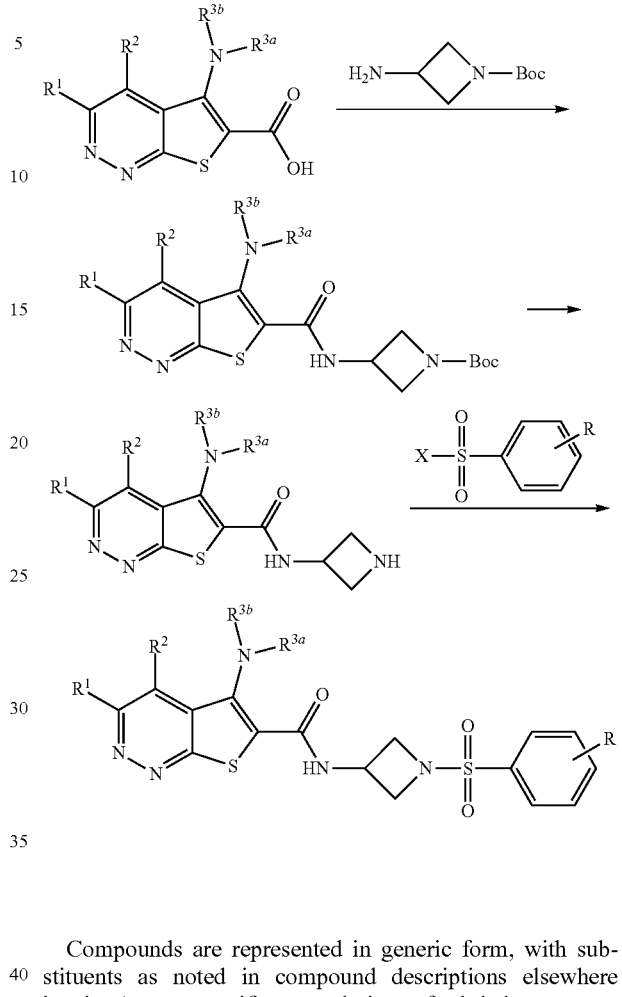

Compounds are represented in generic form, with substituents as noted in compound descriptions elsewhere herein. A more specific example is set forth below.

SCHEME 3B

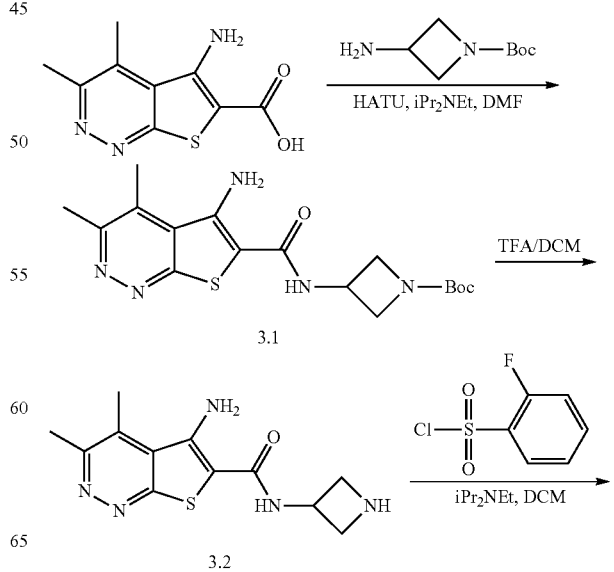

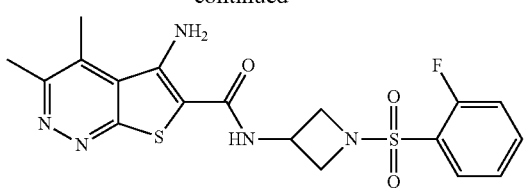

Example 3
(Compound B140, Table I)

In one aspect, compounds of the present invention, e.g. compounds of Formula (3) and other substituted analogs, can be prepared according to Scheme 3b as shown above beginning with a compound of Formula (1.3), or an analog thereof, and subsequent reaction steps as outlined. For example, amidation with a protected azetidin-3-amine, followed by deprotection, yields a compound of Formula (3.2), which can be reacted with an optionally substituted sulfonyl halide to provide a compound of Formula (3), or analog thereof.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

4. Route IV

In one aspect, substituted analogs of the present invention can be prepared generically by the synthetic scheme as shown below.

SCHEME 4A

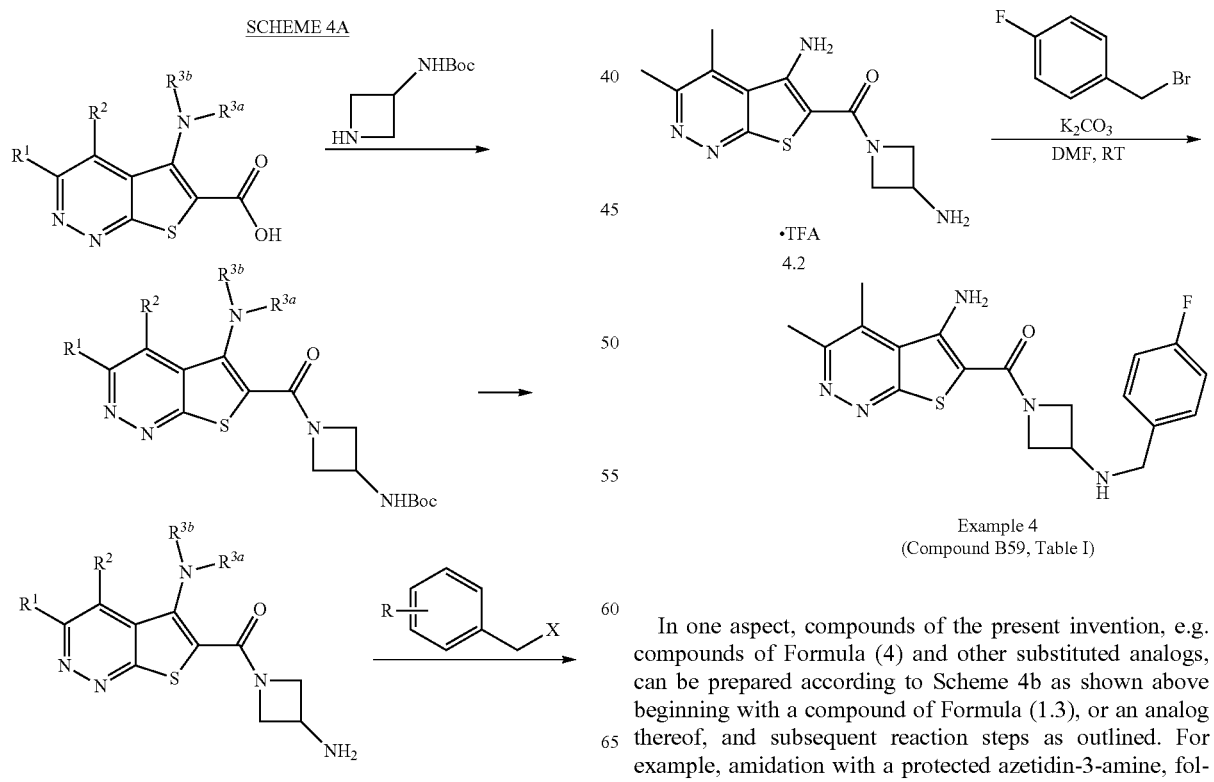

Compounds are represented in generic form, with substituents as noted in compound descriptions elsewhere herein. A more specific example is set forth below.

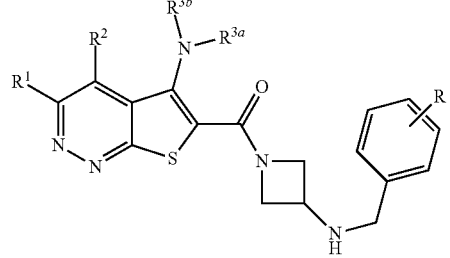

SCHEME 4B

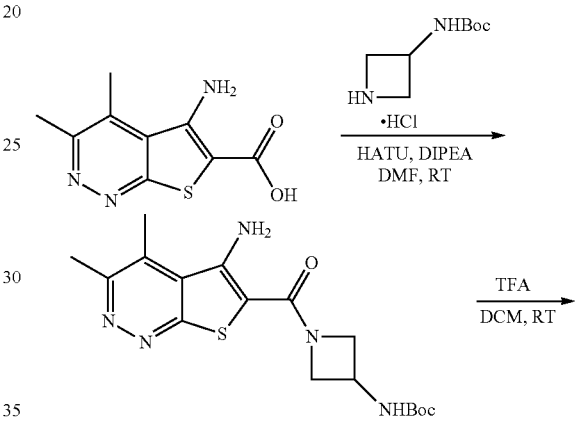

Example 4
(Compound B59, Table I)

In one aspect, compounds of the present invention, e.g. compounds of Formula (4) and other substituted analogs, can be prepared according to Scheme 4b as shown above beginning with a compound of Formula (1.3), or an analog thereof, and subsequent reaction steps as outlined. For example, amidation with a protected azetidin-3-amine, followed by deprotection, yields a compound of Formula (4.2), which can be reacted with an optionally substituted benzyl halide to provide a compound of Formula (4), or analog thereof.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

5. Route V

In one aspect, substituted analogs of the present invention can be prepared generically by the synthetic scheme as shown below.

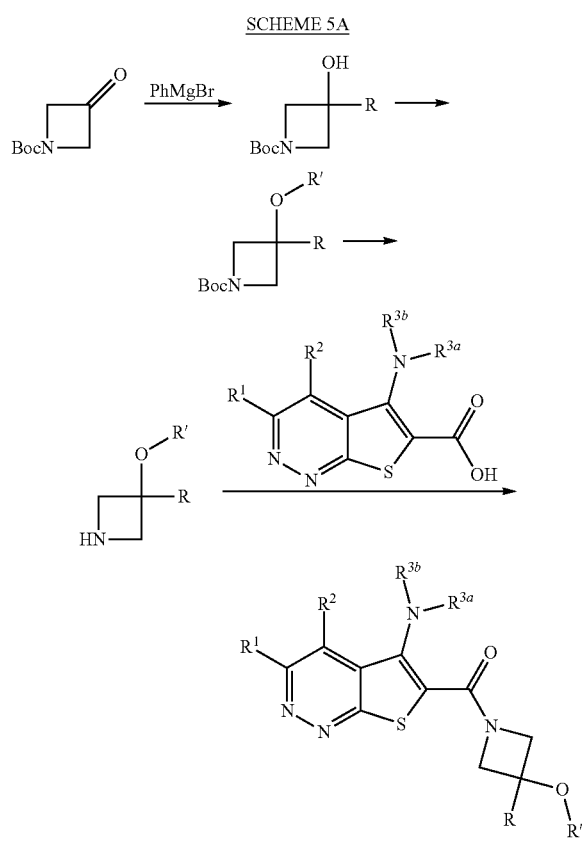

Compounds are represented in generic form, with substituents as noted in compound descriptions elsewhere herein. A more specific example is set forth below.

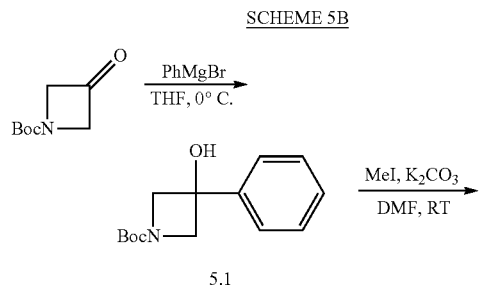

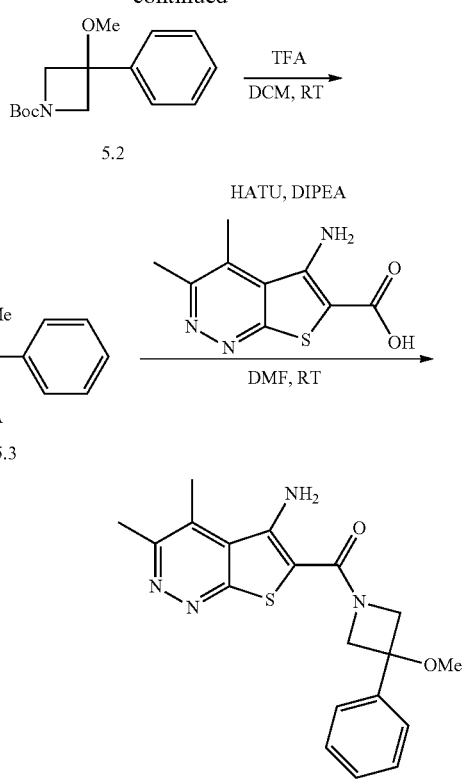

Example 5
(Compound B170, Table I)

In one aspect, compounds of the present invention, e.g. compounds of Formula (5) and other substituted analogs, can be prepared according to Scheme 5b as shown above beginning with a protected azetidin-3-one and subsequent reaction steps as outlined. For example, addition to the carbonyl of the protected azetidin-3-one, with e.g. an alkyl or aryl Grignard reagent, provides the corresponding alcohol, which can be subsequently alkylated to provide the corresponding ether. Deprotection and reaction with a compound of Formula (1.3), or an analog thereof, can produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

6. Route VI

In one aspect, substituted analogs of the present invention can be prepared generically by the synthetic scheme as shown below.

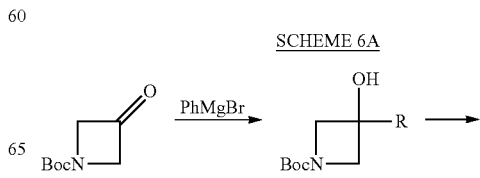

-continued

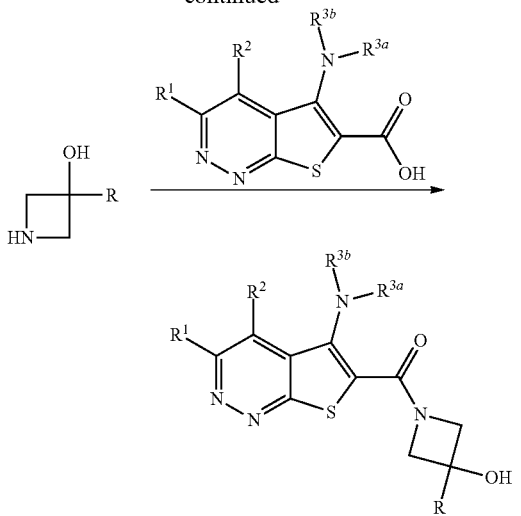

Compounds are represented in generic form, with substituents as noted in compound descriptions elsewhere herein. A more specific example is set forth below.

SCHEME 6B

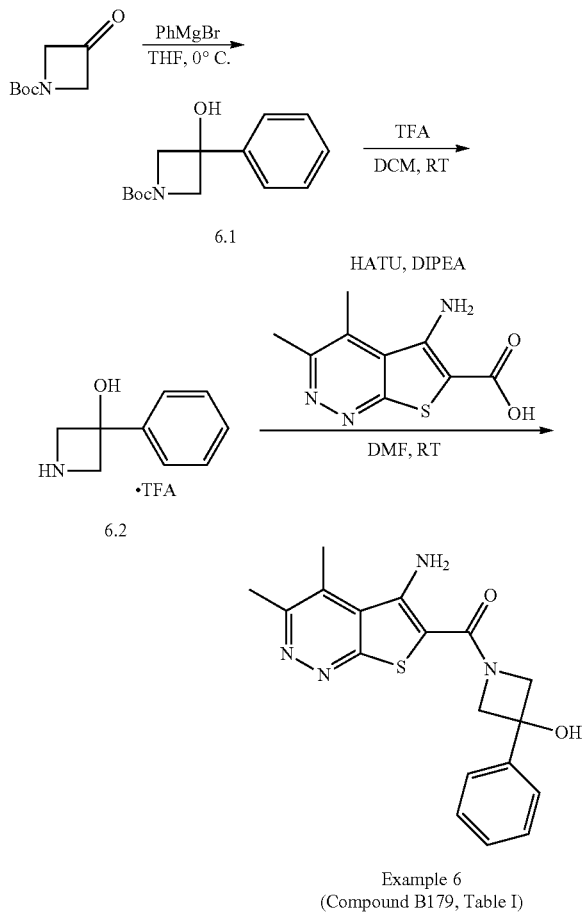

Example 6
(Compound B179, Table I)

In one aspect, compounds of the present invention, e.g. compounds of Formula (6) and other substituted analogs, can be prepared according to Scheme 6b as shown above beginning with a protected azetidin-3-one and subsequent reaction steps as outlined. For example, addition to the carbonyl of the protected azetidin-3-one, with e.g. an alkyl or aryl Grignard reagent, provides the corresponding alcohol. Deprotection and reaction with a compound of Formula (1.3), or an analog thereof, can produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

7. Route VII

In one aspect, substituted analogs of the present invention can be prepared generically by the synthetic scheme as shown below.

SCHEME 7A

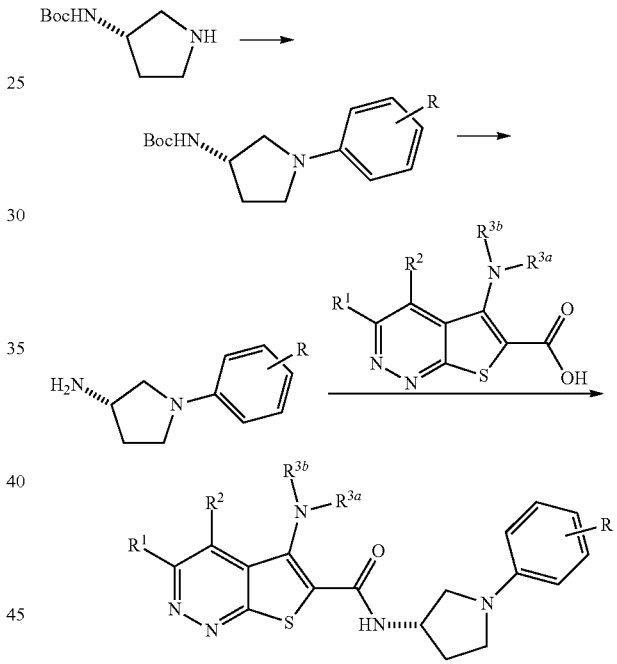

Compounds are represented in generic form, with substituents as noted in compound descriptions elsewhere herein. A more specific example is set forth below.

SCHEME 7B

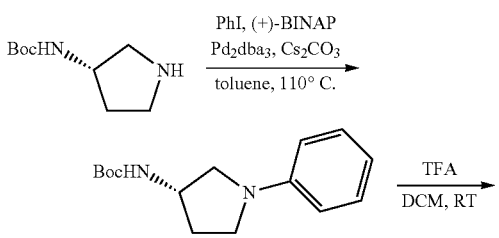

7.1

-continued

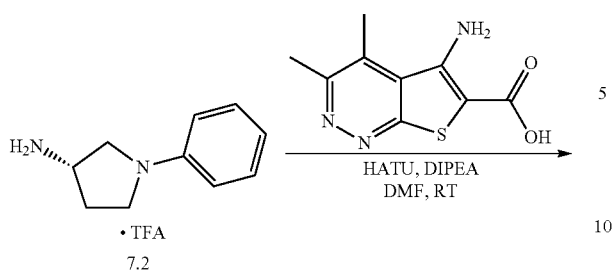

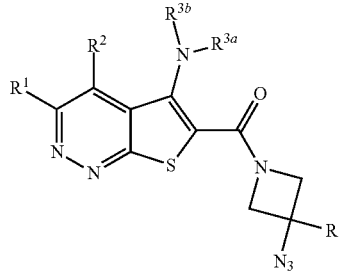

Compounds are represented in generic form, with substituents as noted in compound descriptions elsewhere herein. A more specific example is set forth below.

SCHEME 8B

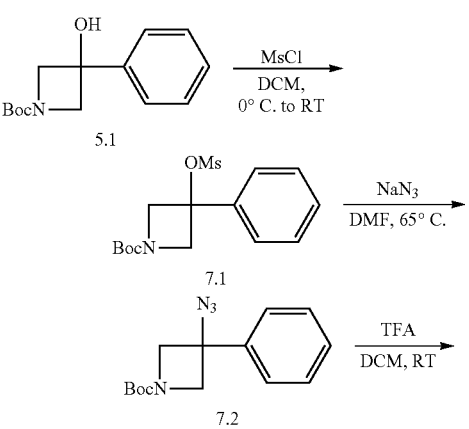

Example 7
(Compound B193, Table I)

In one aspect, compounds of the present invention, e.g. compounds of Formula (7) and other substituted analogs, can be prepared according to Scheme 7b as shown above beginning with an optionally substituted, protected, chiral pyrrolidin-3-amine and subsequent reaction steps as outlined. For example, arylation by metal-mediated coupling of an optionally substituted aryl or heteroaryl halide, optionally in the presence of a chiral catalyst such as BINAP, followed by deprotection and reaction with a compound of Formula (1.3), or an analog thereof, can produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

8. Route VIII

In one aspect, substituted analogs of the present invention can be prepared generically by the synthetic scheme as shown below.

SCHEME 8A

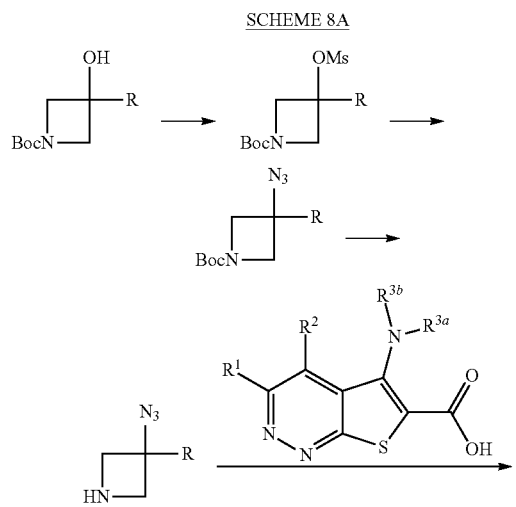

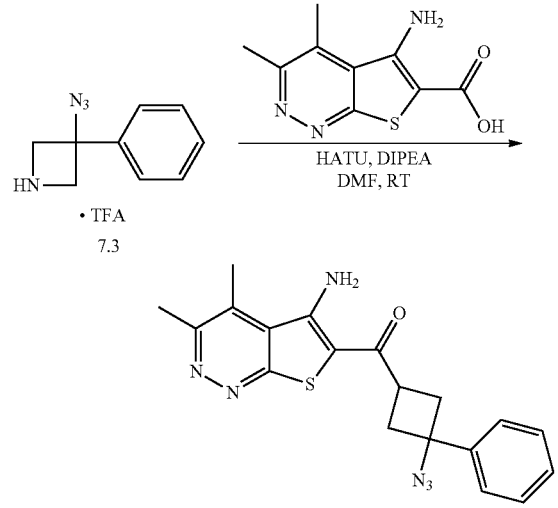

Example 8
(Compound B311, Table I)

In one aspect, compounds of the present invention, e.g. compounds of Formula (8) and other substituted analogs, can be prepared according to Scheme 8b as shown above beginning with an amine-protected 3-substituted azetidin-3-ol (which can be prepared as described above) and subsequent reaction steps as outlined. For example, conversion of the hydroxyl functionality to a psuedohalide, followed by substitution with azide, provides the corresponding amine-protected 3-azido-3-substituted azetidine. This compound can then be subsequently deprotected and reacted with a compound of Formula (1.3), or an analog thereof, can produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

9. Route IX

In one aspect, substituted analogs of the present invention can be prepared generically by the synthetic scheme as shown below.

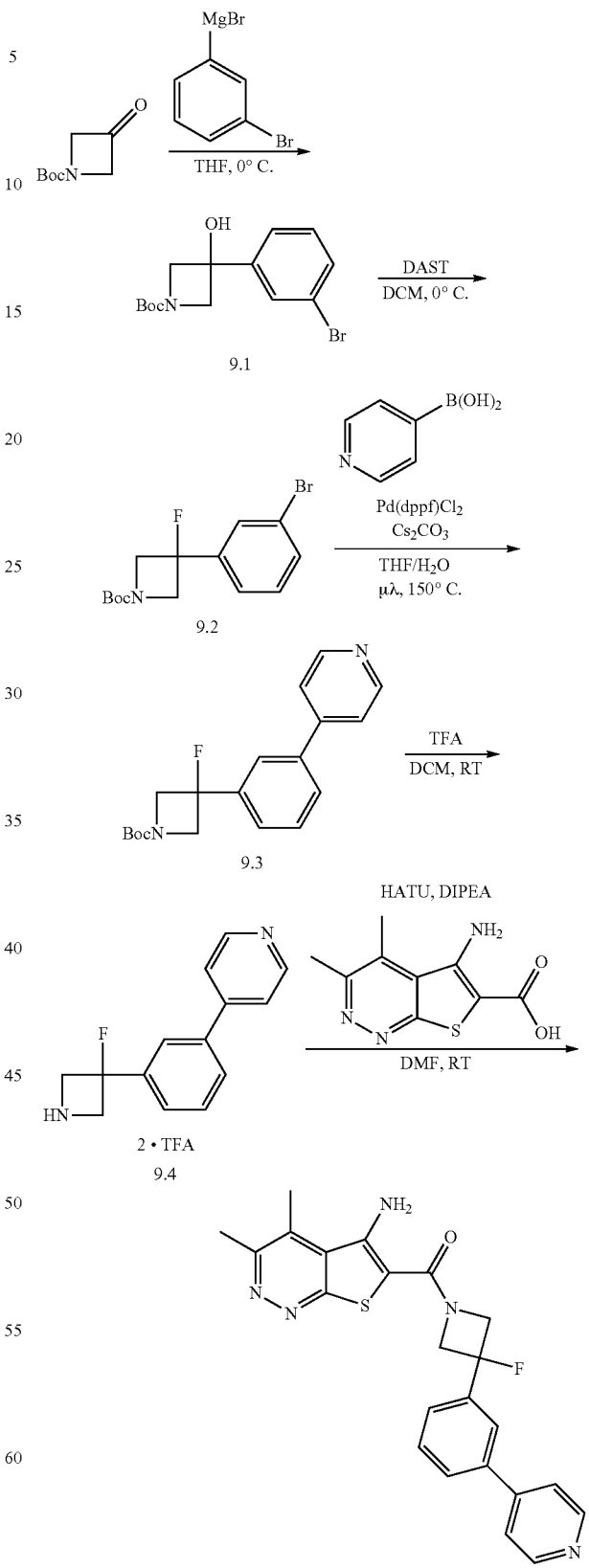

Compounds are represented in generic form, with substituents as noted in compound descriptions elsewhere herein. A more specific example is set forth below.

In one aspect, compounds of the present invention, e.g. compounds of Formula (9) and other substituted analogs, can be prepared according to Scheme 9b as shown above beginning with a protected azetidin-3-one and subsequent reaction steps as outlined. For example, addition to the carbonyl of the protected azetidin-3-one, with e.g. a halo-substituted aryl Grignard reagent, provides the corresponding alcohol, which can be subsequently converted to the corresponding fluoride. Metal-mediated coupling (e.g., Suzuki coupling) with an aryl bononic acid or heteroaryl boronic acid can then be performed. Deprotection and reaction with a compound of Formula (1.3), or an analog thereof, can produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

10. Route X

In one aspect, substituted analogs of the present invention can be prepared generically by the synthetic scheme as shown below.

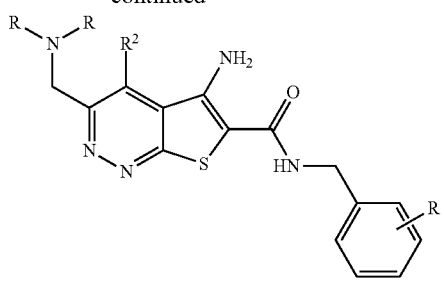

Compounds are represented in generic form, with substituents as noted in compound descriptions elsewhere herein. A more specific example is set forth below.

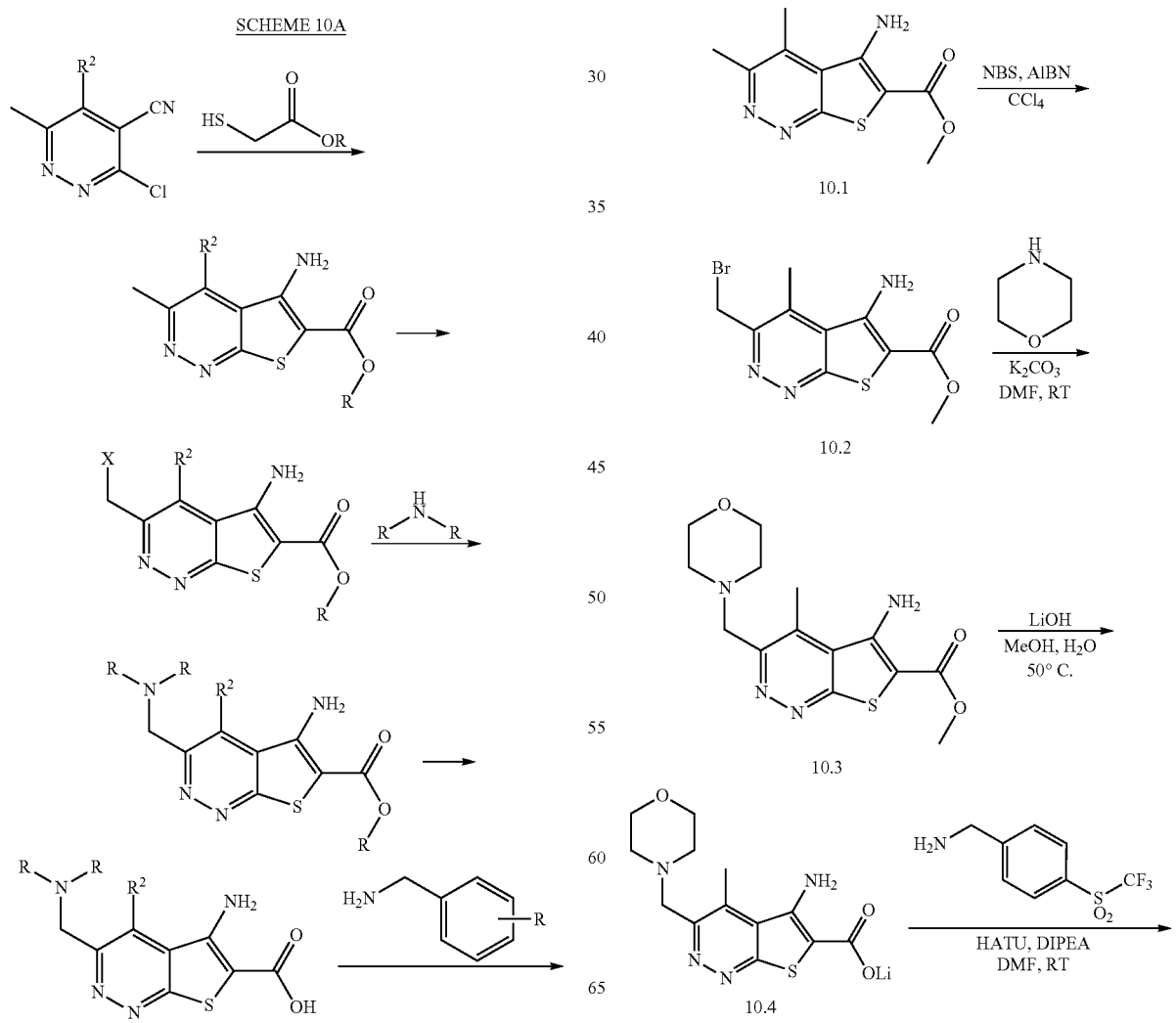

-continued

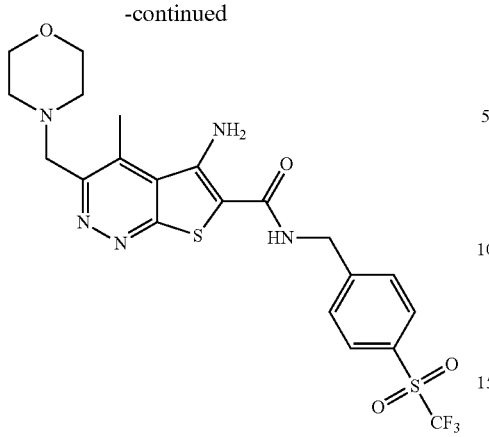

Example 10
(Compound B324, Table I)

In one aspect, compounds of the present invention, e.g. compounds of Formula (10) and other substituted analogs, can be prepared according to Scheme 10b as shown above beginning with cyclization of optionally substituted 3-chloro-6-methylpyridazine-4-carbonitrile with alkyl 2-mercaptoacetate and subsequent reaction steps as outlined. For example, the resultant bicyclic compound can be halogenated and reacted with an amine. Hydrolysis of the ester and reaction with another amine, e.g. optionally substituted benzyl amine, affords the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

11. Route XI

In one aspect, substituted analogs of the present invention can be prepared generically by the synthetic scheme as shown below.

SCHEME 11A

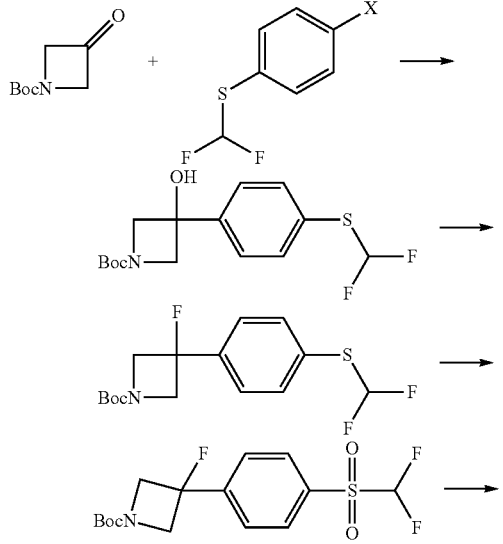

-continued

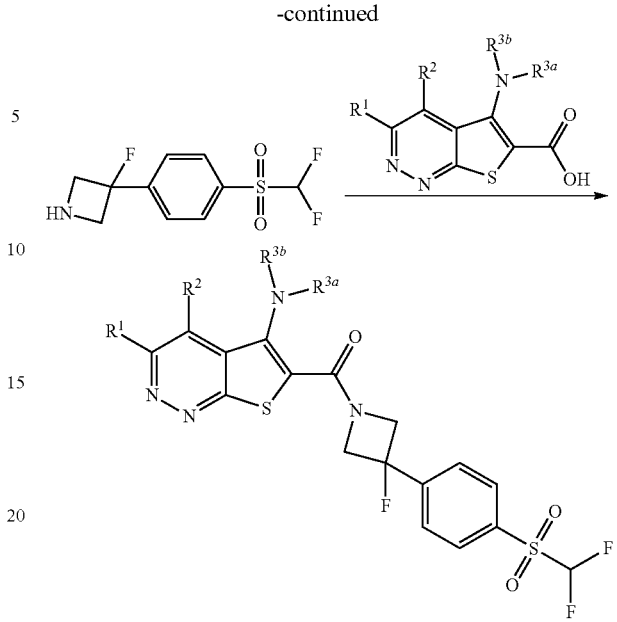

Compounds are represented in generic form, with substituents as noted in compound descriptions elsewhere herein. A more specific example is set forth below.

SCHEME 11B

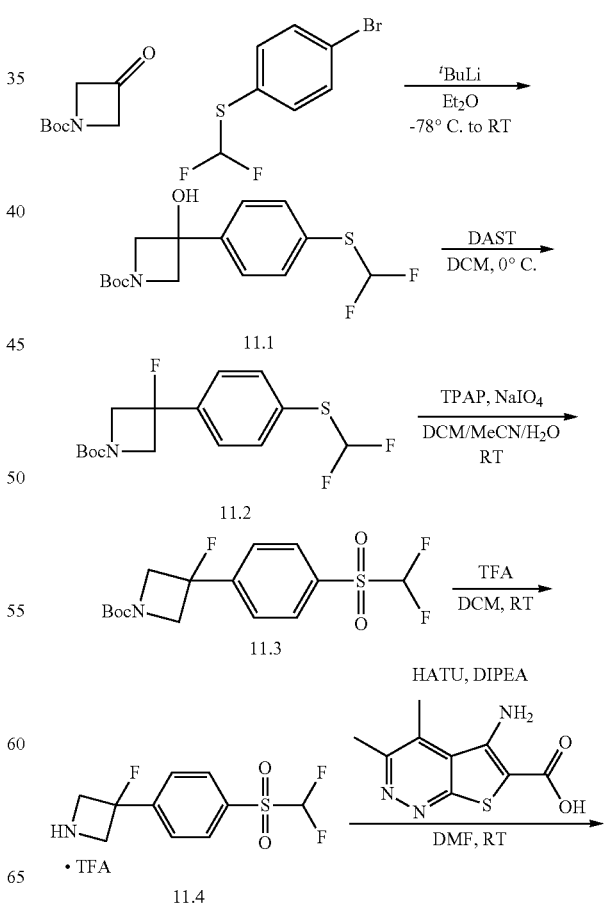

433
-continued

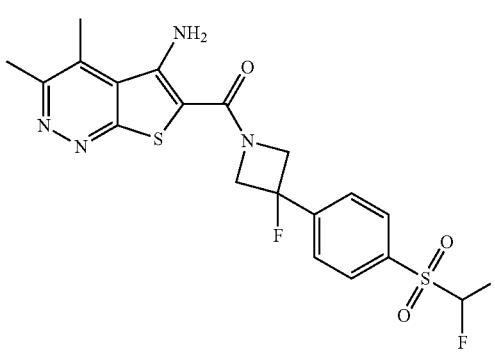

Example 11
(Compound B377, Table I)

In one aspect, compounds of the present invention, e.g. compounds of Formula (11) and other substituted analogs, can be prepared according to Scheme 11b as shown above beginning with lithiation of an optionally substituted aryl or heteroaryl compound and subsequent addition to the carbonyl of a protected azetidin-3-one and subsequent reaction steps as outlined. Conversion of the hydroxyl group to a fluoride substituent and, optionally, oxidation of the sulfur, followed by deprotection, yields an amine, which can be reacted with a compound of Formula (1.3), or an analog thereof, to produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

12. Route XII

In one aspect, substituted analogs of the present invention can be prepared generically by the synthetic scheme as shown below.

SCHEME 12A

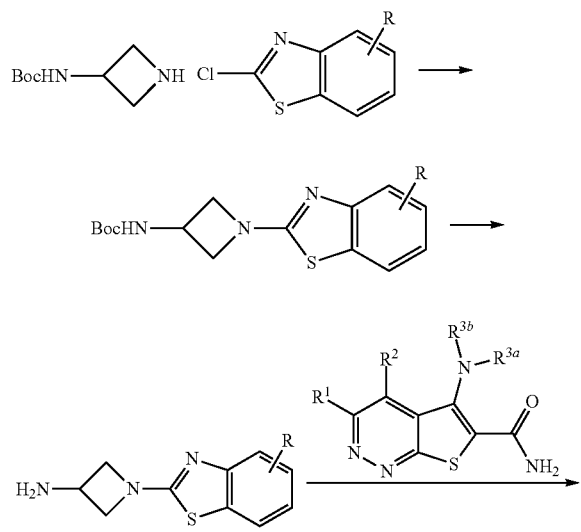

434
-continued

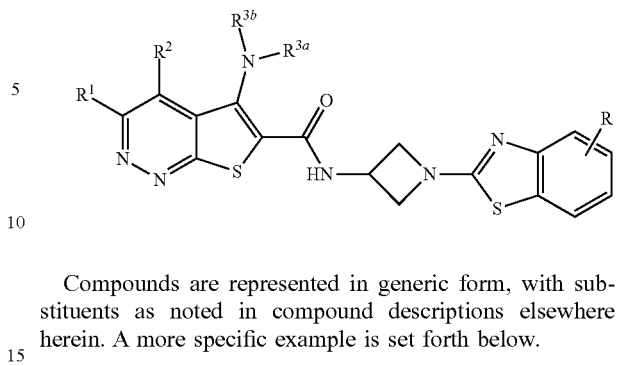

Compounds are represented in generic form, with substituents as noted in compound descriptions elsewhere herein. A more specific example is set forth below.

SCHEME 12B

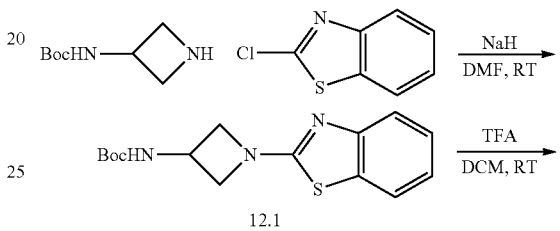

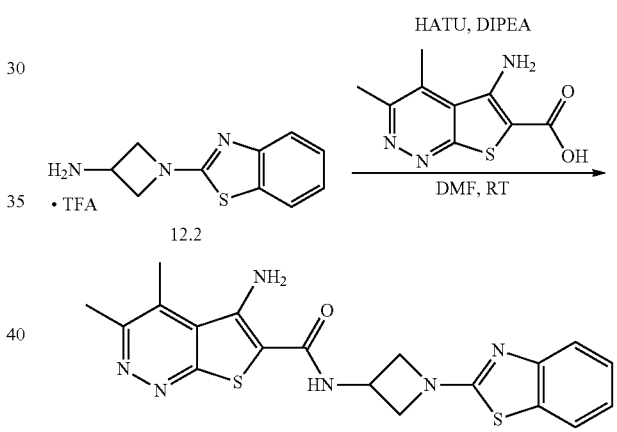

Example 12
(Compound B422, Table I)

In one aspect, compounds of the present invention, e.g. compounds of Formula (12) and other substituted analogs, can be prepared according to Scheme 12b as shown above beginning with nucleophilic substitution of an optionally substituted benzothiazole with a protected azetidin-3-amine and subsequent reaction steps as outlined. Deprotection and subsequent reaction with a compound of Formula (1.3), or an analog thereof, to produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

13. Route XIII

In one aspect, substituted analogs of the present invention can be prepared generically by the synthetic scheme as shown below.

SCHEME 13A

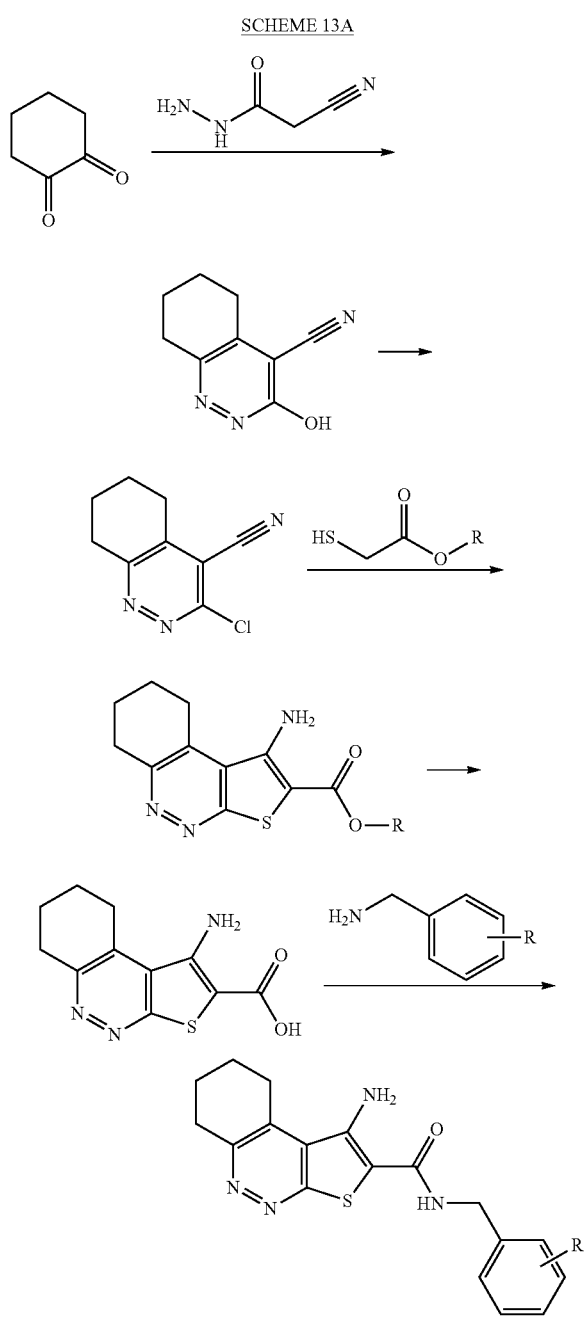

Compounds are represented in generic form, with substituents as noted in compound descriptions elsewhere herein. A more specific example is set forth below.

SCHEME 13B

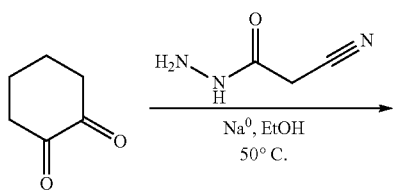

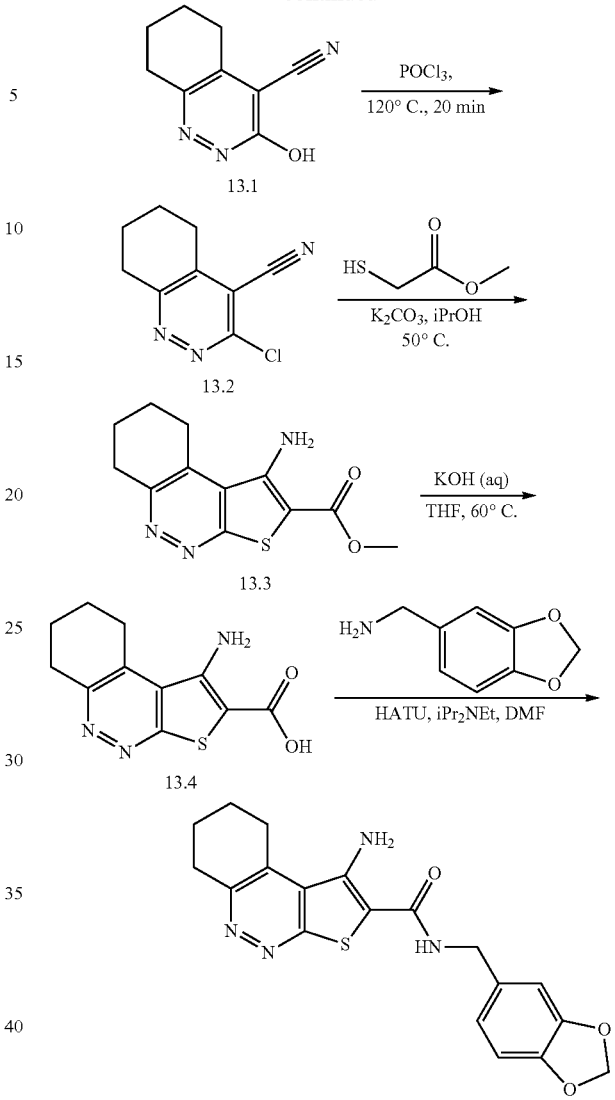

Example 13
(Compound B50, Table I)

In one aspect, compounds of the present invention, e.g. compounds of Formula (13) and other substituted analogs, can be prepared according to Scheme 13b as shown above beginning with cyclization of an optionally substituted cyclohexane-1,2-dione with 2-cyanoacetohydrazide and subsequent reaction steps as outlined. Chlorination of the resultant hydroxyl group, followed by cyclization with an alkyl 2-mercaptoacetate and ester hydrolysis, provides an analog of a compound of Formula (1.3) that can be reacted with an amine, e.g., an optionally substituted benzyl amine, to produce the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

14. Route XIV

In one aspect, substituted analogs of the present invention can be prepared generically by the synthetic scheme as shown below.

SCHEME 14A

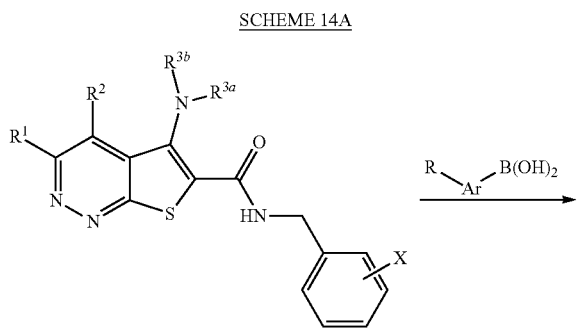

Compounds are represented in generic form, with substituents as noted in compound descriptions elsewhere herein. A more specific example is set forth below.

SCHEME 14B

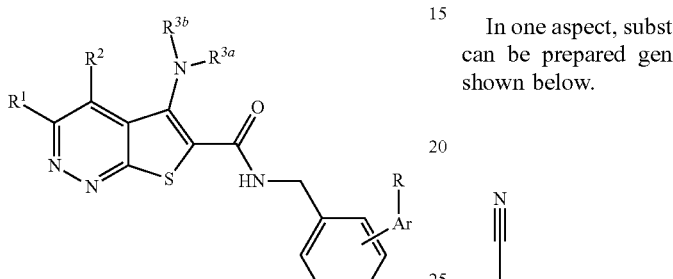

Compound B448

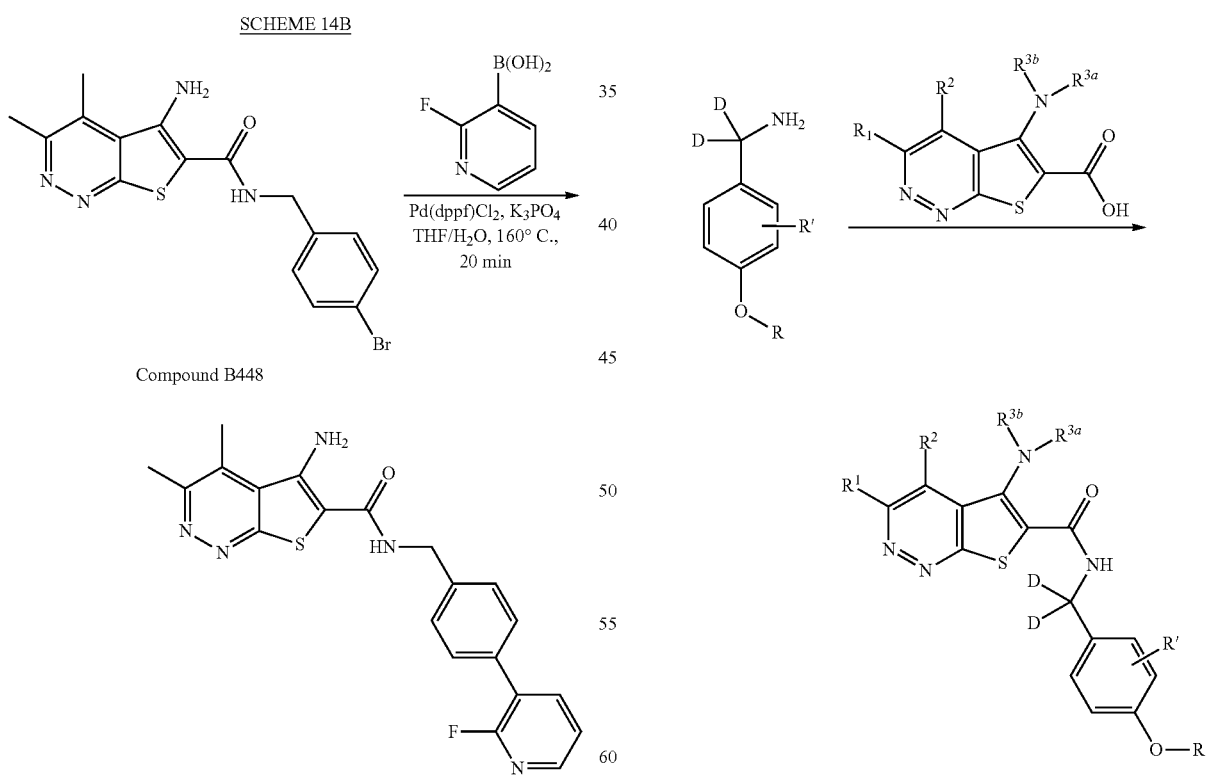

Example 14
(Compound B453, Table I)

In one aspect, compounds of the present invention, e.g. compounds of Formula (14) and other substituted analogs, can be prepared according to Scheme 14b as shown above beginning with an optionally substituted 5-amino-N-(halo)benzylthieno[2,3-c]pyridazine-6-carboxamide and subsequent reaction steps as outlined. Metal-mediated coupling, e.g. Suzuki coupling, with an optionally substituted aryl boronic acid or optionally substituted heteroaryl boronic acid provides the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

15. Route XV

In one aspect, substituted analogs of the present invention can be prepared generically by the synthetic scheme as shown below.

SCHEME 15A

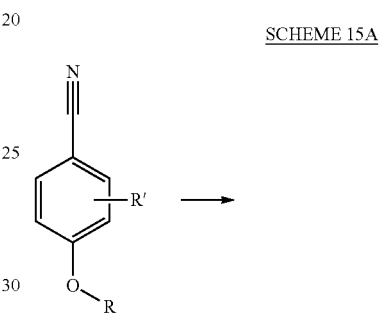

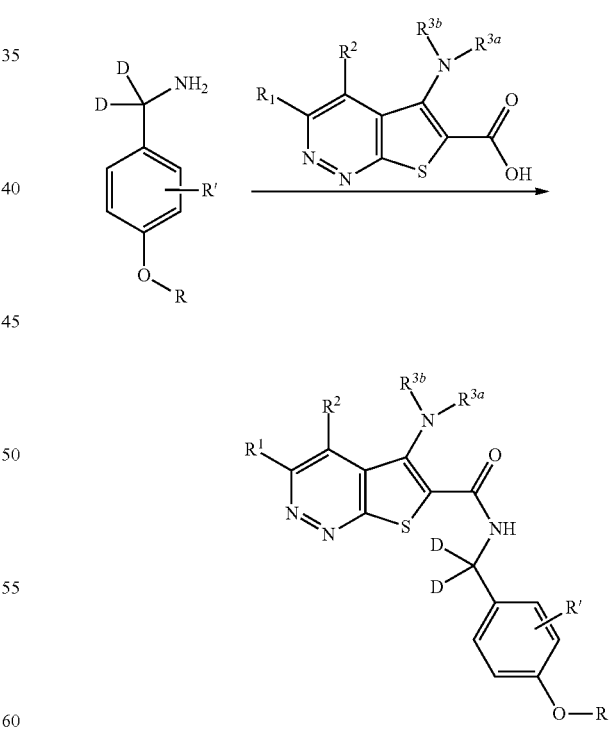

Compounds are represented in generic form, with substituents as noted in compound descriptions elsewhere herein. A more specific example is set forth below.

SCHEME 15B

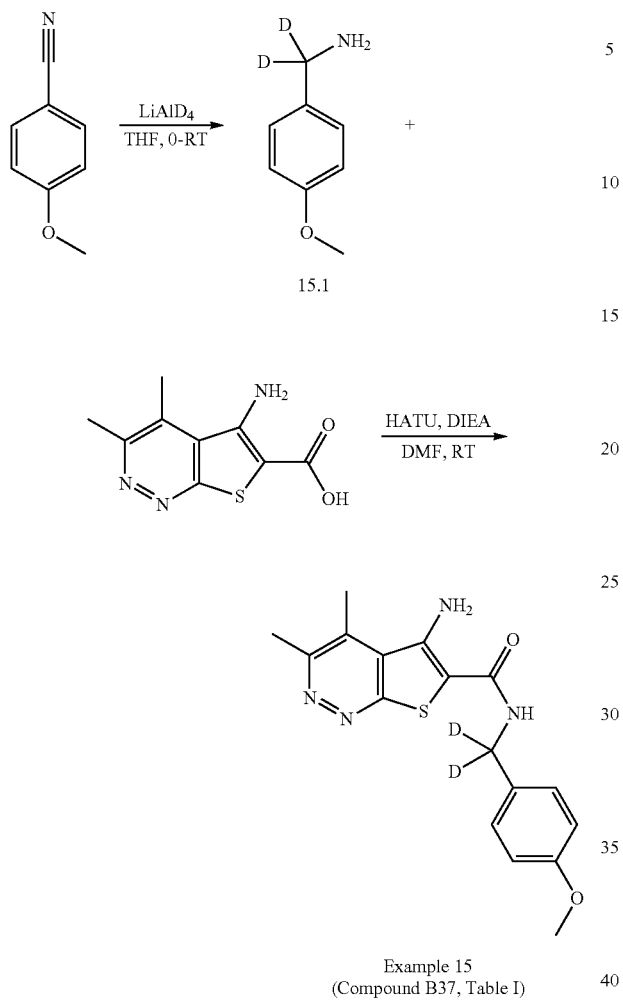

Example 15
(Compound B37, Table I)

In one aspect, compounds of the present invention, e.g. compounds of Formula (15) and other substituted analogs, can be prepared according to Scheme 15b as shown above beginning with reduction of an optionally substituted 4-alkoxybenzonitrile with deuterated lithium aluminum hydride and subsequent reaction steps as outlined. Reaction of the resultant amine with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

16. Route XVI

In one aspect, substituted analogs of the present invention can be prepared generically by the synthetic scheme as shown below.

SCHEME 16A

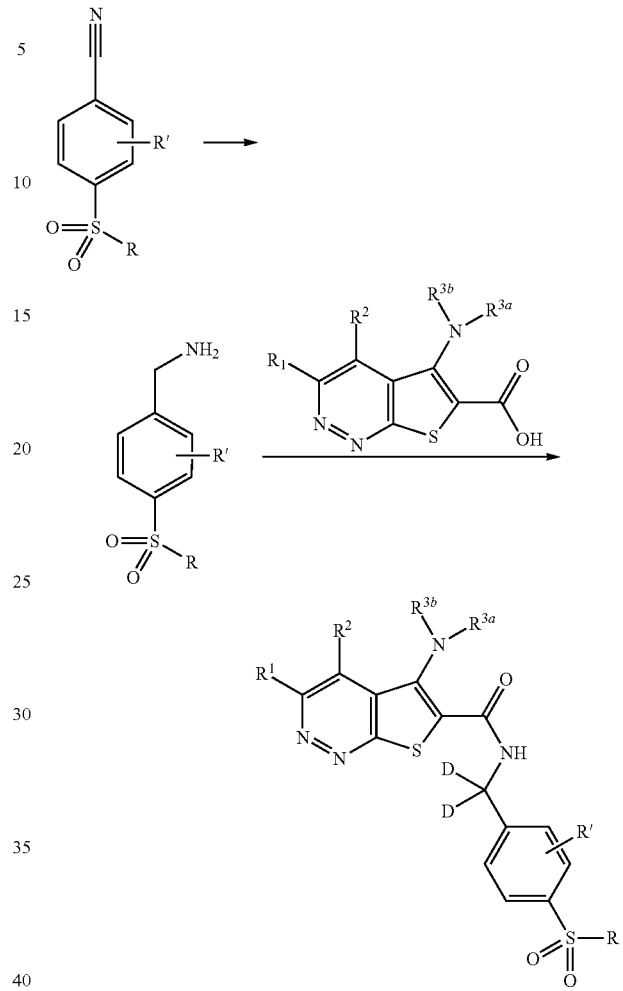

Compounds are represented in generic form, with substituents as noted in compound descriptions elsewhere herein. A more specific example is set forth below.

SCHEME 16B

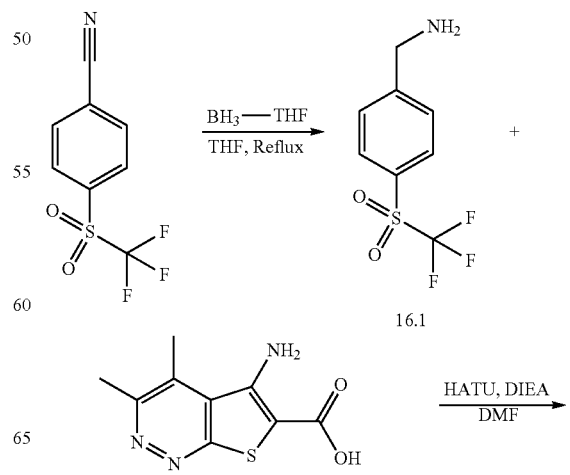

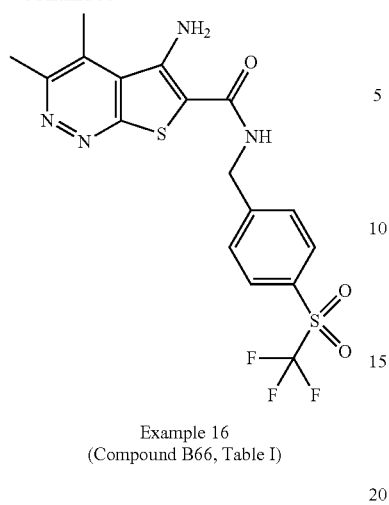

Example 16
(Compound B66, Table I)

In one aspect, compounds of the present invention, e.g. compounds of Formula (16) and other substituted analogs, can be prepared according to Scheme 16b as shown above beginning with reduction of an optionally substituted 4-(alkylsulfonyl)benzonitrile and subsequent reaction steps as outlined. Reaction of the resultant amine with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

17. Route XVII

In one aspect, substituted analogs of the present invention can be prepared generically by the synthetic scheme as shown below.

SCHEME 17A

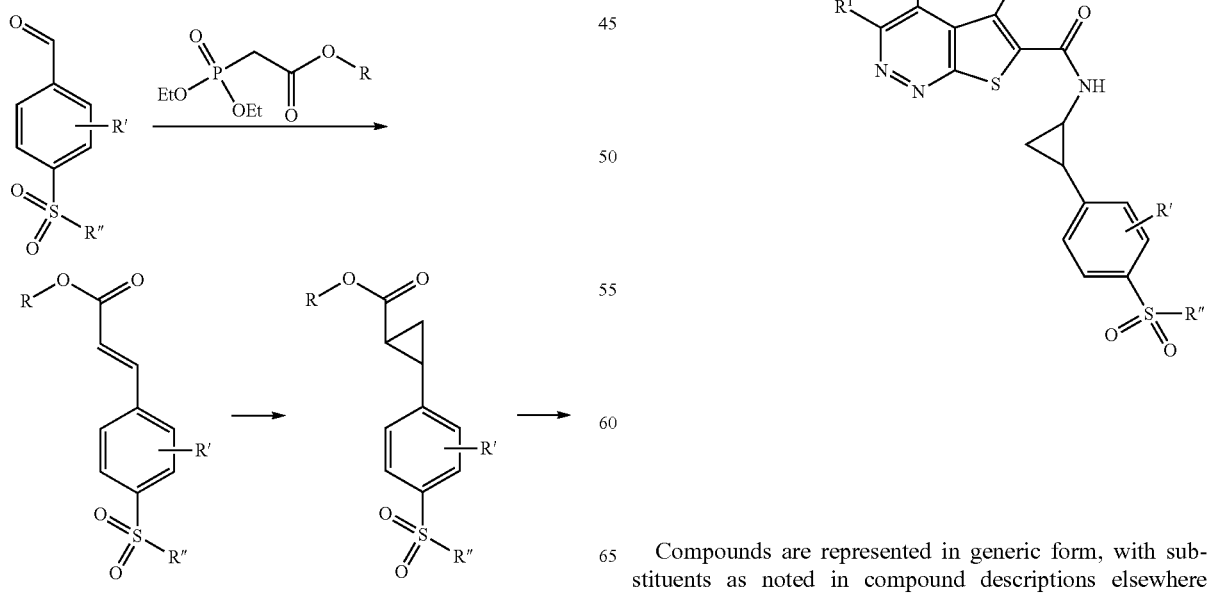

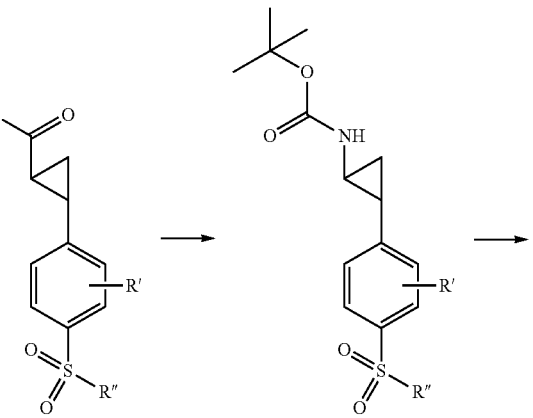

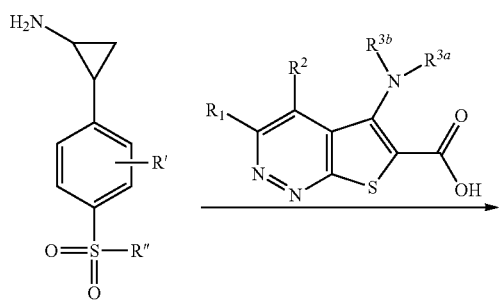

Compounds are represented in generic form, with substituents as noted in compound descriptions elsewhere herein. A more specific example is set forth below.

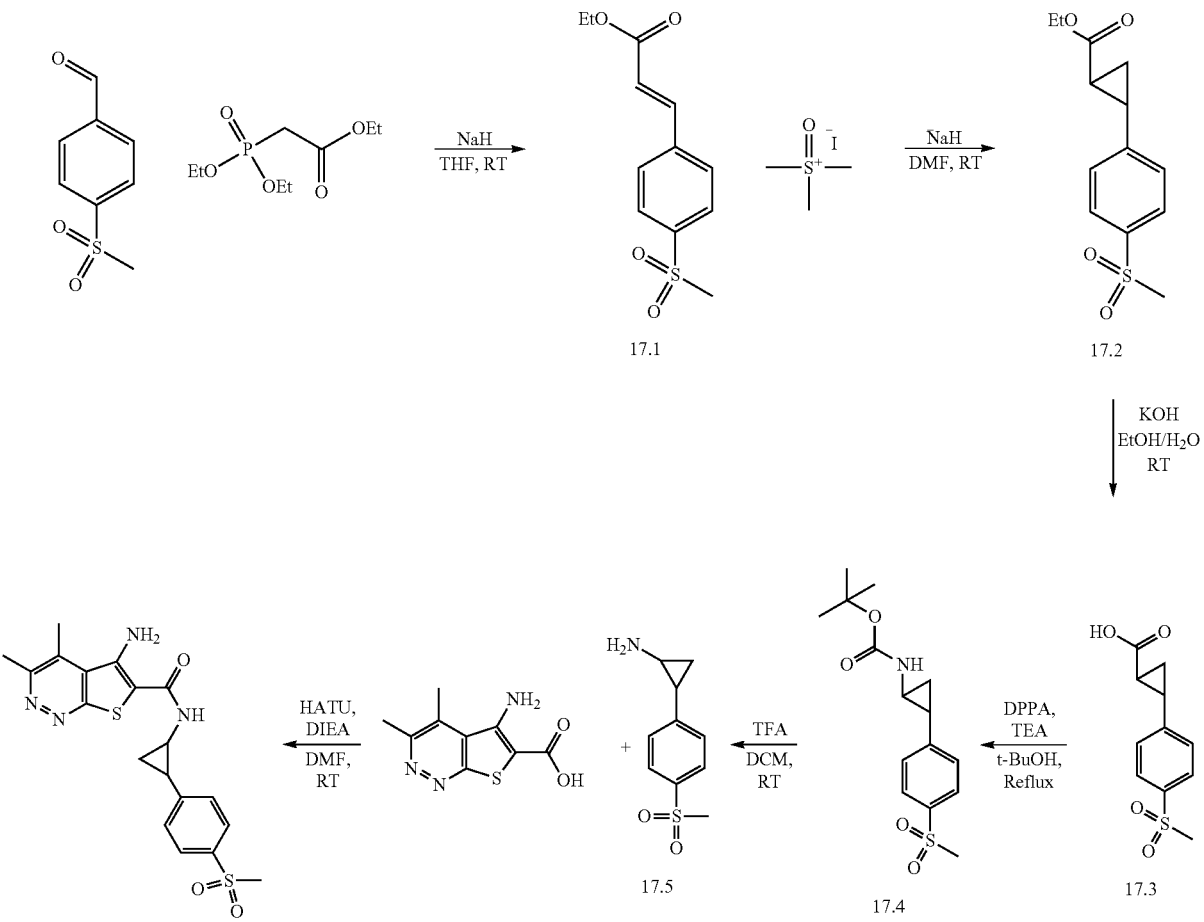

In one aspect, compounds of the present invention, e.g. compounds of Formula (17) and other substituted analogs, can be prepared according to Scheme 17b as shown above beginning by reacting an optionally substituted benzaldehyde, e.g. 4-(methylsulfonyl)benzaldehyde with an alkyl 2-(dialkoxyphosphoryl)acetate to produce the corresponding alkene and subsequent reaction steps as outlined. For example, cyclopropanation and ester hydrolysis provides the corresponding carboxylic acid, which can be converted to the corresponding protected amine by treatment with diphenylphosphoryl azide (DPPA). Deprotection and reaction of the resultant amine with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

18. Route XX

In one aspect, substituted analogs of the present invention can be prepared generically by the synthetic scheme as shown below.

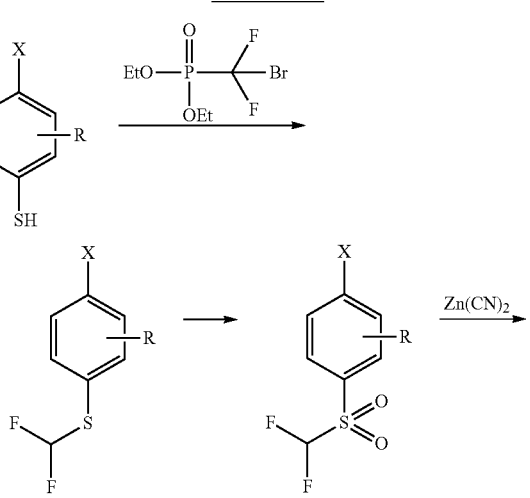

-continued
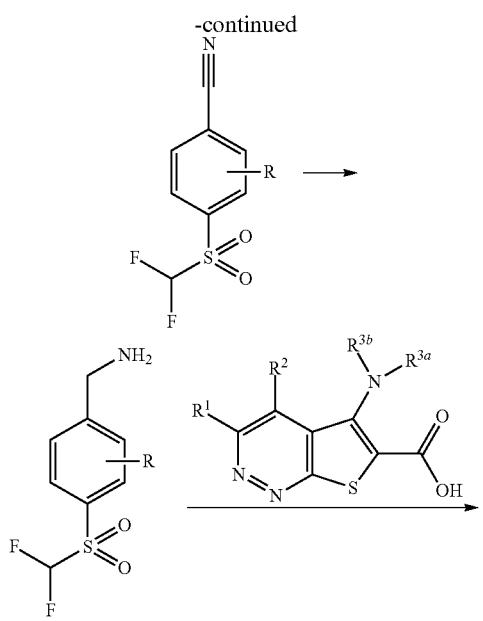
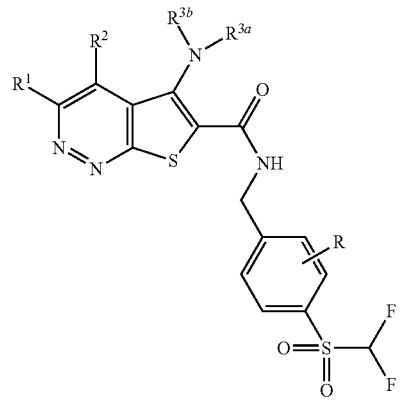
Compounds are represented in generic form, with substituents as noted in compound descriptions elsewhere herein. A more specific example is set forth below.
SCHEME 20B
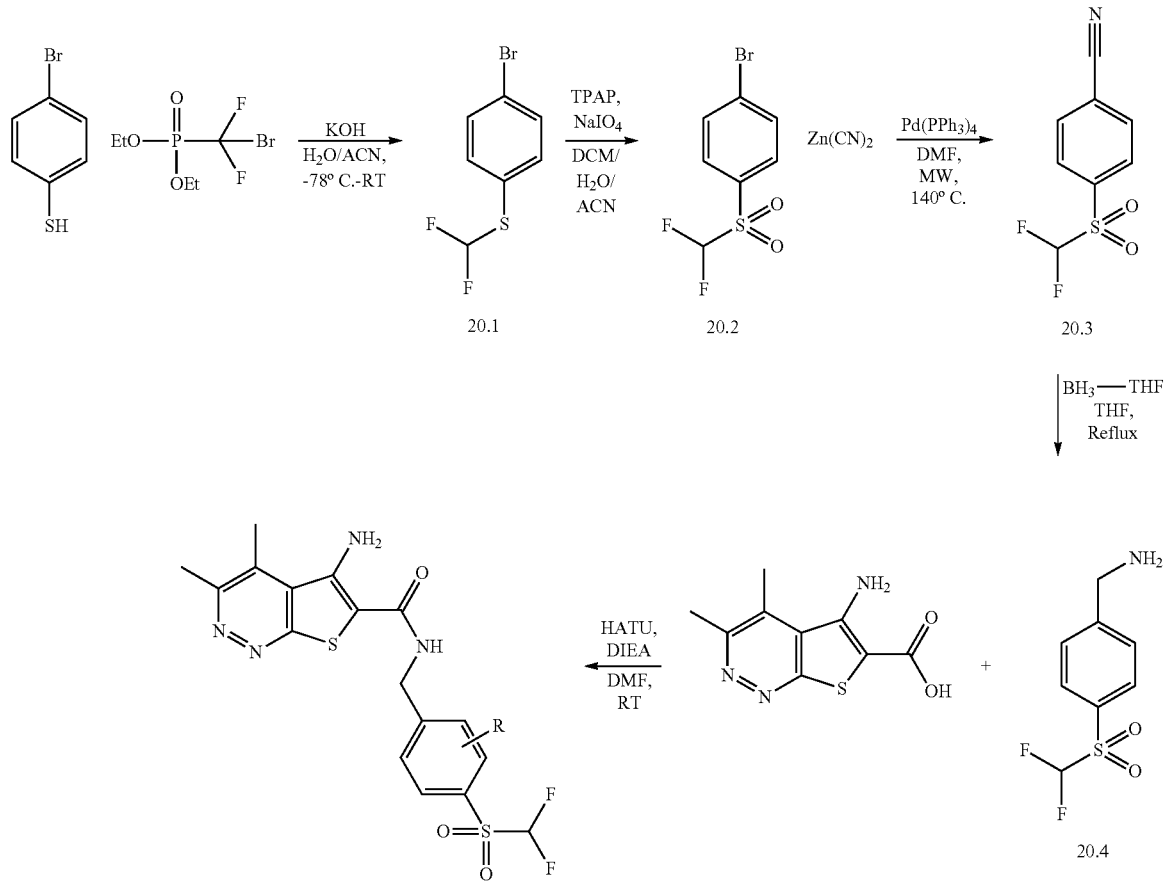
Example 20
(Compound B117, Table I)

In one aspect, compounds of the present invention, e.g. compounds of Formula (20) and other substituted analogs, can be prepared according to Scheme 20b as shown above beginning with an optionally substituted halothiophenol and subsequent reaction steps as outlined. For example, substitution at the thiol group to form a thioether, followed by oxidation, nitrile formation, and reduction, provides the corresponding amine. Reaction with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

19. Route XXI

In one aspect, substituted analogs of the present invention can be prepared generically by the synthetic scheme as shown below.

SCHEME 21A

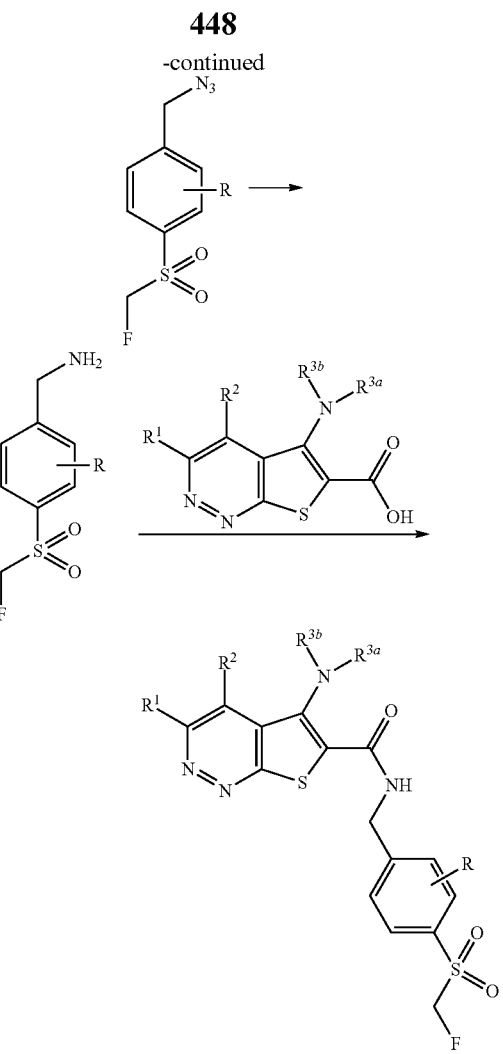

Compounds are represented in generic form, with substituents as noted in compound descriptions elsewhere herein. A more specific example is set forth below.

SCHEME 21B

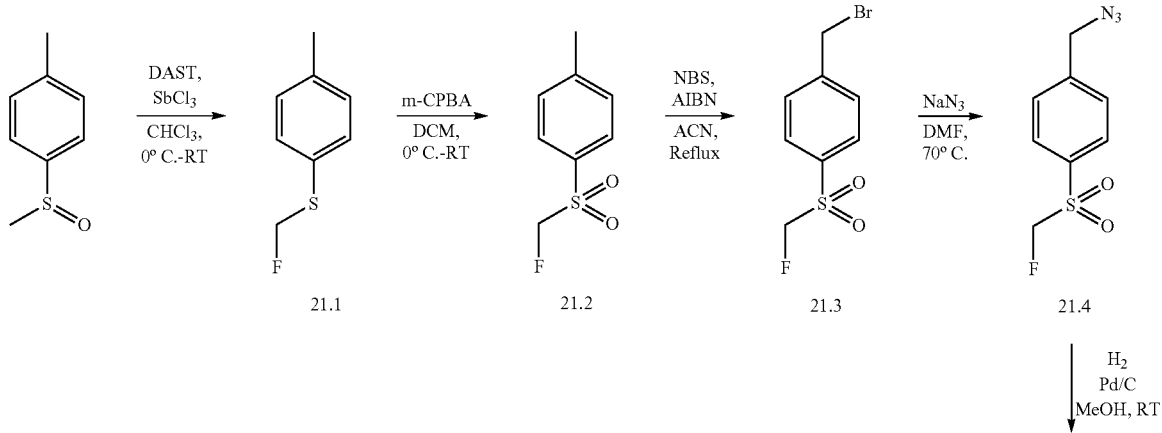

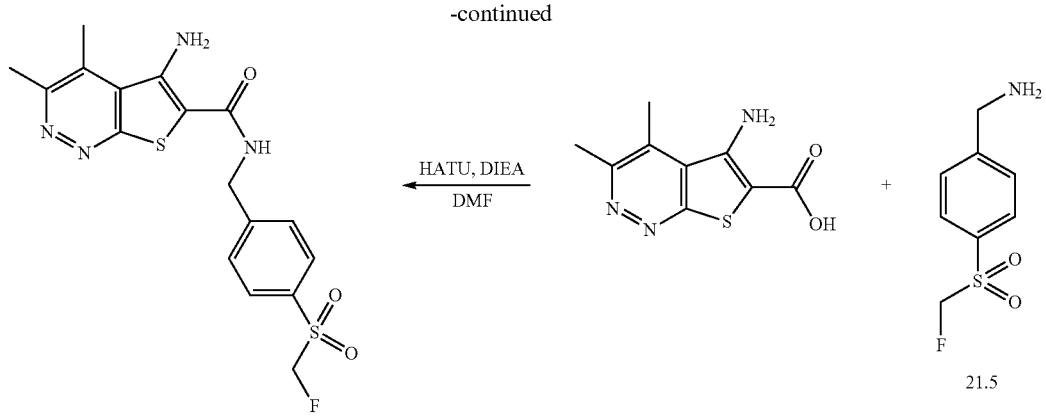

Example 21
(Compound B132, Table I)

In one aspect, compounds of the present invention, e.g. compounds of Formula (21) and other substituted analogs, can be prepared according to Scheme 21b as shown above beginning with elaboration of the sulfur functionality of an optionally substituted 1-methyl-4-(methylsulfinyl)benzene and subsequent reaction steps as outlined. For example, the methylsulfinyl group can be reduced and fluorinated, followed by oxidation. Halogenation of the benzyllic carbon, followed by substitution with azide and reduction, yields the corresponding amine. Reaction with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

20. Route XXII

In one aspect, substituted analogs of the present invention can be prepared generically by the synthetic scheme as shown below.

SCHEME 22A

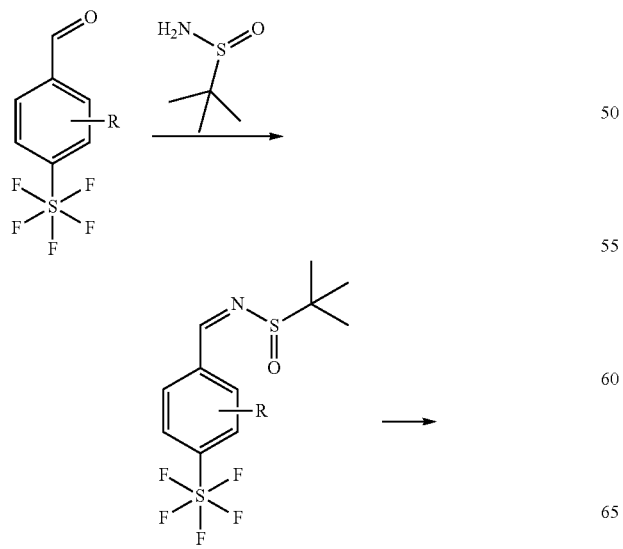

-continued

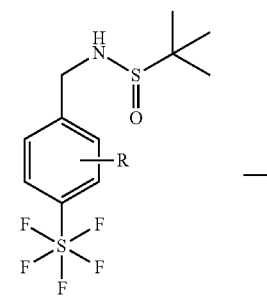

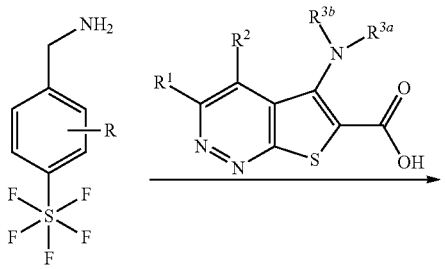

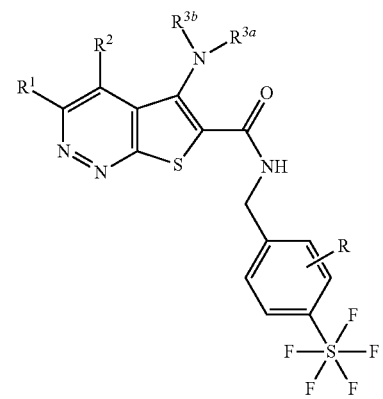

Compounds are represented in generic form, with substituents as noted in compound descriptions elsewhere herein. A more specific example is set forth below.

SCHEME 22B

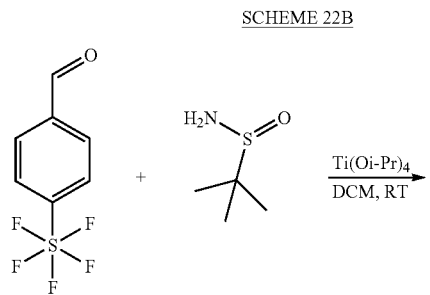

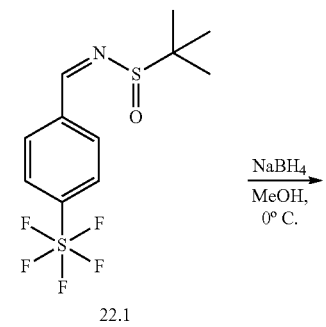

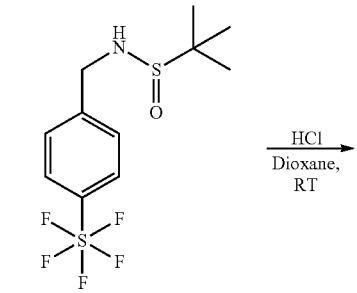

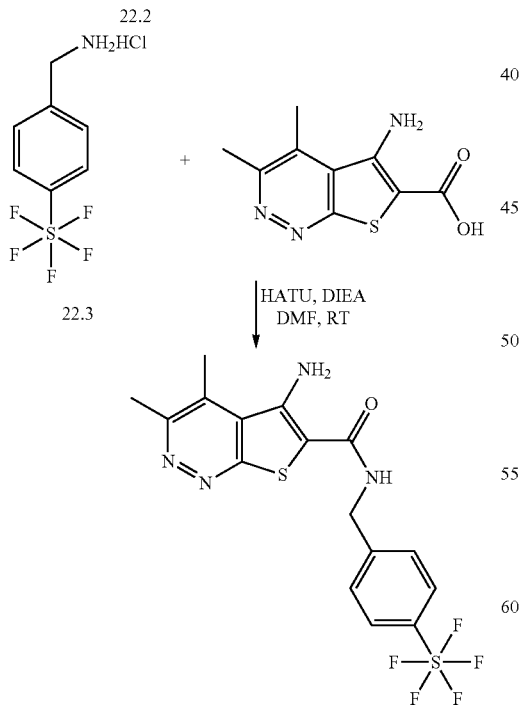

Example 22
(Compound B297, Table I)

In one aspect, compounds of the present invention, e.g. compounds of Formula (22) and other substituted analogs, can be prepared according to Scheme 22b as shown above beginning with conversion of a optionally substituted (e.g., pentafluorosulfanyl) benzaldehyde to the corresponding imine, which is then reduced to the protected amine a compound of Formula (XXX) and subsequent reaction steps as outlined. Deprotection and subsequent reaction with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

21. Route XXIII

In one aspect, substituted analogs of the present invention can be prepared generically by the synthetic scheme as shown below.

SCHEME 23A

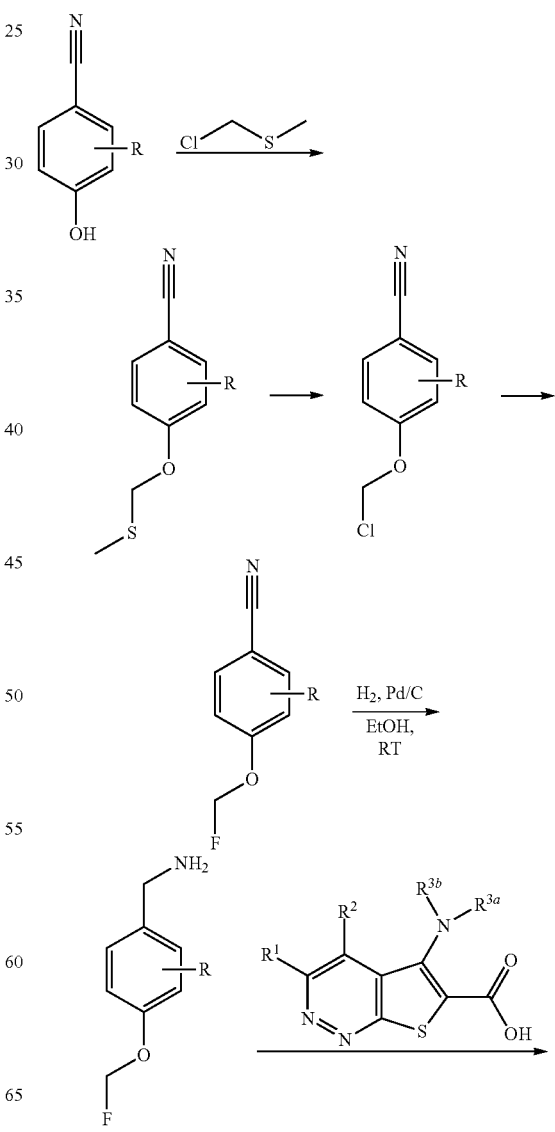

453
-continued

454
-continued

Compounds are represented in generic form, with substituents as noted in compound descriptions elsewhere herein. A more specific example is set forth below.

SCHEME 23B

Example 23
(Compound B411, Table I)

In one aspect, compounds of the present invention, e.g. compounds of Formula (23) and other substituted analogs, can be prepared according to Scheme 23b as shown above beginning with alkylation of an optionally substituted hydroxybenzonitrile to the corresponding imine and subsequent elaboration (e.g., halogenation) of the alkyl group and subsequent reaction steps as outlined. The nitrile can then be reduced to the corresponding amine. Reaction with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

22. Route XXIV

In one aspect, substituted analogs of the present invention can be prepared generically by the synthetic scheme as shown below.

SCHEME 24A

455
-continued

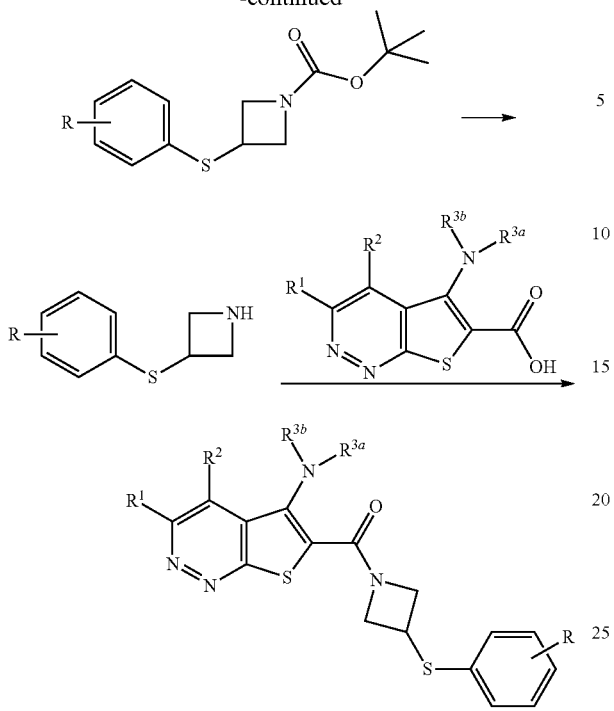

Compounds are represented in generic form, with substituents as noted in compound descriptions elsewhere herein. A more specific example is set forth below.

SCHEME 24B

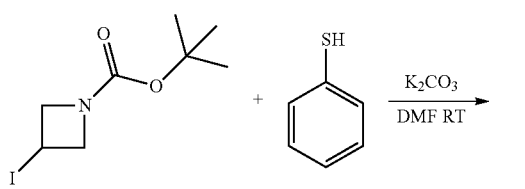

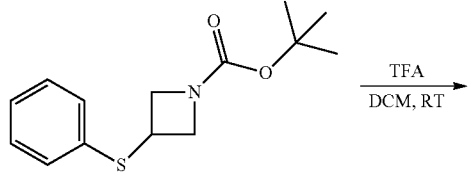

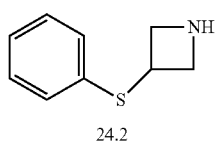

456
-continued

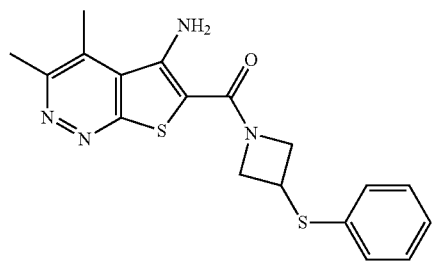

Example 24
(Compound B405, Table I)

In one aspect, compounds of the present invention, e.g. compounds of Formula (24) and other substituted analogs, can be prepared according to Scheme 24b as shown above beginning with reaction of a protected haloazetidine with an optionally substituted thiophenol. Deprotection and subsequent reaction with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

23. Route XXV

In one aspect, substituted analogs of the present invention can be prepared generically by the synthetic scheme as shown below.

SCHEME 25A

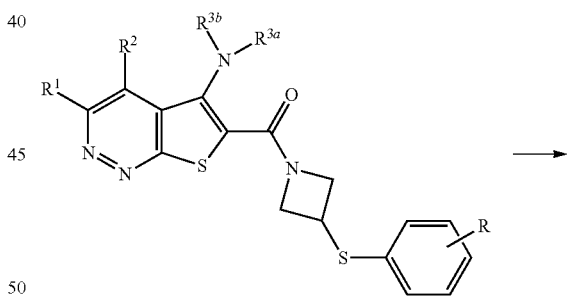

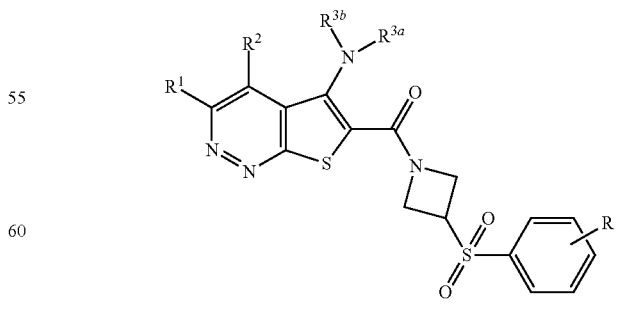

Compounds are represented in generic form, with substituents as noted in compound descriptions elsewhere herein. A more specific example is set forth below.

SCHEME 25B

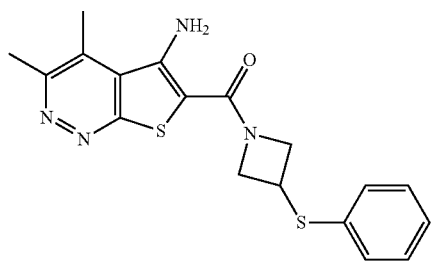

Example 24
(Compound B405, Table I)

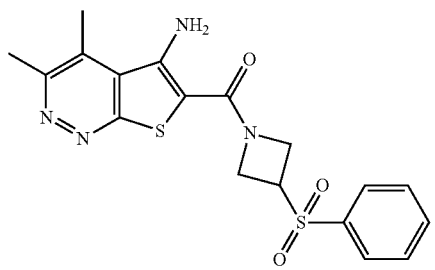

Example 25
(Compound B413, Table I)

In one aspect, compounds of the present invention, e.g. compounds of Formula (25) and other substituted analogs, can be prepared according to Scheme 25b as shown above beginning with an optionally substituted thioether (sulfane) compound and subsequent reaction steps as outlined. The sulfur moiety of the thioether compound can be oxidized to the corresponding sulfinyl compound or sulfonyl compound.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

24. Route XXVI

In one aspect, substituted analogs of the present invention can be prepared generically by the synthetic scheme as shown below.

Compounds are represented in generic form, with substituents as noted in compound descriptions elsewhere herein. A more specific example is set forth below.

SCHEME 26B

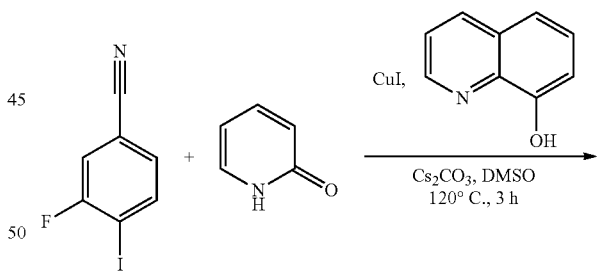

SCHEME 26A

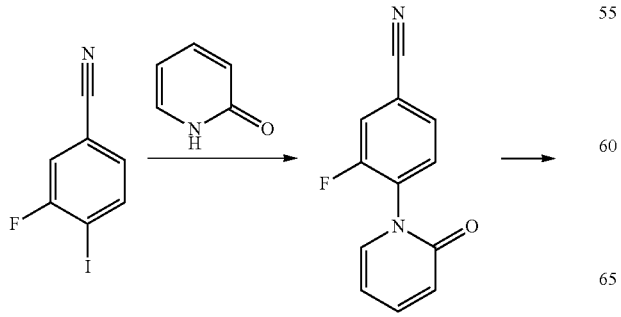

26.1

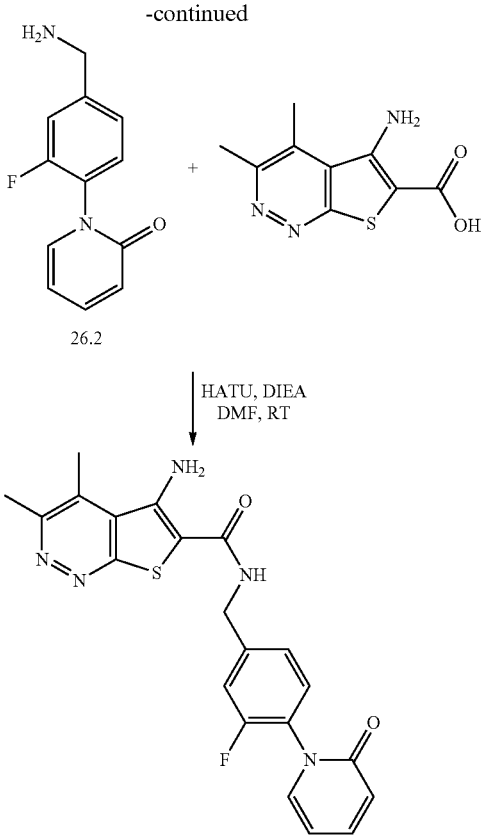

Example 26
(Compound B483, Table I)

In one aspect, compounds of the present invention, e.g. compounds of Formula (26) and other substituted analogs, can be prepared according to Scheme 26b as shown above beginning with reaction of an optionally substituted (e.g., fluoro) halobenzonitrile with an optionally substituted pyridin-2(1H)-one and subsequent reaction steps as outlined. The nitrile can be subsequently reduced to the corresponding amine. Reaction with a compound of Formula (1.3), or an analog thereof, produces the desired amide.

As can be appreciated by one skilled in the art, the above reaction scheme provides an example of a generalized approach wherein compounds similar in structure to the specific reactants illustrated above and appropriate reagents, can be substituted in the reaction to provide substituted analogs similar to those specifically exemplified.

25. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety of specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed D. Pharmaceutical Compositions In one aspect, the invention relates to pharmaceutical compositions comprising the disclosed compounds. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and an effective amount of at least one disclosed compound; or a pharmaceutically acceptable salt, hydrate, solvate, or polymorph thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises a disclosed compound. In a yet further aspect, the pharmaceutical composition comprises a product of a disclosed method of making.

In a further aspect, the pharmaceutical composition exhibits positive allosteric modulation of mAChR $M_4$ with an $EC_{50}$ of less than about 10,000 nM. In a still further aspect, the pharmaceutical composition exhibits positive allosteric modulation of mAChR $M_4$ with an $EC_{50}$ of less than about 5,000 nM. In an even further aspect the pharmaceutical composition exhibits positive allosteric modulation of mAChR $M_4$ with an $EC_{50}$ of less than about 1,000 nM. In a further aspect, the pharmaceutical composition exhibits positive allosteric modulation of mAChR $M_4$ with an $EC_{50}$ of less than about 500 nM. In a yet further aspect, the pharmaceutical composition exhibits positive allosteric modulation of mAChR $M_4$ with an $EC_{50}$ of less than about 100 nM. In a further aspect, the pharmaceutical composition exhibits positive allosteric modulation of mAChR $M_4$ with an $EC_{50}$ of between from about 10,000 nM to about 1 nM. In a yet further aspect, the pharmaceutical composition exhibits positive allosteric modulation of mAChR $M_4$ with an $EC_{50}$ of between from about 1,000 nM to about 1 nM. In a still further aspect, the pharmaceutical composition exhibits positive allosteric modulation of mAChR $M_4$ with an $EC_{50}$ of between from about 100 nM to about 1 nM. In an even further aspect, the pharmaceutical composition exhibits positive allosteric modulation of mAChR $M_4$ with an $EC_{50}$ of between from about 10 nM to about 1 nM.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder. In a further aspect, the pharmaceutical composition is used to treat a neurological and/or psychiatric disorder. In a yet further aspect, the disorder is associated with mAChR $M_4$ dysfunction.

In a further aspect, the pharmaceutical composition is used to treat a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the pharmaceutical composition is used to treat a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, the pharmaceutical composition is used to treat a disorder selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require positive allosteric modulation of mAChR $M_4$ receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating mAChR $M_4$ receptor activity (e.g., treatment of one or more neurological and/or psychiatric disorder associated with mAChR $M_4$ receptor dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, orthosteric muscarinic agonists, muscarinic potentiators, cholinesterase inhibitors, HMG-CoA reductase inhibitors, NSAIDs and anti-amyloid antibodies. In a further aspect, the compounds can be administered in combination with sedatives, hypnotics, anxiolytics, antipsychotics (typical and atypical), selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders associated with selective mAChR $M_4$ receptor activation. For example, a treatment can include selective mAChR $M_4$ receptor activation to an extent effective to affect cholinergic activity. Thus, a disorder can be associated with cholinergic activity, for example cholinergic hypofunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders associated with mAChR $M_4$ receptor activity in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of a disorder in a mammal comprising the step of administering to the mammal at least one disclosed compound, composition, or medicament.

In one aspect, the disclosed compounds have utility in treating a variety of neurological and psychiatric disorders associated with the mAChR $M_4$ receptor, including one or more of the following conditions or diseases: schizophrenia (paranoid, disorganized, catatonic or undifferentiated), psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, Alzheimer's disease, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis. In an even further aspect, the psychotic disorder is due to a general medical condition and substance-induced or drug-induced (phencyclidine, ketamine and other dissociative anesthetics, amphetamine and other psychostimulants and cocaine), In one aspect, the present invention provides a method for treating cognitive disorders, comprising: administering to a patient in need thereof an effective amount of a compound of the present invention. In a further aspect, cognitive disorders include dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In a further specific aspect, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In a still further aspect, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the subject compound can be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound can be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enanthate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HTJA agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require activation of mAChR $M_4$ an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to a method for activating mAChR $M_4$ receptor activity in at least one cell comprising the step of contacting the at least one cell with at least one disclosed compound or at least one product of a disclosed method in an amount effective to activate mAChR $M_4$ in the at least one cell. In a further aspect, the cell is mammalian, for example, human. In a further aspect, the cell has been isolated from a subject prior to the contacting step. In a further aspect, contacting is via administration to a subject.

In a further aspect, the invention relates to a method for activating mAChR $M_4$ activity in a subject comprising the step of administering to the subject at least one disclosed compound or at least one product of a disclosed method in a dosage and amount effective to activating mAChR $M_4$ activity in the subject. In a further aspect, the subject is mammalian, for example, human. In a further aspect, the mammal has been diagnosed with a need for mAChR $M_4$ agonism prior to the administering step. In a further aspect, the mammal has been diagnosed with a need for mAChR $M_4$ activation prior to the administering step. In a further aspect, the method further comprises the step of identifying a subject in need of mAChR $M_4$ agonism.

In a further aspect, the invention relates to a method for the treatment of a disorder associated with selective mAChR $M_4$ activation, for example, a disorder associated with cholinergic activity, in a mammal comprising the step of administering to the mammal at least one disclosed compound or at least one product of a disclosed method in a dosage and amount effective to treat the disorder in the mammal. In a further aspect, the mammal is a human. In a further aspect, the mammal has been diagnosed with a need for treatment for the disorder prior to the administering step. In a further aspect, the method further comprises the step of identifying a subject in need of treatment for the disorder.

In one aspect, the disorder can be selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a further aspect, the disorder is Alzheimer's disease. In a further aspect, the disorder is a neurological and/or psychiatric disorder associated with $M_1$ receptor activity dysfunction.

a. Treating a Disorder Associated with Muscarinic Acetylcholine Receptor Activity In one aspect, the invention relates to a method for the treatment of a neurological and/or psychiatric disorder associated with muscarinic acetylcholine receptor dysfunction in a mammal comprising the step of administering to the mammal an effective amount of at least one disclosed compound; or a pharmaceutically acceptable salt, hydrate, solvate, or polymorph thereof.

In a further aspect, the compound administered is a product of a disclosed method of making. In a still further aspect, an effective amount is a therapeutically effective amount. In a yet further aspect, an effective amount is a prophylactically effective amount.

In a further aspect, the compound administered exhibits potentiation of mAChR $M_4$ with an $EC_{50}$ of less than about 10,000 nM. In a still further aspect, the compound administered exhibits potentiation of mAChR $M_4$ with an $EC_{50}$ of less than about 5,000 nM. In an even further aspect, the compound administered exhibits potentiation of mAChR $M_4$ with an $EC_{50}$ of less than about 1,000 nM. In a further aspect, the compound administered exhibits potentiation of mAChR $M_4$ with an $EC_{50}$ of less than about 500 nM. In a yet further aspect, the compound administered exhibits potentiation of mAChR $M_4$ with an $EC_{50}$ of less than about 100 nM.

In a further aspect, the compound administered exhibits potentiation of mAChR $M_4$ with an $EC_{50}$ of between from about 10,000 nM to about 1 nM. In a yet further aspect, the compound administered exhibits potentiation of mAChR $M_4$ with an $EC_{50}$ of between from about 1,000 nM to about 1 nM. In a still further aspect, the compound administered exhibits potentiation of mAChR $M_4$ with an $EC_{50}$ of between from about 100 nM to about 1 nM. In an even further aspect, the compound administered exhibits potentiation of mAChR $M_4$ with an $EC_{50}$ of between from about 10 nM to about 1 nM.

In one aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is a neurological and/or psychiatric disorder associated with a muscarinic receptor dysfunction. In a still further aspect, the muscarinic receptor is mAChR $M_4$. In a yet further aspect, the disorder is a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder.

In a further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the disorder is a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS dementia complex, dementia of the Alzheimer's type, age-related cognitive decline, and mild cognitive impairment.

In a further aspect, the disorder is selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

b. Potentiation of Muscarinic Acetylcholine Receptor Activity

In one aspect, the invention relates to a method for potentiation of muscarinic acetylcholine receptor activity in a mammal comprising the step of administering to the mammal an effective amount of at least one disclosed compound; or a pharmaceutically acceptable salt, hydrate, solvate, or polymorph thereof.

In a further aspect, the compound administered is a product of a disclosed method of making a compound.

In a further aspect, potentiation of muscarinic acetylcholine receptor activity increases muscarinic acetylcholine receptor activity. In a still further aspect, potentiation of muscarinic acetylcholine receptor activity is partial agonism of the muscarinic acetylcholine receptor. In a yet further aspect, potentiation of muscarinic acetylcholine receptor activity is positive allosteric modulation of the muscarinic acetylcholine receptor.

In a further aspect, the compound administered exhibits potentiation of mAChR $M_4$ with an $EC_{50}$ of less than about 10,000 nM. In a still further aspect, the compound administered exhibits potentiation of mAChR $M_4$ with an $EC_{50}$ of less than about 5,000 nM. In an even further aspect, the compound administered exhibits potentiation of mAChR $M_4$ with an $EC_{50}$ of less than about 1,000 nM. In a further aspect, the compound administered exhibits potentiation of mAChR $M_4$ with an $EC_{50}$ of less than about 500 nM. In a yet further aspect, the compound administered exhibits potentiation of mAChR $M_4$ with an $EC_{50}$ of less than about 100 nM.

In a further aspect, the compound administered exhibits potentiation of mAChR $M_4$ with an $EC_{50}$ of between from about 10,000 nM to about 1 nM. In a yet further aspect, the compound administered exhibits potentiation of mAChR $M_4$ with an $EC_{50}$ of between from about 1,000 nM to about 1 nM. In a still further aspect, the compound administered exhibits potentiation of mAChR $M_4$ with an $EC_{50}$ of between from about 100 nM to about 1 nM. In an even further aspect, the compound administered exhibits potentiation of mAChR $M_4$ with an $EC_{50}$ of between from about 10 nM to about 1 nM.

In one aspect, the mammal is a human. In a further aspect, the mammal has been diagnosed with a need for potentiation of muscarinic acetylcholine receptor activity prior to the administering step. In a yet further aspect, the method further comprises the step of identifying a mammal in need of potentiating muscarinic acetylcholine receptor activity. In a still further aspect, the potentiation of muscarinic acetylcholine receptor activity treats a disorder associated with muscarinic acetylcholine receptor activity in the mammal. In an even further aspect, the muscarinic acetylcholine receptor is mAChR $M_4$.

In a further aspect, potentiation of muscarinic acetylcholine receptor activity in a mammal is associated with the treatment of a neurological and/or psychiatric disorder associated with a muscarinic receptor dysfunction. In a yet further aspect, the muscarinic receptor is mAChR $M_4$. In a still further aspect, the disorder is a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the disorder is a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, disorder is selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

c. Enhancing Cognition

In one aspect, the invention relates to a method for enhancing cognition in a mammal comprising the step of administering to the mammal an effective amount of least one disclosed compound; or a pharmaceutically acceptable salt, hydrate, solvate, or polymorph thereof.

In a further aspect, the compound administered is a product of a disclosed method of making a compound. In a still further aspect, an effective amount is a therapeutically effective amount. In a yet further aspect, an effective amount is a prophylactically effective amount.

In a further aspect, the compound administered exhibits potentiation of mAChR $M_4$ with an $EC_{50}$ of less than about 10,000 nM. In a still further aspect, the compound administered exhibits potentiation of mAChR $M_4$ with an $EC_{50}$ of less than about 5,000 nM. In an even further aspect, the compound administered exhibits potentiation of mAChR $M_4$ with an $EC_{50}$ of less than about 1,000 nM. In a further aspect, the compound administered exhibits potentiation of mAChR $M_4$ with an $EC_{50}$ of less than about 500 nM. In a yet further aspect, the compound administered exhibits potentiation of mAChR $M_4$ with an $EC_{50}$ of less than about 100 nM.

In a further aspect, the compound administered exhibits potentiation of mAChR $M_4$ with an $EC_{50}$ of between from about 10,000 nM to about 1 nM. In a yet further aspect, the compound administered exhibits potentiation of mAChR $M_4$ with an $EC_{50}$ of between from about 1,000 nM to about 1 nM. In a still further aspect, the compound administered exhibits potentiation of mAChR $M_4$ with an $EC_{50}$ of between from about 100 nM to about 1 nM. In an even further aspect, the compound administered exhibits potentiation of mAChR $M_4$ with an $EC_{50}$ of between from about 10 nM to about 1 nM.

In one aspect, the mammal is a human. In a further aspect, the mammal has been diagnosed with a need for cognition enhancement prior to the administering step. In a further aspect, the method further comprises the step of identifying a mammal in need of cognition enhancement. In a further aspect, the need for cognition enhancement is associated with a muscarinic receptor dysfunction. In an even further aspect, the muscarinic receptor is mAChR $M_4$.

In a further aspect, the cognition enhancement is a statistically significant increase in Novel Object Recognition. In a further aspect, the cognition enhancement is a statistically significant increase in performance of the Wisconsin Card Sorting Test.

d. Potentiating Muscarinic Acetylcholine Receptor Activity in Cells

In one aspect, the invention relates to a method for potentiation of muscarinic acetylcholine receptor activity in a mammal comprising the step of administering to the mammal an effective amount of at least one disclosed compound; or a pharmaceutically acceptable salt, hydrate, solvate, or polymorph thereof.

In a further aspect, the compound administered is a product of a disclosed method of making a compound. In a still further aspect, an effective amount is a therapeutically effective amount. In a yet further aspect, an effective amount is a prophylactically effective amount.

In a further aspect, potentiation of muscarinic acetylcholine receptor activity increases muscarinic acetylcholine receptor activity. In a still further aspect, potentiation of muscarinic acetylcholine receptor activity is partial agonism of the muscarinic acetylcholine receptor. In a yet further aspect, potentiation of muscarinic acetylcholine receptor activity is positive allosteric modulation of the muscarinic acetylcholine receptor.

In a further aspect, the compound exhibits potentiation of mAChR $M_4$ with an $EC_{50}$ of less than about 10,000 nM. In a still further aspect, the compound exhibits potentiation of mAChR $M_4$ with an $EC_{50}$ of less than about 5,000 nM. In an even further aspect, the compound exhibits potentiation of mAChR $M_4$ with an $EC_{50}$ of less than about 1,000 nM. In a further aspect, the compound exhibits potentiation of mAChR $M_4$ with an $EC_{50}$ of less than about 500 nM. In a yet further aspect, the compound potentiation of mAChR $M_4$ with an $EC_{50}$ of less than about 100 nM.

In a further aspect, the compound exhibits potentiation of mAChR $M_4$ with an $EC_{50}$ of between from about 10,000 nM to about 1 nM. In a yet further aspect, the compound exhibits potentiation of mAChR $M_4$ with an $EC_{50}$ of between from about 1,000 nM to about 1 nM. In a still further aspect, the compound exhibits potentiation of mAChR $M_4$ with an $EC_{50}$ of between from about 100 nM to about 1 nM. In an even further aspect, the compound exhibits potentiation of mAChR $M_4$ with an $EC_{50}$ of between from about 10 nM to about 1 nM.

In one aspect, the cell is mammalian. In a further aspect, the cell is human. In a still further aspect, the cell has been isolated from a mammal prior to the contacting step. In a yet further aspect, contacting is via administration to a mammal.

In a further aspect, the mammal has been diagnosed with a need for potentiation of muscarinic acetylcholine receptor activity prior to the administering step. In a further aspect, the method further comprises the step of identifying a mammal in need of potentiation of muscarinic acetylcholine receptor activity. In a further aspect, the potentiation of muscarinic acetylcholine receptor activity treats a disorder associated with muscarinic receptor activity in the mammal. In a still further aspect, the muscarinic acetylcholine receptor is mAChR $M_4$.

In a further aspect, potentiation of muscarinic acetylcholine receptor activity in at least one cell is associated with the treatment of a neurological and/or psychiatric disorder associated with mAChR $M_4$ dysfunction. In a still further aspect, the disorder is a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the disorder is a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, disorder is selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

2. Cotherapeutic Methods

The present invention is further directed to administration of a selective mAChR $M_4$ activator for improving treatment outcomes in the context of cognitive or behavioral therapy. That is, in one aspect, the invention relates to a cotherapeutic method comprising the step of administering to a mammal an effective amount and dosage of at least one disclosed compound, or a pharmaceutically acceptable salt, hydrate, solvate, or polymorph thereof.

In a further aspect, the compound administered for the cotherapeutic method is a product of a disclosed method of making. In a still further aspect, an effective amount is a therapeutically effective amount. In a yet further aspect, an effective amount is a prophylactically effective amount.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

3. Manufacture of a Medicament

In one aspect, the invention relates to a medicament comprising one or more disclosed compounds; or a pharmaceutically acceptable salt, hydrate, solvate, or polymorph thereof. In a further aspect, the one or more compounds is a product of a disclosed method of making.

In various aspect, the invention relates methods for the manufacture of a medicament for modulating the activity mAChR $M_4$ (e.g., treatment of one or more neurological and/or psychiatric disorder associated with mAChR $M_4$ dysfunction) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

4. Use of Compounds

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the compound used exhibits potentiation of mAChR $M_4$ activity with an $EC_{50}$ of less than about 10,000 nM. In a still further aspect, the compound used exhibits potentiation of mAChR $M_4$ activity with an $EC_{50}$ of less than about 5,000 nM. In an even further aspect, the compound used exhibits potentiation of mAChR $M_4$ with an $EC_{50}$ of less than about 1,000 nM. In a further aspect, the compound used exhibits potentiation of mAChR $M_4$ activity with an $EC_{50}$ of less than about 500 nM. In a yet further aspect, the compound used potentiation of mAChR $M_4$ activity with an $EC_{50}$ of less than about 100 nM.

In a further aspect, the compound used exhibits potentiation of mAChR $M_4$ activity with an $EC_{50}$ of between from about 10,000 nM to about 1 nM. In a further aspect, the compound used exhibits potentiation of mAChR $M_4$ activity with an $EC_{50}$ of between from about 1,000 nM to about 1 nM. In a still further aspect, the compound used exhibits potentiation of mAChR $M_4$ activity with an $EC_{50}$ of between from about 100 nM to about 1 nM. In an even further aspect, the compound used exhibits potentiation of mAChR $M_4$ activity with an $EC_{50}$ of between from about 10 nM to about 1 nM. In a yet further aspect, potentiation of mAChR $M_4$ activity is positive allosteric modulation of mAChR $M_4$ activity.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for mAChR $M_1$ receptor activation. In one aspect, the use is characterized in that the mammal is a human. In one aspect, the use is characterized in that the disorder is a neurological and/or psychiatric disorder associated with a muscarinic acetylcholine receptor dysfunction. In one aspect, the neurological and/or psychiatric disorder associated with muscarinic acetylcholine receptor dysfunction is treated by potentiation of muscarinic acetylcholine receptor activity in a mammal.

In a further aspect, the use relates to the manufacture of a medicament for the treatment of a disorder associated with a muscarinic acetylcholine receptor dysfunction in a mammal. In a further aspect, the medicament is used in the treatment of a neurological and/or psychiatric disorder associated with a muscarinic acetylcholine receptor dysfunction in a mammal.

In a further aspect, the use relates to potentiation of muscarinic acetylcholine receptor activity in a mammal. In a further aspect, the use relates to partial agonism of muscarinic acetylcholine receptor activity in a mammal. In a further aspect, the use relates to modulating mAChR $M_1$ activity in a mammal. In a still further aspect, the use relates to modulating mAChR $M_1$ activity in a cell. In a yet further aspect, the use relates to partial allosteric agonism of mAChR $M_1$ in a cell. In an even further aspect, the mammal is a human.

In one aspect, the use is associated with the treatment of a neurological and/or psychiatric disorder associated with muscarinic acetylcholine receptor dysfunction. In a further aspect, the use is associated with the treatment of a psychotic disorder. In a still further aspect, the use is associated with the treatment of a psychotic disorder selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the use is associated with the treatment of a neurological disorder selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the use is associated with the treatment of a psychotic disorder selected from schizophrenia, brief psychotic disorder, schizophreniform disorder, schizoaffective disorder, delusional disorder, and shared psychotic disorder. In a still further aspect, the use is associated with the treatment of a schizophrenia selected from catastrophic schizophrenia, catatonic schizophrenia, paranoid schizophrenia, residual schizophrenia, disorganized schizophrenia, and undifferentiated schizophrenia. In a yet further aspect, the use is associated with the treatment of a disorder selected from schizoid personality disorder, schizotypal personality disorder, and paranoid personality disorder.

In a further aspect, the use is associated with the treatment of a cognitive disorder. In a still further aspect, the use is associated with the treatment of a cognitive disorder selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, the use is associated with the treatment of a disorder selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with mAChR $M_4$ receptor dysfunction in a mammal. In a further aspect, the disorder is a neurological and/or psychiatric disorder.

5. Kits

In one aspect, the invention relates to kits comprising at least one disclosed compound; or a pharmaceutically acceptable salt, hydrate, solvate, or polymorph thereof, and one or more of:

(a) at least one agent known to increase mAChR $M_4$ activity;
(b) at least one agent known to decrease mAChR $M_4$ activity;
(c) at least one agent known to treat a disorder associated with cholinergic activity;
(d) instructions for treating a disorder associated with cholinergic activity;
(e) instructions for treating a disorder associated with $M_1$ receptor activity; or
(f) instructions for administering the compound in connection with cognitive or behavioral therapy.

In various further aspects, the invention relates to kits comprising at least one disclosed compound and at least one agent known to have $M_4$ receptor agonist activity.

In various further aspects, the invention relates to kits comprising at least one product of a disclosed method of making and at least one agent known to have $M_4$ receptor agonist activity.

In a further aspect, the kit comprises a disclosed compound or a product of a disclosed method of making.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

6. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by activation or modulation of the muscarinic receptor and/or a need for activation or modulation of muscarinic receptor activity prior to the administering step. In some aspects of the disclosed method, the subject has been diagnosed with anxiety or a related disorder prior to the administering step. In some aspects of the disclosed methods, the subject has been identified with a need for treatment prior to the administering step. In some aspects of the disclosed method, the subject has been identified with a disorder treatable by activation of the muscarinic receptor and/or or a need for activation/modulation of muscarinic activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard. Coupling constants (J-values) are expressed in Hz units.

Microwave assisted reactions were performed in a single-mode reactor: Emrys™ Optimizer microwave reactor (Personal Chemistry A.B., currently Biotage).

Flash column chromatography was performed using ready-to-connect cartridges from: (a) ISCO, on irregular silica gel, particle size 15-40 μm (normal layer disposable flash columns) on a Companion system from ISCO, Inc.; or, (b) Merck, on irregular silica gel, particle size 15-40 μm (normal layer disposable flash columns) on an SPOT or LAFLASH system from Armen Instrument.

Analytical HPLC was performed on an HP 1100 with UV detection at 214 and 254 nm along with ELSD detection and low resolution mass spectra using an Agilent 1200 series 6130 mass spectrometer.

2. LC-MS Methods

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software. [M+H], means the protonated mass of the free base of the compound and where indicated R$_T$ means retention time (in minutes).

In the LC-MS analysis, reversed phase HPLC was carried out on an Agilent 1200 with a Kinetex C18 column (2.6 μm, 2.1×30 mm) from Phenomenex, with a flow rate of 1.5 mL/min, at 45° C. The gradient conditions used are: 93% A (0.1% TFA in water), 7% B (acetonitrile), to 5% A, 95% B in 1.1 minutes. Injection volume was 3.0 μl. Low-resolution ES positive mass spectra (single quadrupole, Agilent 6130) were acquired by scanning from 100 to 700 in 0.25 seconds. The capillary needle voltage was 3 kV.

3. Preparation of 5-amino-N-(benzo[d][1,3]dioxol-5-ylmethyl)-3,4-dimethylthieno[2,3-c]pyridazine-6-carboxamide (Example 1, Method A)

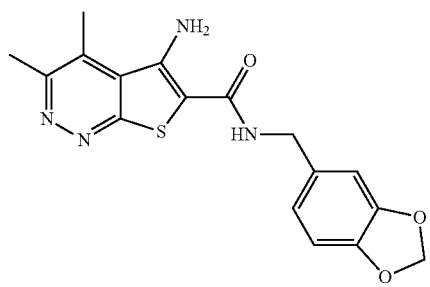 [SMILES: Cc1nnc2sc(C(=O)NCc3ccc4c(c3)OCO4)c(N)c2c1C]

The overall synthesis scheme for the preparation of 5-amino-N-(benzo[d][1,3]dioxol-5-ylmethyl)-3,4-dimethylthieno[2,3-c]pyridazine-6-carboxamide is shown below (Example 1, Method A) is shown below.

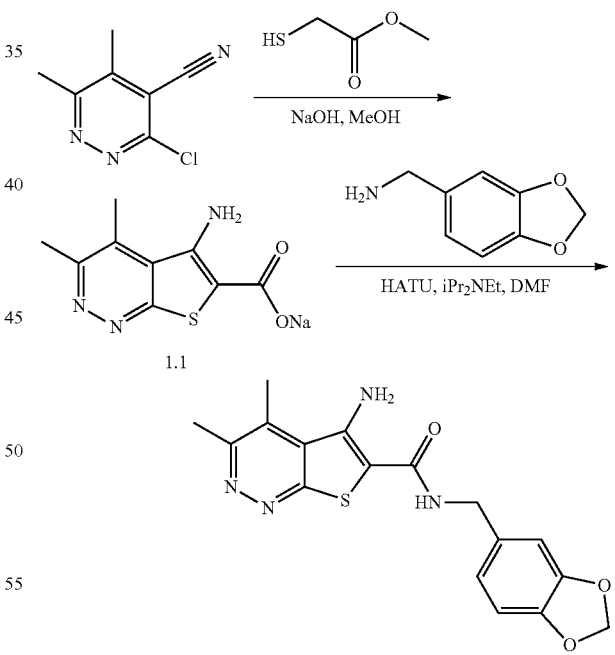

Example 1
(Compound B12, Table I)

a. Sodium 5-amino-3,4-dimethylthieno[2,3-c]pyridazine-6-carboxylate (Compound 1.1)

In a 20 mL microwave vial fitted with a stir bar was added 3-chloro-5,6-dimethylpyridazine-4-carbonitrile (580 mg, 3.50 mmol) and MeOH (7 mL). Methyl thioglycolate (325 µL, 3.60 mmol) was added followed by an aqueous solution of NaOH (1 M, 7.6 mmol). The microwave vial was sealed and heated to 150° C. for 30 min. The vial was cooled and the solution was concentrated to provide sodium 5-amino-3,4-dimethylthieno[2,3-c]pyridazine-6-carboxylate (A) that was used without further purification. LCMS: $R_T$=0.320 min, >99% @ 254 nm, >99% @ 220 nm; m/z (M+1)$^+$=224.

b. 5-amino-N-(benzo[d][1,3]dioxol-5-ylmethyl)-3,4-dimethylthieno[2,3-c]pyridazine-6-carboxamide (Example 1)

In an oven-dried round bottom flask, fitted with a stir bar and a septum, was added sodium 5-amino-3,4-dimethylthieno[2,3-c]pyridazine-6-carboxylate (110 mg, 0.45 mmol) and DMF (1.5 mL). Piperonylamine (62 µL, 0.49 mmol) was added followed by Hünig's base (195 µL, 1.12 mmol) and O-(7-azabenzotriazol-1-yl)-N,N,N',N'-tetramethyluronium hexafluorophosphate (HATU, 171 mg, 0.45 mmol). The reaction mixture was stirred for 2 h at ambient temperature and then 10% NaOH (aq, 15 mL) was added. The mixture was extracted with DCM (3×20 mL) and the organic fractions were combined and passed through a phase separator. The solution was concentrated and the resulting oil was purified on silica gel using ethyl acetate/hexanes as the mobile phase. The desired fractions were combined and concentrated to provide the title compound (51 mg, 47% yield). LCMS: $R_T$=0.589 min, >99% @ 254 nm, >99% @ 220 nm; m/z (M+1)$^+$=357. $^1$H NMR (400 MHz, CDCl$_3$, δ(ppm)): 8.6 (t; J=6.0 Hz; 1H), 6.9 (bs; 2H), 6.8-6.7 (m; 3H), 6.0 (s; 2H), 4.3 (d; J=6.0 Hz; 2H), 2.71 (s; 3H), 2.69 (s; 3H). HRMS calculated for C$_{17}$H$_{17}$N$_4$O$_3$S (M+H)$^+$ m/z: 357.1021, measured: 357.1018.

4. Preparation of 5-amino-3,4-dimethyl-N-(4-(1,1,1-trifluoro-2-hydroxypropan-2-yl)benzyl)thieno[2,3-c]pyridazine-6-carboxamide (Example 2, Method B)

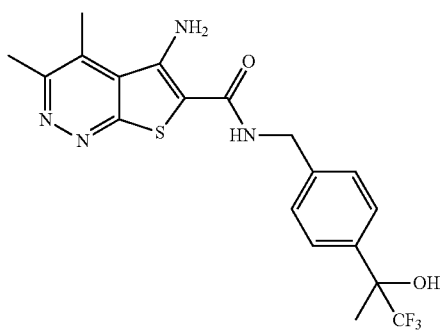 [SMILES: Cc1nnc2sc(C(=O)NCc3ccc(C(C)(O)C(F)(F)F)cc3)c(N)c2c1C]

The overall synthesis scheme for the preparation of 5-amino-3,4-dimethyl-N-(4-(1,1,1-trifluoro-2-hydroxypropan-2-yl)benzyl)thieno[2,3-c]pyridazine-6-carboxamide (Example 2, Method B) is shown below.

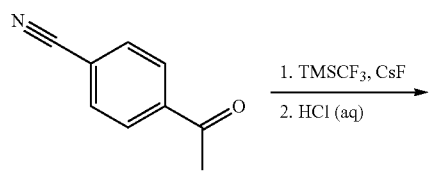

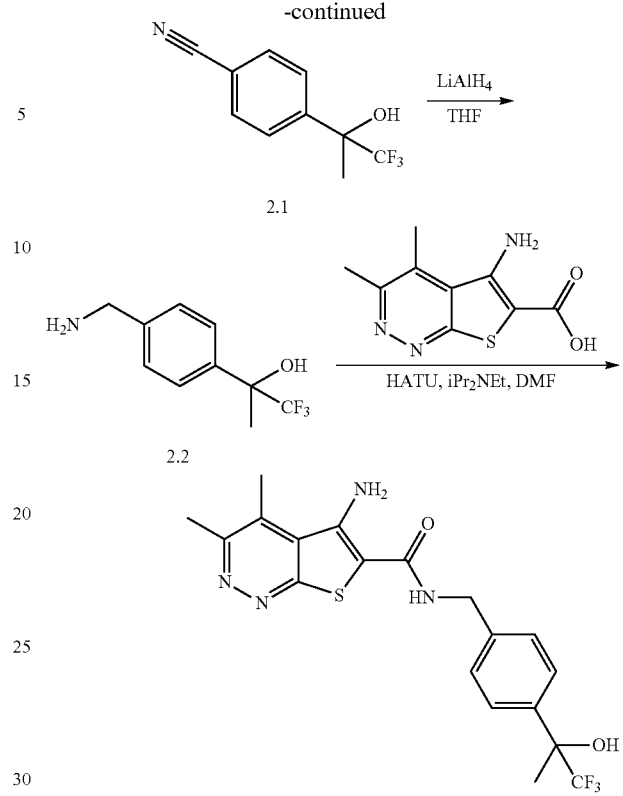

Example 2
(Compound B106, Table I)

a. 4-(1,1,1-trifluoro-2-hydroxypropan-2-yl)benzonitrile (Compound 2.1)

In an oven dried 250 ml round bottom flask fitted with a magnetic stir bar and a septum was added 4-acetylbenzonitrile (1.0 g, 6.9 mmol) and THF (70 mL) at ambient temperature. To this solution was added cesium fluoride (1 mol %) followed by trimethylsilyltrifluoromethane (TMSCF$_3$, 1.2 mL, 7.6 mmol). The solution was stirred at ambient temperature for 3 h and a 2 N HCL aqueous solution (25 mL) was added. The biphasic mixture was vigorously stirred for 18 h. Then, the mixture was diluted with de-ionized H$_2$O (20 mL) and extracted with ethyl acetate (3×25 mL). The organic fractions were combined, dried over MgSO$_4$, filtered and concentrated. It was exposed to high vacuum for 3 h and used without further purification. LCMS: $R_T$=0.604 min, >99% @ 254 nm, >99% @ 220 nm; m/z (M+1)$^+$=216.

b. 2-(4-(aminomethyl)phenyl)-1,1,1-trifluoropropan-2-ol (Compound 2.2)

In an oven dried round bottom flask fitted with a magnetic stir bar and a septum was added lithium aluminum hydride solution (5.1 mL, 2 M in THF, 10.3 mmol) and THF (65 mL) under inert atmosphere. The solution was cooled to 0° C. and 4-(1, 1, 1-trifluoro-2-hydroxypropan-2-yl)benzonitrile (1.5 g, 69 mmol) was added drop-wise as a solution in THF (5 mL) via dropping funnel. After complete addition, the funnel was rinsed with THF (5 mL) and the solution was warmed to ambient temperature and then fitted with a reflux condenser and heated to reflux for 6 h. The solution was cooled to 0° C. and the workup according to Fieser & Fieser (see Fieser, L. F. and Fieser, M. *Reagents for Organic Synthesis*, Vol. 1; John Wiley & Sons: New York, N.Y., 1967, p. 584) was followed to give 2-(4-(aminomethyl)phenyl)-1,1,1-trifluoropropan-2-ol which was used without further purification. LCMS: $R_T$=0.294 min, >99% @ 254 nm, >99% @ 220 nm; m/z $(M+1)^+$=220.

c. 5-amino-3,4-dimethyl-N-(4-(1,1,1-trifluoro-2-hydroxypropan-2-yl)benzyl)thieno[2,3-c]pyridazine-6-carboxamide (Example 2)

In a one dram vial fitted with a magnetic stir bar and a cap was added 5-amino-3,4-dimethylthieno[2,3-c]pyridazine-6-carboxylic acid (35 mg, 0.16 mmol) and DMF (450 μL). 2-(4-(aminomethyl)phenyl)-1,1,1-trifluoropropan-2-ol (36 mg, 0.17 mmol) was added followed by Hünig's base (82 μL, 0.47 mmol) and O-(7-azabenzotriazol-1-yl)-N,N,N',N'-tetramethyluronium hexafluorophosphate (HATU, 60 mg, 0.16 mmol). The reaction mixture was stirred for 2 h at ambient temperature and then 10% NaOH aqueous solution was added (15 mL). The mixture was extracted with DCM (3×20 mL) and the organic fractions were combined and passed through a phase separator. The solution was concentrated and the resulting oil was purified on silica gel using dichloromethane/methanol as a mobile phase. The desired fractions were combined and concentrated to provide the title compound. LCMS: $R_T$=0.609 min, >99% @ 254 nm, >99% @ 220 nm; m/z $(M+1)^+$=425. $^1$H NMR (400 MHz, CDCl$_3$, δ(ppm)): 8.6 (t; J=4.0 Hz; 1H), 7.5 (d; J=8.0 Hz; 2H), 7.3 (d; J=8.0 Hz; 2H), 6.9 (bs; 2H), 6.5 (s; 1H), 4.4 (d; J=8.0 Hz; 2H), 2.71 (s; 3H), 2.69 (s; 3H), 1.6 (s; 3H). HRMS calculated for $C_{19}H_{20}F_3N_4O_2S$ $(M+H)^+$ m/z: 425.1259, measured: 425.1258.

5. Preparation of 5-amino-N-(1-((2-fluorophenyl)sulfonyl)azetidin-3-yl)-3,4-dimethylthieno[2,3-c]pyridazine-6-carboxamide (Example 3, Method C)

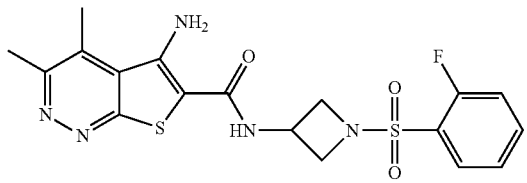

The overall synthesis scheme for the preparation of 5-amino-N-(1-(2-fluorophenyl)sulfonyl)azetidin-3-yl)-3,4-dimethylthieno[2,3-c]pyridazine-6-carboxamide (Example 3, Method C) is shown below.

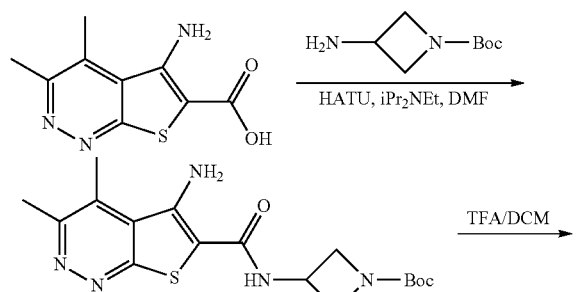

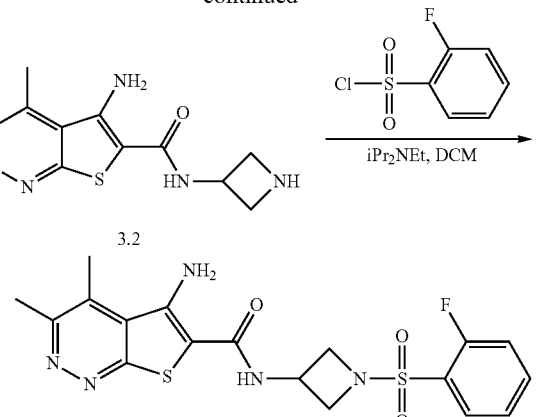

Example 3
(Compound B140, Table I)

a. tert-butyl 3-(5-amino-3,4-dimethylthieno[2,3-c]pyridazine-6-carboxamido)azetidine-1-carboxylate (Compound 3.1)

In an oven dried round bottom flask with a magnetic stir bar and a septum was added 5-amino-3,4-dimethylthieno[2,3-c]pyridazine-6-carboxylic acid (750 mg, 3.4 mmol) and DMF (16 mL). tert-Butyl 3-aminoazetidine-1-carboxylate (630 μL, 3.7 mmol) was added followed by Hünig's base (880 μL, 5.1 mmol) and O-(7-azabenzotriazol-1-yl)-N,N,N',N'-tetramethyluronium hexafluorophosphate (HATU, 1.3 g, 3.4 mmol). The reaction mixture was stirred for 2 h at ambient temperature and then 10% NaOH aqueous solution was added (15 mL). The mixture was extracted with DCM (3×20 mL) and the organic fractions were combined and passed through a phase separator. The solution was concentrated and the resulting oil was purified on silica gel using dichloromethane/methanol as a mobile phase. The desired fractions were combined and concentrated to provide tert-butyl 3-(5-amino-3,4-dimethylthieno[2,3-c]pyridazine-6-carboxamido)azetidine-1-carboxylate. LCMS: $R_T$=0.612 min, >99% @ 254 nm, >99% @ 220 nm; m/z $(M+1)^+$=378.

b. 5-amino-N-(azetidin-3-yl)-3,4-dimethylthieno[2,3-c]pyridazine-6-carboxamide (Compound 3.2)

In a round bottom flask fitted with a magnetic stir bar and a cap, tert-butyl 3-(5-amino-3,4-dimethylthieno[2,3-c]pyridazine-6-carboxamido)azetidine-1-carboxylate was dissolved in DCM (20 mL). To the solution was added trifluoroacetic acid (5 mL) and the solution was stirred at ambient temperature for 1 h and concentrated to yield a residue. The residue was dissolved in MeOH (5 mL) and was purified via ion exchange chromatography (Agilent SCX cartridge, MeOH followed by NH$_4$OH/MeOH eluent). The desired fractions were combined and concentrated to yield 5-amino-N-(azetidin-3-yl)-3,4-dimethylthieno[2,3-c]pyridazine-6-carboxamide and it was used without further purification. LCMS: $R_T$=0.188 min, >99% @ 254 nm, >99% @ 220 nm; m/z $(M+1)^+$=278.

c. 5-amino-N-(1-((2-fluorophenyl)sulfonyl)azetidin-3-yl)-3,4-dimethylthieno[2,3-c]pyridazine-6-carboxamide (Example 3)

In a one dram vial fitted with a magnetic stir bar and a cap was added 5-amino-N-(azetidin-3-yl)-3,4-dimethylthieno[2, 3-c]pyridazine-6-carboxamide (40 mg, 0.14 mmol) and DCM (1.4 mL). Hünig's base (30 μL, 0.17 mmol) was added followed by 2-fluorobenzene-1-sulfonyl chloride (21 μL, 0.16 mmol). The solution was stirred at ambient temperature for 18 h. It was concentrated to yield a residue that was diluted in DMSO and purified on preparative Phenomenex Gemini-C18 column using 0.1% NH$_4$OH in H$_2$O/acetonitrile as a mobile phase. The desired fractions were combined and concentrated to afford the title compound. LCMS: R$_T$=0.590 min, >99% @ 254 nm, >99% @ 220 nm; m/z (M+1)$^+$=436. $^1$H NMR (400 MHz, CDCl$_3$, δ(ppm)): 8.5 (d; J=8.0 Hz; 1H), 7.8-7.7 (m; 2H), 7.5 (dd; J=8.0, 8.0 Hz; 1H), 7.47 (t; J=8.0 Hz; 1H), 6.9 (bs; 2H), 4.5 (ddd; J=12.0, 8.0, 8.0 Hz; 1H), 4.1 (dd; J=8.0, 8.0 Hz; 2H), 4.0 (dd; J=8.0, 8.0 Hz, 2H), 2.70 (s; 3H), 2.67 (s; 3H). HRMS calculated for C$_{18}$H$_{19}$FN$_5$O$_3$S$_2$ (M+H)$^+$ m/z: 436.0913, measured: 436.0910.

6. Preparation of (5-amino-3,4-dimethylthieno[2,3-c]pyridazin-6-yl)(3-((4-fluorobenzyl)amino)azetidin-1-yl)methanone (Example 4, Method D)

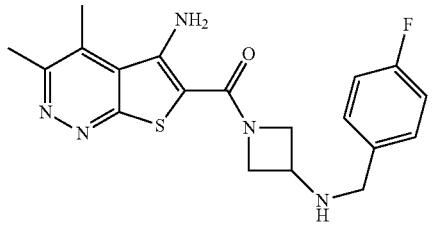 [SMILES: Cc1nnc2sc(C(=O)N3CC(NCc4ccc(F)cc4)C3)c(N)c2c1C]

The overall synthesis scheme for the preparation of (5-amino-3,4-dimethylthieno[2,3-c]pyridazin-6-yl)(3-((4-fluorobenzyl)amino)azetidin-1-yl)methanone (Example 4, Method D) is shown below.

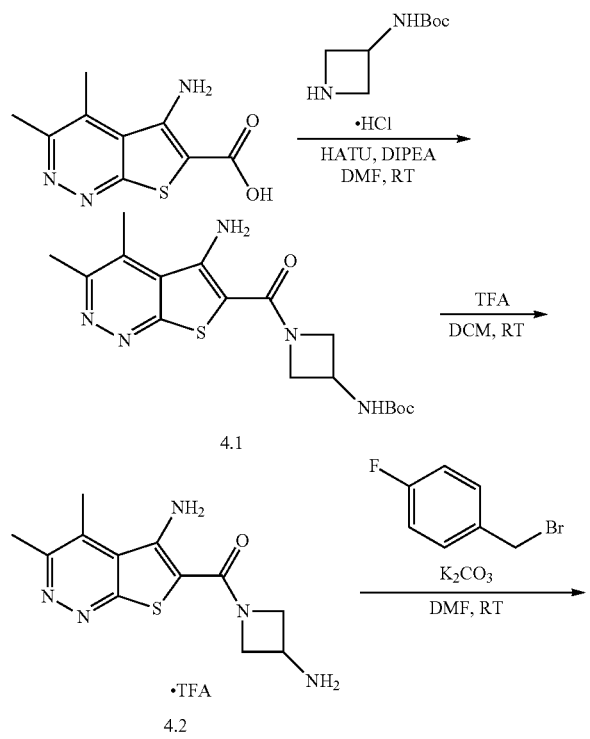

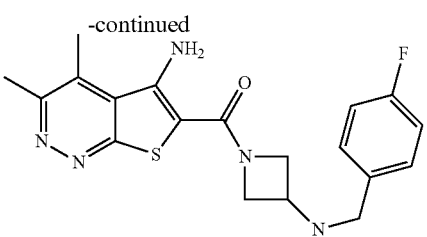

Example 4
(Compound B59, Table I)

a. (5-amino-3,4-dimethylthieno[2,3-c]pyridazin-6-yl)(3-azido-3-phenylazetidin-1-yl)methanone (Compound 4.1)

In a 20-mL scintillation vial equipped with a stir bar, 5-amino-3,4-dimethylthieno[2,3-c]pyridazine-6-carboxylic acid (100 mg, 0.448 mmol) and HATU (190 mg, 0.500 mmol) were massed and dissolved in DMF (4 mL). Diisopropylethyl amine (120 mg, 0.930 mmol) was added, and the reaction was allowed to stir at ambient temperature for 5 min. tert-Butyl azetidin-3-ylcarbamate hydrochloric acid salt (100 mg, 0.481 mmol) in DMF (2 mL) was then added, and the reaction was monitored by LCMS, which confirmed complete consumption of the starting material after 30 min. The reaction was diluted into DCM/H$_2$O (20 mL, 1:1), and the organic layer was separated. The aqueous layer was extracted with DCM (2×10 mL), and the combined organic fractions were dried over MgSO$_4$, filtered, and concentrated under reduced pressure. The crude residue was purified by flash column chromatography using a 12-gram ISCO column and eluting with 0 to 10% MeOH/DCM to afford tert-butyl (1-(5-amino-3,4-dimethylthieno[2,3-c]pyridazine-6-carbonyl)azetidin-3-yl)carbamate (LCMS: R$_T$=0.517 min, m/z=378 [M+H]$^+$).

b. (5-amino-3,4-dimethylthieno[2,3-c]pyridazin-6-yl)(3-aminoazetidin-1-yl)methanone (Compound 4.2)

In a 20-mL scintillation vial equipped with a stir bar, tert-butyl (1-(5-amino-3,4-dimethylthieno[2,3-c]pyridazine-6-carbonyl)azetidin-3-yl)carbamate (160 mg, 0.424 mmol) was massed and dissolved in DCM (10 mL), followed by the addition of TFA (2 mL) at ambient temperature. The reaction was monitored by LCMS until the starting material was completely consumed. After 1 hr, the reaction was concentrated under reduced pressure to afford (5-amino-3,4-dimethylthieno[2,3-c]pyridazin-6-yl)(3-aminoazetidin-1-yl)methanone trifluoroacetic acid salt (LCMS: R$_T$=0.175 min, m/z=278 [M+H]$^+$), which was carried forward without further purification.

c. (5-amino-3,4-dimethylthieno[2,3-c]pyridazin-6-yl)(3-((4-fluorobenzyl)amino)azetidin-1-yl)methanone (Example 4)

In a 20-mL scintillation vial equipped with a stir bar, (5-amino-3,4-dimethylthieno[2,3-c]pyridazin-6-yl)(3-aminoazetidin-1-yl)methanone trifluoroacetic acid salt (26 mg, 0.090 mmol) and K$_2$CO$_3$ (50 mg, 0.362 mmol) were massed and dissolved in DMF (3 mL). 1-(Bromomethyl)-4-fluorobenzene (16 mg, 0.0847 mmol) was dissolved in DMF (1 mL) and added to the reaction via syringe. The reaction was allowed to stir for 16 hr at ambient temperature. The reaction was then diluted into DCM/H$_2$O (20 mL, 1:1) and the organic layer was separated. The aqueous layer was extracted with DCM (2×10 mL). The combined organic fractions were dried over MgSO$_4$, filtered, and concentrated under reduced pressure. The crude product was dissolved in DMSO (1 mL) and purified by reverse phase HPLC, eluting with acetonitrile/water/trifluoroacetic acid. The fractions containing the desired product were partially concentrated, then diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 7.40-7.37 (m, 2H), 7.15 (t, J=8.8 Hz, 2H), 7.01 (s, 2H), 4.43-4.29 (m, 4H), 3.67 (s(br), 1H), 3.62 (m, 2H), 2.98 (s(br), 1H), 2.73 (s, 3H), 2.71 (s, 3H). LCMS: R$_T$=0.405 min, m/z=386 [M+H]$^+$. HRMS calculated for C$_{19}$H$_{21}$N$_5$OFS: 386.1451. found: 386.1451.

7. Preparation of (5-amino-3,4-dimethylthieno[2,3-c]pyridazin-6-yl)(3-methoxy-3-phenylazetidin-1-yl)methanone (Example 5, Method E)

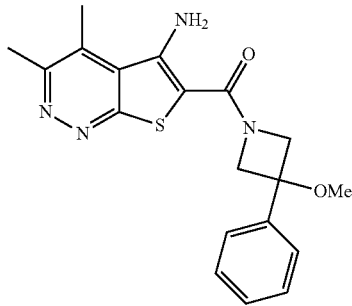 [SMILES: COC1(c2ccccc2)CN(C(=O)c2sc3nnc(C)c(C)c3c2N)C1]

The overall synthesis scheme for the preparation of (5-amino-3,4-dimethylthieno[2,3-c]pyridazin-6-yl)(3-methoxy-3-phenylazetidin-1-yl)methanone (Example 5, Method E) is shown below.

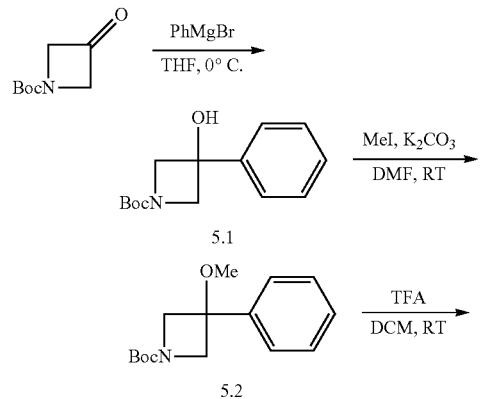

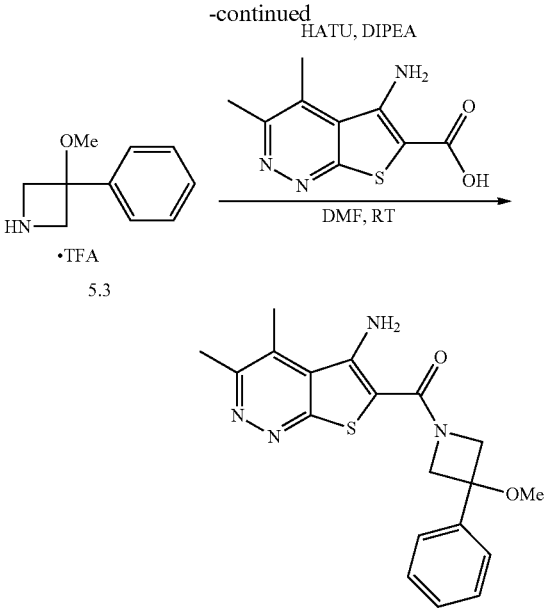

Example 5
(Compound B170, Table I)

a. tert-butyl 3-hydroxy-3-phenylazetidine-1-carboxylate (Compound 5.1)

In a flame-dried 20-mL scintillation vial equipped with a stir bar, tert-butyl 3-oxoazetidine-1-carboxylate (275 mg, 1.61 mmol) was massed under an atmosphere of argon. Tetrahydrofuran (10 mL) was added, and the reaction was cooled to 0° C. Phenylmagnesium bromide (3.0 M in THF, 0.80 mL, 2.40 mmol) was added dropwise over 2 min. The reaction was allowed to stir for 10 min, after which time the starting material was completely consumed, as indicated by LCMS. The reaction was quenched at 0° C. with saturated aqueous NH$_4$Cl. The reaction was diluted into EtOAc/H$_2$O (40 mL, 1:1). The organic layer was separated, and the aqueous layer was extracted with EtOAc (2×20 mL). The combined organic fractions were dried over MgSO$_4$, filtered, and concentrated under reduced pressure to afford intermediate A (LCMS: R$_T$=0.665 min, m/z=194 [M+H−56]).

b. 3-methoxy-3-phenylazetidine (Compounds 5.2 and 5.3)

In an oven-dried 20-mL scintillation vial equipped with a stir bar, tert-butyl 3-hydroxy-3-phenylazetidine-1-carboxylate (100 mg, 0.402 mmol) was massed and dissolved in acetonitrile (4 mL). Sodium hydride (60% dispersion in mineral oil, 30 mg, 0.75 mmol) was added at ambient temperature, and the reaction was allowed to stir for 20 min. Methyl iodide (75 mg, 0.528) was then added in acetonitrile (0.5 mL). The reaction was monitored by LCMS, and the starting material was completely consumed after 2 hr. The reaction was quenched with H$_2$O (1 mL), and then diluted into DCM/H$_2$O (40 mL, 1:1). The organic layer was separated, and the aqueous layer was extracted with DCM (2×20 mL). The combined organic fractions were dried over MgSO$_4$, filtered, and concentrated under reduced pressure to afford 5.2 (LCMS: R$_T$=0.696 min, ionizes poorly). The crude residue was dissolved in DCM (10 mL), followed by the addition of TFA (2 mL) at ambient temperature. The reaction was monitored by LCMS until intermediate 5.2 was completely consumed. After 2 hr, the reaction was concentrated under reduced pressure to afford 3-methoxy-3-phenylazetidine trifluoroacetic acid salt (5.3) (LCMS: $R_T$=0.261 min, m/z=164 [M+H]$^+$), which was carried forward without further purification.

c. (5-amino-3,4-dimethylthieno[2,3-c]pyridazin-6-yl)(3-methoxy-3-phenylazetidin-1-yl)methanone (Example 5)

In a 20-mL scintillation vial equipped with a stir bar, 5-amino-3,4-dimethylthieno[2,3-c]pyridazine-6-carboxylic acid (20 mg, 0.0897 mmol) and HATU (45 mg, 0.118 mmol) were massed and dissolved in DMF (3 mL). Diisopropylethyl amine (35 mg, 0.279 mmol) was added, and the reaction was allowed to stir at ambient temperature for 5 min. 3-Methoxy-3-phenylazetidine trifluoroacetic acid salt (35 mg, 0.126 mmol) in DMF (1 mL) was then added, and the reaction was monitored by LCMS, which confirmed complete consumption of the starting material after 30 min. The reaction was diluted into DCM/H$_2$O (40 mL, 1:1), and the organic layer was separated. The aqueous layer was extracted with DCM (2×20 mL), and the combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid. The fractions containing the desired product were concentrated, and then diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 7.50-7.39 (m, 5H), 7.02 (s, 2H), 4.57-4.51 (m, 4H), 3.03 (s, 3H), 2.72 (s, 3H), 2.71 (s, 3H). LCMS: $R_T$=0.584 min, m/z=369 [M+H]$^+$. HRMS calculated for C$_{19}$H$_{21}$N$_4$O$_2$S: 369.1385. found: 369.1382.

8. Preparation of (5-amino-3,4-dimethylthieno[2,3-c]pyridazin-6-yl)(3-hydroxy-3-phenylazetidin-1-yl)methanone (Example 6, Method F)

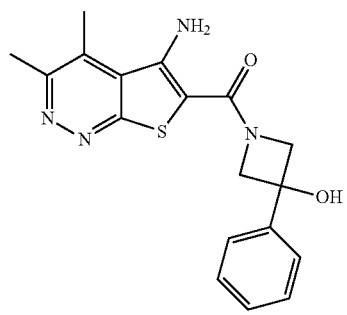 [SMILES: Cc1nnc2sc(C(=O)N3CC(O)(c4ccccc4)C3)c(N)c2c1C]

The overall synthesis scheme for the preparation of (5-amino-3,4-dimethylthieno[2,3-c]pyridazin-6-yl)(3-hydroxy-3-phenylazetidin-1-yl)methanone (Example 6, Method F) is shown below.

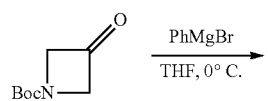

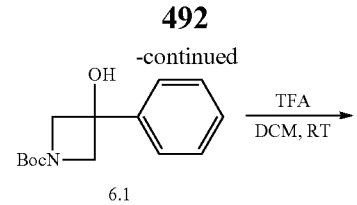

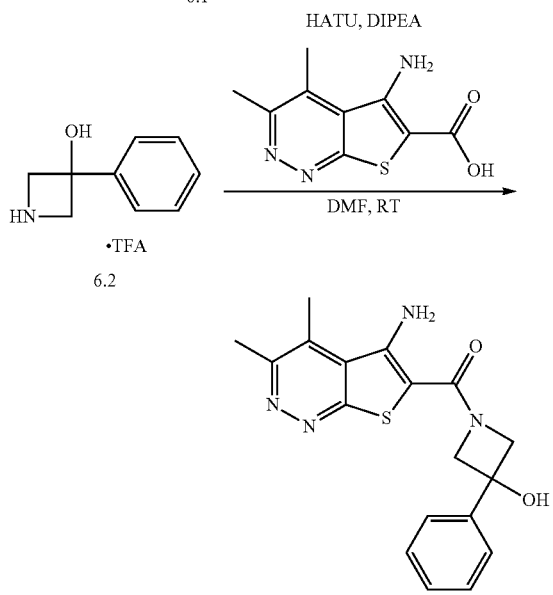

Example 6
(Compound B179, Table I)

a. tert-butyl 3-hydroxy-3-phenylazetidine-1-carboxylate (Compound 6.1)

tert-butyl 3-hydroxy-3-phenylazetidine-1-carboxylate was prepared following the same procedure described for Example 5, Intermediate 6.1.

b. 3-phenylazetidin-3-ol (Compound 6.2)

In a flame-dried 20-mL scintillation vial equipped with a stir bar, tert-butyl 3-oxoazetidine-1-carboxylate (275 mg, 1.61 mmol) was massed under an atmosphere of argon. Tetrahydrofuran (10 mL) was added, and the reaction was cooled to 0° C. Phenylmagnesium bromide (3.0 M in THF, 0.80 mL, 2.40 mmol) was added dropwise over 2 min. The reaction was allowed to stir for 10 min, after which time the starting material was completely consumed as determined by LCMS. The reaction was quenched at 0° C. with saturated aqueous NH$_4$Cl. The reaction was diluted into EtOAc/H$_2$O (40 mL, 1:1). The organic layer was separated, and the aqueous layer was extracted with EtOAc (2×20 mL). The combined organic fractions were dried over MgSO$_4$, filtered, and concentrated under reduced pressure to afford intermediate A (LCMS: $R_T$=0.665 min, m/z=194 [M+H−56]$^+$). The crude residue was dissolved in DCM (20 mL), followed by the addition of TFA (4 mL) at ambient temperature. The reaction was monitored by LCMS until the starting material was completely consumed. After 2 hr, the reaction was concentrated under reduced pressure to afford 3-phenylazetidin-3-ol trifluoroacetic acid salt (LCMS: $R_T$=0.096 min, m/z=150 [M+H]$^+$), which was carried forward without further purification.

c. (5-amino-3,4-dimethylthieno[2,3-c]pyridazin-6-yl)(3-hydroxy-3-phenylazetidin-1-yl)methanone (Example 6)

In a 20-mL scintillation vial equipped with a stir bar, 5-amino-3,4-dimethylthieno[2,3-c]pyridazine-6-carboxylic acid (20 mg, 0.0897 mmol) and HATU (45 mg, 0.118 mmol) were massed and dissolved in DMF (3 mL). Diisopropylethyl amine (35 mg, 0.279 mmol) was added, and the reaction was allowed to stir at ambient temperature for 5 min. 3-Phenylazetidin-3-ol trifluoroacetic acid salt (35 mg, 0.134 mmol) in DMF (1 mL) was then added, and the reaction was monitored by LCMS, which confirmed complete consumption of the starting material after 30 min. The reaction was diluted into DCM/H$_2$O (40 mL, 1:1), and the organic layer was separated. The aqueous layer was extracted with DCM (2×20 mL), and the combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid. The fractions containing the desired product were partially concentrated, then diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 7.58 (d, J=8.0 Hz, 2H), 7.42 (t, J=7.6 Hz, 2H), 7.32 (t, J=7.6 Hz, 1H), 7.08 (s, 2H), 6.53 (s, 1H), 4.52-4.44 (m(br), 4H), 2.74 (s, 3H), 2.73 (s, 3H). LCMS: R$_T$=0.497 min, m/z=355 [M+H]$^+$. HRMS calculated for C$_{18}$H$_{19}$N$_4$O$_2$S: 355.1229. found: 355.1226.

9. Preparation of (S)-5-amino-3,4-dimethyl-N-(1-phenylpyrrolidin-3-yl)thieno[2,3-c]pyridazine-6-carboxamide (Example 7, Method G)

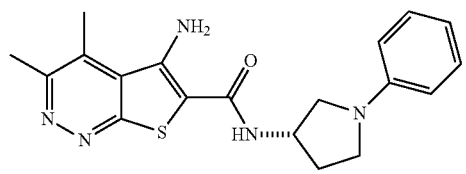

The overall synthesis scheme for the preparation of (S)-5-amino-3,4-dimethyl-N-(1-phenylpyrrolidin-3-yl)thieno[2,3-c]pyridazine-6-carboxamide (Example 7, Method G) is shown below.

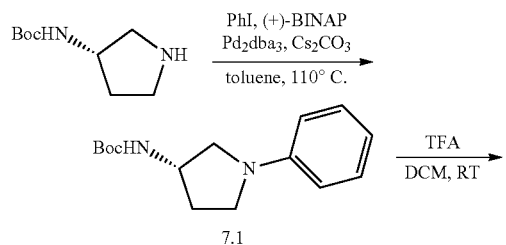

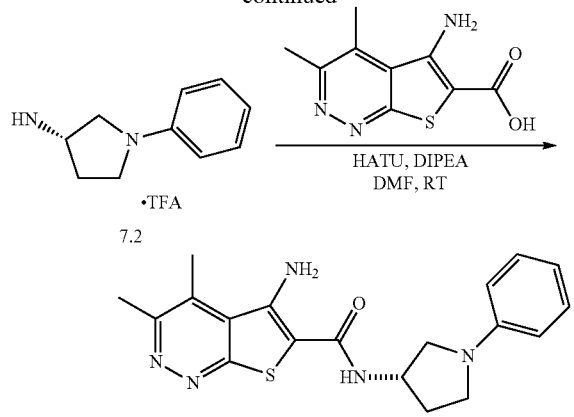

Example 7
(Compound B193, Table I)

a. S)-tert-butyl (1-phenylpyrrolidin-3-yl)carbamate (Compound 7.1)

In an oven-dried 2-dram vial equipped with a stir bar, Pd$_2$dba$_3$ (13 mg, 0.0142 mmol), (±)-BINAP (18 mg, 0.029 mmol), and Cs$_2$CO$_3$ (175 mg, 0.538 mmol) were massed. The vial was purged with argon, dry toluene (2 mL) was added, and the reaction was allowed to stir at ambient temperature for 15 min. In a second oven-dried 2-dram vial, (S)-tert-butyl pyrrolidin-3-ylcarbamate (50 mg, 0.270 mmol) and iodobenzene (80 mg, 0.392 mmol) were massed. The vial was purged with argon, and dry toluene (2 mL) was added. The solution of (S)-tert-butyl pyrrolidin-3-ylcarbamate and iodobenzene were then added to the vial containing the catalyst via syringe. The vials were sealed with a new Teflon cap and heated to 110° C. for 48 hr, after which time the LCMS trace confirmed conversion to the desired product. The reaction was cooled to ambient temperature and diluted into DCM/H$_2$O (20 mL, 1:1). The organic layer was separated, and the aqueous layer was extracted with DCM (2×10 mL). The combined organic layers were dried with a phase separator and concentrated under reduced pressure. The crude product was purified by flash column chromatography using a 4-gram ISCO cartridge and eluting with 0 to 10% MeOH/DCM to afford (S)-tert-butyl (1-phenylpyrrolidin-3-yl)carbamate (LCMS: R$_T$=0.754 min, m/z=263 [M+H]$^+$).

b. (S)-1-phenylpyrrolidin-3-amine (Compound 7.2)

In a 20-mL scintillation vial equipped with a stir bar, (S)-tert-butyl (1-phenylpyrrolidin-3-yl)carbamate (20 mg, 0.0763 mmol) was massed and dissolved in DCM (5 mL), followed by the addition of TFA (1 mL) at ambient temperature. The reaction was monitored by LCMS until the starting material was completely consumed. After 1 hr, the reaction was concentrated under reduced pressure to afford (S)-1-phenylpyrrolidin-3-amine trifluoroacetic acid salt (LCMS: R$_T$=0.352 min, m/z=163 [M+H]$^+$), which was carried forward without further purification.

c. (S)-5-amino-3,4-dimethyl-N-(1-phenylpyrrolidin-3-yl)thieno[2,3-c]pyridazine-6-carboxamide (Example 7)

In a 20-mL scintillation vial equipped with a stir bar, 5-amino-3,4-dimethylthieno[2,3-c]pyridazine-6-carboxylic acid (20 mg, 0.0897 mmol) and HATU (50 mg, 0.132 mmol) were massed and dissolved in DMF (3 mL). Diisopropylethyl amine (50 mg, 0.387 mmol) was added, and the reaction was allowed to stir at ambient temperature for 5 min. (S)-1-Phenylpyrrolidin-3-amine trifluoroacetic acid salt (20 mg, 0.075 mmol) in DMF (1 mL) was then added, and the reaction was monitored by LCMS, which confirmed complete consumption of the starting material after 30 min. The reaction was diluted into DCM/H$_2$O (20 mL, 1:1), and the organic layer was separated. The aqueous layer was extracted with DCM (2×10 mL), and the combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid. The fractions containing the desired product were partially concentrated, diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 8.24 (d, J=6.8 Hz, 1H) 7.17 (t, J=8.4 Hz, 2H) 6.98 (s, 2H), 6.61 (t, J=7.2 Hz, 1H), 6.55 (d, J=8.4 Hz, 2H), 4.66-4.61 (m, 1H), 3.57 (dd, J=7.2 Hz, 9.6 Hz, 1H), 3.44-3.39 (m, 1H), 3.31-3.21 (m, 2H), 2.72 (s, 3H), 2.71 (s, 3H), 2.29-2.25 (m, 1H), 2.15-2.08 (m, 1H). LCMS: R$_T$=0.597 min, m/z=368 [M+H]$^+$. HRMS calculated for C$_{19}$H$_{22}$N$_5$OS: 368.1545. found: 368.1543.

10. Preparation of (5-amino-3,4-dimethylthieno[2,3-c]pyridazin-6-yl)(3-azido-3-phenylazetidin-1-yl)methanone (Example 8, Method H)

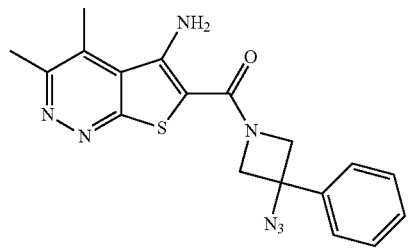 [SMILES: Cc1nnc2sc(C(=O)N3CC(N=[N+]=[N-])(c4ccccc4)C3)c(N)c2c1C]

The overall synthesis scheme for the preparation of (5-amino-3,4-dimethylthieno[2,3-c]pyridazin-6-yl)(3-azido-3-phenylazetidin-1-yl)methanone (Example 8, Method H) is shown below.

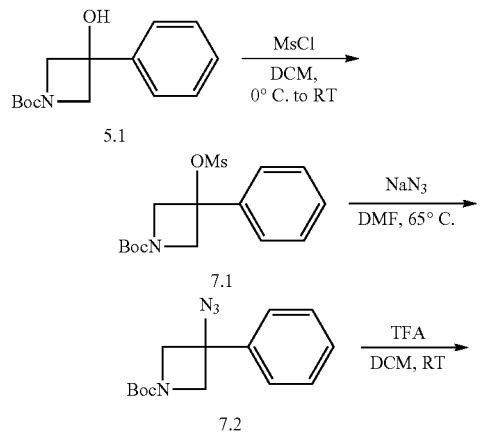

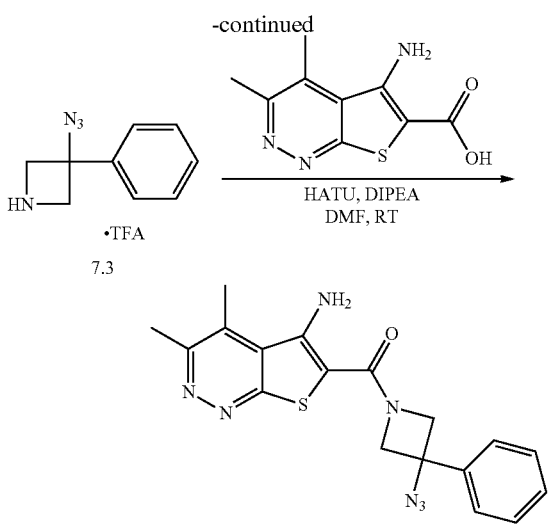

Example 8
(Compound B311, Table I)

a. tert-butyl 3-((methylsulfonyl)oxy)-3-phenylazetidine-1-carboxylate (Compound 7.1)

Intermediate 5.1 was prepared as described herein above. In a 20-mL scintillation vial equipped with a stir bar, tert-butyl 3-hydroxy-3-phenylazetidine-1-carboxylate (A) (275 mg, 1.11 mmol) was massed and dissolved in DCM (6 mL) and cooled to 0° C. Diisopropylethyl amine (290 mg, 2.25 mmol) was added, followed by methanesulfonyl chloride (175 mg, 1.528 mmol). The reaction was allowed to warm to ambient temperature over 1 hr, and then allowed to stir an additional 5 hrs. The reaction was quenched with saturated aqueous NaHCO$_3$, then diluted into DCM/H$_2$O (60 mL, 1:1). The organic layer was separated, and the aqueous layer was extracted with DCM (2×30 mL). The combined organic fractions were dried over MgSO$_4$, filtered, and concentrated under reduced pressure to afford tert-butyl 3-((methylsulfonyl)oxy)-3-phenylazetidine-1-carboxylate, which was carried forward without further purification.

b. tert-butyl 3-azido-3-phenylazetidine-1-carboxylate (Compound 7.2)

In a 20-mL scintillation vial equipped with a stir bar, tert-butyl 3-((methylsulfonyl)oxy)-3-phenylazetidine-1-carboxylate (360 mg, 1.10) was massed and dissolved in DMF (5 mL). Sodium azide (150 mg, 2.308 mmol) was added, and the reaction was heated to 65° C. for 16 hr. The reaction was then cooled to ambient temperature and diluted into DCM/H$_2$O (40 mL, 1:1). The organic layer was separated, and the aqueous layer was extracted with DCM (2×20 mL). The combined organic layers were dried over MgSO$_4$, filtered, and concentrated under reduced pressure. The crude product was purified by flash column chromatography using a 12-gram ISCO column and eluting with 20% to 100% EtOAc/hexanes to afford tert-butyl 3-azido-3-phenylazetidine-1-carboxylate.

c. 3-azido-3-phenylazetidine (Compound 7.3)

In a 20-mL scintillation vial equipped with a stir bar, tert-butyl 3-azido-3-phenylazetidine-1-carboxylate (40 mg, 0.146 mmol) was massed and dissolved in DCM (5 mL), followed by the addition of TFA (1 mL) at ambient temperature. The reaction was monitored by LCMS until the starting material was completely consumed. After 1 hr, the reaction was concentrated under reduced pressure to afford 3-azido-3-phenylazetidine trifluoroacetic acid salt, which was carried forward without further purification.

d. (5-amino-3,4-dimethylthieno[2,3-c]pyridazin-6-yl)(3-azido-3-phenylazetidin-1-yl)methanone (Example 8)

In a 20-mL scintillation vial equipped with a stir bar, 5-amino-3,4-dimethylthieno[2,3-c]pyridazine-6-carboxylic acid (40 mg, 0.179 mmol) and HATU (80 mg, 0.211 mmol) were massed and dissolved in DMF (3 mL). Diisopropylethyl amine (75 mg, 0.566 mmol) was added, and the reaction was allowed to stir at ambient temperature for 5 min. 3-Azido-3-phenylazetidine trifluoroacetic acid salt (41 mg, 0.143 mmol) in DMF (1 mL) was then added, and the reaction was monitored by LCMS, which confirmed complete consumption of the starting material after 30 min. The reaction was diluted into DCM/H$_2$O (20 mL, 1:1), and the organic layer was separated. The aqueous layer was extracted with DCM (2×10 mL), and the combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid. The fractions containing the desired product were partially concentrated, diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 7.58-7.45 (m, 5H), 7.06 (s, 2H), 4.79-4.64 (m(br), 4H), 2.74 (s, 3H), 2.72 (s, 3H). LCMS: R$_T$=0.639 min, m/z=380 [M+H]$^+$. HRMS calculated for C$_{18}$H$_{18}$N$_2$OS: 380.1294. found: 380.1292.

11. Preparation of (5-amino-3,4-dimethylthieno[2,3-c]pyridazin-6-yl)(3-fluoro-3-(3-(pyridin-4-yl)phenyl)azetidin-1-yl)methanone (Example 9, Method I)

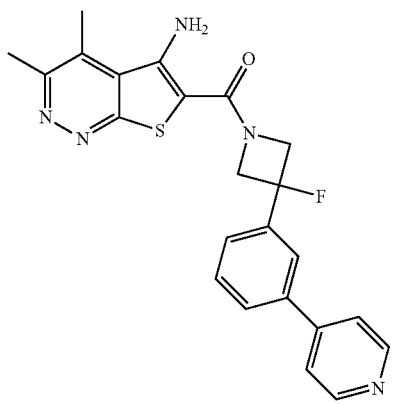 [SMILES: Cc1nnc2sc(C(=O)N3CC(F)(c4cccc(-c5ccncc5)c4)C3)c(N)c2c1C]

The overall synthesis scheme for the preparation of (5-amino-3,4-dimethylthieno[2,3-c]pyridazin-6-yl)(3-fluoro-3-(3-(pyridin-4-yl)phenyl)azetidin-1-yl)methanone (Example 9, Method I) is shown below.

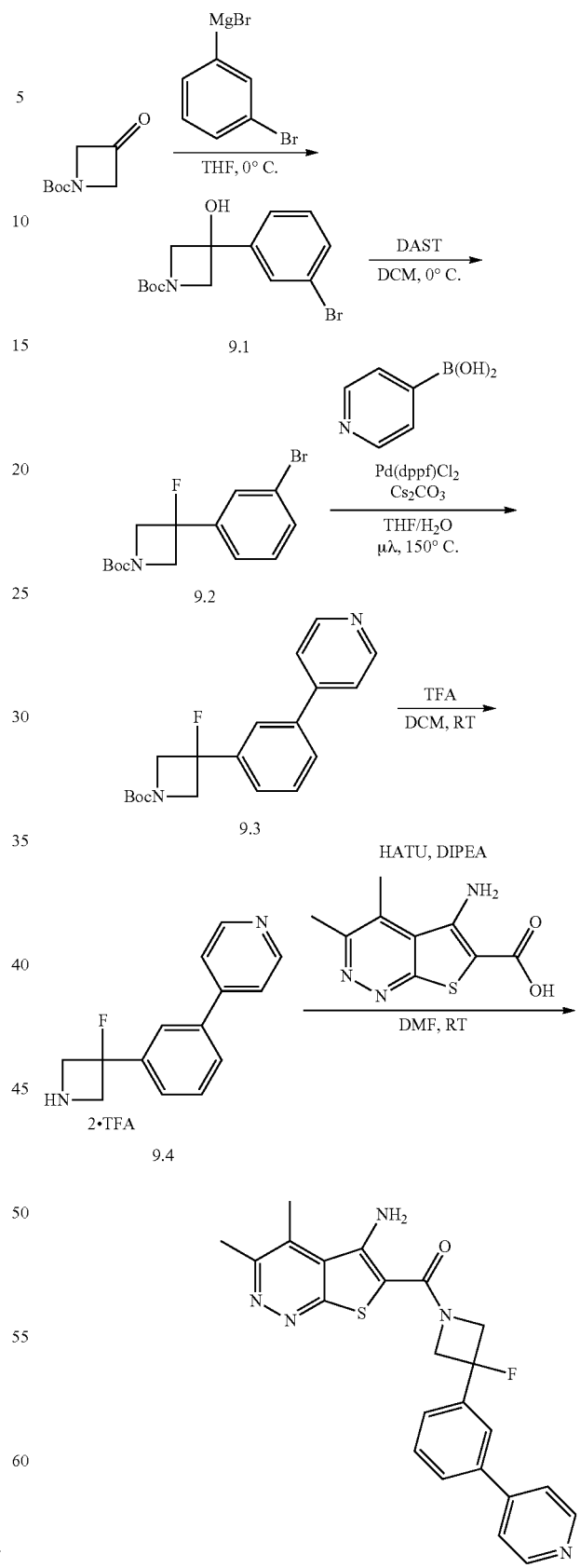

Example 9
(Compound B323, Table I)

a. tert-butyl 3-(3-bromophenyl)-3-hydroxyazetidine-1-carboxylate (Compound 9.1)

In a flame-dried 100-mL round-bottomed flask equipped with a stir bar, magnesium (turnings, 200 mg, 8.33 mmol) was massed and the flask purged with argon. Iodine (20 mg, 0.079 mmol) was added, followed by Et$_2$O (distilled from Na/benzophenone immediately prior to use, 10 mL). A reflux condenser was attached, and the reaction was heated to 40° C. In an oven-dried 20-mL vial, 1,3-dibromobenzene (2.0 g, 8.47 mmol) was massed and dissolved in Et$_2$O (10 mL). The solution of 1,3-dibromobenzene was added via syringe to the suspended magnesium over 20 minutes at 40° C. Reaction was allowed to stir at ambient temperature for 1 hr, followed by addition of THF (10 mL). The reaction was then heated to 45° C. and stirred for 1.5 hr, with the magnesium turnings being consumed. The reaction mixture was cooled to 0° C., and tert-butyl 3-oxoazetidine-1-carboxylate (400 mg, 2.33 mmol) was added in THF (5 mL). The reaction was allowed to stir for 20 min, then quenched with saturated aqueous NH$_4$Cl (20 mL). The reaction mixture was then diluted into EtOAc/H$_2$O (60 mL, 1:1). The organic layer was separated, and the aqueous layer was extracted with EtOAc (3×30 mL). The combined organic fractions were dried over MgSO$_4$, filtered, and concentrated under reduced pressure. The crude product was purified by flash column chromatography on a 24-gram ISCO column eluting with 0 to 100% EtOAc/hexanes to afford tert-butyl 3-(3-bromophenyl)-3-hydroxyazetidine-1-carboxylate.

b. tert-butyl 3-(3-bromophenyl)-3-fluoroazetidine-1-carboxylate (Compound 9.2)

In an oven-dried 100-mL round-bottomed flask equipped with a stir bar, tert-butyl 3-(3-bromophenyl)-3-hydroxyazetidine-1-carboxylate (490 mg, 1.49 mmol) was massed and dissolved in DCM (30 mL). The reaction was cooled to 0° C. and DAST (366 mg, 2.27 mmol) was added via syringe. The reaction was maintained at 0° C. and monitored by LCMS for 15 min. Upon complete consumption of the starting material, the reaction was cautiously quenched with 20 mL of saturated aqueous NaHCO$_3$ at 0° C. The reaction was allowed to stir for 5 minutes, then diluted into DCM/H$_2$O (40 mL, 1:1). The organic layer was separated, and the aqueous layer was extracted with DCM (2×20 mL). The combined organic extracts were dried over MgSO$_4$, filtered, and concentrated under reduced pressure. The crude product was purified by flash column chromatography on a 24-gram ISCO column eluting with 0 to 100% EtOAc/hexanes to afford tert-butyl 3-(3-bromophenyl)-3-fluoroazetidine-1-carboxylate (LCMS: R$_T$=0.873 min, m/z=274 [M+H−56]).

c. tert-butyl 3-fluoro-3-(3-(pyridin-4-yl)phenyl)azetidine-1-carboxylate (Compound 9.3)

In a 5-mL microwave vial equipped with a stir bar, tert-butyl 3-(3-bromophenyl)-3-fluoroazetidine-1-carboxylate (75 mg, 0.227 mmol), pyridin-4-ylboronic acid (55 mg, 0.447 mmol), Pd(dppf)Cl$_2$.DCM (20 mg, 0.025 mmol), and Cs$_2$CO$_3$ (180 mg, 0.554 mmol) were massed. The reagents were dissolved in THF/H$_2$O (5 mL, 4:1). The reaction was capped and heated to 150° C. for 30 min, after which time the LCMS trace showed complete consumption of the starting material. The reaction was diluted into DCM/H$_2$O (20 mL, 1:1), the organic layer was separated, and the aqueous layer was extracted with DCM (2×20 mL). The combined organic fractions were dried over MgSO$_4$, filtered, and concentrated under reduced pressure. The crude product was dissolved in DMSO (1 mL) and purified by reverse phase HPLC, eluting with acetonitrile/water/trifluoroacetic acid. The fractions containing the desired product were partially concentrated, diluted into DCM (20 mL) and saturated aqueous NaHCO$_3$. The organic layer was dried with a phase separator and concentrated under reduced pressure to afford tert-butyl 3-fluoro-3-(3-(pyridin-4-yl)phenyl)azetidine-1-carboxylate (LCMS: R$_T$=0.569 min, m/z=329 [M+H]$^+$).

d. 4-(3-(3-fluoroazetidin-3-yl)phenyl)pyridine (Compound 9.4)

In a 20-mL scintillation vial equipped with a stir bar, tert-butyl 3-fluoro-3-(3-(pyridin-4-yl)phenyl)azetidine-1-carboxylate (12 mg, 0.0365 mmol) was massed and dissolved in DCM (5 mL), followed by the addition of TFA (1 mL) at ambient temperature. The reaction was monitored by LCMS until the starting material was completely consumed. After 2 hr, the reaction was concentrated under reduced pressure to afford 4-(3-(3-fluoroazetidin-3-yl)phenyl)pyridine bis(trifluoroacetic acid) salt (LCMS: R$_T$=0.136 min, m/z=229 [M+H]$^+$), which was carried forward without further purification.

e. (5-amino-3,4-dimethylthieno[2,3-c]pyridazin-6-yl)(3-fluoro-3-(3-(pyridin-4-yl)phenyl)azetidin-1-yl)methanone (Example 9)

In a 20-mL scintillation vial equipped with a stir bar, 5-amino-3,4-dimethylthieno[2,3-c]pyridazine-6-carboxylic acid (10 mg, 0.045 mmol) and HATU (15 mg, 0.039 mmol) were massed and dissolved in DMF (3 mL). Diisopropylethyl amine (30 mg, 0.232 mmol) was added, and the reaction was allowed to stir at ambient temperature for 5 min. 4-(3-(3-fluoroazetidin-3-yl)phenyl)pyridine bis(trifluoroacetic acid) salt (16 mg, 0.035 mmol) in DMF (1 mL) was then added, and the reaction was monitored by LCMS, which confirmed complete consumption of the starting material after 30 min. The reaction was diluted into DCM/H$_2$O (20 mL, 1:1), and the organic layer was separated. The aqueous layer was extracted with DCM (2×10 mL), and the combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid. The fractions containing the desired product were partially concentrated, diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 8.66 (d, J=6.0 Hz, 2H), 8.01 (s, 1H), 7.88 (d, J=7.6 Hz, 1H), 7.81 (d, J=6.0 Hz, 2H), 7.72-7.63 (m, 2H), 7.10 (s, 2H), 4.93-4.72 (m, 4H), 2.74 (s, 3H), 2.73 (s, 3H). LCMS: R$_T$=0.465 min, m/z=434 [M+H]$^+$. HRMS calculated for C$_{23}$H$_{21}$N$_5$OFS: 434.1451. found: 434.1454.

12. Preparation of 5-amino-4-methyl-3-(morpholinomethyl)-N-(4-((trifluoromethyl)sulfonyl)benzyl)-thieno[2,3-c]pyridazine-6-carboxamide (Example 10, Method J)

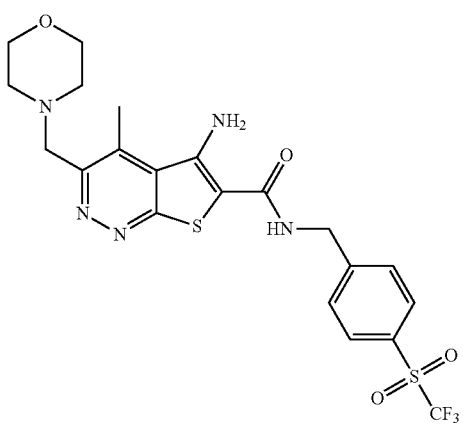 [SMILES: Cc1c(CN2CCOCC2)nnc2sc(C(=O)NCc3ccc(S(=O)(=O)C(F)(F)F)cc3)c(N)c12]

The overall synthesis scheme for the preparation of 5-amino-4-methyl-3-(morpholinomethyl)-N-(4-((trifluoromethyl)sulfonyl)benzyl)-thieno[2,3-c]pyridazine-6-carboxamide (Example 10, Method J) is shown below.

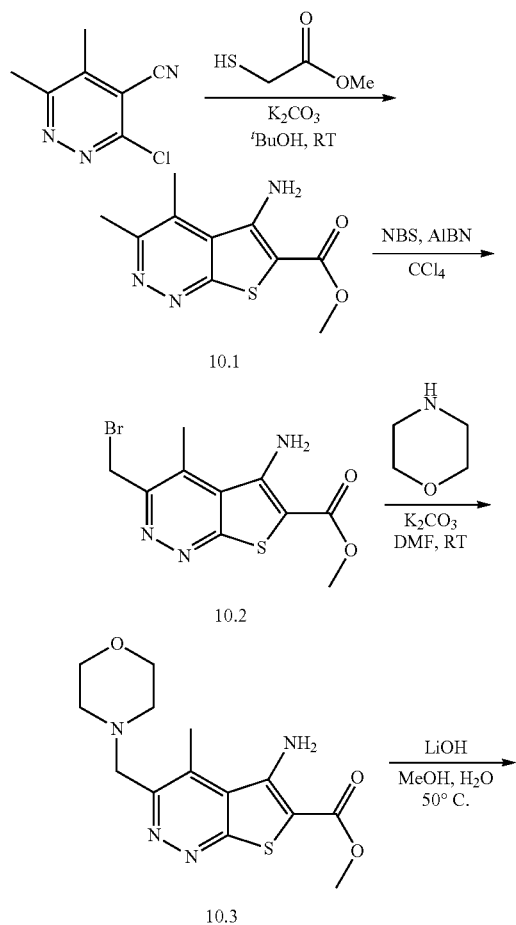

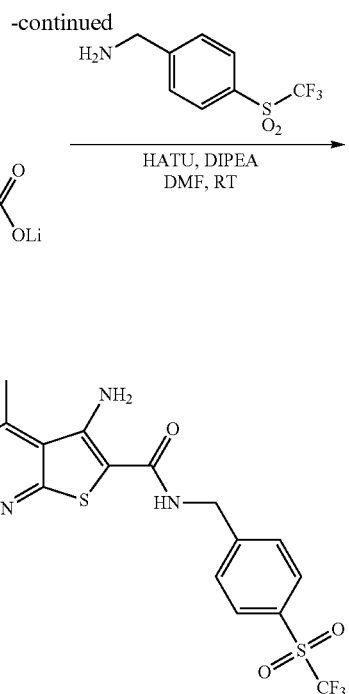

Example 10
(Compound B324, Table I)

a. Methyl 5-amino-3,4-dimethylthieno[2,3-c]pyridazine-6-carboxylate (Compound 10.1)

In a 100-mL round-bottomed flask equipped with a stir bar, 3-chloro-5,6-dimethylpyridazine-4-carbonitrile (750 mg, 4.49 mmol) and methyl thioglycolate (500 mg, 4.717 mmol) were massed. tert-Butanol (50 mL) was added, followed by potassium carbonate (1.00 g, 7.25 mmol) at ambient temperature. The reaction was allowed to stir for 12 hr. LCMS confirmed complete consumption of starting material, with two peaks (m/z=238 [M+H]$^+$), one corresponding the cyclized intermediate A and one to the open-chain adduct. MeOH (20 mL) was added, and the reaction was heated to 45° C. for 3 hr. LCMS confirmed complete conversion to A. The reaction was diluted into DCM (200 mL) and washed with saturated aqueous NaHCO$_3$. The organic layer was dried over MgSO$_4$, filtered, and concentrated under reduced pressure to afford methyl 5-amino-3,4-dimethylthieno[2,3-c]pyridazine-6-carboxylate (LCMS: R$_T$=0.411 min, m/z=238 [M+H]$^+$), which was carried forward without further purification.

b. Methyl 5-amino-3-(bromomethyl)-4-methylthieno[2,3-c]pyridazine-6-carboxylate (Compound 10.2)

In a 40-mL scintillation vial equipped with a stir bar, methyl 5-amino-3,4-dimethylthieno[2,3-c]pyridazine-6-carboxylate (100 mg, 0.420 mmol), N-bromosuccinimide (150 mg, 0.843 mmol), and azobisisobutyronitrile (AIBN, 10 mg, 0.061 mmol) were massed. Carbon tetrachloride (3 mL) was added, and the reaction was heated to 70° C. and the reaction was monitored by LCMS. After 2 hr, the starting material was completely consumed, and the reaction was cooled to ambient temperature. The reaction solution was diluted into DCM (100 mL) and washed with 10% aqueous Na$_2$S$_2$O$_3$, H$_2$O, and brine. The organic layer was dried over MgSO$_4$, filtered, and concentrated under reduced pressure. The crude product was purified by flash column chromatography on a 12-gram ISCO column, eluting with 0 to 100% EtOAc/hexanes to afford methyl 5-amino-3-(bromomethyl)-4-methylthieno[2,3-c]pyridazine-6-carboxylate (LCMS: $R_T$=0.578 min, m/z=316 [M+H]$^+$).

c. Methyl 5-amino-4-methyl-3-(morpholinomethyl)thieno[2,3-c]pyridazine-6-carboxylate (Compound 10.3)

In a 20-mL scintillation vial equipped with a stir bar, methyl 5-amino-3-(bromomethyl)-4-methylthieno[2,3-c]pyridazine-6-carboxylate (60 mg, 0.190 mmol) was added in DMF (3 mL). Morpholine (100 mg, 1.149 mmol) was added in DMF (1 mL), followed by K$_2$CO$_3$ (150 mg, 1.09 mmol). The reaction was allowed to stir at ambient temperature and followed by LCMS until the starting material was completely consumed. After 1 hr, the reaction was diluted into DCM/H$_2$O (20 mL, 1:1). The organic layer was separated, and the aqueous layer was extracted with DCM (3×10 mL). The combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid to afford methyl 5-amino-4-methyl-3-(morpholinomethyl)thieno[2,3-c]pyridazine-6-carboxylate (LCMS: $R_T$=0.507 min, m/z=323 [M+H]$^+$.

d. Lithium 5-amino-4-methyl-3-(morpholinomethyl)thieno[2,3-c]pyridazine-6-carboxylate (Compound 10.4)

In a 20-mL scintillation vial equipped with a stir bar, methyl 5-amino-4-methyl-3-(morpholinomethyl)thieno[2,3-c]pyridazine-6-carboxylate (20 mg, 0.062 mmol) was massed and dissolved in MeOH/H$_2$O/DCM (6 mL, 4:1:1). Lithium hydroxide (5 mg, 0.208 mmol) was added, the reaction was heated to 50° C. and monitored by LCMS until the starting material was completely consumed. After 4 hr, the reaction was cooled to ambient temperature and concentrated under reduced pressure, followed by heating to 50° C. under high vacuum for 1 hr to remove solvent to afford D (LCMS: $R_T$=323 min, m/z=309 [M+H]$^+$).

e. 5-amino-4-methyl-3-(morpholinomethyl)-N-(4-((trifluoromethyl)sulfonyl)benzyl)thieno[2,3-c]pyridazine-6-carboxamide (Example 10)

Intermediate D (19 mg, 0.062 mmol) was dissolved in 3 mL of DMF, followed by addition of DIPEA (20 mg, 0.155 mmol) and HATU (30 mg, 0.079 mmol). The reaction was allowed to stir for 5 minutes, followed by addition of (4-((trifluoromethyl)sulfonyl)-phenyl)methanamine (Example 16, Intermediate A, 20 mg, 0.0836 mmol) in DMF (1 mL). The reaction was stirred at ambient temperature and followed by LCMS until the starting material was completely consumed. After 2 hr, the reaction was diluted into DCM/H$_2$O (20 mL, 1:1). The organic layer was separated, and the aqueous layer was extracted with DCM (3×10 mL). The combined organic fractions were dried over MgSO$_4$, filtered, and concentrated under reduced pressure. The crude residue was dissolved in DMSO (1 mL) and purified by reverse phase HPLC, eluting with acetonitrile/water/trifluoroacetic acid. The fractions containing the desired product were partially concentrated, diluted into DCM (20 mL) and saturated aqueous NaHCO$_3$. The organic layer was dried with a phase separator and concentrated under reduced pressure to afford the title compound. $^1$H NMR (400 MHz, DMSO-d$_6$): δ 8.79 (t, J=5.6 Hz, 1H), 8.13 (d, J=8.4 Hz, 2H), 7.98 (s, 2H), 7.78 (d, J=8.8 Hz, 2H), 4.62 (d, J=5.6 Hz, 2H), 3.89 (s, 2H), 3.58 (s, 4H), 2.84 (s(br) 3H), 2.53 (s(br) 4H). LCMS: $R_T$=0.670 min, m/z=530 [M+H]$^+$. HRMS calculated for C$_{21}$H$_{23}$N$_5$O$_4$F$_3$S$_2$: 530.1144. found: 530.1144.

13. Preparation of (5-amino-3,4-dimethylthieno[2,3-c]pyridazin-6-yl)(3-(4-((difluoromethyl)sulfonyl)-phenyl)-3-fluoroazetidin-1-yl)methanone (Example 11, Method K)

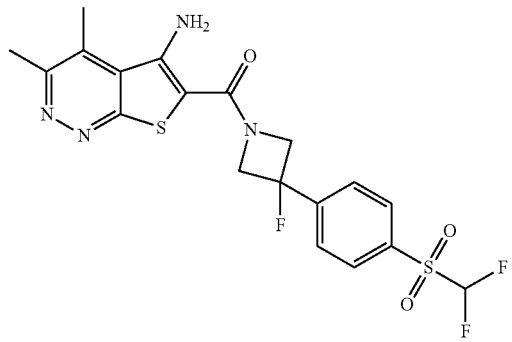

The overall synthesis scheme for the preparation of (5-amino-3,4-dimethylthieno[2,3-c]pyridazin-6-yl)(3-(4-((difluoromethyl)sulfonyl)-phenyl)-3-fluoroazetidin-1-yl)methanone (Example 11, Method K) is shown below.

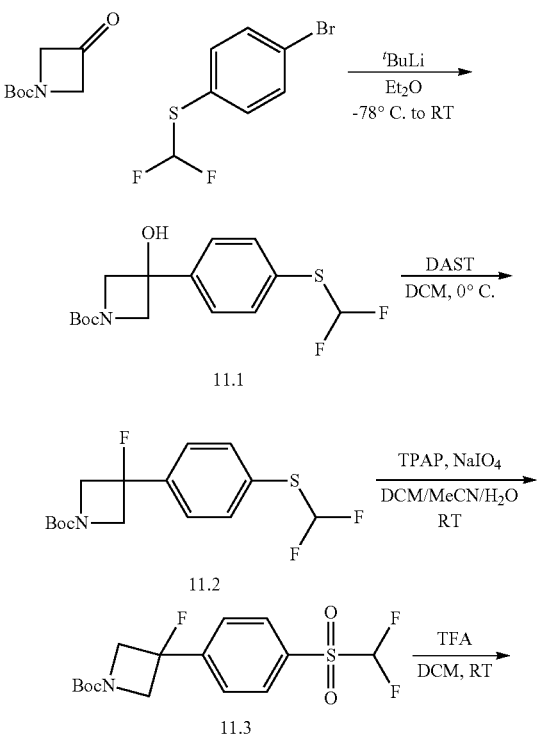

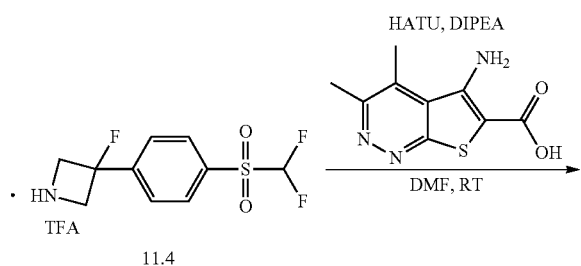

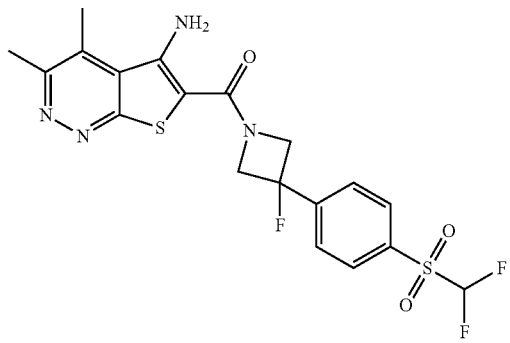 [SMILES: Cc1nnc2sc(C(=O)N3CC(F)(c4ccc(S(=O)(=O)C(F)F)cc4)C3)c(N)c2c1C]

Example 11
(Compound B377, Table I)

a. tert-butyl 3-(4-((difluoromethyl)thio)phenyl)-3-hydroxyazetidine-1-carboxylate (Compound 11.1)

In an oven-dried 20-mL scintillation vial equipped with a stir bar, (4-bromophenyl)(difluoromethyl)sulfane (300 mg, 1.26 mmol) and tert-butyl 3-oxoazetidine-1-carboxylate (200 mg, 1.169 mmol) were massed. The vial was purged with a stream of argon for 5 min, followed by addition of Et₂O (distilled from Na/benzophenone prior to use, 8 mL). The reaction was then cooled to −78° C. tert-Butyllithium (1.7 M in hexanes, 1.7 mL, 2.89 mmol) was added dropwise over 5 min. The reaction was allowed to stir for 1.5 hr at −78° C., then allowed to warm to ambient temperature over 30 min. The reaction was quenched with H₂O (1 mL) and then diluted into EtOAc/saturated NH₄Cl solution (60 mL, 1:1). The organic layer was separated, and the aqueous layer was extracted with EtOAc (2×30 mL). The combined organic layers were dried over MgSO₄, filtered, and concentrated under reduced pressure. The crude residue was purified by flash column chromatography on a 24-gram ISCO cartridge eluting with 0 to 100% EtOAc/hexanes to afford tert-butyl 3-(4-((difluoromethyl)thio)phenyl)-3-hydroxyazetidine-1-carboxylate.

b. tert-butyl 3-(4-((difluoromethyl)thio)phenyl)-3-fluoroazetidine-1-carboxylate (Compound 11.2)

In an oven-dried 20-mL scintillation vial equipped with a stir bar, tert-butyl 3-(4-((difluoromethyl)thio)phenyl)-3-hydroxyazetidine-1-carboxylate (45 mg, 0.136 mmol) was massed and dissolved in DCM (5 mL). The reaction was cooled to 0° C. and DAST (50 mg, 0.311 mmol) was added via syringe. The reaction was maintained at 0° C. and monitored by LCMS for 15 min. Upon complete consumption of the starting material, the reaction was cautiously quenched with 5 mL of saturated aqueous NaHCO₃ at 0° C. The reaction was allowed to stir for 5 minutes, and then diluted into DCM/H₂O (40 mL, 1:1). The organic layer was separated, and the aqueous layer was extracted with DCM (2×20 mL). The combined organic extracts were dried over MgSO₄, filtered, and concentrated under reduced pressure to afford tert-butyl 3-(4-((difluoromethyl)thio)phenyl)-3-fluoroazetidine-1-carboxylate. The crude product was carried forward without further purification.

c. 3-(4-((difluoromethyl)sulfonyl)phenyl)-3-fluoro-azetidine (Compounds 11.2 and 11.4)

In a 20-mL scintillation vial equipped with a stir bar, tert-butyl 3-(4-((difluoromethyl)thio)phenyl)-3-fluoroazetidine-1-carboxylate (25 mg, 0.075 mmol) was massed and dissolved in H₂O (1 mL), DCM (0.6 mL), and acetonitrile (0.6 mL). Tetrabutylammonium perruthenate (3 mg, 0.085 mmol) was added at ambient temperature, followed by sodium periodate (50 mg, 0.234 mmol). The reaction was allowed to stir at ambient temperature and monitored by LCMS until the starting material was consumed. After 15 min, the reaction was diluted into DCM (20 mL). The organic layer was washed with saturated aqueous NaHCO₃ (10 mL), water (10 mL), and brine (10 mL). The organic layer was filtered through a pad of SiO₂ gel, eluting with DCM. The organic layer was then dried over MgSO₄, filtered, and concentrated under reduced pressure to afford tert-butyl 3-(4-((difluoromethyl)sulfonyl)phenyl)-3-fluoro-azetidine-1-carboxylate (11.3). The crude residue was dissolved in DCM (5 mL) and treated with trifluoroacetic acid (1 mL) at ambient temperature. The reaction was monitored by LCMS until the starting material was completely consumed. After 1 hr, the reaction was concentrated under reduced pressure to afford 3-(4-((difluoromethyl)sulfonyl) phenyl)-3-fluoroazetidine, which was used without further purification.

d. (5-amino-3,4-dimethylthieno[2,3-c]pyridazin-6-yl)(3-(4-((difluoromethyl)sulfonyl)phenyl)-3-fluoro-azetidin-1-yl)methanone (Example 11)

In a 20-mL scintillation vial equipped with a stir bar, 5-amino-3,4-dimethylthieno[2,3-c]pyridazine-6-carboxylic acid (15 mg, 0.067 mmol) and HATU (30 mg, 0.079 mmol) were massed and dissolved in DMF (3 mL). DIPEA (25 mg, 0.194 mmol) was added at ambient temperature and the reaction was allowed to stir for 5 minutes. 3-(4-((difluoromethyl)sulfonyl)phenyl)-3-fluoroazetidine (15 mg, 0.065 mmol) was added in DMF (1 mL), and the reaction was monitored by LCMS. Upon complete consumption of the starting material (1 hr), the reaction was diluted into DCM/H₂O (20 mL, 1:1). The organic layer was separated, and the aqueous layer was extracted with DCM (2×10 mL). The combined organic layers were dried over MgSO₄, filtered, and concentrated under reduced pressure. The crude residue was dissolved in 1 mL of DMSO and purified by reverse phase HPLC, eluting with acetonitrile/water/trifluoroacetic acid to afford the title compound. $^1$H NMR (400 MHz, DMSO-d$_6$): δ 8.10 (d, J=8.4 Hz, 2H), 8.03 (d, J=8.4 Hz, 2H), 7.38 (t, J$_{F-H}$=52.0 Hz, 1H), 7.12 (s, 2H), 4.82-4.78 (m(br), 4H), 2.74 (s, 6H). LCMS: R$_T$=0.612 min, m/z=471 [M+H]$^+$. HRMS calculated for C$_{19}$H$_{18}$F$_3$N$_4$O$_3$S$_2$: 471.0772. found: 471.0775.

14. Preparation of 5-amino-N-(1-(benzo[d]thiazol-2-yl)azetidin-3-yl)-3,4-dimethylthieno[2,3-c]pyridazine-6-carboxamide (Example 12, Method L)

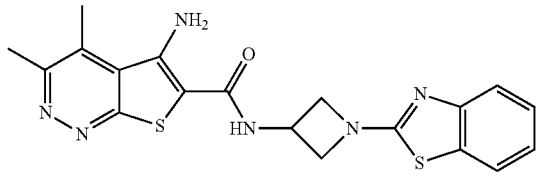 [SMILES: Cc1nnc2sc(C(=O)NC3CN(c4nc5ccccc5s4)C3)c(N)c2c1C]

The overall synthesis scheme for the preparation of 5-amino-N-(1-(benzo[d]thiazol-2-yl)azetidin-3-yl)-3,4-dimethylthieno[2,3-c]pyridazine-6-carboxamide (Example 12, Method L) is shown below.

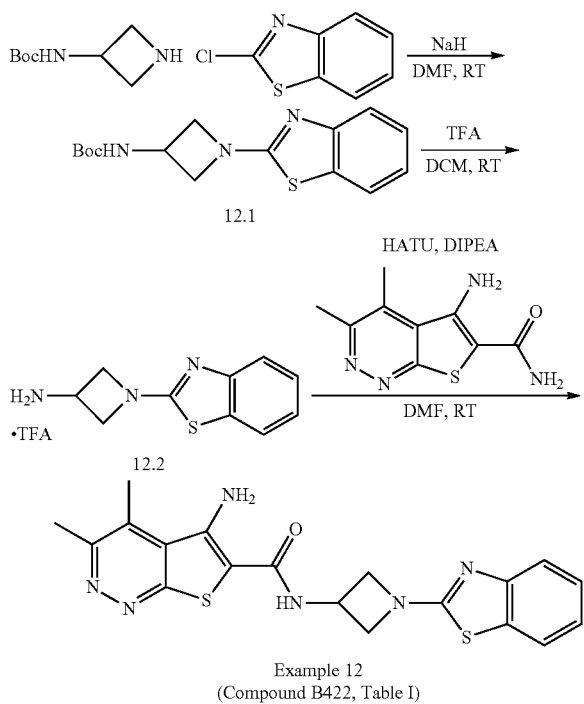

Example 12
(Compound B422, Table I)

a. tert-butyl (1-(benzo[d]thiazol-2-yl)azetidin-3-yl)carbamate (Compound 12.1)

In an oven-dried 2-dram vial equipped with a stir bar, tert-butyl azetidin-3-ylcarbamate (20 mg, 0.116 mmol) and 2-chlorobenzothiazole (22 mg, 0.131 mmol) were massed and dissolved in DMF (2 mL) at ambient temperature. Sodium hydride (60% dispersion in mineral oil, 10 mg, 0.25 mmol) was added and the reaction was allowed to stir at ambient temperature for 1 hr and monitored by LCMS. Upon complete consumption of the starting material, the reaction was quenched with H$_2$O (1 mL). The reaction mixture was diluted into DCM/H$_2$O (20 mL, 1:1). The organic layer was separated, and the aqueous layer was extracted with DCM (2×10 mL). The combined organic fractions were dried over MgSO$_4$, filtered, and concentrated under reduced pressure to afford tert-butyl (1-(benzo[d]thiazol-2-yl)azetidin-3-yl)carbamate (LCMS: R$_T$=0.549 min, m/z=306 [M+H]$^+$). The crude product was carried forward without further purification.

b. 1-(benzo[d]thiazol-2-yl)azetidin-3-amine (Compound 12.2)

In a 20-mL scintillation vial equipped with a stir bar, tert-butyl (1-(benzo[d]thiazol-2-yl)azetidin-3-yl)carbamate (32 mg, 0.105 mmol) was massed and dissolved in DCM (5 mL) at ambient temperature. Trifluoroacetic acid (1 mL) was added, and the reaction was allowed to stir for 1 hr at ambient temperature and monitored by LCMS. Upon complete consumption of the starting material, the reaction was concentrated under reduced pressure to afford 1-(benzo[d]thiazol-2-yl)azetidin-3-amine trifluoracetic acid salt. After drying to a constant weight under vacuum, the crude product was carried forward with without further purification.

c. 5-amino-N-(1-(benzo[d]thiazol-2-yl)azetidin-3-yl)-3,4-dimethylthieno[2,3-c]pyridazine-6-carboxamide (Example 12)

In a 20-mL scintillation vial equipped with a stir bar, 5-amino-3,4-dimethylthieno[2,3-c]pyridazine-6-carboxylic acid (20 mg, 0.0897 mmol) and HATU (35 mg, 0.0921 mmol) were massed. DMF (3 mL) was added, followed by DIPEA (50 mg, 0.388 mmol). The reaction was allowed to stir for 5 min at ambient temperature, followed by addition of 1-(benzo[d]thiazol-2-yl)azetidin-3-amine trifluoracetic acid salt (33 mg, 0.105 mmol) in DMF (1 mL). The reaction was monitored by LCMS and allowed to stir for 30 minutes. Upon complete consumption of the starting material, the reaction was diluted into DCM/H$_2$O (20 mL, 1:1). The organic layer was separated, and the aqueous layer was extracted with DCM (2×10 mL). The combined organic fractions were dried using an Isolute phase separator and concentrated under reduced pressure. The resultant oil was dissolved in DMSO (1 mL) and purified by reverse phase HPLC, eluting with acetonitrile/water/trifluoroacetic acid to afford the title compound. $^1$H NMR (400 MHz, DMSO-d$_6$): δ 8.71 (d, J=7.2 Hz, 1H), 7.80 (d, J=8.0 Hz, 1H), 7.52 (d, J=8.4 Hz, 1H), 7.30 (t, J=7.2 Hz, 1H), 7.10 (t, J=7.6 Hz, 1H), 7.02 (s, 2H), 5.02-4.97 (m, 1H), 4.44 (t, J=8.0 Hz, 2H), 4.21 (dd, J=8.4 Hz, 6.0, Hz, 2H), 2.73 (s, 3H), 2.71 (s, 3H). LCMS: R$_T$=0.472 min, m/z=411 [M+H]$^+$. HRMS calculated for C$_{19}$H$_{19}$N$_6$OS$_2$: 411.1062. found: 411.1065.

15. Preparation of 1-amino-N-(benzo[d][1,3]dioxol-5-ylmethyl)-6,7,8,9-tetrahydrothieno[2,3-c]cinnoline-2-carboxamide (Example 13, Method M)

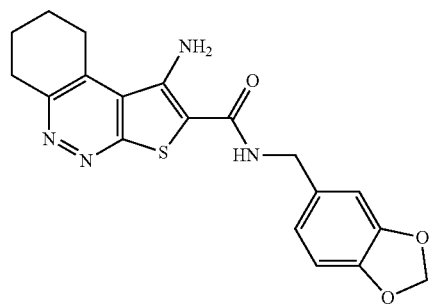 [SMILES: Nc1c(C(=O)NCc2ccc3c(c2)OCO3)sc2nnc3c(c12)CCCC3]

The overall synthesis scheme for the preparation of 1-amino-N-(benzo[d][1,3]dioxol-5-ylmethyl)-6,7,8,9-tetrahydrothieno[2,3-c]cinnoline-2-carboxamide (Example 13, Method M) is shown below.

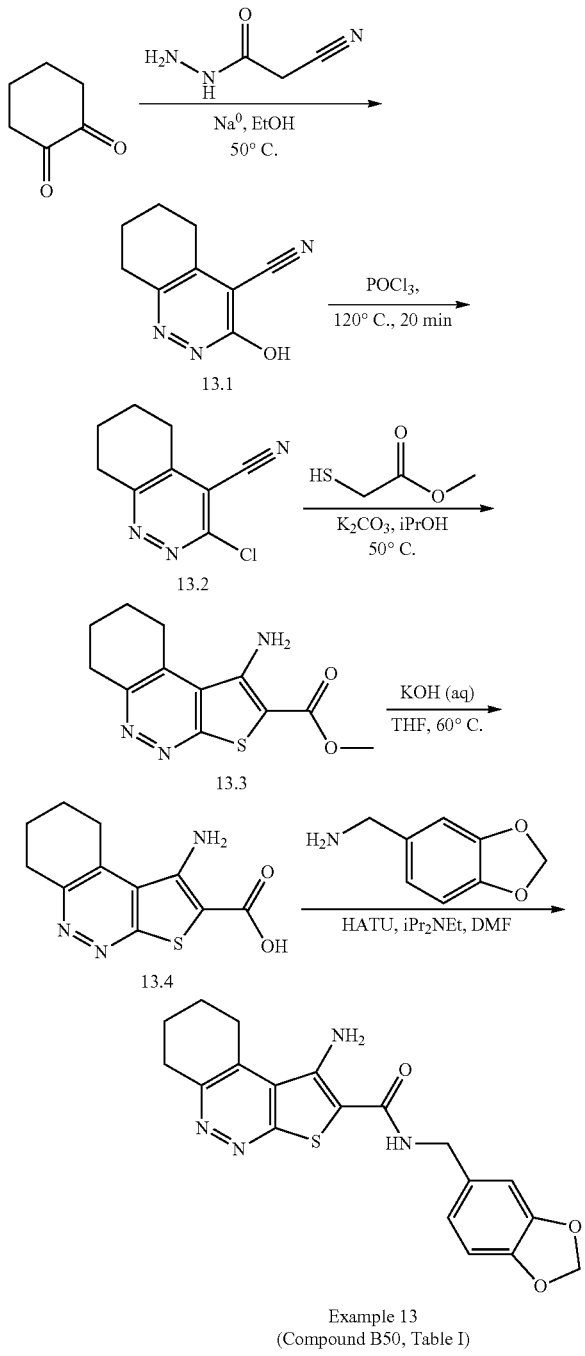

Example 13
(Compound B50, Table I)

a. 3-hydroxy-5,6,7,8-tetrahydrocinnoline-4-carbonitrile (Compound 13.1)

In an oven dried round bottom flask vial fitted with a magnetic stir bar and a septum under inert atmosphere, sodium metal (Na⁰, 107 mg, 4.7 mmol) was added to absolute ethanol (30 mL) and was stirred at ambient temperature until the solid metal was dissolved. To this solution was added cyclohexane-1, 2-dione (500 mg, 4.5 mmol) and cyanoacetohydrazide (440 mg, 4.5 mmol) at ambient temperature. It was stirred for 30 min and then heated to 50° C. for 3 h. The solution was cooled and was concentrated, dissolved in dioxane (30 mL), and concentrated to remove residual water (3×). The residue was dried under high vacuum for 24 h and used without further purification. LCMS: $R_T$=0.380 min, >99% @ 254 nm, >99% @ 220 nm; m/z (M+1)$^+$=176.

b. 3-chloro-5,6,7,8-tetrahydrocinnoline-4-carbonitrile (Compound 13.2)

In a 20 mL microwave vial fitted with a stir bar was suspended 3-hydroxy-5,6,7,8-tetrahydrocinnoline-4-carbonitrile (700 mg, 4.0 mmol) in POCl₃ (5 mL). The vessel was sealed and heated to 120° C. for 20 min. The solution was transferred to a flask and diluted with dichloromethane (20 mL) and concentrated. The residue was suspended in dioxane (30 mL) and was concentrated (3×). The residue was dissolved in dichloromethane (20 mL) and transferred to a separatory funnel. The organic layer was washed with saturated sodium bicarbonate (3×10 mL). The organic fraction was passed through a phase separator and concentrated to yield 3-chloro-5,6,7,8-tetrahydrocinnoline-4-carbonitrile which was used without further purification. LCMS: $R_T$=0.559 min, >99% @ 254 nm, >99% @ 220 nm; m/z (M+1)$^+$=194.

c. Methyl 1-amino-6,7,8,9-tetrahydrothieno[2,3-c]cinnoline-2-carboxylate (Compound 13.3)

In an 8 dram vial fitted with a stir bar was added 3-chloro-5,6,7,8-tetrahydrocinnoline-4-carbonitrile (860 mg, 4.4 mmol) and iPrOH (11 mL). To this solution was added methyl thioglycolate (400 µL, 4.4 mmol) and K₂CO₃ (1.2 g, 8.9 mmol). The mixture was heated to 50° C. for 2 h. It was allowed to cool, diluted with dichloromethane (30 mL), and washed with distilled water (3×10 mL). The organic fraction was passed through a phase separator and concentrated to provide methyl 1-amino-6, 7, 8,9-tetrahydrothieno[2,3-c]cinnoline-2-carboxylate and it was used without further purification. LCMS: $R_T$=0.542 min, >99% @ 254 nm, >99% @ 220 nm; m/z (M+1)$^+$=264.

d. 1-amino-6,7,8,9-tetrahydrothieno[2,3-c]cinnoline-2-carboxylic acid (Compound 13.4)

In an 8 dram vial fitted with a stir bar was added methyl 1-amino-6, 7, 8, 9-tetrahydrothieno[2,3-c]cinnoline-2-carboxylate (130 mg, 0.49 mmol) in THF (5 mL). Aqueous KOH (2N, 2 mL) was added and the solution was heated to 60° C. for 5 h. The suspension was cooled and 2N HCl solution (5 mL) was added to adjust the aqueous mixture to pH=3. The mixture was diluted with dichloromethane (10 mL) and separated. The aqueous layer was extracted with dichloromethane/isopropanol (3:1, 2×10 mL). The organic fractions were combined, passed through a phase separator, and concentrated to provide solids that were used without further purification. LCMS: $R_T$=0.388 min, >99% @ 254 nm, >99% @ 220 nm; m/z (M+1)$^+$=250.

e. 1-amino-N-(benzo[d][1,3]dioxol-5-ylmethyl)-6,7,8,9-tetrahydrothieno[2,3-c]cinnoline-2-carboxamide (Example 13)

In a 2 dram vial fitted with a stir bar was added 1-amino-6, 7, 8, 9-tetrahydrothieno[2,3-c]cinnoline-2-carboxylic acid (10 mg, 0.04 mmol) and DMF (1.5 mL). Piperonylamine (5.5 µL, 0.05 mmol) was added followed by Hünig's base (20 µL, 0.05 mmol) and O-(7-azabenzotriazol-1-yl)-N,N,N′,N′-tetramethyluronium hexafluorophosphate (HATU, 20 mg, 0.04 mmol). The reaction mixture was stirred for 2 h at ambient temperature and then 10% NaOH aqueous solution was added (5 mL). The mixture was extracted with DCM (3×5 mL) and the organic fractions were combined and passed through a phase separator. The solution was concentrated and the resulting residue was dissolved in DMSO and purified on preparative Phenomenex Luna-C18 column using 0.1% TFA in H$_2$O/acetonitrile as a mobile phase. The desired fractions were combined and concentrated to afford the title compound. (10 mg, 65%) LCMS: R$_T$=0.637 min, >99% @ 254 nm, >99% @ 215 nm; m/z (M+1)$^+$=383. $^1$H NMR (400 MHz, CDCl$_3$, δ(ppm)): 8.6 (t; J=5.6 Hz; 1H), 6.9-6.8 (m; 5H), 5.9 (s; 2H), 4.3 (d; J=5.6 Hz; 2H), 3.3 (dd; J=6.4, 6.0 Hz; 2H), 3.1 (dd; J=6.4, 6.0 Hz; 2H), 1.9-1.8 (m; 2H). HRMS calculated for C$_{19}$H$_{19}$N$_4$O$_3$S (M+H)$^+$ m/z: 383.1178, measured: 383.1176.

16. Preparation of 1-amino-N-(benzo[d][1,3]dioxol-5-ylmethyl)-6,7,8,9-tetrahydrothieno[2,3-c]cinnoline-2-carboxamide (Example 14, Method N)

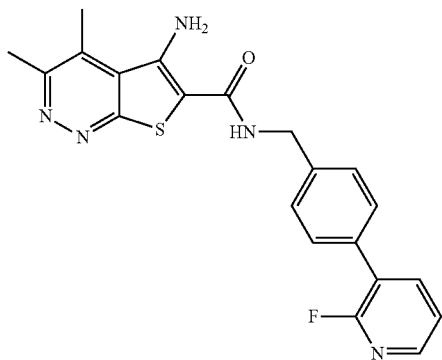 [SMILES: Cc1nnc2sc(C(=O)NCc3ccc(-c4cccnc4F)cc3)c(N)c2c1C]

The overall synthesis scheme for the preparation of 1-amino-N-(benzo[d][1,3]dioxol-5-ylmethyl)-6,7,8,9-tetrahydrothieno[2,3-c]cinnoline-2-carboxamide (Example 14, Method N) is shown below.

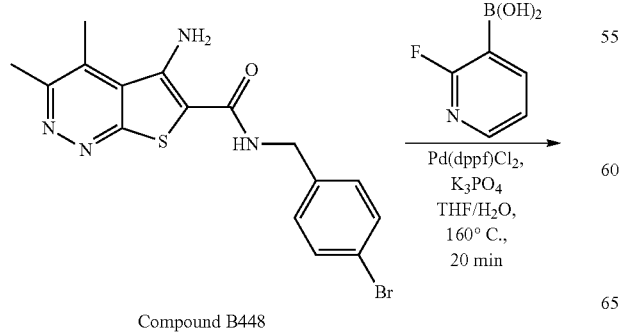

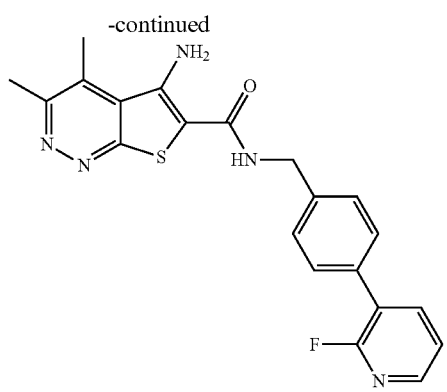

Example 14
(Compound B453, Table I)

In a 5 mL microwave vial fitted with a magnetic stir bar and a crimp cap was added 5-amino-N-(4-bromobenzyl)-3,4-dimethylthieno[2,3-c]pyridazine-6-carboxamide (50 mg, 0.13 mmol), (2-fluoropyridin-3-yl)boronic acid (Compound B448, see Table I; 36 mg, 0.26 mmol), dichloro-1, 1′-bis(diphenylphosphino)-ferrocene palladium(II) dichloromethane adduct (10.3 mg, 0.013 mmol). The microwave vial was sealed, evacuated and back-filled, three times, with argon. An aqueous solution of potassium phosphate tribasic (380 µL, 1M K$_3$PO$_4$ in H$_2$O, 0.38 mmol) was added followed by THF (1.3 mL). The biphasic mixture was then heated to 160° C. under microwave irradiation for 20 min. The vial was cooled and the suspension was diluted with DCM (10 mL). The mixture was passed through a Celite pad as washed with DCM (3×10 mL). The organic fractions were combined and dried. The residue was purified on silica gel using dichloromethane/methanol as a mobile phase. The desired fractions were combined and concentrated to afford the title compound. LCMS: R$_T$=0.623 min, >99% @ 254 nm, >99% @ 215 nm; m/z (M+1)$^+$=408. $^1$H NMR (400 MHz, CDCl$_3$, δ (ppm)): 8.7 (t; J=4.0 Hz; 1H), 8.2 (d; J=4.0 Hz; 1H), 8.1-8.0 (m; 1H), 7.6 (d; J=8.0 Hz; 2H), 7.5-7.4 (m; 3H), 6.9 (bs; 2H), 4.5 (d; J=4.0 Hz; 2H), 2.71 (s; 3H), 2.70 (s; 3H). HRMS calculated for C$_{21}$H$_{19}$FN$_5$OS (M+H)$^+$ m/z: 408.1294, measured: 408.1298.

17. Preparation of 5-amino-N-(dideutero(4-methoxyphenyl)methyl)-3,4-dimethylthieno[2,3-c]pyridazine-6-carboxamide (Example 15, Method O)

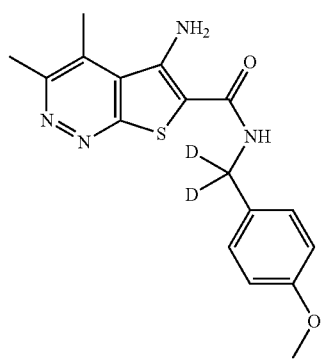 [SMILES: [2H]C([2H])(NC(=O)c1sc2nnc(C)c(C)c2c1N)c1ccc(OC)cc1]

The overall synthesis scheme for the preparation of 5-amino-N-(dideutero(4-methoxyphenyl)methyl)-3,4-dimethylthieno[2,3-c]pyridazine-6-carboxamide (Example 15, Method O) is shown below.

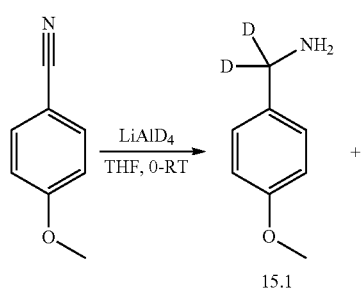

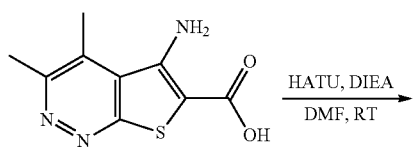

Example 15
(Compound B37, Table I)

a. [dideutero(4-methoxyphenyl)methanamine] (Compound 15.1)

To an oven-dried round-bottom flask equipped with a magnetic stir bar was added lithium aluminum deuteride (473 mg, 11.3 mmol) and tetrahydrofuran (30 mL). After cooling this suspension in an ice bath, 4-methoxybenzonitrile (1 g, 7.5 mmol) was added dropwise as a solution in tetrahydrofuran (5 mL). The mixture was allowed to warm to ambient temperature, and stirred for 24 hours. After again cooling in an ice bath, the mixture was made strongly acidic by the careful addition of 1N HCl solution. This solution was washed with diethyl ether, and the aqueous layer was collected, made strongly basic by addition of 6N sodium hydroxide solution, and again extracted with diethyl ether. The organic layers were collected, dried, and evaporated to afford a colorless oil containing dideutero(4-methoxyphenyl)methanamine, and it was used without further purification.

b. [5-amino-N-(dideutero(4-methoxyphenyl)methyl)-3,4-dimethylthieno[2,3-c]pyridazine-6-carboxamide] (Example 15)

To a suspension of 5-amino-3,4-dimethylthieno[2,3-c]pyridazine-6-carboxylic acid (50 mg, 0.22 mmol) in N,N-dimethylformamide (1 mL) was added N,N-diisopropylethylamine (80 µL, 0.44 mmol) and HATU (100 mg, 0.26 mmol). This mixture was allowed to stir at room temperature for 40 minutes, and then dideutero(4-methoxyphenyl)methanamine (36 mg, 0.26 mmol) was added. This mixture was allowed to continue stirring for an additional 30 minutes, and the mixture was purified by reversed-phase HPLC eluting with acetonitrile/water (w/0.1% TFA) to afford 5-amino-N-(dideutero(4-methoxyphenyl)methyl)-3,4-dimethylthieno[2,3-c]pyridazine-6-carboxamide as a yellow solid. LCMS: $R_T$=0.59 min, >99% @ 254 nm, >99% @ 215 nm; m/z $(M+1)^+$=345. $^1$H NMR (400 MHz, $d_6$-DMSO, δ (ppm)): 8.5 (s, 1H), 7.2-7.3 (m, 2H), 7.0 (br. s, 2H) 6.8-6.9 (m, 2H), 3.7 (s, 3H), 2.6-2.7 (m, 6H) HRMS calculated for $C_{17}H_{16}D_2N_4O_2S$ $(M+H)^+$ m/z: 345.1354, measured: 345.1352.

18. Preparation of 5-amino-3,4-dimethyl-N-(4-((trifluoromethyl)sulfonyl)benzyl)thieno[2,3-c]pyridazine-6-carboxamide (Example 16, Method P)

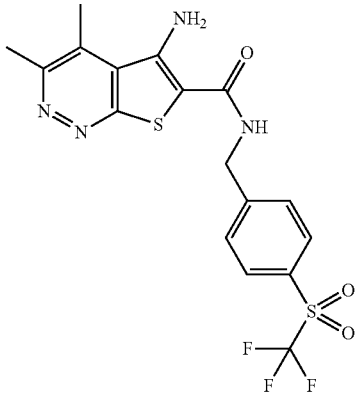 [SMILES: Cc1nnc2sc(C(=O)NCc3ccc(S(=O)(=O)C(F)(F)F)cc3)c(N)c2c1C]

The overall synthesis scheme for the preparation of 5-amino-3,4-dimethyl-N-(4-((trifluoromethyl)sulfonyl)benzyl)thieno[2,3-c]pyridazine-6-carboxamide (Example 16, Method P) is shown below.

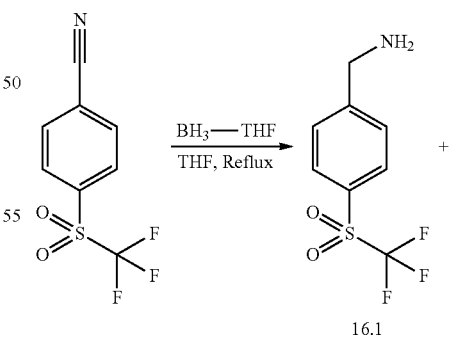

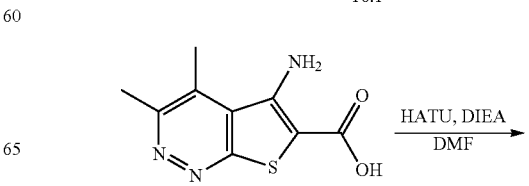

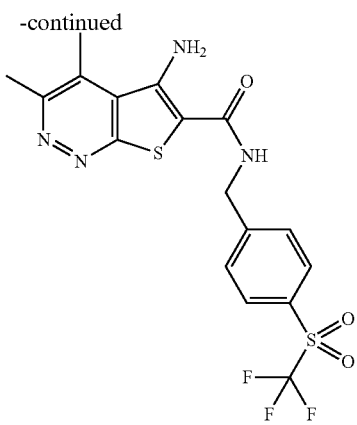

Example 16
(Compound B66, Table I)

a. (4-((trifluoromethyl)sulfonyl)phenyl)methanamine (Compound 16.1)

To a flame-dried flask equipped with a magnetic stir bar was added 4-((trifluoromethyl)sulfonyl)benzonitrile (1 g, 4.3 mmol) and THF (13 mL). To this solution was added a 1M solution of borane-THF in THF (8.4 mL, 8.5 mmol). The flask was fitted with a condenser, and the mixture heated to reflux for 18 h. After cooling to ambient temperature, excess borane-THF was destroyed by careful addition of methanol. Volatiles were removed under reduced pressure, and the resulting residue was redissolved in methanol and loaded onto an SCX cartridge. Elution with methanolic ammonia afforded (4-((trifluoromethyl)sulfonyl)phenyl)methanamine as a yellow oil, which was used without further purification. LCMS: $R_T$=0.46 min, >99% @ 254 nm, >99% @ 215 nm; m/z $(M+1)^+$=240.

b. 5-amino-3,4-dimethyl-N-(4-((trifluoromethyl)sulfonyl)benzyl)thieno[2,3-c]pyridazine-6-carboxamide (Example 16)

To a suspension of 5-amino-3,4-dimethylthieno[2,3-c]pyridazine-6-carboxylic acid (50 mg, 0.22 mmol) in DMF (1 mL) was added N,N-diisopropylethylamine (90 µL, 0.66 mmol), followed by HATU (100 mg, 0.26 mmol). This mixture was allowed to stir at ambient temperature for 45 minutes, then (4-((trifluoromethyl)sulfonyl)phenyl) methanamine (58 mg, 0.24 mmol) was added. After stirring for an additional 20 minutes, the mixture was purified by reversed-phase HPLC eluting with acetonitrile/water (w/0.1% TFA) to afford 5-amino-3,4-dimethyl-N-(4-((trifluoromethyl)sulfonyl)benzyl)thieno[2,3-c]pyridazine-6-carboxamide. LCMS: $R_T$=0.70 min, >99% @ 254 nm, >99% @ 215 nm; m/z $(M+1)^+$=445. $^1$H NMR (400 MHz, $d_6$-DMSO, δ (ppm)): 8.8 (t, J=5.8 Hz, 1H), 8.1 (d, J=8.4 Hz, 2H), 7.8 (d, J=8.4 Hz, 2H), 7.0 (br. s, 2H), 4.6 (d, J=5.8 Hz, 2H), 2.7-2.8 (m, 6H), HRMS calculated for $C_{17}H_{15}F_3N_4O_3S_2$ $(M+H)^+$ m/z: 445.0616, measured: 445.0616.

19. Preparation of 5-amino-3,4-dimethyl-N-(2-(4-(methylsulfonyl)phenyl)cyclopropyl)thieno[2,3-c]pyridazine-6-carboxamide (Example 17, Method Q)

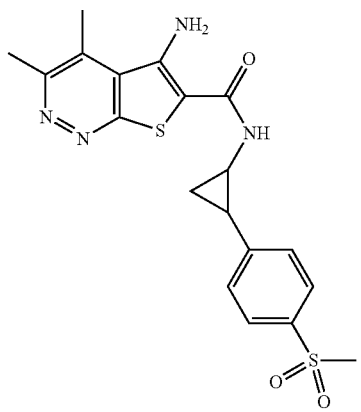

The overall synthesis scheme for the preparation of 5-amino-3,4-dimethyl-N-(2-(4-(methylsulfonyl)phenyl)cyclopropyl)thieno[2,3-c]pyridazine-6-carboxamide (Example 17, Method Q) is shown below.

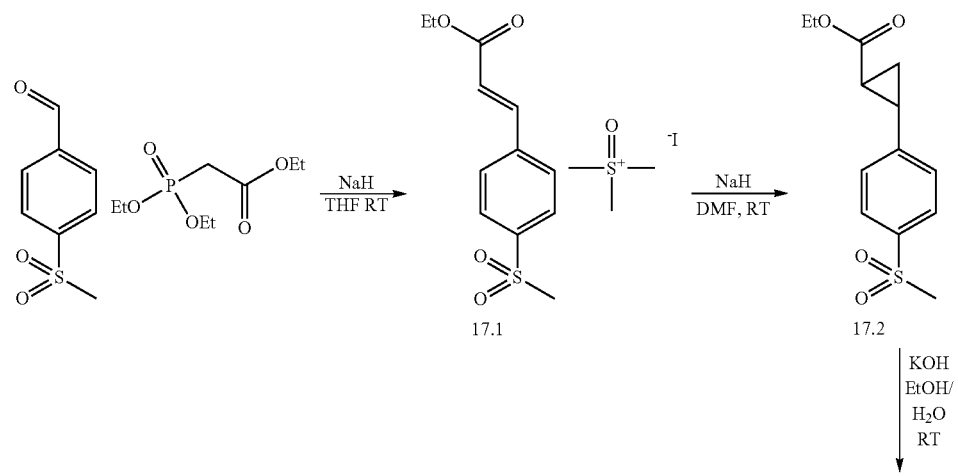

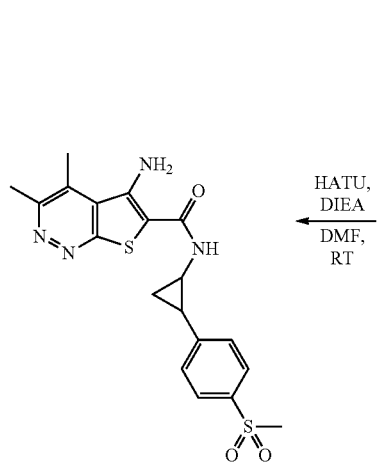

Example 17
(Compound B109, Table I)

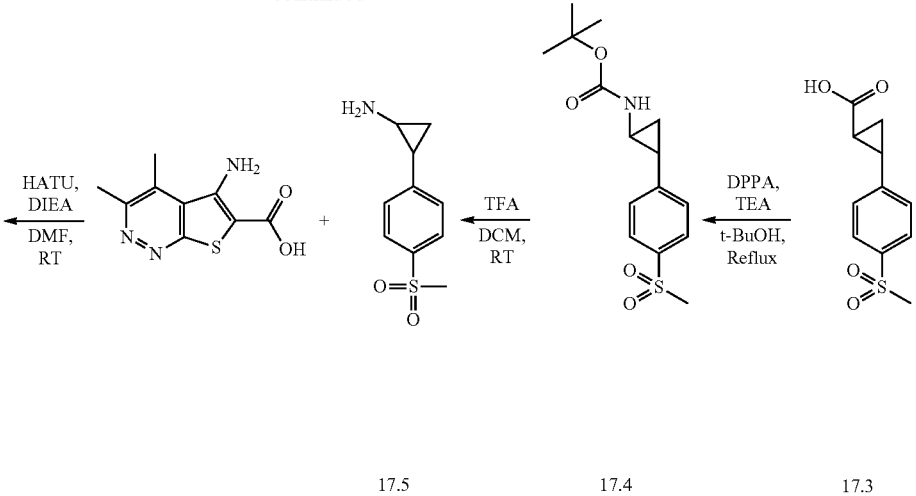

a. Ethyl 3-(4-(methylsulfonyl)phenyl)acrylate (Compound 17.1)

To a flame-dried flask equipped with a magnetic stir bar was added ethyl 2-(diethoxyphosphoryl)acetate (1.45 g, 6.5 mmol) and THF (12 mL). 95% sodium hydride (156 mg, 6.5 mmol) was added portionwise, and the mixture was allowed to stir at ambient temperature until foaming ceased. The resulting solution was then added slowly to a solution of 4-(methylsulfonyl)benzaldehyde (1 g, 5.4 mmol) in THF (12 mL). After allowing this mixture to stir for 15 minutes, the mixture was diluted with water and extracted with ethyl acetate. The organic layers were collected, dried, evaporated and purified by silica gel chromatography (0-50% EtOAc in hexanes) to afford ethyl 3-(4-(methylsulfonyl)phenyl) acrylate as a white solid.

b. Ethyl 2-(4-(methylsulfonyl)phenyl)cyclopropanecarboxylate (Compound 17.2)

To a solution of trimethylsulfoxonium iodide (1.72 g, 7.8 mmol) in DMSO (20 mL) was added 95% sodium hydride (187 mg, 7.8 mmol) portionwise with stirring. After foaming had ceased, ethyl 3-(4-(methylsulfonyl)phenyl)acrylate (1 g, 3.9 mmol) was added as a solution in DMSO (5 mL). This mixture was allowed to stir at ambient temperature for 16 hours, then diluted with water and extracted with diethyl ether. The ether layers were collected, dried, evaporated and purified by silica gel chromatography (20-75% EtOAc in hexanes) to afford ethyl 2-(4-(methylsulfonyl)phenyl)cyclopropanecarboxylate as a colorless solid.

c. 2-(4-(methylsulfonyl)phenyl)cyclopropanecarboxylic acid (Compound 17.3)

To a suspension of ethyl 2-(4-(methylsulfonyl)phenyl) cyclopropanecarboxylate (2 g, 7.9 mmol) in EtOH (30 mL) was added potassium hydroxide (1.32 g, 23.6 mmol) and water (10 mL). This mixture was allowed to stir at room temperature for 2 hours, and then diluted with water. The pH of the mixture was adjusted to ca. 3 by addition of 6N aqueous HCl, and the mixture was extracted with EtOAc. Organic layers were collected, dried, and evaporated to afford 2-(4-(methylsulfonyl)phenyl)cyclopropanecarboxylic acid as a white powder. Product was used without further purification. LCMS: $R_T$=0.54 min, >99% @ 254 nm, >99% @ 215 nm; m/z $(M+1)^+$=241.

d. tert-butyl (2-(4-(methylsulfonyl)phenyl)Cyclopropyl)carbamate (Compound 17.4)

To a suspension of 2-(4-(methylsulfonyl)phenyl)cyclopropanecarboxylic acid (500 mg, 2.1 mmol) in tert-butyl alcohol was added triethylamine (290 µL, 2.1 mmol) and diphenylphosphoryl azide (450 µL, 2.1 mmol). This mixture was heated to reflux for 4 hours. Solvents were removed under reduced pressure, and the residue was re-dissolved in EtOAc and washed with water. The organic layer was collected, dried, evaporated and purified by silica gel chromatography (0-75% EtOAc in hexanes) to afford tert-butyl (2-(4-(methylsulfonyl)phenyl)cyclopropyl)carbamate as a white powder.

e. 2-(4-(methylsulfonyl)phenyl)cyclopropanamine trifluoroacetic acid salt (Compound 17.5)

To a solution of tert-butyl (2-(4-(methylsulfonyl)phenyl) cyclopropyl)carbamate (280 mg, 0.9 mmol) in DCM (10 mL) was added excess trifluoroacetic acid. This mixture was allowed to stir at room temperature for 2 hours. Volatiles were removed under reduced pressure, and the resulting residue containing 2-(4-(methylsulfonyl)phenyl)cyclopropanamine trifluoroacetic acid salt was used without further purification.

f. 5-amino-3,4-dimethyl-N-(2-(4-(methylsulfonyl) phenyl)cyclopropyl)thieno[2,3-c]pyridazine-6-carboxamide (Example 17)

To a suspension of 5-amino-3,4-dimethylthieno[2,3-c] pyridazine-6-carboxylic acid (200 mg, 0.9 mmol) in DMF (7 mL) was added N,N-diisopropylethylamine (630 µL, 3.6 mmol) and HATU (410 mg, 1.1 mmol). This mixture was allowed to stir at room temperature for 1 hour, and then 2-(4-(methylsulfonyl)phenyl)cyclopropanamine trifluoroacetic acid salt (293 mg, 0.9 mmol) was added, and the mixture allowed to stir at room temperature for an additional 2 hours. Purification by reversed-phase HPLC eluting with acetonitrile/water (w/0.1% TFA) afforded 5-amino-3,4-dimethyl-N-(2-(4-(methylsulfonyl)phenyl)cyclopropyl) thieno [2,3-c]pyridazine-6-carboxamide. LCMS: $R_T$=0.60 min, >99% @ 254 nm, >99% @ 215 nm; m/z $(M+1)^+$=417. $^1$H NMR (400 MHz, $d_6$-DMSO, δ (ppm)): 8.4 (d, J=3.8 Hz, 1H), 7.8 (d, J=8.3 Hz, 2H), 7.4 (d, J=8.3 Hz, 2H), 7.0 (br. s, 2H), 3.2 (s, 3H), 3.0-3.1 (m, 1H), 2.6-2.7 (m, 6H), 2.2-2.3 (m, 1H), 1.5-1.6 (m, 1H), 1.3-1.4 (m, 1H), HRMS calculated for $C_{19}H_{20}N_4O_3S_2$ (M+H)$^+$ m/z: 417.1055, measured: 417.1058.

20. Preparation of 5-amino-3,4-dimethyl-N-(2-(4-(methylsulfonyl)phenyl)cyclopropyl)thieno[2,3-c]pyridazine-6-carboxamide, Enantiomer A (Example 18, Method R)

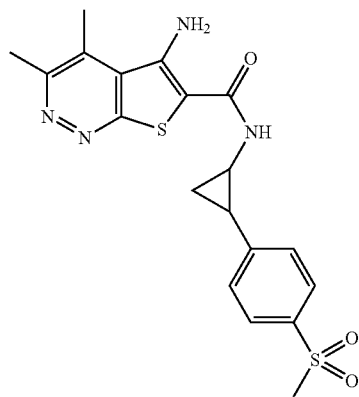

Enantiomer A

The overall preparation scheme for the isolation of the enantiomers of 5-amino-3,4-dimethyl-N-(2-(4-(methylsulfonyl)phenyl)cyclopropyl)thieno[2,3-c]pyridazine-6-carboxamide is shown below.

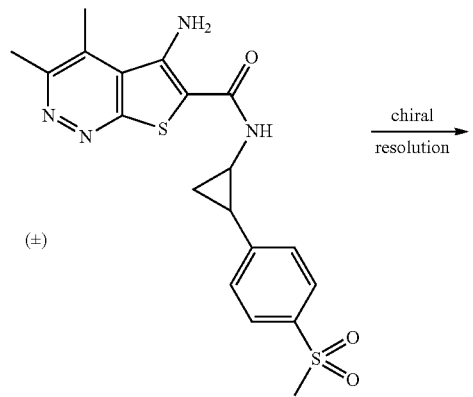

Example 17
(Compound B109, Table I)

$\xrightarrow{\text{chiral resolution}}$

-and-

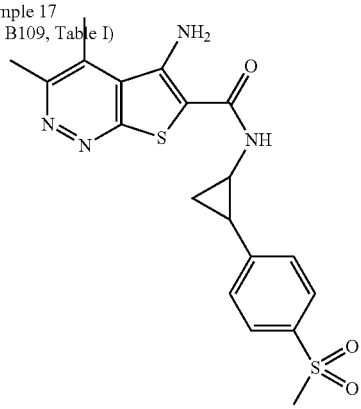

Enantiomer A
Example 18
(Compound B110, Table I)

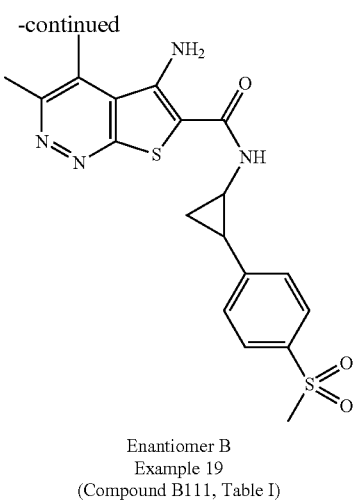

Enantiomer B
Example 19
(Compound B111, Table I)

Racemic 5-amino-3,4-dimethyl-N-(2-(4-(methylsulfonyl)phenyl)cyclopropyl) thieno[2,3-c]pyridazine-6-carboxamide (Example 17, see herein above) was resolved by chiral chromatography using a Chiralpak IC column, with a mobile phase consisting of 2:1 methanol/acetonitrile (w/0.1% DEA) in supercritical carbon dioxide to afford the first eluting enantiomer; $R_T$=3.01 min. LCMS: $R_T$=0.60 min, >99% @ 254 nm, >99% @ 215 nm; m/z (M+1)$^+$=417. $^1$H NMR (400 MHz, d$_6$-DMSO, δ (ppm)): 8.4 (d, J=3.8 Hz, 1H), 7.8 (d, J=8.3 Hz, 2H), 7.4 (d, J=8.3 Hz, 2H), 7.0 (br. s, 2H), 3.2 (s, 3H), 3.0-3.1 (m, 1H), 2.6-2.7 (m, 6H), 2.2-2.3 (m, 1H), 1.5-1.6 (m, 1H), 1.3-1.4 (m, 1H), HRMS calculated for $C_{19}H_{20}N_4O_3S_2$ (M+H)$^+$ m/z: 417.1055, measured: 417.1052.

21. Preparation of 5-amino-3,4-dimethyl-N-(2-(4-(methylsulfonyl)phenyl)cyclopropyl)thieno[2,3-c]pyridazine-6-carboxamide, Enantiomer B (Example 19, Method S)

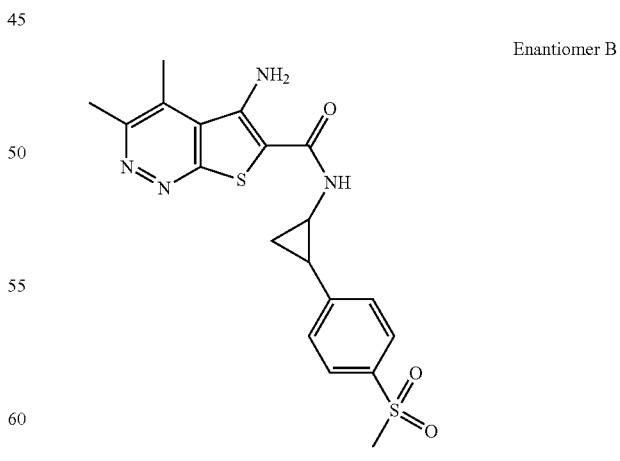

Enantiomer B

The overall preparation scheme for the isolation of the enantiomers of 5-amino-3,4-dimethyl-N-(2-(4-(methylsul fonyl)phenyl)cyclopropyl)thieno[2,3-c]pyridazine-6-carboxamide is shown above for Example 18.

Racemic 5-amino-3,4-dimethyl-N-(2-(4-(methylsulfonyl)phenyl)cyclopropyl) thieno[2,3-c]pyridazine-6-carboxamide (example 17) was resolved by chiral chromatography using a Chiralpak IC column, with a mobile phase consisting of 2:1 methanol/acetonitrile (w/0.1% DEA) in supercritical carbon dioxide to afford the second eluting enantiomer; $R_T$=3.69 min. LCMS: $R_T$=0.60 min, >99% @ 254 nm, >99% @ 215 nm; m/z (M+1)$^+$=417. $^1$H NMR (400 MHz, $d_6$-DMSO, δ (ppm)): 8.4 (d, J=3.8 Hz, 1H), 7.8 (d, J=8.3 Hz, 2H), 7.4 (d, J=8.3 Hz, 2H), 7.0 (br. s, 2H), 3.2 (s, 3H), 3.0-3.1 (m, 1H), 2.6-2.7 (m, 6H), 2.2-2.3 (m, 1H), 1.5-1.6 (m, 1H), 1.3-1.4 (m, 1H), HRMS calculated for $C_{19}H_{20}N_4O_3S_2$ (M+H)$^+$ m/z: 417.1055, measured: 417.1054.

22. Preparation of 5-amino-N-(4-((difluoromethyl)sulfonyl)benzyl)-3,4-dimethylthieno[2,3-c]pyridazine-6-carboxamide (Example 20, Method T)

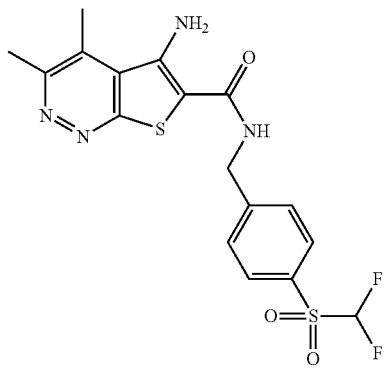 [SMILES: Cc1nnc2sc(C(=O)NCc3ccc(S(=O)(=O)C(F)F)cc3)c(N)c2c1C]

The overall synthesis scheme for the preparation of 5-amino-N-(4-((difluoromethyl)sulfonyl)benzyl)-3,4-dimethylthieno[2,3-c]pyridazine-6-carboxamide (Example 20, Method T) is shown below.

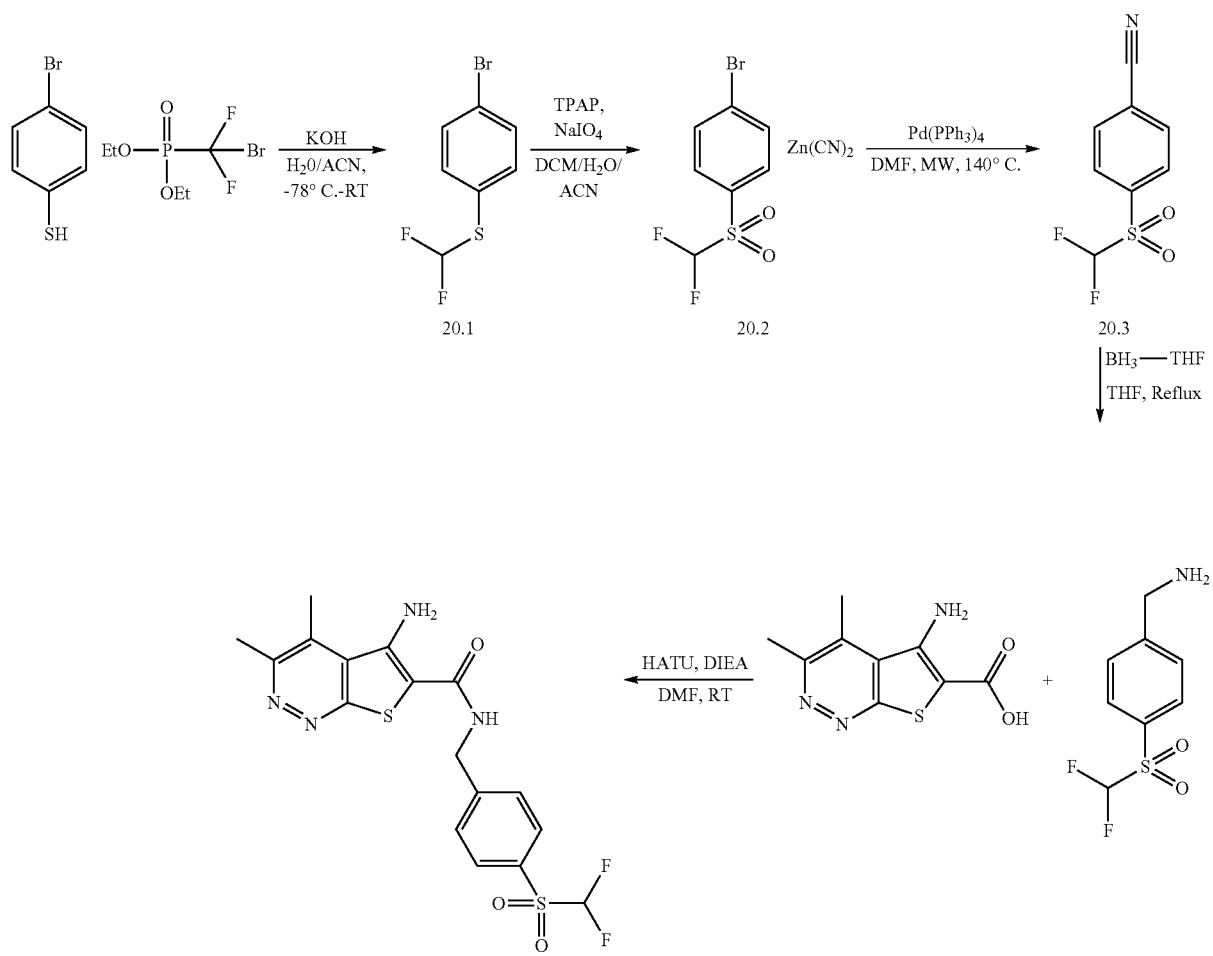

a. (4-bromophenyl)(difluoromethyl)sulfane (Compound 20.1)

4-bromobenzenethiol (2.5 g, 13.2 mmol) was added to a round-bottom flask equipped with a magnetic stir bar and dissolved in acetonitrile (70 mL). Water (70 mL) was added, followed by potassium hydroxide (14.8 g, 264 mmol). The resulting mixture was cooled to −78° C., and diethyl (bromodifluoromethyl)phosphonate (4.7 mL, 26.5 mmol) was added. The mixture was allowed to warm to room temperature, and stirred for an additional hour. After extracting with diethyl ether, the organic layers were collected, dried, and evaporated to afford a colorless oil, containing (4-bromophenyl)(difluoromethyl)sulfane, which was used without further purification.

b. 1-bromo-4-((difluoromethyl)sulfonyl)benzene (Compound 20.2)

To a solution of (4-bromophenyl)(difluoromethyl)sulfane (1.0 g, 4.2 mmol) in water (10 mL), dichloromethane (6 mL), and acetonitrile (6 mL) was added tetrapropylammonium perruthenate (293 mg, 0.84 mmol) and sodium periodate (4.0 g, 19 mmol. After allowing the mixture to stir for 1 hour, dichloromethane was added, and the organic layer was collected, dried, and purified by silica gel chromatography (0-50% EtOAc in hexanes) to afford 1-bromo-4-((difluoromethyl)sulfonyl)benzene as a colorless solid.

c. 4-((difluoromethyl)sulfonyl)benzonitrile (Compound 20.3)

To a microwave vial equipped with a magnetic stir bar were added 1-bromo-4-((difluoromethyl)sulfonyl)benzene (1.75 g, 6.6 mmol), zinc (II) cyanide (1.15 g, 9.9 mmol), Tetrakis(triphenylphosphine)palladium (762 mg, 0.66 mmol). The vial was sealed, evacuated and backfilled with argon three times, and then N,N-dimethylformamide (10 mL) was added. The mixture was briefly purged and backfilled with argon three additional times, and then heated to 140° C. under microwave irradiation for 35 minutes. The resulting mixture was poured into ca. 100 mL water and extracted with ethyl acetate. The organic layers were collected, dried, evaporated and purified by silica gel chromatography (0-50% EtOAc in hexanes) to afford 4-((difluoromethyl)sulfonyl)benzonitrile as a colorless solid.

d. (4-((difluoromethyl)sulfonyl)phenyl)methanamine (Compound 20.4)

To a solution of 4-((difluoromethyl)sulfonyl)benzonitrile (1.55 g, 7.1 mmol) in tetrahydrofuran (20 mL) was added a 1M solution of borane-tetrahydrofuran (14.2 mL, 14.2 mmol). This mixture was heated to reflux for 2 hours, and then allowed to cool to room temperature. Excess borane was destroyed by the careful addition of methanol, and volatiles were removed under reduced pressure. The resulting residue was re-dissolved in methanol, and loaded onto an SCX cartridge. Elution with methanolic ammonia and concentration under reduced pressure afforded (4-((difluoromethyl)sulfonyl)phenyl)methanamine as a yellow oil, which was used without further purification. LCMS: $R_T$=0.18 min, >99% @ 254 nm, >99% @ 215 nm; m/z (M+1)$^+$=222.

e. 5-amino-N-(4-((difluoromethyl)sulfonyl)benzyl)-3,4-dimethylthieno[2,3-c]pyridazine-6-carboxamide (Example 20)

A two dram vial equipped with a magnetic stir bar was charged with 5-amino-3,4-dimethylthieno[2,3-c]pyridazine-6-carboxylic acid (100 mg, 0.45 mmol), which was suspended in N,N-dimethylformamide (2 mL). N,N-diisopropylethylamine was added (235 µL, 1.4 mmol), followed by HATU (205 mg, 0.54 mmol). This mixture was allowed to stir at room temperature for 1 hour, and then (4-((difluoromethyl)sulfonyl)phenyl)methanamine (100 mg, 0.45 mmol) was added. After allowing the mixture to stir for an additional 30 minutes, reversed-phase HPLC eluting with acetonitrile/water (w/0.1% TFA) afforded 5-amino-N-(4-((difluoromethyl)sulfonyl)benzyl)-3,4-dimethylthieno[2,3-c]pyridazine-6-carboxamide as a yellow solid. LCMS: $R_T$=0.60 min, >99% @ 254 nm, >99% @ 215 nm; m/z (M+1)$^+$=427. $^1$H NMR (400 MHz, d$_6$-DMSO, δ (ppm)): 8.8 (t, J=6.0 Hz, 1H), 8.0 (d, J=8.3 Hz, 2H), 7.7 (d, J=8.3 Hz, 2H), 7.3 (t, J=52 Hz, 1H), 7.0 (br. s, 2H), 4.6 (d, J=5.8 Hz, 2H), 2.6-2.7 (m, 6H), HRMS calculated for $C_{17}H_{16}F_2N_4O_3S_2$ (M+H)$^+$ m/z: 427.0710, measured: 427.0707.

23. Preparation of 5-amino-N-(4-((fluoromethyl)sulfonyl)benzyl)-3,4-dimethylthieno[2,3-c]pyridazine-6-carboxamide (Example 21, Method U)

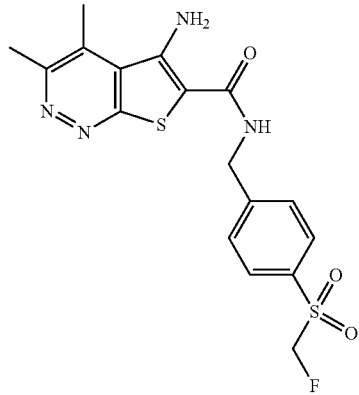 [SMILES: Cc1nnc2sc(C(=O)NCc3ccc(S(=O)(=O)CF)cc3)c(N)c2c1C]

The overall synthesis scheme for the preparation of 5-amino-N-(4-((fluoromethyl)sulfonyl)benzyl)-3,4-dimethylthieno[2,3-c]pyridazine-6-carboxamide (Example 21, Method U) is shown below.

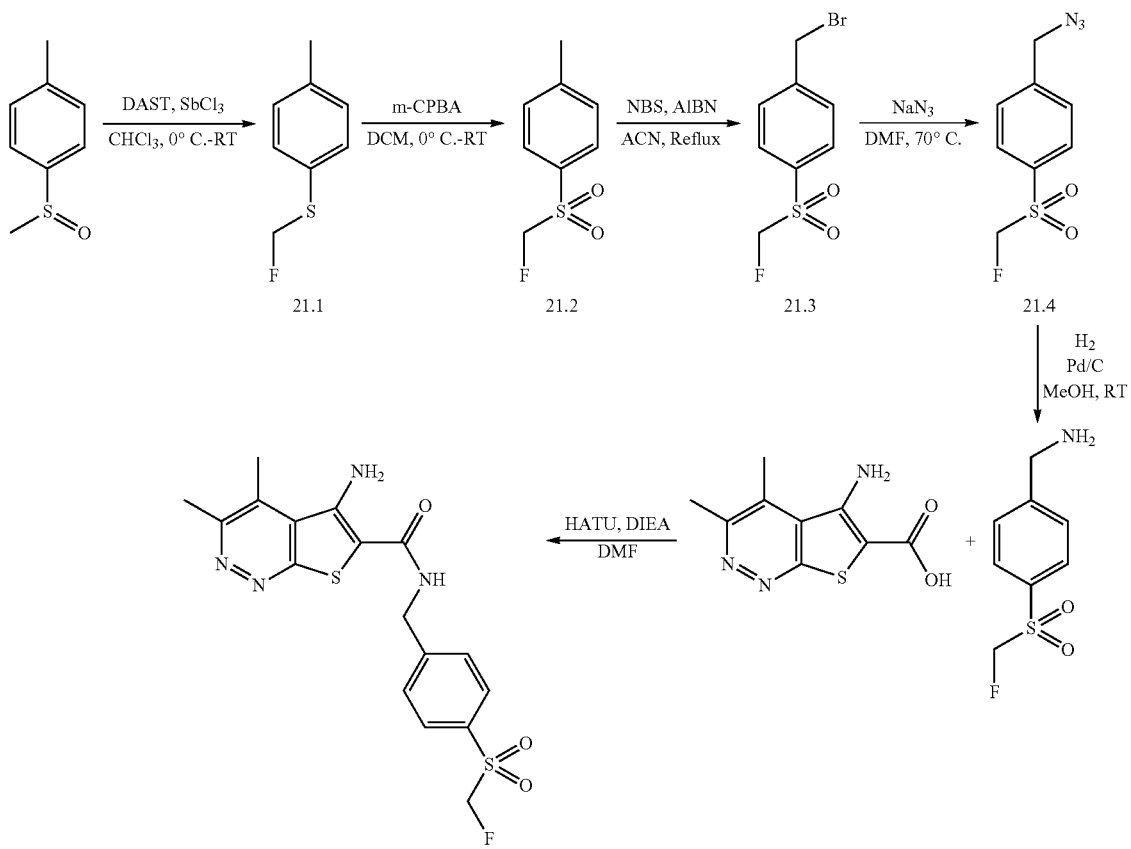

Example 21
(Compound B132, Table I)

a. (fluoromethyl)(p-tolyl)sulfane (Compound 21.1)

1-methyl-4-(methylsulfinyl)benzene (1.65 g, 10.7 mmol) was added to a flame-dried flask equipped with a magnetic stir bar and dissolved in chloroform (50 mL). After cooling the mixture in an ice bath, DAST was added slowly to the mixture, followed by antimony (III) chloride (200 mg, 0.8 mmol). The mixture was allowed to reach room temperature and stirred for an additional 15 minutes, and then poured into an ice cold, saturated solution of sodium bicarbonate. The resulting aqueous suspension was extracted with dichloromethane, and the organic layers collected, dried, evaporated and purified by silica gel chromatography (0-30% EtOAc in hexanes) to afford (fluoromethyl)(p-tolyl)sulfane as an oil.

b. 1-((fluoromethyl)sulfonyl)-4-methylbenzene (Compound 21.2)

A solution of (fluoromethyl)(p-tolyl)sulfane (5.1 g, 32.7 mmol) in DCM (80 mL) was cooled in an ice bath and m-CPBA (13.9 g, 65.4 mmol) was added portionwise. After allowing the mixture to reach ambient temperature, stirring was continued for an additional 1.5 hours. The mixture was washed with aqueous potassium hydroxide solution, and the organic layers were collected, dried, evaporated and purified by silica gel chromatography (0-50% EtOAc in hexanes) to afford 1-((fluoromethyl)sulfonyl)-4-methylbenzene as a colorless solid.

c. 1-(bromomethyl)-4-((fluoromethyl)sulfonyl)benzene (Compound 21.3)

To a solution of 1-((fluoromethyl)sulfonyl)-4-methylbenzene (3.34 g, 17.8 mmol) in acetonitrile (90 mL) was added N-bromosuccinimide (3.5 g, 17.8 mmol) and AIBN (146 mg, 0.89 mmol). The resulting mixture was heated to reflux for 5 hours, and volatiles were removed under reduced pressure. The resulting residue was purified by silica gel chromatography (0-35% EtOAc in hexanes) to afford 1-(bromomethyl)-4-((fluoromethyl)sulfonyl)benzene as a colorless solid.

d. 1-(azidomethyl)-4-((fluoromethyl)sulfonyl)benzene (Compound 21.4)

1-(bromomethyl)-4-((fluoromethyl)sulfonyl)-benzene (4.6 g, 17.2 mmol) was added to a round-bottom flask equipped with a magnetic stir bar and dissolved in DMF (35 mL). Sodium azide (1.34 g, 21 mmol) was added, and the mixture was heated to 70° C. for 1 hour. After cooling to room temperature, the mixture was poured into ice water and extracted with diethyl ether. The organic layers were collected, dried, and evaporated to afford an oil containing 1-(azidomethyl)-4-((fluoromethyl)sulfonyl)benzene, which was used without further purification.

e. (4-((fluoromethyl)sulfonyl)phenyl)methanamine (Compound 21.5)

To a solution of 1-(azidomethyl)-4-((fluoromethyl)sulfonyl)benzene (3.9 g, 17.2 mmol) in methanol was added 10% palladium on charcoal under a stream of argon. The flask was sealed, purged and backfilled with argon three times, before introducing hydrogen (1 atm). After allowing the mixture to stir at room temperature for 16 hours, the vessel was purged and backfilled with argon three additional times. Solids were removed by filtration through Celite®, and the filtrate was concentrated under reduced pressure. The resulting residue was loaded onto an SCX cartridge, eluted with methanolic ammonia and concentrated under reduced pressure to afford an oil containing (4-((fluoromethyl)sulfonyl)phenyl)methanamine, which was used without further purification. LCMS: $R_T$=0.13 min, >99% @ 254 nm, >99% @ 215 nm; m/z (M+1)$^+$=204.

f. 5-amino-N-(4-((fluoromethyl)sulfonyl)benzyl)-3,4-dimethylthieno[2,3-c]pyridazine-6-carboxamide (Example 21)

To a suspension of 5-amino-3,4-dimethylthieno[2,3-c]pyridazine-6-carboxylic acid (200 mg, 0.9 mmol) in DMF (4 mL) was added DIEA (470 μL, 2.7 mmol) and HATU (182 mg, 0.9 mmol) and this mixture was allowed to stir at room temperature for 30 minutes. (4-((fluoromethyl)sulfonyl)phenyl)methanamine (182 mg, 0.9 mmol) was added, and the mixture was allowed to stir for an additional 30 minutes, and then purified by reversed-phase HPLC eluting with acetonitrile/water (w/0.1% TFA) to afford 5-amino-N-(4-((fluoromethyl)sulfonyl)benzyl)-3,4-dimethylthieno[2,3-c]pyridazine-6-carboxamide. LCMS: $R_T$=0.55 min, >99% @ 254 nm, >99% @ 215 nm; m/z (M+1)$^+$=409. $^1$H NMR (400 MHz, d$_6$-DMSO, δ (ppm)): 8.8 (t, J=5.8 Hz, 1H), 7.9 (d, J=8.3 Hz, 2H), 7.6 (d, J=8.3 Hz, 2H), 6.9 (br. s, 2H), 5.7 (d, J=45 Hz, 2H), 4.6 (d, J=5.8 Hz, 2H), 2.6-2.7 (m, 6H), HRMS calculated for C$_{17}$H$_{17}$FN$_4$O$_3$S$_2$ (M+H)$^+$ m/z: 409.0804, measured: 409.0803.

24. Preparation of 5-amino-N-(4-(pentafluorosulfanyl)benzyl)-3,4-dimethylthieno[2,3-c]pyridazine-6-carboxamide (Example 22, Method V)

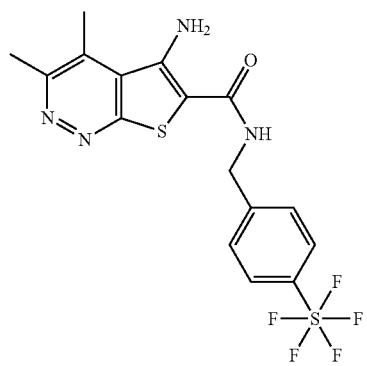 [SMILES: Cc1nnc2sc(C(=O)NCc3ccc(S(F)(F)(F)(F)F)cc3)c(N)c2c1C]

The overall synthesis scheme for the preparation of 5-amino-N-(4-(pentafluorosulfanyl)benzyl)-3,4-dimethylthieno[2,3-c]pyridazine-6-carboxamide (Example 22, Method V) is shown below.

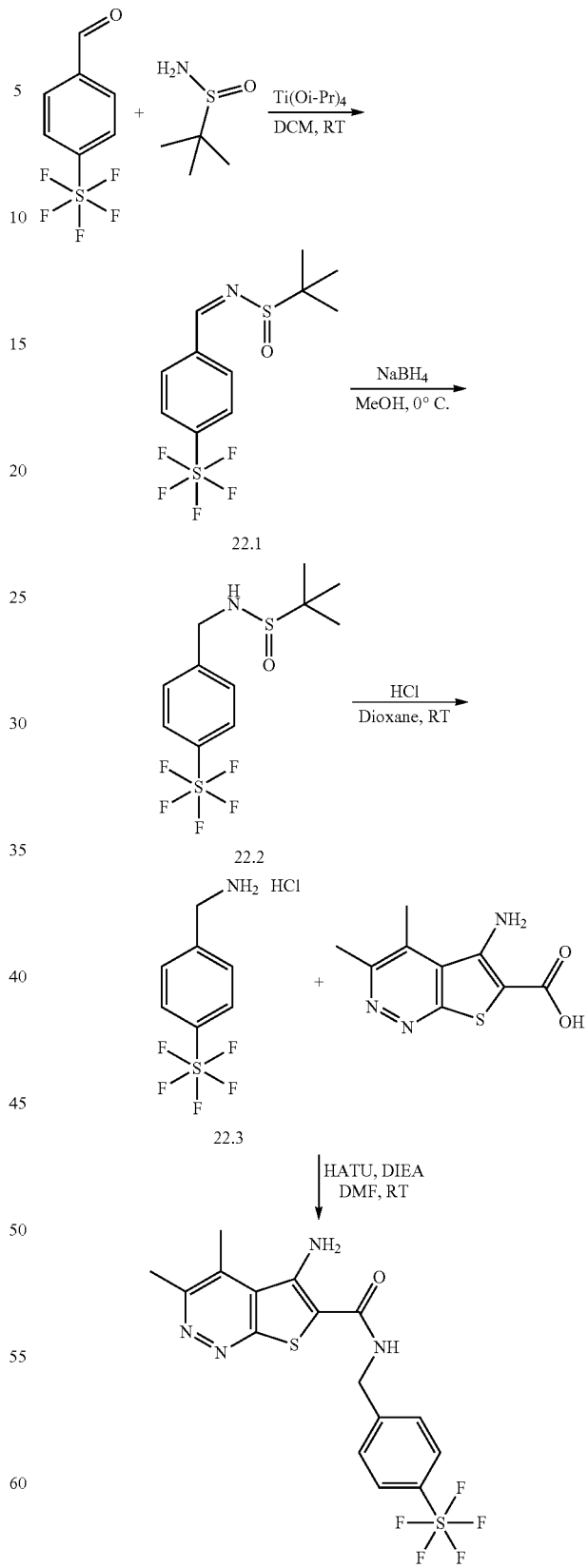

Example 22
(Compound B297, Table I)

a. N-(4-(pentafluorosulfanyl)benzylidene)-2-methyl-propane-2-sulfinamide (Compound 22.1)

To a solution of 4-(pentafluorosulfanyl)benzaldehyde (2 g, 8.6 mmol) in dichloromethane (25 mL) was added 2-methylpropane-2-sulfinamide (1.15 g, 9.5 mmol), followed by titanium tetraisopropoxide (5.1 mL, 17.2 mmol). The resulting mixture was allowed to stir at room temperature for 16 hours and then diluted with water. The organic layer was collected using a phase separator, dried, and evaporated to afford a white solid containing N-(4-(pentafluorosulfanyl)benzylidene)-2-methylpropane-2-sulfinamide, and was used without further purification.

b. 2-methyl-N-(4-(Pentafluorosulfanyl)benzyl)propane-2-sulfinamide (Compound 22.2)

N-(4-(pentafluorosulfanyl)benzylidene)-2-methylpropane-2-sulfinamide (2.9 g, 8.7 mmol) was added to a round-bottom flask equipped with a magnetic stir bar and dissolved in methanol (20 mL). This mixture was cooled in an ice bath, and sodium borohydride (494 mg, 13.1 mmol) was added portionwise. After evolution of hydrogen had ceased, the mixture was diluted with water and extracted with ethyl acetate. The organic layers were collected, dried, and evaporated to afford a colorless oil containing 2-methyl-N-(4-(pentafluorosulfanyl) benzyl)propane-2-sulfinamide and was used without further purification.

c. (4-(pentafluorosulfanyl)phenyl)methanamine hydrochloride (Compound 22.3)

A round-bottom flask equipped with a magnetic stir bar was charged with 2-methyl-N-(4-(pentafluorosulfanyl)benzyl)propane-2-sulfinamide (2.9 g, 8.7 mmol) and 1,4-dioxane (20 mL). To this solution was slowly added an excess of a 4M solution of HCl in dioxane. This mixture was allowed to stir at room temperature for 15 minutes, and then volatiles were removed under reduced pressure to afford a white powder containing (4-(pentafluorosulfanyl)phenyl)methanamine hydrochloride, which was used without further purification.

d. 5-amino-N-(4-(pentafluorosulfanyl)benzyl)-3,4-dimethylthieno[2,3-c]pyridazine-6-carboxamide (Example 22)

To a suspension of 5-amino-3,4-dimethylthieno[2,3-c]pyridazine-6-carboxylic acid (1 g, 4.5 mmol) in N,N-dimethylformamide (10 mL) was added N,N-diisopropyl ethylamine (2.3 mL, 13.5 mmol) and HATU (2.1 g, 5.4 mmol). This mixture was allowed to stir at room temperature for 30 minutes, and (4-(pentafluorosulfanyl)phenyl) methanamine hydrochloride (1.2 g, 4.5 mmol) was added. After stirring for an additional hour, the mixture was purified by reversed-phase HPLC eluting with acetonitrile/water (w/0.1% TFA) to afford 5-amino-N-(4-(pentafluorosulfanyl)benzyl)-3,4-dimethylthieno[2,3-c]pyridazine-6-carboxamide as a yellow solid. LCMS: $R_T$=0.73 min, >99% @ 254 nm, >99% @ 215 nm; m/z (M+1)$^+$=439. $^1$H NMR (400 MHz, d$_6$-DMSO, δ (ppm)): 8.7 (t, J=5.9 Hz, 1H), 7.8-7.9 (m, 2H), 7.5 (d, J=8.4 Hz, 2H), 7.0 (br. s, 2H), 4.5 (d, J=5.8 Hz, 2H), 2.7-2.8 (m, 6H), HRMS calculated for $C_{16}H_{15}F_5N_4OS_2$ (M+H)$^+$ m/z: 439.0686, measured: 439.0689.

25. Preparation of 5-amino-N-(4-(fluoromethoxy)benzyl)-3,4-dimethylthieno[2,3-c]pyridazine-6-carboxamide (Example 23, Method W)

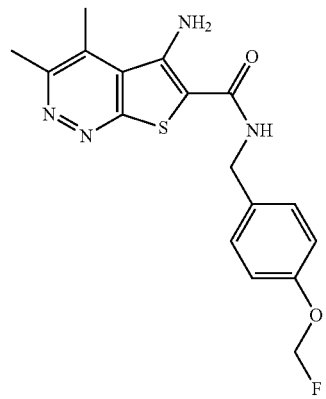 [SMILES: Cc1nnc2sc(C(=O)NCc3ccc(OCF)cc3)c(N)c2c1C]

The overall synthesis scheme for the preparation of 5-amino-N-(4-(fluoromethoxy)benzyl)-3,4-dimethylthieno[2,3-c]pyridazine-6-carboxamide (Example 23, Method W) is shown below.

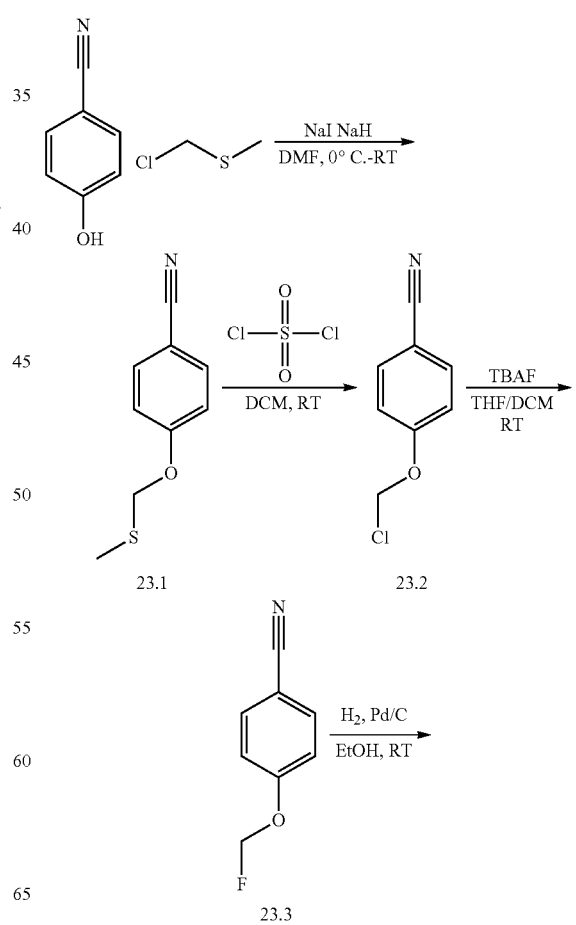

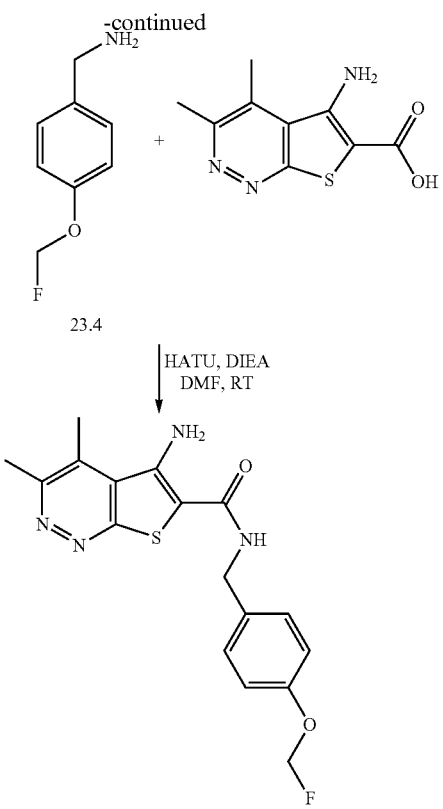

Example 23
(Compound B411, Table I)

a. 4-((methylthio)methoxy)benzonitrile (Compound 23.1)

To a solution of 4-hydroxybenzonitrile (4 g, 33.6 mmol) in N,N-dimethylformamide (70 mL) was added sodium iodide (5.5 g, 37 mmol), and then the mixture was cooled in an ice bath. Sodium hydride (887 mg, 37 mmol) was added portionwise, and the mixture allowed to continue stirring until foaming ceased. (Chloromethyl)(methyl)sulfane (4.2 mL, 50.4 mmol) was added slowly, and the mixture allowed to warm to ambient temperature. After stirring at room temperature for 16 hours, the mixture was diluted with water and extracted with diethyl ether. The organic layers were collected, dried, evaporated and purified by silica gel chromatography (0-50% EtOAc in hexanes) to afford 4-((methylthio)methoxy)benzonitrile as an oil. LCMS: $R_T$=0.90 min, >99% @ 254 nm, >99% @215 nm; m/z (M+1)$^+$=180.

b. 4-(chloromethoxy)benzonitrile (Compound 23.2)

A solution of 4-((methylthio)methoxy)benzonitrile (1 g, 5.6 mmol) in dichloromethane was treated with a 1M solution of sulfuryl chloride in dichloromethane (5.6 mL, 5.6 mmol) and allowed to stir at room temperature for 10 minutes. Volatiles were removed under reduced pressure, and the resulting residue containing 4-(chloromethoxy)benzonitrile was used without further purification.

c. 4-(fluoromethoxy)benzonitrile (Compound 23.3)

4-(chloromethoxy)benzonitrile (933 mg, 5.6 mmol) was taken up in dichloromethane (10 mL), and a 1M solution of tetrabutylammonium fluoride in THF (8.4 mL, 8.4 mmol) was added. The resulting solution was allowed to stir at room temperature for 24 hours, and volatiles were removed under reduced pressure. The resulting residue was purified by silica gel chromatography (0-50% EtOAc in hexanes) to afford 4-(fluoromethoxy)benzonitrile as a colorless oil.

d. (4-(fluoromethoxy)phenyl)methanamine (Compound 23.4)

To a solution of 4-(fluoromethoxy)benzonitrile (1.5 g, 10 mmol) in ethanol (50 mL) was added ca. 4 mL of 6N HCl, followed by 10% palladium on charcoal. After evacuating and backfilling the heterogeneous mixture with argon three times, hydrogen (1 atm.) was introduced, and the mixture allowed to stir at room temperature for 16 hours. The resulting mixture was filtered to remove solids and evaporated to afford an oil, which was loaded onto an SCX cartridge and washed with methanol. Elution with methanolic ammonia and concentration under reduced pressure afforded (4-(fluoromethoxy)phenyl)methanamine as an oil.

e. 5-amino-N-(4-(fluoromethoxy)benzyl)-3,4-dimethylthieno[2,3-c]pyridazine-6-carboxamide (Example 23)

To a suspension of 5-amino-3,4-dimethylthieno[2,3-c]pyridazine-6-carboxylic acid (50 mg, 0.22 mmol) in N,N-dimethylformamide (1 mL) was added N,N-diisopropylamine (76 µL, 0.44 mmol) and HATU (100 mg, 0.24 mmol). This mixture was allowed to stir at room temperature for 30 minutes, and (4-(fluoromethoxy)phenyl)methanamine (35 mg, 0.22 mmol) was added. After stirring for an additional hour, the mixture was purified by reversed-phase HPLC eluting with acetonitrile/water (w/0.1% TFA) to afford 5-amino-N-(4-(fluoromethoxy)benzyl)-3,4-dimethylthieno[2,3-c]pyridazine-6-carboxamide as a solid. LCMS: $R_T$=0.59 min, >99% @ 254 nm, >99% @ 215 nm; m/z (M+1)$^+$=361. $^1$H NMR (400 MHz, d$_6$-DMSO, δ (ppm)): 8.6 (t, J=5.9 Hz, 1H), 7.2-7.3 (m, 2H), 7.0-7.1 (m, 2H), 7.0 (br. s, 2H), 5.8 (d, J=54 Hz, 2H), 4.4 (d, J=5.9 Hz, 2H), 2.7-2.8 (m, 6H), HRMS calculated for C$_{17}$H$_{17}$FN$_4$O$_2$S (M+H)$^+$ m/z: 361.1135, measured: 361.1132.

26. Preparation of (5-amino-3,4-dimethylthieno[2,3-c]pyridazin-6-yl)(3-(phenylthio)azetidin-1-yl)methanone (Example 24, Method X)

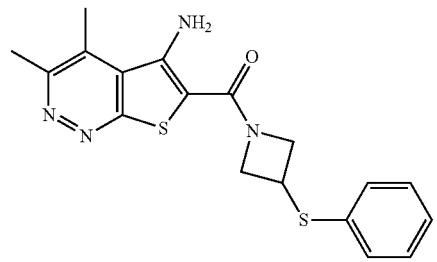 [SMILES: Cc1nnc2sc(C(=O)N3CC(Sc4ccccc4)C3)c(N)c2c1C]

The overall synthesis scheme for the preparation of (5-amino-3,4-dimethylthieno[2,3-c]pyridazin-6-yl)(3-(phenylthio)azetidin-1-yl)methanone (Example 24, Method X) is shown below.

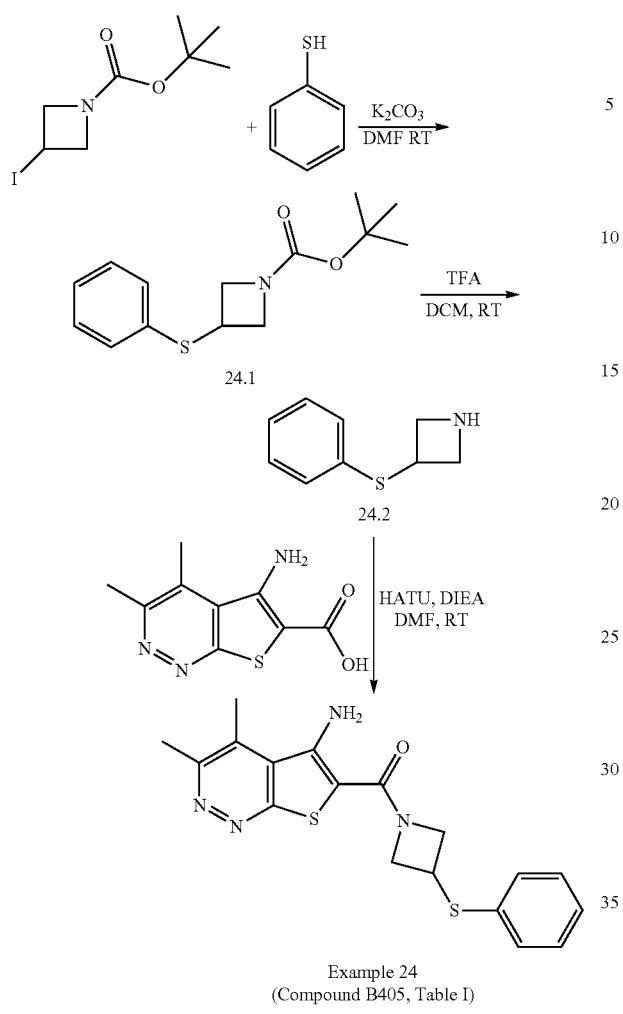

Example 24
(Compound B405, Table I)

a. tert-butyl 3-(phenylthio)azetidine-1-carboxylate (Compound 24.1)

To a stirred solution of thiophenol (0.075 g, 0.7 mmol) in DMF (2 mL) was added K₂CO₃ (122 mg, 0.9 mmol) followed by 1-BOC-3-iodoazetidine (250 mg, 0.9 mmol). The reaction was stirred overnight then diluted with water and EtOAc. The aqueous layer was separated and extracted with EtOAc. The combined organic layers were washed with water (3×), 0.1M HCl, saturated NaHCO₃, brine (2×), dried over Na₂SO₄ and concentrated to give an oil. The oil was purified by chromatography on silica gel (24 g) eluting with a 0-to-20% EtOAc/hexane gradient to give the desired product. $^1$H NMR (400 MHz, DMSO-$d_6$): δ 7.32-7.35 (m, 2H), 7.21-7.26 (m, 3H), 4.30-4.34 (m, 2H), 4.13-4.20 (m, 1H), 3.64-3.67 (m, 2H), 1.35 (s, 9H).

b. 3-(phenylthio)azetidine (Compound 24.2)

The tert-butyl 3-(phenylthio)azetidine-1-carboxylate (0.143 g, 0.54 mmol) was stirred in 15% TFA/DCM (8 mL) for 45 minutes, then concentrated under vacuum. The residue was taken up in MeOH and loaded onto an SCX cartridge. The cartridge was washed with MeOH, then with 2N NH₃/MeOH. The 2N NH₃/MeOH fractions were concentrated under vacuum to give 3-(phenylthio)azetidine.

c. (5-amino-3,4-dimethylthieno[2,3-c]pyridazin-6-yl)(3-(phenylthio)azetidin-1-yl)methanone (Example 24)

A mixture of 5-amino-3,4-dimethylthieno[2,3-c]pyridazine-6-carboxylic acid (60 mg, 0.27 mmol)), 3-(phenylthio)azetidine (76 mg, 0.46 mmol) and HATU (120 mg, 0.31 mmol were stirred in DMF (1.3 mL) at room temperature for 5 minutes. Diisopropyl ethylamine (0.14 mL, 0.81 mmol) was added and the reaction was stirred for about 45 minutes. The reaction was purified by directly injecting the reaction mixture onto a HPLC system (ACN/water/0.1% TFA), followed by free-basing to give the title compound. LCMS: $R_T$=0.68 min, >99% @ 215 and 254 nm and ELSD; m/z (M+1)⁺=371. $^1$H NMR (400 MHz, DMSO-$d_6$): δ 7.26-7.40 (m, 5H), 7.04 (bs, 2H), 4.79 (bs, 2H), 4.32-4.38 (m, 1H), 4.11 (bs, 2H), 2.73 (s, 3H), 2.71 (s, 3H), HRMS calculated for $C_{18}H_{18}N_4OS_2$ (M+H)⁺ m/z: 371.1000, measured: 371.0999.

27. Preparation of (5-amino-3,4-dimethylthieno[2,3-c]pyridazin-6-yl)(3-(phenylsulfonyl)azetidin-1-yl)methanone (Example 25, Method Y)

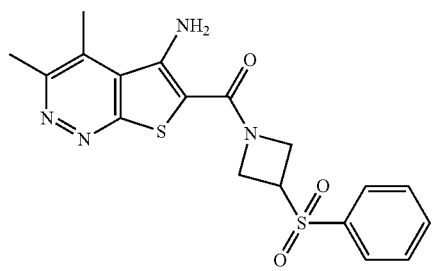 [SMILES: Cc1nnc2sc(C(=O)N3CC(S(=O)(=O)c4ccccc4)C3)c(N)c2c1C]

The overall synthesis scheme for the preparation of (5-amino-3,4-dimethylthieno[2,3-c]pyridazin-6-yl)(3-(phenylsulfonyl)azetidin-1-yl)methanone (Example 25, Method Y) is shown below.

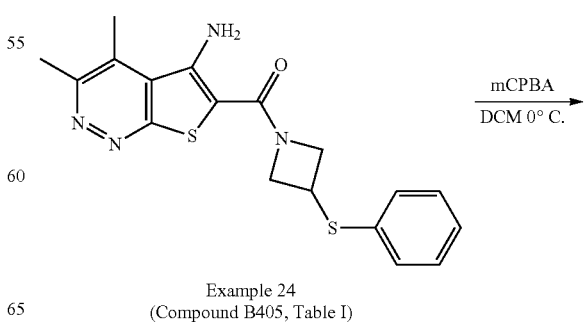

Example 24
(Compound B405, Table I)

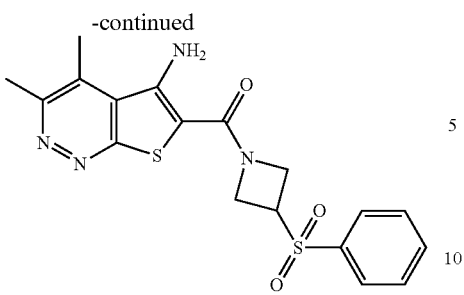

Example 25
(Compound B413, Table I)

To a stirred solution of (5-amino-3,4-dimethylthieno[2,3-c]pyridazin-6-yl)(3-(phenylthio)azetidin-1-yl)methanone (0.023 g, 0.06 mmol) in DCM (2 mL) at 0° C. under argon was added 3-chloroperoxybenzoic acid (30 mg, 0.13 mmol) slowly in two portions. The reaction was stirred about 45 minutes, LC/MS indicated no remaining SM. The reaction was diluted with DCM and washed with aqueous saturated NaHCO$_3$ (2×), water (2×) and brine, then concentrated under vacuum to give a crude oil. Purification by reverse-phase HPLC (ACN/water/0.1% TFA), followed by free-basing gave the title compound. LCMS: R$_T$=0.55 min, >99% @ 215 and 254 nm and ELSD; m/z (M+1)$^+$=403. HRMS calculated for C$_{18}$H$_{18}$N$_4$O$_3$S$_2$ (M+H)$^+$ m/z: 403.0899, measured: 403.0899.

28. Preparation of 5-amino-N-(3-fluoro-4-(2-oxopyridin-1(2H)-yl)benzyl)-3,4-dimethylthieno[2,3-c]pyridazine-6-carboxamide, (Example 26, Method Z)

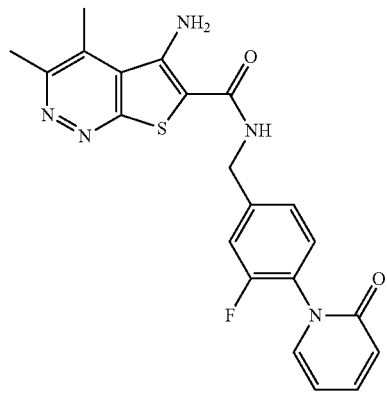 [SMILES: Cc1nnc2sc(C(=O)NCc3ccc(-n4ccccc4=O)c(F)c3)c(N)c2c1C]

The overall synthesis scheme for the preparation of 5-amino-N-(3-fluoro-4-(2-oxopyridin-1(2H)-yl)benzyl)-3,4-dimethylthieno[2,3-c]pyridazine-6-carboxamide, (Example 26, Method Z) is shown below.

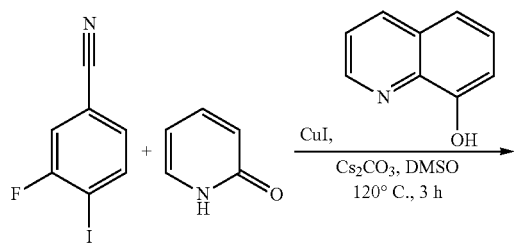

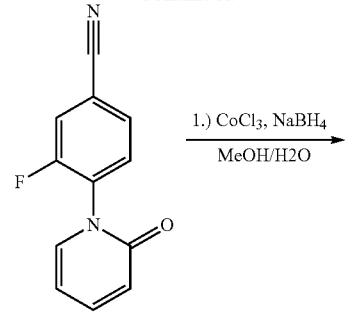

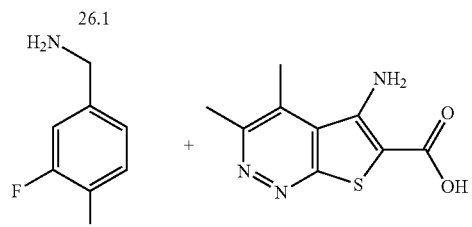

Example 26
(Compound B483, Table I)

a. 3-fluoro-4-(2-oxopyridin-1(2H)-yl)benzonitrile (Compound 26.1)

To a microwave vial equipped with a magnetic stir bar were charged 3-fluoro-4-iodobenzonitrile (250 mg, 1.0 mmol), pyridin-2(1H)-one (192 mg, 2.0 mmol), copper (I) iodide (57 mg, 0.30 mmol), quinolin-8-ol (44 mg, 0.30 mmol), and cesium carbonate (650 mg, 2.0 mmol). The vial was sealed, evacuated and backfilled with argon three times, and then dimethyl sulfoxide (2.5 mL) was introduced via syringe. The resulting suspension was purged and backfilled with argon an additional three times, and heated to 120° C. for three hours. After cooling to ambient temperature, the mixture was poured into water and extracted with ethyl acetate. The organic layers were collected, dried, evaporated and purified by silica gel chromatography (0-50% EtOAc in hexanes) to afford 3-fluoro-4-(2-oxopyridin-1(2H)-yl)benzonitrile.

b. 1-(4-(Aminomethyl)-2-fluorophenyl)pyridin-2(1H)-one (Compound 26.2)

To a solution of 3-fluoro-4-(2-oxopyridin-1(2H)-yl)benzonitrile (520 mg, 2.4 mmol) in methanol (10 mL) and water (10 µL) was added cobalt (II) chloride hexahydrate (1.13 g, 4.8 mmol). Sodium borohydride (888 mg, 24 mmol) was added in small portions over the course of 30 minutes, and the mixture was allowed to continue stirring at room temperature for an additional hour. The mixture was diluted with water and extracted with dichloromethane. The organic layers were collected, dried, and evaporated. The resulting residue was re-dissolved in methanol, loaded onto an SCX cartridge and washed with additional methanol. Elution with methanolic ammonia followed by concentration under reduced pressure afforded an oil containing 1-(4-(aminomethyl)-2-fluorophenyl)pyridin-2(1H)-one, which was used without further purification.

c. 5-amino-N-(3-fluoro-4-(2-oxopyridin-1(2H)-yl)benzyl)-3,4-dimethylthieno[2,3-c]pyridazine-6-carboxamide (Example 26)

5-amino-3,4-dimethylthieno[2,3-c]pyridazine-6-carboxylic acid (100 mg, 0.45 mmol) was charged to a screw-cap vial equipped with a magnetic stir bar and suspended in N,N-dimethylformamide. N,N-diisopropylethylamine (235 µL) was added, followed by HATU (205 mg, 0.54 mmol). This mixture was allowed to stir at room temperature for 30 minutes, and 1-(4-(aminomethyl)-2-fluorophenyl)pyridin-2(1H)-one (98 mg, 0.45 mmol) was added. The mixture was allowed to continue stirring at room temperature for an additional hour. Purification by reversed-phase HPLC eluting with acetonitrile/water (w/0.1% TFA) afforded 5-amino-N-(3-fluoro-4-(2-oxopyridin-1(2H)-yl)benzyl)-3,4-dimethylthieno[2,3-c]pyridazine-6-carboxamide. LCMS: $R_T$=0.65 min, >99% @ 254 nm, >99% @ 215 nm; m/z (M+1)$^+$=424. $^1$H NMR (400 MHz, d$_6$-DMSO, δ (ppm)): 8.6-8.8 (m, 1H), 8.0-8.1 (m, 1H), 7.8-7.9 (m, 1H), 7.2-7.3 (m, 2H), 7.1-7.2 (m, 1H), 7.1-7.2 (m, 2H), 7.0-7.1 (br. s, 2H), 4.5 (d, J=5.9 Hz, 2H), 2.7-2.8 (m, 6H). HRMS calculated for $C_{19}H_{20}N_4O_3S_2$ (M+H)$^+$ m/z: 424.1244, measured: 424.1242.

29. Characterization of Exemplary Compounds

The compounds in Table I were synthesized with methods identical or analogous to those described herein, e.g. the column denoted as "Synthesis Method" refers to the designated synthesis method described herein above. For example, "A" refers to "Method A" described herein above for the preparation of Example 1 (5-amino-N-(benzo[d][1,3]dioxol-5-ylmethyl)-3,4-dimethylthieno[2,3-c]pyridazine-6-carboxamide). The other methods identified in Table I are similarly associated with the appropriate method as described herein above. The requisite starting materials were commercially available, described in the literature, or readily synthesized by one skilled in the art of organic synthesis. The mass spectrometry data were obtained using the general LC-MS methods as described above.

TABLE I

| No. | Compound | M + H | Synthetic Method |
|---|---|---|---|
| B1 | | 235 | A |
| B2 | | 315 | A |
| B3 | | 315 | A |

TABLE I-continued

| No. | Compound | M + H | Synthetic Method |
|---|---|---|---|
| B4 | | 328 | A |
| B5 | | 349 | A |
| B6 | | 277 | A |
| B7 | | 331 | A |
| B8 | | 263 | A |
| B9 | | 313 | A |

TABLE I-continued

| No. | Compound | M + H | Synthetic Method |
|---|---|---|---|
| B10 | | 315 | A |
| B11 | | 320 | A |
| B12 | | 357 | A |
| B13 | | 314 | A |
| B14 | | 314 | A |
| B15 | | 349 | A |

TABLE I-continued

| No. | Compound | M + H | Synthetic Method |
|---|---|---|---|
| B16 | | 343 | A |
| B17 | | 315 | A |
| B18 | | 321 | A |
| B19 | | 285 | A |
| B20 | | 363 | A |
| B21 | | 303 | A |

TABLE I-continued
| No. | Compound | M + H | Synthetic Method |
|---|---|---|---|
| B22 | 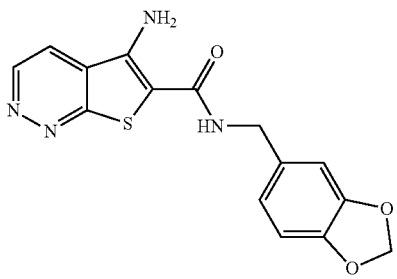 [SMILES: Nc1c(C(=O)NCc2ccc3c(c2)OCO3)sc2nnccc12] | 329 | A |
| B23 | 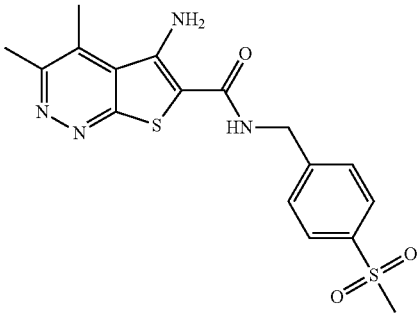 [SMILES: Cc1nnc2sc(C(=O)NCc3ccc(S(C)(=O)=O)cc3)c(N)c2c1C] | 391 | A |
| B24 | 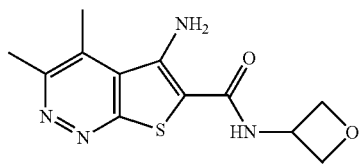 [SMILES: Cc1nnc2sc(C(=O)NC3COC3)c(N)c2c1C] | 279 | A |
| B25 | 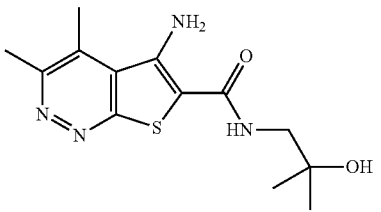 [SMILES: Cc1nnc2sc(C(=O)NCC(C)(C)O)c(N)c2c1C] | 295 | A |
| B26 | 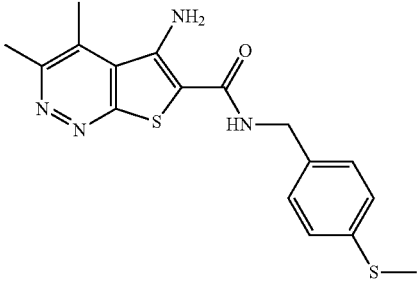 | 359 | A |

TABLE I-continued

| No. | Compound | M + H | Synthetic Method |
|---|---|---|---|
| B27 | | 355 | A |
| B28 | | 336 | A |
| B29 | | 371 | A |
| B30 | | 369 | A |
| B31 | | 369 | S |

Enantiomer B (See Note 1 below)

TABLE I-continued

| No. | Compound | M + H | Synthetic Method |
|---|---|---|---|
| B32 | [structure] Enantiomer A (See Note 2 below) | 369 | R |
| B33 | [structure] | 409 | V |
| B34 | [structure] | 375 | A |
| B35 | [structure] | 293 | A |
| B36 | [structure] | 300 | A |

TABLE I-continued

| No. | Compound | M + H | Synthetic Method |
|---|---|---|---|
| B37 | | 345 | O |
| B38 | | 300 | A |
| B39 | | 438 | A |
| B40 | | 467 | A |
| B41 | | 515 | A |

TABLE I-continued

| No. | Compound | M + H | Synthetic Method |
|---|---|---|---|
| B42 | | 393 | A |
| B43 | | 355 | A |
| B44 | | 391 | A |
| B45 | | 367 | A |
| B46 | | 386 | D |

TABLE I-continued

| No. | Compound | M + H | Synthetic Method |
|---|---|---|---|
| B47 | | 433 | A |
| B48 | | 419 | A |
| B49 | | 405 | A |
| B50 | | 383 | M |
| B51 | | 339 | M |

TABLE I-continued

| No. | Compound | M + H | Synthetic Method |
|---|---|---|---|
| B52 | | 369 | M |
| B53 | | 419 | M |
| B54 | | 303 | M |
| B55 | | 395 | M |
| B56 | | 397 | M |

TABLE I-continued

| No. | Compound | M + H | Synthetic Method |
|---|---|---|---|
| B57 | | 375 | M |
| B58 | | 417 | M |
| B59 | | 386 | D |
| B60 | | 369 | D |

TABLE I-continued

| No. | Compound | M + H | Synthetic Method |
|-----|----------|-------|------------------|
| B61 | | 398 | D |
| B62 | | 369 | D |
| B63 | | 348 | D |
| B64 | | 358 | D |

TABLE I-continued

| No. | Compound | M + H | Synthetic Method |
|---|---|---|---|
| B65 | | 368 | D |
| B66 | | 445 | P |
| B67 | | 339 | A |
| B68 | | 279 | A |
| B69 | | 295 | A |
| B70 | | 306 | A |

TABLE I-continued

| No. | Compound | M + H | Synthetic Method |
|---|---|---|---|
| B71 | | 314 | A |
| B72 | | 330 | A |
| B73 | | 371 | A |
| B74 | | 405 | A |
| B75 | | 383 | A |
| B76 | | 397 | A |

TABLE I-continued

| No. | Compound | M + H | Synthetic Method |
|---|---|---|---|
| B77 | | 370 | A |
| B78 | | 409 | V |
| B79 | | 383 | A |
| B80 | | 356 | C |
| B81 | | 278 | C |
| B82 | | 370 | C |

TABLE I-continued

| No. | Compound | M + H | Synthetic Method |
|---|---|---|---|
| B83 | | 378 | C |
| B84 | | 277 | A |
| B85 | | 383 | A |
| B86 | | 363 | A |
| B87 | | 291 | A |
| B88 | | 314 | A |
| B89 | | 317 | V |

TABLE I-continued

| No. | Compound | M + H | Synthetic Method |
|---|---|---|---|
| B90 | | 361 | A |
| B91 | | 357 | A |
| B92 | | 417 | A |
| B93 | | 328 | A |
| B94 | | 328 | A |

TABLE I-continued

| No. | Compound | M + H | Synthetic Method |
|---|---|---|---|
| B95 | | 329 | A |
| B96 | | 307 | A |
| B97 | | 305 | A |
| B98 | | 438 | C |
| B99 | | 408 | C |
| B100 | | 408 | C |
| B101 | | 507 | C |

TABLE I-continued

| No. | Compound | M + H | Synthetic Method |
|---|---|---|---|
| B102 | | 303 | A |
| B103 | | 453 | C |
| B104 | | 419 | A |
| B105 | | 431 | A |
| B106 | | 425 | B |

TABLE I-continued

| No. | Compound | M + H | Synthetic Method |
|---|---|---|---|
| B107 | | 367 | A |
| B108 | | 487 | A |
| B109 | | 417 | Q |
| B110 | | 417 | R |

Enantiomer A (See Note 3 below).

TABLE I-continued

| No. | Compound | M + H | Synthetic Method |
|---|---|---|---|
| B111 | Enantiomer B (See Note 4 below). | 417 | S |
| B112 | | 353 | A |
| B113 | | 368 | A or G |
| B114 | | 460 | C |
| B115 | | 367 | A |

TABLE I-continued

| No. | Compound | M + H | Synthetic Method |
|---|---|---|---|
| B116 | | 339 | A |
| B117 | | 427 | T |
| B118 | | 441 | A |
| B119 | | 424 | C |
| B120 | | 424 | C |

TABLE I-continued

| No. | Compound | M + H | Synthetic Method |
|-----|----------|-------|------------------|
| B121 | | 362 | C |
| B122 | | 360 | C |
| B123 | | 388 | C |
| B124 | | 412 | C |
| B125 | | 389 | C |
| B126 | | 383 | C |

TABLE I-continued

| No. | Compound | M + H | Synthetic Method |
|---|---|---|---|
| B127 | | 412 | C |
| B128 | | 388 | C |
| B129 | | 410 | C |
| B130 | | 432 | C |
| B131 | | 418 | C |

TABLE I-continued

| No. | Compound | M + H | Synthetic Method |
|---|---|---|---|
| B132 | | 409 | U |
| B133 | | 426 | C |
| B134 | | 320 | C |
| B135 | | 346 | C |
| B136 | | 422 | C |
| B137 | | 448 | C |
| B138 | | 432 | C |

TABLE I-continued
| No. | Compound | M + H | Synthetic Method |
|---|---|---|---|
| B139 | 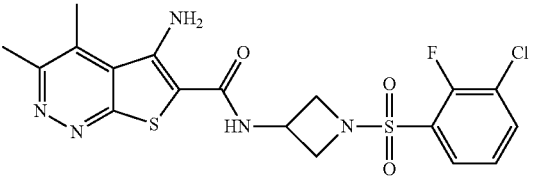 [SMILES: Cc1nnc2sc(C(=O)NC3CN(S(=O)(=O)c4cccc(Cl)c4F)C3)c(N)c2c1C] | 470 | C |
| B140 | 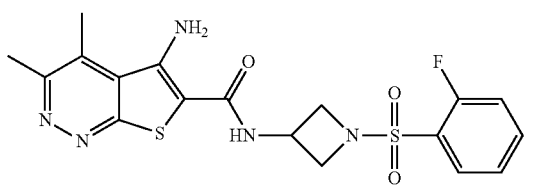 | 436 | C |
| B141 | 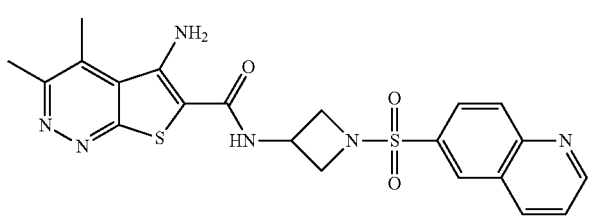 [SMILES: Cc1nnc2sc(C(=O)NC3CN(S(=O)(=O)c4ccc5ncccc5c4)C3)c(N)c2c1C] | 469 | C |
| B142 | 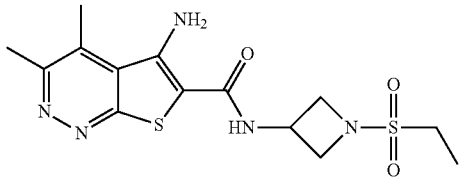 [SMILES: CCS(=O)(=O)N1CC(NC(=O)c2sc3nnc(C)c(C)c3c2N)C1] | 370 | C |
| B143 | 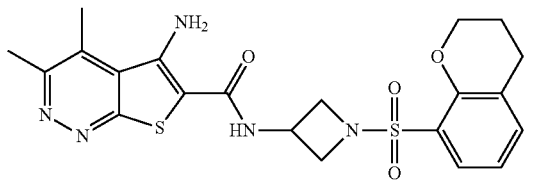 [SMILES: Cc1nnc2sc(C(=O)NC3CN(S(=O)(=O)c4cccc5c4OCCC5)C3)c(N)c2c1C] | 474 | C |
| B144 | 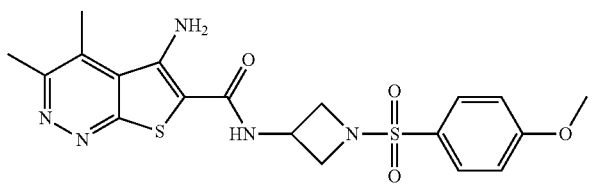 | 448 | C |
| B145 | 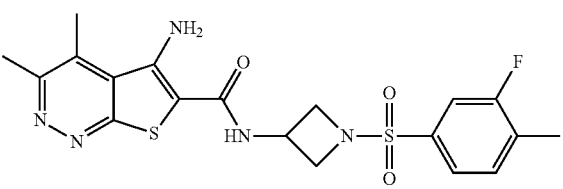 | 450 | C |
| B146 | 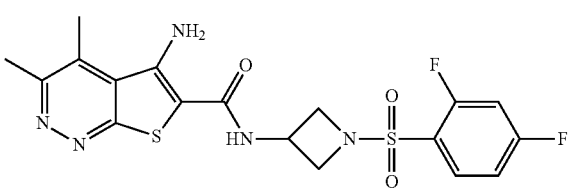 [SMILES: Cc1nnc2sc(C(=O)NC3CN(S(=O)(=O)c4ccc(F)cc4F)C3)c(N)c2c1C] | 454 | C |

TABLE I-continued

| No. | Compound | M + H | Synthetic Method |
|-----|----------|-------|------------------|
| B147 | | 486 | C |
| B148 | | 355 | A |
| B149 | | 369 | A |
| B150 | | 383 | C |
| B151 | | 398 | C |
| B152 | | 376 | C |

TABLE I-continued

| No. | Compound | M + H | Synthetic Method |
|---|---|---|---|
| B153 | | 336 | C |
| B154 | | 402 | C |
| B155 | | 400 | C |
| B156 | | 354 | A |
| B157 | | 320 | C |
| B158 | | 347 | A |

TABLE I-continued

| No. | Compound | M + H | Synthetic Method |
|---|---|---|---|
| B159 | | 418 | C |
| B160 | | 382 | C |
| B161 | | 442 | C |
| B162 | | 391 | A |
| B163 | | 367 | A |

TABLE I-continued

| No. | Compound | M + H | Synthetic Method |
|---|---|---|---|
| B164 | | 383 | A |
| B165 | | 400 | C |
| B166 | | 346 | C |
| B167 | | 398 | C |
| B168 | | 379 | A |

TABLE I-continued

| No. | Compound | M + H | Synthetic Method |
|---|---|---|---|
| B169 | | 382 | C |
| B170 | | 369 | E |
| B171 | | 411 | V |
| B172 | | 356 | C |
| B173 | | 357 | I |

TABLE I-continued

| No. | Compound | M + H | Synthetic Method |
|---|---|---|---|
| B174 | | 422 | C |
| B175 | | 376 | C |
| B176 | | 393 | A |
| B177 | | 410 | C |
| B178 | | 364 | C |

TABLE I-continued

| No. | Compound | M + H | Synthetic Method |
|---|---|---|---|
| B179 | | 355 | F |
| B180 | | 469 | C |
| B181 | | 397 | A |
| B182 | | 422 | C |
| B183 | | 432 | C |

TABLE I-continued

| No. | Compound | M + H | Synthetic Method |
|---|---|---|---|
| B184 | | 383 | C |
| B185 | | 388 | C |
| B186 | Enantiomer A (See Note 5 below) | 425 | B + R |
| B187 | Enantiomer B (See Note 6 below) | 425 | B + S |

TABLE I-continued

| No. | Compound | M + H | Synthetic Method |
|---|---|---|---|
| B188 | | 451 | B + M |
| B189 | | 471 | M + P |
| B190 | | 412 | C |
| B191 | | 417 | H |
| B192 | | 368 | G |

TABLE I-continued

| No. | Compound | M + H | Synthetic Method |
|---|---|---|---|
| B193 | | 368 | G |
| B194 | | 418 | A |
| B195 | | 352 | A |
| B196 | | 366 | A |
| B197 | | 392 | A |

TABLE I-continued

| No. | Compound | M + H | Synthetic Method |
|-----|----------|-------|------------------|
| B198 | | 357 | A |
| B199 | | 325 | A |
| B200 | | 402 | C |
| B201 | | 405 | C |
| B202 | | 436 | C |
| B203 | | 412 | C |
| B204 | | 397 | C |

TABLE I-continued

| No. | Compound | M + H | Synthetic Method |
|---|---|---|---|
| B205 | | 412 | C |
| B206 | | 426 | C |
| B207 | | 432 | C |
| B208 | | 405 | C |
| B209 | | 516 | C |
| B210 | | 378 | C |
| B211 | | 450 | C |

TABLE I-continued

| No. | Compound | M + H | Synthetic Method |
|---|---|---|---|
| B212 | | 468 | C |
| B213 | | 462 | C |
| B214 | | 462 | C |
| B215 | | 452 | C |
| B216 | | 414 | C |
| B217 | | 432 | C |
| B218 | | 390 | C |

TABLE I-continued
| No. | Compound | M + H | Synthetic Method |
|---|---|---|---|
| B219 | 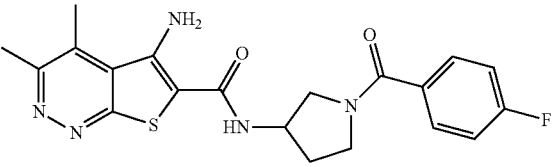 [SMILES: Cc1nnc2sc(C(=O)NC3CCN(C(=O)c4ccc(F)cc4)C3)c(N)c2c1C] | 414 | C |
| B220 | 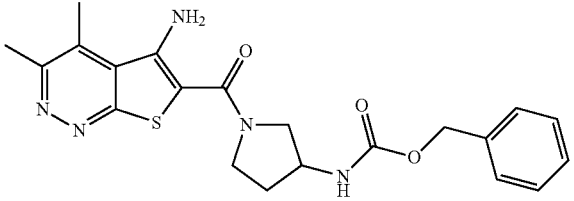 [SMILES: Cc1nnc2sc(C(=O)N3CCC(NC(=O)OCc4ccccc4)C3)c(N)c2c1C] | 426 | C |
| B221 | 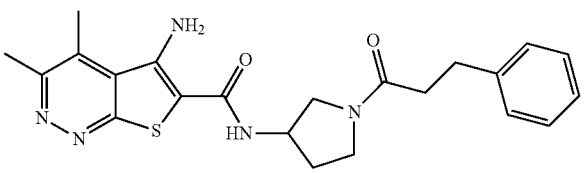 [SMILES: Cc1nnc2sc(C(=O)NC3CCN(C(=O)CCc4ccccc4)C3)c(N)c2c1C] | 424 | C |
| B222 | 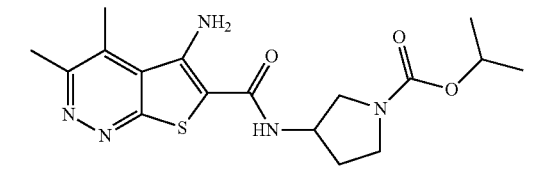 [SMILES: Cc1nnc2sc(C(=O)NC3CCN(C(=O)OC(C)C)C3)c(N)c2c1C] | 378 | C |
| B223 | 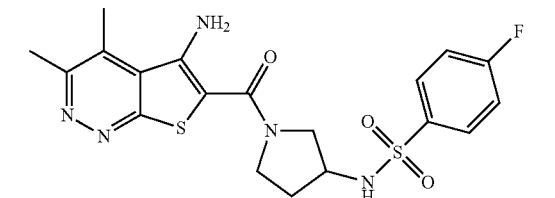 | 450 | C |
| B224 | 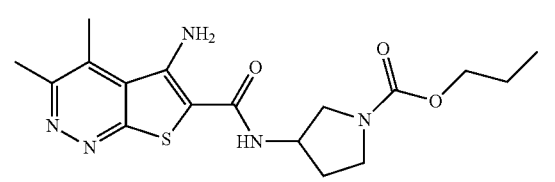 [SMILES: CCCOC(=O)N1CCC(NC(=O)c2sc3nnc(C)c(C)c3c2N)C1] | 378 | C |
| B225 | 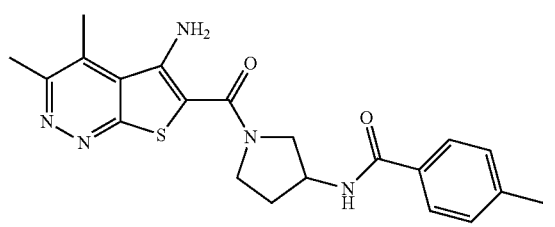 | 410 | C |
| B226 | 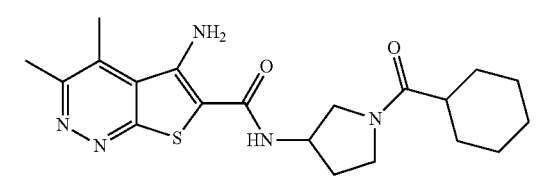 [SMILES: Cc1nnc2sc(C(=O)NC3CCN(C(=O)C4CCCCC4)C3)c(N)c2c1C] | 402 | C |

TABLE I-continued

| No. | Compound | M + H | Synthetic Method |
|---|---|---|---|
| B227 | | 416 | C |
| B228 | | 432 | C |
| B229 | | 432 | C |
| B230 | | 416 | C |
| B231 | | 426 | C |
| B232 | | 390 | C |
| B233 | | 387 | A |

TABLE I-continued

| No. | Compound | M + H | Synthetic Method |
|---|---|---|---|
| B234 | | 474 | C |
| B235 | | 410 | C |
| B236 | | 360 | C |
| B237 | | 402 | C |
| B238 | | 396 | A |

TABLE I-continued

| No. | Compound | M + H | Synthetic Method |
|---|---|---|---|
| B239 | | 374 | C |
| B240 | | 397 | C |
| B241 | | 416 | C |
| B242 | | 360 | C |
| B243 | | 432 | C |
| B244 | | 446 | C |
| B245 | | 516 | C |

TABLE I-continued

| No. | Compound | M + H | Synthetic Method |
|---|---|---|---|
| B246 | | 396 | C |
| B247 | | 436 | C |
| B248 | | 289 | A |
| B249 | | 424 | C |
| B250 | | 380 | A |
| B251 | | 367 | A |

TABLE I-continued
| No. | Compound | M + H | Synthetic Method |
|---|---|---|---|
| B252 | 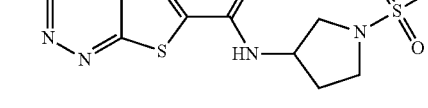 | 370 | C |
| B253 | 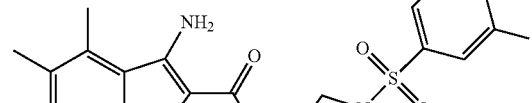 | 450 | C |
| B254 | 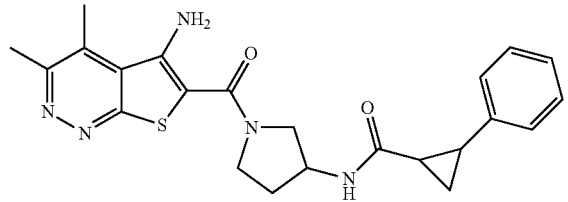 [SMILES: Cc1nnc2sc(C(=O)N3CCC(NC(=O)C4CC4c4ccccc4)C3)c(N)c2c1C] | 436 | C |
| B255 | 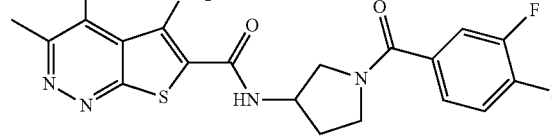 | 432 | C |
| B256 | 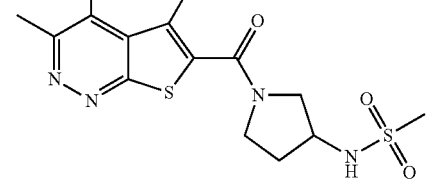 | 370 | C |
| B257 | 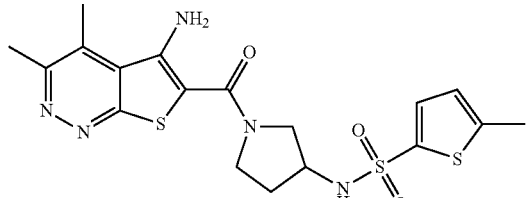 | 452 | C |
| B258 | 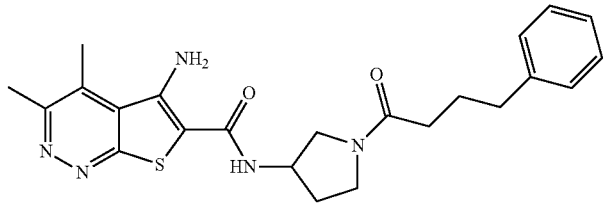 [SMILES: Cc1nnc2sc(C(=O)NC3CCN(C(=O)CCCc4ccccc4)C3)c(N)c2c1C] | 438 | C |

TABLE I-continued
| No. | Compound | M + H | Synthetic Method |
|---|---|---|---|
| B259 | 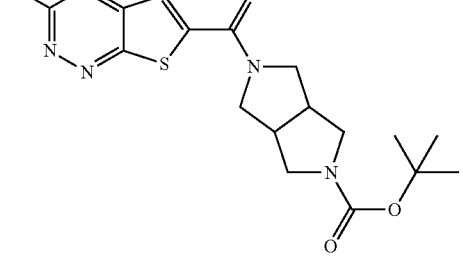 | 418 | C |
| B260 | 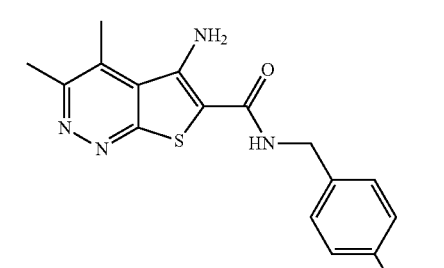 | 363 | A |
| B261 | 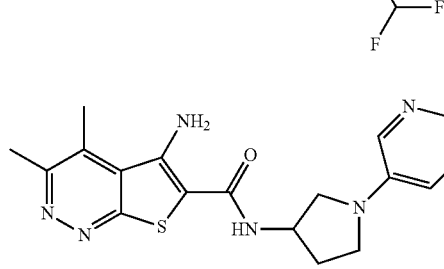 | 369 | G |
| B262 | 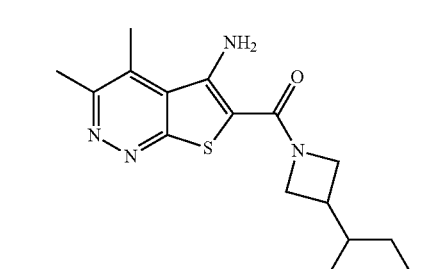 | 345 | A |
| B263 | 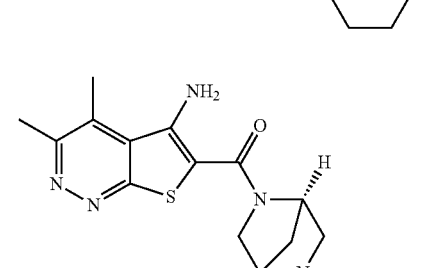 | 408 | C |

TABLE I-continued

| No. | Compound | M + H | Synthetic Method |
|---|---|---|---|
| B264 | | 402 | G |
| B265 | | 382 | G |
| B266 | | 369 | G |
| B267 | | 382 | C |
| B268 | | 402 | G |
| B269 | | 382 | G |
| B270 | | 424 | C |

TABLE I-continued

| No. | Compound | M + H | Synthetic Method |
|---|---|---|---|
| B271 | | 398 | G |
| B272 | | 307 | A |
| B273 | | 452 | G |
| B274 | | 402 | G |
| B275 | | 353 | A |
| B276 | | 368 | A |

TABLE I-continued
| No. | Compound | M + H | Synthetic Method |
|---|---|---|---|
| B277 | 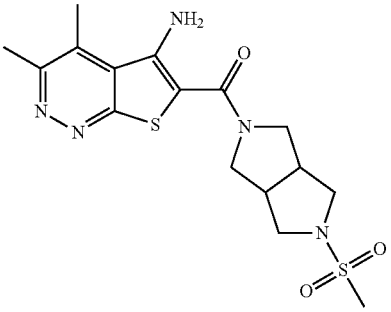 [SMILES: Cc1nnc2sc(C(=O)N3CC4CN(S(C)(=O)=O)CC4C3)c(N)c2c1C] | 396 | C |
| B278 | 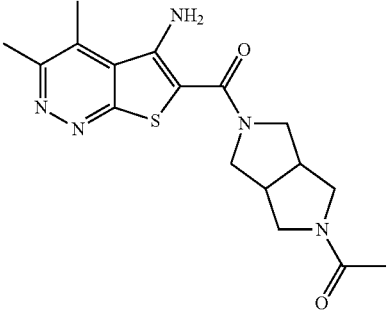 [SMILES: CC(=O)N1CC2CN(C(=O)c3sc4nnc(C)c(C)c4c3N)CC2C1] | 360 | C |
| B279 | 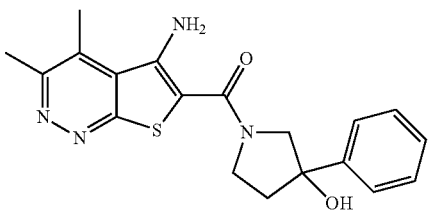 [SMILES: Cc1nnc2sc(C(=O)N3CCC(O)(c4ccccc4)C3)c(N)c2c1C] | 369 | F |
| B280 | 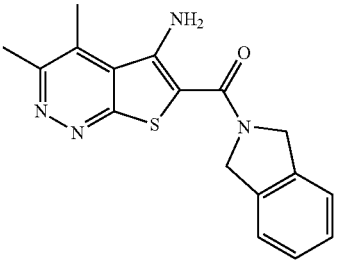 [SMILES: Cc1nnc2sc(C(=O)N3Cc4ccccc4C3)c(N)c2c1C] | 325 | A |
| B281 | 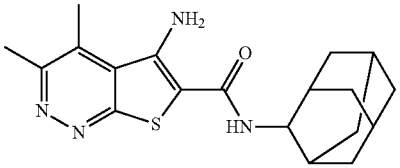 [SMILES: Cc1nnc2sc(C(=O)NC3C4CC5CC(C4)CC3C5)c(N)c2c1C] | 357 | A |
| B282 | 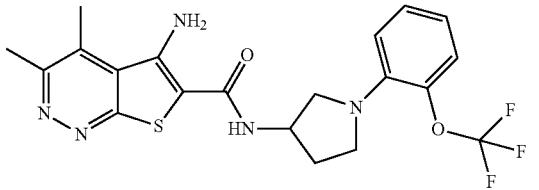 [SMILES: Cc1nnc2sc(C(=O)NC3CCN(c4ccccc4OC(F)(F)F)C3)c(N)c2c1C] | 452 | G |

TABLE I-continued

| No. | Compound | M + H | Synthetic Method |
|---|---|---|---|
| B283 | | 436 | G |
| B284 | | 436 | G |
| B285 | | 390 | C |
| B286 | | 386 | D |
| B287 | | 395 | G |

TABLE I-continued

| No. | Compound | M + H | Synthetic Method |
|---|---|---|---|
| B288 | | 344 | V |
| B289 | | 344 | V |
| B290 | | 399 | E |
| B291 | | 395 | I |
| B292 | | 307 | E |

TABLE I-continued

| No. | Compound | M + H | Synthetic Method |
|---|---|---|---|
| B293 | | 375 | I |
| B294 | | 399 | E |
| B295 | | 391 | I |
| B296 | | 363 | I |
| B297 | | 439 | V |

TABLE I-continued

| No. | Compound | M + H | Synthetic Method |
|---|---|---|---|
| B298 | | 407 | E |
| B299 | | 387 | E |
| B300 | | 387 | I |
| B301 | | 369 | A |
| B302 | | 295 | I |

TABLE I-continued

| No. | Compound | M + H | Synthetic Method |
|---|---|---|---|
| B303 | | 358 | I |
| B304 | | 375 | E |
| B305 | | 349 | E |
| B306 | | 354 | H |
| B307 | | 337 | I |

TABLE I-continued
| No. | Compound | M + H | Synthetic Method |
|---|---|---|---|
| B308 | 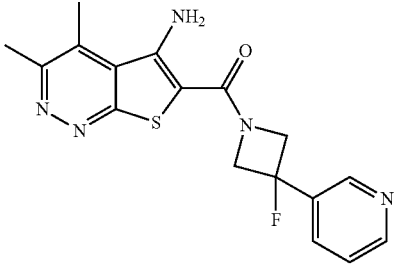 [SMILES: Cc1nnc2sc(C(=O)N3CC(F)(c4cccnc4)C3)c(N)c2c1C] | 358 | I |
| B309 | 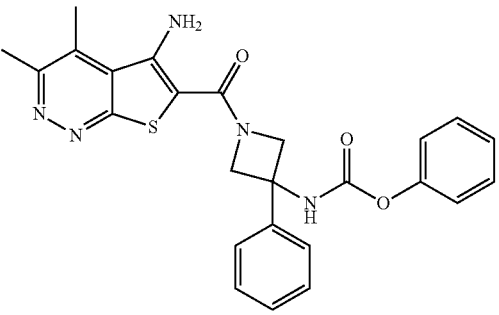 [SMILES: Cc1nnc2sc(C(=O)N3CC(NC(=O)Oc4ccccc4)(c4ccccc4)C3)c(N)c2c1C] | 474 | H |
| B310 | 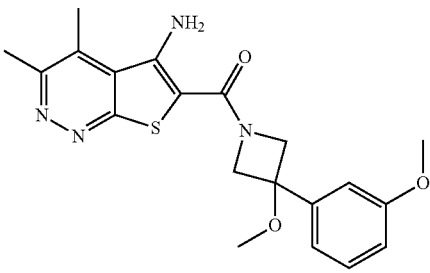 | 399 | E |
| B311 | 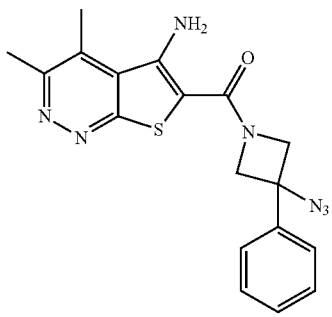 [SMILES: Cc1nnc2sc(C(=O)N3CC(N=[N+]=[N-])(c4ccccc4)C3)c(N)c2c1C] | 380 | H |
| B312 | 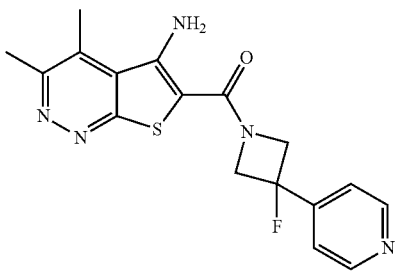 [SMILES: Cc1nnc2sc(C(=O)N3CC(F)(c4ccncc4)C3)c(N)c2c1C] | 358 | I |

TABLE I-continued
| No. | Compound | M + H | Synthetic Method |
|-----|----------|-------|------------------|
| B313 | 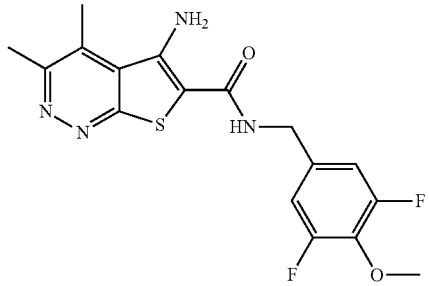 | 379 | A |
| B314 | 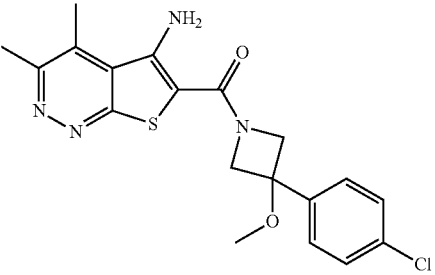 [SMILES: COC1(c2ccc(Cl)cc2)CN(C(=O)c2sc3nnc(C)c(C)c3c2N)C1] | 403 | E |
| B315 | 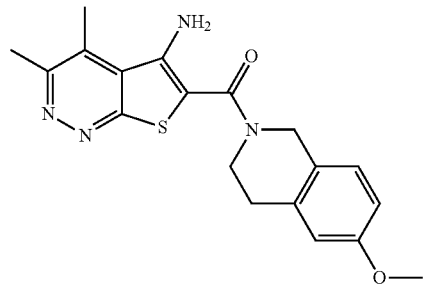 | 369 | A |
| B316 | 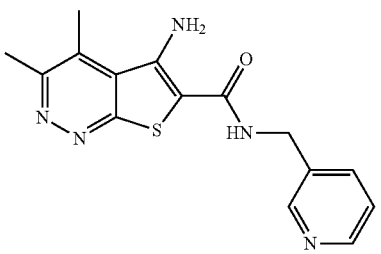 [SMILES: Cc1nnc2sc(C(=O)NCc3cccnc3)c(N)c2c1C] | 314 | A |
| B317 | 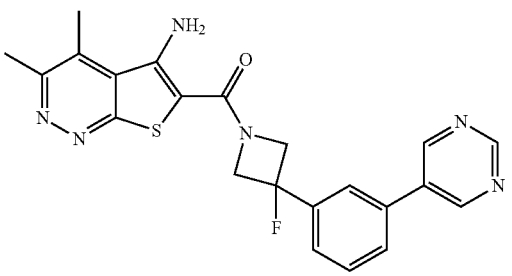 [SMILES: Cc1nnc2sc(C(=O)N3CC(F)(c4cccc(-c5cncnc5)c4)C3)c(N)c2c1C] | 435 | I |

TABLE I-continued

| No. | Compound | M + H | Synthetic Method |
|---|---|---|---|
| B318 | | 434 | I |
| B319 | | 437 | I |
| B320 | | 434 | I |
| B321 | | 434 | I |
| B322 | | 382 | H |

TABLE I-continued

| No. | Compound | M + H | Synthetic Method |
|---|---|---|---|
| B323 | | 434 | I |
| B324 | | 530 | J + P |
| B325 | | 437 | I |
| B326 | | 435 | I |

TABLE I-continued

| No. | Compound | M + H | Synthetic Method |
|---|---|---|---|
| B327 | | 398 | A |
| B328 | | 370 | A |
| B329 | | 392 | A |
| B330 | | 392 | A |

TABLE I-continued

| No. | Compound | M + H | Synthetic Method |
|---|---|---|---|
| B331 | | 440 | C |
| B332 | | 386 | C |
| B333 | | 402 | C |
| B334 | | 428 | C |

TABLE I-continued

| No. | Compound | M + H | Synthetic Method |
|---|---|---|---|
| B335 | | 659 | A |
| B336 | | 438 | C |
| B337 | | 448 | C |
| B338 | | 415 | C |
| B339 | | 386 | G |

TABLE I-continued
| No. | Compound | M + H | Synthetic Method |
|---|---|---|---|
| B340 | 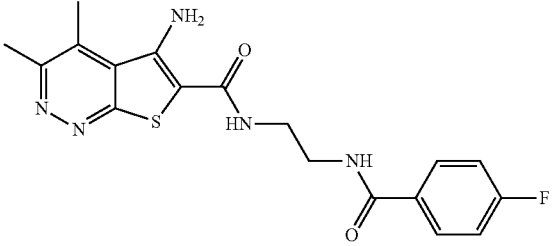 [SMILES: Cc1nnc2sc(C(=O)NCCNC(=O)c3ccc(F)cc3)c(N)c2c1C] | 388 | C |
| B341 | 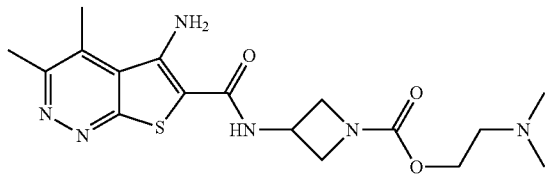 | 393 | C |
| B342 | 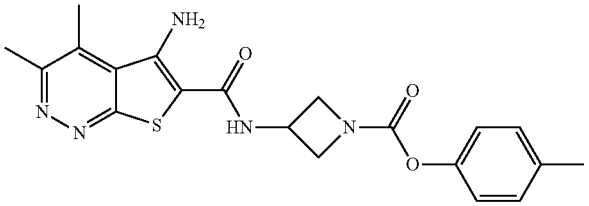 | 412 | C |
| B343 | 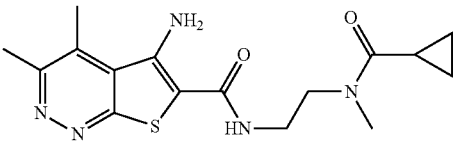 [SMILES: Cc1nnc2sc(C(=O)NCCN(C)C(=O)C3CC3)c(N)c2c1C] | 348 | C |
| B344 | 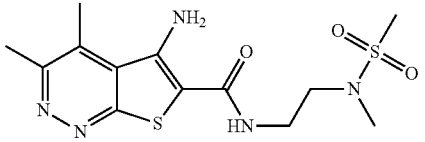 [SMILES: Cc1nnc2sc(C(=O)NCCN(C)S(C)(=O)=O)c(N)c2c1C] | 358 | C |
| B345 | 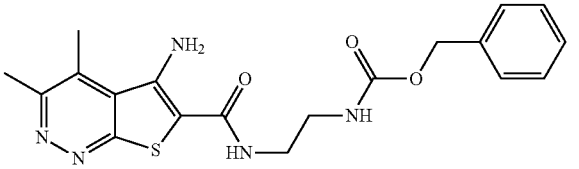 [SMILES: Cc1nnc2sc(C(=O)NCCNC(=O)OCc3ccccc3)c(N)c2c1C] | 400 | C |
| B346 | 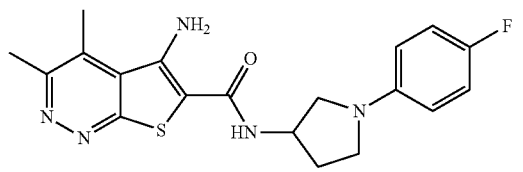 [SMILES: Cc1nnc2sc(C(=O)NC3CCN(c4ccc(F)cc4)C3)c(N)c2c1C] | 386 | G |
| B347 | 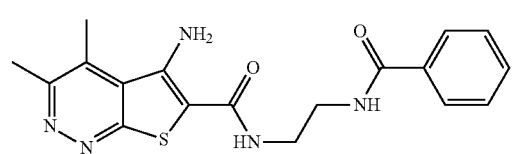 [SMILES: Cc1nnc2sc(C(=O)NCCNC(=O)c3ccccc3)c(N)c2c1C] | 370 | C |

TABLE I-continued

| No. | Compound | M + H | Synthetic Method |
|---|---|---|---|
| B348 | | 440 | C |
| B349 | | 439 | C |
| B350 | | 399 | C |
| B351 | | 415 | C |
| B352 | | 344 | C |
| B353 | | 424 | C |
| B354 | | 386 | C |
| B355 | | 432 | C |

TABLE I-continued

| No. | Compound | M + H | Synthetic Method |
|---|---|---|---|
| B356 | | 466 | C |
| B357 | | 402 | C |
| B358 | | 438 | C |
| B359 | | 432 | C |
| B360 | | 406 | C |
| B361 | | 412 | C |
| B362 | | 397 | C |

TABLE I-continued

| No. | Compound | M + H | Synthetic Method |
|---|---|---|---|
| B363 | | 463 | C |
| B364 | | 371 | C |
| B365 | | 412 | C |
| B366 | | 308 | C |
| B367 | | 334 | C |
| B368 | | 428 | C |
| B369 | | 384 | C |
| B370 | | 434 | C |
| B371 | | 427 | C |

TABLE I-continued

| No. | Compound | M + H | Synthetic Method |
|---|---|---|---|
| B372 | | 416 | C |
| B373 | | 367 | A |
| B374 | | 386 | C |
| B375 | | 420 | C |
| B376 | | 428 | C |
| B377 | | 471 | K |

TABLE I-continued

| No. | Compound | M + H | Synthetic Method |
|---|---|---|---|
| B378 | | 489 | K |
| B379 | | 359 | A |
| B380 | | 343 | A |
| B381 | | 331 | A |
| B382 | | 291 | A |
| B383 | | 435 | K |

TABLE I-continued

| No. | Compound | M + H | Synthetic Method |
|---|---|---|---|
| B384 | | 419 | K |
| B385 | | 400 | C |
| B386 | | 442 | C |
| B387 | | 421 | A |

TABLE I-continued

| No. | Compound | M + H | Synthetic Method |
|---|---|---|---|
| B388 | | 388 | C |
| B389 | | 402 | C |
| B390 | | 357 | A |
| B391 | | 418 | C |
| B392 | | 416 | C |

TABLE I-continued

| No. | Compound | M + H | Synthetic Method |
|---|---|---|---|
| B393 | | 453 | K |
| B394 | | 444 | C |
| B395 | | 341 | A |
| B396 | | 400 | C |
| B397 | | 412 | C |

TABLE I-continued

| No. | Compound | M + H | Synthetic Method |
|---|---|---|---|
| B398 | | 438 | C |
| B399 | | 345 | V |
| B400 | | 412 | C |
| B401 | | 398 | I |
| B402 | | 400 | C |

TABLE I-continued

| No. | Compound | M + H | Synthetic Method |
|---|---|---|---|
| B403 | | 400 | C |
| B404 | | 408 | C |
| B405 | | 371 | X |
| B406 | | 341 | A |
| B407 | | 410 | A |
| B408 | | 418 | C |

TABLE I-continued

| No. | Compound | M + H | Synthetic Method |
|---|---|---|---|
| B409 | | 466 | C |
| B410 | | 397 | A |
| B411 | | 361 | W |
| B412 | | 380 | T |
| B413 | | 403 | Y |

TABLE I-continued

| No. | Compound | M + H | Synthetic Method |
|---|---|---|---|
| B414 | | 407 | X |
| B415 | | 439 | Y |
| B416 | | 401 | X |
| B417 | | 433 | Y |

TABLE I-continued

| No. | Compound | M + H | Synthetic Method |
|---|---|---|---|
| B418 | | 401 | X |
| B419 | | 407 | Y |
| B420 | | 364 | A |
| B421 | | 439 | C |
| B422 | | 411 | L |
| B423 | | 411 | C |

TABLE I-continued

| No. | Compound | M + H | Synthetic Method |
|---|---|---|---|
| B424 | | 439 | C |
| B425 | | 395 | L |
| B426 | | 437 | L |
| B427 | | 453 | M + T |
| B428 | | 435 | M + U |
| B429 | | 434 | L |

TABLE I-continued

| No. | Compound | M + H | Synthetic Method |
|-----|----------|-------|------------------|
| B430 | | 361 | L |
| B431 | | 338 | A |
| B432 | | 439 | Y |
| B433 | | 433 | Y |
| B434 | | 396 | L |

TABLE I-continued
| No. | Compound | M + H | Synthetic Method |
|---|---|---|---|
| B435 | 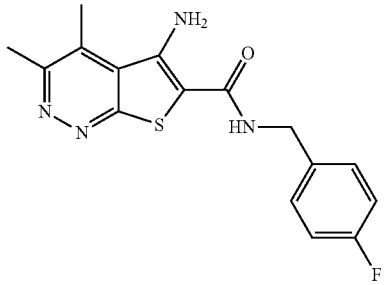 [SMILES: Cc1nnc2sc(C(=O)NCc3ccc(F)cc3)c(N)c2c1C] | 331 | A |
| B436 | 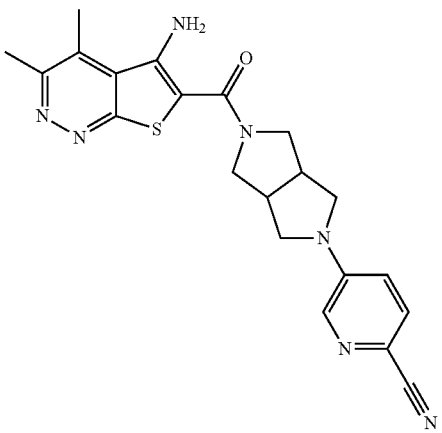 [SMILES: Cc1nnc2sc(C(=O)N3CC4CN(c5ccc(C#N)nc5)CC4C3)c(N)c2c1C] | 420 | L |
| B437 | 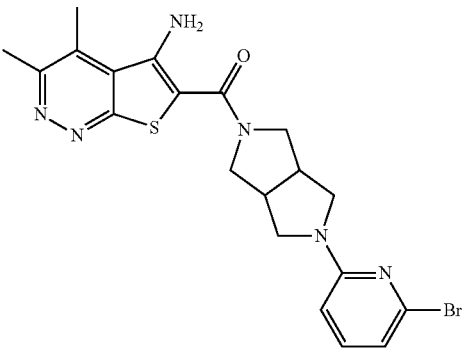 [SMILES: Cc1nnc2sc(C(=O)N3CC4CN(c5cccc(Br)n5)CC4C3)c(N)c2c1C] | 473 | L |
| B438 | 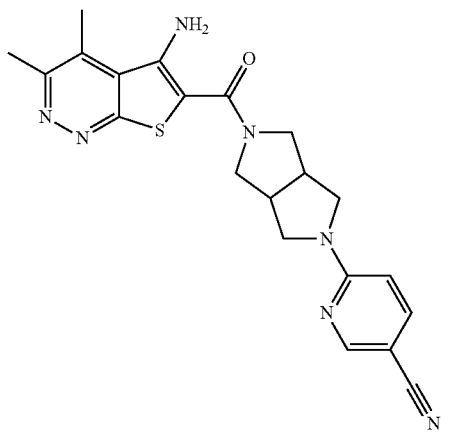 [SMILES: Cc1nnc2sc(C(=O)N3CC4CN(c5ccc(C#N)cn5)CC4C3)c(N)c2c1C] | 420 | L |

TABLE I-continued

| No. | Compound | M + H | Synthetic Method |
|---|---|---|---|
| B439 | | 362 | A |
| B440 | | 332 | A |
| B441 | | 412 | A |
| B442 | | 413 | L |
| B443 | | 382 | A |

TABLE I-continued

| No. | Compound | M + H | Synthetic Method |
|---|---|---|---|
| B444 | | 344 | A |
| B445 | | 329 | A |
| B446 | | 377 | A |
| B447 | | 393 | N |
| B448 | | 391 | A |

TABLE I-continued

| No. | Compound | M + H | Synthetic Method |
|-----|----------|-------|------------------|
| B449 | | 356 | A |
| B450 | | 420 | A |
| B451 | | 356 | A |
| B452 | | 332 | A |

TABLE I-continued
| No. | Compound | M + H | Synthetic Method |
|---|---|---|---|
| B453 | 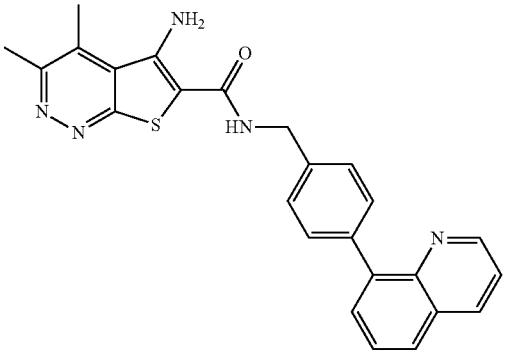 [SMILES: Cc1nnc2sc(C(=O)NCc3ccc(-c4cccc5cccnc45)cc3)c(N)c2c1C] | 440 | N |
| B454 | 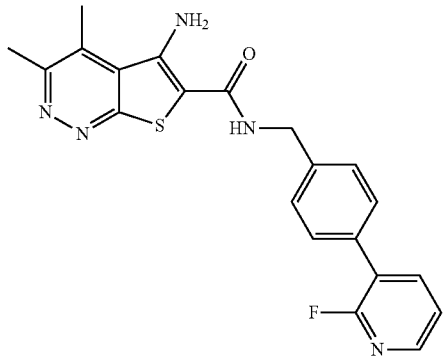 [SMILES: Cc1nnc2sc(C(=O)NCc3ccc(-c4cccnc4F)cc3)c(N)c2c1C] | 408 | N |
| B455 | 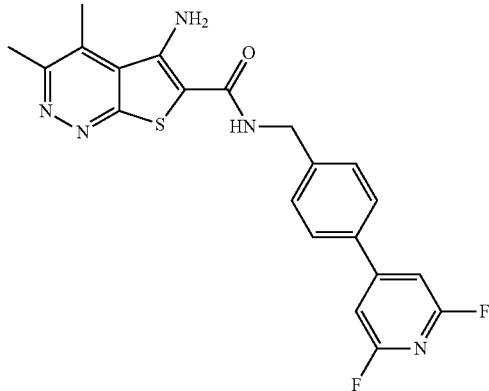 [SMILES: Cc1nnc2sc(C(=O)NCc3ccc(-c4cc(F)nc(F)c4)cc3)c(N)c2c1C] | 426 | N |
| B456 | 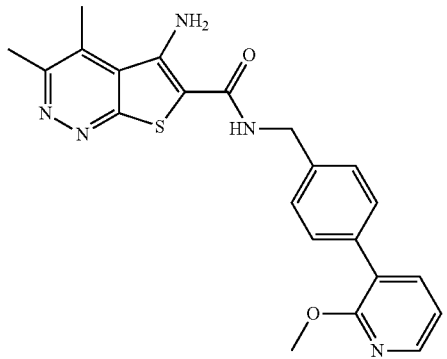 [SMILES: COc1ncccc1-c1ccc(CNC(=O)c2sc3nnc(C)c(C)c3c2N)cc1] | 420 | N |

TABLE I-continued

| No. | Compound | M + H | Synthetic Method |
|---|---|---|---|
| B457 | | 390 | N |
| B458 | | 438 | N |
| B459 | | 408 | N |
| B460 | | 395 | N |

TABLE I-continued

| No. | Compound | M + H | Synthetic Method |
|---|---|---|---|
| B461 | | 408 | N |
| B462 | | 391 | N |
| B463 | | 429 | N |
| B464 | | 390 | N |

TABLE I-continued

| No. | Compound | M + H | Synthetic Method |
|---|---|---|---|
| B465 | | 429 | T |
| B466 | | 344 | A |
| B467 | | 339 | A |
| B468 | | 445 | T |
| B469 | | 389 | A or N |

TABLE I-continued

| No. | Compound | M + H | Synthetic Method |
|---|---|---|---|
| B470 | | 328 | A |
| B471 | | 392 | A |
| B472 | | 389 | A or N |
| B473 | | 443 | N |

| No. | Compound | M + H | Synthetic Method |
|---|---|---|---|
| B474 | | 443 | N |
| B475 | | 361 | A |
| B476 | | 429 | T |
| B477 | | 429 | O + T |

TABLE I-continued

| No. | Compound | M + H | Synthetic Method |
|---|---|---|---|
| B478 | | 411 | T |
| B479 | | 355 | G |
| B480 | | 380 | T |
| B481 | | 354 | G |
| B482 | | 421 | A |

TABLE I-continued

| No. | Compound | M + H | Synthetic Method |
|---|---|---|---|
| B483 | | 424 | Z |
| B484 | | 422 | N |
| B485 | | 421 | N |
| B486 | | 420 | N |

TABLE I-continued

| No. | Compound | M + H | Synthetic Method |
|---|---|---|---|
| B487 | | 408 | N |
| B488 | | 420 | N |
| B489 | | 461 | T |
| B490 | | 379 | Z |

TABLE I-continued

| No. | Compound | M + H | Synthetic Method |
|---|---|---|---|
| B491 | (structure) Enantiomer B (See Note 8 below) | 411 | T + S |
| B492 | (structure) | 396 | A |
| B493 | (structure) | 428 | A |
| B494 | (structure) | 405 | N |

TABLE I-continued

| No. | Compound | M + H | Synthetic Method |
|---|---|---|---|
| B495 | | 426 | N |
| B496 | | 441 | N |
| B497 | | 440 | N |
| B498 | | 422 | N |

TABLE I-continued

| No. | Compound | M + H | Synthetic Method |
|---|---|---|---|
| B499 | | 404 | N |
| B500 | | 439 | N |
| B501 | | 433 | N |
| B502 | | 395 | N |

TABLE I-continued

| No. | Compound | M + H | Synthetic Method |
|-----|----------|-------|------------------|
| B503 | | 440 | N |
| B504 | | 410 | A |
| B505 | | 453 | A |
| B506 | | 379 | Z |

TABLE I-continued

| No. | Compound | M + H | Synthetic Method |
|---|---|---|---|
| B507 | | 461 | T |
| B508 | | 344 | A |
| B509 | | 332 | A |
| B510 | | 411 | T + R |

Enantiomer A (See Note 8 below)

TABLE I-continued

| No. | Compound | M + H | Synthetic Method |
|---|---|---|---|
| B511 | 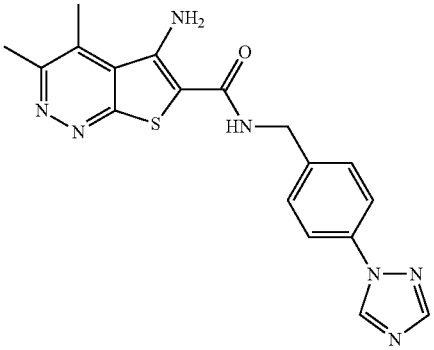 [SMILES: Cc1nnc2sc(C(=O)NCc3ccc(-n4cncn4)cc3)c(N)c2c1C] | 380 | Z |

Note 1:
Separated on Chiralpak IB using MeOH/0.1% DEA, flow rate = 5 mL/min; retention time = 4.03 min.
Note 2:
Separated on Chiralpak IB using MeOH w/0.1% DEA, flow rate = 5 mL/min; retention time = 3.48 min.
Note 3:
Separated on Chiralpak IC, 2:1 MeOH:ACN (0.1% DEA). >99% by SFC; retention time = 3.02 min.
Note 4:
Separated on Chiralpak IC, 2:1 MeOH:ACN (0.1% DEA). >99% by SFC; retention time = 3.69 min.
Note 5:
Separated by Chiral SFC: 3.5 mL/min analytical, 10 min run, Lux Cellulose-3 (OJ) 2:1 MeOH/ACN 0.1% DEA (50% isocratic); retention time = 1.627 min.
Note 6:
Separated on Chiral SFC: 3.5 mL/min analytical, 10 min run, Lux Cellulose-3 (OJ) 2:1 MeOH/ACN 0.1% DEA (50% isocratic; retention time = 2.500 min.
Note 7:
Separated on Chiral SFC CHIRALPAK IA: $CO_2$:MeOH (0.1% DEA) isocratic 1:1 (4.6 × 250 mm analytical; 10 × 250 mm prep) 3.5 mL/min analytical; 15 mL/min preparative run; retention time = 4.26 min.
Note 8:
Separated on Chiral SFC CHIRALPAK IA: $CO_2$:MeOH (0.1% DEA) isocratic 1:1 (4.6 × 250 mm analytical; 10 × 250 mm prep) 3.5 mL/min analytical; 15 mL/min preparative run; retention time = 5.19 min.

30. Cell Lines Expressing Muscarinic Acetylcholine Receptors

Chinese hamster ovary (CHO-K1) cells stably expressing rat (r)$M_1$ were purchased from the American Type Culture Collection and cultured according to their indicated protocol. CHO cells stably expressing human (h)$M_2$, h$M_3$, and h$M_5$ were described previously (Levey et al., 1991); h$M_1$ and h$M_4$ cDNAs were purchased from Missouri S&T cDNA Resource; r$M_4$ cDNA was provided by T. I. Bonner (National Institutes of Health, Bethesda, Md.). r$M_2$ and r$M_3$ were cloned from a rat brain cDNA library and sequence verified. h$M_1$, r$M_2$, r$M_3$, h$M_4$, and r$M_4$ cDNAs were used to stably transfect CHO-K1 cells purchased from the American Type Culture Collection using Lipofectamine 2000. To make stable r$M_2$, h$M_2$, h$M_4$, and r$M_4$ cell lines for use in calcium mobilization assays, these cells also were stably transfected with a chimeric G-protein ($G_{qi5}$) (provided by B. R. Conklin, University of California, San Francisco) using Lipofectamine 2000. r$M_1$, h$M_1$, r$M_3$, h$M_3$, r$M_5$, and h$M_5$ cells were grown in Ham's F-12 medium containing 10% heat-inactivated fetal bovine serum (FBS), 20 mM HEPES, and 50 μg/mL G418 sulfate. r$M_2$-$G_{qi5}$, h$M_2$-$G_{qi5}$, and h$M_4$-$G_{qi5}$ cells were grown in the same medium also containing 500 μg/mL Hygromycin B. Stable r$M_4$-$G_{qi5}$ cells were grown in DMEM containing 10% heat-inactivated FBS, 20 mM HEPES, 400 μg/mL G418 sulfate, and 500 μg/mL Hygromycin B.

31. Cell-Based Functional Assay of Muscarinic Acetylcholine Receptor Activity For high throughput measurement of agonist-evoked increases in intracellular calcium, CHO-K1 cells stably expressing muscarinic receptors were plated in growth medium lacking G418 and hygromycin at 15,000 cells/20 μL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with four washes (80 μL) of assay buffer then aspirated to 20 μL. Next, 20 μL of 16 μM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer was added to the wells and the cell plates were incubated for 50 mM at 37° C. and 5% $CO_2$. Dye was removed by washing with the ELX 405 (four 80 μL washes of assay buffer) then aspirated to 20 μL. Compound master plates were formatted in an 11 point CRC format (1:3 dilutions) in 100% DMSO with a starting concentration of 10 mM using the BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 μL) to a 2× stock using a Thermo Fisher Combi (Thermo Fisher Scientific, Waltham, Mass.).

Calcium flux was measured using the Functional Drug Screening System (FDSS) 6000 (Hamamatsu Corporation, Tokyo, Japan) as an increase in the fluorescent static ratio. Compounds were applied to cells (20 μL, 2×) using the automated system of the FDSS 6000 at 4 s into the 300 s protocol and the data were collected at 1 Hz. At 144 s into the 300 s protocol, 10 μL of an $EC_{20}$ concentration of the muscarinic receptor agonist acetylcholine was added (5×), followed by the addition of 12 μL an $EC_{80}$ concentration of acetylcholine at the 230 s time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response. Concentration-response curves were generated using a four-parameter logistical equation in XLFit curve fitting software (IDBS, Bridgewater, N.J.) for Excel (Microsoft, Redmond, Wash.) or Prism (GraphPad Software, Inc., San Diego, Calif.).

The above described assay was also operated in a second mode where an appropriate fixed concentration of the present compounds were added to the cells after establishment of a fluorescence baseline for about 3 seconds, and the response in cells was measured. 140 s later the appropriate concentration of agonist was added and readings taken for an additional 106 s. Data were reduced as described above and the $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

32. Activity of Substituted 5-aminothieno[2,3-c]pyridazine-6-carboxamide Analogs in a mAChR $M_4$ Cell-Based Assay Substituted 5-aminothieno[2,3-c]pyridazine-6-carboxamide analogs were synthesized as described above. Activity ($EC_{50}$ and $E_{max}$) was determined in the mAChR $M_4$ cell-based functional assay as described above and the data are shown in Table II. The compound number corresponds to the compound numbers used in Table I.

TABLE II

| No. | $EC_{50}$ (nM) | $E_{max}$ (%)* |
|---|---|---|
| B1 | >10,000 | 40 |
| B2 | >10,000 | 61 |
| B3 | >10,000 | 46 |
| B4 | 640 | 96 |
| B5 | 180 | 86 |
| B6 | 500 | 89 |
| B7 | 140 | 97 |
| B8 | 260 | 97 |
| B9 | 170 | 97 |
| B10 | >10,000 | 82 |
| B11 | 1,500 | 82 |
| B12 | 93 | 90 |
| B13 | 1,000 | 58 |
| B14 | 320 | 100 |
| B15 | 100 | 97 |
| B16 | 250 | 99 |
| B17 | >10,000 | 83 |
| B18 | >10,000 | 60 |
| B19 | >10,000 | 53 |
| B20 | >10,000 | 41 |
| B21 | >10,000 | 59 |
| B22 | 2,800 | 63 |
| B23 | 450 | 83 |
| B24 | 520 | 80 |
| B25 | >10,000 | 56 |
| B26 | 11 | 76 |
| B27 | 42 | 76 |
| B28 | >10,000 | 54 |
| B29 | 30 | 76 |
| B30 | 14 | 76 |
| B31 | 7.5 | 79 |
| B32 | 300 | 73 |
| B33 | 37 | 73 |
| B34 | 140 | 82 |
| B35 | 840 | 77 |
| B36 | 1,700 | 29 |
| B37 | 32 | 68 |
| B38 | 600 | 54 |
| B39 | >10,000 | 40 |
| B40 | 2,700 | 47 |
| B41 | >10,000 | 48 |
| B42 | 26 | 76 |
| B43 | 270 | 75 |
| B44 | 420 | 75 |
| B45 | 45 | 71 |
| B46 | >10,000 | 38 |
| B47 | 41 | 76 |
| B48 | 48 | 77 |
| B49 | 48 | 64 |
| B50 | 61 | 49 |
| B51 | 130 | 51 |
| B52 | 77 | 54 |
| B53 | 170 | 42 |
| B54 | 790 | 37 |
| B55 | 47 | 48 |
| B56 | 72 | 54 |
| B57 | 100 | 47 |
| B58 | 240 | 64 |
| B59 | 4,100 | 56 |
| B60 | >10,000 | 41 |
| B61 | 4,600 | 55 |
| B62 | >10,000 | 34 |
| B63 | >10,000 | 41 |
| B64 | >10,000 | 41 |
| B65 | 3,600 | 56 |
| B66 | 24 | 62 |
| B67 | 350 | 51 |
| B68 | 2,600 | 68 |
| B69 | >10,000 | 48 |
| B70 | 1,200 | 37 |
| B71 | 460 | 31 |
| B72 | 380 | 30 |
| B73 | 350 | 40 |
| B74 | 170 | 69 |
| B75 | 360 | 41 |
| B76 | 490 | 55 |
| B77 | 3,500 | 53 |
| B78 | 230 | 63 |
| B79 | >10,000 | 35 |
| B80 | 210 | 68 |
| B81 | >10,000 | 34 |
| B82 | 460 | 59 |
| B83 | 29 | 58 |
| B84 | 1,000 | 61 |
| B85 | 47 | 58 |
| B86 | 80 | 62 |
| B87 | 280 | 57 |
| B88 | 400 | 43 |
| B89 | 320 | 58 |
| B90 | 40 | 58 |
| B91 | 97 | 53 |
| B92 | 23 | 53 |
| B93 | 2,300 | 49 |
| B94 | 5,000 | 47 |
| B95 | 47 | 66 |
| B96 | >10,000 | 64 |
| B97 | 1,500 | 75 |
| B98 | 63 | 66 |
| B99 | 160 | 65 |
| B100 | 180 | 68 |
| B101 | 84 | 66 |

TABLE II-continued

| No. | EC$_{50}$ (nM) | E$_{max}$ (%)* |
|---|---|---|
| B102 | 1,300 | 81 |
| B103 | 94 | 69 |
| B104 | 150 | 63 |
| B105 | 55 | 66 |
| B106 | 20 | 71 |
| B107 | 1,700 | 52 |
| B108 | 44 | 61 |
| B109 | 120 | 78 |
| B110 | 18 | 62 |
| B111 | 240 | 60 |
| B112 | 630 | 61 |
| B113 | 24 | 66 |
| B114 | 1,600 | 48 |
| B115 | 3,900 | 38 |
| B116 | 160 | 75 |
| B117 | 18 | 66 |
| B118 | 10 | 66 |
| B119 | 82 | 68 |
| B120 | 190 | 86 |
| B121 | 840 | 92 |
| B122 | 180 | 88 |
| B123 | 130 | 97 |
| B124 | 22 | 58 |
| B125 | 1,000 | 58 |
| B126 | 290 | 92 |
| B127 | 85 | 82 |
| B128 | 31 | 78 |
| B129 | 110 | 80 |
| B130 | 97 | 79 |
| B131 | 150 | 76 |
| B132 | 19 | 66 |
| B133 | 76 | 74 |
| B134 | 520 | 67 |
| B135 | 230 | 73 |
| B136 | 1,000 | 72 |
| B137 | 100 | 70 |
| B138 | 57 | 65 |
| B139 | 54 | 65 |
| B140 | 43 | 72 |
| B141 | 85 | 92 |
| B142 | 290 | 77 |
| B143 | 120 | 90 |
| B144 | 140 | 87 |
| B145 | 130 | 82 |
| B146 | 66 | 82 |
| B147 | 87 | 95 |
| B148 | >10,000 | 50 |
| B149 | >10,000 | 44 |
| B150 | 190 | 62 |
| B151 | 9.5 | 57 |
| B152 | 110 | 85 |
| B153 | 230 | 83 |
| B154 | 70 | 88 |
| B155 | 93 | 91 |
| B156 | 2,200 | 53 |
| B157 | >10,000 | 32 |
| B158 | 28 | 66 |
| B159 | 81 | 56 |
| B160 | 78 | 71 |
| B161 | 200 | 61 |
| B162 | 17 | 66 |
| B163 | 240 | 54 |
| B164 | 280 | 39 |
| B165 | >10,000 | 32 |
| B166 | 3,100 | 41 |
| B167 | 470 | 65 |
| B168 | 13 | 76 |
| B169 | 1,500 | 68 |
| B170 | 470 | 60 |
| B171 | 23 | 71 |
| B172 | >10,000 | 51 |
| B173 | 170 | 56 |
| B174 | 6,700 | 51 |
| B175 | >10,000 | 52 |
| B176 | 23 | 73 |
| B177 | 970 | 53 |
| B178 | 1,700 | 60 |
| B179 | 920 | 33 |
| B180 | 1,100 | 43 |
| B181 | 30 | 68 |
| B182 | 2,300 | 59 |
| B183 | 490 | 47 |
| B184 | 1,900 | 48 |
| B185 | 1,800 | 54 |
| B186 | 19 | 75 |
| B187 | 20 | 84 |
| B188 | 900 | 56 |
| B189 | 420 | 42 |
| B190 | 560 | 53 |
| B191 | 2,100 | 45 |
| B192 | 1,800 | 51 |
| B193 | 14 | 63 |
| B194 | 4,700 | 30 |
| B195 | 65 | 62 |
| B196 | 61 | 69 |
| B197 | >10,000 | 35 |
| B198 | 25 | 63 |
| B199 | >10,000 | 52 |
| B200 | 91 | 74 |
| B201 | >10,000 | 56 |
| B202 | 3,800 | 69 |
| B203 | 100 | 74 |
| B204 | 5,000 | 64 |
| B205 | 570 | 71 |
| B206 | 31 | 64 |
| B207 | 1,300 | 64 |
| B208 | 2,100 | 73 |
| B209 | 310 | 68 |
| B210 | >10,000 | 58 |
| B211 | 1,400 | 70 |
| B212 | 870 | 76 |
| B213 | 4,500 | 65 |
| B214 | 820 | 73 |
| B215 | 340 | 75 |
| B216 | >10,000 | 62 |
| B217 | 1,100 | 53 |
| B218 | 5,000 | 61 |
| B219 | 350 | 77 |
| B220 | 830 | 67 |
| B221 | 1,300 | 72 |
| B222 | >10,000 | 50 |
| B223 | 2,400 | 61 |
| B224 | 610 | 77 |
| B225 | 1,400 | 62 |
| B226 | 430 | 84 |
| B227 | 920 | 76 |
| B228 | 350 | 81 |
| B229 | 550 | 68 |
| B230 | 3,400 | 63 |
| B231 | 230 | 78 |
| B232 | 530 | 77 |
| B233 | 99 | 78 |
| B234 | 810 | 50 |
| B235 | 360 | 72 |
| B236 | 5,000 | 66 |
| B237 | 3,400 | 62 |
| B238 | 130 | 68 |
| B239 | 1,200 | 84 |
| B240 | >10,000 | 53 |
| B241 | 860 | 64 |
| B242 | 1,300 | 79 |
| B243 | 590 | 78 |
| B244 | 580 | 79 |
| B245 | 1,200 | 73 |
| B246 | 4,600 | 78 |
| B247 | 390 | 73 |
| B248 | 630 | 81 |
| B249 | >10,000 | 48 |
| B250 | 190 | 75 |
| B251 | 190 | 79 |
| B252 | 1,700 | 83 |
| B253 | 390 | 71 |
| B254 | 1,400 | 65 |
| B255 | 430 | 71 |
| B256 | >10,000 | 65 |
| B257 | 1,100 | 62 |

TABLE II-continued

| No. | EC$_{50}$ (nM) | E$_{max}$ (%)* |
|---|---|---|
| B258 | 520 | 64 |
| B259 | 900 | 53 |
| B260 | 34 | 81 |
| B261 | 620 | 53 |
| B262 | 50 | 66 |
| B263 | >10,000 | 41 |
| B264 | 38 | 71 |
| B265 | 120 | 60 |
| B266 | 220 | 70 |
| B267 | 5,100 | 51 |
| B268 | 180 | 68 |
| B269 | 110 | 68 |
| B270 | >10,000 | 62 |
| B271 | 3000 | 71 |
| B272 | >10,000 | 55 |
| B273 | 230 | 71 |
| B274 | 41 | 69 |
| B275 | 200 | 65 |
| B276 | 360 | 67 |
| B277 | >10,000 | 56 |
| B278 | >10,000 | 54 |
| B279 | 4,300 | 48 |
| B280 | 1,700 | 46 |
| B281 | 2,000 | 62 |
| B282 | 220 | 80 |
| B283 | 180 | 76 |
| B284 | 150 | 71 |
| B285 | 2,500 | 73 |
| B286 | 4,800 | 19 |
| B287 | 250 | 58 |
| B288 | 150 | 71 |
| B289 | 230 | 69 |
| B290 | 440 | 45 |
| B291 | >10,000 | 46 |
| B292 | >10,000 | 62 |
| B293 | 150 | 46 |
| B294 | 1,100 | 43 |
| B295 | >10,000 | 54 |
| B296 | 280 | 67 |
| B297 | 30 | 76 |
| B298 | 4,300 | 43 |
| B299 | 350 | 35 |
| B300 | 330 | 52 |
| B301 | 6,400 | 48 |
| B302 | 860 | 73 |
| B303 | 500 | 57 |
| B304 | 1,100 | 43 |
| B305 | 870 | 68 |
| B306 | 1,100 | 51 |
| B307 | 180 | 55 |
| B308 | 850 | 42 |
| B309 | >10,000 | 48 |
| B310 | 1,900 | 39 |
| B311 | 180 | 43 |
| B312 | 2,800 | 55 |
| B313 | 18 | 84 |
| B314 | 2,800 | 49 |
| B315 | 840 | 57 |
| B316 | 310 | 73 |
| B317 | 290 | 47 |
| B318 | 290 | 35 |
| B319 | 390 | 51 |
| B320 | 130 | 42 |
| B321 | 290 | 48 |
| B322 | 2,200 | 42 |
| B323 | 87 | 44 |
| B324 | 460 | 72 |
| B325 | 590 | 62 |
| B326 | 390 | 50 |
| B327 | 120 | 67 |
| B328 | 130 | 73 |
| B329 | 780 | 74 |
| B330 | 150 | 68 |
| B331 | 3,600 | 58 |
| B332 | 1,600 | 58 |
| B333 | >10,000 | 53 |
| B334 | 13 | 69 |
| B335 | 890 | 74 |
| B336 | 980 | 49 |
| B337 | 600 | 55 |
| B338 | 44 | 62 |
| B339 | 76 | 74 |
| B340 | 370 | 38 |
| B341 | 120 | 74 |
| B342 | 9 | 67 |
| B343 | >10,000 | 33 |
| B344 | >10,000 | 41 |
| B345 | 3,600 | 64 |
| B346 | 170 | 79 |
| B347 | 1,500 | 59 |
| B348 | 54 | 72 |
| B349 | 26 | 71 |
| B350 | 38 | 66 |
| B351 | 32 | 57 |
| B352 | >10,000 | 51 |
| B353 | 3,400 | 57 |
| B354 | 2,000 | 73 |
| B355 | 16 | 58 |
| B356 | 25 | 61 |
| B357 | >10,000 | 27 |
| B358 | 4,500 | 49 |
| B359 | 16 | 55 |
| B360 | 2,500 | 52 |
| B361 | 11 | 76 |
| B362 | 18 | 64 |
| B363 | 27 | 74 |
| B364 | 3,900 | 49 |
| B365 | 7.9 | 58 |
| B366 | >10,000 | 32 |
| B367 | >10,000 | 52 |
| B368 | 12 | 69 |
| B369 | >10,000 | 25 |
| B370 | 10 | 61 |
| B371 | 48 | 61 |
| B372 | 24 | 62 |
| B373 | 170 | 66 |
| B374 | >10,000 | 33 |
| B375 | 4,000 | 51 |
| B376 | 17 | 59 |
| B377 | 72 | 50 |
| B378 | 4,200 | 46 |
| B379 | 3,900 | 45 |
| B380 | >10,000 | 34 |
| B381 | 710 | 63 |
| B382 | >10,000 | 45 |
| B383 | 510 | 51 |
| B384 | 1,100 | 71 |
| B385 | 2,600 | 55 |
| B386 | 820 | 44 |
| B387 | 68 | 77 |
| B388 | >10,000 | 55 |
| B389 | 1,300 | 47 |
| B390 | >10,000 | 46 |
| B391 | 300 | 88 |
| B392 | 74 | 60 |
| B393 | 400 | 44 |
| B394 | 1,100 | 47 |
| B395 | 47 | 71 |
| B396 | 200 | 70 |
| B397 | 430 | 64 |
| B398 | 1,000 | 47 |
| B399 | 290 | 62 |
| B400 | 52 | 63 |
| B401 | 3,100 | 54 |
| B402 | 3,300 | 46 |
| B403 | 110 | 71 |
| B404 | >10,000 | 50 |
| B405 | 92 | 46 |
| B406 | 1,700 | 54 |
| B407 | 220 | 61 |
| B408 | 270 | 65 |
| B409 | 120 | 65 |
| B410 | 200 | 53 |
| B411 | 53 | 82 |
| B412 | 67 | 85 |
| B413 | 350 | 54 |

TABLE II-continued

| No. | EC$_{50}$ (nM) | E$_{max}$ (%)* |
|---|---|---|
| B414 | 340 | 63 |
| B415 | 1,300 | 44 |
| B416 | 110 | 61 |
| B417 | 750 | 46 |
| B418 | 160 | 56 |
| B419 | 220 | 56 |
| B420 | 270 | 71 |
| B421 | 15 | 84 |
| B422 | 17 | 73 |
| B423 | 53 | 59 |
| B424 | 7.9 | 68 |
| B425 | 28 | 74 |
| B426 | 440 | 67 |
| B427 | 59 | 39 |
| B428 | 88 | 51 |
| B429 | 23 | 67 |
| B430 | 2,100 | 58 |
| B431 | 120 | 56 |
| B432 | 820 | 40 |
| B433 | 590 | 34 |
| B434 | 1,100 | 48 |
| B435 | 180 | 68 |
| B436 | 980 | 49 |
| B437 | 98 | 54 |
| B438 | 170 | 45 |
| B439 | 25 | 78 |
| B440 | 190 | 80 |
| B441 | 80 | 79 |
| B442 | 310 | 66 |
| B443 | 120 | 69 |
| B444 | >10,000 | 65 |
| B445 | >10,000 | 31 |
| B446 | 17 | 59 |
| B447 | >10,000 | 64 |
| B448 | 18 | 75 |
| B449 | 69 | 71 |
| B450 | 65 | 65 |
| B451 | 340 | 66 |
| B452 | 240 | 59 |
| B453 | 240 | 74 |
| B454 | 19 | 66 |
| B455 | 27 | 64 |
| B456 | 99 | 68 |
| B457 | 19 | 75 |
| B458 | 32 | 82 |
| B459 | 15 | 88 |
| B460 | 28 | 76 |
| B461 | 23 | 84 |
| B462 | 38 | 65 |
| B463 | 150 | 70 |
| B464 | 11 | 63 |
| B465 | 15 | 61 |
| B466 | 1,200 | 60 |
| B467 | 1,200 | 69 |
| B468 | 16 | 85 |
| B469 | 430 | 64 |
| B470 | 510 | 48 |
| B471 | 390 | 60 |
| B472 | 230 | 64 |
| B473 | 89 | 61 |
| B474 | 460 | 82 |
| B475 | 24 | 61 |
| B476 | 1,600 | 66 |
| B477 | 23 | 74 |
| B478 | 23 | 71 |
| B479 | 12 | 67 |
| B480 | >10,000 | 74 |
| B481 | 12 | 62 |
| B482 | 87 | 67 |
| B483 | 47 | 69 |
| B484 | 110 | 63 |
| B485 | 48 | 58 |
| B486 | 230 | 61 |
| B487 | 37 | 71 |
| B488 | 49 | 76 |
| B489 | 35 | 73 |
| B490 | 20 | 61 |
| B491 | 120 | 63 |
| B492 | 38 | 76 |
| B493 | 82 | 68 |
| B494 | 190 | 75 |
| B495 | 210 | 72 |
| B496 | 250 | 66 |
| B497 | 710 | 46 |
| B498 | 330 | 82 |
| B499 | 200 | 71 |
| B500 | 1,800 | 72 |
| B501 | 990 | 44 |
| B502 | 580 | 66 |
| B503 | 1,100 | 56 |
| B504 | 80 | 68 |
| B505 | 110 | 63 |
| B506 | 150 | 70 |
| B507 | 510 | 66 |
| B508 | 770 | 54 |
| B509 | 1,400 | 59 |
| B510 | 500 | 70 |
| B511 | 78 | 67 |

*% ACh maximum at 30 μM.

For compounds showing low potency (as indicated by a lack of a plateau in the concentration response curve) but greater than a 20% increase in ACh response, a potency of >10 μM (pEC$_{50}$<5) is estimated.

The selectivity of the disclosed compounds for mAChR M$_4$ compared to mAChR M$_1$, M$_2$, M$_3$, and M$_5$ was determined using the cell-based functional assay described below using the appropriate cell-lines (prepared as described below). The EC$_{50}$ for each of mAChR M$_1$, M$_2$, M$_3$, and M$_5$ was greater than at least 30 μM for representative compounds (i.e., there was no receptor response up to a concentration of about 30 μM, the upper limit of compound used in the assay).

33. Prophetic Pharmaceutical Composition Examples

"Active ingredient" as used throughout these examples relates to one or more disclosed compounds or products of disclosed methods of making as described hereinbefore, or a pharmaceutically acceptable salt, hydrate, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

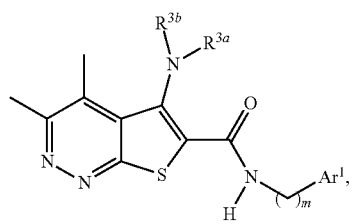

wherein:
each of $R^{3a}$ and $R^{3b}$ is independently selected from hydrogen, C1-C6 alkyl, C1-C6 haloalkyl, C1-C6 polyhaloalkyl, C3-C9 cycloalkyl, C2-C7 heterocycloalkyl, (C1-C8 alkyl)(C3-C9 cycloalkyl), and —(C1-C8 alkyl)-(C2-C7 heterocycloalkyl);
wherein $R^{3a}$ and $R^{3b}$ are optionally covalently bonded and, together with the intermediate nitrogen, form a 3- to 7-membered heterocycloalkyl substituted with 0, 1, 2, or 3 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, and C1-C6 dialkylamino;
m is an integer from 1 to 3;
$Ar^1$ is selected from phenyl and heterocyclyl, and $Ar^1$ is substituted with 0-2 groups selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$;
n is an integer from 0 to 2; and
$R^5$, when present, is selected from hydrogen, C1-C8 alkyl, C1-C8 haloalkyl, and C1-C8 polyhaloalkyl;
or a pharmaceutically acceptable salt, solvate, or polymorph thereof.

2. A pharmaceutical composition comprising a therapeutically effective amount of a compound of any claim 1, or pharmaceutically acceptable salt, hydrate, solvate, or polymorph thereof, and a pharmaceutically acceptable carrier.

3. The compound of claim 1, wherein each of $R^{3a}$ and $R^{3b}$ is independently selected from hydrogen and methyl.

4. The compound of claim 1, wherein each of $R^{3a}$ and $R^{3b}$ is hydrogen.

5. The compound of claim 1, wherein $Ar^1$ is phenyl substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

6. The compound of claim 5, wherein $Ar^1$ is phenyl substituted with 0-2 groups independently selected from —F, —Cl, —NH$_2$, —OH, —CN, methyl, —CHF$_2$, and —CF$_3$.

7. The compound of claim 1, wherein $Ar^1$ is heterocyclyl substituted with 0-2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$.

8. The compound of claim 1, wherein $Ar^1$ has a structure represented by a formula selected from:

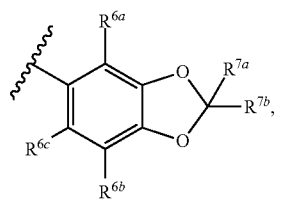
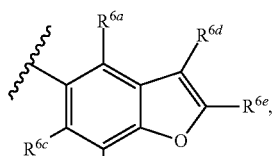
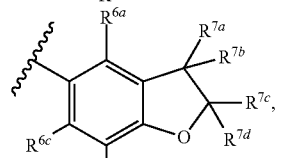
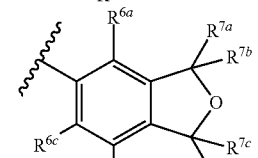
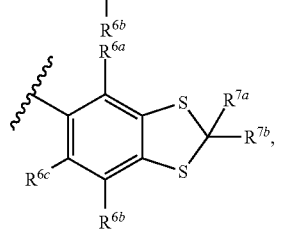
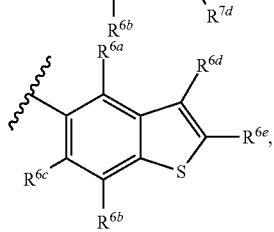

-continued

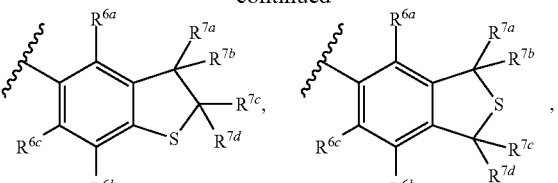
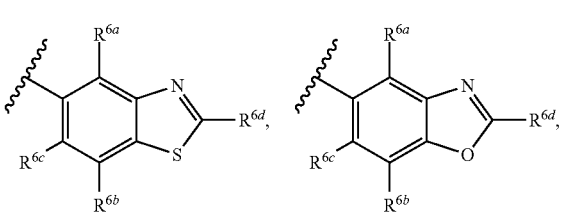
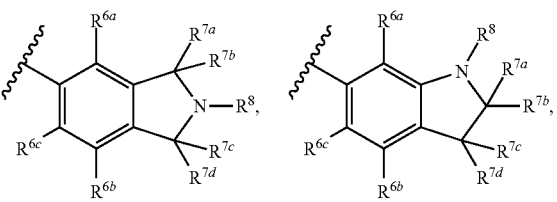
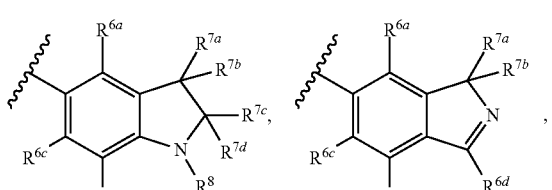
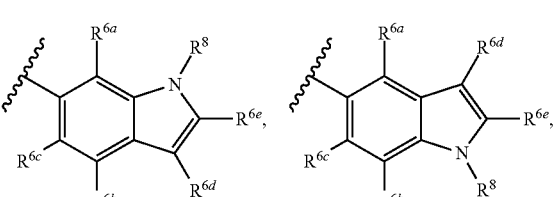
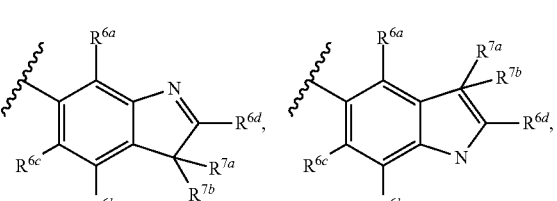
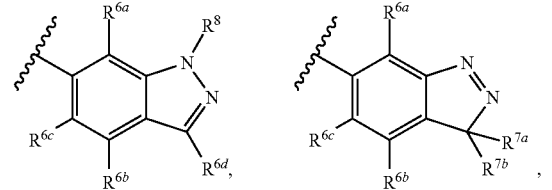
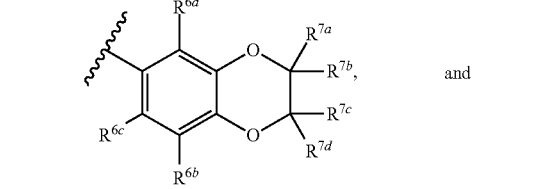

and

-continued

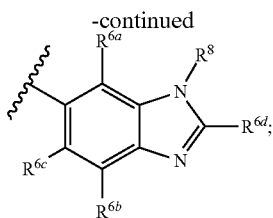

wherein:

each of $R^{6a}$, $R^{6b}$, $R^{6c}$, $R^{6d}$, and $R^{6e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$;

each of $R^{7a}$, $R^{7b}$, $R^{7c}$, and $R^{7d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_n$R$^5$; and $R^8$, when present, is selected from hydrogen and C1-C8 alkyl.

* * * * *

UNITED STATES PATENT AND TRADEMARK OFFICE
CERTIFICATE OF CORRECTION

Page 1 of 1

PATENT NO. : 9,868,746 B2
APPLICATION NO. : 15/283508
DATED : January 16, 2018
INVENTOR(S) : Craig W Lindsley et al.

It is certified that error appears in the above-identified patent and that said Letters Patent is hereby corrected as shown below:

In the Specification

Column 1, Line 22:

Replace the paragraph: [[This invention was made with government support under grant numbers MH87965, MH86601, MH82867, MH73676, MH89870, NS65867, MH77607, MH84659 and MH74427 awarded by the National Institutes of Health. The United States government has certain rights in the invention.]]

With the paragraph: --This invention was made with government support under grant numbers MH074427, NS065867, MF089870, MH086601, MH087965, MH082867, MH073676, MH077607, and MH084659 awarded by the National Institutes of Health. The government has certain rights in the invention.--

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*